(12) United States Patent
Jin et al.

(10) Patent No.: US 11,472,799 B2
(45) Date of Patent: Oct. 18, 2022

(54) SERINE THREONINE KINASE (AKT) DEGRADATION / DISRUPTION COMPOUNDS AND METHODS OF USE

(71) Applicant: Icahn School of Medicine at Mount Sinai, New York, NY (US)

(72) Inventors: Jian Jin, New York, NY (US); Jing Liu, New York, NY (US); Ramon E. Parsons, Manhasset, NY (US); Jia Xu, New York, NY (US); Xufen Yu, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 65 days.

(21) Appl. No.: 16/977,654

(22) PCT Filed: Mar. 6, 2019

(86) PCT No.: PCT/US2019/021014
§ 371 (c)(1),
(2) Date: Sep. 2, 2020

(87) PCT Pub. No.: WO2019/173516
PCT Pub. Date: Sep. 12, 2019

(65) Prior Publication Data
US 2020/0399266 A1  Dec. 24, 2020

Related U.S. Application Data

(60) Provisional application No. 62/639,240, filed on Mar. 6, 2018.

(51) Int. Cl.
*C07D 417/14* (2006.01)
*C07D 401/14* (2006.01)
*C07D 487/04* (2006.01)
*G01N 33/50* (2006.01)
*A61P 35/00* (2006.01)
*A61K 31/436* (2006.01)
*A61K 31/496* (2006.01)
*A61K 31/517* (2006.01)
*A61K 31/519* (2006.01)
*A61K 45/06* (2006.01)

(52) U.S. Cl.
CPC .......... *C07D 417/14* (2013.01); *A61K 31/436* (2013.01); *A61K 31/496* (2013.01); *A61K 31/517* (2013.01); *A61K 31/519* (2013.01); *A61K 45/06* (2013.01); *A61P 35/00* (2018.01); *C07D 401/14* (2013.01); *C07D 487/04* (2013.01); *G01N 33/5011* (2013.01); *G01N 2333/90* (2013.01); *G01N 2333/912* (2013.01)

(58) Field of Classification Search
CPC .. C07D 417/14; C07D 401/14; C07D 487/04; G01N 33/5011; G01N 2333/90; G01N 2333/912; A61P 35/00; A61K 31/436; A61K 31/496; A61K 31/517; A61K 31/519; A61K 45/06
See application file for complete search history.

(56) References Cited

U.S. PATENT DOCUMENTS

| | | | |
|---|---|---|---|
| 5,691,147 A | 10/1997 | Draetta et al. | |
| 8,377,937 B2 | 2/2013 | Bencsik et al. | |
| 8,648,096 B2 | 2/2014 | Muller et al. | |
| 9,809,603 B1 | 11/2017 | Jacques | |
| 9,822,094 B2 | 11/2017 | Man et al. | |
| 2002/0098161 A1 | 7/2002 | Uhrich | |
| 2004/0063773 A1 | 4/2004 | Tang et al. | |
| 2011/0172107 A1 | 7/2011 | Katz et al. | |
| 2011/0196150 A1 | 8/2011 | Man et al. | |
| 2014/0031325 A1 | 1/2014 | Bartlett et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0045504 A1 | 2/2016 | Grembecka et al. | |
| 2017/0008904 A1 | 1/2017 | Crew et al. | |
| 2017/0114098 A1 | 4/2017 | Aivado et al. | |
| 2017/0283807 A1 | 10/2017 | Mounir et al. | |
| 2018/0072741 A1 | 3/2018 | Vechorkin et al. | |
| 2018/0086767 A1 | 3/2018 | Fesik et al. | |
| 2018/0134684 A1 | 5/2018 | Bradner et al. | |
| 2018/0186800 A1 | 7/2018 | Yamamoto et al. | |
| 2019/0092768 A1 | 3/2019 | Gray et al. | |
| 2019/0255041 A1 | 8/2019 | Jin et al. | |
| 2019/0336503 A1 | 11/2019 | Jin et al. | |
| 2019/0367525 A1 | 12/2019 | Ioannidis et al. | |
| 2020/0338070 A1 | 10/2020 | Jin et al. | |
| 2021/0261538 A1 | 8/2021 | Jin et al. | |

(Continued)

FOREIGN PATENT DOCUMENTS

CN  102822165  12/2012
CN  104736569   6/2015
(Continued)

OTHER PUBLICATIONS

EP Office Action in European Appln. No. 17877800.7, dated May 24, 2022, 6 pages.
PCT International Search Report and Written Opinion in International Appln. No. PCT/US2022/013225, dated Jun. 6, 2022, 24 pages.
Abramovich et al., "Hox regulation of normal and leukemic hematopoietic stem cells," Curr. Opin. Hematol., May 2005, 12(3):210-216.
Addie et al., "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases," J. Med. Chem., Mar. 2013, 56(5):2059-2073.

(Continued)

*Primary Examiner* — Erich A Leeser
(74) *Attorney, Agent, or Firm* — Fish & Richardson P.C.

(57) ABSTRACT

Disclosed herein are serine threonine kinase (AKT) degradation/disruption compounds including an AKT ligand, a degradation/disruption tag, and a linker, and methods of using such compounds in the treatment of AKT-mediated diseases.

30 Claims, 47 Drawing Sheets

(56) References Cited

U.S. PATENT DOCUMENTS

| | | |
|---|---|---|
| 2021/0283261 A1 | 9/2021 | Jin et al. |
| 2021/0395244 A1 | 12/2021 | Jin et al. |
| 2022/0054488 A1 | 2/2022 | Jin et al. |

FOREIGN PATENT DOCUMENTS

| | | | |
|---|---|---|---|
| CN | 105085620 | 11/2015 | |
| CN | 108137507 | 6/2018 | |
| CN | 109071552 | 12/2018 | |
| CN | 109790143 | 5/2019 | |
| JP | 2018-526430 | 9/2018 | |
| JP | 2019-514883 | 5/2020 | |
| MX | 2018000471 | 4/2018 | |
| MX | 2018000360 | 6/2018 | |
| WO | WO 2008/109104 | 9/2008 | |
| WO | WO 2014/100719 | 6/2014 | |
| WO | WO 2015/101293 | 7/2015 | |
| WO | WO 2015/104677 | 7/2015 | |
| WO | WO 2015/192123 | * 12/2015 | ............ A61K 47/48 |
| WO | WO 2016/073956 | 5/2016 | |
| WO | WO 2016/105518 | 6/2016 | |
| WO | WO 2016/106518 | 7/2016 | |
| WO | WO 2016/115480 | 7/2016 | |
| WO | WO 2016/149668 | 9/2016 | |
| WO | WO 2016/174130 | 11/2016 | |
| WO | WO 2017/011371 | 1/2017 | |
| WO | WO 2017/011590 | 1/2017 | |
| WO | WO 2017/147700 | 9/2017 | |
| WO | WO 2017/147701 | 9/2017 | |
| WO | WO 2017/185031 | 10/2017 | |
| WO | WO 2017/197051 | 11/2017 | |
| WO | WO 2017/197055 | 11/2017 | |
| WO | WO 2018/106870 | 6/2018 | |
| WO | WO 2018/117177 | 6/2018 | |
| WO | WO 2019/222380 | 11/2019 | |
| WO | WO 2019/246570 | 12/2019 | |
| WO | WO 2020/252043 | 12/2020 | |
| WO | WO 2021/021904 | 2/2021 | |

OTHER PUBLICATIONS

Aguilar et al., "Discovery of 4-((3'R,4'S,5'R)-6"-Chloro-4'-(3-chloro-2-fluorophenyl)1'ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development," Journal of Medicinal Chemistry, Mar. 2017, 60(7):2819-2839.

Alinari et al., "Selective inhibition of protein arginine methyltransferase 5 blocks initiation and maintenance of B-cell transformation," Blood, Apr. 2015, 125(16):2530-2543.

Alzabin et al., "Hematopoietic progenitor kinase 1 is a critical component of prostaglandin E2-mediated suppression of the antitumor immune response," Cancer Immunol. Immunother., 2010, 59:419-429.

Alzabin et al., "Hematopoietic Progenitor Kinase 1 Is a Negative Regulator of Dendritic Cell Activation," J Immunol, 2009, 182:6187-6194.

Anders et al., "Differential expression analysis for sequence count data," Genome Biol., 2010 11:R106.

Armstrong et al., "MLL translocations specify a distinct gene expression profile that distinguishes a unique leukemia," Nat Genet., Jan. 2002, 30:41-47.

Artinger et al., "An MLL-dependent network sustains hematopoiesis," Proc. Natl. Acad. Sci. USA, Jul. 2013, 110(29):12000-12005.

Asiaban et al., "Cell-Based Ligand Discovery for the ENL YEATS Domain," ACS Chem. Biol., Apr. 2020, 15(4):895-903.

AU Notice of Allowance in Australian Appln. No. 2017348322, dated Dec. 14, 2021, 3 pages.

AU Office Action in Australian Appln. No. 2017348322, dated Dec. 10, 2020, 7 pages.

AU Office Action in Australian Appln. No. 2017348322, dated Sep. 27, 2021, 2 pages.

Ayton et al., "Molecular mechanisms of leukemogenesis mediated by MLL fusion proteins," Oncogene, Oct. 2001, 20:5695-5707.

Bachman et al., "EZH2 Expression Is Associated With High Proliferation Rate and Aggressive Tumor Subgroups in Cutaneous Melanoma and Cancers of the Endometrium, Prostate, and Breast," J. Clin. Oncol., 2006, 24(2):268-273.

Bai et al., "Targeted degradation of BET proteins in triple-negative breast cancer," Cancer Res., May 1, 2017, 77(9):2476-2487.

Basiorka et al. "Lenalidomide Stabilizes the Erythropoietin Receptor by Inhibiting the E3 Ubiquitin Ligase RNF41," Cancer Res., Apr. 2016, 76:3531-3540.

Bennett et al., "The Role of Nuclear Receptor-Binding SET Domain Family Histone Lysine Methyltransferases in Cancer," Cold Spring Harb. Perspect. Med., Jun. 2017, 7(6):a026708.

Berge et al., "Pharmaceutical Salts," Journal of Pharmaceutical Science, 1997, 66:1-19.

Bilsland et al., "Behavioral and neurochemical alterations in mice deficient in anaplastic lymphoma kinase suggest therapeutic potential for psychiatric indications," Neuropsychopharmacology, 2008, 33:685-700.

Biondi et al., "Biological and therapeutic aspects of infant leukemia.," Blood, Jul. 2000, 96:24-3 3.

Biswas et al., "Function of leukemogenic mixed lineage leukemia 1 (MLL) fusion proteins through distinct partner protein complexes," Proc. Natl. Acad. Sci. USA, Sep. 2011, 108(38):15751-15756.

Bitoun et al., "The mixed-lineage leukemia fusion partner 10 AF4 stimulates RNA polymerase II transcriptional elongation and mediates coordinated chromatin remodeling," Human Molecular Genetics, Jan. 2007, 16:92-106.

Blake et al., "Discovery and preclinical pharmacology of a selective ATP-competitive Akt inhibitor (GDC-0068) for the treatment of human tumors," J. Med. Chem., Sep. 2012, 55(18):8110-8127.

Bolshan et al., "Synthesis, optimization, and evaluation of novel small molecules as antagonists of WDR5-MLL interaction," ACS Medicinal Chemistry Letters, Mar. 2013, 4(3):353-357.

Bondeson et al., "Catalytic in vivo protein knockdown by small-molecule PROTACs," Nature Chemical Biology, 2015, 11(8):611-617.

Bondeson et al., "Lessons in PROTAC design from selective degradation with a promiscuous warhead," Cell Chem. Biol., Jan. 2018, 25:78-87e5.

Bottcher et al., "Fragment-based discovery of a chemical probe for the PWWP1 domain of NSD3," Nat. Chem. Biol., Aug. 2019, 15:822-829.

Bourdi et al., "Safety Assessment of Metarrestin in Dogs: A Clinical Candidate Targeting a Subnuclear Structure Unique to Metastatic Cancer Cell," Regul. Toxicol. Pharmacol., Aug. 2020, 116:104716.

Bracken et al., "EZH2 is downstream of the pRB-E2F pathway, essential for proliferation and amplified in cancer," EMBO J., 2003, 22(20)5323-5335.

Bradley et al., "EZH2 Inhibitor Efficacy in Non-Hodgkin's Lymphoma Does Not Require Suppression of H3K27 Monomethylation," Chem. Biol., 2014, 21(11):1463-1475.

Brand et al., "Homolog-selective degradation as a strategy to probe the function of CDK6 in AML," Cell Chem. Biol., Feb. 2019, 26(2):300-306e9.

Brauer et al., "Building a better understanding of the intracellular tyrosine kinase PTK6—BRK by BRK," Biochim, Biophys. Acta., Aug. 2010, 1806:66-73.

Braun et al., "Coordinated Splicing of Regulatory Detained Introns within Oncogenic Transcripts Creates an Exploitable Vulnerability in Malignant Glioma," Cancer Cell, Oct. 2017, 32(4):411-426.

Brooun et al., "Polycomb repressive complex 2 structure with inhibitor reveals a mechanism of activation and drug resistance," Nat. Commun., Apr. 28, 2016, 7:11384, 12 pages.

Browne et al., "Regulation of peptide-chain elongation in mammalian cells," Eur. J. Biochem., Nov. 2002, 269:5360-5368.

Buckley et al., "HaloPROTACS: use of small molecule PROTACs to induce degradation of HaloTag fusion proteins," ACS Chemical Biology, Aug. 2015, 10(8):1831-1837.

(56) References Cited

OTHER PUBLICATIONS

Buckley et al., "Small-molecule control of intracellular protein levels through modulation of the ubiquitin proteasome system," Angew Chem. Int. Ed. Engl., 2014, 53(9):2312-2330.

Buckley et al., "Small-molecule inhibitors of the interaction between the E3 ligase VHL and HIF1α," Angew Chem Int. Ed. Engl., 2012, 51(46):11463-11467.

Buckley et al., "Targeting the von Hippel-Lindau E3 ubiquitin ligase using small molecules to dismpt the VHL/HIF-1α interaction," Journal of the American Chemical Society, 2012, 134(10):4465-4468.

Burkhart et al., "Cellular mechanisms of tumour suppression by the retinoblastoma gene," Nature Reviews Cancer, 2008, 8(9):671-682.

Burnet, "The concept of immunological surveillance," Progress Exp. Tumor Res., 1970, 13:1-27.

Burslem et al., "Small-molecule modulation of protein homeostasis," Chem. Rev., Aug. 2017, 117(17):11269-11301.

Burslem et al., "The advantages of targeted protein degradation over inhibition: An RTK case study," Cell Chem. Biol., Jan. 2018, 25:67-77e3.

Cai et al., "Subunit composition and substrate specificity of a MOF-containing histone acetyltransferase distinct from the male-specific lethal (MSL) complex," The Journal of Biological Chemistiy, Feb. 2010, 285(7):4268-4272.

Cai et al., "ZFX Mediates Non-canonical Oncogenic Functions of the Androgen Receptor Splice Variant 7 in Castrate-Resistant Prostate Cancer," 2018, Mol. Cell 72, 341-354 e346.

Campbell et al., "EPZ011989, A Potent, Orally-Available EZH2 Inhibitor with Robust in Vivo Activity," ACS Med. Chem. Lett., 2015, 6(5):491-495.

Cao et al., "Regulation and functional role of eEF1 A2 in pancreatic carcinoma," Biochem. Biophys. Res. Commun., 2009, 380(1):11-16.

Cao et al., "Role of Histone H3 Lysine 27 Methylation in Polycomb-Group Silencing," Science, 2002, 298(5595):1039-1043.

Cao et al., "Targeting MLL1 H3K4 methyltransferase activity in mixed-lineage leukemia," Molecular Cell, Jan. 2014, 53(2):247-261.

Cappuzzo et al., "Erlotinib as maintenance treatment in advanced non-small-cell lung cancer: a multicentre, randomised, placebo-controlled phase 3 study," Lancet Oncol., Jun. 2010, 11:521-529.

Cardenas et al., "Enantioselective Synthesis of Pyrrolopyrimidine Scaffolds through Cation-Directed Nucleophilic Aromatic Substitution," Org. Lett., Mar. 2018, 20:2037-2041.

Carugo et al., "In vivo functional platform targeting patient-derived xenografts identifies WDR5-Myc association as a critical determinant of pancreatic cancer," Cell Reports, Jun. 2016, 16(1):133-147.

Castro et al., "Breast tumor kinase and extracellular signal-regulated kinase 5 mediate Met receptor signaling to cell migration in breast cancer cells," Breast Cancer Research, 2010, 12:R60, 15 pages.

Chamberlain et al., "Structure of the human Cereblon-DDB1-lenalidomide complex reveals basis for responsiveness to thalidomide analogs," Nat. Struct. Mol. Biol., 2014, 21(9):803-809.

Chang et al., "EZH2 promotes expansion of breast tumor initiating cells through activation of RAF1-β-catenin signaling," Cancer Cell, 2011, 19(1):86-100.

Chan-Penebre et al., "A selective inhibitor of PRMT5 with in vivo and in vitro potency in MCL models," Nature Chemical Biology, Apr. 2015, 11:432-437.

Chau et al., "An Anatomical Site and Genetic-Base Prognostic Model for Patients With Nuclear Protein in Testis (NUT) Midline Carcinoma: Analysis of 124 Patients," JNCI Cancer Spectr 4, 2020, pkz094 2020.

Chawade et al., "Normalyzer: a tool for rapid evaluation of normalization methods for omics data sets," J. Proteome. Res., 2014, 13:3114-31202014.

Chen et al., "Design, synthesis, and initial evaluation of affinity-based small molecular probe for detection of WDR5," Bioorganic Chemistiy, Feb. 2018, 76:380-385.

Chen et al., "Gene expression profiling of WDR5 regulated genes in bladder cancer," Genomics Data, Sep. 2015, 5:27-29.

Chen et al., "PTK6 promotes hepatocellular carcinoma cell proliferation and invasion," Am. J. Transl. Res., Oct. 2016, (10)4354-4361.

Chen et al., "Upregulated WDR5 promotes proliferation, self-renewal and chemoresistance in bladder cancer via mediating H3K4 trimethylation," Scientific Reports, Feb. 2015, 5: 12 pages.

Chi et al., "Covalent histone modifications—miswritten, misinterpreted and mis-erased in human cancers," Nat. Rev. Cancer, 2010, 10:457-469.

Choi et al., "EML4-ALK mutations in lung cancer that confer resistance to ALK inhibitors," N. Engl. J. Med., Oct. 2010, 363(18)4734-1739.

Choi et al., "Identification of novel isoforms of the EML4-ALK transforming gene in non-small cell lung cancer," Cancer Res., Jul. 2008, 68(13)4971-4976.

Christott et al., "Discovery of a Selective Inhibitor for the YEATS Domains of ENL/AF9.," SLAS Discov., 2019, 24:133-141.

Chung et al., "Cbx8 acts non-canonically with Wdr5 to promote mammary tumorigenesis," Cell Reports, Jul. 2016, 16(2)472-486.

Clinicaltrials.gov [online], "Metarrestin (ML-246) in Subjects with Metastatic Solid Tumors," Jan. 10, 2020, retrieved on Mar. 16, 2022, retrieved from URL<https://clinicaltrials.gov/ct2/show/NCT04222413>, 12 pages.

CN Office Action in Chinese Appln. No. 201780081246.8, dated Dec. 2, 2021, 18 pages (with English Translation).

CN Office Action in Chinese Appln. No. 201780081246.8, dated Jun. 4, 2021, 19 pages (with English Translation).

CN Office Action in Chinese Appln. No. 201780085879.6, dated Jan. 5, 2022, 18 pages (with English Translation).

Corthay, "Does the immune system naturally protect against cancer?" Front. Immunol., May 2014, 5(197): 1-8.

Cromm et al., "Addressing kinase-independent functions of Fak via PROTAC-mediated degradation," J. Am. Chem. Soc., Nov. 2018, 140(49): 17019-17026.

Cromm et al., "Targeted protein degradation: from chemical biology to drug discovery," Cell Chem. Biol., Sep. 2017, 24(9):1181-1190.

Czermin et al., "*Drosophila* enhancer of Zeste/ESC complexes have a histone H3 methyltransferase activity that marks chromosomal Polycomb sites," Cell, 2002, 111(2):185-196.

Dai et al., "WDR5 expression is prognostic of breast cancer outcome," PLoS One, Sep. 2015, 10: 15 pages.

Davies et al., "Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery," Journal of Medicinal Chemistry, Apr. 2016, 59(8):3991-4006.

Dawson et al., "Inhibition of BET recruitment to chromatin as an effective treatment for MLL-fusion leukaemia," Nature, 2011, 478:529-15 533.

Deng et al., "Protein arginine methyltransferase 5 functions as an epigenetic activator of the androgen receptor to promote prostate cancer cell growth," Oncogene, 2017, 36:1223-1231.

Derry et al., "Altered localization and activity of the intracellular tyrosine kinase BRK/Sik in prostate tumor cells," Oncogene, Jul. 2003, 22:4212-4220.

Deshpande et al., "Chromatin modifications as therapeutic targets in MLL-rearranged leukemia," Trends Immunol., Nov. 2012, 33(11):563-570.

Dias et al., "Structural analysis of the KANSL1/WDR5/KANSL2 complex reveals that WDR5 is required for efficient assembly and chromatin targeting of the NSL complex," Genes & Development, May 2014, 28(9):929-942.

Douglass, Jr. et al., "A comprehensive mathematical model for three-body binding equilibria," J. Am. Chem. Soc., Apr. 2013, 135(16):6092-6099.

Du et al., "FOXC1, a target of polycomb, inhibits metastasis of breast cancer cells," Breast Cancer Res. Treat., 2012, 131(1):65-73.

Duanmin et al., "eEF1A2 protein expression correlates with lymph node metastasis and decreased survival in pancreatic ductal adenocarcinoma," Hepatogastroenterology, Jun. 2013, 60(124):870-875.

(56) References Cited

OTHER PUBLICATIONS

Dumble et al., "Discovery of novel AKT inhibitors with enhanced anti-tumor effects in combination with the MEK inhibitor," PloS One, Jun. 2014, 9(6), 11 pages.
EA Office Action in Eurasian Appln. No. 201991071, dated Jun. 10, 2020, 4 pages (with English translation).
Ee et al., "An embryonic stem cell-specific NuRD complex functions through interaction with WDR5," Stem Cell Reports, Jun. 2017, 8(6): 9 pages.
EP Extended European Search Report in European Appln. No. 17863645.2, dated Aug. 6, 2020, 10 pages.
EP Extended European Search Report in European Appln. No. 17877800.7, dated Feb. 19, 2021, 9 pages.
EP Extended European Search Report in European Appln. No. 19757825.5, dated Jan. 26, 2022, 14 pages.
EP Extended European Search Report in European Appln. No. 19763958.6, dated Dec. 8, 2021, 12 pages.
EP Extended European Search Report in European Appln. No. 19830269.7, dated Mar. 7, 2022, 6 pages.
EP Office Action in European Appln. No. 17863645.2, dated Apr. 6, 2021, 7 pages.
EP Office Action in European Appln. No. 17863645.2, dated Mar. 11, 2022, 5 pages.
EP Office Action in European Appln. No. 19821826.5, dated Jan. 13, 2022, 4 pages.
EP Partial Supplementary Search Report in European Appln. No. 19757825.5, dated Oct. 18, 2021, 16 pages.
Erb et al. (2017). Transcription control by the ENL YEATS domain in acute leukaemia. Nature 543, 270-274.
Fabian et al., "A small molecule-kinase interaction map for clinical kinase inhibitors," Nat. Biotechnol., Mar. 2005, 23(3):329-336.
Fan et al., "A Kinase Inhibitor Targeted to mTORC1 Drives Regression in Glioblastoma," Cancer Cell, Mar. 2017, 31(3):424-435.
Fan et al., "BAHCC1 binds H3K27me3 via a conserved BAH module to mediate gene silencing and oncogenesis," Nature genetics, 2020, 52:1384-1396.
fda.gov [online], "Data Standards Manual (Monographs)," Feb. 27, 2018, retrieved on Feb. 7, 2022, retrieved from URL <https://www.fda.gov/drugs/electronic-regulatory-submission-and-review/data-standards-manual-monographs>, 1 page.
fda.gov [online], "Development & Approval Process | Drugs," Oct. 28, 2019, retrieved on Feb. 4, 2022, retrieved from URL <https://www.fda.gov/drugs/development-approval-process-drugs>, 4 pages.
Fei et al., "PROTAC and its Application in the Treatment of Cancer," Chemistry of Life, Aug. 2014, 34(4):549-554 (with English abstract).
Ferguson et al., "Kinase inhibitors: the road ahead," Nat. Rev. Drug Discov., May 2018, 17:353-377.
Ferrando et al., "Gene expression signatures in *MLL*-rearranged T-lineage and B-precursor acute leukemias: dominance of *HOX* dysregulation," Blood, Jul. 2003, 102(1):262-268.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," The Lancet Oncology, 2015, 16(1):25-35.
Fischer et al., "Structure of the DDB1-CRBN E3 ubiquitin ligase in complex with thalidomide," Nature, Aug. 2014, 512(7512):49-53.
Frankowski et al., "Metarrestin, a perinucleolar compartment inhibitor, effectively suppresses metastasis," Science Translational Medicine, May 2018, 10(441), 13 pages.
Frost et al., "Potent and selective chemical probe of hypoxic signalling downstream of HIF-α hydroxylation via VHL inhibition," Nat. Commun., Nov. 2016, 7:13312, 12 pages.
Fujii et al., "Enhancer of Zeste Homologue 2 (EZH2) Downregulates RUNX3 by Increasing Histone H3 Methylation," J. Biol. Chem., 2008, 283(25):47324-17332.
Fujii et al., "MEKERK pathway regulates EZH2 overexpression in association with aggressive breast cancer subtypes," Oncogene, 2011, 30(39):4118-4128.
Gadd et al., "A Children's Oncology Group and TARGET initiative exploring the genetic landscape of Wilms tumor," Nat. Genet., Oct. 2017, 49:1487-1494.
Galdeano et al., "Structure-guided design and optimization of small molecules targeting the proteinprotein interaction between the von Hippel-Lindau (VHL) E3 ubiquitin ligase and the hypoxia inducible factor (HIF) alpha subunit with in vitro nanomolar affinities," J. Med. Chem., 2014, 57(20):8657-8663.
Gao et al., "ZLD1122, a novel EZH2 and EZHI small molecular inhibitor, blocks H3K27 methylation and diffuse large B cell lymphoma cell growth," RSC Adv., 2016, 6:28512-28521.
Garapaty-Rao et al., "Identification of EZH2 and EZHI small molecule inhibitors with selective impact on diffuse large B cell lymphoma cell growth," Chem. Biol., 2013, 20(11):1329-1339.
Gamar-Wortzel et al., "Chemical Inhibition of ENL/AF9 YEATS Domains in Acute Leukemia," ACS Central Science, Apr. 2021, 7(5):815-830.
Ge et al., "WDR5 high expression and its effect on tumorigenesis in leukemia," Oncotarget, Jun. 2016, 7(25):37740-37754.
Gehling et al., "Discovery, design, and synthesis of indole-based EZH2 inhibitors," Bioorg. Med. Chem. Lett., 2015, 25(17):3644-3649.
Genscript.com [online], "Gen Script Make Research Easy," available on or before Mar. 3, 2015, retrieved on Mar. 17, 2022, retrieved from URL<https://www.genscript.com/gRNAdatabase.html>.
Getlik et al., "Structure-based optimization of a small molecule antagonist of the interaction between WD repeat-containing protein 5 (WDR5) and mixed-lineage leukemia 1 (MLL1)," Journal of Medicinal Chemistry, Mar. 2016, 59(6):2478-2496.
Gillis et al., "Biochemical and biological characterization of lymphocyte regulatory molecules; V. Identification of an interleukin 2-producing human leukemia T cell line," The Journal of experimental medicine, Dec. 1980,152:1709-1719.
Github.com [online], "PreprocessCore," Oct. 26, 2021, retrieved on Mar. 17, 2022, retrieved fromURL<Gihttps://github.com/bmbolstad/preprocessCore>, 1 pages.
Github.com [online], "ProteiNorm," Jul. 27, 2020, retrieved on Mar. 17, 2022, retrieved from URL <https://github.com/ByrumLab/proteiNorm>, 3 page.
Gluz et al., "Triplenegative breast cancer—current status and future directions," Ann. Oncol., 2009, 20(12):1913-1927.
Godin-Heymann et al., "The T790M 'gatekeeper' mutation in EGFR mediates resistance to low concentrations of an irreversible EGFR inhibitor," Mol. Cancer Ther., Apr. 2008, 7(4):874-879.
Gonzalez et al., "Downregulation of EZH2 decreases growth of estrogen receptor-negative invasive breast carcinoma and requires BRCA1," Oncogene, 2009, 28(6):843-853.
Gonzalez et al., "EZH2 expands breast stem cells through activation of NOTCH1 signaling," Proc. Natl. Acad. Sci. USA, 2014, 111(8):3098-3103.
Grabe et al., "C797S Resistance: The undruggable EGFR mutation in non-small cell lung cancer?" ACS Med. Chem. Lett., 2018, 9:779-782.
Grebien et al., "Pharmacological targeting of the Wdr5-MLL interaction in C/EBPα N-terminal leukemia," Nature Chemical Biology, Aug. 2015, 11(8): 11 pages.
Guarnaccia et al., "Moonlighting with WDR5: A cellular multitasker," Journal of Clinical Medicine, Feb. 2018, 7(2): 17 pages.
Gullà et al., "Protein arginine methyltransferase 5 has prognostic relevance and is a druggable target in multiple myeloma," Leukemia, 2018, 32:996-1002.
Haegebarth et al., "Protein tyrosine kinase 6 negatively regulates growth and promotes enterocyte differentiation in the small intestine," Mol. Cell Biol., Jul. 2006, 26:4949-4957.
Hallberg et al., "Mechanistic insight into ALK receptor tyrosine kinase in human cancer biology," Nature Reviews Cancer, Oct. 2013, 13:685-700.
Hamilton et al., "Targeting CDK4/6 in patients with cancer," Cancer Treatment Reviews, 2016, 45:129-138.

(56) References Cited

OTHER PUBLICATIONS

Han et al., "Discovery of ARD-69 as a Highly Potent Proteolysis Targeting Chimera (PROTAC) Degrader of Androgen Receptor (AR) for the Treatment of Prostate Cancer," Journal of Medicinal Chemistry, Jan. 2019, 62:941-964.
Harvey et al., "Brk protects breast cancer cells from autophagic cell death induced by loss of anchorage," The American Journal of Pathology, Sep. 2009, 175:1226-1234.
Harvey et al., "Use of RNA interference to validate Brk as a novel therapeutic target in breast cancer: Brk promotes breast carcinoma cell proliferation," Oncogene, Aug. 2003, 22:5006-5010.
He et al., "HIV-1 Tat and Host AFF4 Recruit Two Transcription Elongation Factors into a Bifunctional Complex for Coordinated Activation of HIV-I Transcription," Mol. Cell., May 2010, 38(3):428-438.
He et al., "Human Polymerase-Associated Factor complex (PAFc) connects the Super Elongation Complex (SEC) to RNA polymerase II on chromatin," Proc. Natl. Acad. Sci. USA, Sep. 2011, 108(36):E636-E645.
Heerding et al., "Identification of 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol (GSK690693), a novel inhibitor of AKT kinase," Journal of Medicinal Chemistry, Sep. 2008, 51(18):5663-5679.
Heidemeich et al., "Structure-Based Approach toward Identification of Inhibitory Fragments for Eleven-Nineteen-Leukemia Protein (ENL)," J. Med. Chem., Nov. 2018, 61(23):10929-10934.
Henning et al., "Degradation of Akt using protein-catalyzed capture agent," Journal of Peptide Science, 2016, 22:196-200.
Herbst et al., "Gefitinib—a novel targeted approach to treating cancer," Nat. Rev. Cancer, Dec. 2004, 4:956-965.
Hernandez et al., "The Kinase Activity of Hematopoietic Progenitor Kinase 1 Is Essential for the Regulation of T Cell Function," Cell reports, Oct. 2018, 25:80-94.
Herrera-Abreu et al., "Early adaptation and acquired resistance to CDK4/6 inhibition in estrogen receptor-positive breast cancer," Cancer Research, 2016, 76(8):2301-2313.
Hess, "MLL: a histone methyltransferase disrupted in leukemia," Trends Mol. Med., Oct. 2004, 10(10):500-507.
Higa et al., "CUL4-DDB 1 ubiquitin ligase interacts with multiple WD40-repeat proteins and regulates histone methylation," Nature Cell Biology, Nov. 2006, 8(11):1277-1283.
Hirai et al., "MK-2206, an allosteric Akt inhibitor, enhances antitumor efficacy by standard chemotherapeutic agents or molecular targeted drugs *in vitro* and *in vivo*," Molecular Cancer Therapeutics, Jul. 2010, 9(7): 1956-1967.
Hiroyuki et al., "The structure of bestatin," The Journal of Antibiotics, Jan. 1976, 29(1):100-101.
Hirsch et al., "Lung cancer: current therapies and new targeted treatments," Lancet, Jan. 2017, 389:299-311.
Holm et al., "Global H3K27 trimethylation and EZH2 abundance in breast tumor subtypes," Mol. Oncol., 2012, 6(5):494-506.
Hsu et al., "Recognition of histone acetylation by the GAS41 YEATS domain promotes H2A.Z deposition in non-small cell lung cancer," Genes Dev., 2018, 32:58-69.
Hu et al., "Human HPK1, a novel human hematopoietic progenitor kinase that activates the JNK/SAPK kinase cascade," Genes Dev., Sep. 1996, 10:2251-2264.
Hu et al., "Small Molecule Inhibitors of Protein Arginine Methyltransferases," Expert Opinion Investigational Drugs, 2016, 25:335-358.
Huang et al., "A Chemoproteomic Approach to Query the Degradable Kinome Using a Multi-kinase Degrader," Cell Chemical Biology, Jan. 2018, 25(1):88-99.
Huang et al., "Covalent inhibition of NSD1 histone methyltransferase," Nat. Chem. Biol, 2020, 16:1403-1410.
Huber et al., "Variance stabilization applied to microarray data calibration and to the quantification of differential expression," Bioinformatics, 2002, 18 Suppl 1:S96-104.

IN Office Action in Indian Appln. No. 201917020814, dated Jun. 23, 2021, 6 pages (with English Translation).
Irie et al., "PTK6 regulates IGF-1-induced anchorage-independent survival," PLoS One, Jul. 2010, 5(7):e11729.
Ito et al., "Identification of a primary target of thalidomide teratogenicity," Science, Mar. 2010, 327(5971):1345-1350.
Ito et al., "PTK6 Inhibition Suppresses Metastases of Triple-Negative Breast Cancer via SNAIL-Dependent E-Cadherin regulation," Cancer Res., Aug. 2016, 76:4406-4417.
Ito et al., "PTK6 regulates growth and survival of endocrine therapy-resistant ER+ breast cancer cells," NPJ Breast Cancer, Nov. 2017, 3:45.
Iwahara et al., "Molecular characterization of ALK, a receptor tyrosine kinase expressed specifically in the nervous system," Oncogene, Jan. 30, 1997, 14:439-449.
Jakobsson et al., "The dual methyltransferase METTL13 targets N terminus and Lys55 of eEF1A and modulates codon-specific translation rates," Nature Communications, Aug. 2018, 15 pages.
Jiang et al., "Development of dual and selective degraders of cyclin-dependent kinases 4 and 6," Angew. Chem, Int. Ed. Engl., May 2019, 58(19):6321-6326.
Jiang et al., "Targeting BRK-Positive Breast Cancers with Small-Molecule Kinase Inhibitors," Cancer Res., Jan. 2017, 77:175-186.
Jiao et al., "Structural basis of histone H3K27 trimethylation by an active polycomb repressive complex 2," Science, 2015, 350(6258):aac4383.
Jin et al., "Targeting methyltransferase PRMT5 eliminates leukemia stem cells in chronic myelogenous leukemia," The Journal of Clinical Investigation, Oct. 2016, 126:3961-3980.
JP Office Action in Japanese Appln. No. 2019-522841, dated Oct. 5, 2021, 14 pages (with English Translation).
JP Office Action in Japanese Appln. No. 2019-530811, dated Dec. 14, 2021, 4 pages (with English Translation).
Jude et al., "Unique and independent roles for MLL in adult hematopoietic stem cells and progenitors," Cell Stem Cell, Sep. 2007, 1(3):324-337.
Justin et al., "Structural basis of oncogenic histone H3K27M inhibition of human polycomb repressive complex 2," Nat. Commun., 2016, 7:11316.
Kanda et al., "Protein arginine methyltransferase 5 is associated with malignant phenotype and peritoneal metastasis in gastric cancer," International Journal of Oncology, Jun. 2016, 49:1195-1202.
Kanis et al., "A small molecule inhibitor of the perinucleolar compartment, ML246, attenuates growth and spread of ovarian cancer," Gynecol. Oncol. Res. Pract., 2018, 5:7.
Kanis et al., "Metarrestin: A novel compound active against ovarian cancer," Gynecol Oncol., Oct. 2015, 139(1):190.
Kaniskan et al., "Inhibitors of Protein Methyltransferases and Demethylases," Chem. Rev., 2018, 118(3):989-1068.
Kaniskan et al., "Selective inhibitors of protein methyltransferases," Journal of Medicinal Chemistry, 2015, 58:1596-1629.
Karatas et al., "Discovery of a highly potent, cell-permeable macrocyclic peptidomimetic (MM-589) targeting the WD repeat domain 5 protein (WDR5)-mixed lineage leukemia (MLL) protein-protein interaction," Journal of Medicinal Chemistiy, Jun. 2017, 60(12)4818-4839.
Khalyfa et al., "Characterization of elongation factor-1A (eEF1A-1) and eEF1A-2/S1 protein expression in normal and *wasted* mice," Journal of Biological Chemistry, 2001, 276:22915-22922.
Kiefer et al., "HPK1, a hematopoietic protein kinase activating the SAPK/JNK pathway," Embo J., Dec. 1996, 15(24):7013-7025.
Kim et al. "Targeted disruption of the EZH2-EED complex inhibits EZH2-dependent cancer" Nature Chemical Biology, 2013, 9:643-650.
Kim et al., "Targeting EZH2 in cancer," Nat. Med., 2016, 22(2)428-134.
Kleer et al., "EZH2 is a marker of aggressive breast cancer and promotes neoplastic transformation of breast epithelial cells," PNAS, 2003, 100(20)41606-11611.
Klein et al., "Yaf9 subunit of the NuA4 and SWR1 complexes targets histone H3K27ac through its YEATS domain," Nucleic Acids Res., Jan. 2018, 46:421-430.

(56) References Cited

OTHER PUBLICATIONS

Knutson et al., "A selective inhibitor of EZH2 blocks H3K27 methylation and kills mutant lymphoma cells," Nat. Chem. Biol., 8(11):890-896.
Knutson et al., "Durable tumor regression in genetically altered malignant rhabdoid tumors by inhibition of methyltransferase EZH2," Proc. Natl. Acad. Sci. USA., 2013, 110(19):7922-7927.
Kobayashi et al., "EGFR mutation and resistance of non-small-cell lung cancer to gefitinib," N. Engl. J. Med., Feb. 2005, 352(8):786-792.
Koivunen et al., "*EML4-ALK* fusion gene and efficacy of an ALK kinase inhibitor in lung cancer," Clinical Cancer Research, Jul. 1, 2008, 14(13):4275-4283.
Konze et al., "An Orally Bioavailable Chemical Probe of the Lysine Methyltransferases EZH2 and EZHI," ACS Chem. Biol., 2013, 8(6)4324-1334.
Krause et al., "Tyrosine kinases as targets for cancer therapy," N. Engl. J. Med., Jul. 2005, 353(2):172-187.
Krivtsov et al., "*MLL* translocations, histone modifications and leukaemia stem-cell development," Nat. Rev. Cancer, Nov. 2007, 7:823-833.
Kryukov et al., "*MTAP* deletion confers enhanced dependency on the PRMT5 arginine methyltransferase in cancer cells," Science, 2016, 351(6278):1214-1218.
Kuenzi et al., "Polypharmacology-based ceritinib repurposing using integrated functional proteomics," Nat. Chem. Biol., Dec. 2017, 13(12):1222-1231.
Kung et al., "Design and Synthesis of Pyridone-Containing 3,4-Dihydroisoquinoline-1(2*H*)-ones as a Novel Class of Enhancer of Zeste Homolog 2 (EZH2) Inhibitors," J. Med. Chem., 2016, 59(18):8306-8325.
Kuzmichev et al., "Histone methyltransferase activity associated with a human multiprotein complex containing the Enhancer of Zeste protein," Genes Dev., 2002, 16(22):2893-2905.
Kwak et al., "Anaplastic lymphoma kinase inhibition in non-small-cell lung cancer," New England Journal of Medicine, Oct. 28, 2010, 363(18):1693-1703.
Lai et al., "Induced protein degradation: an emerging drug discovery paradigm," Nat. Rev. Drug Discov., Feb. 2017, 16(2):101-114.
Lai et al., "Modular PROTAC design for the degradation of oncogenic BCR-ABL, "Angewandte Chemie International Edition English, Jan. 2016, 55(2):807-810.
Lapierre et al., "Discovery of 3-(3-(4-(1-Aminocyclobutyl)phenyl)-5-phenyl-3*H*-imidazo[4,5-α]pyridin-2-yl)pyridin-2-amine (ARQ 092): An orally bioavailable, selective, and potent allosteric AKT inhibitor," Journal of Medicinal Chemistry, 2016, 59:6455-6469.
Lebraud et al., "Protein Degradation by In-Cell Self-Assembly of Proteolysis Targeting Chimeras," ACS Central Science, 2016, 2:927-934.
Li et al., "AF9 YEATS domain links histone acetylation to DOT1L-mediated H3K79 methylation," Cell, Oct. 2014, 159(3):558-571.
Li et al., "Discovery of MD-224 as a first-in-class, highly potent, and efficacious proteolysis targeting chimera Murine Double Minute 2 degrader capable of achieving complete and durable tumor regression," J, Med. Chem., 2019, 62(2):448-466.
Li et al., "Discovery of potent and noncovalent reversible EGFR kinase inhibitors of EGFR$^{L858R/T790M/C7978}$," ACS Med. Chem. Lett., Jun. 2019, 10(6):869-873.
Li et al., "High-affinity small molecular blockers of mixed lineage leukemia 1 (MLL1)-WDR5 interaction inhibit MILL1 complex H3K4 methyltransferase activity," European Journal of Medicinal Chemistiy, Nov. 2016, 124:480-489.
Li et al., "Molecular Coupling of Histone Crotonylation and Active Transcription by AF9 Yeats Domain," Mol, Cell., Apr. 2016, 62(2):181-193.
Li et al., "RSEM: accurate transcript quantification from RNA-Seq data with or without a reference genome," Bmc Bioinformatics, 2011, 12:323.
Li et al., "Structure-based design and synthesis of small molecular inhibitors disturbing the interaction of MLL1-WDR5," European Journal of Medicinal Chemistiy, Aug. 2016, 118:1-8.
Li et al., "Structure-guided development of YEATS domain inhibitors by targeting π-π-π stacking," Nat. Chem. Biol., Dec. 2018, 14:1140-1149.
Li et al., "The OncoPPi network of cancer-focused protein-protein interactions to inform biological insights and therapeutic strategies," Nat. Commun., Feb. 2017, 8:14356.
Li et al., "Understanding histone H3 lysine 36 methylation and its deregulation in disease," Cell. Mol. Life Sci., Aug. 2019, 76(15)2899-2916.
Li et al., "ZMYND11-MBTD1 induces leukemogenesis through hijacking NuA4/TIP60 acetyltransferase complex and a PWWP-mediated chromatin association mechanism," Nat. Commun., 2021, 12(1), 18 pages.
Lim et al., "CDK4/6 inhibitors: promising opportunities beyond breast cancer," Cancer Discovery, 2016, 6(7):697-699.
Lin et al., "AFF4, a component of the ELL/PTEFb elongation complex and a shared subunit of MLL chimeras, can link transcription elongation to leukemia," Mol. Cell., Feb. 2010, 37(3):429-437.
Lin et al., "Clinicopathologic features, patterns of recurrence, and survival among women with triplenegative breast cancer in the National Comprehensive Cancer Network," Cancer, 2012, 118(22):5463-5472.
Lin et al., "Targeting ALK: Precision Medicine Takes on Dmg Resistance," Cancer Discovery, Feb. 2017, 7(2):137-155.
Ling et al., "Involvement of hematopoietic progenitor kinase 1 in T cell receptor signaling," The Journal of biological chemistiy, Jun. 2001, 276:18908-18914.
Liou et al., "HPK1 is activated by lymphocyte antigen receptors and negatively regulates AP-1," Immunity, Apr. 2000, 12(4):399-408.
Liu et al., "Calcineurin is a common target of cyclophilin-cyclosporin A and FKBP-FK506 complexes," Cell, Aug. 1991, 66(4):807-815.
Liu et al., "Critical role of kinase activity of hematopoietic progenitor kinase 1 in anti-tumor immune surveillance," PloS one, Mar. 2019, 14:e02 12670.
Liu et al., "METTL13 Methylation of eEF1A Increases Translational Output to Promote Tumorigenesis," Cell, Jan. 2019, 176:491-504,e421.
Liu et al., "Widening Synthesis Bottlenecks: Realization of Ultrafast and Continuous-Flow Synthesis of High-Silica Zeolite SSZ-13 for NOx Removal," Angew. Chem., May 4, 2015, 127(19):5775-5779.
Losada et al., "Binding of *eEF1A2* to the RNA-dependent protein kinase PKR modulates its activity and promotes tumour cell survival," British Journal of Cancer, Nov. 2018, 119(11):1410-1420.
Lu et al., "Epigenetic Perturbations by Arg882-Mutated DNMT3 A Potentiate Aberrant Stem Cell Gene-Expression Program and Acute Leukemia Development," Cancer Cell, 2016, 30:92-107.
Lu et al., "Hijacking the E3 ubiquitin ligase cereblon to efficiently target BRD4," Chemistry & Biology, Jun. 2015, 22(6):755-763.
Lu et al., "Targeting EGFR$^{L858R/T790M}$ and EGFR$^{L858R/T790M/C7978}$ resistance mutations in NSCLC: Current developments in medicinal chemistiy," Med. Res. Rev., Jan. 2018, 38(5):1550-1581.
Mahara et al., "HIFI-β activation underlies a functional switch in the paradoxical role of Ezh2/PRC2 in breast cancer," PNAS, 2016, 113(26):E3735-E3744.
Mahmoud et al., "Discovery of 4-anilino β-carbolines as novel Brk inhibitors," Bioorganic & Medicinal Chemistry Letters, Apr. 2014, 24:1948-1951.
Majer et al., "A687V EZH2 is a gain-offunction mutation found in lymphoma patients," FEBS Lett., 2012, 586(19):3448-3451.
Maniaci et al., "Homo-PROTACs: bivalent small-molecule dimerizers of the VHL E3 ubiquitin ligase to induce self-degradation," Nature Communication, Oct. 2017, 8, 14 pages.
Manning et al., "AKT/PKB signaling: navigating the network," Cell, Apr. 2017, 169(3):381-405.
Marjon et al., "*MTAP* Deletions in Cancer Create Vulnerability to Targeting of the MAT2A/PRMT5/RIOK1 Axis," Cell Reports, Apr. 2016, 15:574-587.
Marschalek, "MLL Leukemia and Future Treatment Strategies," Arch. Pharm. Chem. Life Sci., Apr. 2015, 348(4):221-228.

(56) References Cited

OTHER PUBLICATIONS

Matsushime et al., "Identification and properties of an atypical catalytic subunit ($p34^{PSK-J3}$/cdk4) for mammalian D type G1 cyclins," Cell, 1992, 71(2):323-334.
Mavrakis et al., "Disordered methionine metabolism in MTAP/CDKN2A-deleted cancers leads to dependence onPRMT5," Science, Febmaiy 2016, 351(6278):1208-1213.
McApine et al., "Abstract 4857: Discovery of PF-06855800, a SAM competitive PRMT5 inhibitor with potent antitumor activity," American Association for Cancer Research Annual Meeting, 2018, 78(13 Supplement), 4 pages.
McCabe et al., "EZH2 inhibition as a therapeutic strategy for lymphoma with EZH2-activating mutations," Nature, 2012, 492(7427): 108-112.
McCabe et al., "Mutation of A677 in histone methyltransferase EZH2 in human B-cell lymphoma promotes hypertrimethylation of histone H3 on lysine 27 (H3K27)," Proc. Natl. Acad. Sci. USA, 2012, 109(8):2989-2994.
Meyer et al., "New insights to the *MLL* recombinome of acute leukemias," Leukemia, Aug. 2009, 23:1490-1499.
Meyer et al., "The *MLL* recombinome of acute leukemias in 2013," Leukemia, Nov. 2013, 27:2165-2176.
Meyer et al., "The *MLL* recombinome of acute leukemias," Leukemia, May 2006, 20:777-784.
Meyerson et al., "Identification of $G_1$ kinase activity for cdk6, a novel cyclin D partner," Molecular and Cellular Biology, 1994, 14(3)2077-2086.
Mi et al., "YEATS2 links histone acetylation to tumorigenesis of non-small cell lung cancer," Nat. Commun,, Oct. 2017, 8:1088, 14 pages.
Migliori et al., "Symmetric dimethylation of H3R2 is a newly identified histone mark that supports euchromatin maintenance," Nature Structural and Molecular Biology, Feb. 2012, 19(2):136-144.
Miller et al., "COMPASS: a complex of proteins associated with atrithorax-related SET domain protein," Proceedings of the National Academy of Sciences, Nov. 2001, 98(23): 12902-12907,.
Mitchell et al., "Cloning and characterisation of cDNAs encoding a novel non-receptor tyrosine kinase, brk, expressed in human breast tumours," Oncogene, Aug. 1994, 9:2383-2390.
Mohan et al., "Licensed to elongate: a molecular mechanism for MLL-based leukaemogenesis," Nat. Rev. Cancer, Oct. 2010, 10:721-728.
Mohan et al., "Linking H3K79 trimethylation to Wnt signaling through a novel Dot1-containing complex (DotCom)," Genes Dev., 2010, 24:574-589.
Molander et al., "Efficient hydrolysis of organotrifluoroborates via silica gel and water," Journal of Organic Chemistiy, Oct. 2009, 74(19):364-7369.
Morin et al., "Somatic mutations altering EZH2 (Y641) in follicular and diffuse large B-cell lymphomas of germinal-center origin," Nat. Genet., 2010, 42(2): 181-185.
Morris et al., "*ALK*, the chromosome 2 gene locus altered by the t(2;5) in non-Hodgkin's lymphoma, encodes a novel neural receptor tyrosine kinase that is highly related to leukocyte tyrosine kinase (LTK)," Oncogene, Mar. 8, 1997, 14:2175-2188.
Morris et al., "Fusion of a kinase gene, *ALK*, to a nucleolar protein gene, *NPM*, in non-Hodgkin's lymphoma," Science, Mar. 4, 1994, 263(5151):1281-1284.
Moustakim et al., "Discovery of an MLLT1/3 Yeats Domain Chemical Probe," Angew. Chem. Int. Ed. Engl,, Dec. 2018, 57(50): 16302-16307.
Mueller et al., "A role for the MLL fusion partner ENL in transcriptional elongation and chromatin modification," Blood, Dec. 2007, 110(13):4445-4454.
Mueller et al., "Misguided Transcriptional Elongation Causes Mixed Lineage Leukemia," Plos Biol., Nov. 2009, 7(11):e1000249, 15 pages.
Muller et al., "Histone methyltransferase activity of a Drosophila Poly comb group repressor complex," Cell, 2002, 111(2): 197-208.

MX Office Action in Mexican Appln. No. MX/a/2019/004950, dated Aug. 6, 2021, 6 pages (with English translation).
MX Office Action in Mexican Appln. No. MX/a/2019/004950, dated Nov. 23, 2021, 8 pages (with English Translation).
Nadeem Abbas et al., "Advances in targeting the epidermal growth factor receptor pathway by synthetic products and its regulation by epigenetic modulators as a therapy for glioblastoma," Cells, Apr. 2019, 8:350, 22 pages.
Neklesa et al., "Small-molecule hydrophobic tagging induced degradation of HaloTag fusion proteins," Nat. Chem. Biol., 2011, 7(8):538-543.
Ni et al., "Structural Insights into Interaction Mechanisms of Alternative Piperazine-urea YEATS Domain Binders in MLLT1," ACS Med. Chem. Lett., Dec. 2019, 10(12):1661-1666.
Nicholson et al., "EGFR and cancer prognosis," Eur. J. Cancer, Sep. 2001, 37(Supp. 4):9-15.
Noble et al., "Protein kinase inhibitors: insights into drug design from structure," Science, Mar. 2004, 303:1800-1805.
Odho et al., "Characterization of a novel WDR5-binding site that recruits RbBP5 through a conserved motif to enhance methylation of histone H3 lysine 4 by mixed lineage leukemia protein-1," Journal of Biological Chemistiy, Oct. 2010, 285(43):32967-32976.
Ohoka et al., "In vivo knockdown of pathogenic proteins via specific and nongenetic inhibitor of apoptosis protein (IAP)-dependent protein erasers (SNIPERs)," Journal of Biological Chemistry, Mar. 2017, 292(11):4556-4570.
Okada et al., "hDOTIL links histone methylation to leukemogenesis," Cell, Apr. 2005, 121(2):167-178.
Okuhira et al., "Specific degradation of CRABP-II via cIAPI-mediated ubiquitylation induced by hybrid molecules that crosslink cIAPI and the target protein," FEBS Lett., Apr. 2011, 585(8): 1147-1152.
Olson et al., "Pharmacological perturbation of CDK9 using selective CDK9 inhibition or degradation," Nat. Chem, Biol., Feb. 2018, 14:163-170.
Ono et al., "PTK6 promotes cancer migration and invasion in pancreatic cancer cells dependent on ERK signaling," PLoS One, 2014, 9:e96060.
Ostrander et al., "Brk/PTK6 signaling in normal and cancer cell models," Curr. Opin. Pharmacol., 2010, 10:662-669.
Ottis et al., "Proteolysis-targeting chimeras: induced protein degradation as a therapeutic strategy," ACS Chem. Biol., Mar. 2017, 12(4):892-898.
Paez et al., "*EGFR mutations* in lung cancer: correlation with clinical response to gefitinib therapy," Science, Jun. 2004, 304:1497-500.
Pao et al., "Acquired resistance of lung adenocarcinomas to gefitinib or erlotinib is associated with a second mutation in the EGFR kinase domain," PLoS Med., Feb. 2005, 2(3):e73.
Papazimas et al., "A General Strategy for the Preparation of Thalidomide-Conjugate Linkers," Synlett, Aug. 23, 2017, 28:2881-2885.
Park et al., "Discovery of EGF receptor inhibitors that are selective for the d746-750/T790M/C797S mutant through structure-based *de novo* design," Angew. Chem, Int. Ed., Jun. 2017, 56(26):7634-7638.
Park et al., "PTK6 inhibition promotes apoptosis of Lapatinib-resistant Her2+breast cancer cells by inducing Bim," Breast Cancer Res, 2015, 17:86.
Patel et al., "A conserved arginine-containing motif crucial for the assembly and enzymatic activity of the mixed lineage leukemia protein-I core complex," The Journal of Biological Chemistry, Nov. 2008, 283(47):32162-32175.
Patel et al., "Recent updates on third generation EGFR inhibitors and emergence of fourth generation EGFR inhibitors to combat C797S resistance," Eur. J. Med. Chem., Dec. 2017, 142:32-47.
Patel et al., "Structure of WDR5 bound to mixed lineage leukemia protein-I peptide," The Journal of Biological Chemistry, Nov. 2008, 283(47):32158-32161.
PCT International Preliminary Report on Patentability in International Appln No. PCT/US2018/063847, dated Jun. 18, 2020, 8 pages.

(56) References Cited

OTHER PUBLICATIONS

PCT International Preliminary Report on Patentability in International Appln. No. PCT/US2019/019123, dated Aug. 27, 2020, 10 pages.
PCT International Preliminary Report on Patentability in International Appln. No. PCT/US2019/038560, dated Dec. 30, 2020, 9 pages.
PCT International Preliminary Report on Patentability in International Appln. No. PCT/US2019/040507, dated Jan. 5, 2021, 7 pages.
PCT International Preliminary Report on Patentability in International Appln. No. PCT/US2020/031527, dated Nov. 2, 2021, 8 pages.
PCT International Search Report and Written Opinion in International Appln. No. PCT/US2017/058718, dated Jan. 28, 2018, 8 pages.
PCT International Search Report and Written Opinion in International Appln. No. PCT/US2017/065027, dated Mar. 6, 2018, 8 pages.
PCT International Search Report and Written Opinion in International Appln. No. PCT/US2018/063847, dated Mar. 27, 2019, 11 pages.
PCT International Search Report and Written Opinion in International Appln. No. PCT/US2019/019123, dated Jun. 20, 2019, 15 pages.
PCT International Search Report and Written Opinion in International Appln. No. PCT/US2019/021014, dated Jun. 27, 2019, 11 pages.
PCT International Search Report and Written Opinion in International Appln. No. PCT/US2019/038560, dated Oct. 10, 2019, 12 pages.
PCT International Search Report and Written Opinion in International Appln. No. PCT/US2019/040507, dated Nov. 12, 2019, 10 pages.
PCT International Search Report and Written Opinion in International Appln. No. PCT/US2020/031527, dated Sep. 14, 2020, 11 pages.
PCT International Search Report and Written Opinion in International Appln. No. PCT/US2021/055574, dated Feb. 25, 2022, 11 pages.
PCT Invitation to Pay Additional Fees in International Appln. No. PCT/US2019/019123, dated Apr. 8, 2019, 3 pages.
PCT Invitation to Pay Additional Fees in International Appln. No. PCT/US2019/021014, dated Apr. 22, 2019, 2 pages.
PCT Invitation to Pay Additional Fees in International Appln. No. PCT/US2019/038560, dated Aug. 14, 2019, 2 pages.
PCT Invitation to Pay Additional Fees in International Appln. No. PCT/US2021/055574, dated Dec. 22, 2021, 2 pages.
Pellegrino et al., "EEF1A2 inactivates p53 by way of PI3K/AKT/mTOR-dependent stabilization of MDM4 in hepatocellular carcinoma," Hepatology, May 2014, 59(5):1886-1899.
Peng et al., "Protein tyrosine kinase 6 promotes ERBB2-induced mammary gland tumorigenesis in the mouse," Cell Death Dis., 2015, 6:e1848.
Perlman et al., "*MLLT1* YEATS domain mutations in clinically distinctive Favourable Histology Wilms tumours," Nat. Commun,, Dec. 2015, 6:10013, 10 pages.
Peters et al., "Alectinib versus Crizotinib in Untreated ALK Positive Non-Small-Cell Lung Cancer," New England Journal of Medicine, Aug. 31, 2017, 377(9):829-838.
Pettersson et al., "PROteolysis TArgeting Chimeras (PROTACs)—past, present and future," Drug Discov. Today Technol., Apr. 2019, 31:15-27.
Pieters et al., "A treatment protocol for infants younger than 1 year with acute lymphoblastic leukaemia (Interfant-99): an observational study and a multicentre randomised trial," Lancet, Jul. 2007, 370:240-250.
Prabhu et al., "Adapting AlphaLISA high throughput screen to discover a novel small-molecule inhibitor targeting protein arginine methyltransferase 5 in pancreatic and colorectal cancers," Oncotarget, May 2017, 8(25):39963-39977.

Pretre et al., "Inhibition of Akt and other AGC kinases: A target for clinical cancer therapy?," Accepted Manuscript, Seminars in Cancer Biology, 2018, 48:70-77.
PubChem-CID-44631912, NIH, National Center for Biotechnology Information, Create Date: Mar. 8, 2010, 30 pages.
Pui et al., "Treating Childhood Acute Lymphoblastic Leukemia without Cranial Irradiation," N. Engl. J. Med., Jun. 2009, 360(26):2730-2741.
Pulford et al., "Detection of anaplastic lymphoma kinase (ALK) and nucleolar protein nucleophosmin (NPM)-ALK proteins in normal and neoplastic cells with the monoclonal antibody ALK1," Blood, Feb. 15, 1997, 89(4):1394-1404.
Qi et al., "Selective inhibition of Ezh2 by a small molecule inhibitor blocks tumor cells proliferation," Proc. Natl. Acad. Sci. USA, 2012, 109(52):21360-21365.
Quentmeier et al., "EZH2 Y641 mutations in follicular lymphoma," Leukemia, 2011, 25(4):726-729.
Raina et al., "PROTACinduced BET protein degradation as a therapy for castration-resistant prostate cancer," Proceedings of the National Academy of Sciences of the United States of America, Jun. 2016, 113(26):7124-7129.
Rao et al., "Hijacked in cancer: the KMT2 (MLL) family of methyltransferases," Nat. Rev. Cancer, Jun. 2015, 15:334-346.
Ren et al., "PHF19 promotes multiple myeloma tumorigenicity through PRC2 activation and broad H3K27me3 domain formation," Blood, 2019, 134:1176-1189.
Ren et al., "Polycomb protein EZH2 regulates tumor invasion via the transcriptional repression of the metastasis suppressor RKIP in breast and prostate cancer," Cancer Res., 2012, 72(12):3091-3104.
Ribas et al., "Cancer immunotherapy using checkpoint blockade," Science (New York, NY), Mar. 2018, 359(6382)4350-1355.
Rikova et al., "Global survey of phosphotyrosine signaling identifies oncogenic kinases in lung cancer," Cell, Dec. 14, 2007, 131(6):1190-1203.
Ritchie et al., "*limma* powers differential expression analyses for RNA-sequencing and microarray studies," Nucleic Acids Res., 2015, 43(7):e47.
Rodrik-Outmezguine et al., "Overcoming mTOR resistance mutations with a new-generation mTOR inhibitor," Nature, Jun. 2016, 534:272-276.
Roguev et al., "The *Saccharomyces cerevisiae* Set1 complex includes an ash2 homologue and methylates histone 3 lysine," The EMBO journal, Dec. 2001, 20(24):7137-7148.
Rosati et al., "*NUP98* is fused to the NSD3 gene in acute myeloid leukemia associated with t(8;11)(p11.2;p15)," Blood, 2002, 99:3857-3860.
Sakamoto et al., "Protacs: chimeric molecules that target proteins to the Skpl-Cullin-F box complex for ubiquitination and degradation," Proc. Natl. Acad. Sci. USA, Jul. 2001, 98(15):8554-8559.
Salami et al., "Waste disposal-An attractive strategy for cancer therapy," Science, Mar. 2017, 355:1163-1167.
Saura et al., "A first-in-human phase I study of the ATP-competitive AKT inhibitor ipatasertib demonstrates robust and safe targeting of AKT in patients with solid tumors," Cancer Discovery, January 2017, 7(1):102-113.
Sauvageau et al., "Poly comb group proteins: multi-faceted regulators of somatic stem cells and cancer," Cell Stem Cell., 2010, 7(3):299-313.
Sawasdikosol et al., "Hematopoietic progenitor kinase 1 (HPK1) regulates prostaglandin Ez-induced fos gene transcription," Blood, May 2003, 101(9):3687-3689.
Sawasdikosol et al., "HPK1 as a novel target for cancer immunotherapy," Immunologic Research, Dec. 2012, 54(1-3):262-265.
Sawasdikosol et al., "Prostaglandin $E_2$ activates HPK 1 kinase activity via a PKA-dependent pathway," The Journal of biological chemistiy, Nov. 2007, 282(48):34693-34699.
Schapira et al., "Targeted protein degradation: expanding the toolbox," Nat. Rev. Drug Discov., Dec. 2019, 18(12):949-963.
Schmandt et al., "The BRK tyrosine kinase is expressed in high-grade serous carcinoma of the ovary," Cancer Biol. Ther., 2006, 5:1136-1141.
Schneider et al. "Characterization of EBV-genome negative 'null' and T cell lines derived from children with acute lymphoblastic

(56) References Cited

OTHER PUBLICATIONS leukemia and leukemic transformed non-Hodgkin lymphoma," International Journal of Cancer, May 1977, 19(5): 621-626.
Schramm et al., "Novel BQCA- and TBPB-derived M1 receptor hybrid ligands: orthosteric carbachol differentially regulates partial agonism," ChemMedChem, Jul. 2019, 14(14): 1349-1358.
Senisterra et al., "Small-molecule inhibition of MLL activity by disruption of its interaction with WDR5," Biochemical Journal, Jan. 2013, 449(1):151-159.
Seshacharyulu et al., "Targeting the EGFR signaling pathway in cancer therapy," Expert Opin. Ther. Targets, Jan. 2012, 16:15-31.
Shanle et al., "Association of Taf14 with acetylated histone H3 directs gene transcription and the DNA damage response," Genes Dev., 2015, 29:1795-1800.
Sharma et al., "Epidermal growth factor receptor mutations in lung cancer," Nat. Rev. Cancer, Mar. 2007, 7:169-181.
Shaw et al., "Ceritinib in *ALK*-rearranged non-small-cell lung cancer," New England Journal of Medicine, Mar. 27, 2014, 370(13):1189-1197.
Shen et al., "Identification of LEM-14 inhibitor of the oncoprotein NSD2," Biochem Biophys. Res. Commun., Jan. 2019, 508(1):102-108.
Shen et al., "NSD3-Short Is an Adaptor Protein that Couples BRD4 to the CHD8 Chromatin Remodeler," Mol. Cell., Dec. 2015, 60(6):847-859.
Shen et al., "Structure-based design of 5-methylpyrimidopyridone derivatives as new wild-type sparing inhibitors of the epidermal growth factor receptor triple mutant (EGFR$^{L858R/T790M/C797S}$)," J Med. Chem., Jul. 2019, 62:7302-7308.
Sherr et al., "Targeting CDK4 and CDK6: from discovery to therapy," Cancer Discovery, 2016, 6(4):353-367.
Shibata et al., "Development of protein degradation inducers of oncogenic BCR-ABL protein by conjugation of ABL kinase inhibitors and IAP ligands," Cancer Science, Aug. 2017, 108(8):1657-1666.
Shimizu et al., "The protein arginine methyltransferase 5 promotes malignant phenotype of hepatocellular carcinoma cells and is associated with adverse patient outcomes after curative hepatectomy," International Journal of Oncology, Jan. 2017, 50(2):381-386.
Shiota et al., "Hyperphosphorylation of a novel 80 kDa protein-tyrosine kinase similar to Ltk in a human 40 Ki-1 lymphoma cell line, AMS3," Oncogene, Jun. 1994, 9(6)4567-1574.
Shui et al., "Hematopoietic progenitor kinase 1 negatively regulates T-cell receptor signaling and T cell-mediated immune responses," Nature Immunology, Jan. 2007, 8(1):84-91.
Slany, "When epigenetics kills: MLL fusion proteins in leukemia," Hematol. Oncol., Mar. 2005, 23:1-9.
Sneeringer et al., "Coordinated activities of wild-type plus mutant EZH2 drive tumor-associated hypertrimethylation of lysine 27 on histone H3 (H3K27) in human B-cell lymphomas," Proc. Natl. Acad. Sci. USA, Dec. 7, 2010, 107(49):20980-20985.
Soda et al., "Identification of the transforming *EML4-ALK* fusion gene in non-small-cell lung cancer," Nature, Aug. 2, 2007, 448:561-566.
Solomon et al., "First-line crizotinib versus chemotherapy in *ALK*-positive lung cancer," New England Journal of Medicine, Dec. 4, 2014, 371(23):2167-2177.
Song et al., "Selective inhibition of EZH2 by ZLD1039 blocks H3K27methylation and leads to potent anti-tumor activity in breast cancer," Sci. Rep., 2016, 6:20864.
Song et al., "WDR5 interacts with mixed lineage leukemia (MLL) protein via the histone HJ-binding pocket," The Journal of Biological Chemistiy, Dec. 2008, 283(50):35258-35264.
Soucy et al., "An inhibitor of NEDD 8-activating enzyme as a new approach to treat cancer," Nature, Apr. 2009, 458:732-736.
Subramanian et al., "Gene set enrichment analysis: a knowledge-based approach for interpreting genome-wide expression profiles," Proc. Natl. Acad. Sci. USA, Sep. 2005, 102(43):15545-15550.
Suda et al., "The structure of bestatin," The Journal of Antibiotic, Jan. 1976, 29(1):100-101.

Sun et al., "Discovery of AMG 232, a potent, selective, and orally bioavailable MDM2-p53 inhibitor in clinical development," Journal of Medicinal Chemistiy, Febmaiy 2014, 57(4):1454-1472.
Sun et al., "PROTAC-induced BTK degradation as a novel therapy for mutated Btk C481S induced ibrutinib-resistant B-cell malignancies," Cell Research, Jul. 2018, 28(7):779-781.
Sun et al., "Up-regulated WDR5 promotes gastric cancer formation by induced cyclin DI expression," Journal of Cellular Biochemistiy, Apr. 2018, 119(4): 28 pages.
Sun et al., "WDR5 supports an N-Myc transcriptional complex that drives a protumorigenic gene expression signature in neuroblastoma," Cancer Research, Dec. 2015 75(23):5143-5154.
Tahirovic et al., "Discovery of *N-alkyl* piperazine side chain based CXCR4 antagonists with improved drug-like properties," ACS Med. Chem. Lett., May 2018, 9(5):446-451.
Takeuchi et al., "KIF5B-ALK, a novel fusion oncokinase identified by an immunohistochemistrybased diagnostic system for ALK-positive lung cancer," Clinical Cancer Research, May 1, 2009, 15(9):3143-3149.
Tan et al., "A kinase-independent role for EGF receptor in autophagy initiation," Cell, Jan. 2015, 160(1-2):145-160.
Tan et al., "Next-generation epidermal growth factor receptor tyrosine kinase inhibitors in epidermal growth factor receptor -mutant non-small cell lung cancer," Lung Cancer, Mar. 2016, 93:59-68.
Tan et al., "PBK/AKT-mediated upregulation of WDR5 promotes colorectal cancer metastasis by directly targeting ZNF407," Cell Death and Disease, Mar. 2017, 8(3): 12 pages.
Taniguchi et al., "Silencing of Kruppel-like factor 2 by the histone methyltransferase EZH2 in human cancer," Oncogene, 2012, 31(15):1988-1994.
Tarighat et al., "The dual epigenetic role of PRMT5 in acute myeloid leukemia: gene activation and repression via histone arginine methylation," Leukemia, Nov. 2016, 30:789-799.
Thomas et al., "Interaction with WDR5 promotes target gene recognition and tumorigenesis by MYC," Molecular Cell, May 2015, 58(3)440-452.
Thomas et al., "The MYC-WDR5 nexus and cancer," Cancer Research, Oct. 2015, 75(19)4012-4015.
Thress et al., "Acquired *EGFR* C797S mutation mediates resistance to AZD9291 in non-small cell lung cancer harboring *EGFR* T790M," Nat. Med., May 2015, 21:560-562.
Toure et al., "Small-Molecule PROTACS: New Approaches to Protein Degradation," Angewandte Chemie-Intemational Edition, Febmaiy 2016, 55(6)4966-1973.
Trievel et al., "WDR5, a complexed protein," Nature Structural & Molecular Biology, Jul. 2009, 16(7):678-680.
Turner et al., "Palbociclib in hormone-receptor-positive advanced breast cancer," New England Journal of Medicine, 2015, 373(3):209-219.
Tumer-Ivey et al., "Development of mammary hyperplasia, dysplasia, and invasive ductal carcinoma in transgenic mice expressing the 8p1 1 amplicon oncogene NSD3," Breast Cancer Res. Treat., Jul. 2017, 164(2):349-358.
Varambally et al., "The polycomb group protein EZH2 is involved in progression of prostate cancer," Nature, 2002, 419(6907):624-629.
Varfolomeev et al., "IAP antagonists induce autoubiquitination of c-IAPs, NF-KB activation, and TNFa-dependent apoptosis," Cell, Nov. 2007, 131(4):669-681.
Vassilev et al., "In vivo activation of the p53 pathway by small-molecule antagonists of MDM2," Science, Febmaiy 2004, 303(5659):844-848.
Verma et al., "Identification of Potent, Selective, Cell-Active Inhibitors of the Histone Lysine Methyltransferase EZH2," ACS Med. Chem. Lett., 2012, 3(12):1091-1096.
Vivanco et al., "A kinase-independent function of AKT promotes cancer cell survival," eLIFE, 2014, 3:e03751.
Vu et al., "Discovery of RG7112: a small-molecule MDM2 inhibitor in clinical development," ACS Medicinal Chemistiy Letters, May 2013, 4(5)466-469.
Wakeling, "Use of pure antioestrogens to elucidate the mode of action of oestrogens," Biochemical Pharmacology, May 1995, 49(11): 1545-1549.

(56) References Cited

OTHER PUBLICATIONS

Wan et al., "ENL links histone acetylation to oncogenic gene expression in acute myeloid leukaemia," Nature, Mar. 2017, 543:265-269.
Wan et al., "Impaired cell fate through gain-of-function mutations in a chromatin reader," Nature, Jan. 2020, 577:121-126.
Wang et al., "EAI045: The fourth-generation EGFR inhibitor overcoming T790M and C797S resistance," Cancer Lett, Jan. 2017, 385:51-54.
Wang et al., "MapSplice: accurate mapping of RNA-seq reads for splice junction discovery," Nucleic Acids Res., 2010, 38:e178.
Wang et al., "NUP98-NSD1 links H3K36 methylation to Hox-A gene activation and leukaemogenesis," Nat. Cell. Biol., Jul. 2007, 9(7):804-812.
Wang et al., "Polycomb genes, miRNA, and their deregulation in B-cell malignancies," Blood, 2015, 125(8):1217-1225.
Wei et al., "Protein arginine methylation of non-histone proteins and its role in diseases," Cell Cycle, 2014, 13(1):32-41.
Weisberg et al., "Smac mimetics: implications for enhancement of targeted therapies in leukemia," Leukemia, Dec. 2010, 24:2100-2109.
Weiss et al., "Anaplastic lymphoma kinase and leukocyte tyrosine kinase: functions and genetic interactions in learning, memory and adult neurogenesis," Pharmacology, Biochemistry and Behavior, Jan. 2012, 100(3):566-574.
Weiss et al., "The role of T3 surface molecules in the activation of human T cells: a two-stimulus requirement for IL 2 production reflects events occurring at a pre-translational level," Journal of Immunology, Aug. 1984, 133(1): 123-128.
Wieduwilt et al., "The epidermal growth factor receptor family: biology driving targeted therapeutics," Cell. Mol, Life Sci., May 2008, 65(10): 1566-1584.
Winter et al., "Phthalimide conjugation as a strategy for in vivo target protein degradation," Science, May 2015, 348(6241): 1376-1381.
Wood et al., "Lack of the t(2;5) or other mutations resulting in expression of anaplastic lymphoma kinase catalytic domain in CD30+ primary cutaneous lymphoproliferative disorders and Hodgkin's disease," Blood, Sep. 1, 1996, 88(5)4765-1770.
Wu et al., "Overexpression of WD repeat domain 5 associates with aggressive clinicopathological features and unfavorable prognosis in head neck squamous cell carcinoma," International Association of Oral Pathologists and the American Academy of Oral Pathology, Apr. 2018, 47(5): 27 pages.
Xie et al., "Pharmacological targeting of the pseudokinase Her3," Nature Chemical Biology, Dec. 2014, 10(12):1006-1012.
Xie et al., "WDR5 positively regulates p53 stability by inhibiting p53 ubiquitination," Biochemical and Biophysical Research Communications, May 2017, 487(2):333-338.
Xu et al., "eEF1 A2 promotes cell migration, invasion and metastasis in pancreatic cancer by upregulating MMP-9 expression through Akt activation," Clin. Exp. Metastasis, May 2013, 30(7):933-944.
Xu et al., "Selective inhibition of EZH2 and EZHI enzymatic activity by a small molecule suppresses MLL-rearranged leukemia," Blood, Jan. 2015, 125:346-357.
Xu et al., "Targeting EZH2 and PRC2 dependence as novel anticancer therapy," Exp. Hematol., 2015, 43(8):698-712.
Yang et al., "Structure-Activity Relationship Studies for Enhancer of Zeste Homologue 2 (EZH2) and Enhancer of Zeste Homologue 1 (EZHI) Inhibitors," J. Med. Chem., 2016, 59(16):7617-7633.
Yokoyama et al., "A Higher-Order Complex Containing AF4 and ENL Family Proteins with P-TEFb Facilitates Oncogenic and Physiologic MLL-Dependent Transcription," Cancer Cell, Febmary 2010, 17(2): 198-212.
You et al., "Discovery of an AKT degrader with prolonged inhibition of downstream signaling," Cell Chemical Biology, 2020, 27(1):66-73.
Yu et al., "Altered *Hox* Expression and Segmental Identity in *MII*-Mutant Mice," Nature, Nov. 1995, 378:505-508.
Yu et al., "Requirement for CDK4 kinase function in breast cancer," Cancer Cell, 2006, 9(1):23-32.
Yu et al., "Targeting AKT1-E17K and the PI3K/AKT pathway with an allosteric AKT inhibitor, ARQ 092," PLOS One, Oct. 2015, 10(10):e0140479.
Yun et al., "The T790M mutation in EGFR kinase causes dmg resistance by increasing the affinity for ATP," Proc. Natl. Acad. Sci. USA, Feb. 2008, 105(6)2070-2075.
Zeng et al., "Discovery of novel imidazo[1,2-a]pyrazin-8-amines as Brk/PTK6 inhibitors," Bioorg. Med. Chem. Lett., Oct. 2011, 21(19):5870-5875.
Zengerle et al., "Selective Small Molecule Induced Degradation of the BET Bromodomain Protein BRD4," ACS Chemical Biology, Jun. 2015, 10(8): 1770-1777.
Zhang et al., "Proteolysis targeting chimeras (PROTACs) of anaplastic lymphoma linase (ALK)," Eur. J. Med. Chem., May 2018, 151:304-314.
Zhang et al., "Structural Insights into Histone Crotonyl-Lysine Recognition by the AF9 Yeats Domain," Structure, Sep. 2016, 24(9):1606-1612.
Zhao et al., "PROTACs suppression of CDK4/6, cmcial kinases for cell cycle regulation in cancer," Chem. Commun. (Camb)., 2019, 55:2704-2707.
Zhao et al., "The language of chromatin modification in human cancers," Nat. Rev. Cancer, Jul. 2021, 21:413-430.
Zheng et al., "PTK6 activation at the membrane regulates epithelial-mesenchymal transition in prostate cancer," Cancer Res., Sep. 2013, 73(17):5426-5437.
Zhou et al., "Discovery of a Small-Molecule Degrader of Bromodomain and Extra-Terminal (BET) Proteins with Picomolar Cellular Potencies and Capable of Achieving Tumor Regression," Journal of Medicinal Chemistiy, 2018, 61(2):462-481.
Zuber et al., "RNAi screen identifies Brd4 as a therapeutic target in acute myeloid leukaemia," Nature, 2011, 478:524-528.
EP Extended European Search Report in European Appln. No. 19821826.5, dated May 3, 2022, 10 pages.
Fisher et al., "Targeted protein degradation and the enzymology of degraders," Current Opinion in Chemical Biology, 2018, 44:47-55.

\* cited by examiner

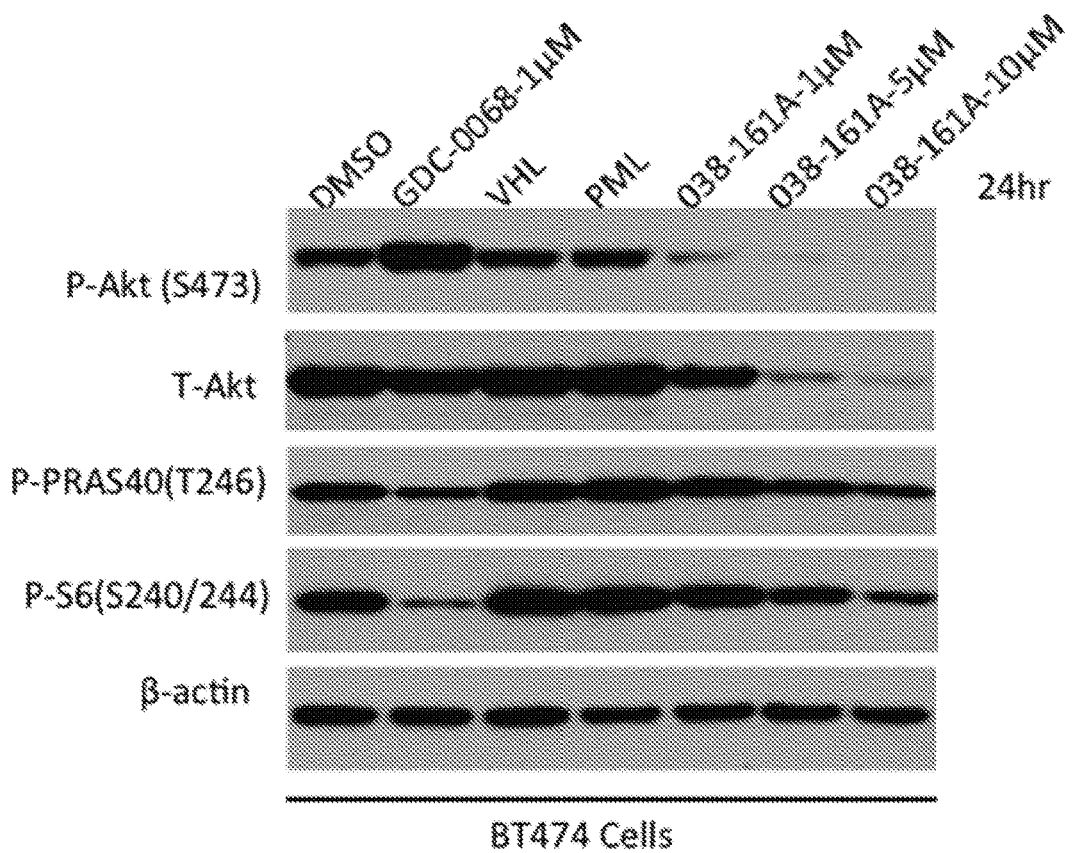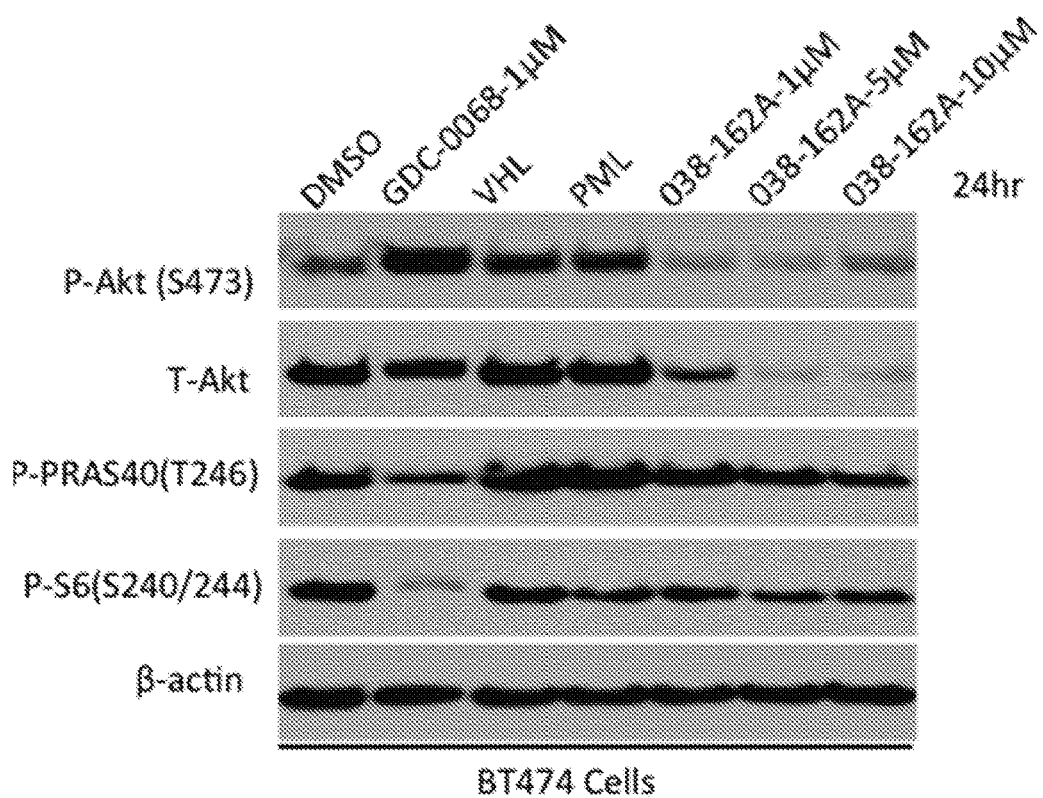
FIG. 1A-3

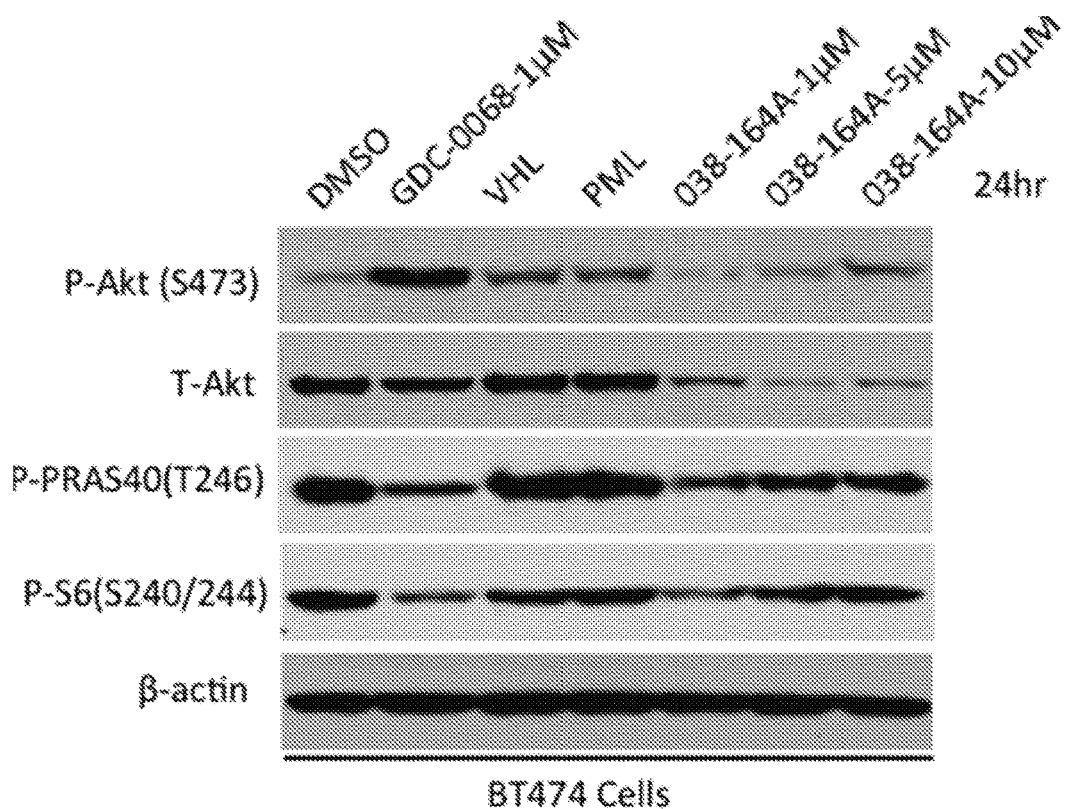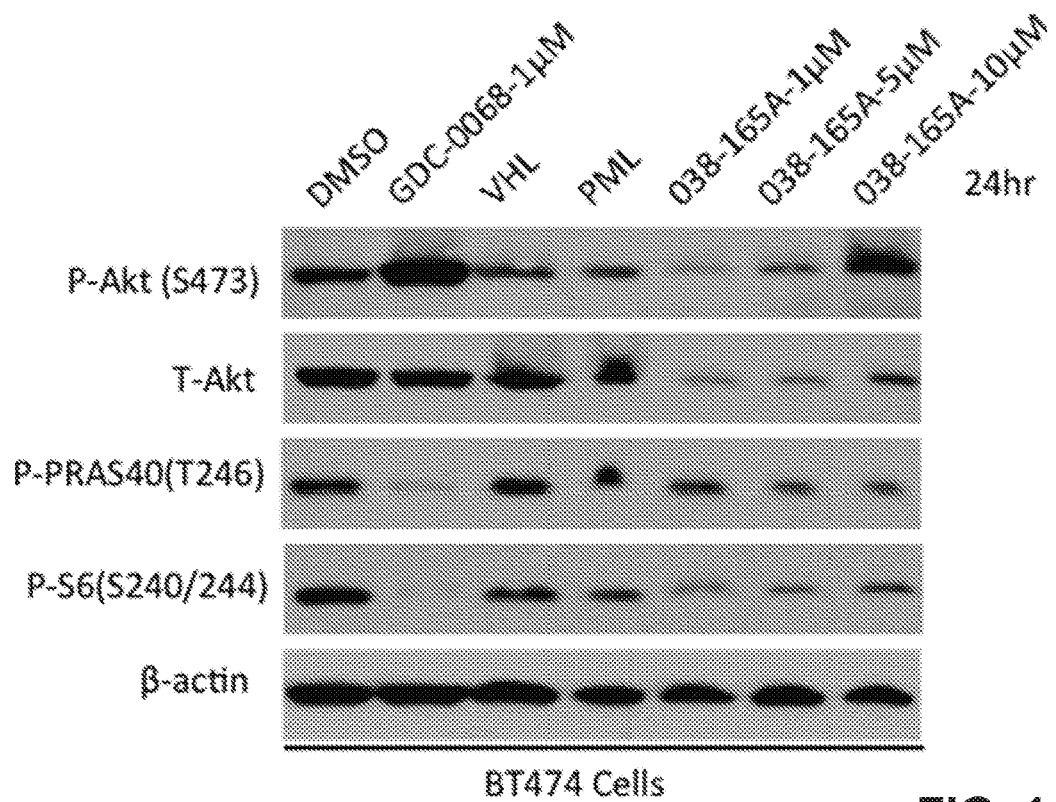
FIG. 1A-4

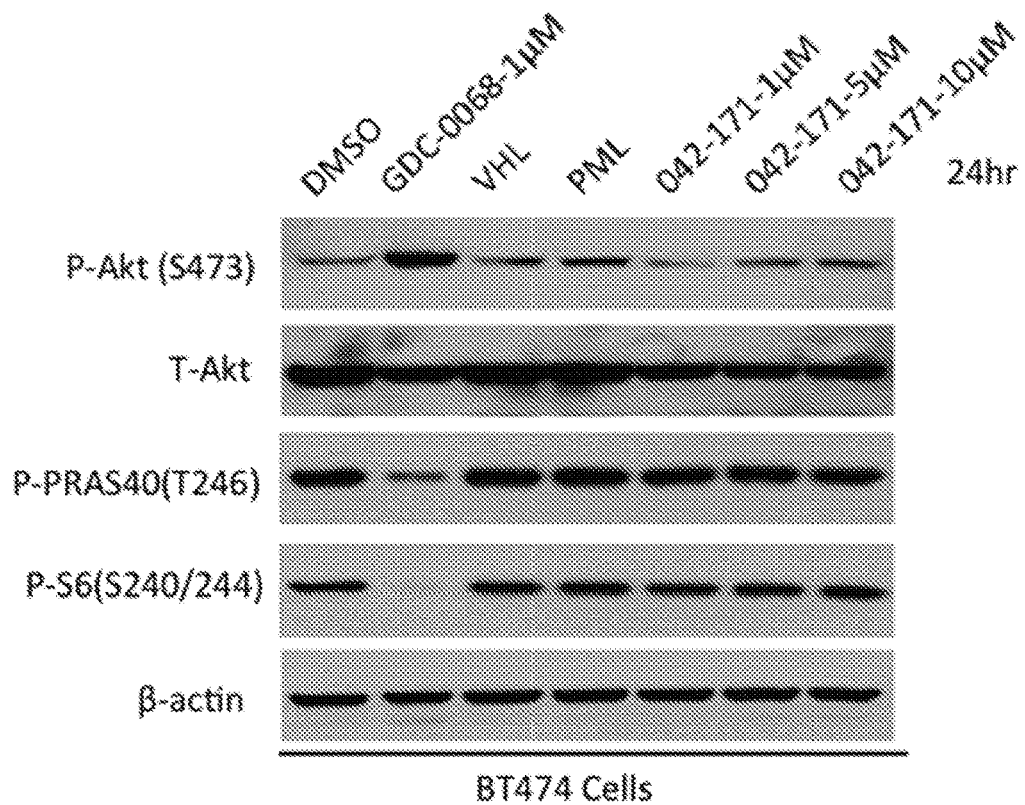
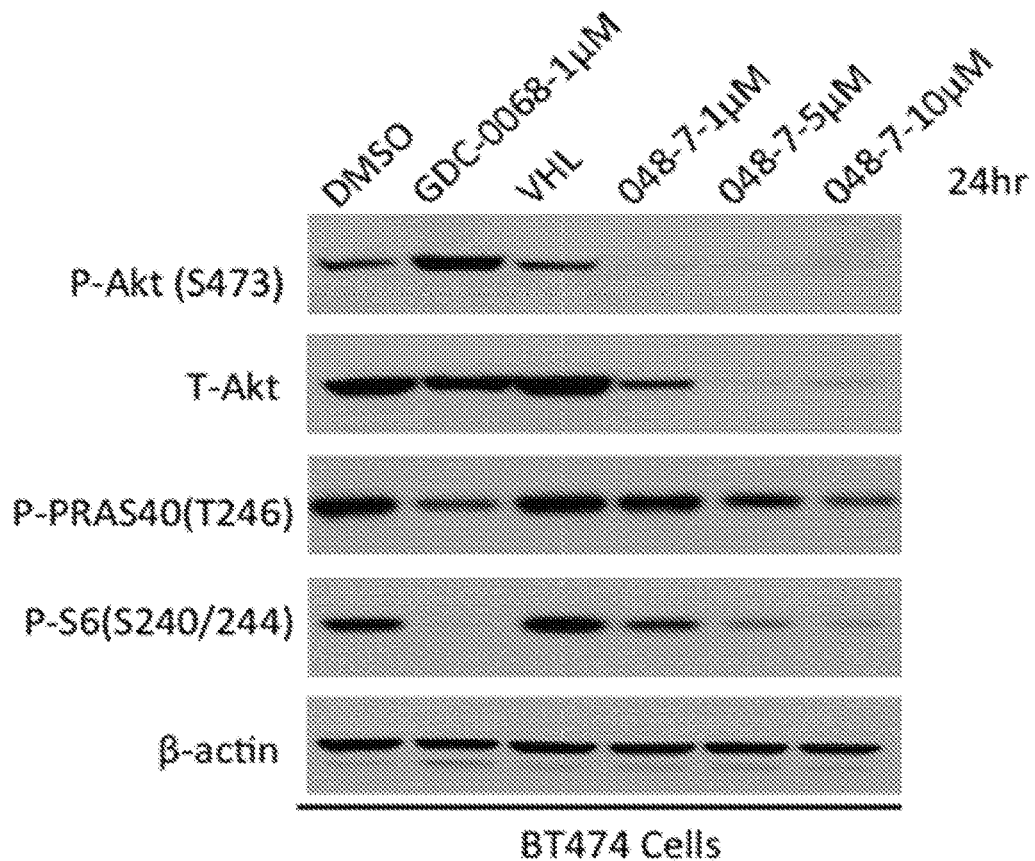
FIG. 1B-2

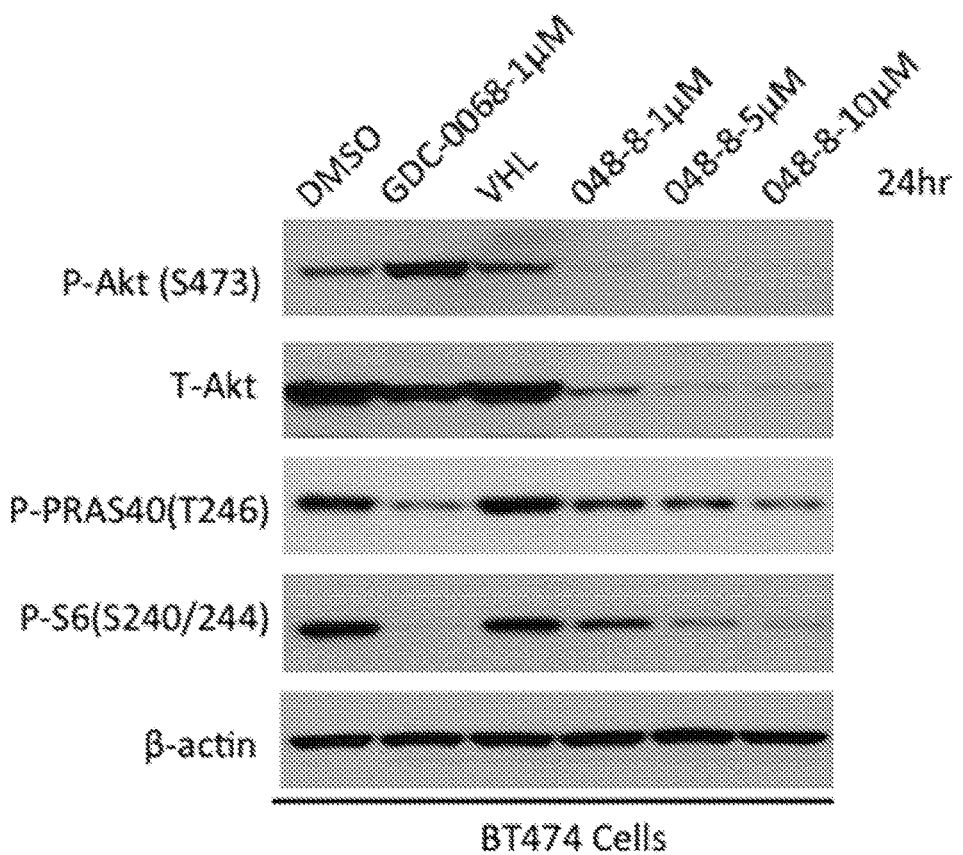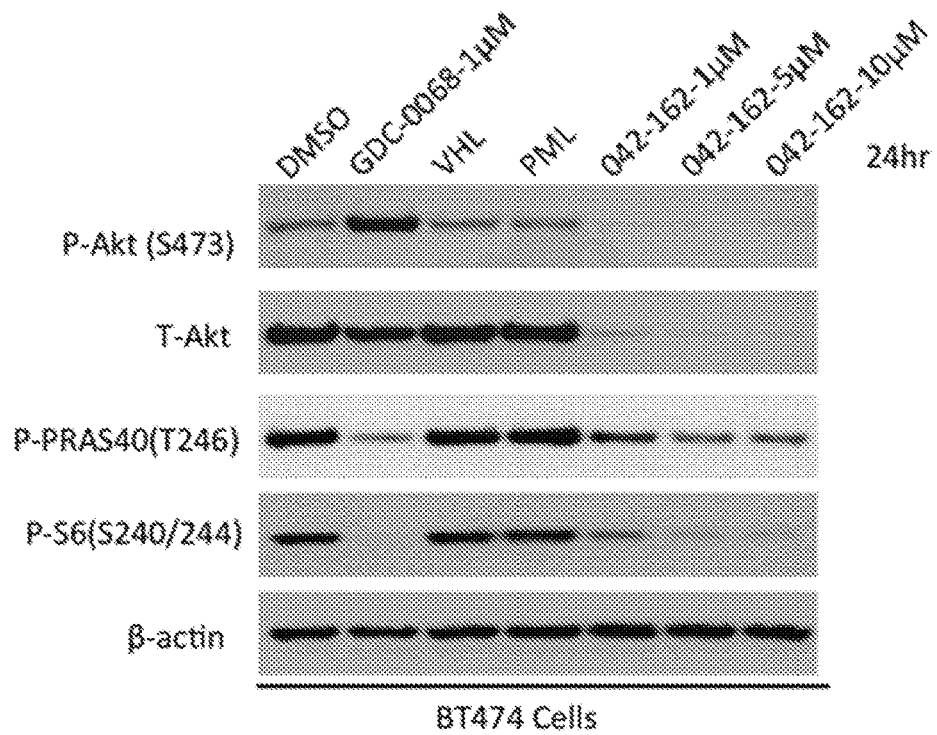
FIG. 1B-3

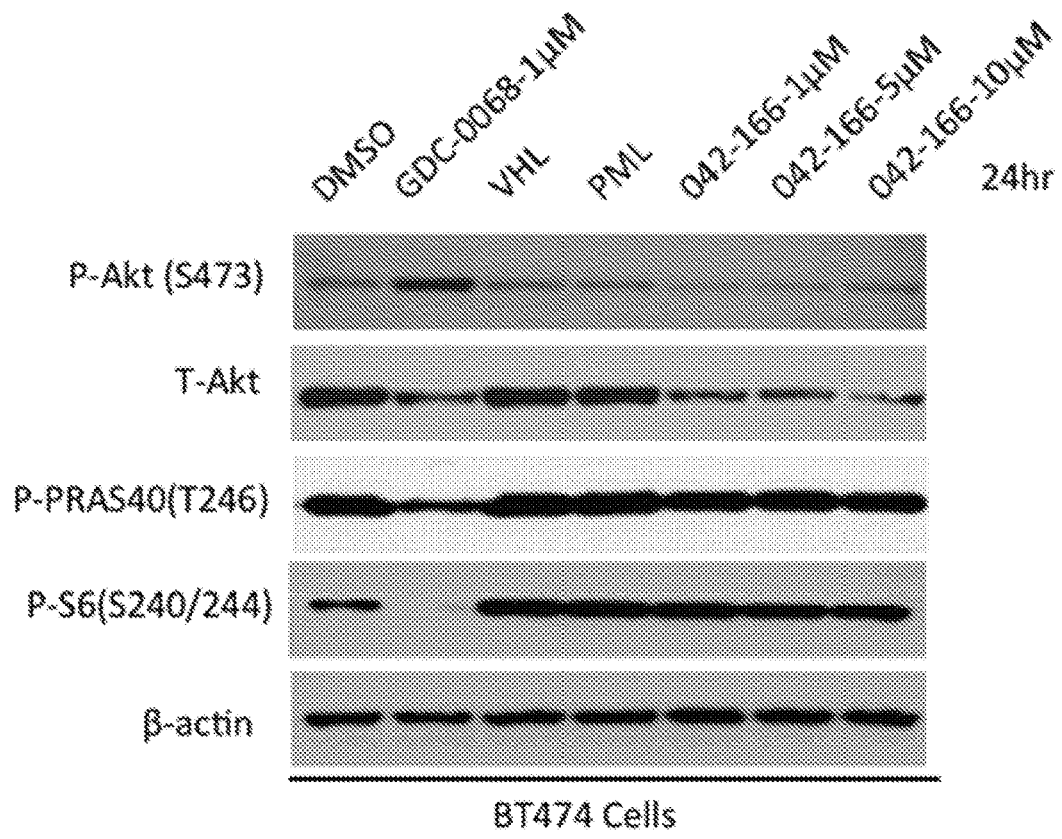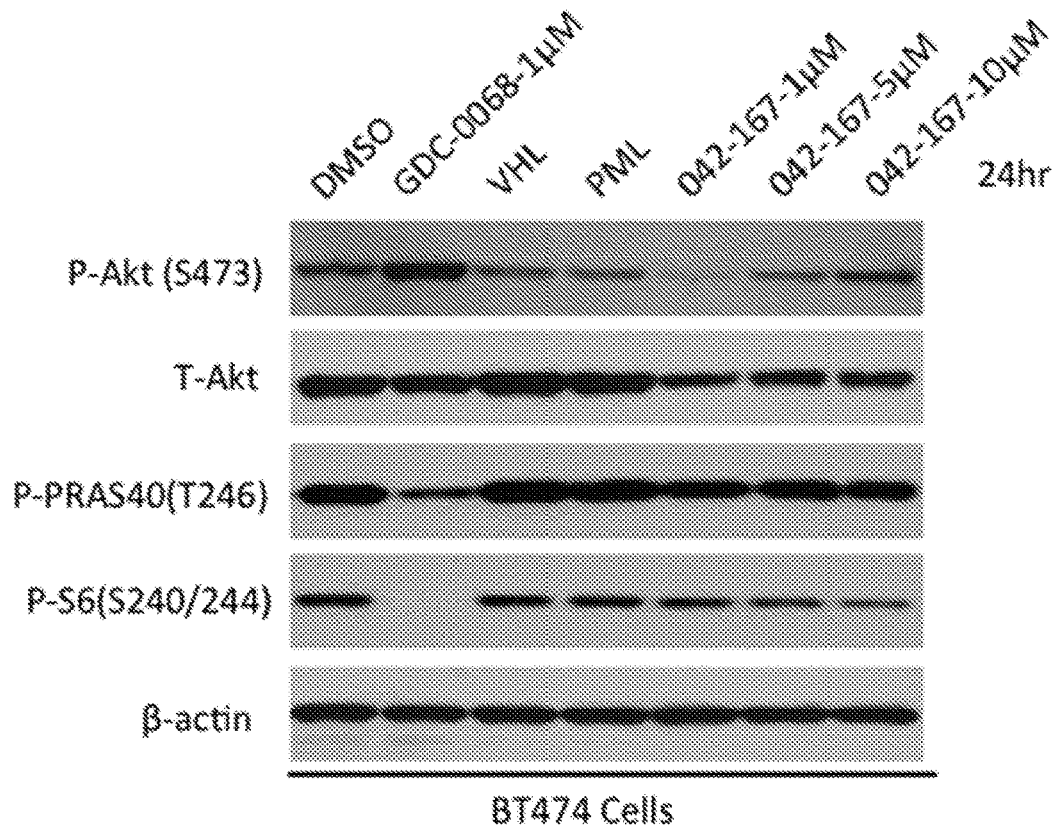
FIG. 1B-4

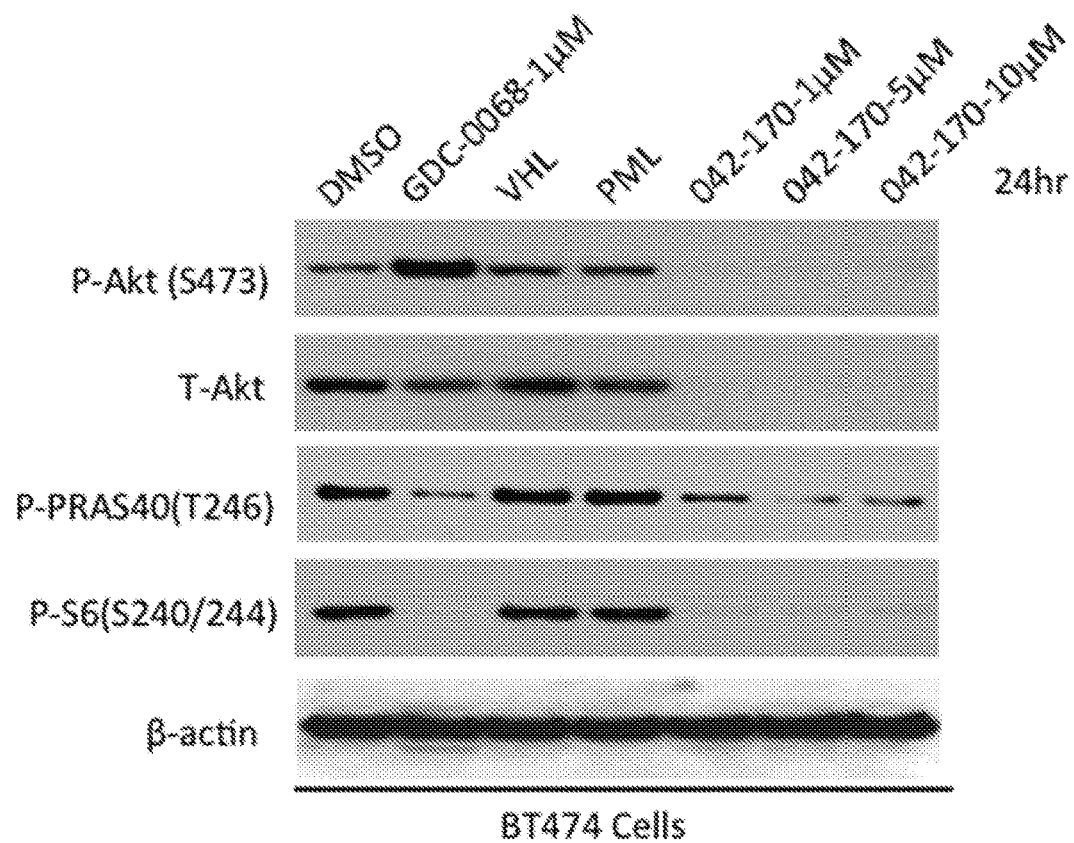
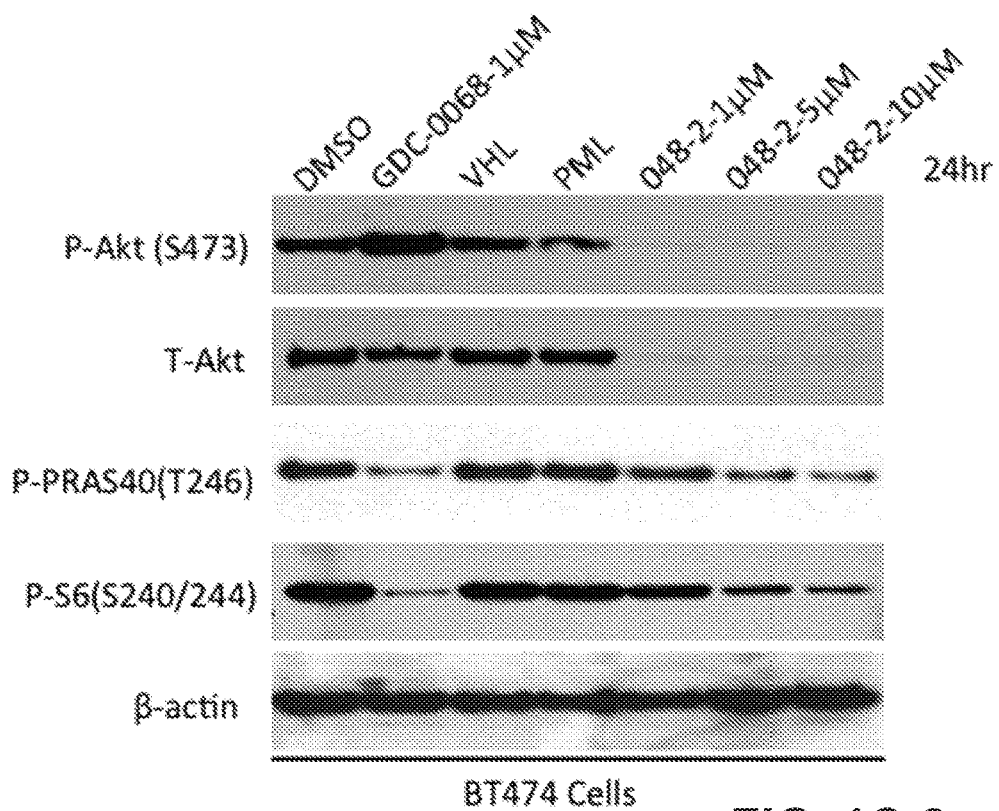
FIG. 1C-2

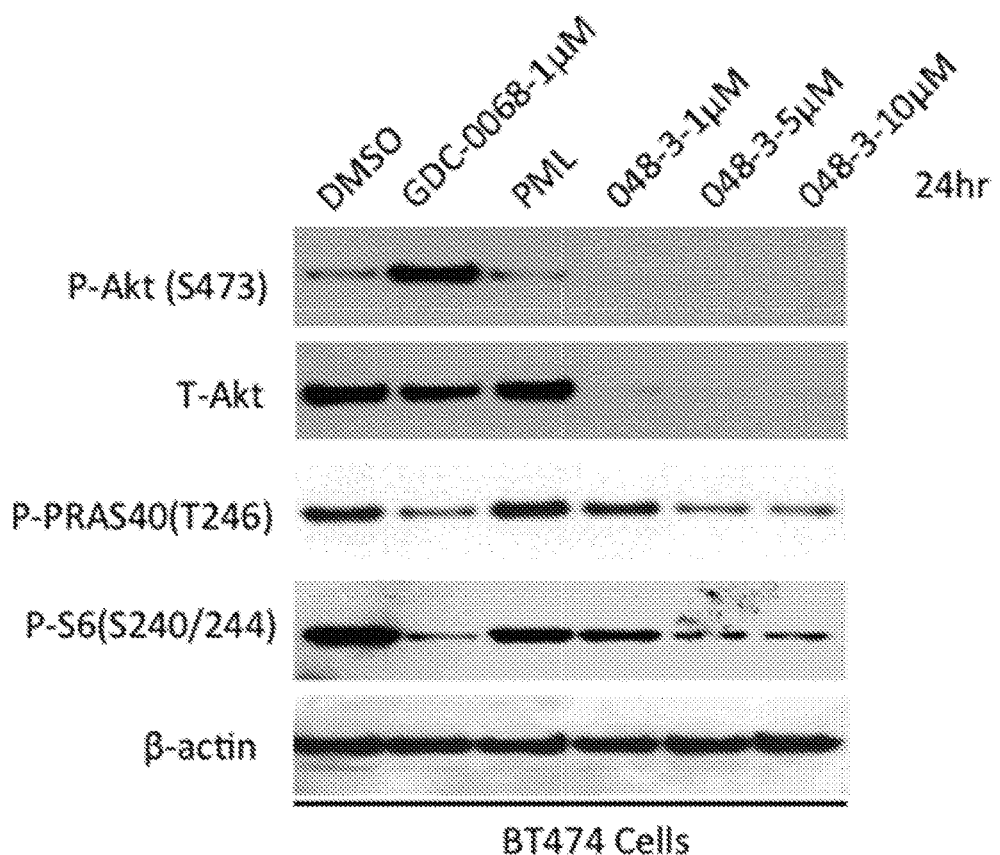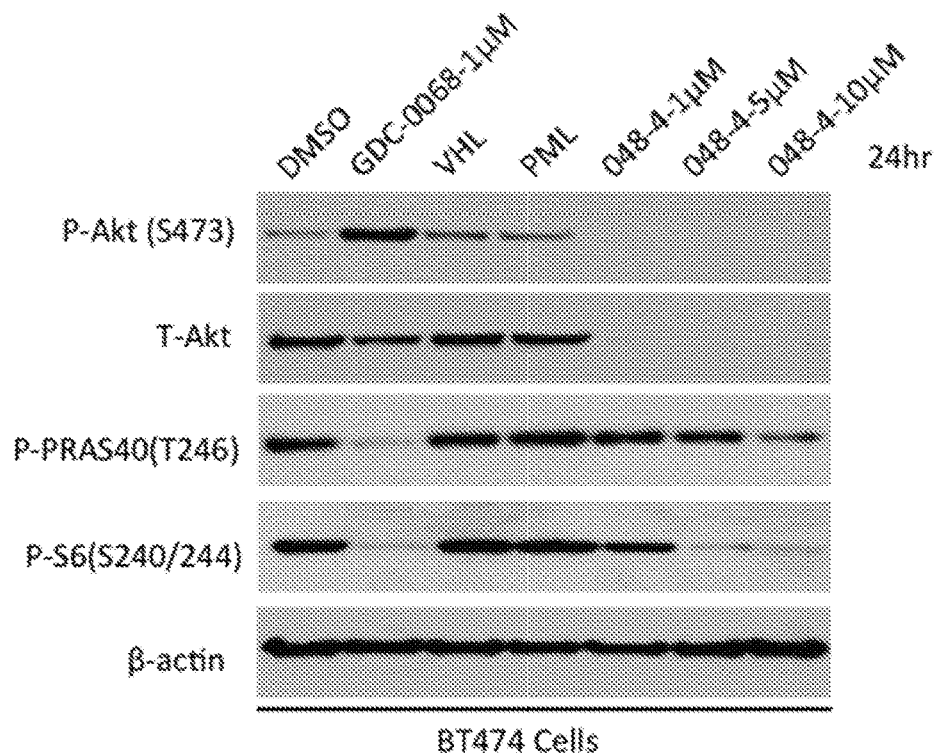
FIG. 1C-3

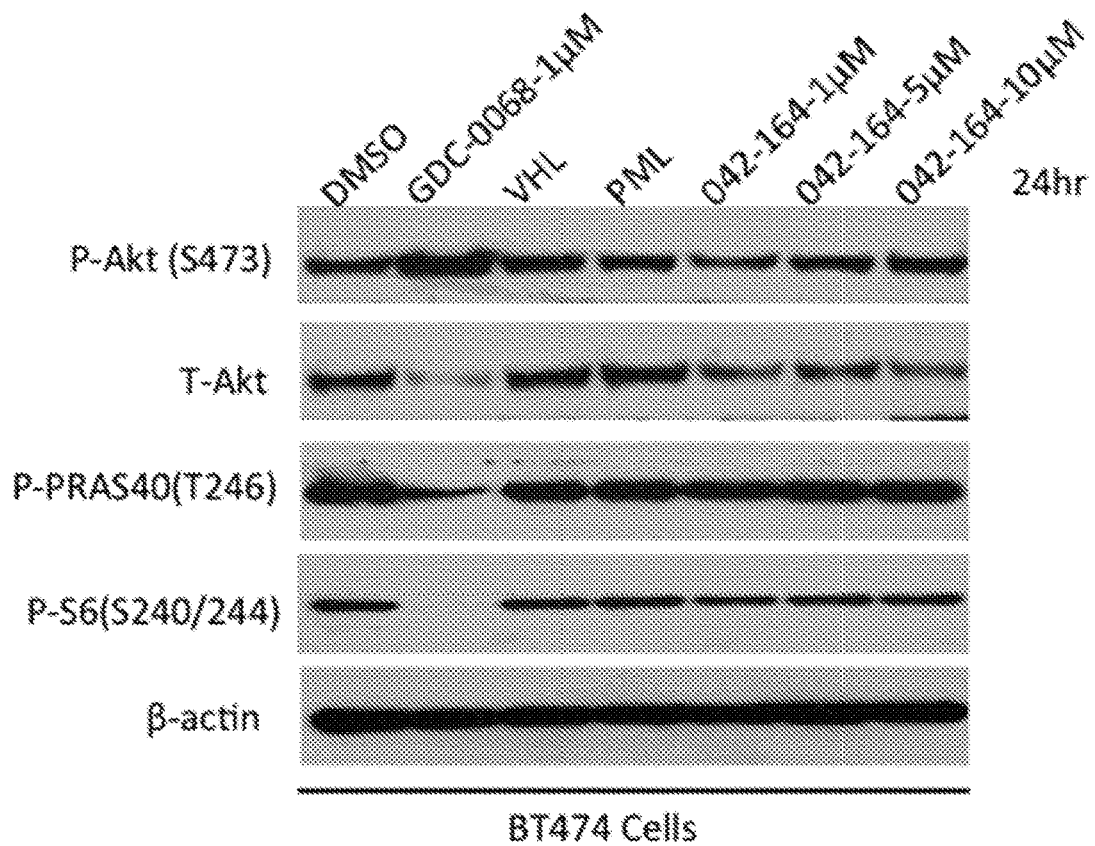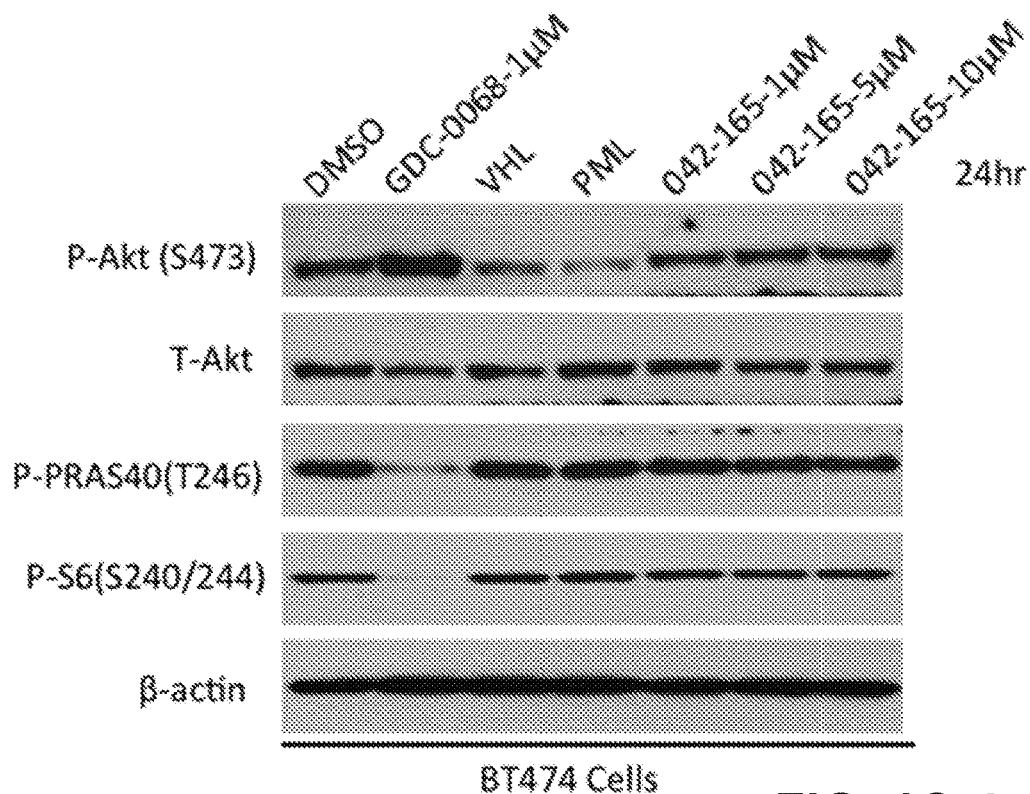
FIG. 1C-4

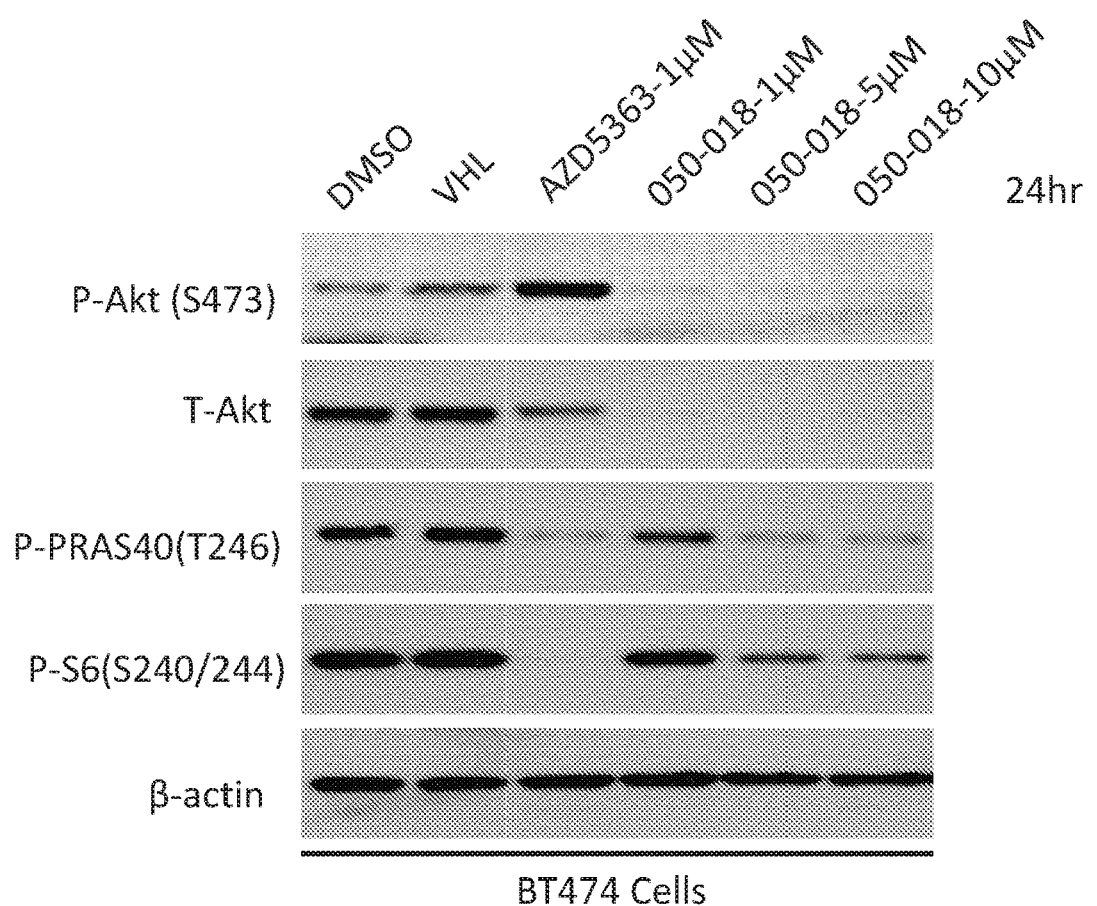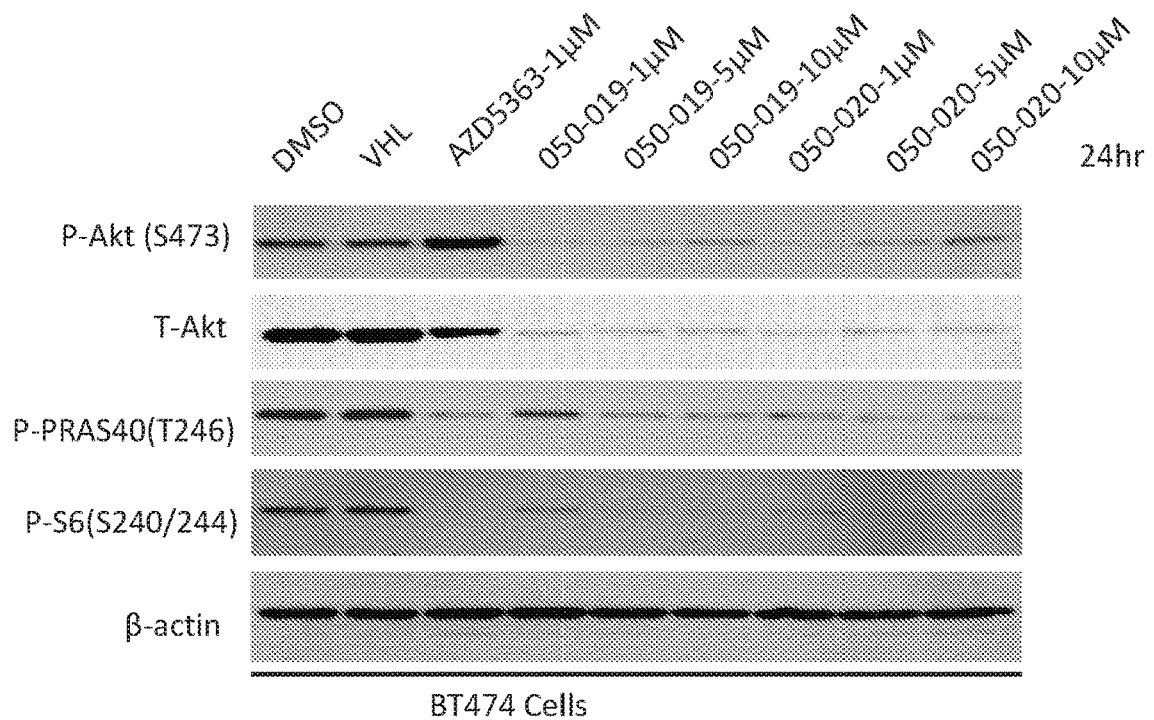
FIG. 3A-4

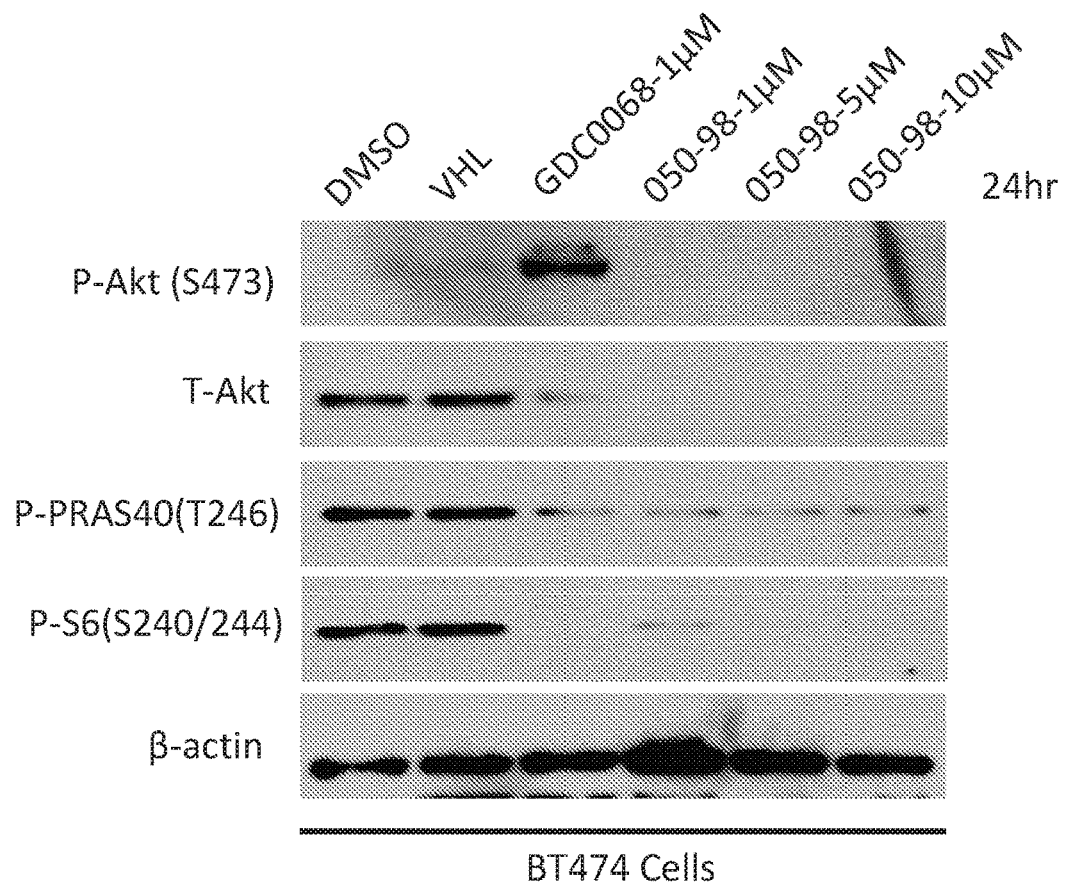
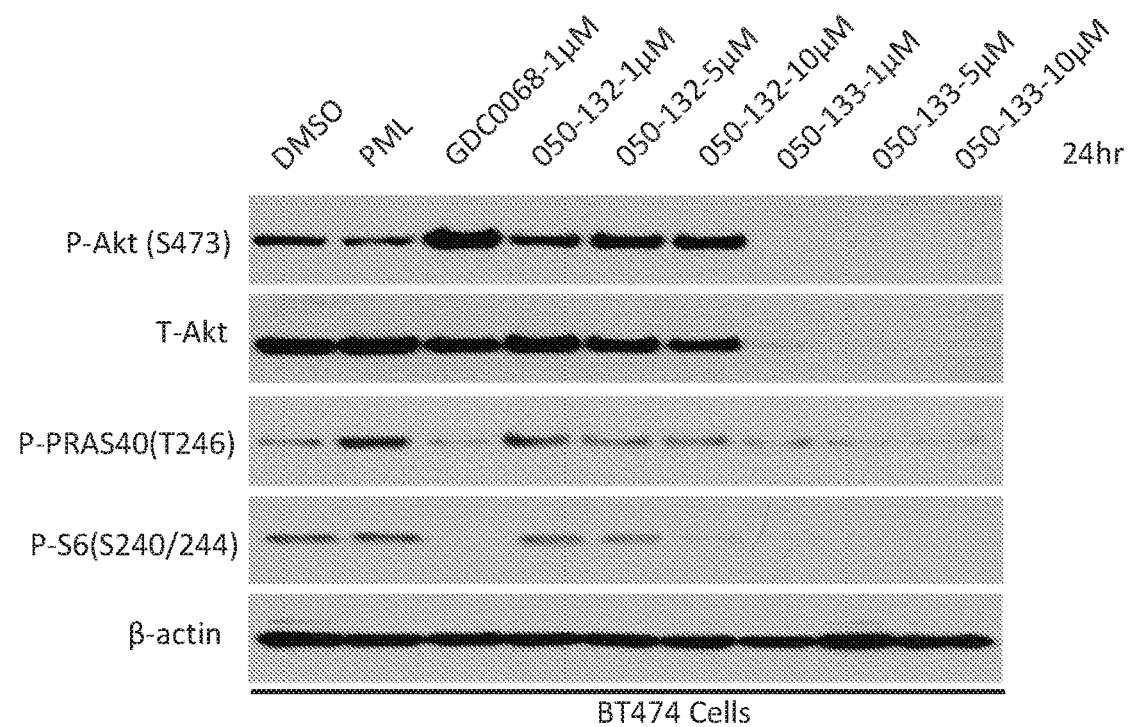
FIG. 3B-4

SERINE THREONINE KINASE (AKT) DEGRADATION / DISRUPTION COMPOUNDS AND METHODS OF USE

CROSS-REFERENCE TO RELATED APPLICATION

This application claims the benefit of U.S. Provisional Application No. 62/639,240 filed Mar. 6, 2018. The entire contents of the foregoing are incorporated herein by reference.

TECHNICAL FIELD

This disclosure relates to bivalent compounds (e.g., bifunctional small molecule compounds) which degrade and/or disrupt the serine threonine kinase AKT (also known as protein kinase B or PKB), compositions comprising one or more of the bivalent compounds, and to methods of use thereof for the treatment of AKT-mediated disease in a subject in need thereof. The disclosure also relates to methods for designing such bivalent compounds.

BACKGROUND OF THE INVENTION

Significant efforts have been spent attempting to develop small molecule inhibitors of the kinase activity of the serine threonine kinase AKT (also known as protein kinase B or PKB) because over-activation of AKT is frequently associated with many human malignancies, including colon cancer, ovarian cancer, brain cancer, lung cancer, pancreatic cancer, breast cancer, prostate cancer, and gastric carcinomas. In addition to cancer, aberrant AKT activation has been associated with a variety of other severe human diseases, including developmental and overgrowth syndromes, cardiovascular disease, diabetes, inflammatory and autoimmune disorders, and neurological disorders (Manning and Toker, 2017). AKT is encoded by three closely related genes (AKT1 (PKB-$\alpha$), AKT2 (PKB-$\beta$), and AKT3 (PKB-$\gamma$)) and is the central node of the PI3K-AKT-mTOR signaling pathway. The AKT signaling pathway can be aberrantly activated by multiple mechanisms in cancers, including, e.g., loss of the tumor suppressor PTEN; activating mutations in AKT, the p110$\alpha$ subunit of PI3K, and/or the PIK3CA gene; and/or increased receptor tyrosine kinase signaling.

However, traditional catalytic inhibition of AKT has not been an optimal solution for treating AKT overexpression. For example, although ATP-competitive inhibitors like GDC0068 (Blake et al., 2012) function as pan-AKT inhibitors, they also stabilize AKT in its active conformation, resulting in AKT hyperphosphorylation. Moreover, AKT has functions in addition to the (catalytic) activity targeted by small molecule inhibitors. AKT's kinase-independent functions promote cancer cell survival in a pleckstrin homology (PH)-domain dependent manner. Studies have shown that the enzymatic inhibitor GDC00068 alone was not very effective in a colon cancer xenograft with RAS/RAF activation albeit with PIK3CA mutation. Similarly, GDC0068 also failed to result in significant objective tumor shrinkage in a phase I clinical trial (Saura et al., 2017).

Unlike traditional enzyme inhibitors, which only inhibit the catalytic activity of the target enzyme, the AKT degradation/disruption compounds ("AKT degraders") disclosed herein bind and induce degradation of AKT, thus eliminating any scaffolding functions of AKT in addition to eliminating its enzymatic activity. The AKT degraders disclosed herein are bivalent compounds, including an AKT ligand conjugated to a degradation/disruption tag via a linker.

The AKT degraders disclosed herein offer a novel mechanism for treating AKT-mediated diseases. In particular, the ability of the AKT degraders to target AKT for degradation, as opposed to merely inhibiting AKT's catalytic activity, is expected to overcome resistance, regardless of whether specific drugs were used in a prior treatment and regardless of whether the resistance is caused by gene mutation, amplification, or otherwise.

In an aspect, this disclosure provides a method of treating AKT-mediated diseases, the method including administering one or more AKT degraders to a subject who has an AKT-mediated disease, the AKT degraders being bivalent compounds including an AKT ligand conjugated to a degradation/disruption tag via a linker. The AKT-mediated disease can be a disease resulting from AKT activation. The AKT-mediated disease can have elevated AKT enzymatic activity relative to a wild-type tissue of the same species and tissue type. Non-limiting examples of AKT-mediated diseases include inflammatory, hyperproliferative cardiovascular, neurodegenerative, gynecological, and dermatological diseases and disorders.

In an aspect, the AKT degraders of the present disclosure can be employed for the treatment of hyperproliferative disorders, including cancers angiosarcoma, fibrosarcoma, rhabdomyosarcoma, liposarcoma, myxoma, rhabdomyoma, fibroma, lipoma, teratoma, squamous cell carcinoma, undifferentiated small cell carcinoma, undifferentiated large cell carcinoma, adenocarcinoma, alveolar carcinoma, bronchial adenoma, sarcoma, lymphoma, chondromatous hamartoma, mesothelioma, non-small cell lung cancer, small cell lung cancer, leiomyosarcoma, stomach carcinoma, ductal adenocarcinoma, insulinoma, glucagonoma, gastrinoma, carcinoid tumors, vipoma, carcinoid tumors, Kaposi's sarcoma, leiomyoma, hemangioma, neurofibroma, tubular adenoma, villous adenoma, hamartoma, kidney cancer, Wilm's tumor, nephroblastoma, leukemia, bladder cancer, urethra cancer, transitional cell carcinoma, prostate cancer, seminoma, embryonal carcinoma, teratocarcinoma, choriocarcinoma, interstitial cell carcinoma, fibroadenoma, adenomatoid tumors, hepatoma, hepatocellular carcinoma, cholangiocarcinoma, hepatoblastoma, hepatocellular adenoma, osteogenic sarcoma, osteosarcoma, malignant fibrous histiocytoma, chondrosarcoma, Ewing's sarcoma, malignant lymphoma, reticulum cell sarcoma, multiple myeloma, malignant giant cell tumor chordoma, osteochronfroma, osteocartilaginous exostoses, benign chondroma, chondroblastoma, chondromyxofibroma, osteoid osteoma, giant cell tumors, osteoma, granuloma, xanthoma, osteitis deformans, meningioma, meningiosarcoma, gliomatosis, astrocytoma, medulloblastoma, glioma, ependymoma, germinoma, pinealoma, glioblastoma multiforme, oligodendroglioma, schwannoma, retinoblastoma, congenital tumors, spinal cord neurofibroma, endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, intraepithelial carcinoma, melanoma, clear cell carcinoma, botryoid sarcoma, embryonal fallopian tubes carcinoma, acute myeloid leukemia, chronic myeloid leukemia, acute lymphoblastic leukemia, chronic lymphocytic leukemia, myeloproliferative diseases, myelodysplastic syndrome, Hodgkin's disease, non-Hodgkin's lymphoma, advanced melanoma, malignant melanoma, basal cell carcinoma, moles dysplastic nevi, angioma, dermatofibroma, keloids, psoriasis, neuroblastoma, metastatic breast cancer, colon cancer, oral cancer, hairy cell leukemia, head and neck cancer, refractory metastatic disease; Kaposi's sarcoma, Bannayan-Zonana syndrome, Cowden disease and Lhermitte-Duclos disease.

The compounds and methods of this disclosure can be also used to treat diseases and conditions such as rheumatoid arthritis, osteoarthritis, Crohn's disease, angiofibroma, retinal vascularization, diabetic retinopathy, age-related macular degeneration, macular degeneration, multiple sclerosis, obesity, Alzheimer's disease, restenosis, autoimmune diseases, allergy, asthma, endometriosis, atherosclerosis, vein graft stenosis, peri-anastomatic prosthetic graft stenosis, prostate hyperplasia, chronic obstructive pulmonary disease, psoriasis, inhibition of neurological damage due to tissue repair, scar tissue formation, multiple sclerosis, inflammatory bowel disease, infections, particularly bacterial, viral, retroviral or parasitic infections, pulmonary disease, neoplasm, Parkinson's disease, transplant rejection, and septic shock.

The AKT-mediated disease can be a relapsed disease. The AKT-mediated disease can have been refractory to one or more previous treatments by different therapies.

SUMMARY OF THE INVENTION

The present disclosure relates generally to bivalent compounds (e.g., bi-functional compounds) which degrade and/or disrupt AKT, and to methods for the treatment of AKT-mediated cancer (i.e., a cancer which depends on AKT protein; or cancer having elevated levels of AKT, or AKT activity relative to a wild-type tissue of the same species and tissue type). Because the AKT degraders/disruptors have dual functions (enzyme inhibition plus protein degradation/disruption), the bivalent compounds of the present disclosure can be significantly more effective therapeutic agents than current AKT inhibitors, which inhibit the enzymatic activity of AKT, but do not affect AKT protein levels. The present disclosure further provides methods for identifying AKT degraders/disruptors as described herein.

More specifically, the present disclosure provides a bivalent compound including an AKT ligand conjugated to a degradation/disruption tag via a linker.

In some aspects, the AKT degraders/disruptors have the form "PI-Linker-EL", as shown below:

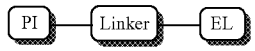

wherein PI (a ligand for a "protein of interest," i.e., the protein to be degraded) comprises an AKT ligand (e.g., an AKT inhibitor), and EL (e.g., a ligand for an E3 ligase) comprises a degradation/disruption tag (e.g., E3 ligase ligand). Exemplary AKT ligands (PI), exemplary degradation/disruption tags (EL), and exemplary linkers (Linker) are illustrated below:

AKT Ligands
AKT Ligands include but are not limited to:

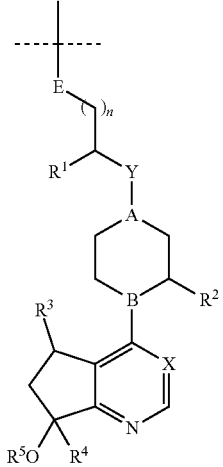

FORMULA 1 wherein
A, B, and X are independently N, CH, or $CR^6$,
Y is $CH_2$, CO, SO, $SO_2$, $CR^7R^8$, $CONR^7$, or $SO_2NR^7$,
E is NH, $NR^9$, O, $C_1$-$C_8$ alkyl, $C_1$-$C_8$ alkoxy, $C_1$-$C_8$ alkoxyalkyl, $C_1$-$C_8$ haloalkyl, $C_1$-$C_8$ hydroxyalkyl, $C_3$-$C_8$ cycloalkyl, $C_3$-$C_7$ heterocyclyl, $C_2$-$C_8$ alkenyl, $C_2$-$C_8$ alkynyl, $OR^9$, $SR^9$, $NR^9R^{10}$, CN, $NO_2$, $(CR^9R^{10})mNR^{11}R^{12}$, $(CR^9R^{10})mC(O)R^{11}$, $(NR^9R^{10})mNR^{11}R^{12}$, $(NR^9R^{10})mC(O)R^{11}$, $COR^9$, $CO_2R^9$, $CONR^9R^{10}$, $NR^9COR^{10}$, $NR^9SOR^{10}$, $NR^9SO_2R^{10}$, $SOR^9$, $SO_2R^9$, $SO_2NR^9R^{10}$, $(CR^9R^{10})$m-aryl, or $(CR^9R^{10})$m-heteroaryl,
$R^1$ is H, $C_1$-$C_8$ alkyl, $C_3$-$C_8$ cycloalkyl, $C_1$-$C_8$ alkoxy, $C_1$-$C_8$ alkoxyalkyl, aryl, $C_1$-$C_8$ alkylaryl, haloaryl, arylalkyl, heteroaryl, or heteroarylalkyl,
$R^2$, $R^3$, $R^4$, and $R^6$ are independently hydrogen, halogen, amino, $C_1$-$C_8$ alkylamino, arylamino, $C_1$-$C_8$ alkyl, $C_3$-$C_8$ cycloalkyl, $C_1$-$C_8$ alkoxy, or $C_1$-$C_8$ alkoxyalkyl,
$R^5$, $R^7$, and $R^8$ are independently H, $C_1$-$C_8$ alkyl, $C_3$-$C_8$ cycloalkyl, or $C_1$-$C_8$ alkoxyalkyl,
$R^9$, $R^{10}$, $R^{11}$, and $R^{12}$ are independently H, $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, arylalkyl, cycloalkyl, heterocycloalkyl, aryl, heteroaryl, or heteroarylalkyl,
$R^9$ and $R^{10}$, $R^{11}$ and $R^{12}$ can independently form 4-8 membered alkyl or heterocyclyl rings,
m=0-8,
and
n=0-8; and

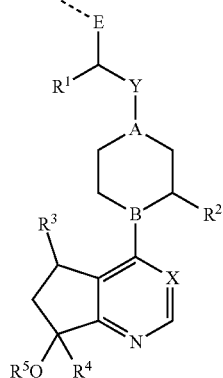

FORMULA 2 wherein

A, B and X are independently selected from N and $CR^6$, wherein $R^6$ is independently selected from hydrogen, halogen, cyano, nitro, hydroxyl, amino, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted amino, optionally substituted $C_1$-$C_8$ alkylamino, optionally substituted $C_1$-$C_8$ alkylamino$C_1$-$C_8$ alkyl, optionally substituted 3-10 membered carbocyclyl, and optionally substituted 4-10 membered heterocyclyl;

Y is selected from $CR^7R^8$, CO, SO, $SO_2$, $CONR^7$, and $SO_2NR^7$, wherein $R^7$ and $R^8$ is independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl; optionally substituted $C_1$-$C_8$ alkylamino, optionally substituted $C_1$-$C_8$ alkylamino $C_1$-$C_8$ alkyl, optionally substituted 3 to 10 membered carbocyclyl, and optionally substituted 4-10 membered heterocyclyl, or $R^7$ and $R^8$ together with the atom to which they are connected form an optionally substituted 3-10 membered carbocyclyl or an optionally substituted 4-10 membered heterocyclyl ring;

E is connected to the "linker" moiety of the bivalent compound, and is selected from null, R'—R" R'OR", R'SR", $R'NR^9R"$, R'OC(O)R", R'OC(O)OR", $R'OCONR^9R"$, R'C(O)R", R'C(O)OR", $R'CONR^9R"$, R'S(O)R", $R'S(O)_2R"$, $R'SO_2NR^9R"$, $R'NR^{10}C(O)OR"$, $R'NR^{10}C(O)R"$, $R'NR^{10}C(O)NR^9R"$, $R'NR^{10}S(O)R"$, $R'NR^{10}S(O)_2R"$, and $R'NR^{10}S(O)_2NR^9R"$, wherein R' and R" are independently selected from null, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ haloalkylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted ($C_1$-$C_8$ alkylene)O($C_1$-$C_8$ alkylene), optionally substituted ($C_1$-$C_8$ alkylene)N($C_1$-$C_8$ alkylene), optionally substituted 3-10 membered carbocyclyl, optionally substituted 4-10 membered heterocyclyl, optionally substituted $C_3$-$C_{13}$ fused carbocyclyl, optionally substituted $C_3$-$C_{13}$ fused heterocyclyl, optionally substituted $C_3$-$C_{13}$ bridged carbocyclyl, optionally substituted $C_3$-$C_{13}$ bridged heterocyclyl, optionally substituted $C_3$-$C_{13}$ spiro carbocyclyl, optionally substituted $C_3$-$C_{13}$ spiro heterocyclyl, optionally substituted aryl, and optionally substituted heteroaryl;

$R^9$ and $R^{10}$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^9$ and $R^{10}$, R' and $R^9$, R' and $R^{10}$, R" and $R^9$, R" and $R^{10}$ together with the atom to which they are connected form a 4-20 membered heterocyclyl ring;

$R^1$ is selected from hydrogen, halogen, and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ alkylamino, optionally substituted $C_1$-$C_8$ alkylamino $C_1$-$C_8$ alkyl, optionally substituted 3-10 membered carbocyclyl, optionally substituted 4-10 membered heterocyclyl, optionally substituted aryl, and optionally substituted heteroaryl;

$R^2$, $R^3$ and $R^4$ are independently selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted aryloxy, optionally substituted $C_1$-$C_8$ alkoxy$C_1$-$C_8$ alkyl, optionally substituted amino, optionally substituted $C_1$-$C_8$ alkylamino, optionally substituted $C_1$-$C_8$ alkylamino$C_1$-$C_8$ alkyl, optionally substituted arylamino, optionally substituted 3-10 membered carbocyclyl, and optionally substituted 4-10 membered heterocyclyl;

$R^5$ is selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy$C_1$-$C_8$ alkyl, optionally substituted $C_1$-$C_8$ alkylamino$C_1$-$C_8$ alkyl, optionally substituted 3-10 membered carbocyclyl, and optionally substituted 4-10 membered heterocyclyl; and In one embodiment, A is selected from N, CH and $CNH_2$.

In another embodiment, A is N.

In one embodiment, B and X are independently selected from N and CH.

In another embodiment, B is N.

In another embodiment, X is N.

In another embodiment, Y is selected from $CH_2$, CO, CONH and NHCO.

In another embodiment, Y is CO.

In another embodiment, E is selected from null, O, N, optionally substituted $C_1$-$C_8$ alkylene, optionally substituted ($C_1$-$C_8$ alkylene)O, optionally substituted ($C_1$-$C_8$ alkylene)N, optionally substituted 3-10 membered carbocyclylene, optionally substituted (3-10 membered carbocyclylene)O, optionally substituted (3-10 membered carbocyclylene)N, optionally substituted 4-10 membered heterocyclylene, optionally substituted (4-10 membered heterocyclylene)O, optionally substituted (4-10 membered heterocyclylene)N, optionally substituted aryl, and optionally substituted heteroaryl.

In another embodiment, $R^1$ is selected from optionally substituted aryl and optionally substituted heteroaryl.

In another embodiment, $R^1$ is selected from optionally substituted phenyl.

In another embodiment, $R^1$ is 4-chlorophenyl.

In another embodiment, $R^2$, $R^3$, $R^4$ and $R^5$ are independently selected from H, F, Cl, CN, $NO_2$, $CH_3$, $CF_3$, iPr, and cPr.

In another embodiment, $R^2$, $R^4$ and $R^5$ are H.

In another embodiment, $R^3$ is $CH_3$.

FORMULA 3

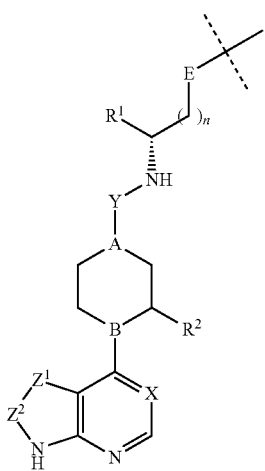

wherein
A, B, and X are independently N or $CR^3$,
Y is $CH_2$, CO, SO, $SO_2$, $CR^4R^5$, $CONR^4$, or $SO_2NR^4$,
E is NH, $NR^6$, O, $C_1$-$C_8$ alkyl, $C_1$-$C_8$ alkoxy, $C_1$-$C_8$ alkoxyalkyl, $C_1$-$C_8$ haloalkyl, $C_1$-$C_8$ hydroxyalkyl, $C_3$-$C_8$ cycloalkyl, $C_3$-$C_8$ heterocyclyl, $C_2$-$C_8$ alkenyl, $C_2$-$C_8$ alkynyl, $OR^6$, $SR^6$, $NR^6R^7$, CN, $NO_2$, $(CR^6R^7)mNR^8R^9$, $(CR^6R^7)mC(O)R^8$, $(NR^6R^7)mNR^8R^9$, $(NR^6R^7)mC(O)R^8$, $COR^6$, $CO_2R^6$, $CONR^6R^7$, $NR^6COR^7$, $NR^6SOR^7$, $NR^6SO_2R^7$, $SOR^6$, $SO_2R^6$, $SO_2NR^6R^7$, $(CR^6R^7)m$-aryl, or $(CR^6R^7)m$-heteroaryl,
$Z^1$—$Z^2$ is $CR^{10}$=CH, N+CH, or $CR^{10}$=N,
$R^1$ is hydrogen, $C_1$-$C_8$ alkyl, $C_3$-$C_8$ cycloalkyl, $C_1$-$C_8$ alkoxy, $C_1$-$C_8$ alkoxyalkyl, aryl, $C_1$-$C_8$ alkylaryl, haloaryl, arylalkyl, heteroaryl, or heteroarylalkyl,
$R^2$, $R^3$, and $R^4$ are independently hydrogen, halogen, amino, $C_1$-$C_8$ alkylamino, arylamino, $C_1$-$C_8$ alkyl, $C_3$-$C_8$ cycloalkyl, $C_1$-$C_8$ alkoxy, or $C_1$-$C_8$ alkoxyalkyl,
$R^6$, $R^7$, $R^8$, and $R^9$ are independently H, $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, arylalkyl, cycloalkyl, heterocycloalkyl, aryl, heteroaryl, or heteroarylalkyl,
$R^6$ and $R^7$, $R^8$ and $R^9$ can independently form 4-8 membered alkyl or heterocyclyl rings,
$R^{10}$ is hydrogen, halogen, $C_1$-$C_8$ alkyl, $C_3$-$C_8$ cycloalkyl, $C_1$-$C_8$ alkoxy, $C_1$-$C_8$ alkoxyalkyl,
m=0-8,
and
n=0-8.

FORMULA 4

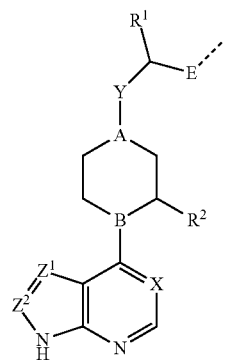

wherein
A, B and X are independently selected from N and $CR^3$, wherein
$R^3$ is independently selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino $C_1$-$C_8$ alkyl, optionally substituted 3-10 membered carbocyclyl, and optionally substituted 4-10 membered heterocyclyl;
$Z^1$ is selected for $CR^8$ and N, wherein
$R^8$ is selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3-10 membered carbocyclyl, and optionally substituted 4-10 membered heterocyclyl;
$Z^2$ is selected for CH and N;
Y is selected from CO, SO, $SO_2$, $CR^4R^5$, $CONR^4$, and $SO_2NR^4$, wherein
$R^4$ and $R^5$ is independently selected from hydrogen and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3 to 10 membered carbocyclyl, and optionally substituted 4-10 membered heterocyclyl;
E is connected to the "linker" moiety of the bivalent compound, and is selected from null, R'—R", R'OR", R'SR", R'$NR^6$R", R'OC(O)R", R'OC(O)OR", R'OCO$NR^6$R", R'C(O)R", R'C(O)OR", R'CO$NR^6$R", R'S(O)R", R'S(O)$_2$R", R'SO$_2$$NR^6$R", R'$NR^7$C(O)OR", R'$NR^7$C(O)R", R'$NR^7$C(O)$NR^6$R", R'$NR^7$S(O)R", R'$NR^7$S(O)$_2$R", and R'$NR^7$S(O)$_2$$NR^6$R", wherein
R' and R" are independently selected form null, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ haloalkylene, optionally substituted $C_1$-$C_8$ hydroxyalkylene, optionally substituted $C_1$-$C_8$alkoxy$C_1$-$C_8$alkylene, optionally substituted ($C_1$-$C_8$ alkylene)O($C_1$-$C_8$ alkylene), optionally substituted ($C_1$-$C_8$ alkylene)N($C_1$-$C_8$ alkylene), optionally substituted 3-10 membered carbocyclyl, optionally substituted 4-10 membered heterocyclyl, optionally substituted $C_3$-$C_{13}$ fused carbocyclyl, optionally substituted $C_3$-$C_{13}$ fused heterocyclyl, optionally substituted $C_3$-$C_{13}$ bridged carbocyclyl, optionally substituted $C_3$-$C_{13}$ bridged heterocyclyl, optionally substituted $C_3$-$C_{13}$ spiro carbocyclyl, optionally substituted $C_3$-$C_{13}$ spiro heterocyclyl, optionally substituted aryl, and optionally substituted heteroaryl;
$R^6$ and $R^7$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl, or R' and R", R⁶ and R⁷, R' and R⁶, R' and R⁷, R" and R⁶, R" and R⁷ together with the atom to which they are connected form a 4-20 membered heterocyclyl ring;

R¹ is selected from selected from hydrogen, halogen, and optionally substituted C₁-C₈ alkyl, optionally substituted C₂-C₈ alkenyl, optionally substituted C₂-C₈ alkynyl, optionally substituted C₁-C₈ alkoxy, optionally substituted C₁-C₈ alkoxyC₁-C₈ alkyl, optionally substituted amino, optionally substituted C₁-C₈ alkylaminoC₁-C₈ alkyl, optionally substituted 3-10 membered carbocyclyl, optionally substituted 4-10 membered heterocyclyl, optionally substituted aryl, and optionally substituted heteroaryl; and R² is selected from hydrogen, halogen, cyano, nitro, hydroxyl, optionally substituted C₁-C₈ alkyl, optionally substituted C₂-C₈ alkenyl, optionally substituted C₂-C₈ alkynyl, optionally substituted C₁-C₈ alkoxy, or optionally substituted C₁-C₈ alkoxy C₁-C₈ alkyl, optionally substituted amino, optionally substituted C₁-C₈ alkylaminoC₁-C₈ alkyl, optionally substituted 3-10 membered carbocyclyl, and optionally substituted 4-10 membered heterocyclyl;

In one embodiment, A is selected from N, CH and CNH₂.
In another embodiment, A is CNH₂.
In one embodiment, B and X are independently selected from N and CH.
In another embodiment, B is N.
In another embodiment, X is N.
In another embodiment, Z¹ is selected from CH and CCH₃.
In another embodiment, Z¹ is CH.
In another embodiment, Z² is CH.
In another embodiment, Y is selected from CH₂, CO, CONH and NHCO.
In another embodiment, Y is CONH.
In another embodiment, E is selected from null, O, N, optionally substituted C₁-C₈ alkylene, optionally substituted (C₁-C₈ alkylene)O, optionally substituted (C₁-C₈ alkylene)N, optionally substituted 3-10 membered carbocyclylene, optionally substituted (3-10 membered carbocyclylene)O, optionally substituted (3-10 membered carbocyclylene)N, optionally substituted 4-10 membered heterocyclylene, optionally substituted (4-10 membered heterocyclylene)O, optionally substituted (4-10 membered heterocyclylene)N, optionally substituted aryl, and optionally substituted heteroaryl.
In another embodiment, R¹ is selected from optionally substituted aryl and optionally substituted heteroaryl.
In another embodiment, R¹ is selected from optionally substituted phenyl.
In another embodiment, R¹ is 4-chlorophenyl.
In another embodiment, R² is selected from H, F, Cl, CN, NO₂, CH₃, CF₃, iPr, and cPr.
In another embodiment, R² is H.

The AKT ligand can be an AKT inhibitor, such as, for example, GSK690693 (Heerding et al., 2008), GSK2110183 (Dumble et al., 2014), GSK2141795 (Dumble et al., 2014), AZD5363 (Addie et al., 2013), GDC0068 (Blake et al., 2012), MK-2206 (Hirai et al., 2010), and ARQ-092 (Yu et al., 2015), and/or analogs thereof.

In some aspects, the AKT ligand can be, e.g.:

FORMULA 3A

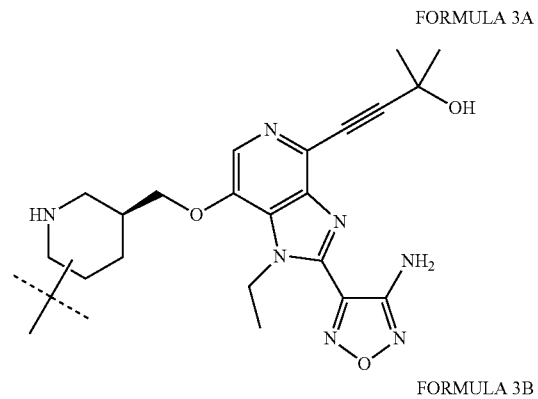

FORMULA 3B

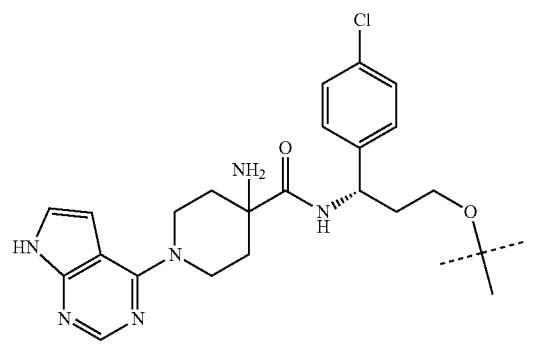

FORMULA 3C

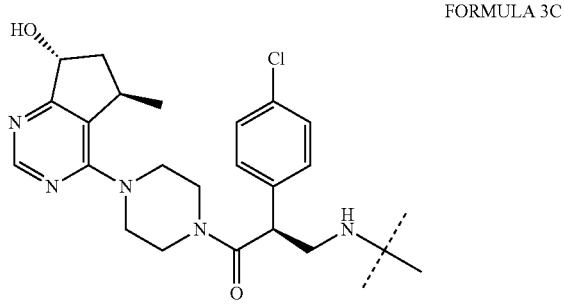

FORMULA 3D

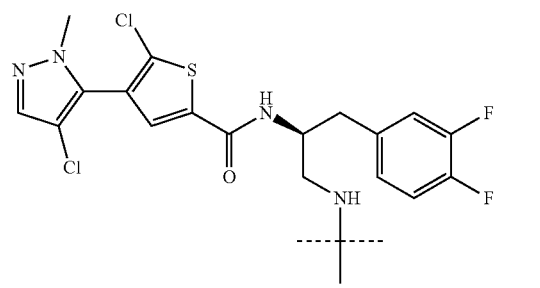

FORMULA 3E

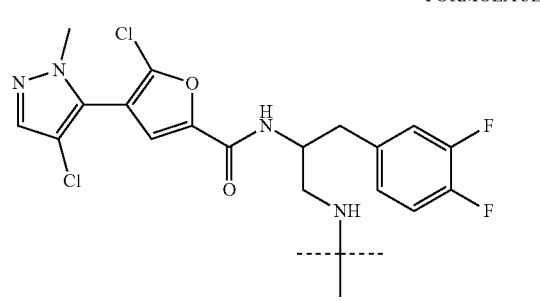

FORMULA 3F
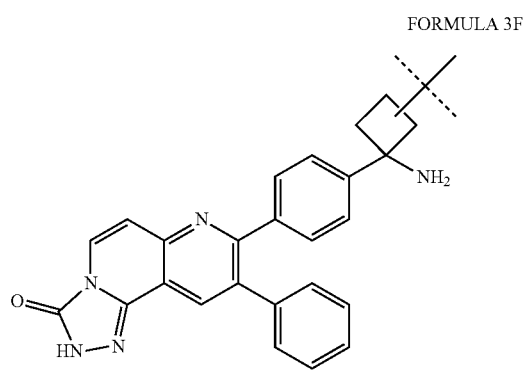
FORMULA 3G
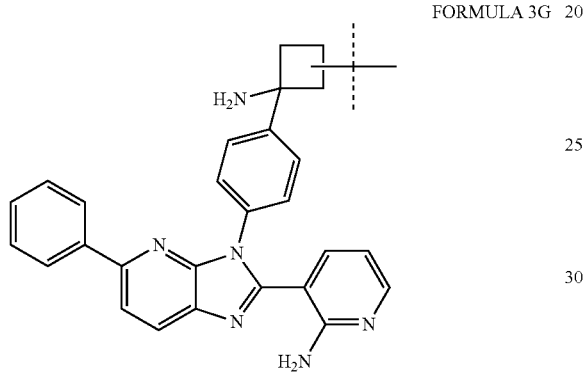
FORMULA 3H
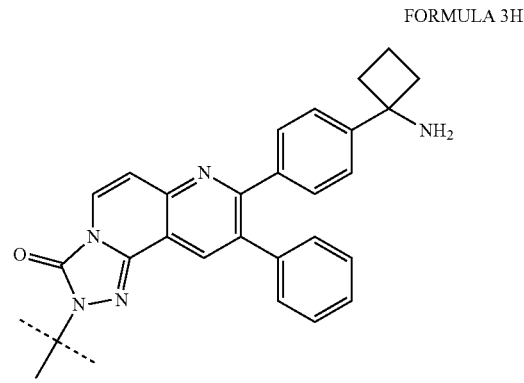
FORMULA 3I
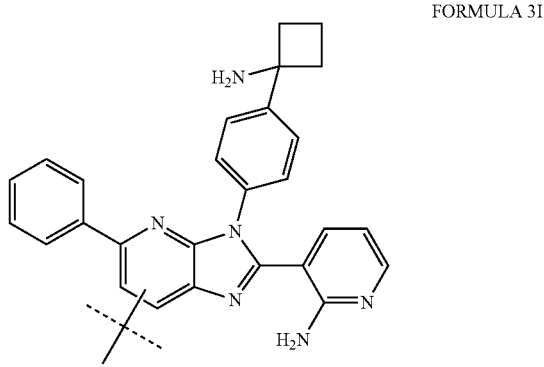
FORMULA 3J
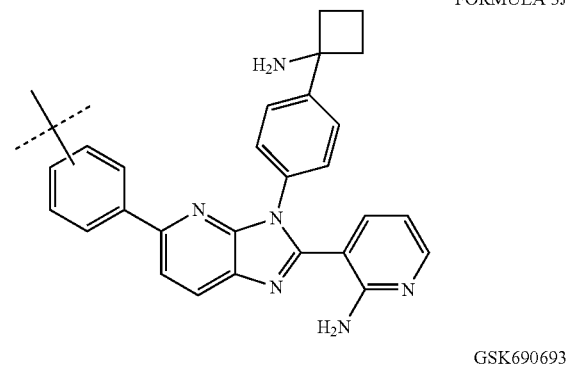
GSK690693
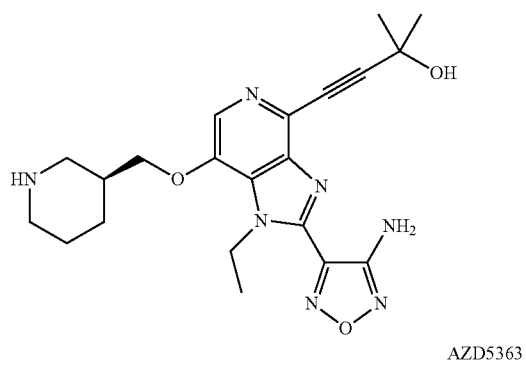
AZD5363
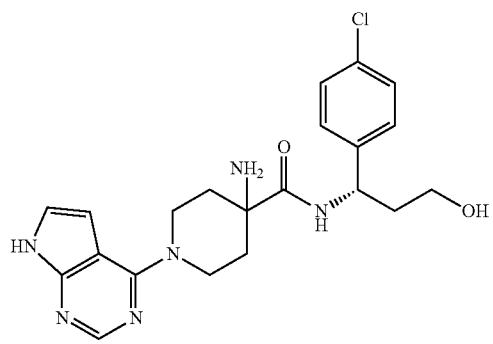
GDC0068
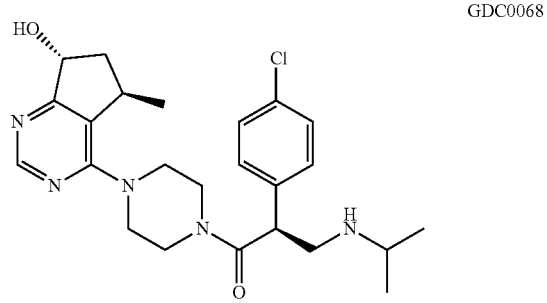
GSK2110183
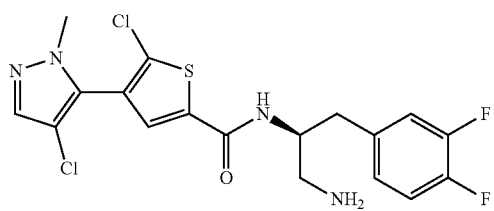

GSK2141795

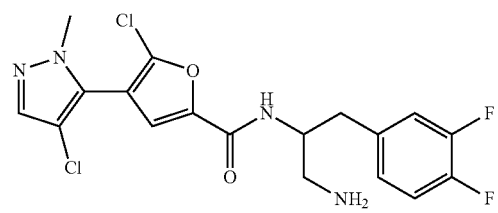

MK2206

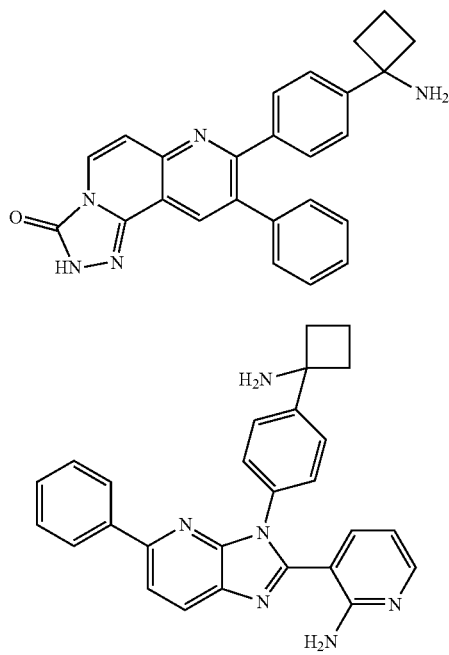

ARQ 092

The AKT ligand can be bound to AKT and/or AKT mutant proteins, such as, e.g., AKT with an E17K mutation.

Degradation/Disruption Tags

Degradation/Disruption Tags (EL) include but are not limited to:

FORMULA 5A

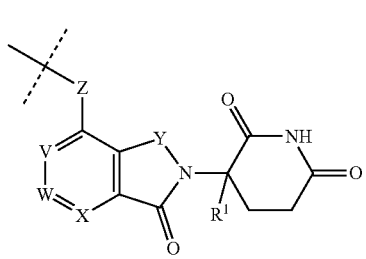

FORMULA 5B

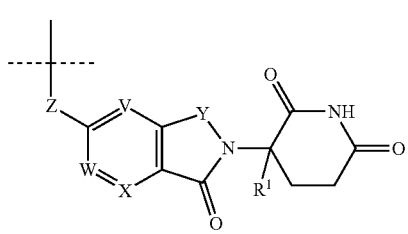

FORMULA 5C

FORMULA 5D

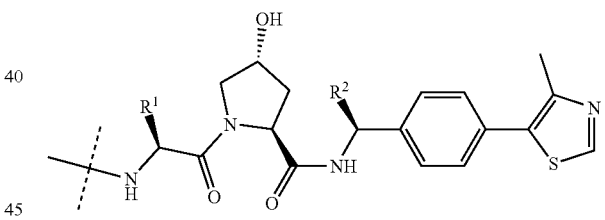

wherein
V, W, and X are independently $CR^2$ or N,
Y is CO or $CH_2$,
Z is $CH_2$, NH, or O,
$R^1$ is hydrogen, methyl, or fluoro, and
$R^2$ is hydrogen, halogen, or $C_1$-$C_5$ alkyl;
wherein
V, W, and X are independently selected from $CR^2$ and N;
Y is selected from CO, $CH_2$, and N=N;
Z is selected from $CH_2$, NH and O; and
$R^1$ and $R^2$ are independently selected from hydrogen, halogen, cyano, nitro, and $C_1$-$C_5$ alkyl.

FORMULA 6

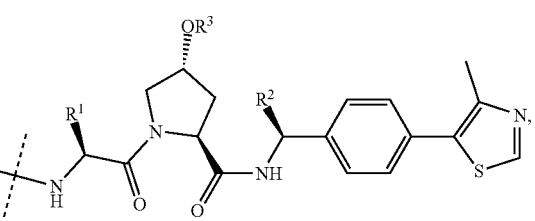

wherein
$R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl;

FORMULA 7 wherein
$R^1$ and $R^2$ are independently selected from hydrogen, hydroxyl, amino, cyano, nitro, optionally substituted $C_1$-$C_8$ alkyl, optionally substituted $C_2$-$C_8$ alkenyl, and optionally substituted $C_2$-$C_8$ alkynyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted 3-10 membered carbocyclyl, and optionally substituted 4-10 membered heterocyclyl.

$R^3$ is selected from hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)(3-10 membered carbocyclyl), optionally substituted C(O)(4-10 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$alkyl, optionally substituted C(O)O(3-10 membered carbocyclyl), optionally substituted C(O)O(4-10 membered heterocyclyl), optionally substituted C(O)O$C_2$-$C_8$ alkenyl, optionally substituted C(O)O$C_2$-$C_8$ alkynyl, optionally substituted C(O)N$C_1$-$C_8$alkoxy$C_1$-$C_8$alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$alkyl, optionally substituted C(O)N(3-10 membered carbocyclyl), optionally substituted C(O)N(4-10 membered heterocyclyl), optionally substituted C(O)N$C_2$-$C_8$ alkenyl, optionally substituted C(O)N$C_2$-$C_8$ alkynyl, optionally substituted P(O)(OH)$_2$, optionally substituted P(O)(O$C_1$-$C_8$ alkyl)$_2$, and optionally substituted P(O)(O$C_1$-$C_8$ aryl)$_2$.
and

FORMULA 8

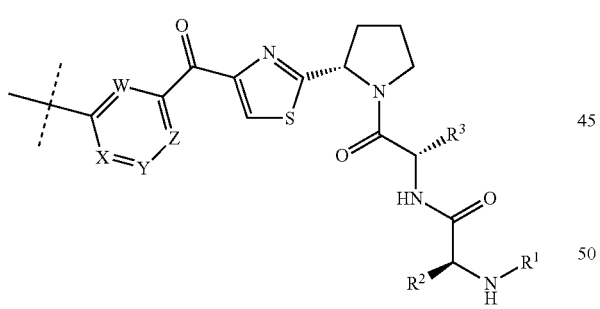

wherein
$R^1$, $R^2$, $R^3$, and $R^4$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl, and
V, W, X, and Z are independently $CR^4$ or N.
wherein
V, W, X, and Z are independently selected from $CR^4$ and N; and
$R^1$, $R^2$, $R^3$, and $R^4$ are independently selected from hydrogen, halogen, cyano, nitro, optionally substituted $C_1$-$C_8$ alkyl, optionally substituted $C_2$-$C_8$ alkenyl, and optionally substituted $C_2$-$C_8$ alkynyl; optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkoxy, optionally substituted $C_1$-$C_8$alkylamino, optionally substituted 3-10 membered carbocyclyl, and optionally substituted 4-10 membered heterocyclyl.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), and/or analogs thereof.

In some aspects, the degradation/disruption tag can be, e.g., one of the following structures:

FORMULA 8A

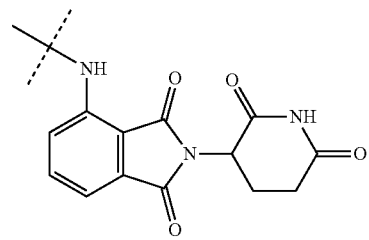

FORMULA 8B

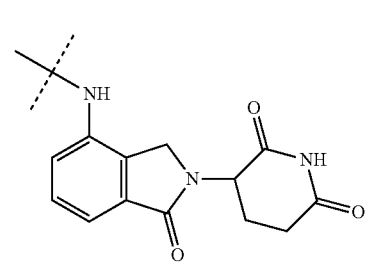

FORMULA 8C

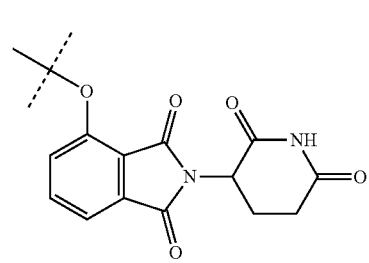

FORMULA 8D

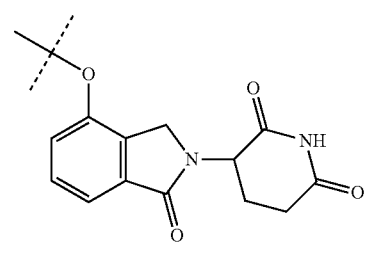

FORMULA 8E
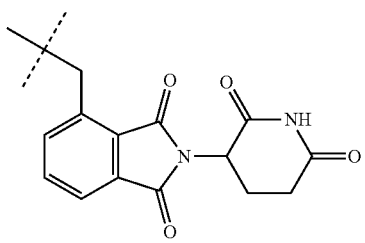
FORMULA 8F
FORMULA 8G
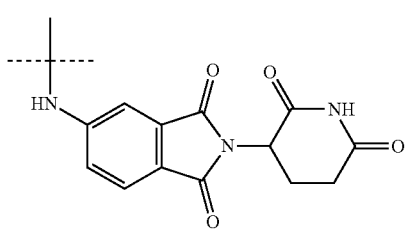
FORMULA 8H
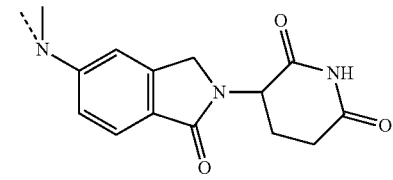
FORMULA 8I
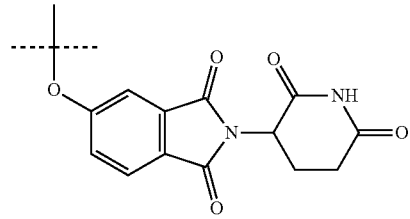
FORMULA 8J
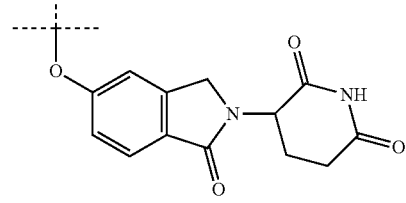
FORMULA 8K
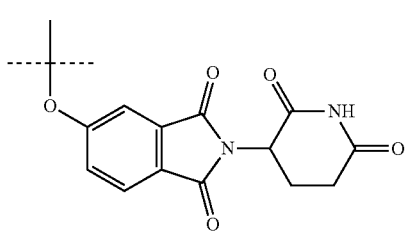
FORMULA 8L
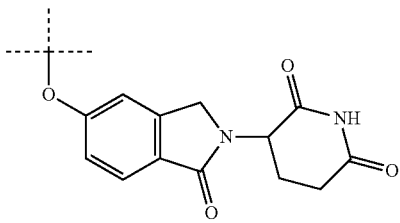
FORMULA 8M
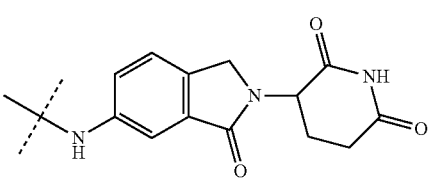
FORMULA 8N
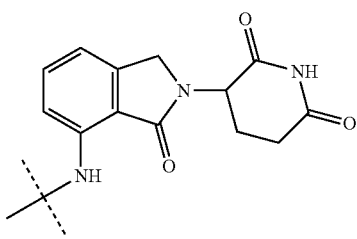
FORMULA 8O
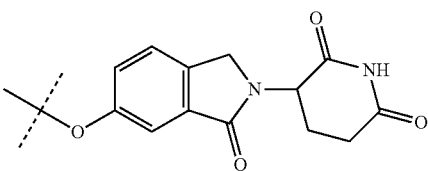
FORMULA 8P
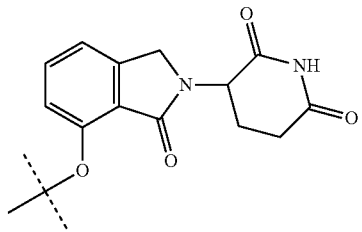
FORMULA 8Q
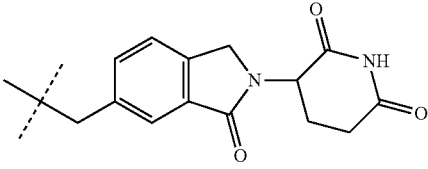
FORMULA 8R
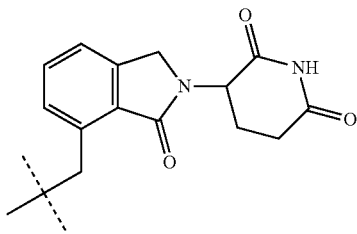

FORMULA 8S
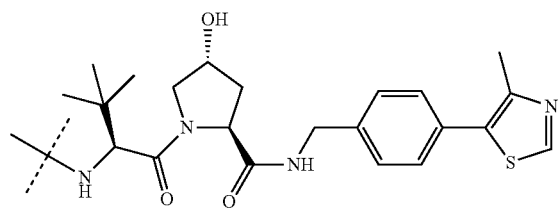
FORMULA 8T
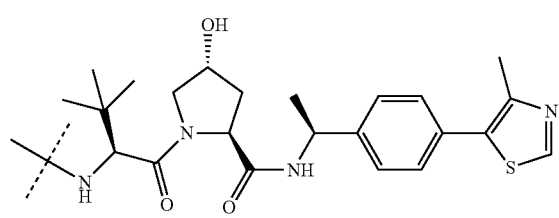
FORMULA 8U
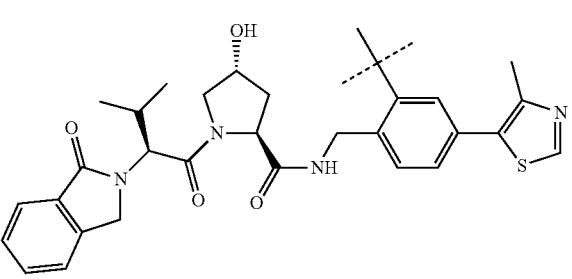
FORMULA 8V
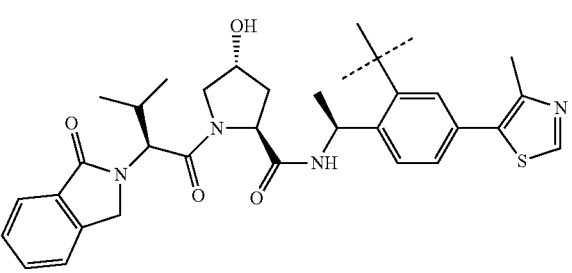
FORMULA 8W
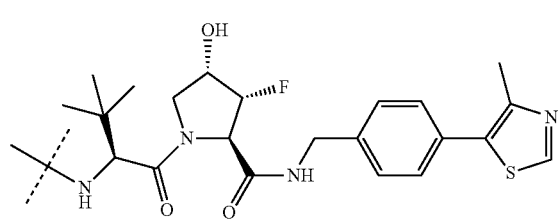
FORMULA 8X
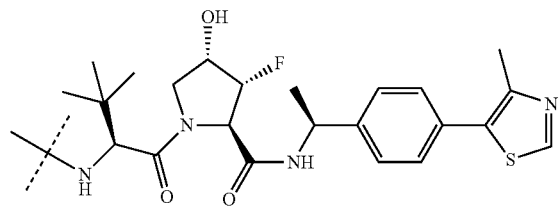
FORMULA 8Y
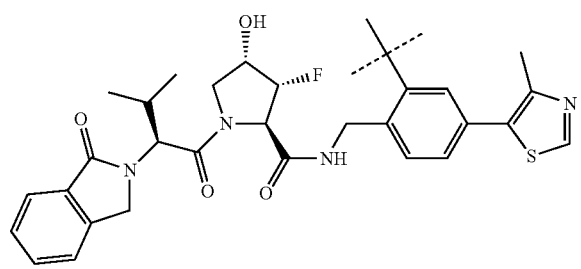
FORMULA 8Z
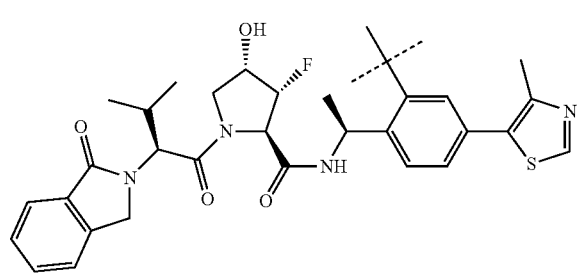
FORMULA 8AA
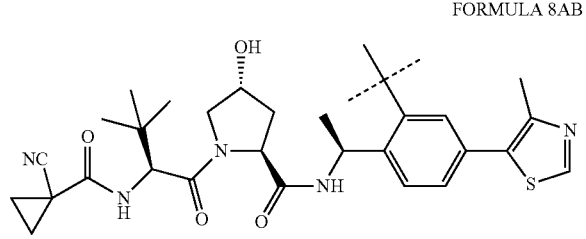
FORMULA 8AB
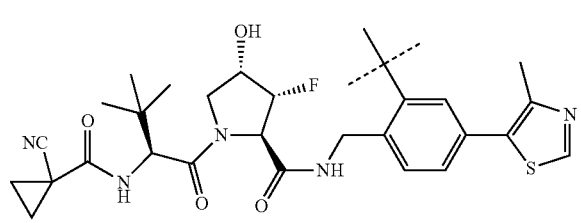
FORMULA 8AC
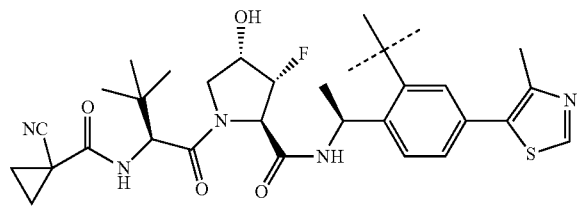
FORMULA 8AD FORMULA 8AE
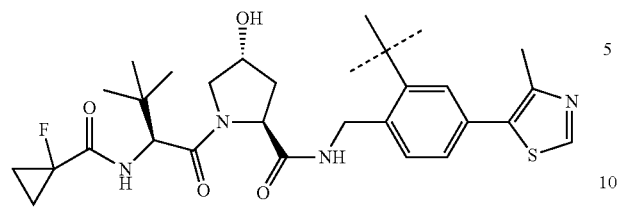
FORMULA 8AF
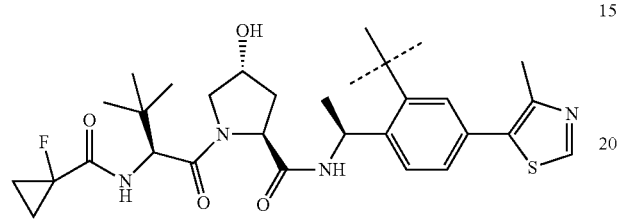
FORMULA 8AG

FORMULA 8AH

FORMULA 8AI
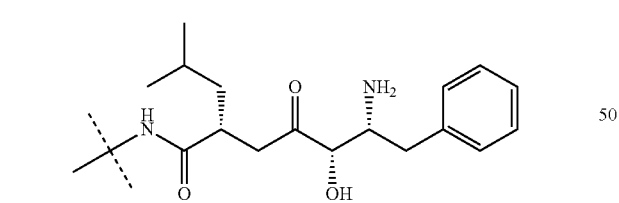
FORMULA 8AJ
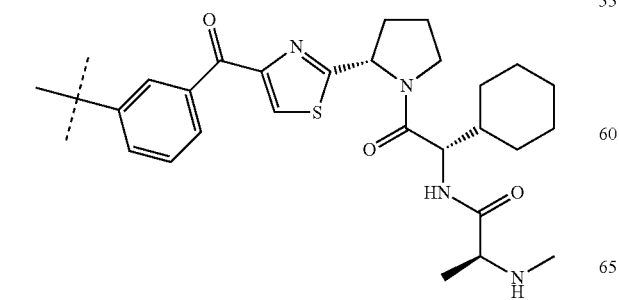
FORMULA 8AK
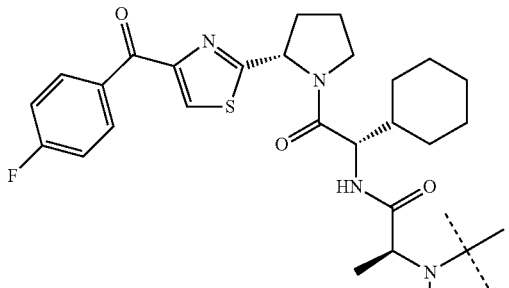
FORMULA 8AL
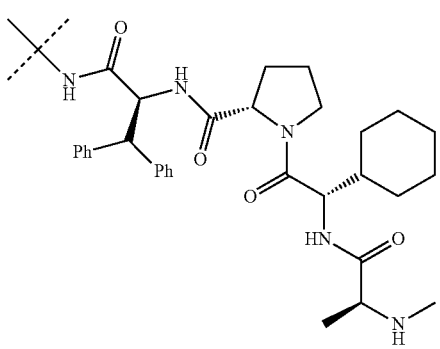
FORMULA 8AM
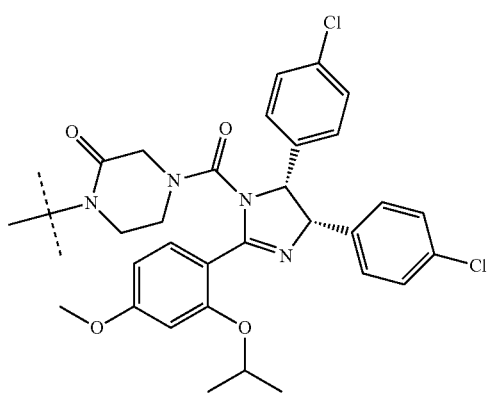
FORMULA 8AN
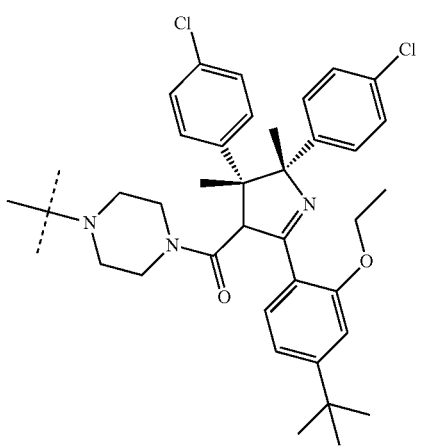

FORMULA 8AO
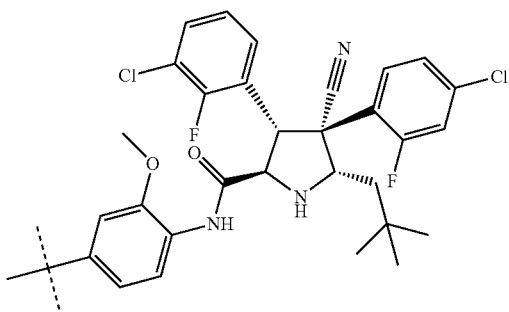
FORMULA 8AP
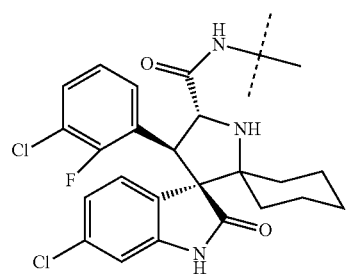
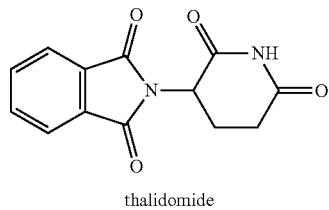
thalidomide
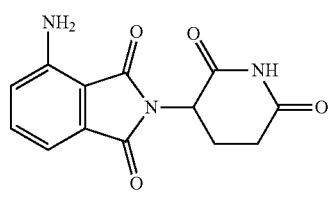
pomalidomide
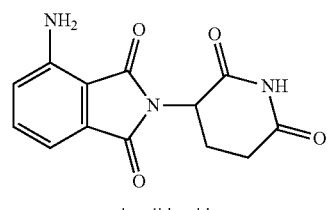
lenalidomide
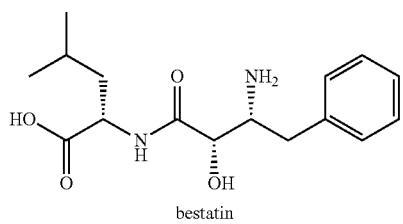
bestatin
MV1
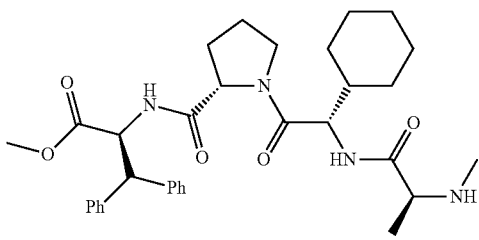
LCL161
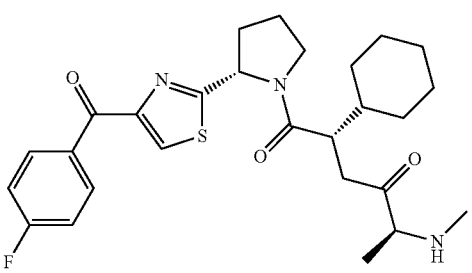
nutlin-3a
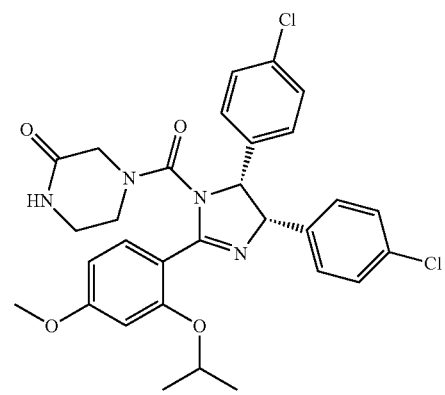
RG7112
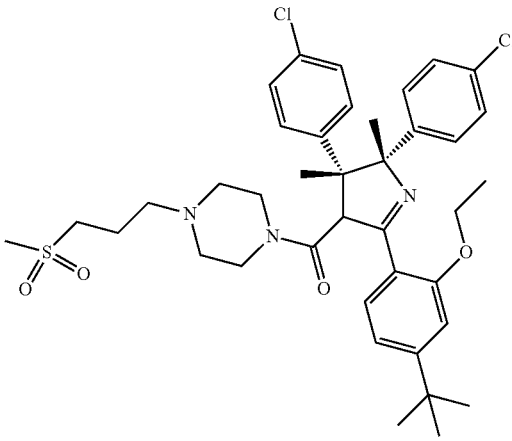

-continued

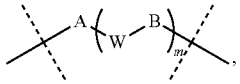

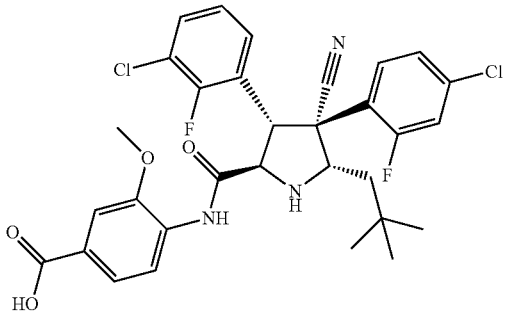

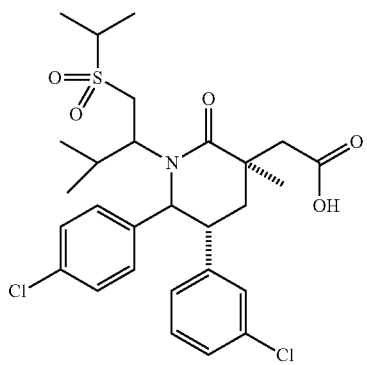

In some aspects, the degradation/disruption tag can bind to aubiquitin ligase (e.g., an E3 ligase such as a cereblon E3 ligase, a VHL E3 ligase, a MDM2 ligase, a TRIM21 ligase, a TRIM24 ligase, and/or an IAP ligase) and/or serve as a hydrophobic group that leads to AKT protein misfolding.

Linkers

In all of the above-described compounds, the AKT ligand is conjugated to the degradation/disruption tag through a linker. The linker can include, for example, acyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

FORMULA 9

$$\text{---}A\text{---}(W\text{---}B)_m\text{---}$$

wherein

A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

R$^1$ and R$^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R' and R$^2$, R" and R$^1$, R" and R$^2$ together with the atom to which they are connected form a 3-20 membered cycloalkyl or 4-20 membered heterocyclyl ring; and m is 0 to 15.

In one embodiment, the linker moiety is of FORMULA 9A:

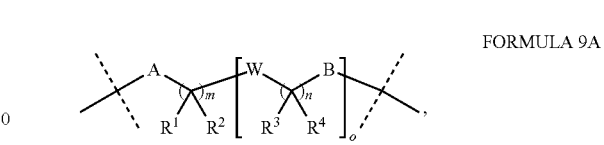

FORMULA 9A wherein

R$^1$, R$^2$, R$^3$ and R$^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted C₁-C₈ alkoxy, optionally substituted C₁-C₈ alkoxyalkyl, optionally substituted C₁-C₈ haloalkyl, optionally substituted C₁-C₈ hydroxyalkyl, optionally substituted C₁-C₈ alkylamino, and optionally substituted C₁-C₈ alkylaminoC₁-C₈ alkyl, optionally substituted 3-10 membered carbocyclyl, optionally substituted 3-10 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'—R", R'COR", R'CO₂R", R'C(O)NR"R¹, R'C(S)NR"R¹, R'OR", R'OC(O)R", R'OC(O)OR", R'OCONR¹R", R'SR", R'SOR", R'SO₂R", R'SO₂NR"R¹, R'NR"R¹, R'NR¹COR", R'NR¹C(O)OR", R'NR¹CONR"R², R'NR¹C(S)R", R'NR¹S(O)R", R'NR¹S(O)₂R", and R'NR¹S(O)₂NR²R", wherein R and R" are independently selected from null, or a moiety comprising of optionally substituted C₁-C₈ alkyl, optionally substituted C₂-C₈ alkenyl, optionally substituted C₂-C₈ alkynyl, optionally substituted C₁-C₈ hydroxyalkyl, optionally substituted C₁-C₈alkoxyC₁-C₈alkyl, optionally substituted C₁-C₈alkylaminoC₁-C₈alkyl, optionally substituted C₁-C₈ haloalkyl, optionally substituted C₁-C₈ alkylene, optionally substituted C₂-C₈ alkenylene, optionally substituted C₂-C₈ alkynylene, optionally substituted C₁-C₈ hydroxyalkylene, optionally substituted C₁-C₈alkoxyC₁-C₈alkylene, optionally substituted C₁-C₈alkylaminoC₁-C₈alkylene, optionally substituted C₁-C₈ haloalkylene, optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

$R^5$ and $R^6$ are independently selected from hydrogen, optionally substituted C₁-C₈ alkyl, optionally substituted C₂-C₈ alkenyl, optionally substituted C₂-C₈ alkynyl, optionally substituted C₁-C₈ alkoxyalkyl, optionally substituted C₁-C₈ haloalkyl, optionally substituted C₁-C₈ hydroxyalkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;
n, at each occurrence, is 0 to 15; and
o is 0 to 15.

In another embodiment, the linker moiety is of FORMULA 9B:

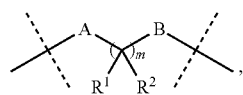

FORMULA 9B wherein $R^1$ and $R^2$, at each occurrence, are independently selected from hydrogen, halogen, hydroxyl, amino, cyano, nitro, and optionally substituted C₁-C₈ alkyl, optionally substituted C₁-C₈ alkoxy, optionally substituted C₁-C₈ alkoxy C₁-C₈ alkyl, optionally substituted C₁-C₈ haloalkyl, optionally substituted C₁-C₈ hydroxyalkyl, optionally substituted C₁-C₈ alkylamino, C₁-C₈alkylaminoC₁-C₈alkyl, optionally substituted 3-10 membered carbocyclyl, optionally substituted 3-10 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'CO₂R", R'C(O)NR"R¹, R'C(S)NR"R¹, R'OR", R'OC(O)R", R'OC(O)OR", R'OCONR¹R", R'SR", R'SOR", R'SO₂R", R'SO₂NR"R¹, R'NR"R¹, R'NR¹COR", R'NR¹C(O)OR", R'NR¹CONR"R², R'NR¹C(S)R", R'NR¹S(O)R", R'NR¹S(O)₂R", and R'NR¹S(O)₂NR²R", wherein R' and R" are independently selected from null, or a moiety comprising of optionally substituted C₁-C₈ alkyl, optionally substituted C₂-C₈ alkenyl, optionally substituted C₂-C₈ alkynyl, optionally substituted C₁-C₈ hydroxyalkyl, optionally substituted C₁-C₈alkoxyC₁-C₈alkyl, optionally substituted C₁-C₈alkylaminoC₁-C₈alkyl, optionally substituted C₁-C₈ haloalkyl, optionally substituted C₁-C₈ alkylene, optionally substituted C₂-C₈ alkenylene, optionally substituted C₂-C₈ alkynylene, optionally substituted C₁-C₈ hydroxyalkylene, optionally substituted C₁-C₈alkoxyC₁-C₈alkylene, optionally substituted C₁-C₈alkylaminoC₁-C₈alkylene, optionally substituted C₁-C₈ haloalkylene, optionally substituted 3-10 membered carbocyclyl, optionally substituted 4-10 membered heterocyclyl, optionally substituted C₃-C₁₃ fused cycloalkyl, optionally substituted C₃-C₁₃ fused heterocyclyl, optionally substituted C₃-C₁₃ bridged cycloalkyl, optionally substituted C₃-C₁₃ bridged heterocyclyl, optionally substituted C₃-C₁₃ spiro cycloalkyl, optionally substituted C₃-C₁₃ spiro heterocyclyl, optionally substituted aryl, and optionally substituted heteroaryl;

$R^3$ and $R^4$ are independently selected from hydrogen, optionally substituted C₁-C₈ alkyl, optionally substituted C₂-C₈ alkenyl, optionally substituted C₂-C₈ alkynyl, optionally substituted C₁-C₈ alkoxyalkyl, optionally substituted C₁-C₈ haloalkyl, optionally substituted C₁-C₈ hydroxyalkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

each m is 0 to 15; and
n is 0 to 15.

In another embodiment, the linker moiety is of FORMULA 9C:

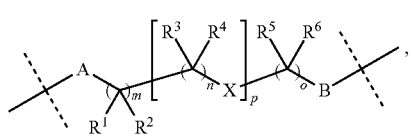
FORMULA 9C wherein

X is selected from O, NH, and $NR^7$;

$R^1$, $R^2$, $R^3$, $R^4$, $R^5$, $R^6$, and $R^7$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-10 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;

m, at each occurrence, is 0 to 15;

n, at each occurrence, is 0 to 15;

o is 0 to 15; and p is 0 to 15.

In another embodiment, A and B, at each occurrence, are independently selected from null, CO, NH, NH—CO, CO—NH, CH$_2$—NH—CO, CH$_2$—CO—NH, NH—CO—CH$_2$, CO—NH—CH$_2$, CH$_2$—NH—CH$_2$—CO—NH, CH$_2$—NH—CH$_2$—NH—CO, —CO—NH, CO—NH—CH$_2$—NH—CH$_2$, CH$_2$—NH—CH$_2$.

In another embodiment, o is 0 to 5.

In another embodiment, the linker moiety comprises a ring selected from the group consisting of a 3 to 13 membered ring, a 3 to 13 membered fused ring, a 3 to 13 membered bridged ring, and a 3 to 13 membered spiro ring.

In another embodiment, the linker moiety comprises one or more rings selected from the group consisting of FORMULAE C1, C2, C3, C4 and C5:

FORMULA C1

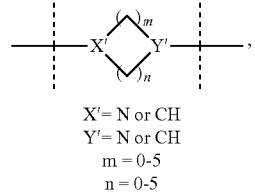

X' = N or CH
Y' = N or CH
m = 0-5
n = 0-5

FORMULA C2

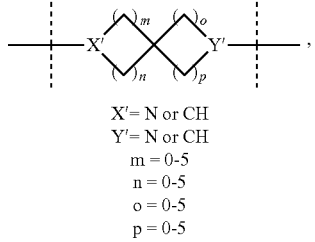

X' = N or CH
Y' = N or CH
m = 0-5
n = 0-5
o = 0-5
p = 0-5

FORMULA C3

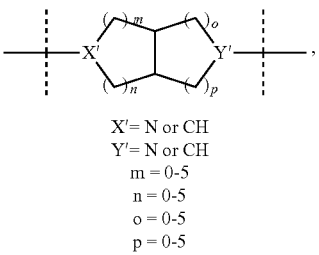

X' = N or CH
Y' = N or CH
m = 0-5
n = 0-5
o = 0-5
p = 0-5

FORMULA C4

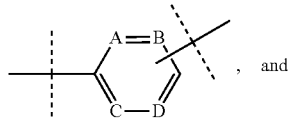
, and

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N -continued

FORMULA C5

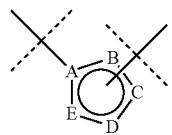

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S·

Formula A

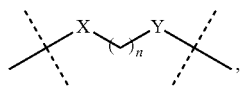

wherein X is C=O or CH$_2$,
Y is C=O or CH$_2$, and
n is 0-15;

Formula B

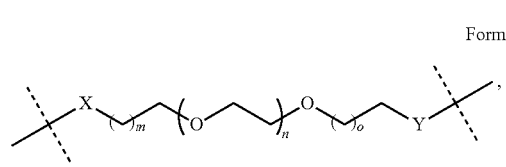

wherein X is C=O or CH$_2$,
Y is C=O or CH$_2$,
m is 0-15,
n is 0-6, and
o is 0-15; or Formula C

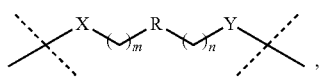

wherein
X is C=O or CH$_2$,
Y is C=O or CH$_2$,
R is —CH$_2$—, —CF$_2$—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C≡C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of:

Formula C1

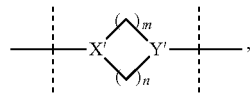

X'= N or CH
Y'= N or CH
m = 0-5
n = 0-5

Formula C2

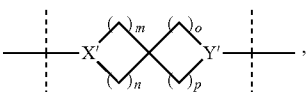

X'= N or CH
Y'= N or CH
m = 0-5
n = 0-5
o = 0-5
p = 0-5

Formula C3

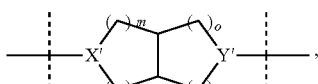

X'= N or CH
Y'= N or CH
m = 0-5
n = 0-5
o = 0-5
p = 0-5

Formula C4

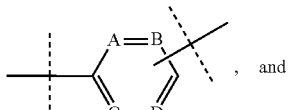
, and

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N Formula C5

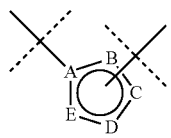

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S·

In some aspects, the bivalent compound is a compound selected from the following compounds, as identified in Table 1 below: XF038-157A, XF038-158A, XF038-159A, XF038-160A, XF038-161A, XF038-162A, XF038-164A, XF038-165A, XF038-166A, XF038-176A, XF038-177A, XF042-162, XF042-164, XF042-165, XF042-166, XF042-167, XF042-168, XF042-170, XF042-171, XF048-1, XF048-2, XF048-3, XF048-4, XF048-5, XF048-7, XF048-8, XF050-5, XF050-6, XF050-7, XF050-8, XF050-9, XF050-10, XF050-11, XF050-12, XF050-13, XF050-14, XF050-15, XF050-16, XF050-17, XF050-18, XF050-19, XF050-20, XF050-21, XF050-22, XF050-23, XF050-24, XF050-25, XF050-26, XF050-27, XF050-28, XF050-29, XF050-30, XF050-31, XF050-32, XF050-33, XF050-98, XF050-132, XF050-133, XF050-134, XF056-93, XF050-143, XF050-144, XF050-145, XF050-167, XF056-33, XF056-34, XF056-35, XF056-36, XF056-37, XF056-73, XF061-10, XF067-1, XF067-2, XF067-3, XF067-4, XF067-5, XF067-6, XF067-7, XF067-8, XF067-9, XF067-10, XF067-11, XF067-12, XF067-13, XF067-14, XF067-15, XF067-16, XF067-17, XF067-18, XF067-19, XF067-20, XF067-21, XF067-22, XF067-23, XF067-24, XF067-25, XF067-26, XF067-27, XF067-28, XF067-29, XF067-30, XF067-31, XF067-32, XF067-33, XF067-34, XF067-35, XF067-36, XF067-37, XF067-38, XF067-39, XF067-40, XF067-41, XF067-42, XF067-43, XF067-44, XF067-45, XF067-46, XF067-47, XF067-48, XF067-49, XF067-50, XF067-51, XF067-52, XF067-53, XF067-54, XF067-55, XF067-56, XF067-57, XF067-58, XF067-59, XF067-84, XF067-85, XF067-86, XF067-87, XF067-88, XF067-89, XF067-90, XF067-91, XF067-92, XF067-93, XF067-94, XF067-95, XF067-96, XF067-97, XF067-98, XF067-99, XF067-100, XF067-101, XF067-102, XF067-103, XF067-104, XF067-105, XF067-106, XF067-107, XF067-108, XF067-109, XF067-110, XF067-111, XF067-112, XF067-113, or analogs thereof.

In some aspects, this disclosure provides a method of treating AKT-mediated cancers, the method including administering to a subject in need thereof one or more bivalent compounds including an AKT ligand conjugated to a degradation/disruption tag via a linker. The AKT-mediated cancer can be a cancer resulting from (aberrant) AKT activation. The AKT-mediated cancer can have elevated AKT enzymatic activity relative to a wild-type tissue of the same species and tissue type. Non-limiting examples of AKT-mediated diseases include inflammatory, hyperproliferative cardiovascular, neurodegenerative, gynecological, and dermatological diseases and disorders. In an aspect, the AKT degraders of the present disclosure can be employed for the treatment of hyperproliferative disorders, including cancers angiosarcoma, fibrosarcoma, rhabdomyosarcoma, liposarcoma, myxoma, rhabdomyoma, fibroma, lipoma, teratoma, squamous cell carcinoma, undifferentiated small cell carcinoma, undifferentiated large cell carcinoma, adenocarcinoma, alveolar carcinoma, bronchial adenoma, sarcoma, lymphoma, chondromatous hamartoma, mesothelioma, non-small cell lung cancer, small cell lung cancer, leiomyosarcoma, stomach carcinoma, ductal adenocarcinoma, insulinoma, glucagonoma, gastrinoma, carcinoid tumors, vipoma, carcinoid tumors, Kaposi's sarcoma, leiomyoma, hemangioma, neurofibroma, tubular adenoma, villous adenoma, hamartoma, kidney cancer, Wilm's tumor, nephroblastoma, leukemia, bladder cancer, urethra cancer, transitional cell carcinoma, prostate cancer, seminoma, embryonal carcinoma, teratocarcinoma, choriocarcinoma, interstitial cell carcinoma, fibroadenoma, adenomatoid tumors, hepatoma, hepatocellular carcinoma, cholangiocarcinoma, hepatoblastoma, hepatocellular adenoma, osteogenic sarcoma, osteosarcoma, malignant fibrous histiocytoma, chondrosarcoma, Ewing's sarcoma, malignant lymphoma, reticulum cell sarcoma, multiple myeloma, malignant giant cell tumor chordoma, osteochronfroma, osteocartilaginous exostoses, benign chondroma, chondroblastoma, chondromyxofibroma, osteoid osteoma, giant cell tumors, osteoma, granuloma, xanthoma, osteitis deformans, meningioma, meningiosarcoma, gliomatosis, astrocytoma, medulloblastoma, glioma, ependymoma, germinoma, pinealoma, glioblastoma multiforme, oligodendroglioma, schwannoma, retinoblastoma, congenital tumors, spinal cord neurofibroma, endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, intraepithelial carcinoma, melanoma, clear cell carcinoma, botryoid sarcoma, embryonal fallopian tubes carcinoma, acute myeloid leukemia, chronic myeloid leukemia, acute lymphoblastic leukemia, chronic lymphocytic leukemia, myeloproliferative diseases, myelodysplastic syndrome, Hodgkin's disease, non-Hodgkin's lymphoma, advanced melanoma, malignant melanoma, basal cell carcinoma, moles dysplastic nevi, angioma, dermatofibroma, keloids, psoriasis, neuroblastoma, metastatic breast cancer, colon cancer, oral cancer, hairy cell leukemia, head and neck cancer, refractory metastatic disease; Kaposi's sarcoma, Bannayan-Zonana syndrome, Cowden disease, Lhermitte-Duclos disease.

The compounds and methods of this disclosure can be also used to treat diseases and conditions such as rheumatoid arthritis, osteoarthritis, Crohn's disease, angiofibroma, retinal vascularization, diabetic retinopathy, age-related macular degeneration, macular degeneration, multiple sclerosis, obesity, Alzheimer's disease, restenosis, autoimmune diseases, allergy, asthma, endometriosis, atherosclerosis, vein graft stenosis, peri-anastomatic prosthetic graft stenosis, prostate hyperplasia, chronic obstructive pulmonary disease, psoriasis, inhibition of neurological damage due to tissue repair, scar tissue formation, multiple sclerosis, inflammatory bowel disease, infections, particularly bacterial, viral, retroviral or parasitic infections, pulmonary disease, neoplasm, Parkinson's disease, transplant rejection, and septic shock.

The AKT-mediated disease can be a relapsed disease. The AKT-mediated disease can have been refractory to one or more previous treatments by different therapies.

In any of the above-described methods, the bivalent compounds can be XF038-157A, XF038-158A, XF038-159A, XF038-160A, XF038-161A, XF038-162A, XF038-164A, XF038-165A, XF038-166A, XF038-176A, XF038-177A, XF042-162, XF042-164, XF042-165, XF042-166, XF042-167, XF042-168, XF042-170, XF042-171, XF048-1, XF048-2, XF048-3, XF048-4, XF048-5, XF048-7, XF048-8, XF050-5, XF050-6, XF050-7, XF050-8, XF050-9, XF050-10, XF050-11, XF050-12, XF050-13, XF050-14, XF050-15, XF050-16, XF050-17, XF050-18, XF050-19, XF050-20, XF050-21, XF050-22, XF050-23, XF050-24, XF050-25, XF050-26, XF050-27, XF050-28, XF050-29, XF050-30, XF050-31, XF050-32, XF050-33, XF050-98, XF050-132, XF050-133. XF050-134, XF056-93, XF050-143, XF050-144, XF050-145, XF050-167, XF056-33, XF056-34, XF056-35, XF056-36, XF056-37, XF056-73, XF061-10, XF067-1, XF067-2, XF067-3, XF067-4, XF067-5, XF067-6, XF067-7, XF067-8, XF067-9, XF067-10, XF067-11, XF067-12, XF067-13, XF067-14, XF067-15, XF067-16, XF067-17, XF067-18, XF067-19, XF067-20, XF067-21, XF067-22, XF067-23, XF067-24, XF067-25, XF067-26, XF067-27, XF067-28, XF067-29, XF067-30, XF067-31, XF067-32, XF067-33, XF067-34, XF067-35, XF067-36, XF067-37, XF067-38, XF067-39, XF067-40, XF067-41, XF067-42, XF067-43, XF067-44, XF067-45, XF067-46, XF067-47, XF067-48, XF067-49, XF067-50, XF067-51, XF067-52, XF067-53, XF067-54, XF067-55, XF067-56, XF067-57, XF067-58, XF067-59, XF067-84, XF067-85, XF067-86, XF067-87, XF067-88, XF067-89, XF067-90, XF067-91, XF067-92, XF067-93, XF067-94, XF067-95, XF067-96, XF067-97, XF067-98, XF067-99, XF067-100, XF067-101, XF067-102, XF067-103, XF067-104, XF067-105, XF067-106, XF067-107, XF067-108, XF067-109, XF067-110, XF067-111, XF067-112, XF067-113, or analogs thereof.

In some aspects of the methods described herein, the bivalent compounds can be administered, e.g., orally, parenterally, intradermally, subcutaneously, topically, and/or rectally.

Any of the above-described methods can further include treating a subject with one or more additional therapeutic regimens for treating cancer. The one or more additional therapeutic regimens for treating cancer can be, e.g., one or more of surgery, chemotherapy, radiation therapy, hormone therapy, or immunotherapy.

This disclosure additionally provides a method for identifying a bivalent compound which mediates degradation/disruption of AKT, the method including providing a heterobifunctional test compound including a AKT ligand conjugated to a degradation/disruption tag via a linker, contacting the heterobifunctional test compound with a cell (e.g., a cancer cell such as a AKT-mediated cancer cell) including a ubiquitin ligase and AKT.

As used herein, the terms "about" and "approximately" are defined as being within plus or minus 10% of a given value or state, preferably within plus or minus 5% of said value or state. The terms "bivalent" and "bi-functional" are used interchangeably herein. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DEFINITION OF TERMS

Figure 1A:
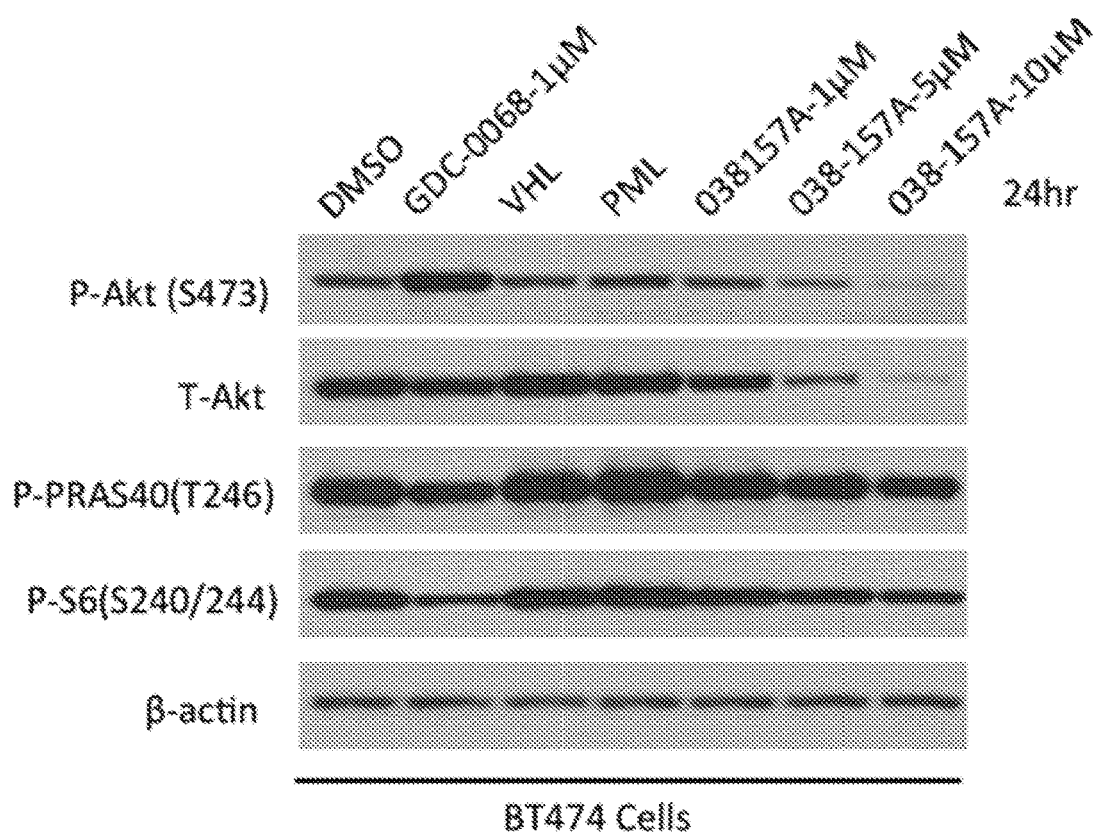
FIGS. 1A-C are a series of Western blots showing the effect of various AKT degraders on reducing AKT, p-AKT, P-PRAS40 (T246), and P-S6 (S240/244) protein levels at various concentrations in BT474 cells. (Note: "XF" portion of the degrader compound code was omitted).

As used herein, the terms "comprising" and "including" are used in their open, non-limiting sense.

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a —CH$_2$CH=CH$_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+2) π-electron system in accordance with the Hickel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a —C$_6$H$_5$ group.

The term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hickel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent O atoms or two adjacent S atoms. A heterocyclyl group may include fused, bridged or spirocyclic ring systems. In certain embodiments, a heterocyclyl group comprises 3 to 8 ring atoms ($C_3$-$C_8$ heterocyclyl; or 3-8 membered heterocyclyl). In certain embodiments, a heterocyclyl group comprises 3 to 10 ring atoms ($C_3$-$C_{10}$ heterocyclyl; or 3-10 membered heterocyclyl). In certain embodiments, a heterocyclyl group comprises 4 to 8 ring atoms ($C_4$-$C_8$ heterocyclyl; or 4-8 membered heterocyclyl). In certain embodiments, a heterocyclyl group comprises 4 to 10 ring atoms ($C_4$-$C_{10}$ heterocyclyl; or 4-10 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" or "carbocyclyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 6 carbon ring atoms ($C_3$-$C_6$ cycloalkyl; 3-6 membered cycloalkyl; or 3-6 membered carbocyclyl). In certain embodiments, a cycloalkyl comprises 3 to 8 carbon ring atoms ($C_3$-$C_8$ cycloalkyl; 3-8 membered cycloalkyl; or 3-8 membered carbocyclyl). In certain embodiments, a cycloalkyl comprises 3 to 10 carbon ring atoms ($C_3$-$C_{10}$ cycloalkyl; 3-10 membered cycloalkyl; or 3-10 membered carbocyclyl). Examples of such groups include, but are not limited to, cyclopropyl, cyclobutyl, cyclopentyl, cyclopentenyl, cyclohexyl, cycloheptyl, adamantyl, and the like.

The term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term "cyano" refers to a —C≡N group.

An "aldehyde" group refers to a —C(O)H group.

An "alkoxy" group refers to both an —O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refer to a —SO$_2$alkyl, as defined herein.

An "amino" group refers to an optionally substituted —NH$_2$.

An "aminoalkyl" group refers to an -alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)-aryloxy, as defined herein.

An "arylsulfonyl" group refers to a —SO$_2$aryl, as defined herein.

A "carbonyl" group refers to a —C(O)— group, as defined herein.

A "carboxylic acid" group refers to a —C(O)OH group.

A "cycloalkoxy" refers to a —O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —NO$_2$ group.

An "oxo" group refers to the =O substituent.

A "trihalomethyl" group refers to a methyl substituted with three halogen atoms.

The term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "null" or "bond" means the absence of an atom or moiety, and there is a bond between adjacent atoms in the structure.

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein, the same symbol in different FORMULAE refers to a different definition, for example, the definition of R1 in FORMULA 1 is as defined with respect to FORMULA 1 and the definition of R1 in FORMULA 6 is as defined with respect to FORMULA 6.

As used herein, when m (or n or o or p) is defined by a range, for example, "m is 0 to 15" or "m=0-3" mean that m is an integer from 0 to 15 (i.e. m is 0, 1, 2, 3, 4, 5, 6, 7, 8, 9, 10, 11, 12, 13, 14, or 15) or m is an integer from 0 to 3 (i.e. m is 0, 1, 2, or 3) or is any integer in the defined range.

"Pharmaceutically acceptable salt" includes both acid and base addition salts. A pharmaceutically acceptable salt of any one of the bivalent compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al.

DETAILED DESCRIPTION

The present disclosure is based in part, on the discovery that novel heterobifunctional small molecules which degrade AKT and/or AKT mutant proteins are useful in the treatment of AKT-mediated diseases, particularly developmental and over-growth syndromes, cardiovascular disease, diabetes, inflammatory and autoimmune disorders, neurological disorders, and cancer, including but not limited to colon cancer, ovarian cancer, brain cancer, lung cancer, pancreatic cancer, breast cancer, prostate cancer, and gastric carcinoma.

Successful strategies for selective degradation/disruption of the target protein induced by a bifunctional small molecule include recruiting an E3 ubiquitin ligase and mimicking protein misfolding with a hydrophobic tag (Buckley and Crews, 2014). The bifunctional molecules have three moieties: one E3-binder moiety that binds an E3 ubiquitin ligase; one targeted protein-binder moiety that binds the protein target of interest; and a linker moiety that connects the E3-binder and the targeted protein-binder moieties (Buckley and Crews, 2014). The induced proximity leads to selective ubiquitination of the target followed by its degradation at the proteasome. Several types of high affinity small-molecule E3 ligase ligands have been identified/developed: immunomodulatory drugs (IMiDs) such as thalidomide and pomalidomide, which bind cereblon (CRBN or CRL4CRBN), a component of a cullin-RING ubiquitin ligase (CRL) complex (Bondeson et al., 2015; Chamberlain et al., 2014; Fischer et al., 2014; Ito et al., 2010; Winter et al., 2015); and VHL-1, a hydroxyproline-containing ligand, which binds van Hippel-Lindau protein (VHL or CRL2VHL), a component of another CRL complex (Bondeson et al., 2015; Buckley et al., 2012a; Buckley et al., 2012b; Galdeano et al., 2014; Zengerle et al., 2015). This bifunctional molecule technology has been successfully applied to degradation of multiple targets (Bondeson et al., 2015; Buckley et al., 2015; Lai et al., 2016; Lu et al., 2015; Winter et al., 2015; Zengerle et al., 2015). Recently, peptidic VHL-recruiting bifunctional molecule has been reported (Henning et al., 2016). However, there are no reported small molecule-based bifunctional molecules that lead to the degradation of AKT or AKT mutant proteins. In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has been successfully applied to selective degradation of the pseudokinase Her3 (Xie et al., 2014), but not to degradation of AKT or AKT mutant proteins.

As discussed in the following examples, this disclosure provides specific examples of novel AKT degraders/disruptors, and examines the effect of exemplary degraders/disruptors on reducing AKT protein levels, inhibiting/disrupting AKT activity, and inhibiting cancer cell proliferation. The results indicate that these novel small molecules can be beneficial in treating human disease, especially developmental and over-growth syndromes, cardiovascular disease, diabetes, inflammatory and autoimmune disorders, neurological disorders, and cancer, including but not limited to colon cancer, ovarian cancer, brain cancer, lung cancer, pancreatic cancer, breast cancer, prostate cancer, and gastric carcinoma.

A number of selective small-molecule AKT catalytic inhibitors, such as GSK690693 (Heerding et al., 2008), GSK2110183 (Dumble et al., 2014), GSK2141795 (Dumble et al., 2014), AZD5363 (Addie et al., 2013), GDC00068 (Blake et al., 2012), MK-2206 (Hirai et al., 2010), and ARQ-092 (Yu et al., 2015) have been in clinical trials for treating ovarian cancer, fallopian tube cancer, peritoneal cancer, neuroendocrine tumor, acute myelogenous leukemia, lymphoma, gastric and gastroesophageal junction cancer, biliary cancer, non-small cell lung cancer, pancreatic cancer, nasopharyngeal carcinoma, adenoid cystic carcinoma, endometrial cancer, colorectal cancer, breast cancer, renal cell carcinoma, prostate, glioblastoma, gliosarcoma, chronic lymphocytic leukemia, melanoma (Pretre and Wicki, 2017). Despite effectiveness in preclinical animal models, the majority of these inhibitors lack efficacy in human patients (Manning and Toker, 2017).

Currently compounds targeting AKT generally focus on inhibition of its catalytic activity. In the present disclosure, a different approach is taken: to develop compounds that directly and selectively target not only the catalytic function of AKT, but also its protein level in cells. Strategies for inducing protein degradation include recruiting E3 ubiquitin ligases, mimicking protein misfolding with hydrophobic tags, and inhibiting chaperones. For example, a thalidomide-JQ1 bivalent compound has been used to hijack the cereblon E3 ligase, inducing highly selective BET protein degradation in vitro and in vivo and resulting in a demonstrated delay in leukemia progression in mice (Winter et al., 2015).

Similarly, BET protein degradation has also been induced via another E3 ligase, VHL (Zengerle et al., 2015). Partial degradation of Her3 has been induced using an adamantane-modified compound (Xie et al., 2014). Such an approach, based on the use of bivalent small molecule compounds, permits more flexible regulation of protein levels in vitro and in vivo compared with techniques such as gene knockout or knockdown via RNA interference. Unlike gene knockout or knockdown, this chemical approach further provides an opportunity to study dose and time dependency in a disease model through varying the concentrations and frequencies of administration of the relevant compound.

This disclosure includes all stereoisomers, geometric isomers, tautomers and isotopes of the structures depicted and compounds named herein. This disclosure also includes compounds described herein, regardless of how they are prepared, e.g., synthetically, through biological process (e.g., metabolism or enzyme conversion), or a combination thereof.

This disclosure includes pharmaceutically acceptable salts of the structures depicted and compounds named herein.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms. In some embodiments, the compound includes at least one fluorine atom. In some embodiments, the compound includes two or more fluorine atoms. In some embodiments, the compound includes 1-2, 1-3, 1-4, 1-5, or 1-6 fluorine atoms. In some embodiments, all of the hydrogen atoms in a compound can be replaced or substituted by fluorine atoms.

Degraders

In some aspects, the present disclosure provides bivalent compounds, also referred to herein as degraders, comprising an AKT ligand (or targeting moiety) conjugated to a degradation tag. Linkage of the AKT ligand to the degradation tag can be direct, or indirect via a linker.

As used herein, the terms "serine threonine kinase (AKT) ligand" or "AKT ligand" or "AKT targeting moiety" are to be construed broadly, and encompass a wide variety of molecules ranging from small molecules to large proteins that associate with or bind to AKT. The AKT ligand or targeting moiety can be, for example, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

The AKT ligand or targeting moiety can be an AKT inhibitor (e.g., GSK690693 (Heerding et al., 2008), GSK2110183 (Dumble et al., 2014), GSK2141795 (Dumble et al., 2014), AZD5363 (Addie et al., 2013), GDC0068 (Blake et al., 2012), MK-2206 (Hirai et al., 2010), and ARQ-092 (Yu et al., 2015), and analogs thereof), which is capable of interfering with the enzymatic activity of AKT. As used herein, an "inhibitor" refers to an agent that restrains, retards, or otherwise causes inhibition of a physiological, chemical or enzymatic action or function and causes a decrease in enzyme activity of at least 5%. An inhibitor can also or alternately refer to a drug, compound, or agent that prevents or reduces the expression, transcription, or translation of a gene or protein. An inhibitor can reduce or prevent the function of a protein, e.g., by binding to or activating/inactivating another protein or receptor.

Exemplary AKT ligands include, but are not limited to, the compounds listed below:

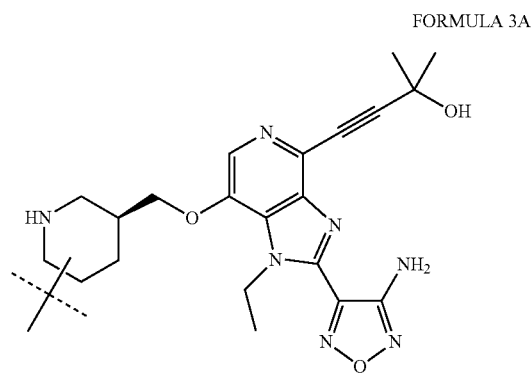

FORMULA 3A

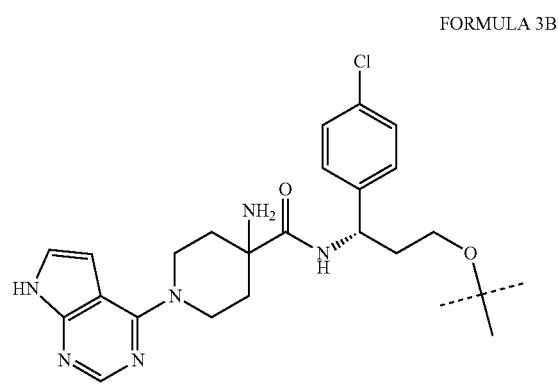

FORMULA 3B

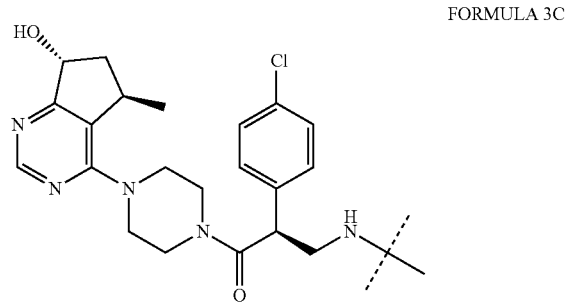

FORMULA 3C

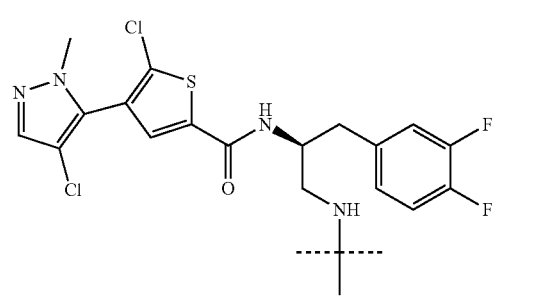

FORMULA 3D

FORMULA 3E
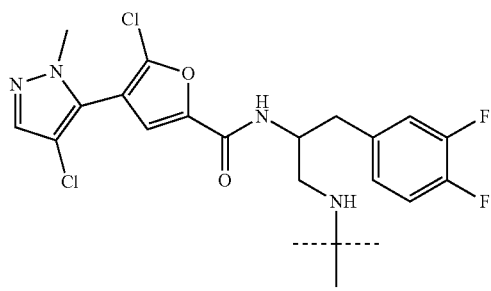
FORMULA 3I
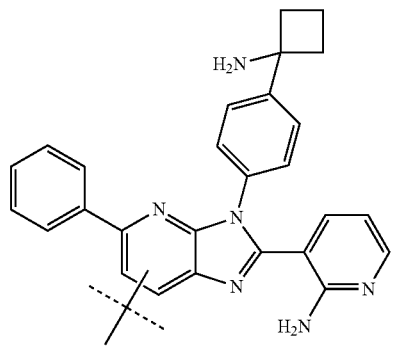
FORMULA 3F
FORMULA 3J
FORMULA 3G
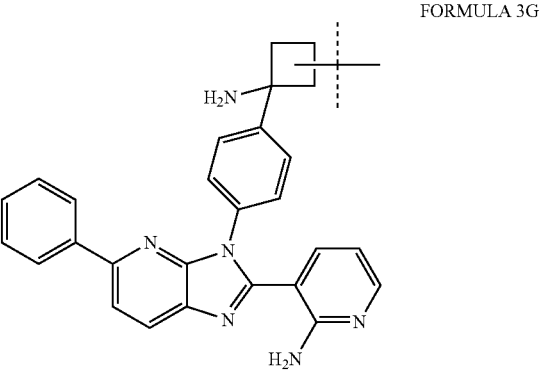
GSK690693
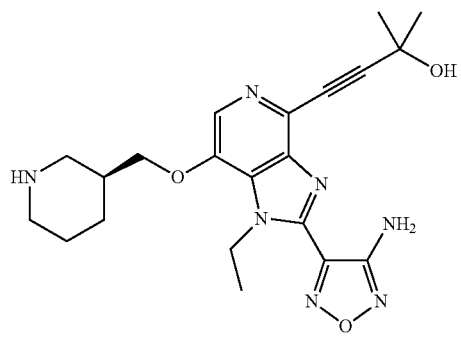
FORMULA 3H
AZD5363
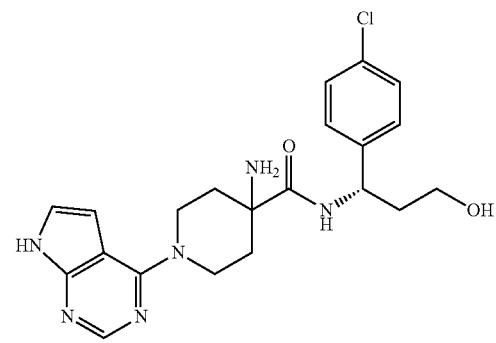

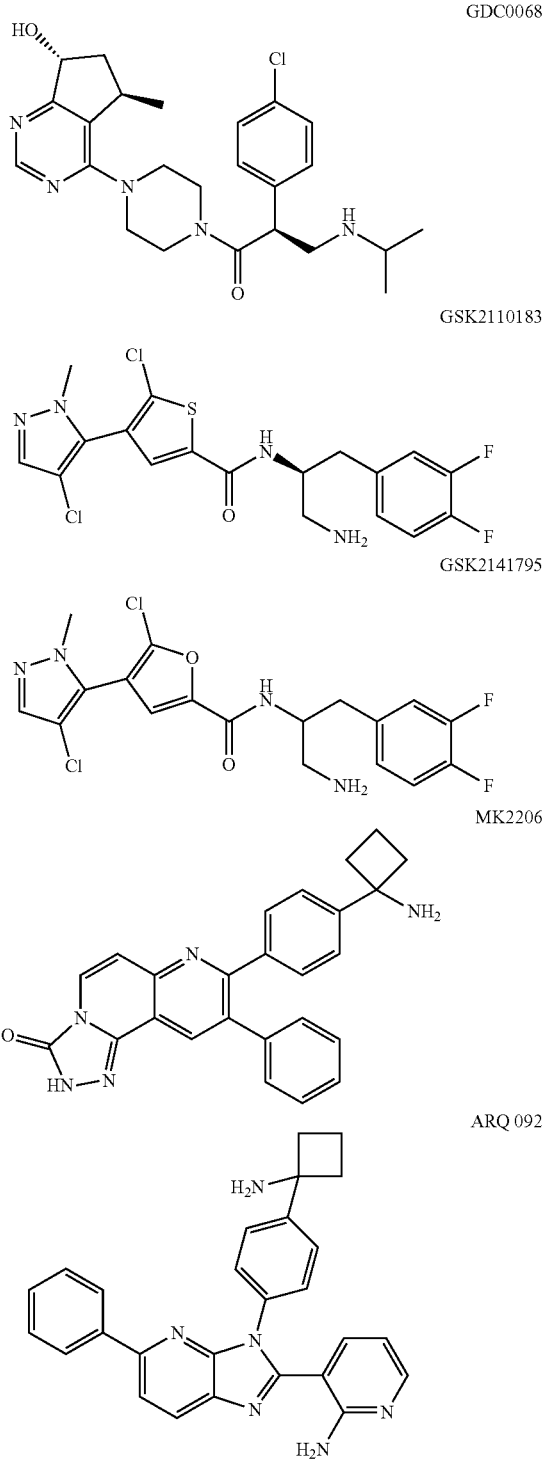

As used herein, the term "degradation/disruption tag" refers to a compound which associates with or binds to a ubiquitin ligase for recruitment of the corresponding ubiquitination machinery to AKT or induces AKT protein misfolding and subsequent degradation at the proteasome or loss of function.

In some aspects, the degradation/disruption tags of the present disclosure include, e.g., pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), and/or analogs thereof.

As used herein, a "linker" is a bond, molecule, or group of molecules that binds two separate entities to one another. Linkers provide for optimal spacing of the two entities. The term "linker" in some aspects refers to any agent or molecule that bridges the AKT ligand to the degradation/disruption tag. One of ordinary skill in the art recognizes that sites on the AKT ligand or the degradation/disruption tag, which are not necessary for the function of the bifunctional molecule of the present disclosure, are ideal sites for attaching a linker, provided that the linker, once attached to the conjugate of the present disclosures, does not interfere with the function of the bifunctional molecule, i.e., its ability to target AKT, and its ability to recruit a ubiquitin ligase.

The length of the linker of the bivalent compound can be adjusted to minimize the molecular weight of the disruptors/degraders and avoid the clash of the AKT ligand or targeting moiety with the ubiquitin ligase or induce AKT misfolding by the hydrophobic tag at the same time.

In some aspects, the degradation/disruption tags of the present disclosure include, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV (Varfolomeev et al., 2007), LCL161 (Weisberg et al., 2010), and analogs thereof. The degradation/disruption tags can be attached to each portion of interest in the structure of an AKT ligand or targeting moiety (e.g., GSK690693 (Heerding et al., 2008), GSK2110183 (Dumble et al., 2014), GSK2141795 (Dumble et al., 2014), AZD5363 (Addie et al., 2013), GDC00068 (Blake et al., 2012), MK-2206 (Hirai et al., 2010), and ARQ-092 (Yu et al., 2015)) with linkers of different types and lengths in order to generate effective bivalent compounds. In particular, attaching pomalidomide or VHL-1 to either portion of the molecule can recruit the cereblon E3 ligase to AKT.

The bivalent compounds disclosed herein can selectively affect AKT-mediated disease cells compared to WT (wild type) cells (i.e., an AKT degrader/disruptor able to kill or inhibit the growth of an AKT-mediated disease cell while also having a relatively low ability to lyse or inhibit the growth of a WT cell), e.g., possess a $GI_{50}$ for one or more AKT-mediated disease cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its $GI_{50}$ for one or more WT cells, e.g., WT cells of the same species and tissue type as the AKT-mediated disease cells.

Additional bivalent compounds (i.e., AKT degraders/disruptors) can be developed using the principles and methods disclosed herein. For example, other linkers, degradation/disruption tags, and AKT binding/inhibiting moieties (not limited to GSK690693 (Heerding et al., 2008), GSK2110183 (Dumble et al., 2014), GSK2141795 (Dumble et al., 2014), AZD5363 (Addie et al., 2013), GDC0068 (Blake et al., 2012), MK-2206 (Hirai et al., 2010), and ARQ-092 (Yu et al., 2015)) can be synthesized and tested.

In some aspects, the AKT degraders/disruptors have the form "PI-Linker-EL", as shown below:

wherein PI (a ligand for a "protein of interest," i.e., the protein to be degraded) comprises an AKT ligand (e.g., an AKT inhibitor), and EL (e.g., a ligand for an E3 ligase) comprises a degradation/disruption tag (e.g., E3 ligase ligand). Exemplary AKT ligands (PI), exemplary degradation/disruption tags (EL), and exemplary linkers (Linker) are illustrated below:

AKT Ligands

AKT Ligands (PI) include but are not limited to:

FORMULA 1

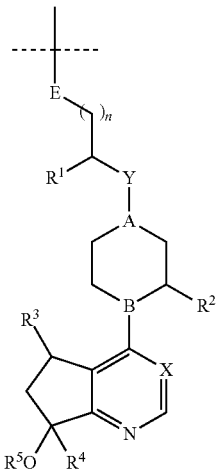

wherein

A, B, and X are independently N, CH, or $CR^6$,

Y is $CH_2$, CO, SO, $SO_2$, $CR^7R^8$, $CONR^7$, or $SO_2NR^7$,

E is NH, $NR^9$, O, $C_1$-$C_8$ alkyl, $C_1$-$C_8$ alkoxy, $C_1$-$C_8$ alkoxyalkyl, $C_1$-$C_8$ haloalkyl, $C_1$-$C_8$ hydroxyalkyl, $C_3$-$C_8$ cycloalkyl, $C_3$-$C_7$ heterocyclyl, $C_2$-$C_8$ alkenyl, $C_2$-$C_8$ alkynyl, $OR^9$, $SR^9$, $NR^9R^{10}$, CN, $NO_2$, $(CR^9R^{10})mNR^{11}R^{12}$, $(CR^9R^{10})mC(O)R^{11}$, $(NR^9R^{10})mNR^{11}R^{12}$, $(NR^9R^{10})mC(O)R^{11}$, $COR^9$, $CO_2R^9$, $CONR^9R^{10}$, $NR^9COR^{10}$, $NR^9SOR^{10}$, $NR^9SO_2R^{10}$, $SOR^9$, $SO_2R^9$, $SO_2NR^9R^{10}$, $(CR^9R^{10})$m-aryl, or $(CR^9R^{10})$m-heteroaryl, $R^1$ is H, $C_1$-$C_8$ alkyl, $C_3$-$C_8$ cycloalkyl, $C_1$-$C_8$ alkoxy, $C_1$-$C_8$ alkoxyalkyl, aryl, $C_1$-$C_8$ alkylaryl, haloaryl, arylalkyl, heteroaryl, or heteroarylalkyl, $R^2$, $R^3$, $R^4$, and $R^6$ are independently hydrogen, halogen, amino, $C_1$-$C_8$ alkylamino, arylamino, $C_1$-$C_8$ alkyl, $C_3$-$C_8$ cycloalkyl, $C_1$-$C_8$ alkoxy, or $C_1$-$C_8$ alkoxyalkyl, $R^5$, $R^7$, and $R^8$ are independently H, $C_1$-$C_8$ alkyl, $C_3$-$C_8$ cycloalkyl, or $C_1$-$C_8$ alkoxyalkyl, $R^9$, $R^{10}$, $R^{11}$, and $R^{12}$ are independently H, $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, arylalkyl, cycloalkyl, heterocycloalkyl, aryl, heteroaryl, or heteroarylalkyl, $R^9$ and $R^{10}$, $R^{11}$ and $R^{12}$ can independently form 4-8 membered alkyl or heterocyclyl rings, m=0-8, and n=0-8; and

FORMULA 2

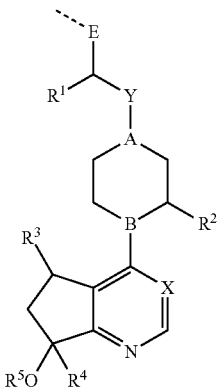

wherein

A, B and X are independently selected from N and $CR^6$, wherein $R^6$ is independently selected from hydrogen, halogen, cyano, nitro, hydroxyl, amino, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted amino, optionally substituted $C_1$-$C_8$ alkylamino, optionally substituted $C_1$-$C_8$ alkylamino$C_1$-$C_8$ alkyl, optionally substituted 3-10 membered carbocyclyl, and optionally substituted 4-10 membered heterocyclyl;

Y is selected from $CR^7R^8$, CO, SO, $SO_2$, $CONR^7$, and $SO_2NR^7$, wherein $R^7$ and $R^8$ is independently selected from hydrogen, halogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl; optionally substituted $C_1$-$C_8$ alkylamino, optionally substituted $C_1$-$C_8$ alkylamino $C_1$-$C_8$ alkyl, optionally substituted 3 to 10 membered carbocyclyl, and optionally substituted 4-10 membered heterocyclyl, or $R^7$ and R' together with the atom to which they are connected form an optionally substituted 3-10 membered carbocyclyl or an optionally substituted 4-10 membered heterocyclyl ring;

E is connected to the "linker" moiety of the bivalent compound, and is selected from null, R'—R" R'OR", R'SR", $R'NR^9R"$, R'OC(O)R", R'OC(O)OR", $R'OCONR^9R"$, R'C(O)R", R'C(O)OR", $R'CONR^9R"$, R'S(O)R", $R'S(O)_2R"$, $R'SO_2NR^9R"$, $R'NR^{10}C(O)OR"$, $R'NR^{10}C(O)R"$, $R'NR^{10}C(O)NR^9R"$, $R'NR^{10}S(O)R"$, $R'NR^{10}S(O)_2R"$, and $R'NR^{10}S(O)_2NR^9R"$, wherein R' and R" are independently selected from null, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ haloalkylene, optionally substituted $C_1$-$C_8$ hydroxyalkylene, optionally substituted C₁-C₈alkoxyC₁-C₈alkylene, optionally substituted C₁-C₈alkylaminoC₁-C₈alkylene, optionally substituted (C₁-C₈ alkylene)O(C₁-C₈ alkylene), optionally substituted (C₁-C₈ alkylene)N(C₁-C₈ alkylene), optionally substituted 3-10 membered carbocyclyl, optionally substituted 4-10 membered heterocyclyl, optionally substituted C₃-C₁₃ fused carbocyclyl, optionally substituted C₃-C₁₃ fused heterocyclyl, optionally substituted C₃-C₁₃ bridged carbocyclyl, optionally substituted C₃-C₁₃ bridged heterocyclyl, optionally substituted C₃-C₁₃ spiro carbocyclyl, optionally substituted C₃-C₁₃ spiro heterocyclyl, optionally substituted aryl, and optionally substituted heteroaryl;

$R^9$ and $R^1$ are independently selected from hydrogen, optionally substituted C₁-C₈ alkyl, optionally substituted C₂-C₈ alkenyl, optionally substituted C₂-C₈ alkynyl, optionally substituted C₁-C₈alkoxyC₁-C₈alkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R", $R^9$ and $R^{10}$, R' and $R^9$, R' and $R^{10}$, R" and $R^9$, R" and $R^{10}$ together with the atom to which they are connected form a 4-20 membered heterocyclyl ring;

$R^1$ is selected from hydrogen, halogen, and optionally substituted C₁-C₈ alkyl, optionally substituted C₂-C₈ alkenyl, optionally substituted C₂-C₈ alkynyl, optionally substituted C₁-C₈ alkoxy, optionally substituted C₁-C₈ alkoxy C₁-C₈ alkyl, optionally substituted C₁-C₈ alkylamino, optionally substituted C₁-C₈ alkylamino C₁-C₈ alkyl, optionally substituted 3-10 membered carbocyclyl, optionally substituted 4-10 membered heterocyclyl, optionally substituted aryl, and optionally substituted heteroaryl;

$R^2$, $R^3$ and $R^4$ are independently selected from hydrogen, halogen, cyano, nitro, hydroxyl, optionally substituted C₁-C₈ alkyl, optionally substituted C₂-C₈ alkenyl, optionally substituted C₂-C₈ alkynyl, optionally substituted C₁-C₈ alkoxy, optionally substituted aryloxy, optionally substituted C₁-C₈ alkoxyC₁-C₈ alkyl, optionally substituted amino, optionally substituted C₁-C₈ alkylamino, optionally substituted C₁-C₈ alkylaminoC₁-C₈ alkyl, optionally substituted arylamino, optionally substituted 3-10 membered carbocyclyl, and optionally substituted 4-10 membered heterocyclyl;

$R^5$ is selected from hydrogen, optionally substituted C₁-C₈ alkyl, optionally substituted C₂-C₈ alkenyl, optionally substituted C₂-C₈ alkynyl, optionally substituted C₁-C₈ alkoxyC₁-C₈ alkyl, optionally substituted C₁-C₈ alkylaminoC₁-C₈ alkyl, optionally substituted 3-10 membered carbocyclyl, and optionally substituted 4-10 membered heterocyclyl; and In one embodiment, A is selected from N, CH and CNH₂.
In another embodiment, A is N.
In one embodiment, B and X are independently selected from N and CH.
In another embodiment, B is N.
In another embodiment, X is N.
In another embodiment, Y is selected from CH₂, CO, CONH and NHCO.
In another embodiment, Y is CO.
In another embodiment, E is selected from null, O, N, optionally substituted C₁-C₈ alkylene, optionally substituted (C₁-C₈ alkylene)O, optionally substituted (C₁-C₈ alkylene)N, optionally substituted 3-10 membered carbocyclylene, optionally substituted (3-10 membered carbocyclylene)O, optionally substituted (3-10 membered carbocyclylene)N, optionally substituted 4-10 membered heterocyclylene, optionally substituted (4-10 membered heterocyclylene)O, optionally substituted (4-10 membered heterocyclylene)N, optionally substituted aryl, and optionally substituted heteroaryl.

In another embodiment, $R^1$ is selected from optionally substituted aryl and optionally substituted heteroaryl.

In another embodiment, $R^1$ is selected from optionally substituted phenyl.

In another embodiment, $R^1$ is 4-chlorophenyl.

In another embodiment, $R^2$, $R^3$, $R^4$ and $R^5$ are independently selected from H, F, Cl, CN, NO₂, CH₃, CF₃, iPr, and cPr.

In another embodiment, $R^2$, $R^4$ and $R^5$ are H.

In another embodiment, $R^3$ is CH₃.

FORMULA 3

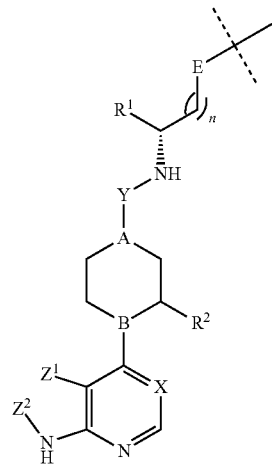

wherein
A, B, and X are independently N or $CR^3$,
Y is CH₂, CO, SO, SO₂, $CR^4R^5$, $CONR^4$, or $SO_2NR^4$,
E is NH, $NR^6$, O, C₁-C₈ alkyl, C₁-C₈ alkoxy, C₁-C₈ alkoxyalkyl, C₁-C₈ haloalkyl, C₁-C₈ hydroxyalkyl, C₃-C₈ cycloalkyl, C₃-C₈ heterocyclyl, C₂-C₈ alkenyl, C₂-C₈ alkynyl, $OR^6$, $SR^6$, $NR^6R^7$, CN, NO₂, $(CR^6R^7)mNR^8R^9$, $(CR^6R^7)mC(O)R^8$, $(NR^6R^7)mNR^8R^9$, $(NR^6R^7)mC(O)R^8$, $COR^6$, $CO_2R^6$, $CONR^6R^7$, $NR^6COR^7$, $NR^6SOR^7$, $NR^6SO_2R^7$, $SOR^6$, $SO_2R^6$, $SO_2NR^6R^7$, $(CR^6R^7)$m-aryl, or $(CR^6R^7)$m-heteroaryl,
$Z^1$—$Z^2$ is $CR^{10}$=CH, N+CH, or $CR^{10}$=N,
$R^1$ is hydrogen, C₁-C₈ alkyl, C₃-C₈ cycloalkyl, C₁-C₈ alkoxy, C₁-C₈ alkoxyalkyl, aryl, C₁-C₈ alkylaryl, haloaryl, arylalkyl, heteroaryl, or heteroarylalkyl,
$R^2$, $R^3$, and $R^4$ are independently hydrogen, halogen, amino, C₁-C₈ alkylamino, arylamino, C₁-C₈ alkyl, C₃-C₈ cycloalkyl, C₁-C₈ alkoxy, or C₁-C₈ alkoxyalkyl,
$R^6$, $R^7$, $R^8$, and $R^9$ are independently H, C₁-C₈ alkyl, C₃-C₈ cycloalkyl, C₁-C₈ alkoxy, C₂-C₈ alkenyl, C₂-C₈ alkynyl, arylalkyl, cycloalkyl, heterocycloalkyl, aryl, heteroaryl, or heteroarylalkyl,
$R^6$ and $R^7$, $R^8$ and $R^9$ can independently form 4-8 membered alkyl or heterocyclyl rings,
$R^{10}$ is hydrogen, halogen, C₁-C₈ alkyl, C₃-C₈ cycloalkyl, C₁-C₈ alkoxy, C₁-C₈ alkoxyalkyl, and
n=0-8.

FORMULA 4

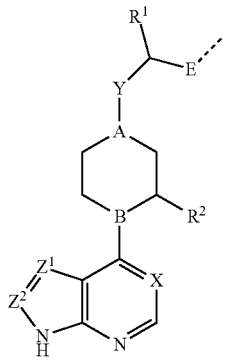

wherein
A, B and X are independently selected from N and $CR^3$, wherein
$R^3$ is independently selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino $C_1$-$C_8$ alkyl, optionally substituted 3-10 membered carbocyclyl, and optionally substituted 4-10 membered heterocyclyl;
$Z^1$ is selected for $CR^8$ and N, wherein
$R^8$ is selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3-10 membered carbocyclyl, and optionally substituted 4-10 membered heterocyclyl;
$Z^2$ is selected for CH and N;
Y is selected from CO, SO, $SO_2$, $CR^4R^5$, $CONR^4$, and $SO_2NR^4$, wherein
$R^4$ and $R^5$ is independently selected from hydrogen and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3 to 10 membered carbocyclyl, and optionally substituted 4-10 membered heterocyclyl;
E is connected to the "linker" moiety of the bivalent compound, and is selected from null, R'—R", R'OR", R'SR", $R'NR^6R"$, R'OC(O)R", R'OC(O)OR", $R'OCONR^6R"$, R'C(O)R", R'C(O)OR", $R'CONR^6R"$, R'S(O)R", $R'S(O)_2R"$, $R'SO_2NR^6R"$, $R'NR^7C(O)OR"$, $R'NR^7C(O)R"$, $R'NR^7C(O)NR^6R"$, $R'NR^7S(O)R"$, $R'NR^7S(O)_2R"$, and $R'NR^7S(O)_2NR^6R"$, wherein
R' and R" are independently selected form null, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ haloalkylene, optionally substituted $C_1$-$C_8$ hydroxyalkylene, optionally substituted $C_1$-$C_8$alkoxy$C_1$-$C_8$alkylene, optionally substituted ($C_1$-$C_8$ alkylene)O($C_1$-$C_8$ alkylene), optionally substituted ($C_1$-$C_8$ alkylene)N($C_1$-$C_8$ alkylene), optionally substituted 3-10 membered carbocyclyl, optionally substituted 4-10 membered heterocyclyl, optionally substituted $C_3$-$C_{13}$ fused carbocyclyl, optionally substituted $C_3$-$C_{13}$ fused heterocyclyl, optionally substituted $C_3$-$C_{13}$ bridged carbocyclyl, optionally substituted $C_3$-$C_{13}$ bridged heterocyclyl, optionally substituted $C_3$-$C_{13}$ spiro carbocyclyl, optionally substituted $C_3$-$C_{13}$ spiro heterocyclyl, optionally substituted aryl, and optionally substituted heteroaryl;
$R^6$ and $R^7$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl, or
R' and R", $R^6$ and $R^7$, R' and $R^6$, R' and $R^7$, R" and $R^6$, R" and $R^7$ together with the atom to which they are connected form a 4-20 membered heterocyclyl ring;
$R^1$ is selected from selected from hydrogen, halogen, and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3-10 membered carbocyclyl, optionally substituted 4-10 membered heterocyclyl, optionally substituted aryl, and optionally substituted heteroaryl; and
$R^2$ is selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, or optionally substituted $C_1$-$C_8$ alkoxy $C_1$-$C_8$ alkyl, optionally substituted amino, optionally substituted $C_1$-$C_8$ alkylamino$C_1$-$C_8$ alkyl, optionally substituted 3-10 membered carbocyclyl, and optionally substituted 4-10 membered heterocyclyl;
In one embodiment, A is selected from N, CH and $CNH_2$.
In another embodiment, A is $CNH_2$.
In one embodiment, B and X are independently selected from N and CH.
In another embodiment, B is N.
In another embodiment, X is N.
In another embodiment, $Z^1$ is selected from CH and $CCH_3$.
In another embodiment, $Z^1$ is CH.
In another embodiment, $Z^2$ is CH.
In another embodiment, Y is selected from $CH_2$, CO, CONH and NHCO.
In another embodiment, Y is CONH.
In another embodiment, E is selected from null, O, N, optionally substituted $C_1$-$C_8$ alkylene, optionally substituted ($C_1$-$C_8$ alkylene)O, optionally substituted ($C_1$-$C_8$ alkylene)N, optionally substituted 3-10 membered carbocyclylene, optionally substituted (3-10 membered carbocyclylene)O, optionally substituted (3-10 membered carbocyclylene)N, optionally substituted 4-10 membered heterocyclylene, optionally substituted (4-10 membered heterocyclylene)O, optionally substituted (4-10 membered heterocyclylene)N, optionally substituted aryl, and optionally substituted heteroaryl.

In another embodiment, $R^1$ is selected from optionally substituted aryl and optionally substituted heteroaryl.

In another embodiment, $R^1$ is selected from optionally substituted phenyl.

In another embodiment, $R^1$ is 4-chlorophenyl.

In another embodiment, $R^2$ is selected from H, F, Cl, CN, $NO_2$, $CH_3$, $CF_3$, iPr, and cPr, In another embodiment, $R^2$ is H.

The AKT ligand can be an AKT inhibitor, such as, for example, GSK690693 (Heerding et al., 2008), GSK2110183 (Dumble et al., 2014), GSK2141795 (Dumble et al., 2014), AZD5363 (Addie et al., 2013), GDC0068 (Blake et al., 2012), MK-2206 (Hirai et al., 2010), and ARQ-092 (Yu et al., 2015), and/or analogs thereof.

In some aspects, the AKT ligand can be, e.g.:

FORMULA 3A

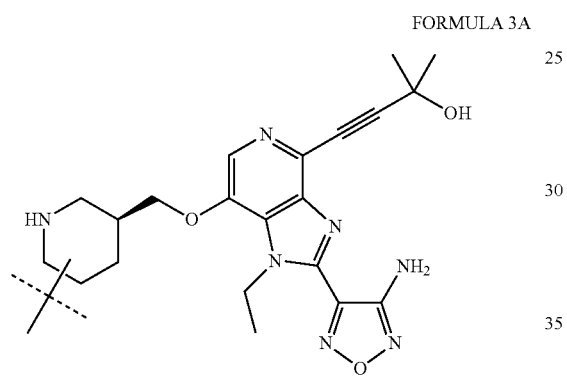

FORMULA 3B

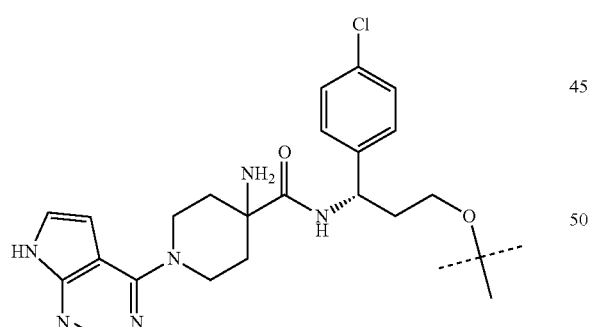

FORMULA 3C

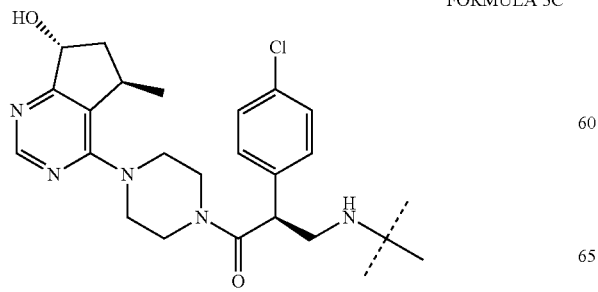

FORMULA 3D

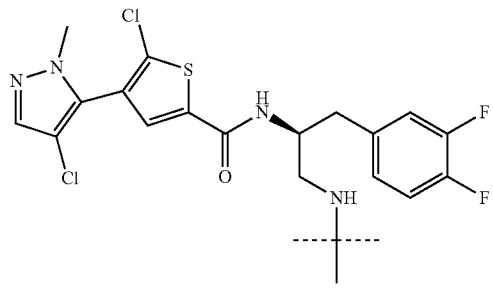

FORMULA 3E

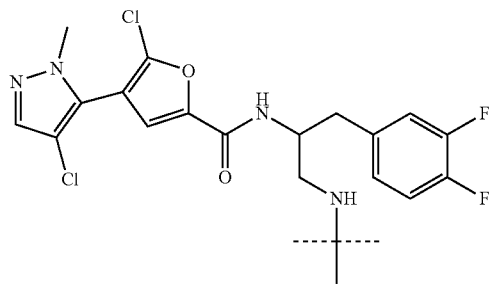

FORMULA 3F

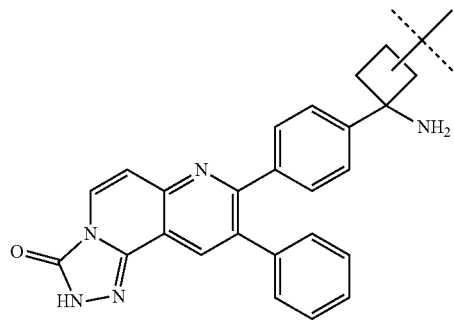

FORMULA 3G

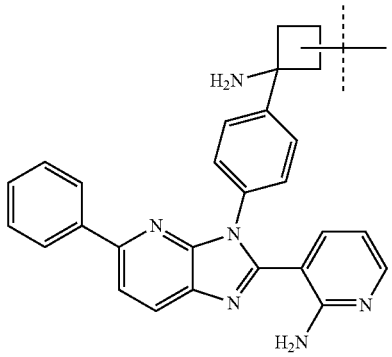

FORMULA 3H
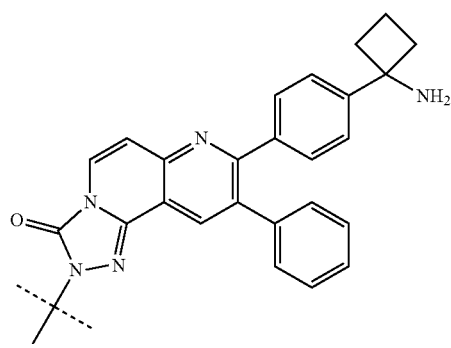
FORMULA 3I
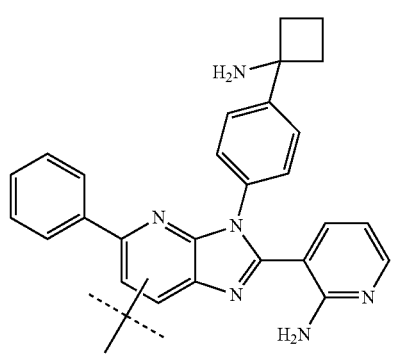
FORMULA 3J
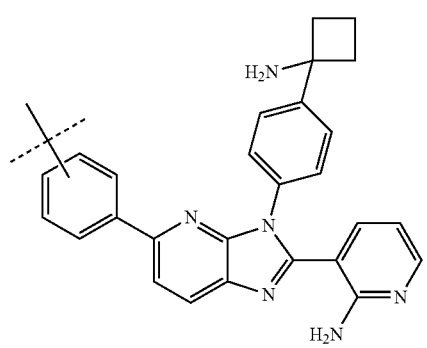
GSK690693
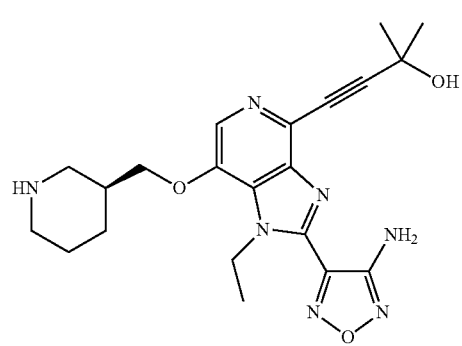
AZD5363
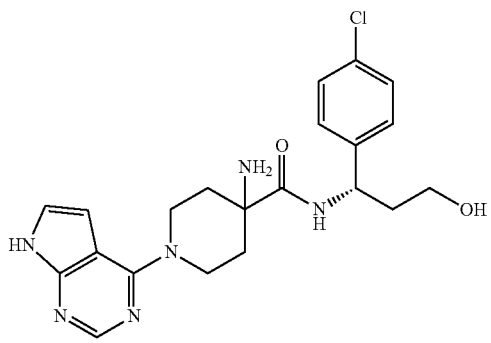
GDC0068
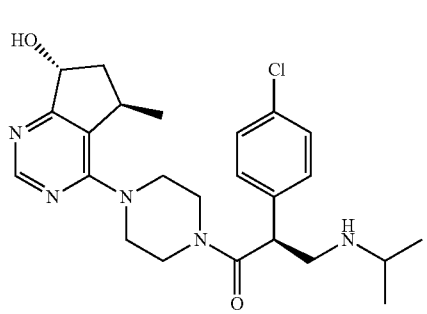
GSK2110183
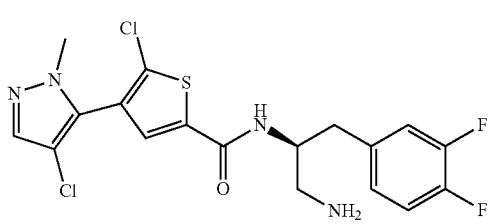
GSK2141795
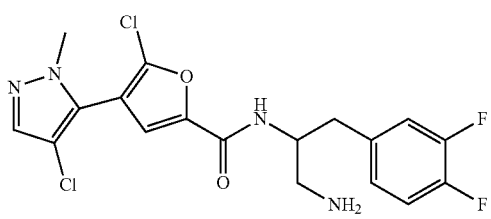
MK2206
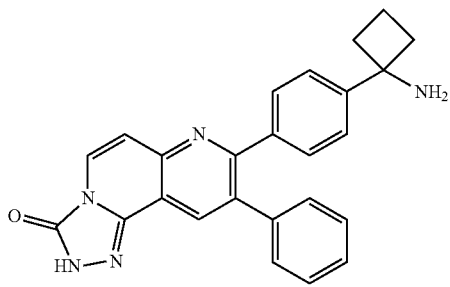

-continued

ARQ 092

The AKT ligand can be bound to AKT and/or AKT mutant proteins, such as, e.g., AKT with an E17K mutation.

Degradation/Disruption Tags

Degradation/Disruption Tags (EL) include but are not limited to:

FORMULA 5A

FORMULA 5B

FORMULA 5C

FORMULA 5D wherein
V, W, and X are independently $CR^2$ or N,
Y is CO or $CH_2$,
Z is $CH_2$, NH, or O,
$R^1$ is hydrogen, methyl, or fluoro, and
$R^2$ is hydrogen, halogen, or $C_1$-$C_5$ alkyl;
wherein
V, W, and X are independently selected from $CR^2$ and N;
Y is selected from CO, $CH_2$, and N=N;
Z is selected from $CH_2$, NH and O; and
$R^1$ and $R^2$ are independently selected from hydrogen, halogen, cyano, nitro, and $C_1$-$C_5$ alkyl.

FORMULA 6 wherein
$R^1$ and $R^2$ are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl;

FORMULA 7 wherein
$R^1$ and $R^2$ are independently selected from hydrogen, hydroxyl, amino, cyano, nitro, optionally substituted $C_1$-$C_8$ alkyl, optionally substituted $C_2$-$C_8$ alkenyl, and optionally substituted $C_2$-$C_8$ alkynyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted 3-10 membered carbocyclyl, and optionally substituted 4-10 membered heterocyclyl.
$R^3$ is selected from hydrogen, optionally substituted C(O) $C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)(3-10 membered carbocyclyl), optionally substituted C(O)(4-10 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O) O$C_1$-$C_8$alkylamino$C_1$-$C_8$alkyl, optionally substituted C(O) O(3-10 membered carbocyclyl), optionally substituted C(O) O(4-10 membered heterocyclyl), optionally substituted C(O)OC$_2$-C$_8$ alkenyl, optionally substituted C(O)OC$_2$-C$_8$ alkynyl, optionally substituted C(O)NC$_1$-C$_8$alkoxyC$_1$-C$_8$alkyl, optionally substituted C(O)NC$_1$-C$_8$ haloalkyl, optionally substituted C(O)NC$_1$-C$_8$ hydroxyalkyl, optionally substituted C(O)NC$_1$-C$_8$ aminoalkyl, optionally substituted C(O)NC$_1$-C$_8$alkylaminoC$_1$-C$_8$alkyl, optionally substituted C(O)N(3-10 membered carbocyclyl), optionally substituted C(O)N(4-10 membered heterocyclyl), optionally substituted C(O)NC$_2$-C$_8$ alkenyl, optionally substituted C(O)NC$_2$-C$_8$ alkynyl, optionally substituted P(O)(OH)$_2$, optionally substituted P(O)(OC$_1$-C$_8$ alkyl)$_2$, and optionally substituted P(O)(OC$_1$-C$_8$ aryl)$_2$.

and

FORMULA 8 wherein

R$^1$, R$^2$, R$^3$, and R$^4$ are independently hydrogen, C$_1$-C$_8$ alkyl, C$_1$-C$_8$ alkoxyalkyl, C$_1$-C$_8$ haloalkyl, C$_1$-C$_8$ hydroxyalkyl, C$_3$-C$_7$ cycloalkyl, C$_3$-C$_7$ heterocyclyl, C$_2$-C$_8$ alkenyl, or C$_2$-C$_8$ alkynyl, and V, W, X, and Z are independently CR$^4$ or N.

wherein

V, W, X, and Z are independently selected from CR$^4$ and N; and

R$^1$, R$^2$, R$^3$, and R$^4$ are independently selected from hydrogen, halogen, cyano, nitro, optionally substituted C$_1$-C$_8$ alkyl, optionally substituted C$_2$-C$_8$ alkenyl, and optionally substituted C$_2$-C$_8$ alkynyl; optionally substituted C$_1$-C$_8$alkoxyC$_1$-C$_8$alkyl, optionally substituted C$_1$-C$_8$ haloalkyl, optionally substituted C$_1$-C$_8$ hydroxyalkyl, optionally substituted C$_1$-C$_8$alkoxy, optionally substituted C$_1$-C$_8$alkylamino, optionally substituted 3-10 membered carbocyclyl, and optionally substituted 4-10 membered heterocyclyl.

In some aspects, the degradation/disruption tag can be, for example, pomalidomide (Fischer et al., 2014), thalidomide (Fischer et al., 2014), lenalidomide (Fischer et al., 2014), VH032 (Galdeano et al., 2014; Maniaci et al., 2017), adamantine (Xie et al., 2014), 1-((4,4,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), and/or analogs thereof.

In some aspects, the degradation/disruption tag can be, e.g., one of the following structures:

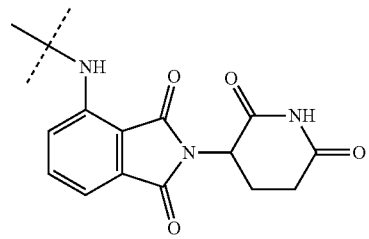

FORMULA 8A

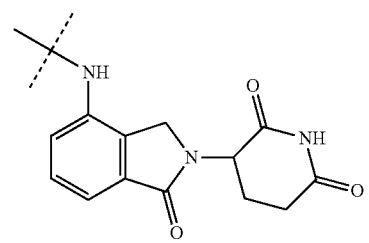

FORMULA 8B

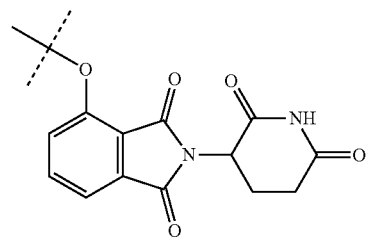

FORMULA 8C

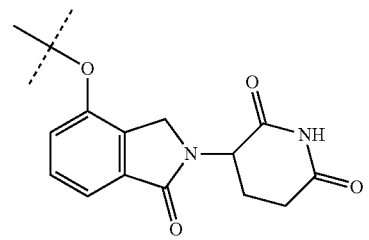

FORMULA 8D

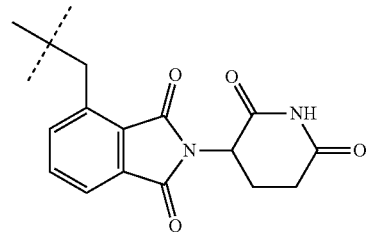

FORMULA 8E

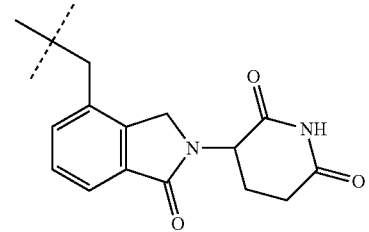

FORMULA 8F

FORMULA 8G
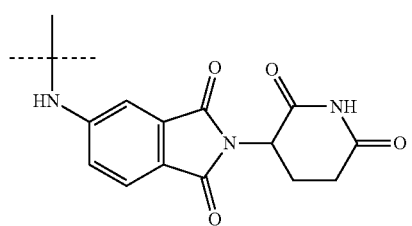
FORMULA 8H
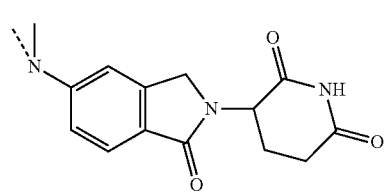
FORMULA 8I
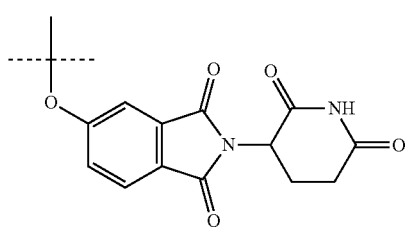
FORMULA 8J
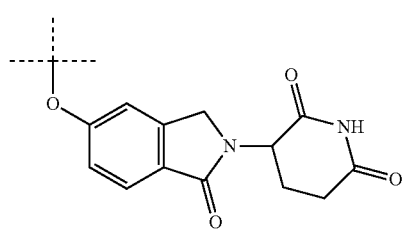
FORMULA 8K
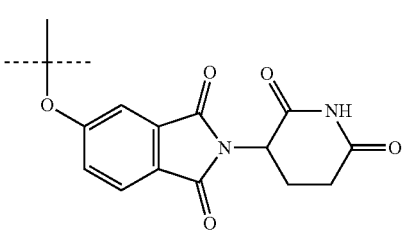
FORMULA 8L
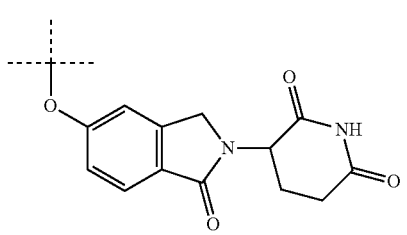
FORMULA 8M
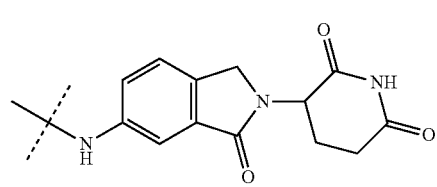
FORMULA 8N
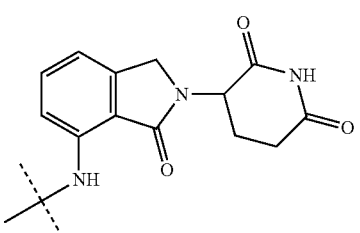
FORMULA 8O
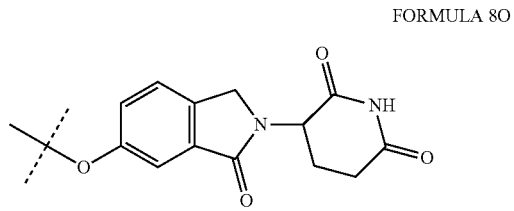
FORMULA 8P
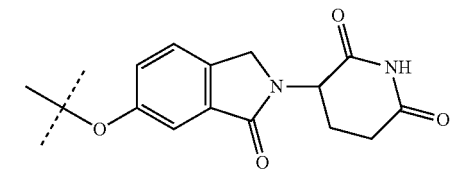
FORMULA 8Q
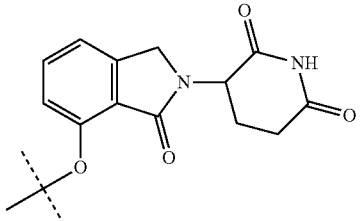
FORMULA 8R
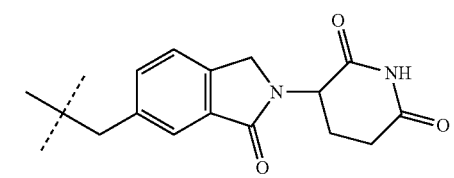
FORMULA 8S
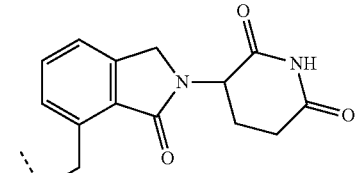
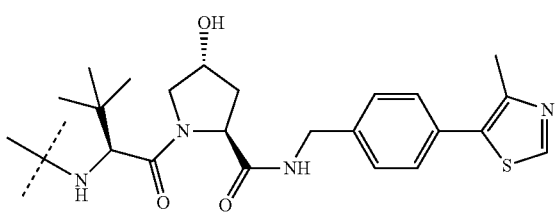
FORMULA 8T
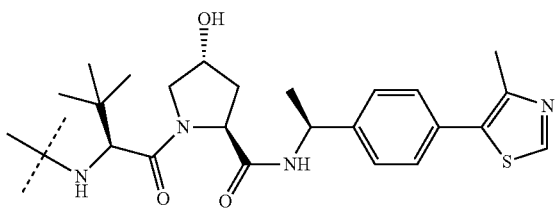

FORMULA 8U
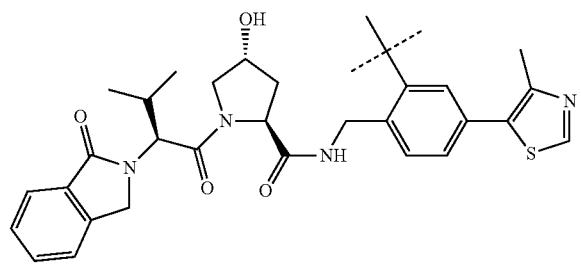
FORMULA 8V
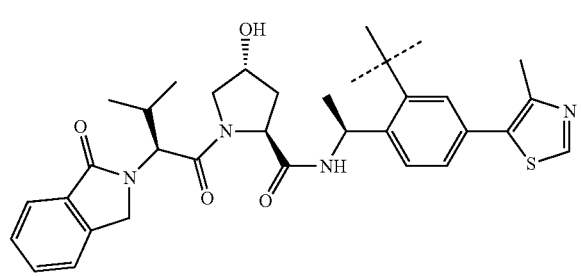
FORMULA 8W
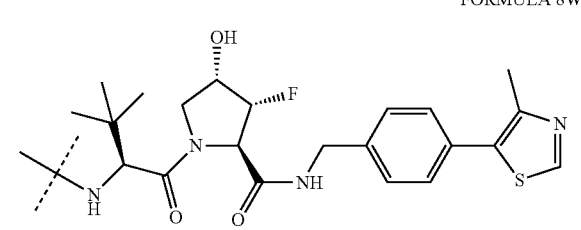
FORMULA 8X
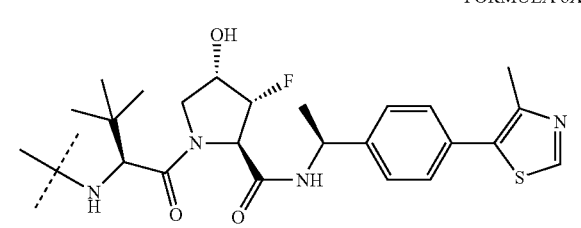
FORMULA 8Y
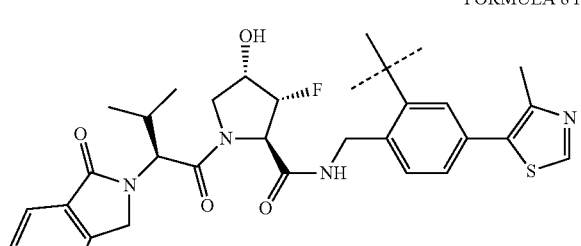
FORMULA 8Z
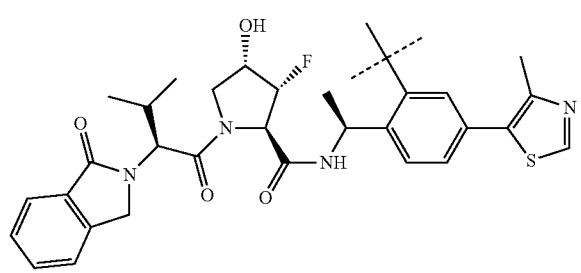
FORMULA 8AA
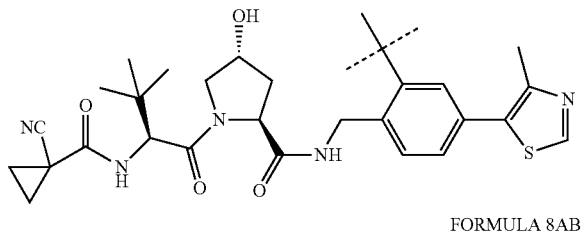
FORMULA 8AB
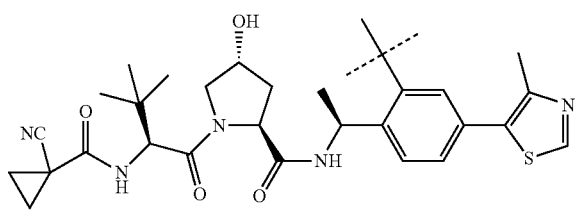
FORMULA 8AC
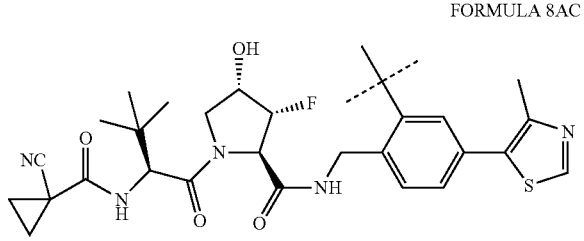
FORMULA 8AD
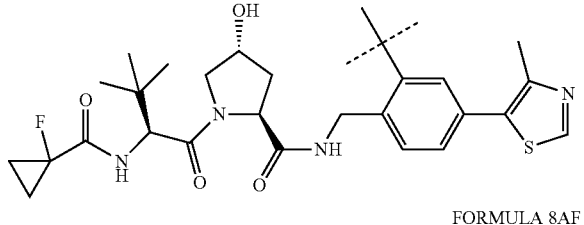
FORMULA 8AE
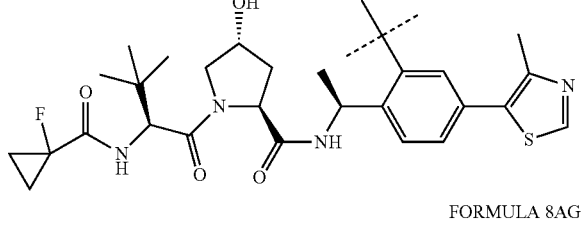
FORMULA 8AF
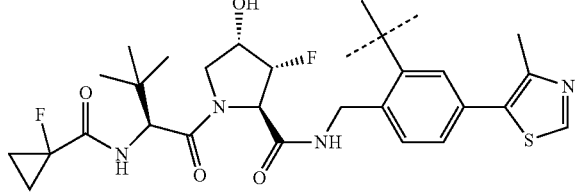
FORMULA 8AG -continued
FORMULA 8AH
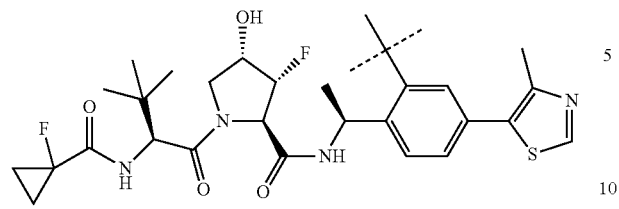
FORMULA 8AI
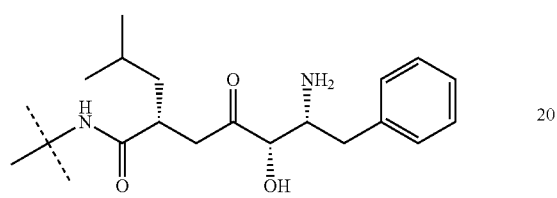
FORMULA 8AJ
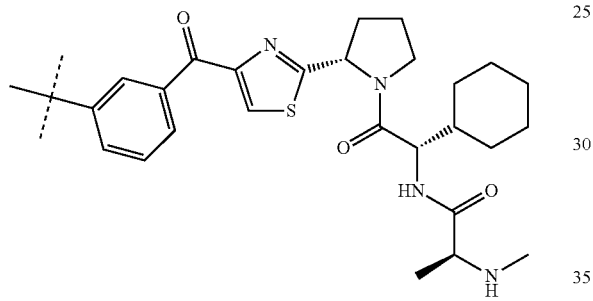
FORMULA 8AK
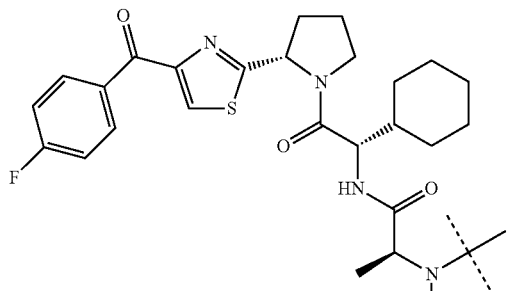
FORMULA 8AL
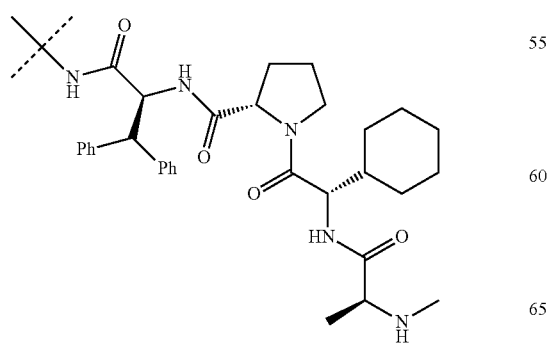
-continued
FORMULA 8AM
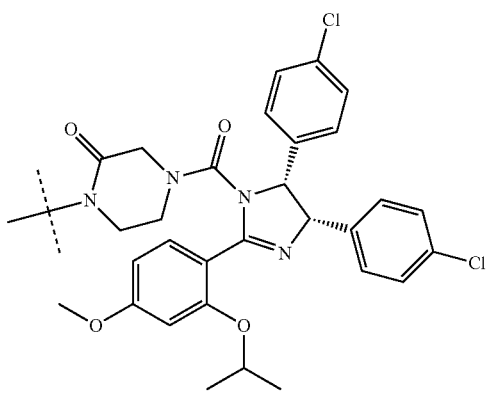
FORMULA 8AN
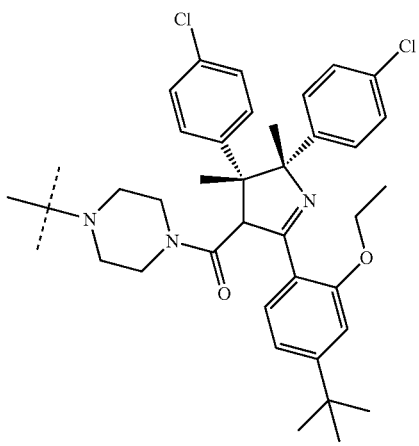
FORMULA 8AO
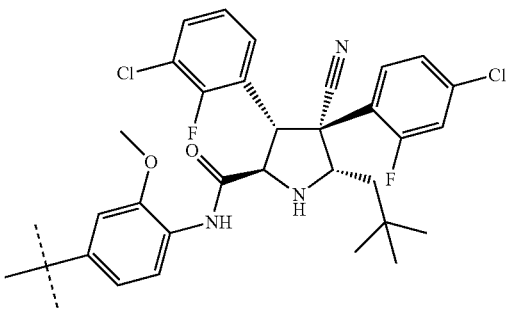
FORMULA 8AP
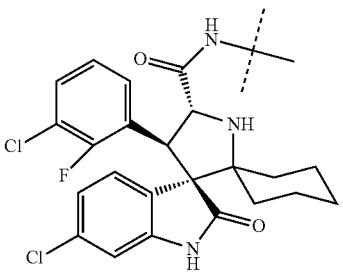

-continued
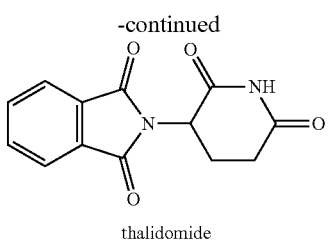
thalidomide
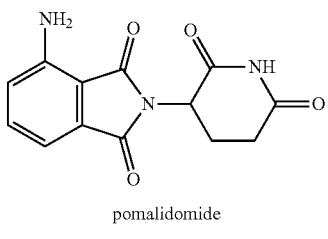
pomalidomide
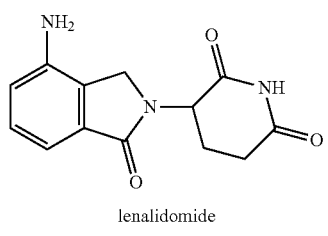
lenalidomide
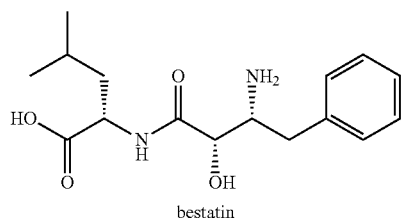
bestatin
MV1
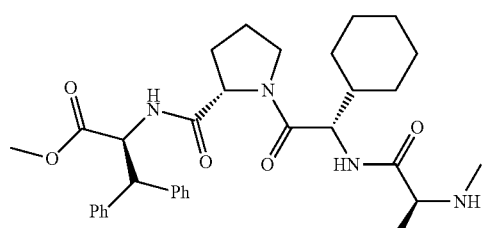
LCL161
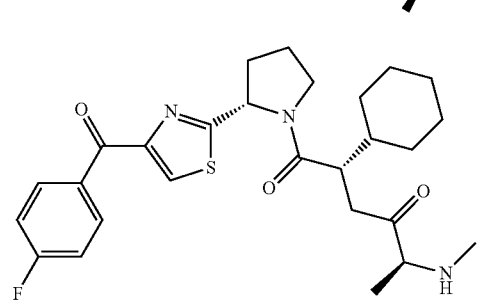
-continued
nutlin-3a
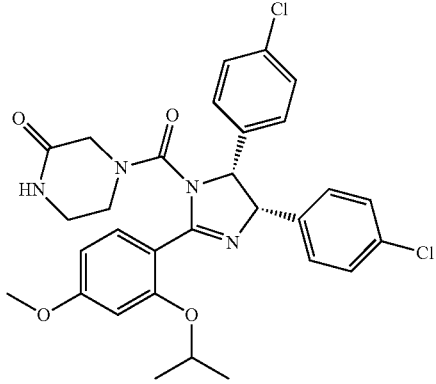
RG7112
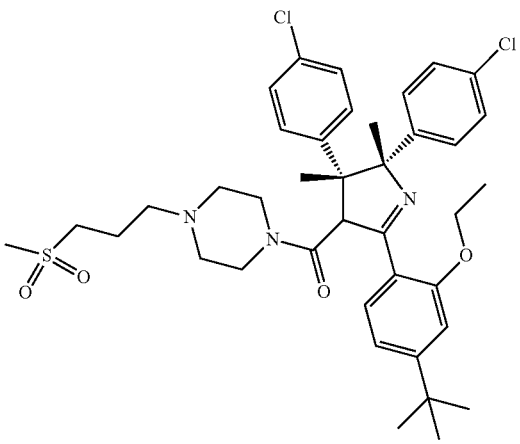
RG7338
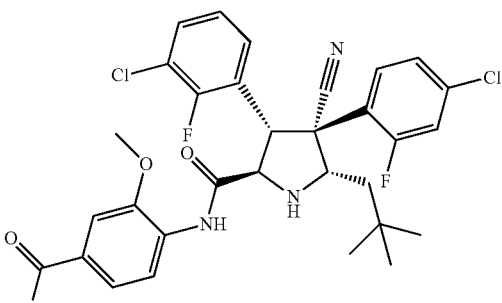
AMG232
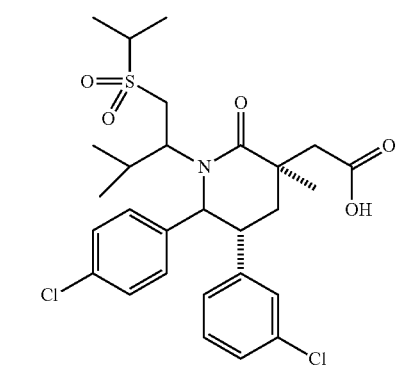

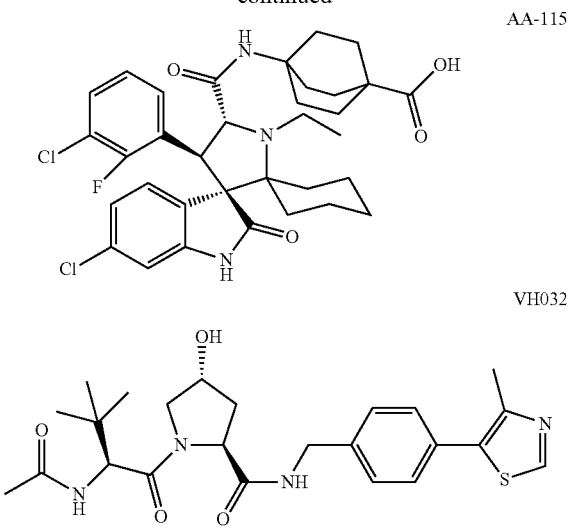

AA-115

VH032

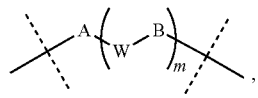

In some aspects, the degradation/disruption tag can bind to a ubiquitin ligase (e.g., an E3 ligase such as acereblonE3 ligase, a VHL E3 ligase, a MDM2 ligase, a TRIM21 ligase, a TRIM24 ligase, and/or an IAP ligase) and/or serve as a hydrophobic group that leads to AKT protein misfolding.

Linkers

In all of the above-described compounds, the AKT ligand is conjugated to the degradation/disruption tag through a linker. The linker can include, for example, a cyclic or cyclic saturated or unsaturated carbon, ethylene glycol, amide, amino, ether, urea, carbamate, aromatic, heteroaromatic, heterocyclic and/or carbonyl containing groups with different lengths.

In some aspects, the linker can be a moiety of:

FORMULA 9

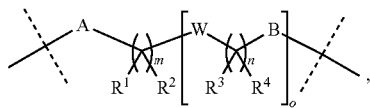

wherein

A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^1$ and R$^2$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R' and R$^2$, R" and R$^1$, R" and R$^2$ together with the atom to which they are connected form a 3-20 membered cycloalkyl or 4-20 membered heterocyclyl ring; and m is 0 to 15.

In one embodiment, the linker moiety is of FORMULA 9A:

FORMULA 9A wherein

R$^1$, R$^2$, R$^3$ and R$^4$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$ alkylamino, and optionally substituted C$_1$-C$_8$ alkylaminoC$_1$-C$_8$ alkyl, optionally substituted 3-10 membered carbocyclyl, optionally substituted 3-10 membered cycloalkoxy, optionally substituted 3-10 membered carbocyclylamino, optionally substituted 4-8 membered heterocyclyl, optionally substituted aryl, and optionally substituted heteroaryl, or R$^1$ and R$^2$, R$^3$ and R$^4$ together with the atom to which they are connected form a 3-20 membered cycloalkyl or 4-20 membered heterocyclyl ring;

A, W and B, at each occurrence, are independently selected from null, or bivalent moiety selected from R'—R, R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^5$ and R$^6$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^5$ and R$^6$, R' and R$^5$, R' and R$^6$, R" and R$^5$, R" and R$^6$ together with the atom to which they are connected form a 3-20 membered cycloalkyl or 4-20 membered heterocyclyl ring;

m is 0 to 15;
n, at each occurrence, is 0 to 15; and
o is 0 to 15.

In another embodiment, the linker moiety is of FORMULA 9B:

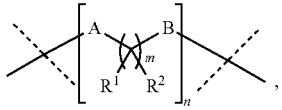

FORMULA 9B wherein

R$^1$ and R$^2$, at each occurrence, are independently selected from hydrogen, halogen, hydroxyl, amino, cyano, nitro, and optionally substituted C$_1$-C$_8$ alkyl, optionally substituted C$_1$-C$_8$ alkoxy, optionally substituted C$_1$-C$_8$ alkoxy C$_1$-C$_8$ alkyl, optionally substituted C$_1$-C$_8$ haloalkyl, optionally substituted C$_1$-C$_8$ hydroxyalkyl, optionally substituted C$_1$-C$_8$ alkylamino, C$_1$-C$_8$alkylaminoC$_1$-C$_8$alkyl, optionally substituted 3-10 membered carbocyclyl, optionally substituted 3-10 membered cycloalkoxy, optionally substituted 3-10 membered carbocyclylamino, optionally substituted 4-10 membered heterocyclyl, optionally substituted aryl, and optionally substituted heteroaryl, or R$^1$ and R$^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^3$ and R$^4$ are independently selected from hydrogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxyalkyl, optionally substituted C$_1$-C$_8$ haloalkyl, optionally substituted C$_1$-C$_8$ hydroxyalkyl, optionally substituted C$_1$-C$_8$alkylaminoC$_1$-C$_8$alkyl, optionally substituted 3-10 membered carbocyclyl, optionally substituted 4-10 membered heterocyclyl, optionally substituted aryl, and optionally substituted heteroaryl;

R' and R", R$^3$ and R$^4$, R' and R$^3$, R' and R$^4$, R" and R$^3$, R" and R$^4$ together with the atom to which they are connected form a 3-20 membered cycloalkyl or 4-20 membered heterocyclyl ring;

each m is 0 to 15; and
n is 0 to 15.

In another embodiment, the linker moiety is of FORMULA 9C:

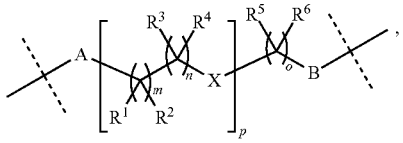

FORMULA 9C wherein

X is selected from O, NH, and NR$^7$;

R$^1$, R$^2$, R$^3$, R$^4$, R$^5$, R$^6$, and R$^7$, at each occurrence, are independently selected from hydrogen, halogen, hydroxyl, amino, cyano, nitro, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxy C$_1$-C$_8$ alkyl, optionally substituted C$_1$-C$_8$ haloalkyl, optionally substituted C$_1$-C$_8$ hydroxyalkyl, optionally substituted C$_1$-C$_8$ alkylamino, optionally substituted C$_1$-C$_8$ alkylaminoC$_1$-C$_8$ alkyl, optionally substituted 3-10 membered carbocyclyl, optionally substituted 3-10 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein

- R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;
- $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;
- R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;
- m, at each occurrence, is 0 to 15;
- n, at each occurrence, is 0 to 15;
- o is 0 to 15; and
- p is 0 to 15.

In another embodiment, A and B, at each occurrence, are independently selected from null, CO, NH, NH—CO, CO—NH, CH$_2$—NH—CO, CH$_2$—CO—NH, NH—CO—CH$_2$, CO—NH—CH$_2$, CH$_2$—NH—CH$_2$—CO—NH, CH$_2$—NH—CH$_2$—NH—CO, —CO—NH, CO—NH—CH$_2$—NH—CH$_2$, CH$_2$—NH—CH$_2$.

In another embodiment, o is 0 to 5.

In another embodiment, the linker moiety comprises a ring selected from the group consisting of a 3 to 13 membered ring, a 3 to 13 membered fused ring, a 3 to 13 membered bridged ring, and a 3 to 13 membered spiro ring.

In another embodiment, the linker moiety comprises one or more rings selected from the group consisting of FORMULAE C1, C2, C3, C4 and C5:

FORMULA C1

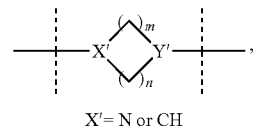

X' = N or CH
Y' = N or CH
m = 0-5
n = 0-5

FORMULA C2

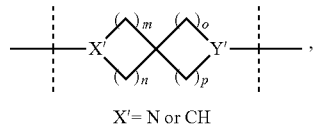

X' = N or CH
Y' = N or CH
m = 0-5
n = 0-5
o = 0-5
p = 0-5

FORMULA C3

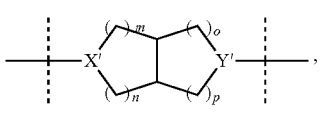

X' = N or CH
Y' = N or CH
m = 0-5
n = 0-5
o = 0-5
p = 0-5

FORMULA C4

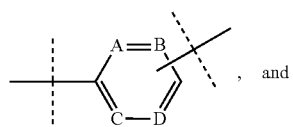, and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N

FORMULA C5

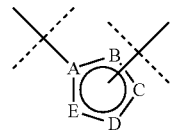

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S.

Formula A

wherein X is C=O or CH$_2$,
Y is C=O or CH$_2$, and
n is 0-15;

Formula B

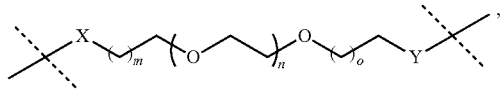

wherein X is C=O or CH$_2$,
Y is C=O or CH$_2$,
m is 0-15,
n is 0-6, and
o is 0-15; or Formula C

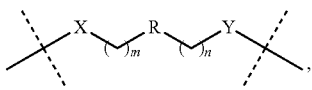

wherein
X is C=O or CH$_2$,
Y is C=O or CH$_2$,
R is —CH$_2$—, —CF$_2$—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C=C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

In some aspects of Formula C, R is a 3-13 membered ring, a 3-13 membered fused ring, a 3-13 membered bridged ring, and/or a 3-13 membered spiro ring, one or more of which can contain one or more heteroatoms.

In some aspects of Formula C, R has a structure of:

Formula C1

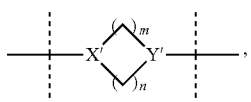

X'= N or CH
Y'= N or CH
m = 0-5
n = 0-5

Formula C2

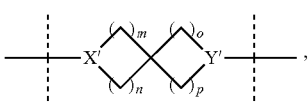

X'= N or CH
Y'= N or CH
m = 0-5
n = 0-5
o = 0-5
p = 0-5

Formula C3

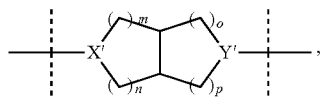

X'= N or CH
Y'= N or CH
m = 0-5
n = 0-5
o = 0-5
p = 0-5

Formula C4

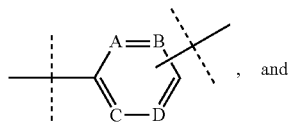

, and

A = CH, C(C$_{1-3}$ alkyl), or N
B = CH, C(C$_{1-3}$ alkyl), or N
C = CH, C(C$_{1-3}$ alkyl), or N
D = CH, C(C$_{1-3}$ alkyl), or N Formula C5

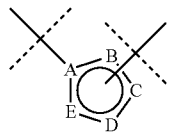

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3alkyl), O, S·

Synthesis and Testing of Bivalent Compounds

The binding affinity of novel synthesized bivalent compounds (i.e., AKT degraders/disruptors) can be assessed using standard biophysical assays known in the art (e.g., isothermal titration calorimetry (ITC)). Cellular assays can then be used to assess the bivalent compound's ability to induce AKT degradation and inhibit cancer cell proliferation. Besides evaluating a bivalent compound's induced changes in the protein expression of AKT or AKT mutant proteins, enzymatic activity can also be assessed. Assays suitable for use in any or all of these steps are known in the art, and include, e.g., Western blotting, quantitative mass spectrometry (MS) analysis, flow cytometry, enzymatic inhibition, ITC, SPR, cell growth inhibition and xenograft and PDX models. Suitable cell lines for use in any or all of these steps are known in the art and include, e.g., LNCaP cells (androgen-sensitive human prostate adenocarcinoma cells), PC3 (PC-3) cells (PTEN homozygous deletion mutant human prostate cancer cell lines), MCF7-neo/HER2 cells (PIK3CAE545K mutant stably expressing a HER2 transgene breast cancer cells), BT474M1 cells (PIK3CAK111N mutant and HER2-amplified human breast carcinoma), and IGROV-1 cells (PTENT319fsX1/Y155C and PIK3CA1069 Wovarian cancer cells), MDA-MB-468 cells (PTEN loss breast cancer cells), HCC1143 cells (Triple Negative Breast Cancer cells, TP53R248Q mutant), MDA-MB-231 (Triple Negative Breast Cancer cells), and U87MG cells (PTEN Loss Glioblastoma cells). Suitable mouse models for use in any or all of these steps are known in the art and include, e.g., PC3 prostate cancer model, MCF7-neo/HER2 breast cancer model, LNCaP prostate adenocarcinoma model, MDA-MB-468 breast cancer model, HCC1143 breast cancer model, and TOV-21G.x1 ovarian cancer xenograft model.

By way of non-limiting example, detailed synthesis protocols are described in the Examples for specific exemplary AKT degraders/disruptors.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^{2}H$, $^{3}H$, $^{13}C$, $^{14}C$, $^{15}N$, $^{17}O$, $^{18}O$, $^{32}P$, $^{35}S$, $^{18}F$, and $^{36}Cl$.

Isotopic variations (e.g., isotopic variations containing $^{2}H$) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^{3}H$) and carbon-14 ($^{14}C$) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Characterization of Exemplary AKT Degraders/Disruptors

Figure 1:
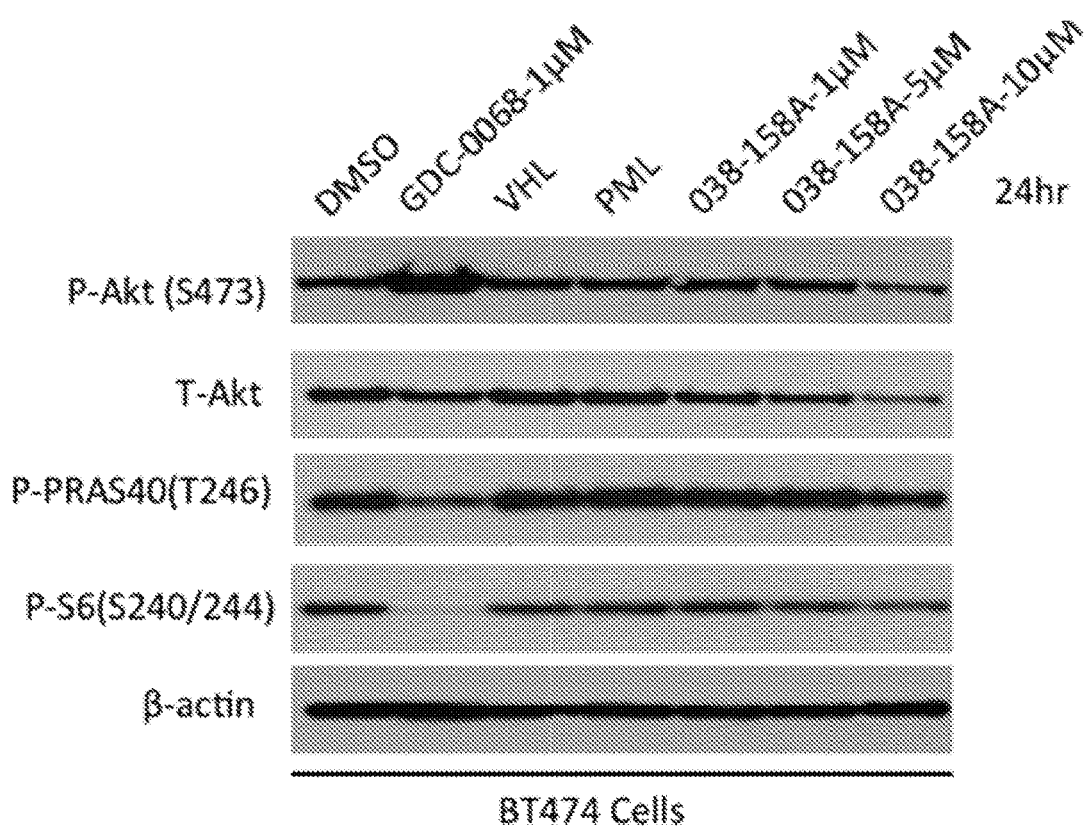
Figures 1, 1A, 2:
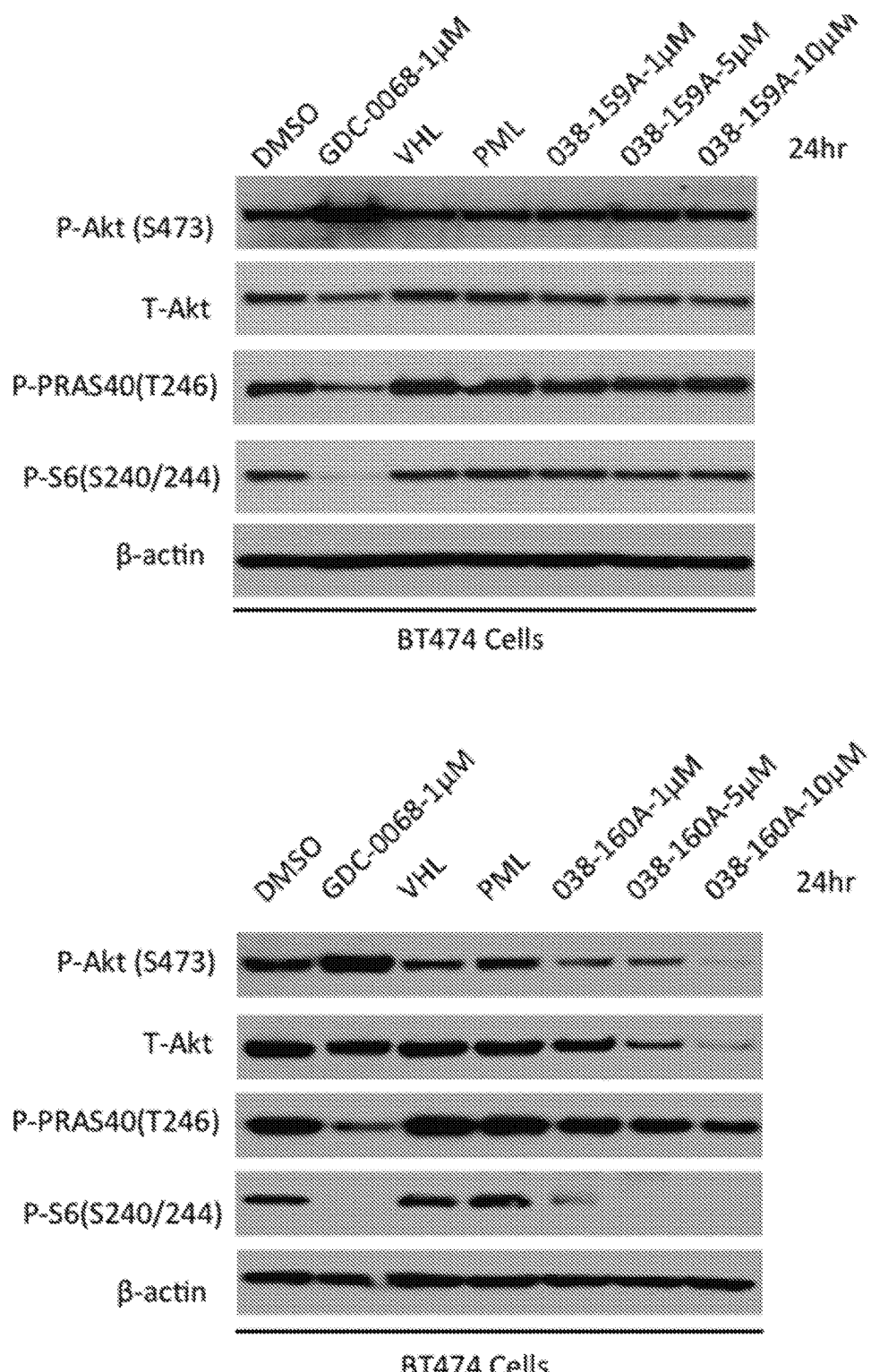
FIG. 2 is a Western blot showing that XF038-166A time-dependently reduces AKT, p-AKT, P-PRAS40 (T246), and P-S6 (S240/244) protein levels in BT474 cells.
Figures 1, 1A, 2, 3, 4, 5:
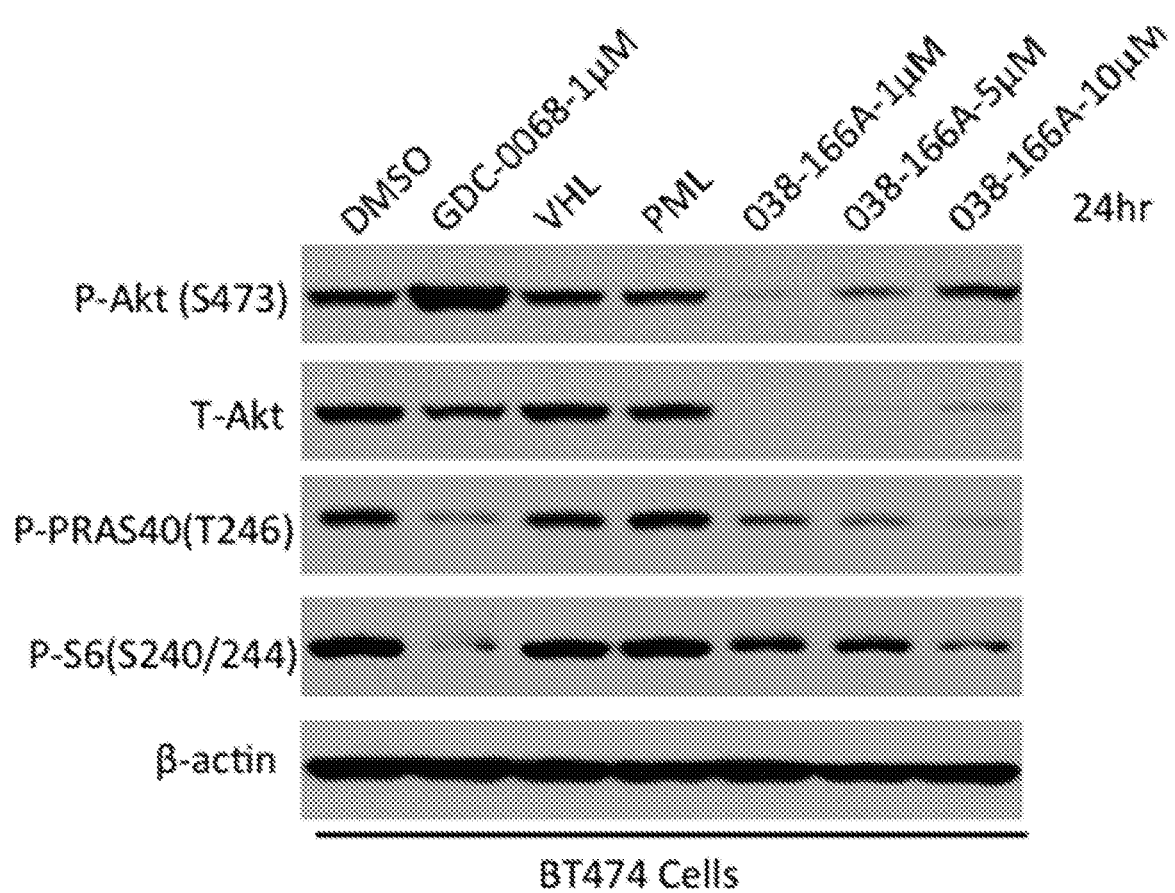
Figure 1B:
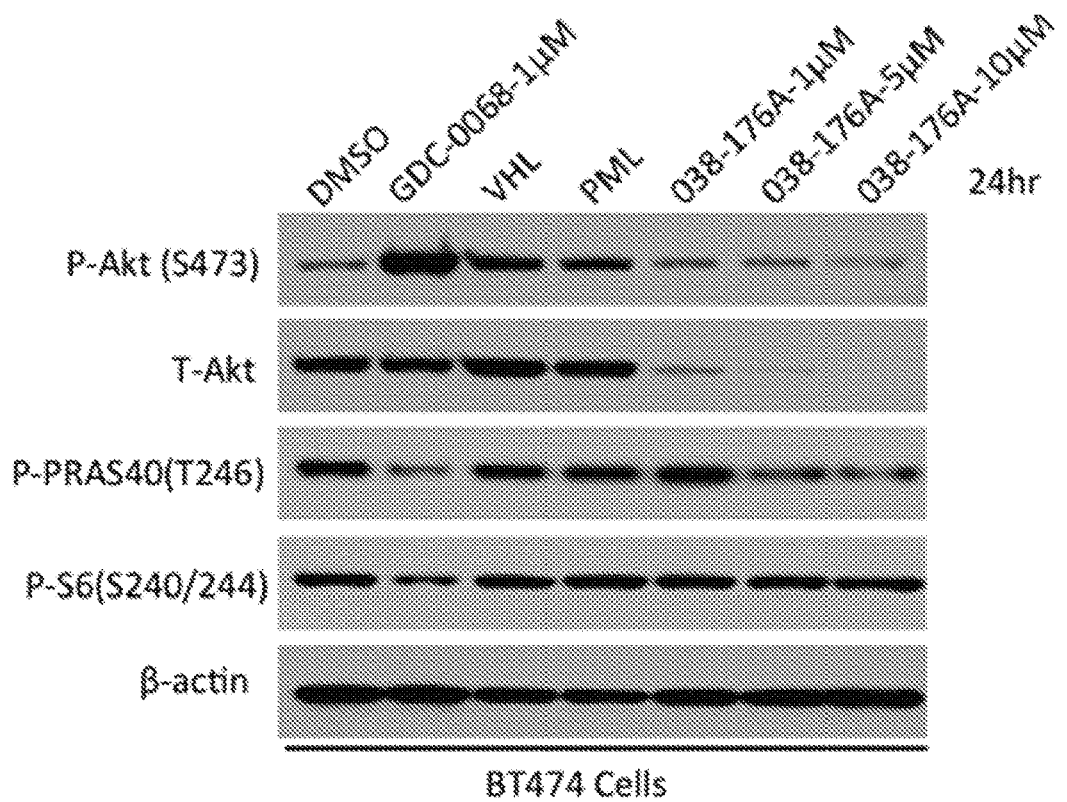
Figure 1:
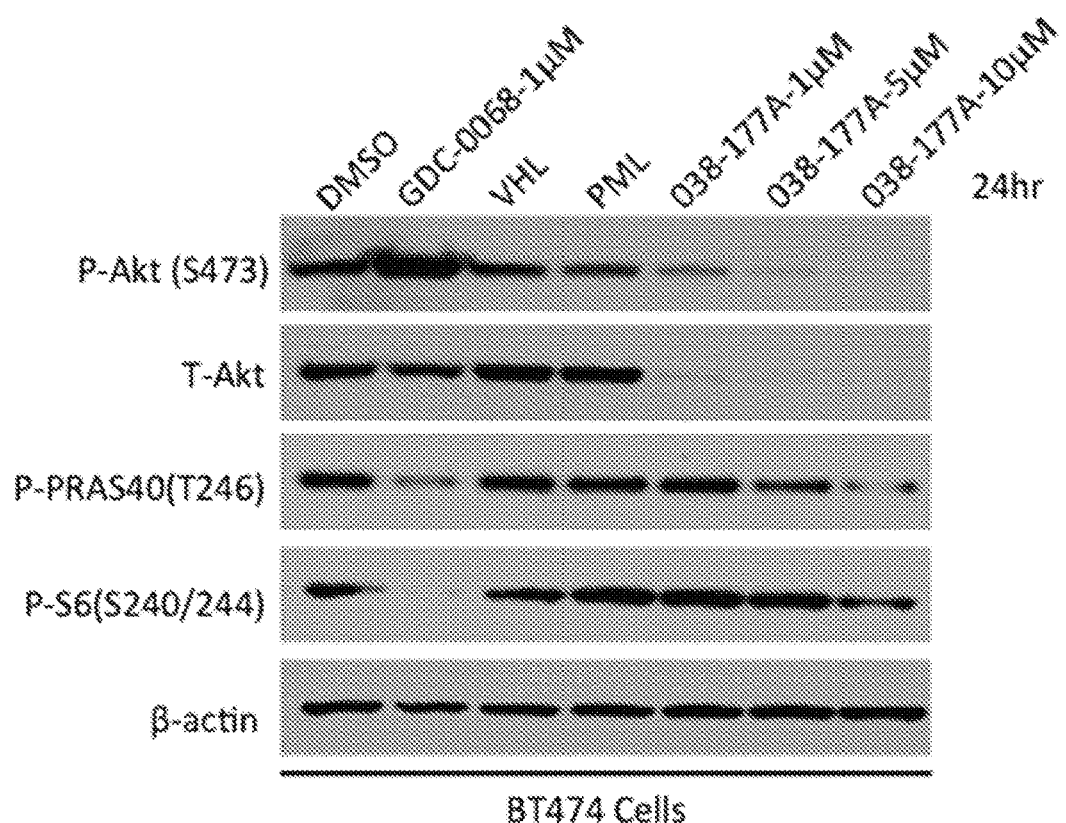
Figures 1, 1B, 2, 3, 4, 5:
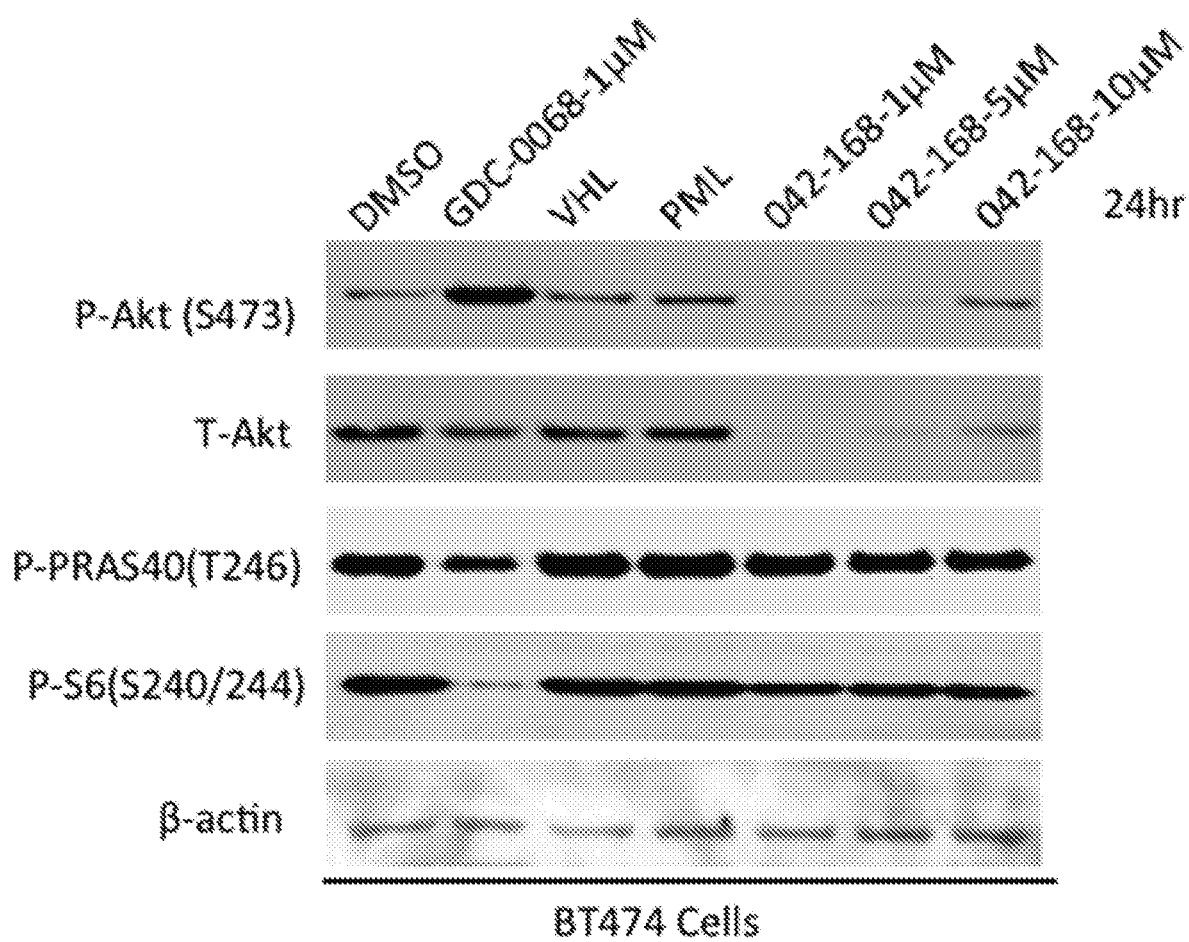
Figure 1C:
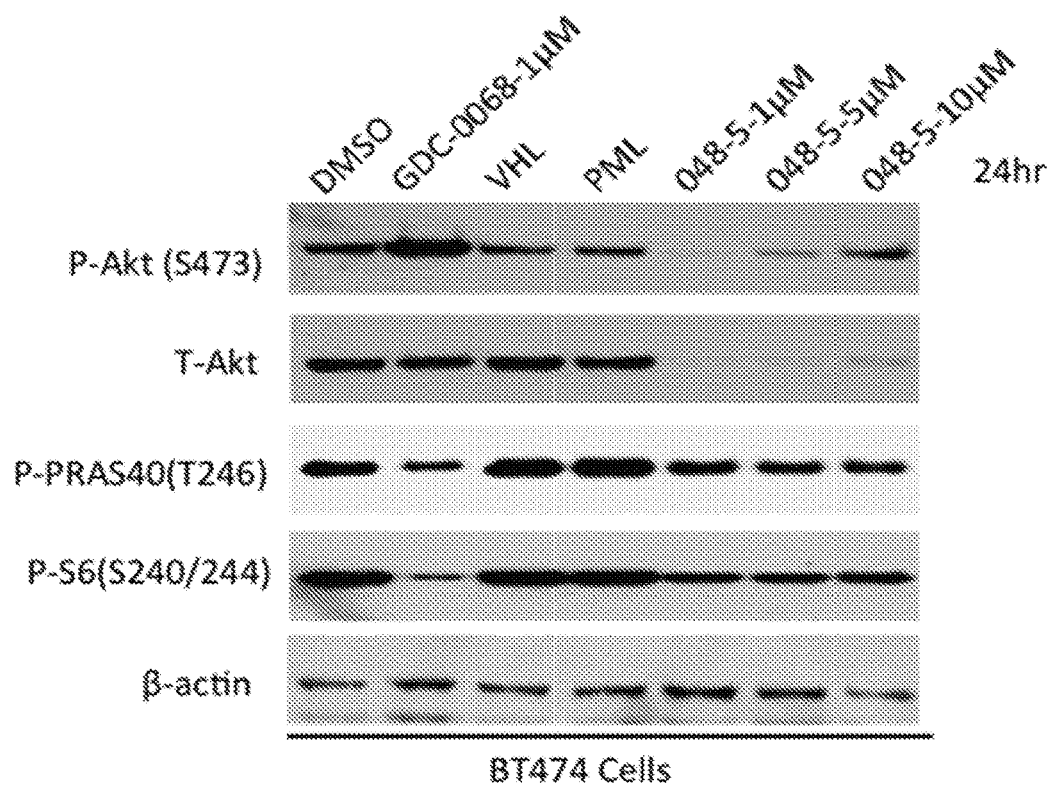
Figure 1:
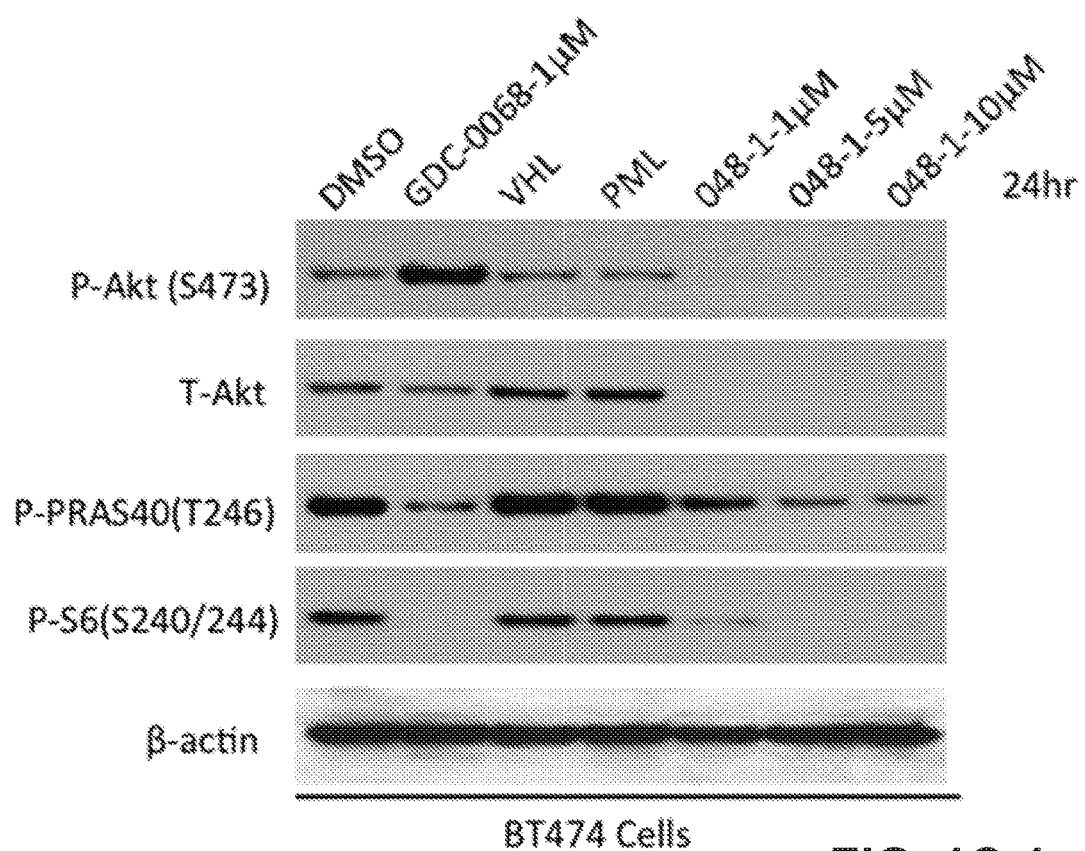
Figure 2:
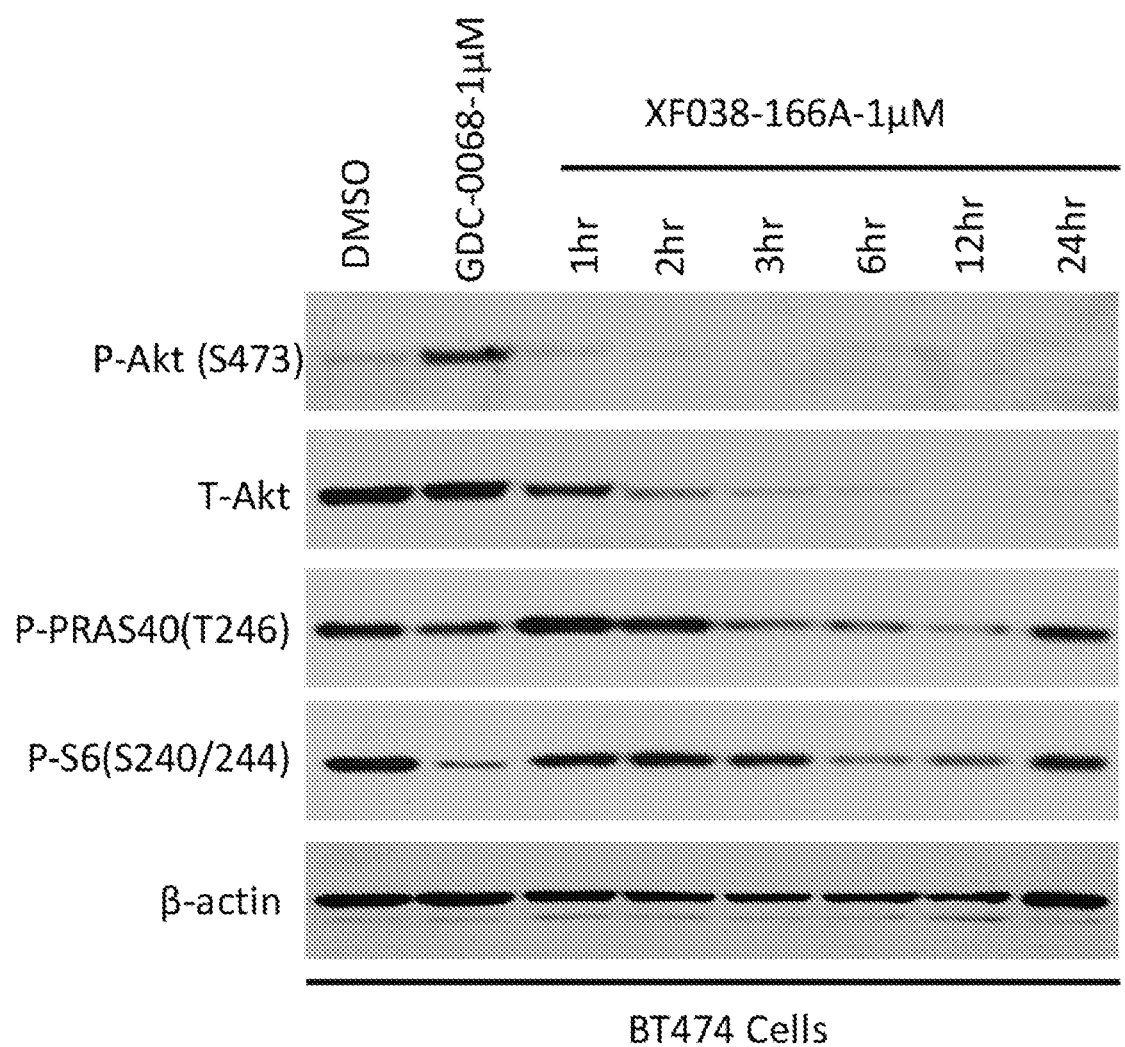
Figure 3A:
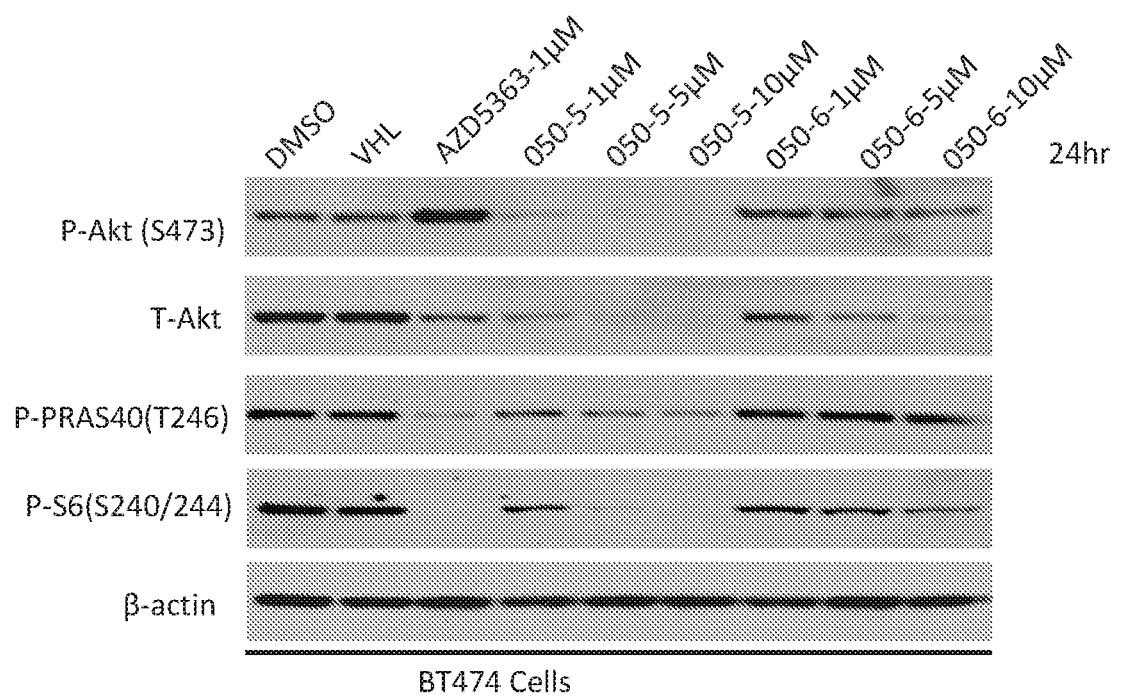
FIG. 3A-C are a series of Western blots showing the effect of various AKT degraders on reducing AKT, p-AKT, P-PRAS40 (T246), and P-S6 (S240/244) protein levels at various concentrations in BT474 cells. (Note: "XF" portion of the degrader compound code was omitted)
Figure 1:
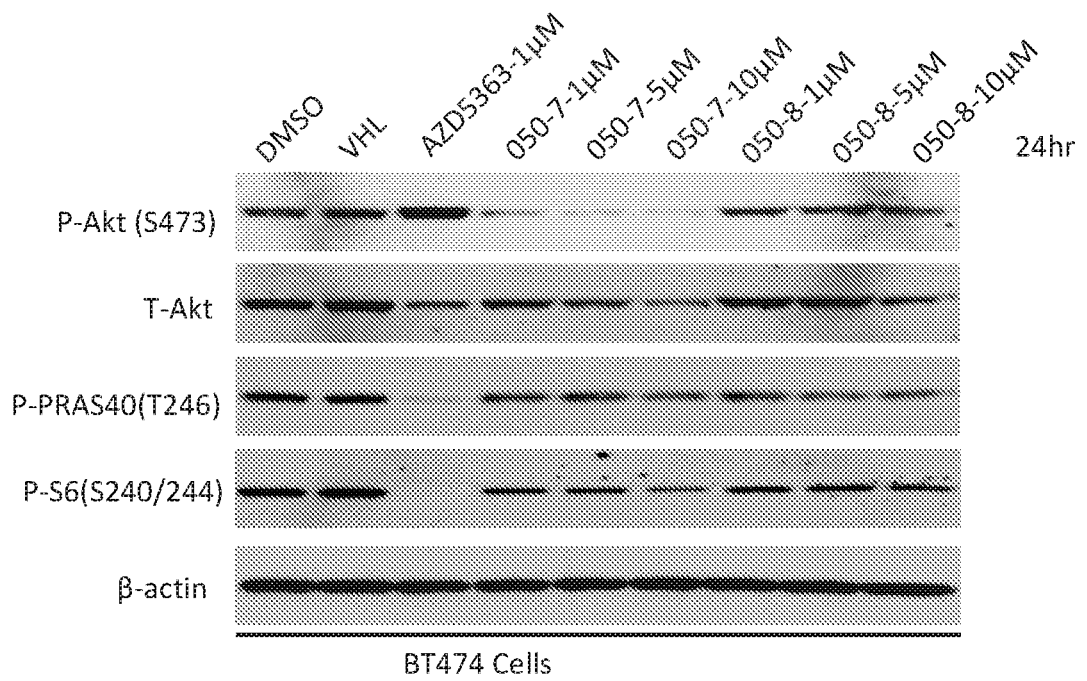
Figures 2, 3A:
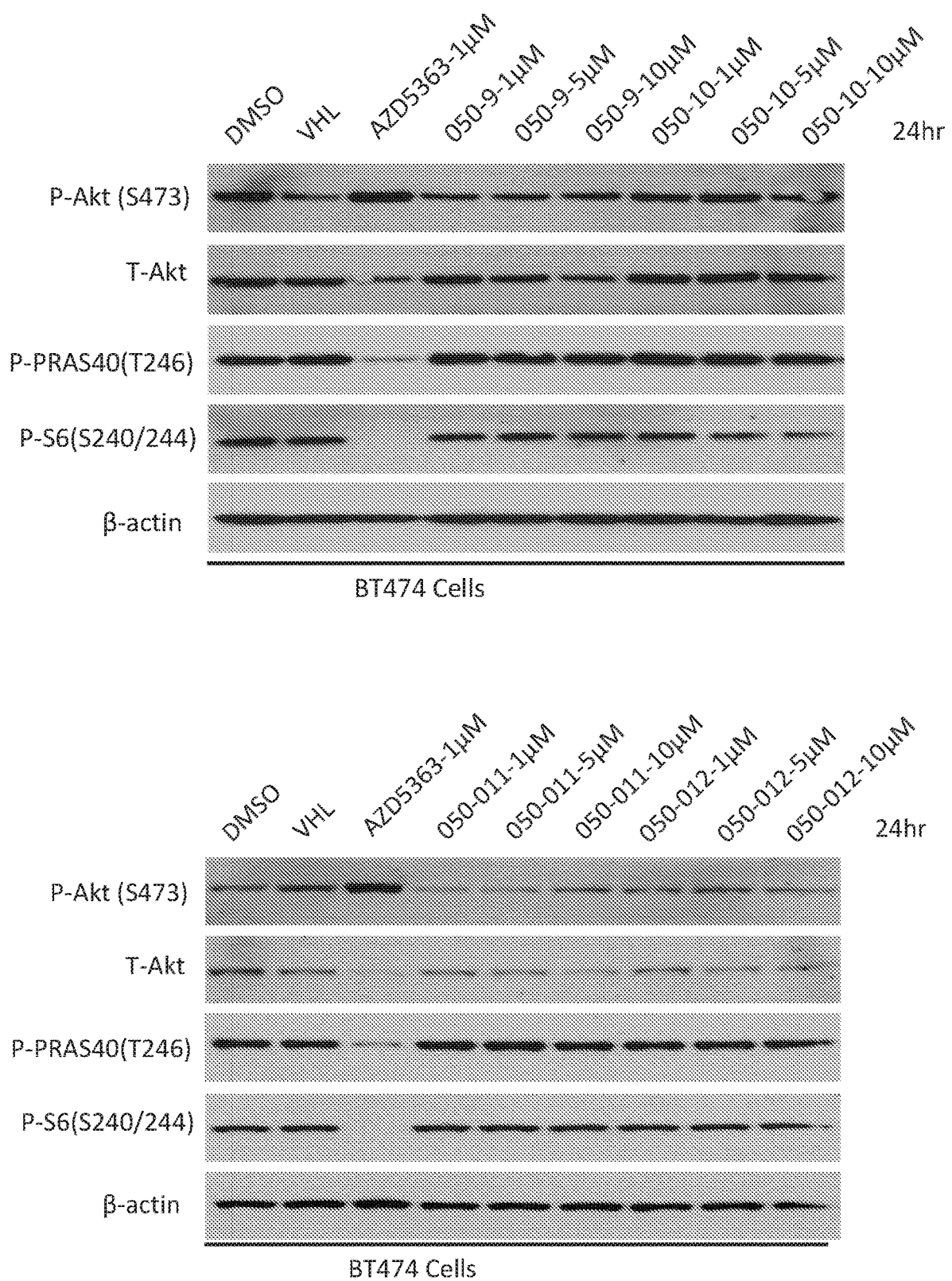
Figure 3A:
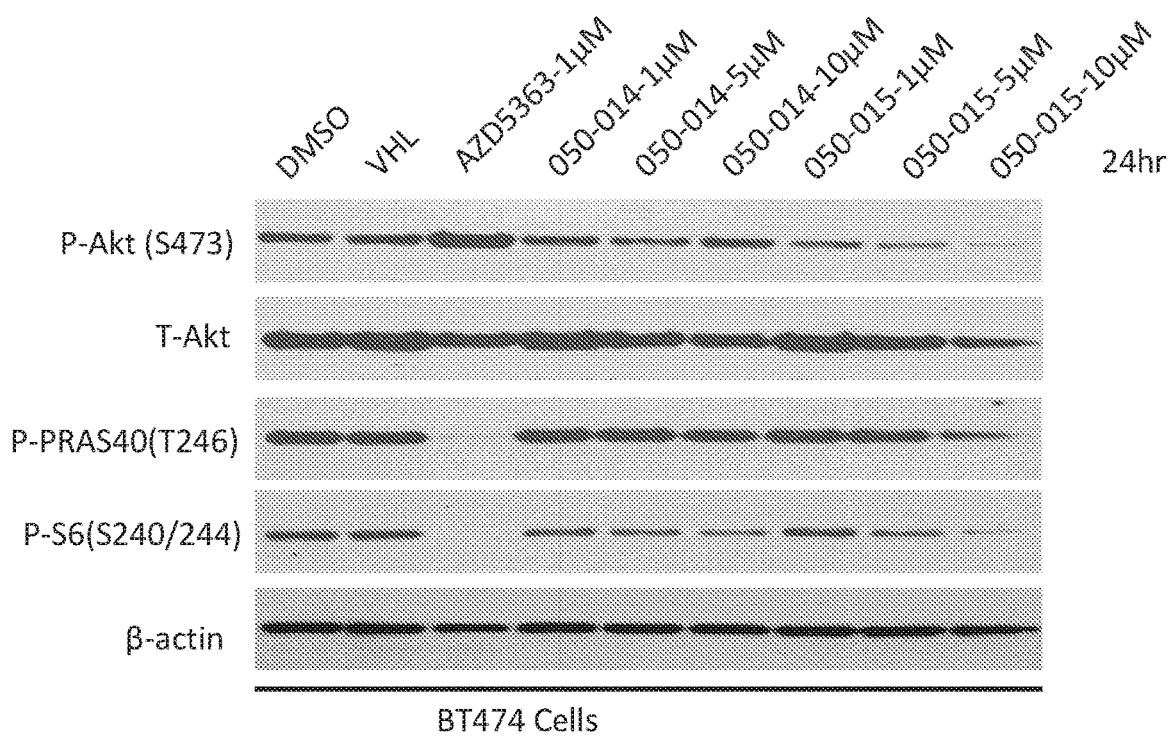
Figure 3:
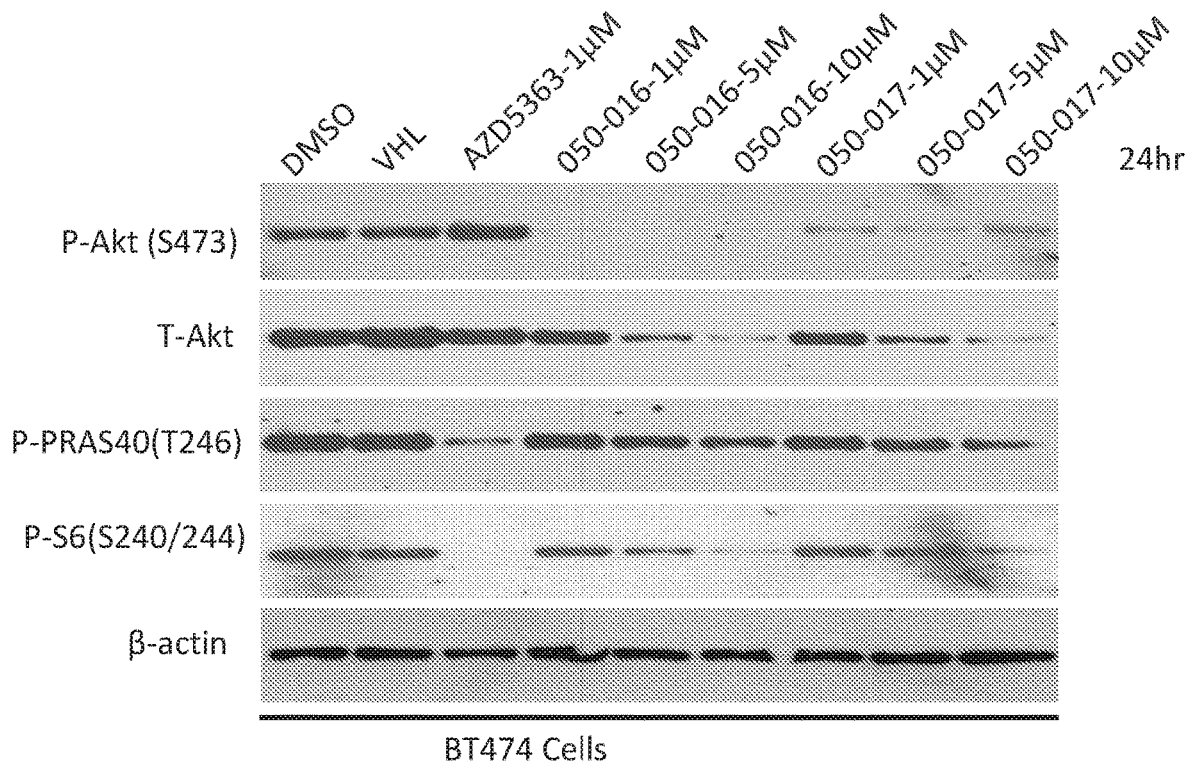
Figures 3, 3A, 4, 5:
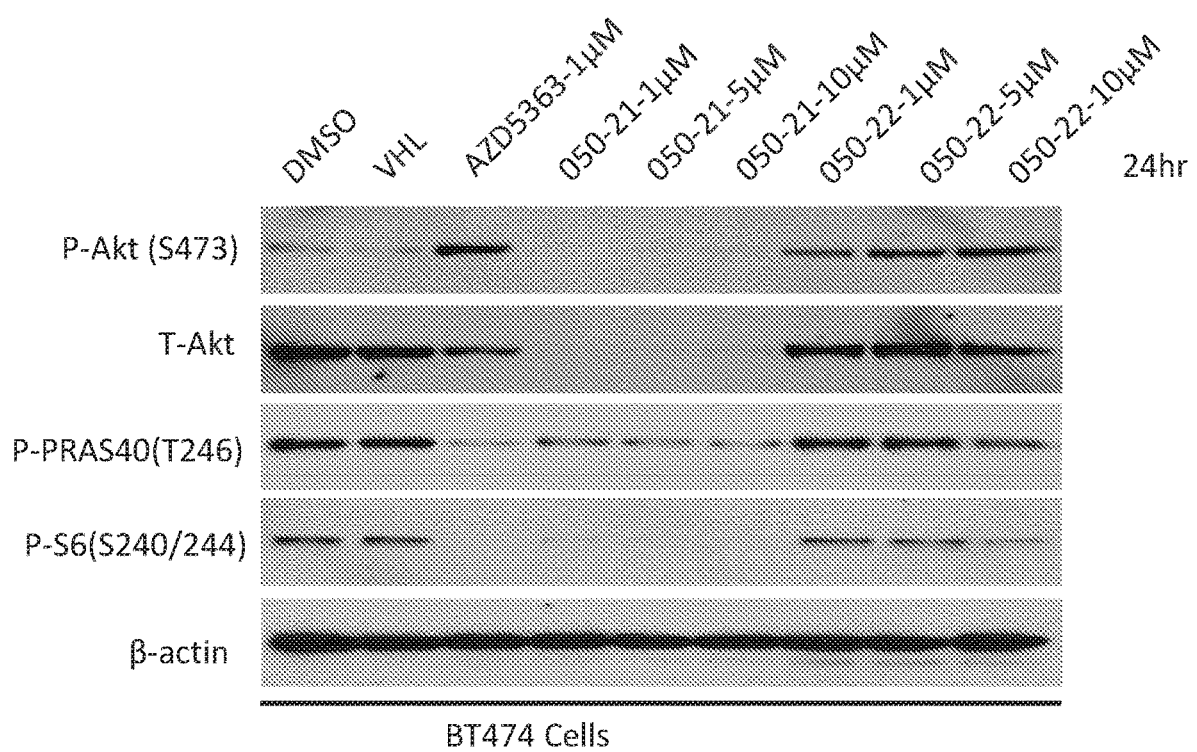
Figure 3B:
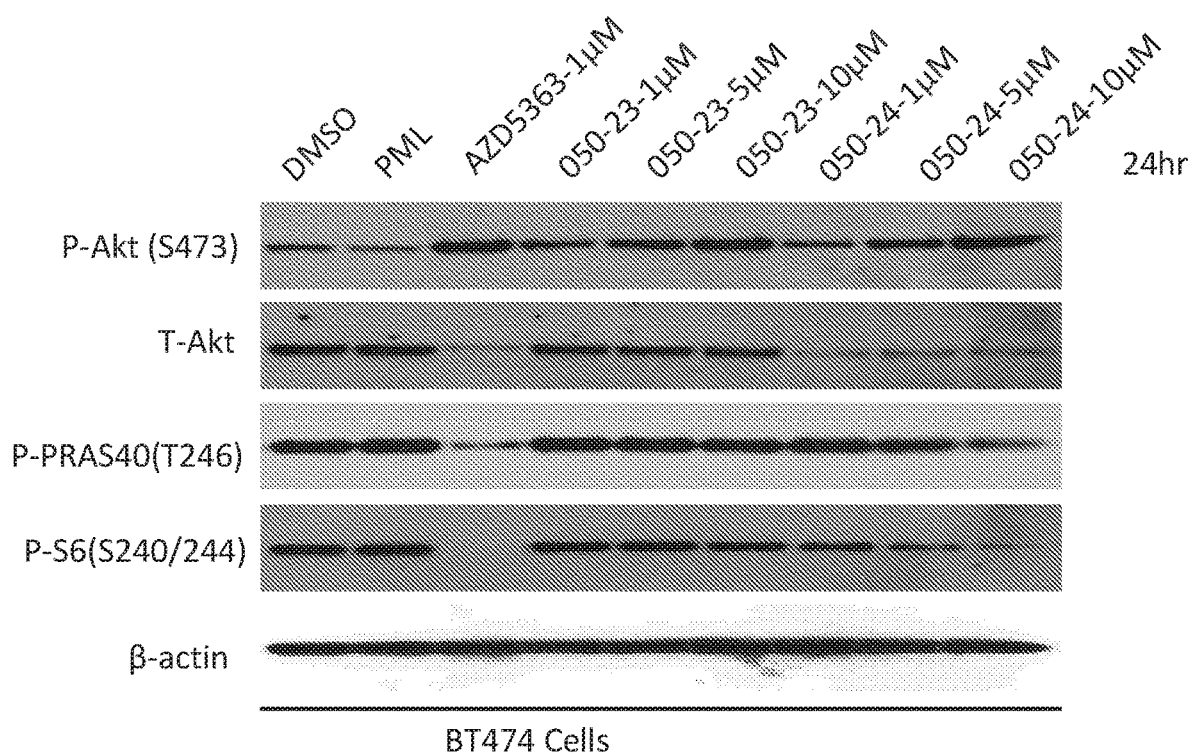
Figure 1:
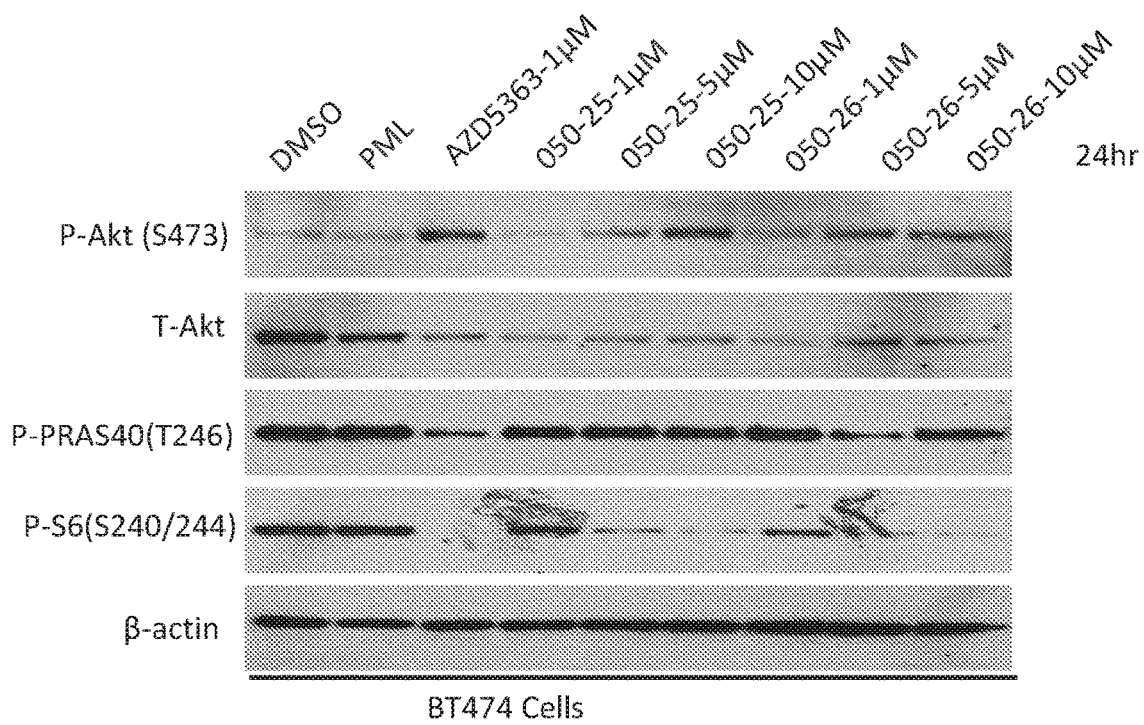
Figure 3B:
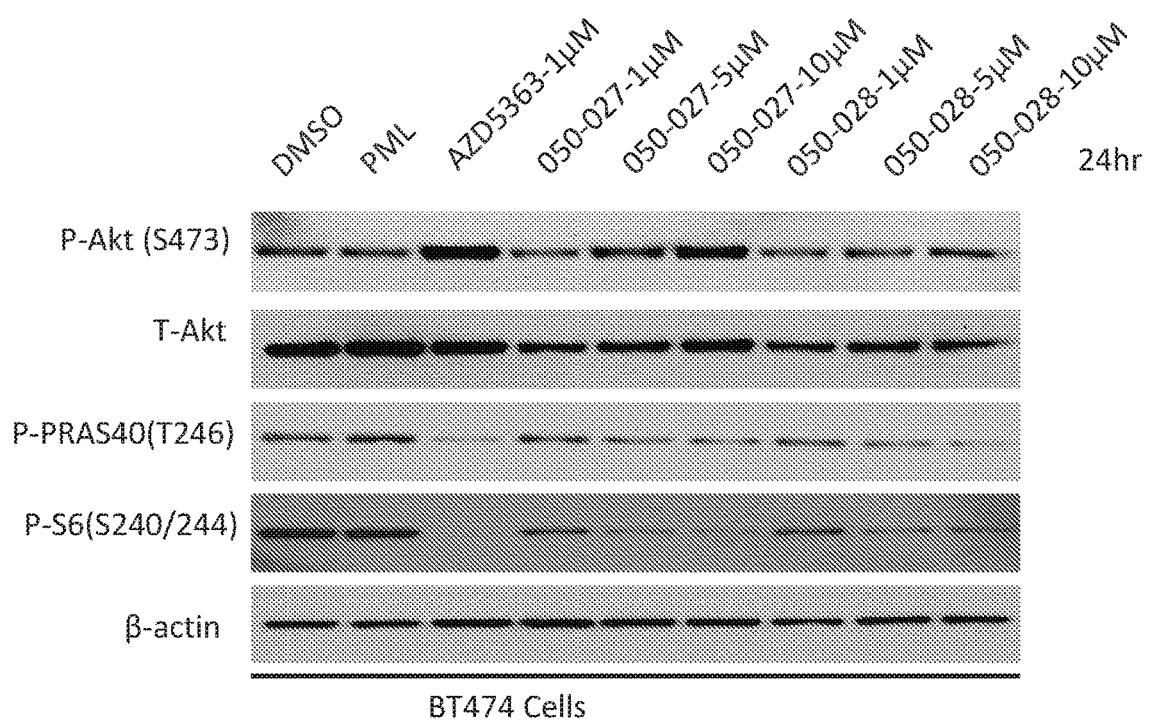
Figure 2:
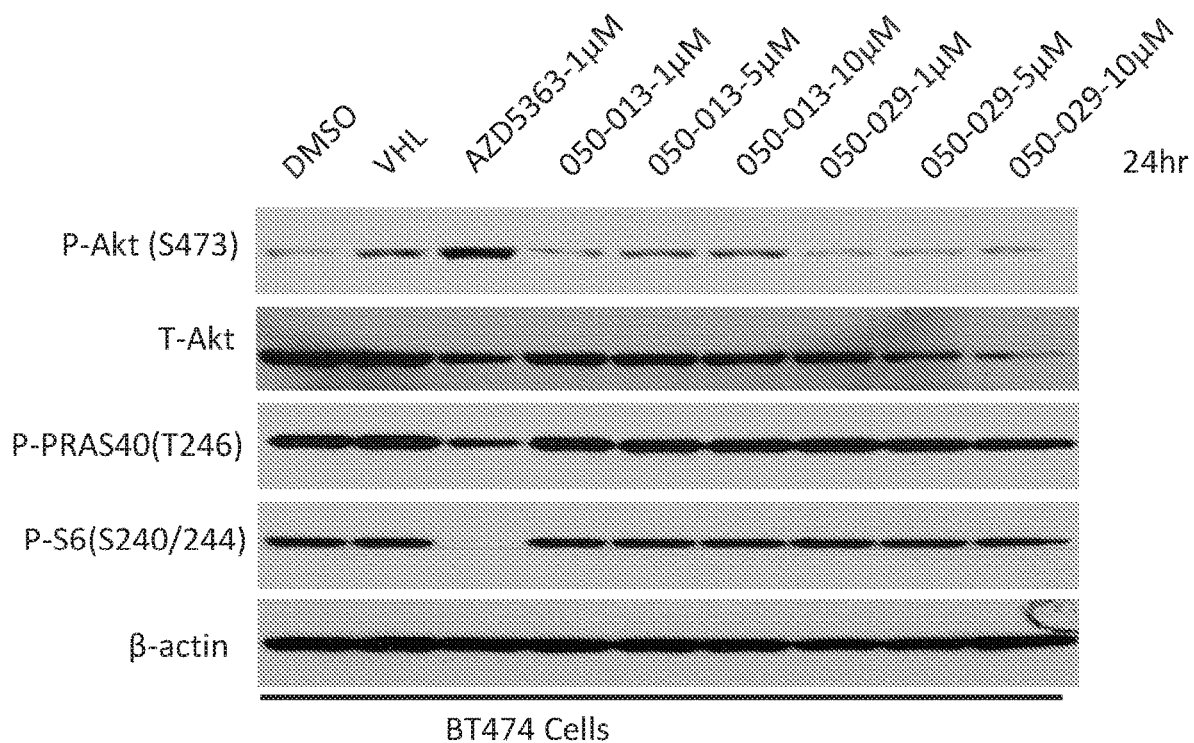
Figure 3B:
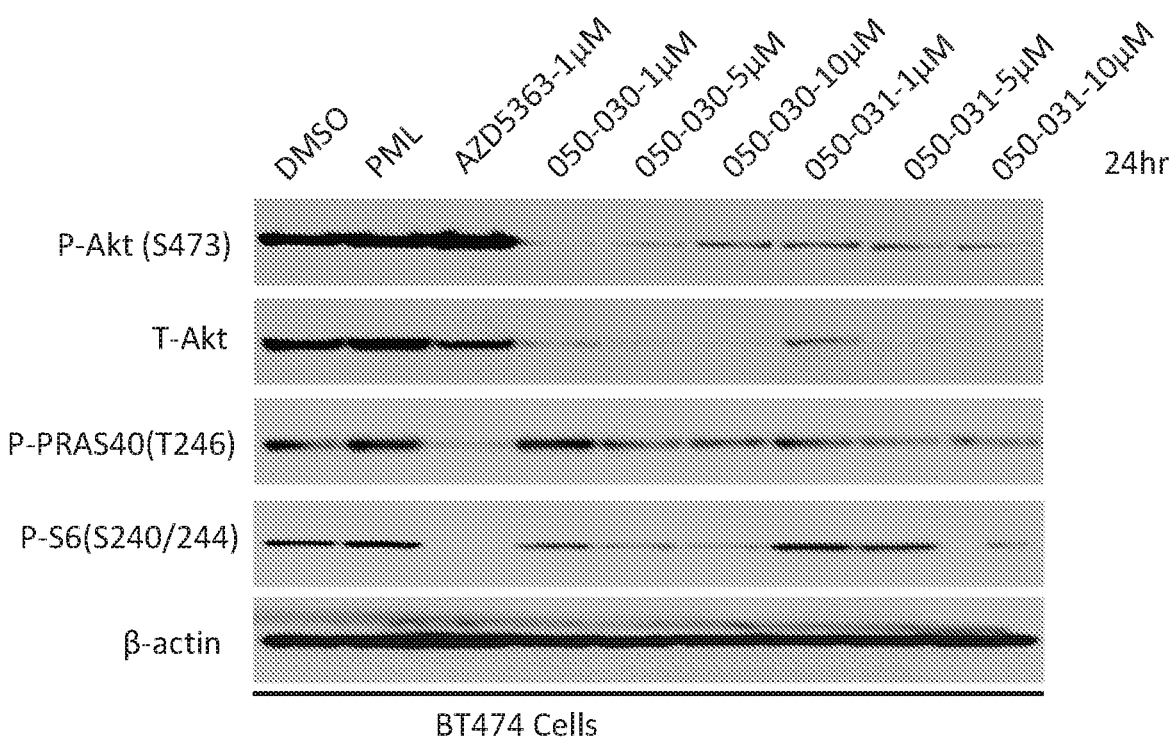
Figure 3:
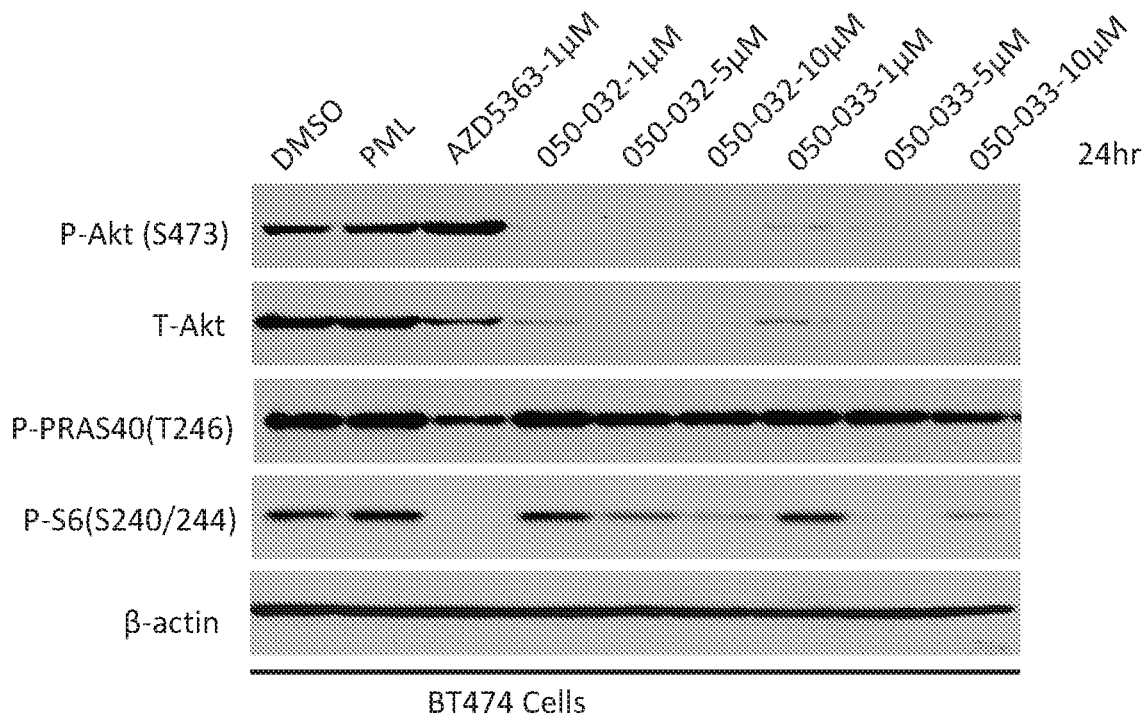
Figures 3, 3B, 4, 5:
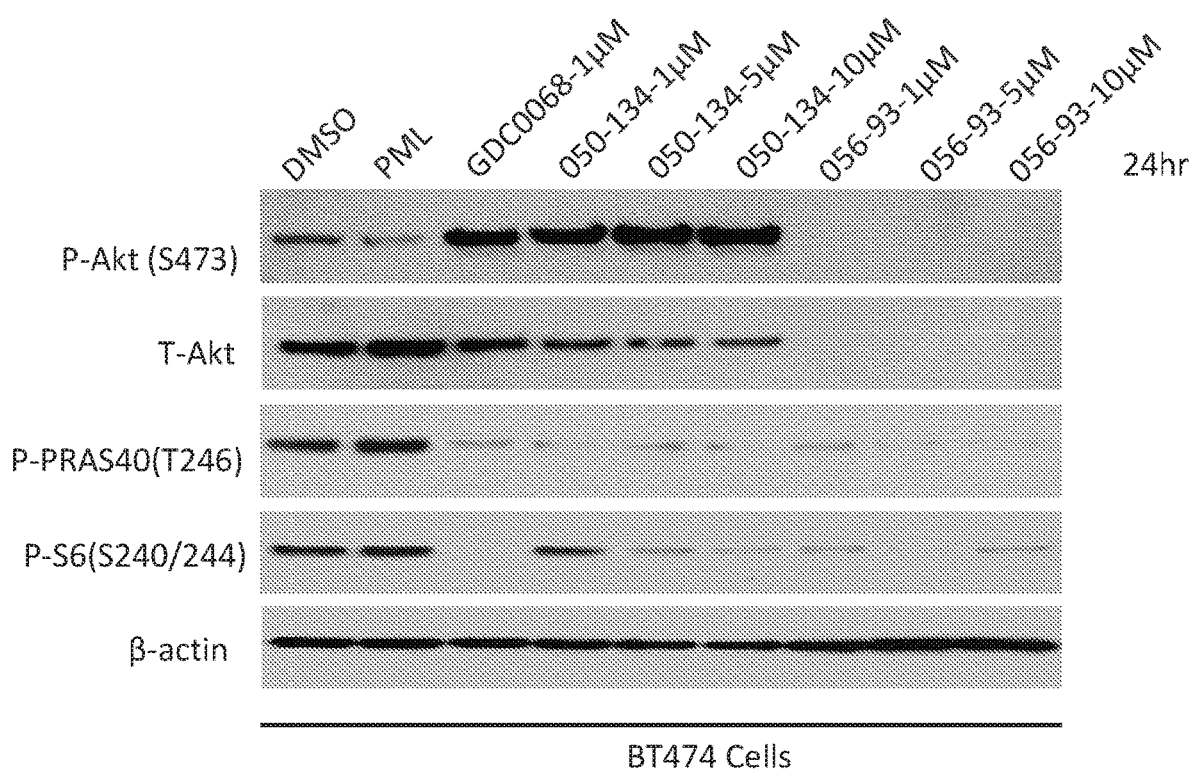
Figure 3C:
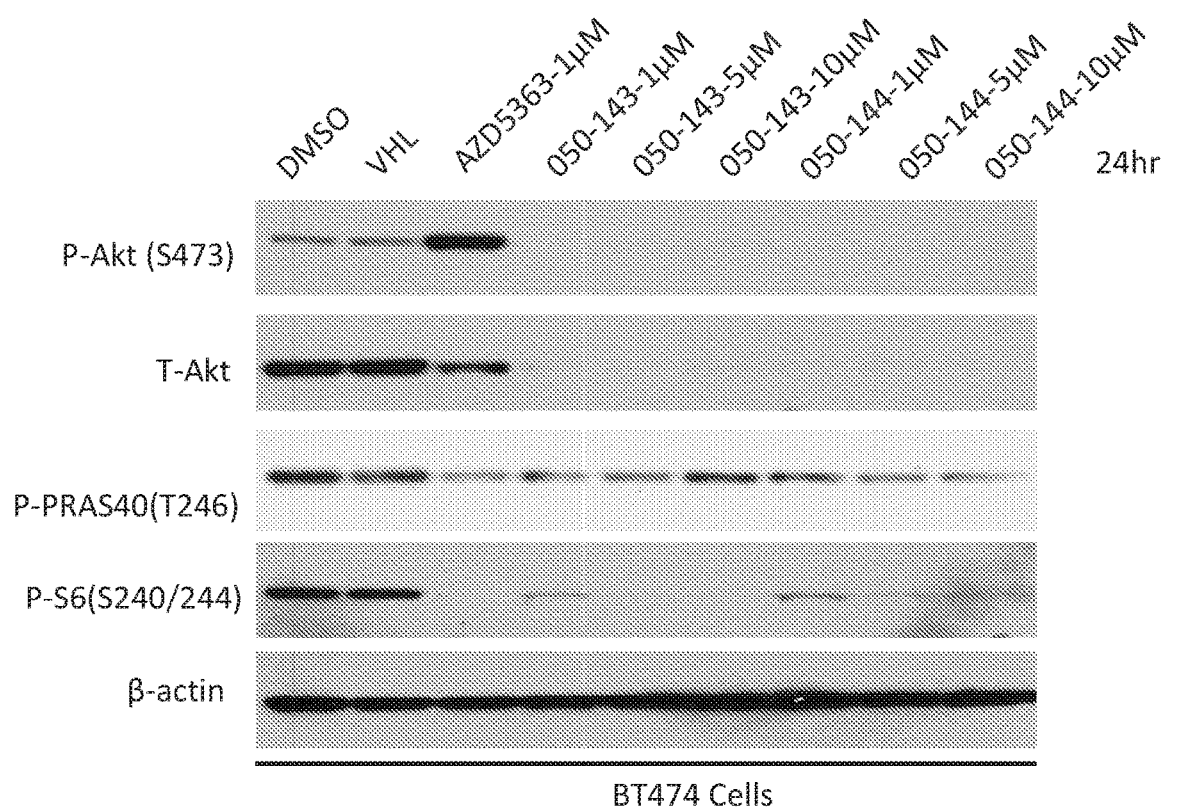
Figure 1:
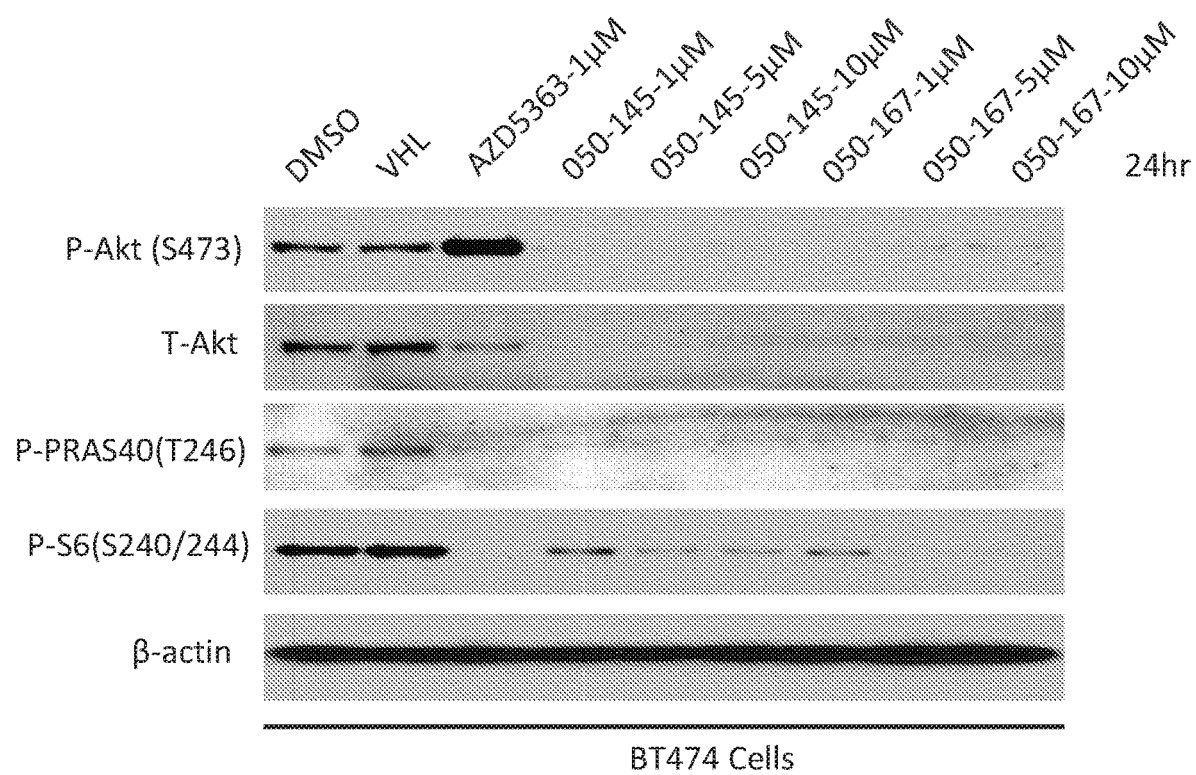
Figure 3C:
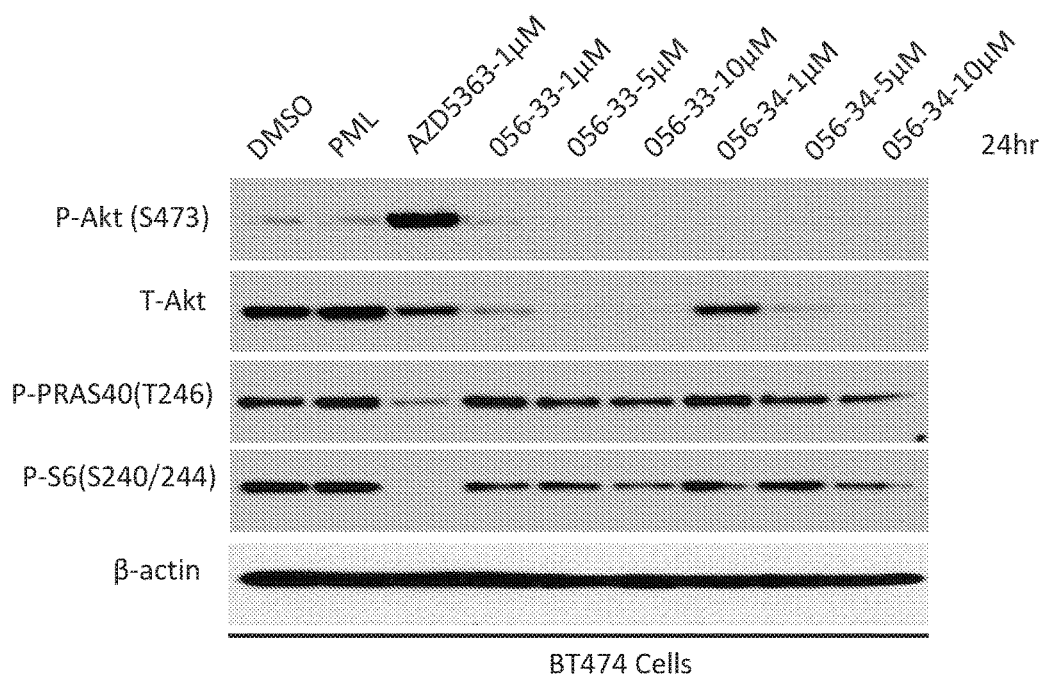
Figure 2:
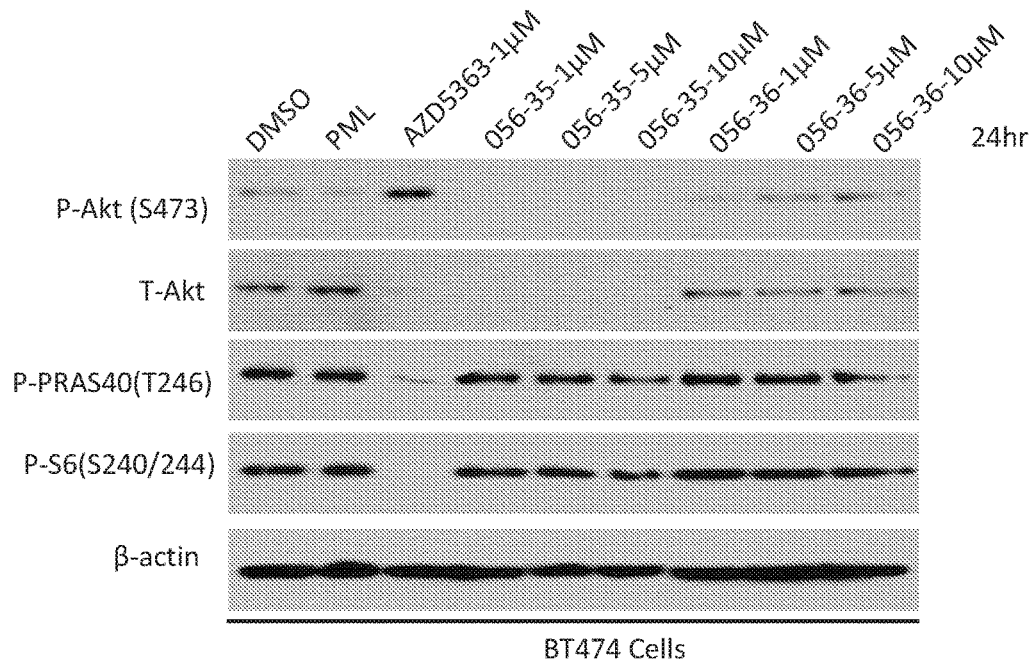
Figures 3, 3C:
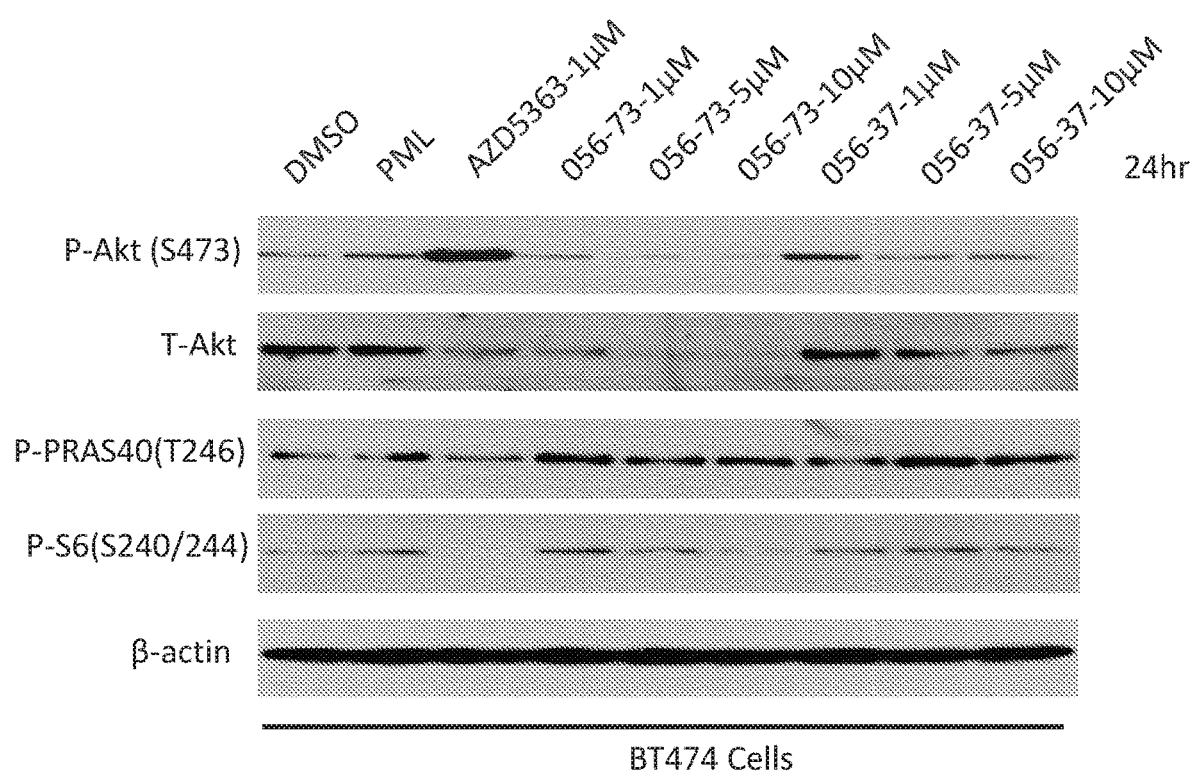
Figure 6:
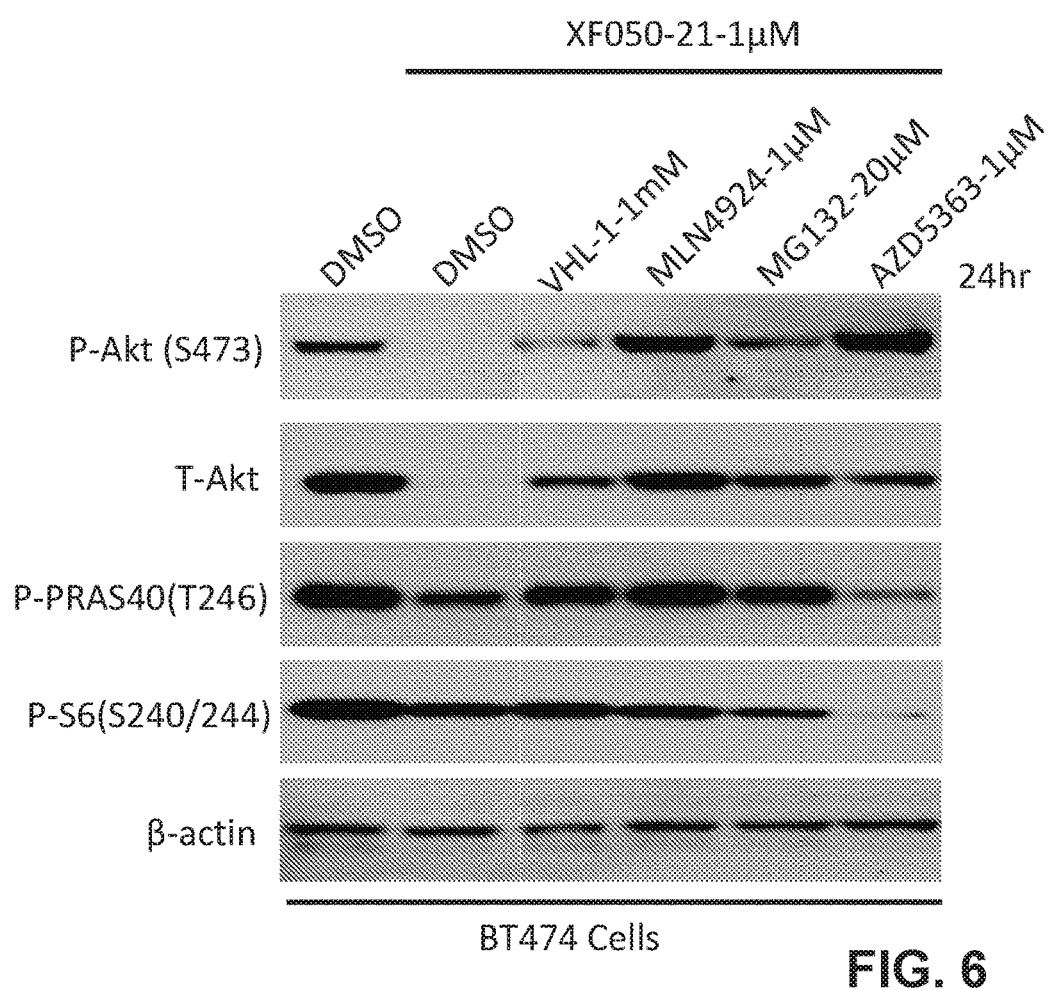
FIG. 6 is a Western blot showing the effect of XF050-21 on reducing the AKT and p-AKT levels can be blocked by pretreatment of VHL-1, MLN4924, MG132, and AZD5363 in BT474 cells.
Figure 7:
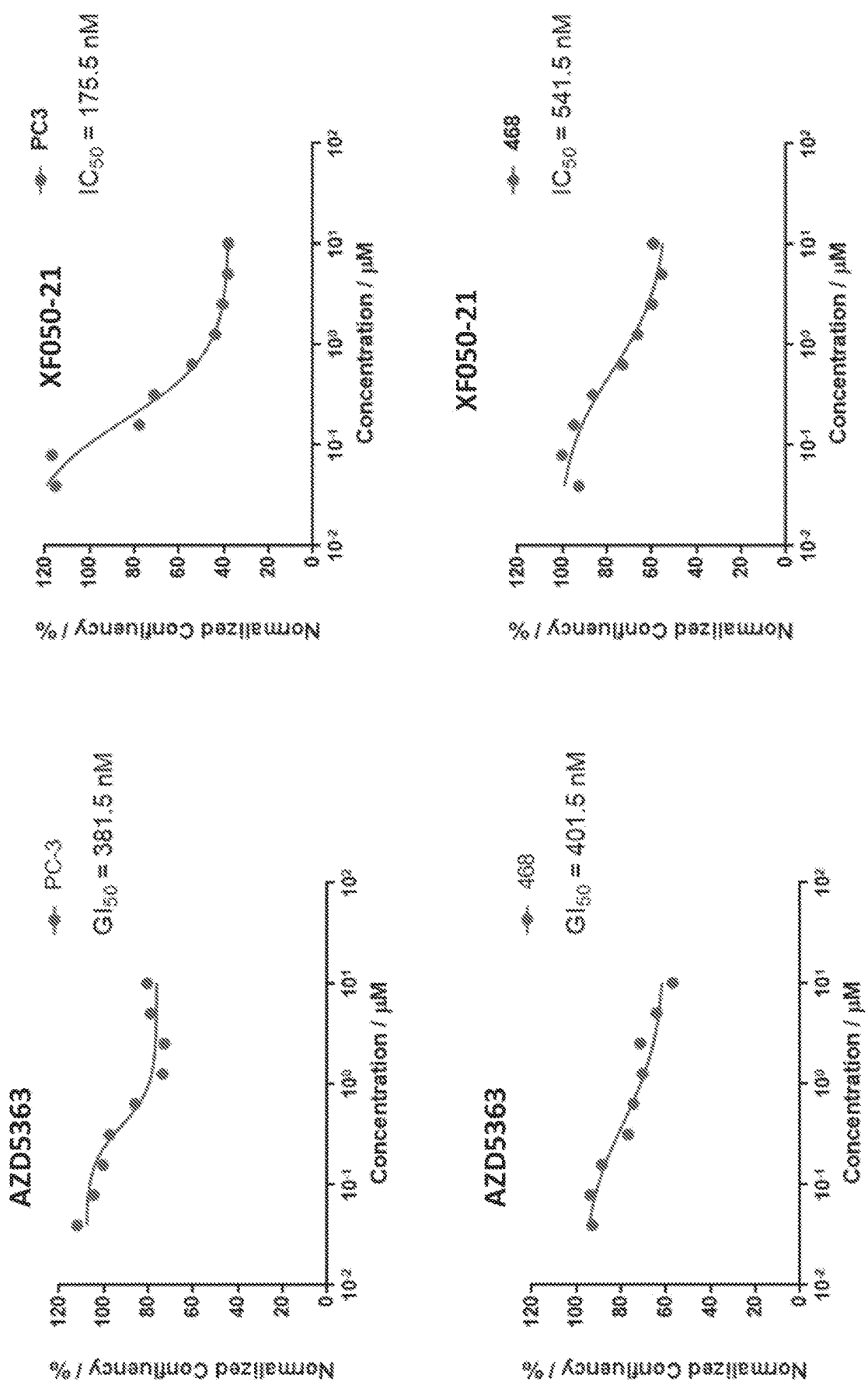
FIG. 7 is a series of concentration-response curves showing that XF050-21 was more effective than AZD5363 in inhibiting cell growth of PC-3 and MDA-MB-468 cells.
Figure 8A:
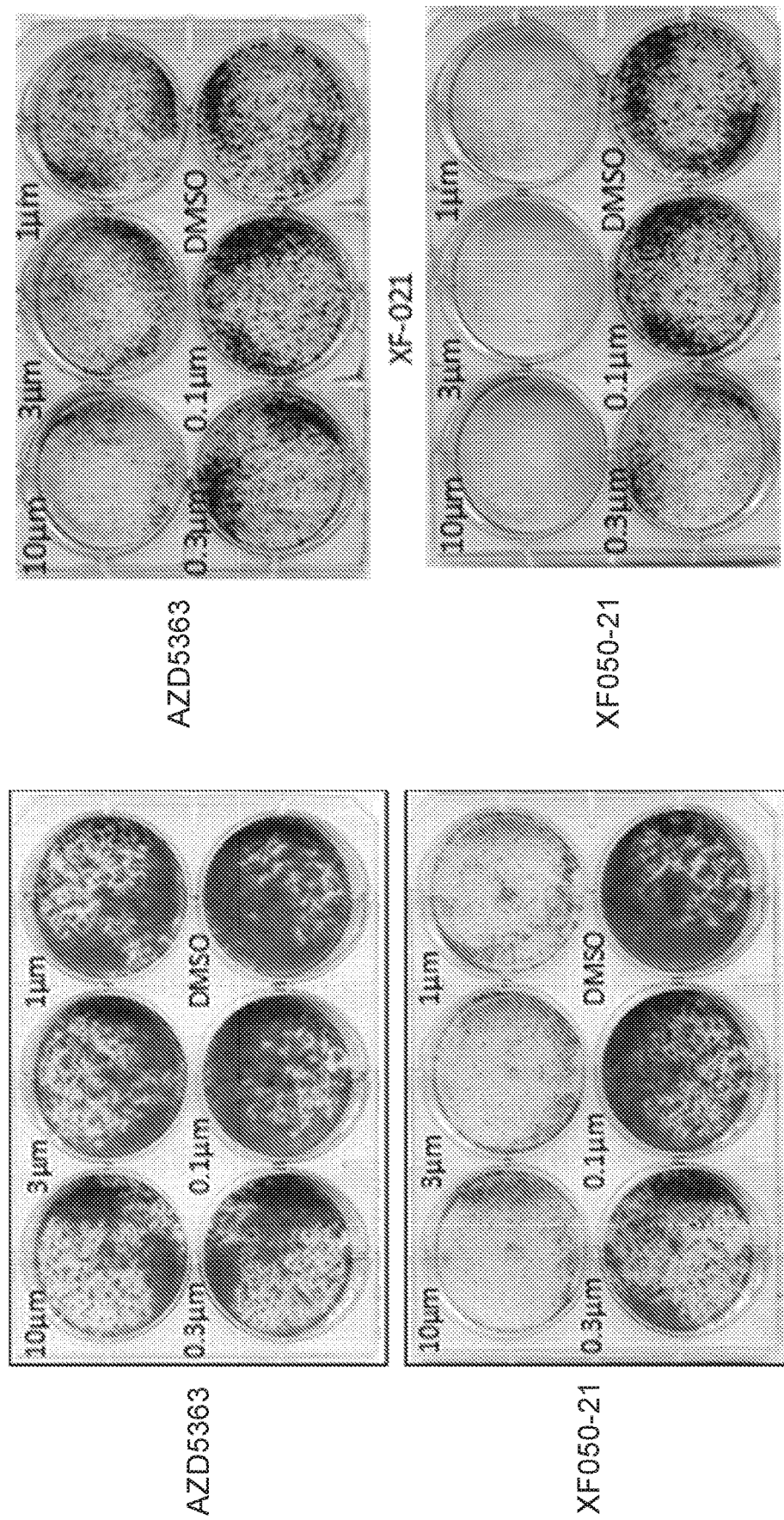
FIG. 8A-B are a series of cell culture dish pictures showing that XF050-21 was more effective than AZD5363 in inhibiting colony formation of PC-3, MDA-MB-468, HCC 1143, and MDA-MB-231 cells.
Figure 8B:
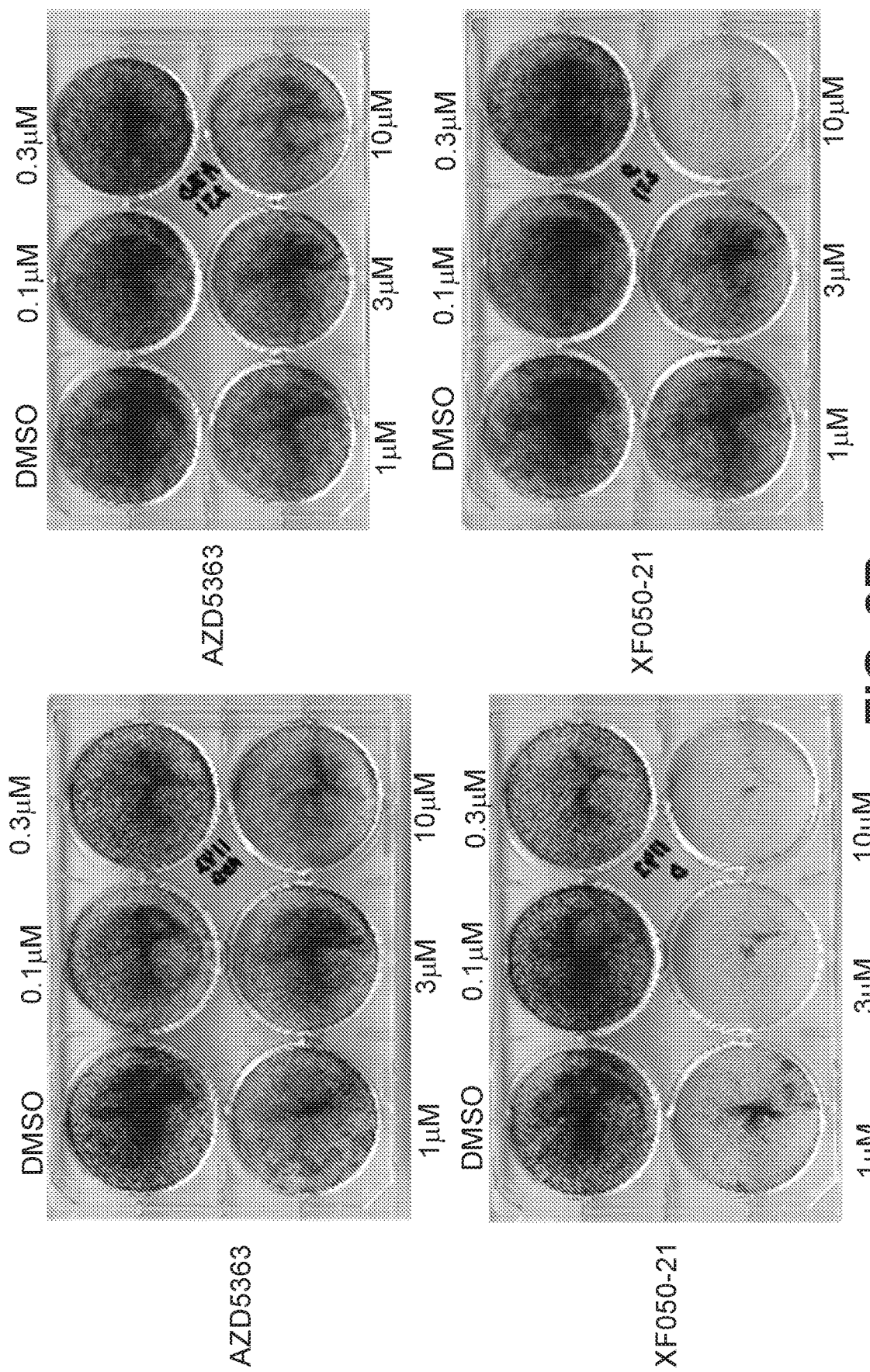
Figure 9:
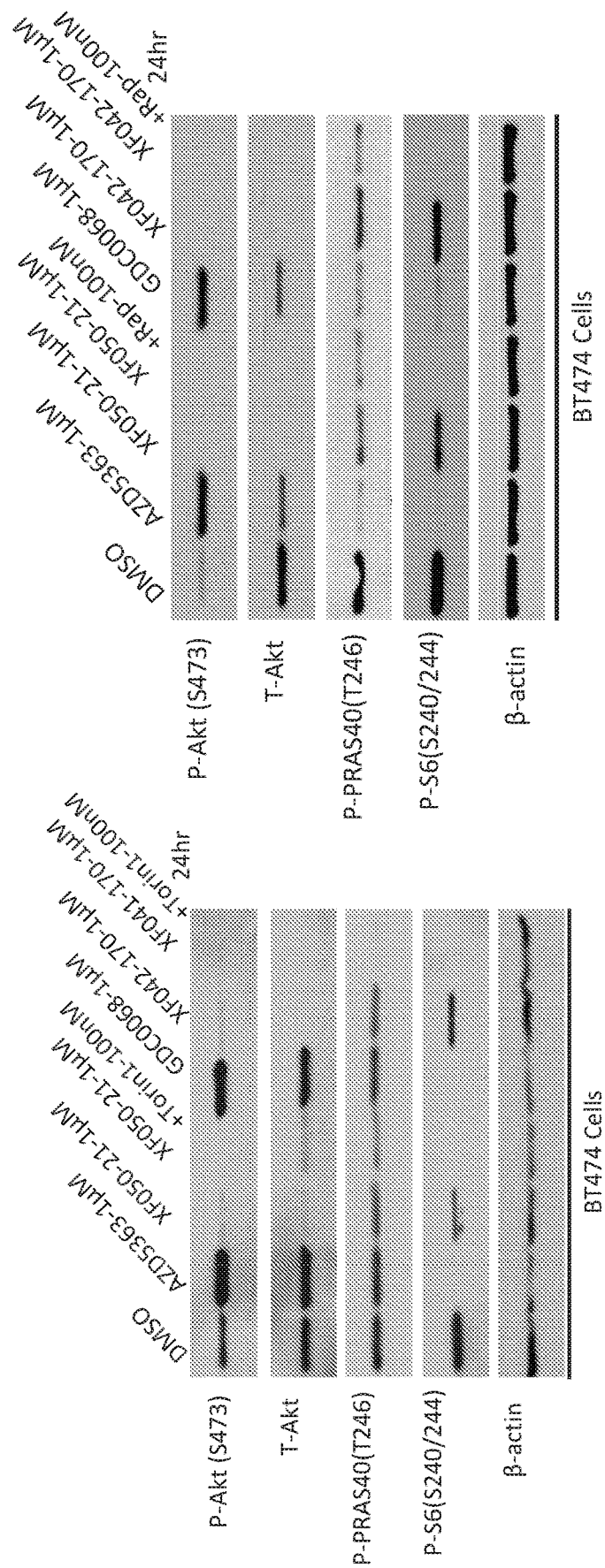
FIG. 9 is a series of Western blots showing the combination effect of an AKT degrader (XF050-21 or XF041-170) with an mTOR inhibitor (Torin1 or Rapamycin) in BT474 cells.
Figure 10:
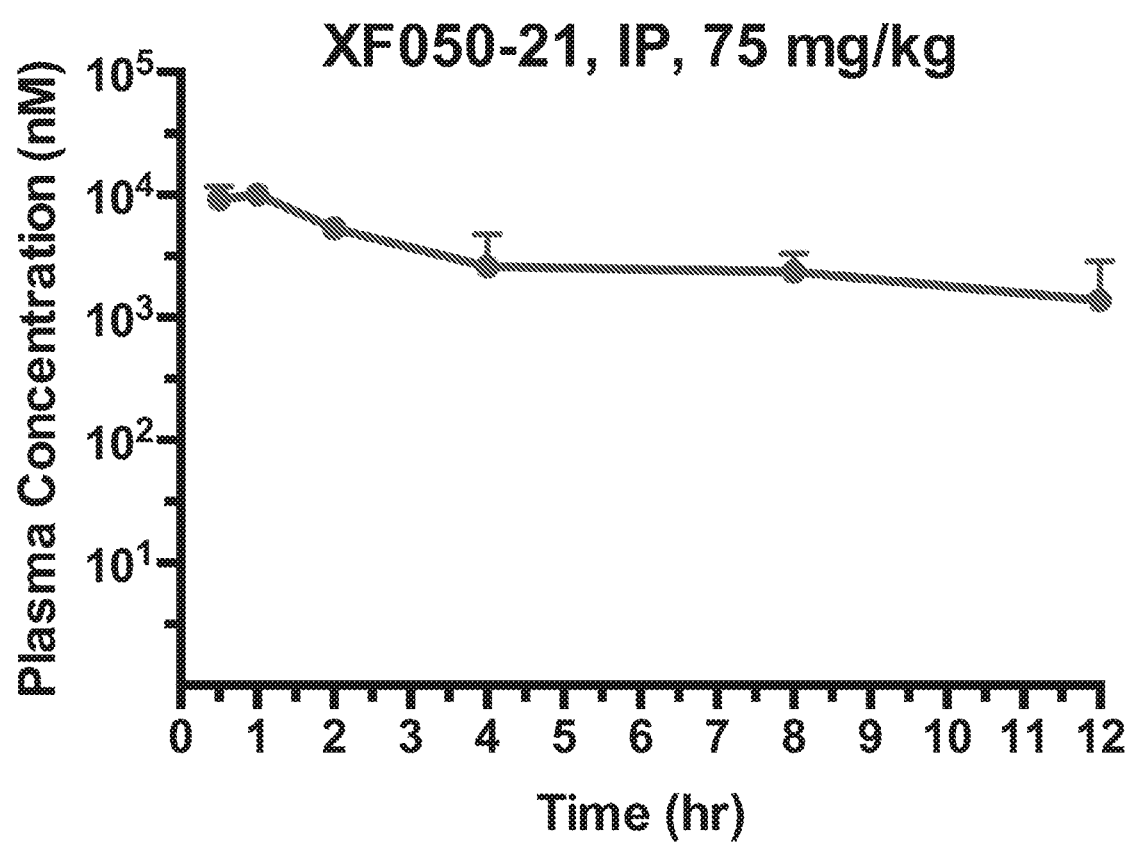
FIG. 10 is the mouse plasma exposure curve of XF050-21.
Figures 1, 11:
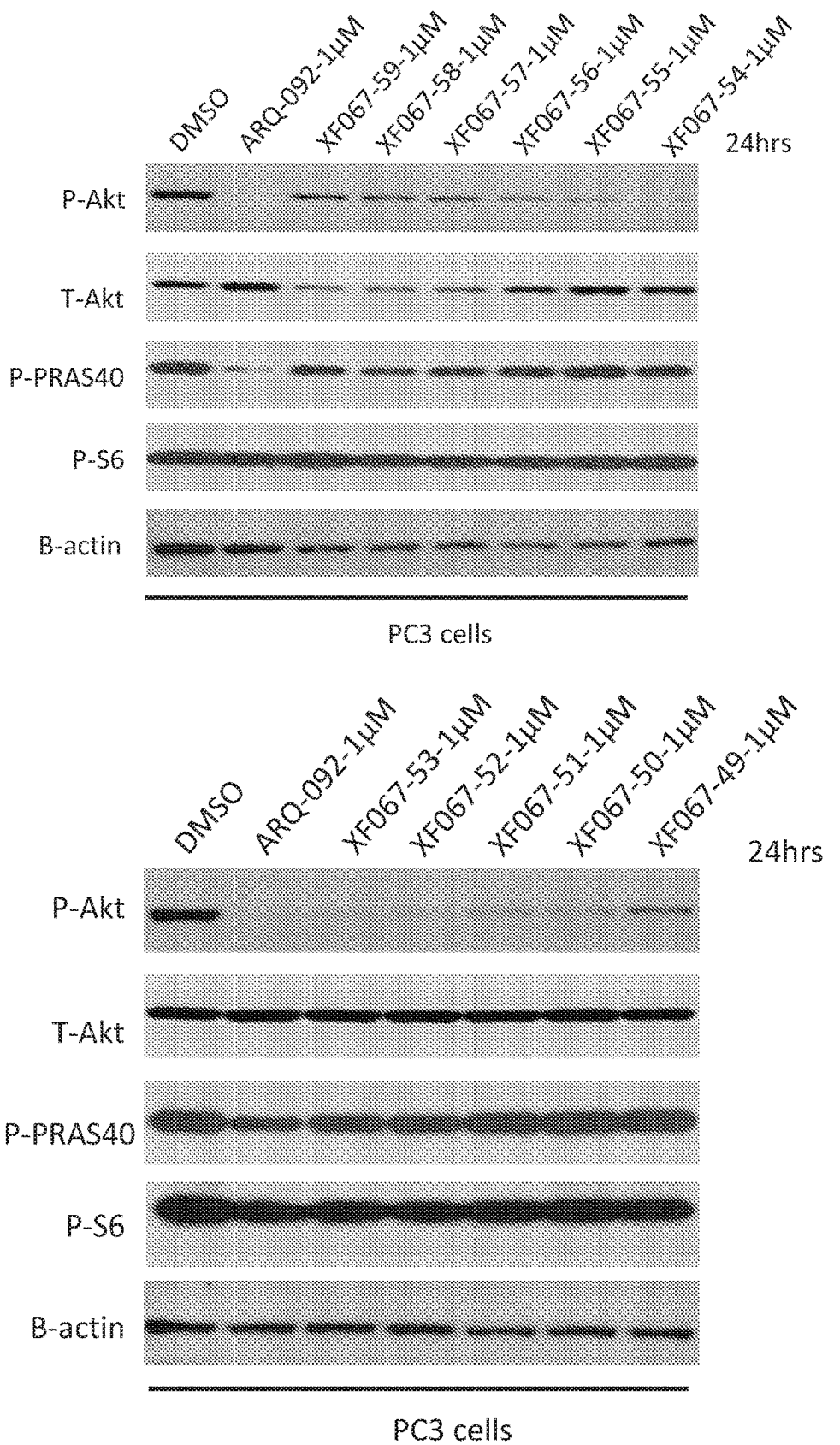
FIG. 11 is a series of Western blots showing the effect of various AKT degraders on reducing AKT, p-AKT, P-PRAS40 (T246), and P-S6 (S240/244) protein levels at 1 μM compound concentration in PC-3 cells.
Figure 11:
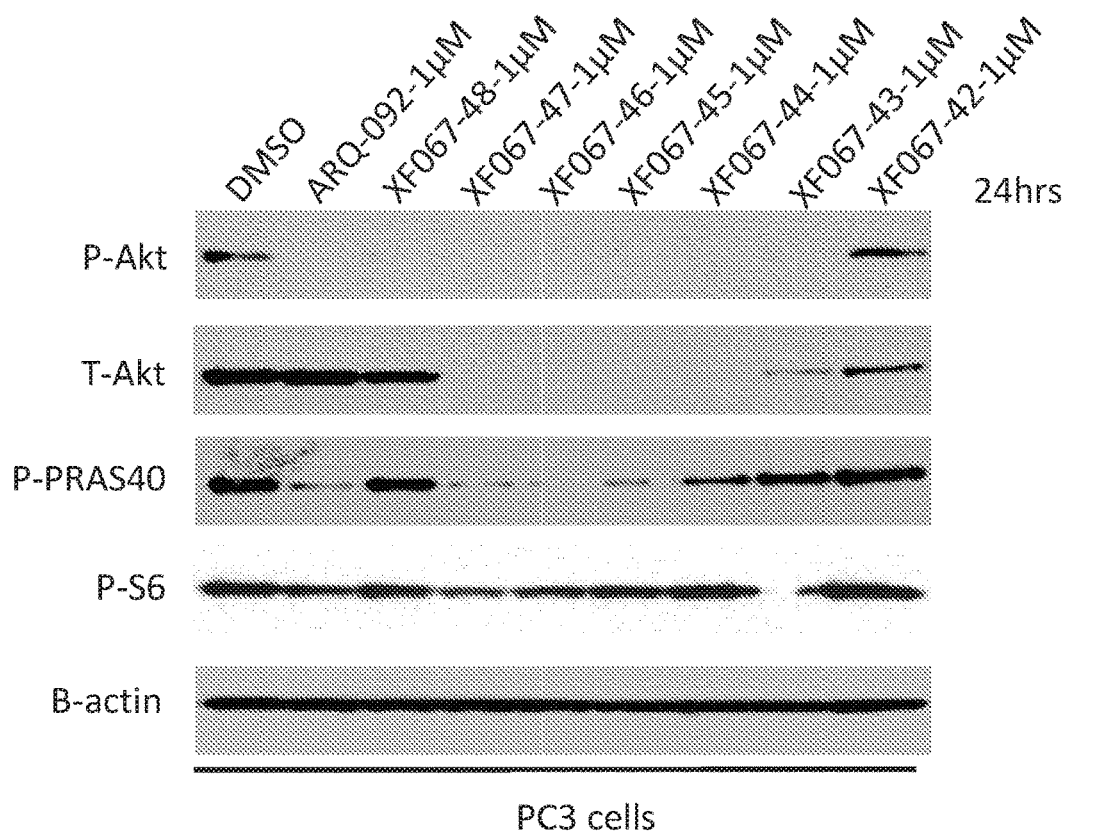
Figure 2:
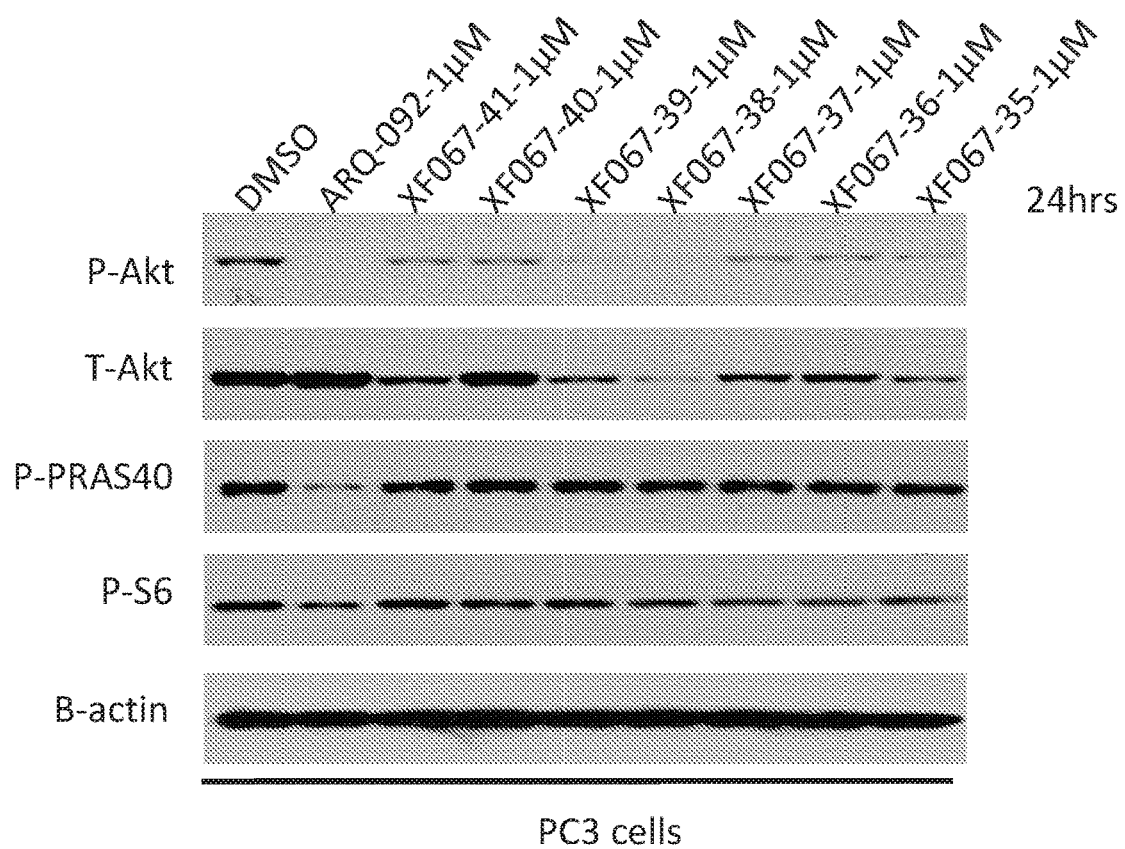
Figure 11:
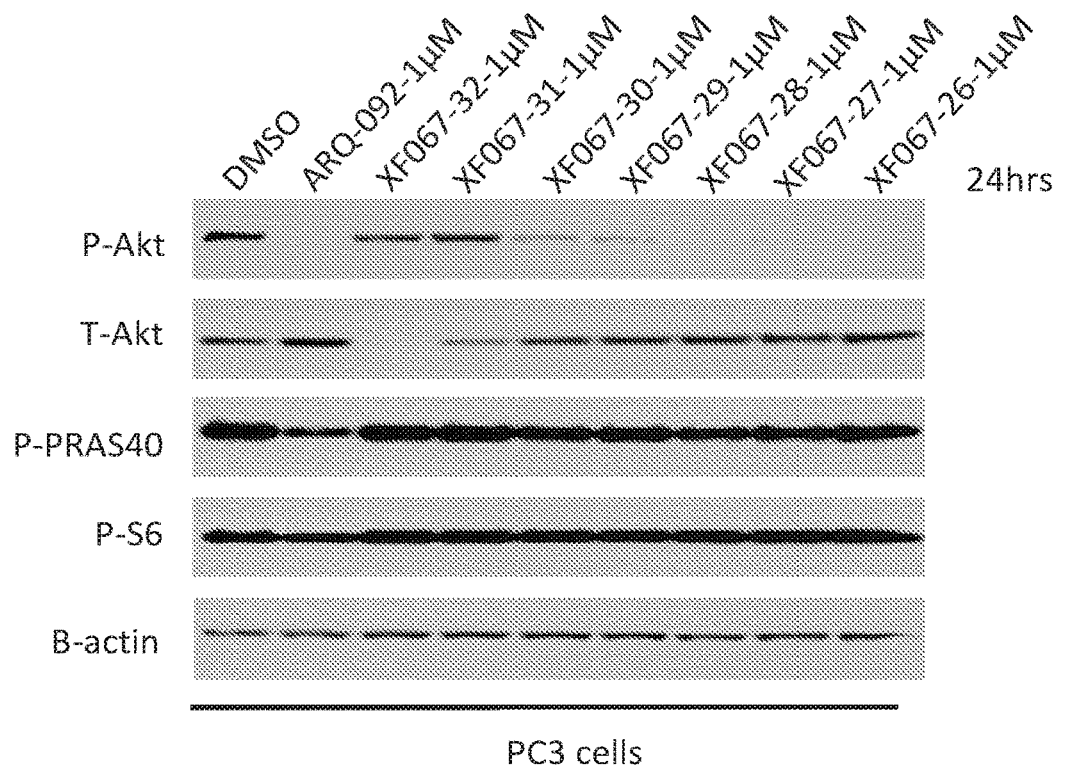
Figure 3:
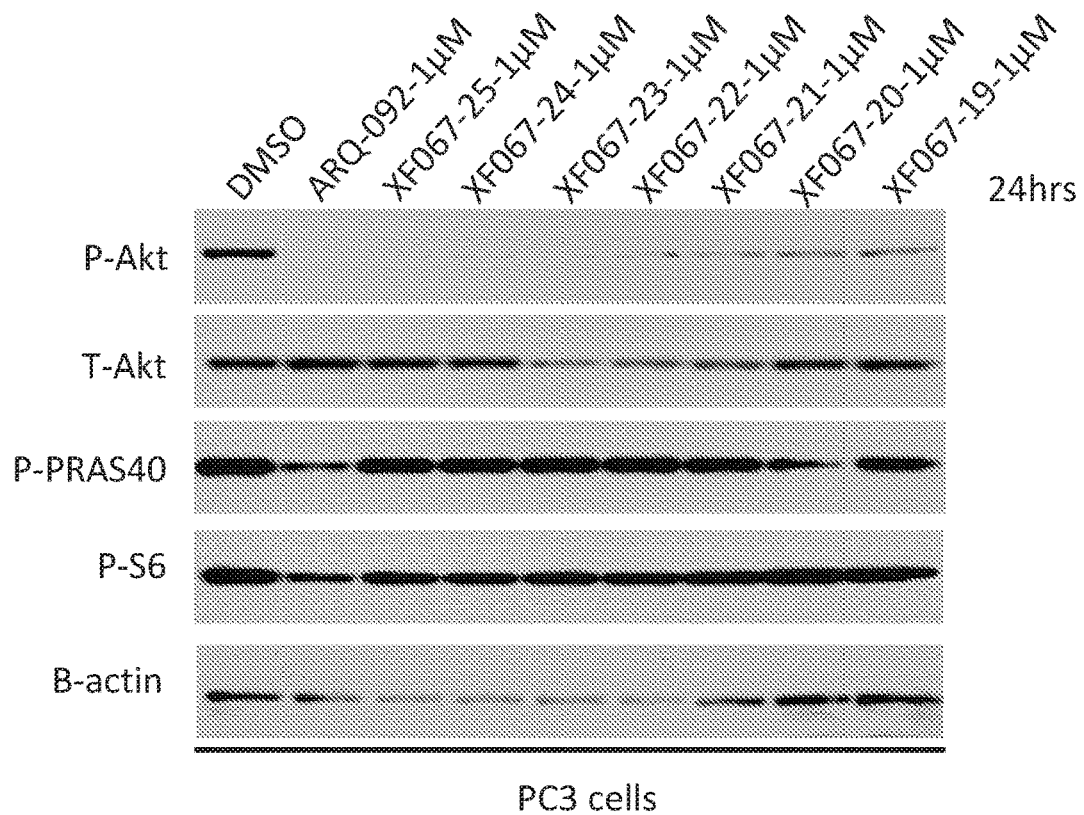
Figure 11:
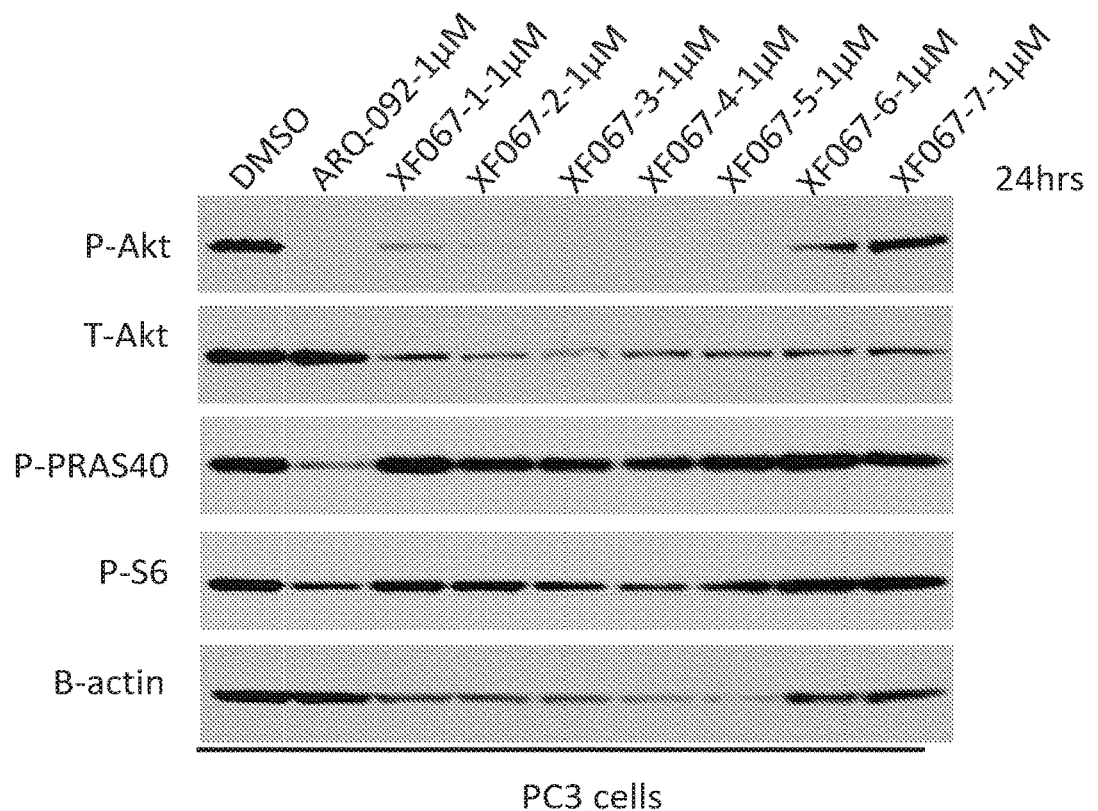
Figure 4:
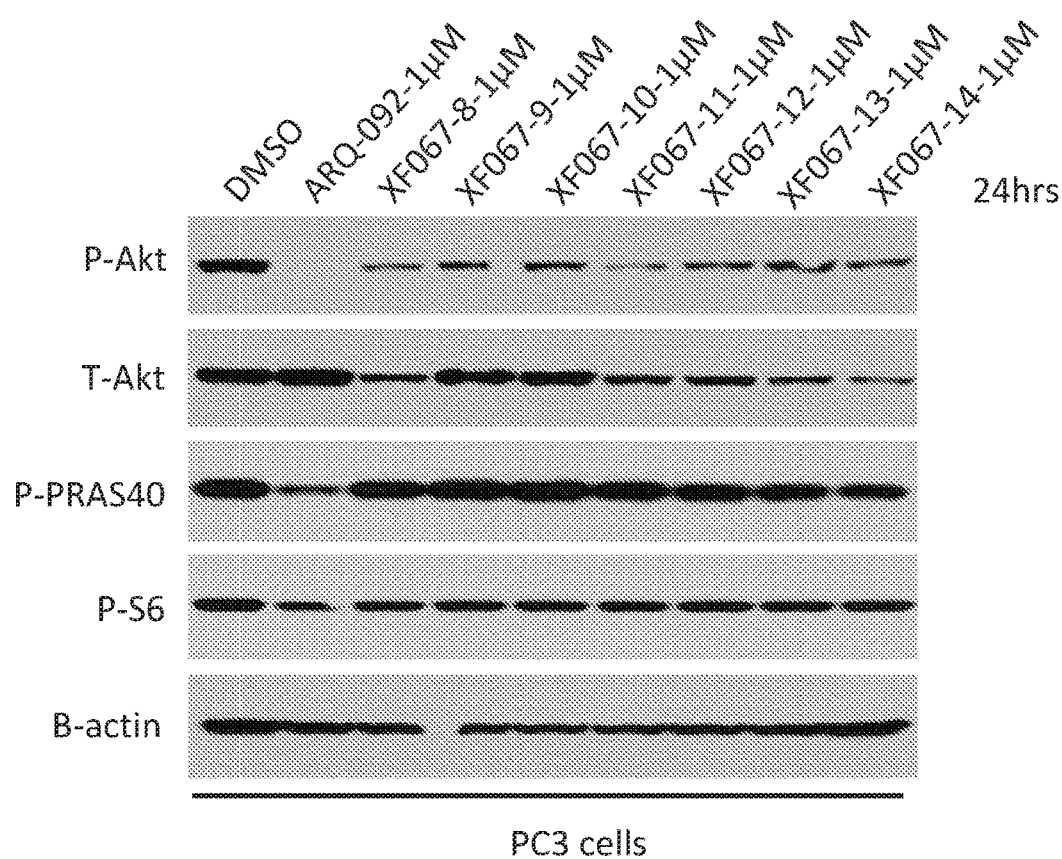
Figures 5, 11:
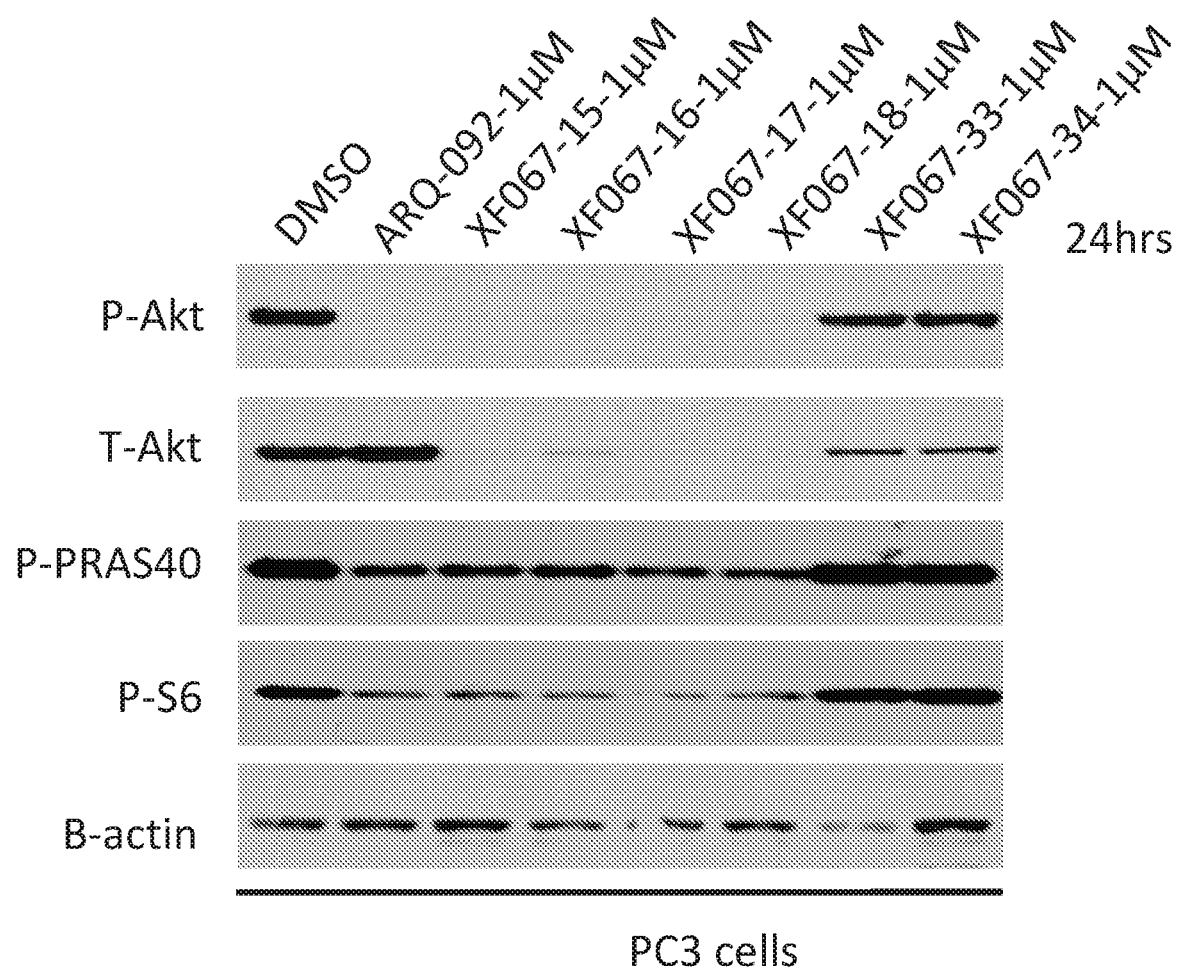
Figure 12:
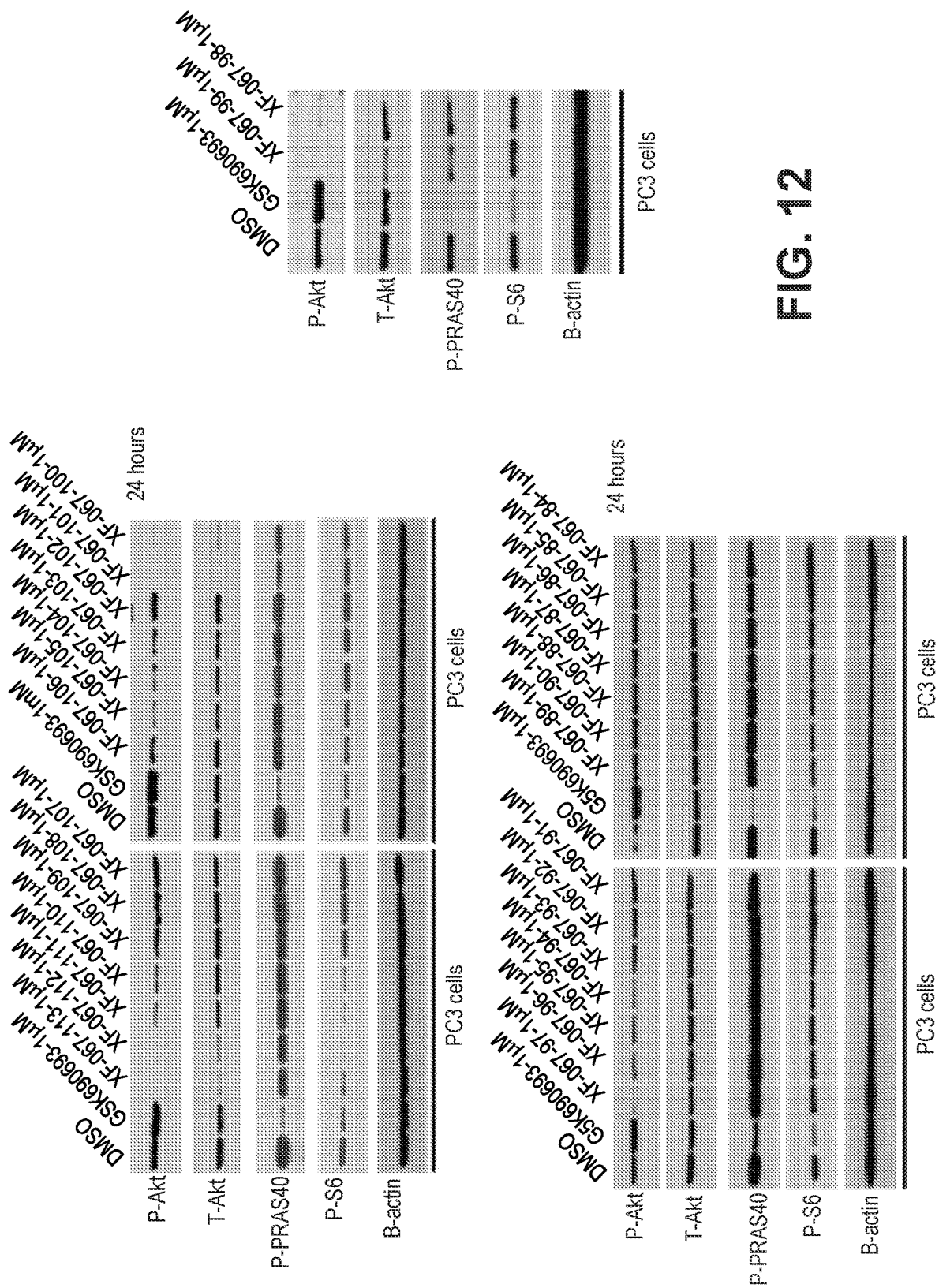
FIG. 12 is a series of Western blots showing the effect of various AKT degraders on reducing AKT, p-AKT, P-PRAS40 and P-S6 (S240/244) protein levels at 1 μM compound concentration in PC-3 cells.

Specific exemplary AKT degraders/disruptors were characterized in various cells and mice (Examples 167-178, FIGS. 1-12). Bifunctional compounds XF038-165A, XF038-166A, XF038-176A, XF038-177A, XF042-162, XF042-168, XF042-170, XF048-1, XF048-2, XF048-3, XF048-4, XF048-5, XF048-7, XF048-8, XF050-5, XF050-7, XF050-16, XF050-17, XF050-18, XF050-19, XF050-20, XF050-21, XF050-30, XF050-31, XF050-32, XF050-33, XF050-98, XF050-133, XF056-93, XF050-143, XF050-144, XF050-145, XF050-167, XF056-33, XF056-34, XF056-35, and XF056-37, in particular were found to be effective in suppressing both AKT protein level and AKT activity in BT474 cells (FIGS. 1, 3, and 4). We further demonstrated that XF038-166A, XF042-162, XF042-170, XF050-21, and XF050-33 induced AKT degradation is time-dependent with 24 h being the time point for the most significant AKT degradation in BT474 cells (FIGS. 2 and 5). Using XF050-21, we showed that the observed AKT degradation can be rescued by pretreatment of the cells with VHL-1, MLN4924, MG132 and AZD5363 (FIG. 6). In FIG. 7, we compared the cell proliferation inhibition effects of AZD5363 and XF050-21. XF050-21 displayed better cell proliferation inhibition activity than AZD5363 in PC3 and MDA-MB-468 cells. In FIG. 8, XF050-21 showed better colony formation inhibition than AZD5363 in PC3, MDA-MB-468, HCC1143, and MDA-MB-231 cells. In FIG. 9, we showed that the combination treatment using an AKT degrader (XF050-21 or XF041-170) and a MTOR inhibitor (torin1 or rapamycin) significantly reduced the AKT protein levels and AKT downstream signaling in BT474 cells. In mice, XF050-21-22 was bioavailable at 75 mg/kg via IP administration (FIG. 10). Additional bifunctional compounds were tested at 1 uM concentration in PC-3 cells. Compounds XF067-15, XF067-16, XF067-17, XF067-18, XF067-44, XF067-45, XF067-46, XF067-47, XF067-98, XF067-99, XF067-100, XF067-101, XF067-112 and XF067-113 were found to be effective in suppressing AKT protein level and AKT activity at 1 µM concentration in PC-3 cells (FIGS. 11 and 12).

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents known in the art. When co-administered, AKT degraders/disruptors disclosed herein can operate in conjunction with conventional chemotherapeutic agents to produce mechanistically additive or synergistic therapeutic effects.

In some aspects, the pH of the compositions disclosed herein can be adjusted with pharmaceutically acceptable acids, bases, or buffers to enhance the stability of the AKT degraders/disruptor or its delivery form.

Pharmaceutical compositions typically include a pharmaceutically acceptable carrier, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable carrier, adjuvant, or vehicle is a composition that can be administered to a patient, together with a compound of the invention, and which does not destroy the pharmacological activity thereof and is nontoxic when administered in doses sufficient to deliver a therapeutic amount of the compound. Exemplary conventional nontoxic pharmaceutically acceptable carriers, adjuvants, and vehicles include saline, solvents, dispersion media, coatings, antibacterial and antifungal agents, isotonic and absorption delaying agents, and the like, compatible with pharmaceutical administration.

In particular, pharmaceutically acceptable carriers, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

As used herein, the AKT degraders/disruptors disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, 5$^{th}$ Edition, Vol. 1: Principles and Practice, which is incorporated herein by reference to the extent of teaching such derivatives.

The AKT degraders/disruptors disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivatives thereof.

In particular, pharmaceutically acceptable salts of the AKT degraders/disruptors disclosed herein include, e.g., those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate, trifluoromethylsulfonate, and undecanoate. Salts derived from appropriate bases include, e.g., alkali metal (e.g., sodium), alkaline earth metal (e.g., magnesium), ammonium and N-(alkyl)4+ salts. The invention also envisions the quaternization of any basic nitrogen-containing groups of the AKT degraders/disruptors disclosed herein. Water or oil-soluble or dispersible products can be obtained by such quaternization.

In some aspects, the pharmaceutical compositions disclosed herein can include an effective amount of one or more AKT degraders/disruptors. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium.

For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of a compound of the formulae described herein (e.g., an AKT degraders/disruptors) and one or more additional compounds (e.g., one or more additional compounds, drugs, or agents used for the treatment of cancer or any other condition or disease, including conditions or diseases known to be associated with or caused by cancer), both the compound and the additional compound should be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, the present disclosure provides methods for using a composition comprising an AKT degrader/disruptor, including pharmaceutical compositions (indicated below as 'X') disclosed herein in the following methods: Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition from which the subject is suffering (e.g., an AKT-mediated disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of a degrader/disruptor (e.g., an AKT degrader/disruptor) described herein.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention. Exemplary AKT-mediated diseases that can be treated with AKT degraders/disruptors include, for example, cancer, inflammatory, hyperproliferative cardiovascular, neurodegenerative, gynecological, and dermatological diseases and disorders.

In an aspect, the AKT degraders of the present disclosure can be employed for the treatment of hyperproliferative disorders, including cancers angiosarcoma, fibrosarcoma, rhabdomyosarcoma, liposarcoma, myxoma, rhabdomyoma, fibroma, lipoma, teratoma, squamous cell carcinoma, undifferentiated small cell carcinoma, undifferentiated large cell carcinoma, adenocarcinoma, alveolar carcinoma, bronchial adenoma, sarcoma, lymphoma, chondromatous hamartoma, mesothelioma, non-small cell lung cancer, small cell lung cancer, leiomyosarcoma, stomach carcinoma, ductal adenocarcinoma, insulinoma, glucagonoma, gastrinoma, carcinoid tumors, vipoma, carcinoid tumors, Karposi's sarcoma, leiomyoma, hemangioma, neurofibroma, tubular adenoma, villous adenoma, hamartoma, kidney cancer, Wilm's tumor, nephroblastoma, leukemia, bladder cancer, urethra cancer, transitional cell carcinoma, prostate cancer, seminoma, embryonal carcinoma, teratocarcinoma, choriocarcinoma, interstitial cell carcinoma, fibroadenoma, adenomatoid tumors, hepatoma, hepatocellular carcinoma, cholangiocarcinoma, hepatoblastoma, hepatocellular adenoma, osteogenic sarcoma, osteosarcoma, malignant fibrous histiocytoma, chondrosarcoma, Ewing's sarcoma, malignant lymphoma, reticulum cell sarcoma, multiple myeloma, malignant giant cell tumor chordoma, osteochronfroma, osteocartilaginous exostoses, benign chondroma, chondroblastoma, chondromyxofibroma, osteoid osteoma, giant cell tumors, osteoma, granuloma, xanthoma, osteitis deformans, meningioma, meningiosarcoma, gliomatosis, astrocytoma, medulloblastoma, glioma, ependymoma, germinoma, pinealoma, glioblastoma multiforme, oligodendroglioma, schwannoma, retinoblastoma, congenital tumors, spinal cord neurofibroma, endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, intraepithelial carcinoma, melanoma, clear cell carcinoma, botryoid sarcoma, embryonal fallopian tubes carcinoma, acute myeloid leukemia, chronic myeloid leukemia, acute lymphoblastic leukemia, chronic lymphocytic leukemia, myeloproliferative diseases, myelodysplastic syndrome, Hodgkin's disease, non-Hodgkin's lymphoma, advanced melanoma, malignant melanoma, basal cell carcinoma, moles dysplastic nevi, angioma, dermatofibroma, keloids, psoriasis, neuroblastoma, metastatic breast cancer, colon cancer, oral cancer, hairy cell leukemia, head and neck cancer, refractory metastatic disease; Kaposi's sarcoma, Bannayan-Zonana syndrome, Cowden disease, Lhermitte-Duclos disease.

The compounds and methods of this disclosure can be also used to treat diseases and conditions such as rheumatoid arthritis, osteoarthritis, Crohn's disease, angiofibroma, retinal vascularization, diabetic retinopathy, age-related macular degeneration, macular degeneration, multiple sclerosis, obesity, Alzheimer's disease, restenosis, autoimmune diseases, allergy, asthma, endometriosis, atherosclerosis, vein graft stenosis, peri-anastomatic prosthetic graft stenosis, prostate hyperplasia, chronic obstructive pulmonary disease, psoriasis, inhibition of neurological damage due to tissue repair, scar tissue formation, multiple sclerosis, inflammatory bowel disease, infections, particularly bacterial, viral, retroviral or parasitic infections, pulmonary disease, neoplasm, Parkinson's disease, transplant rejection, and septic shock.

The AKT-mediated disease can be a relapsed disease. The AKT-mediated disease can have been refractory to one or more previous treatments by different therapies.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The present disclosure is also described and demonstrated by way of the following examples. However, the use of these and other examples anywhere in the specification is illustrative only and in no way limits the scope and meaning of the invention or of any exemplified term. Likewise, the invention is not limited to any particular preferred embodiment or aspect described herein. Indeed, many modifications and variations may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1: Synthesis of Intermediate 2

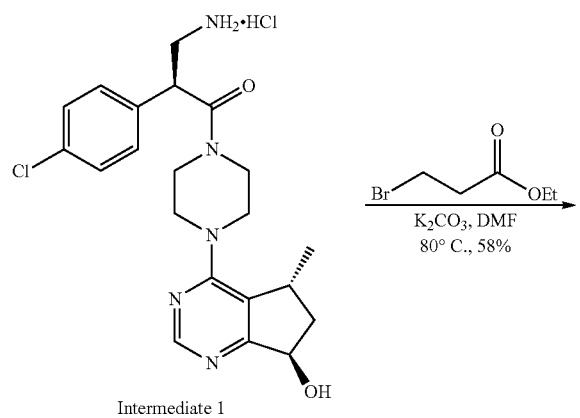

Intermediate 1

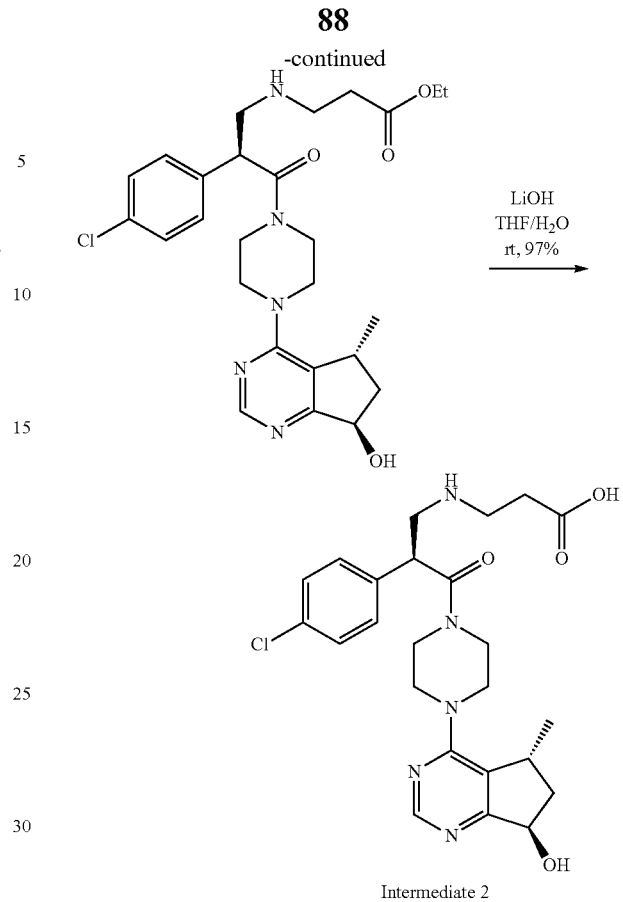

Intermediate 2

To a solution of intermediate 1 (Blake et al., 2012) (360 mg, 0.86 mmol) in DMF (10 mL) was added potassium carbonate (358 mg, 2.6 mmol, 3 equiv). The resulting suspension was stirred at 80° C. for 15 min, before ethyl 3-bromopropanoate (310 mg, 1.72 mmol, 2 equiv) was added to the solution. After the reaction was stirred overnight, water was added to quench the reaction. The mixture was extracted with ethyl acetate (3×10 mL), dried over $Na_2SO_4$, filtered and evaporated. The resulting residue was purified by silica gel column (DCM/MeOH=10:1) to afford the pure product ethyl 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)propanoate (257 mg, yield 58%). The obtained intermediate was dissolved in $THF/H_2O$ (1:1). To the resulting solution was added lithium hydroxide (12 mg, 0.5 mmol). After being stirred overnight at room temperature, the reaction mixture was concentrated and the residue was purified by reverse phase C18 column (10%-100% methanol/0.1% TFA zin $H_2O$) to afford intermediate 2 as white solid in TFA salt form (238 mg, 97% yield). $^1$H NMR (600 MHz, $CD_3OD$) δ 8.57 (d, J=4.5 Hz, 1H), 7.47 (dt, J=8.7, 2.3 Hz, 2H), 7.36 (dd, J=8.4, 6.0 Hz, 2H), 5.28 (t, J=7.9 Hz, 1H), 4.50 (ddd, J=9.7, 6.6, 4.1 Hz, 1H), 4.37 (td, J=7.9, 4.6 Hz, 1H), 4.24-4.10 (m, 1H), 4.09-4.01 (m, 1H), 3.95-3.81 (m, 4H), 3.65 (dd, J=12.9, 8.9 Hz, 3H), 3.52-3.38 (m, 2H), 3.21 (dd, J=12.8, 4.6 Hz, 1H), 2.78 (t, J=6.4 Hz, 2H), 2.28 (dd, J=12.9, 7.4 Hz, 1H), 2.17 (ddt, J=12.6, 8.3, 4.1 Hz, 1H), 1.19 (dd, J=21.1, 7.0 Hz, 3H). HRMS (m/z) for $C_{24}H_{31}ClN_5O_4^+$ [M+H]$^+$: molecular weight calculated 488.2059, found 488.2057.

Example 2

Synthesis of XF038-157A

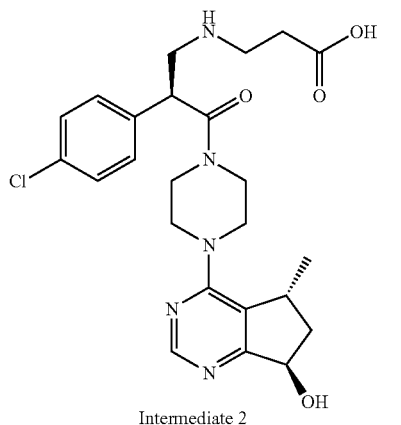

Intermediate 2

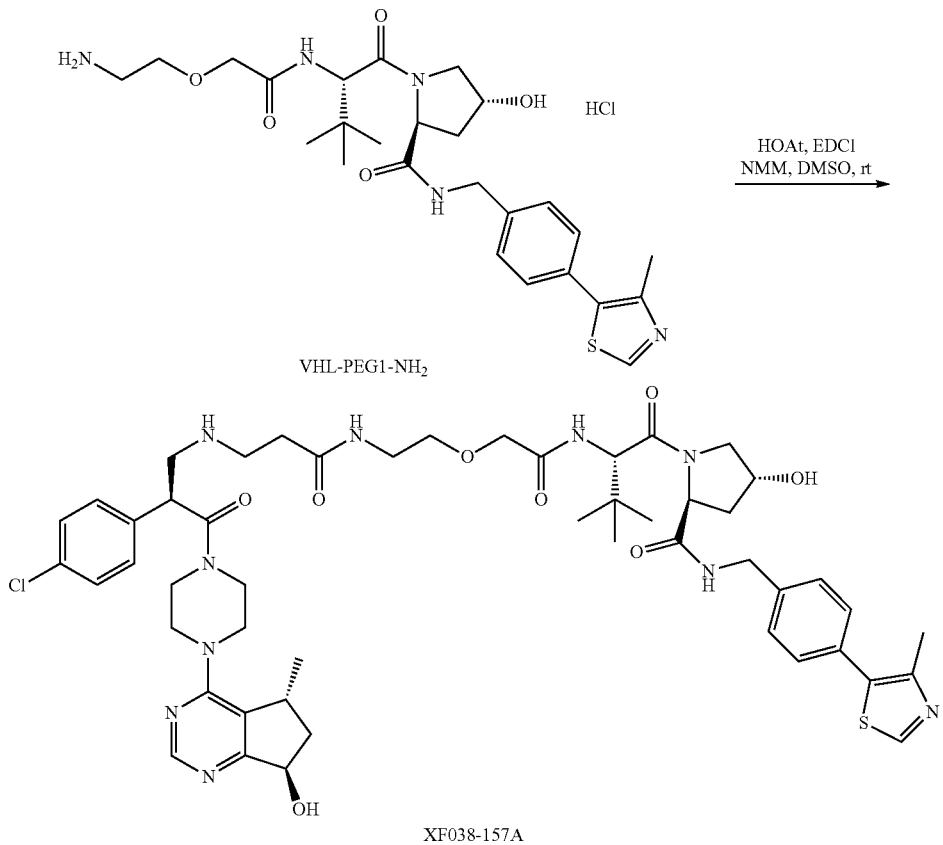

To a solution of Intermediate 2 (12 mg, 0.02 mmol) in DMSO (1 mL) were added VHL-PEG1-NH$_2$ (11.3 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirred overnight at room temperature, the resulting mixture was purified by preparative HPLC (10%-100% methanol/0.1% TFA in H$_2$O) to afford XF038-157A as white solid in TFA salt form (18.2 mg, 91%). $^1$H NMR (600 MHz, CD$_3$OD) δ 8.97 (s, 1H), 8.58 (s, 1H), 7.54-7.39 (m, 6H), 7.39-7.30 (m, 2H), 5.31 (t, J=8.0 Hz, 1H), 4.71 (s, 1H), 4.61-4.45 (m, 4H), 4.42-4.36 (m, 1H), 4.17 (s, 1H), 4.08-4.03 (m, 1H), 3.99-3.76 (m, 7H), 3.71-3.54 (m, 7H), 3.47-3.36 (m, 3H), 3.28-3.23 (m, 1H), 2.80-2.64 (m, 3H), 2.48 (s, 3H), 2.33-2.22 (m, 2H), 2.17 (dt, J=12.7, 8.2 Hz, 1H), 2.09 (ddd, J=13.4, 9.4, 4.4 Hz, 1H), 1.17 (d, J=6.9 Hz, 3H), 1.04 (s, 9H). HRMS (m/z) for C$_{50}$H$_{66}$ClN$_{10}$O$_8$S$^+$ [M+H]$^+$: molecular weight calculated 1001.4469, found 1001.4472.

Example 3

Synthesis of XF038-158A

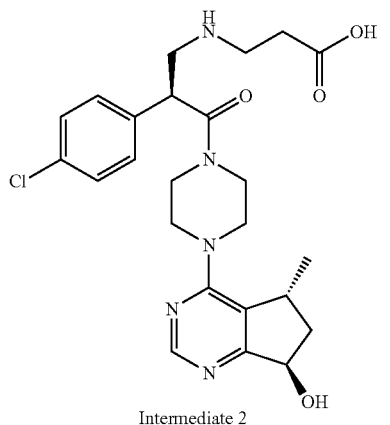

Intermediate 2

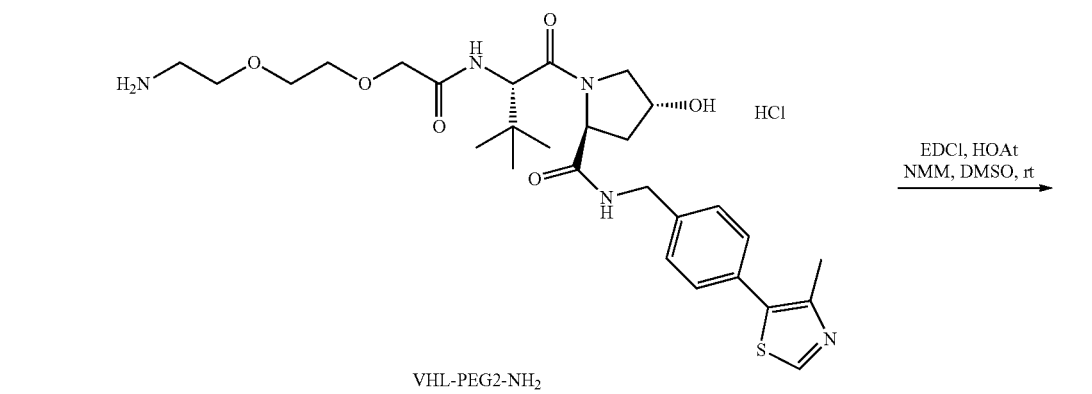

VHL-PEG2-NH$_2$

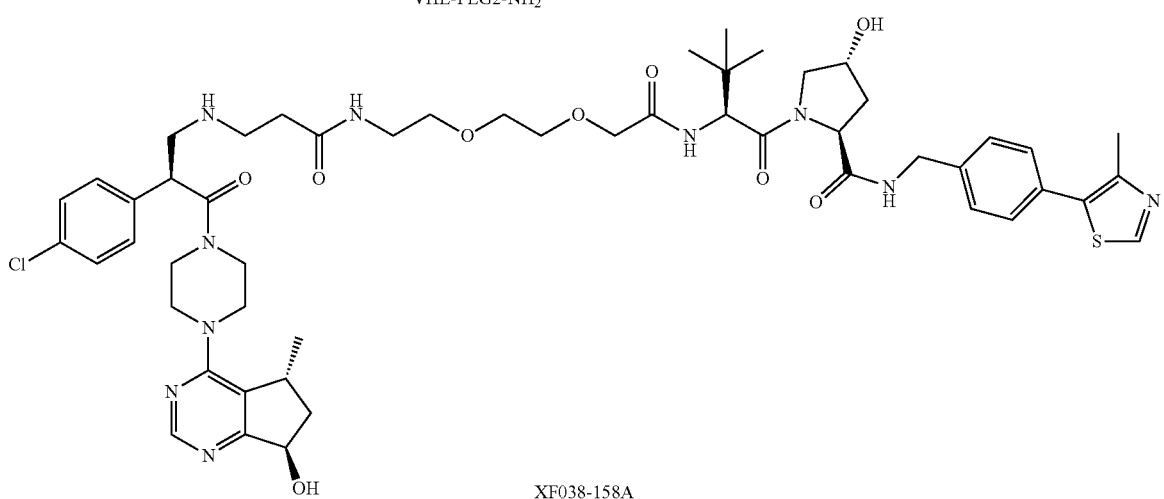

XF038-158A

XF038-158A was synthesized following the standard procedure for preparing XF038-157A from intermediate 2 (12 mg, 0.02 mmol), VHL-PEG2-NH$_2$ (12.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-158A was obtained as white solid in TFA salt form (9.4 mg, 45%). $^1$H NMR (600 MHz, CD$_3$OD) δ 8.95 (s, 1H), 8.57 (s, 1H), 7.53-7.37 (m, 6H), 7.34 (dd, J=8.5, 2.1 Hz, 2H), 5.31 (t, J=7.9 Hz, 1H), 4.75 (s, 1H), 4.63-4.45 (m, 4H), 4.40 (d, J=15.5 Hz, 1H), 4.17 (s, 1H), 4.03 (d, J=2.0 Hz, 2H), 3.96-3.79 (m, 6H), 3.74-3.47 (m, 13H), 3.39 (t, J=9.5 Hz, 1H), 3.28-3.22 (m, 3H), 2.68 (t, J=6.3 Hz, 1H), 2.47 (s, 3H), 2.32-2.24 (m, 2H), 2.17 (dt, J=12.7, 8.1 Hz, 1H), 2.08 (ddd, J=13.5, 9.6, 4.3 Hz, 1H), 1.17 (dd, J=7.0, 2.0 Hz, 3H), 1.04 (s, 9H). HRMS (m/z) for C$_{52}$H$_{70}$ClN$_{10}$O$_9$S$^+$ [M+H]$^+$: molecular weight calculated 1045.4731, found 1045.4738.

Example 4

Synthesis of XF038-159A

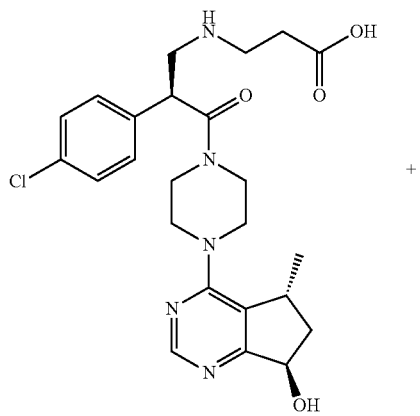

Intermediate 2

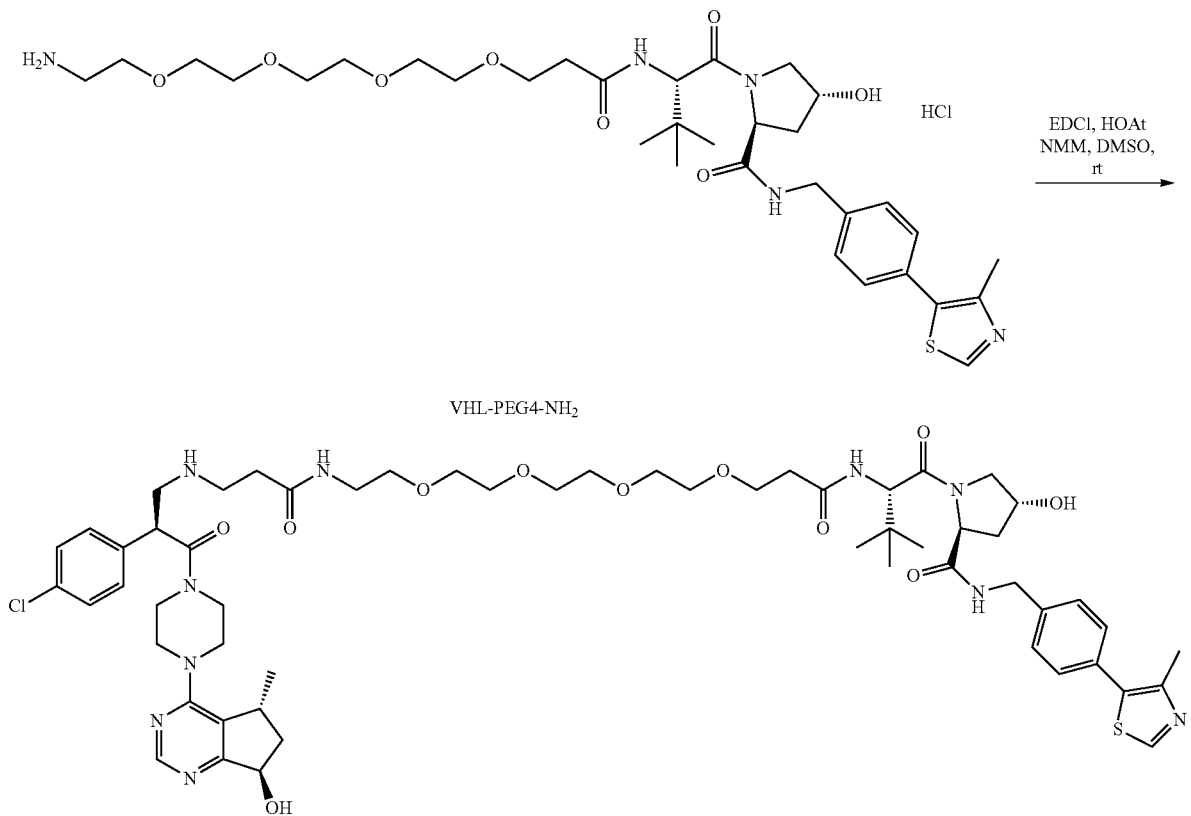

XF038-159A was synthesized following the standard procedure for preparing XF038-157A from intermediate 2 (12 mg, 0.02 mmol), VHL-PEG4-NH$_2$ (14.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-159A was obtained as white solid in TFA salt form (11.2 mg, 48%). $^1$H NMR (600 MHz, CD$_3$OD) δ 8.95 (s, 1H), 8.58 (s, 1H), 7.54-7.39 (m, 6H), 7.39-7.28 (m, 2H), 5.31 (t, J=8.0 Hz, 1H), 4.65 (s, 1H), 4.60-4.47 (m, 4H), 4.36 (d, J=15.5 Hz, 1H), 4.18 (s, 1H), 3.98-3.77 (m, 6H), 3.76-3.57 (m, 19H), 3.53 (t, J=5.4 Hz, 2H), 3.44-3.33 (m, 4H), 3.29-3.23 (m, 2H), 2.67 (t, J=6.3 Hz, 2H), 2.58 (ddd, J=15.0, 7.5, 5.2 Hz, 1H), 2.48 (s, 3H), 2.33-2.26 (m, 1H), 2.25-2.15 (m, 2H), 2.12-2.04 (m, 1H), 1.17 (d, J=6.9 Hz, 3H), 1.04 (s, 9H). HRMS (m/z) for C$_{57}$H$_{80}$ClN$_{10}$O$_{11}$S$^+$ [M+H]$^+$: molecular weight calculated 1147.5412, found 1147.5412.

Example 5
Synthesis of XF038-160A
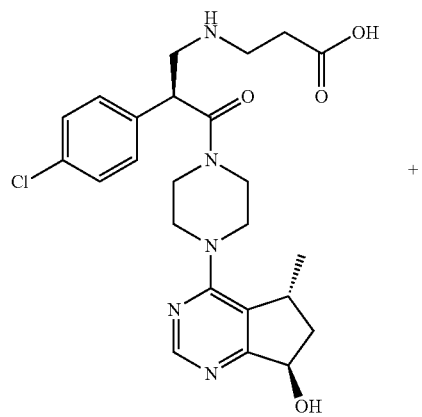
Intermediate 2
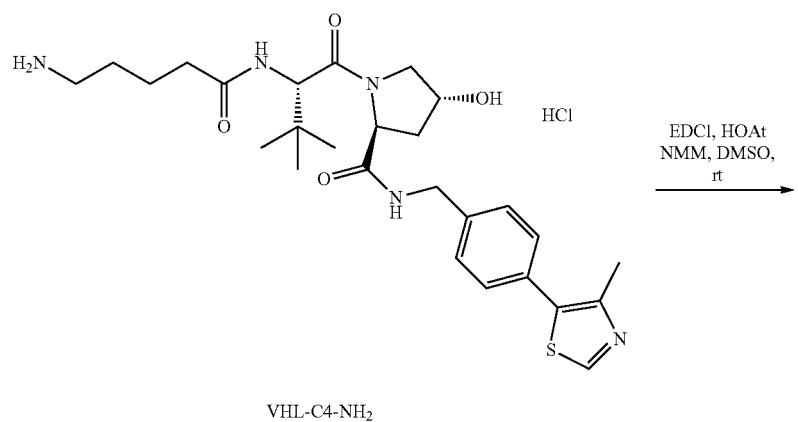
VHL-C4-NH₂
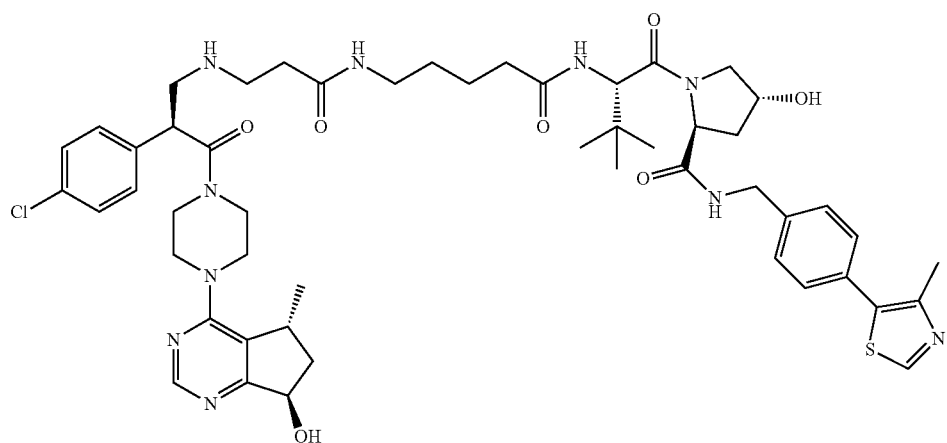
XF038-160A XF038-160A was synthesized following the standard procedure for preparing XF038-157A from intermediate 2 (12 mg, 0.02 mmol), VHL-C4-NH$_2$ (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-160A was obtained as white solid in TFA salt form (7.6 mg, 38%). $^1$H NMR (600 MHz, CD$_3$OD) δ 8.93 (s, 1H), 8.57 (s, 1H), 7.51-7.39 (m, 6H), 7.39-7.32 (m, 2H), 5.31 (t, J=7.9 Hz, 1H), 4.62 (s, 1H), 4.59-4.48 (m, 4H), 4.36 (d, J=15.4 Hz, 1H), 4.18 (s, 1H), 3.96-3.86 (m, 4H), 3.81 (dt, J=10.9, 6.1 Hz, 2H), 3.70-3.60 (m, 5H), 3.40 (t, J=8.9 Hz, 1H), 3.27 (dd, J=12.6, 3.8 Hz, 2H), 3.22-3.16 (m, 2H), 2.67-2.63 (m, 2H), 2.47 (s, 3H), 2.33-2.26 (m, 3H), 2.23-2.16 (m, 2H), 2.08 (ddd, J=13.3, 9.1, 4.5 Hz, 1H), 1.65-1.57 (m, 2H), 1.51 (t, J=7.4 Hz, 2H), 1.17 (d, J=7.3 Hz, 3H), 1.03 (s, 9H). HRMS (m/z) for C$_{51}$H$_{68}$ClN$_{10}$O$_7$S$^+$ [M+H]$^+$: molecular weight calculated 999.4676, found 999.4678.

Example 6

Synthesis of XF038-161A

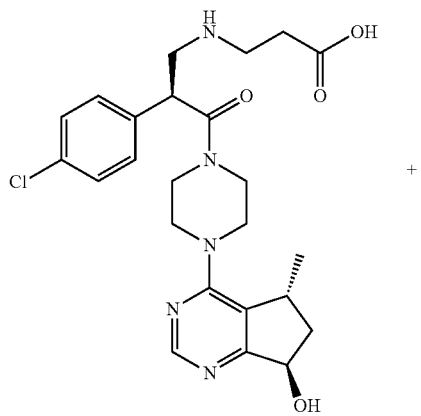

Intermediate 2

+

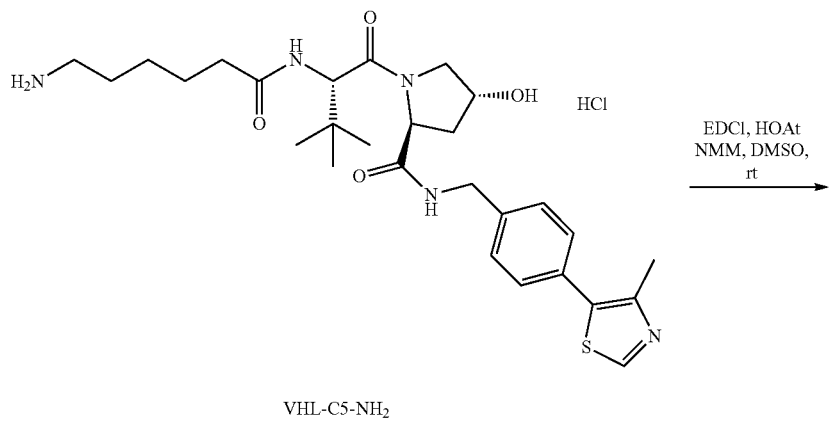

VHL-C5-NH$_2$

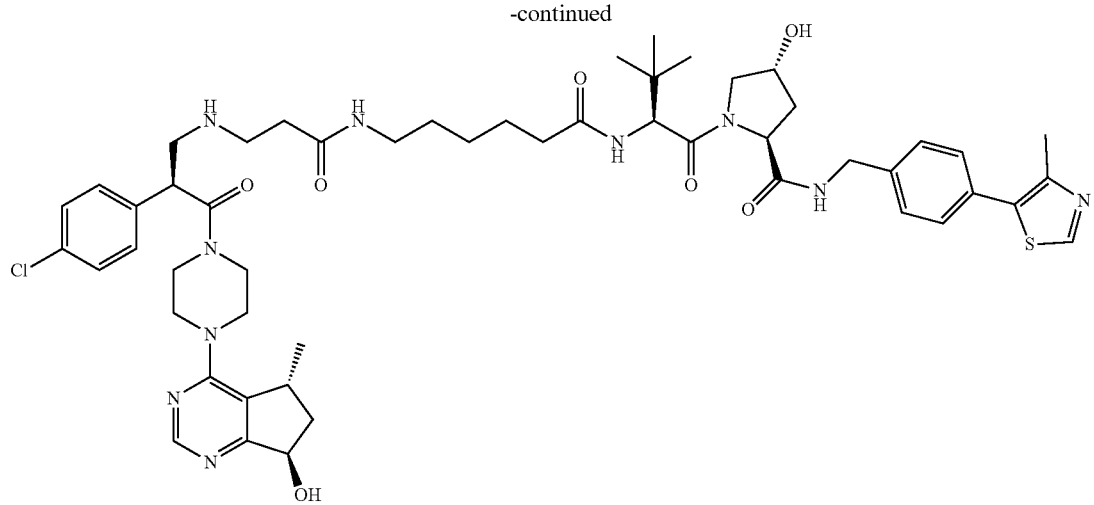

XF038-161A

XF038-161A was synthesized following the standard procedure for preparing XF038-157A from intermediate 2 (12 mg, 0.02 mmol), VHL-C5-NH$_2$ (11.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-161A was obtained as white solid in TFA salt form (12.7 mg, 63%). $^1$H NMR (600 MHz, CD$_3$OD) δ 8.97 (s, 1H), 8.58 (d, J=4.4 Hz, 1H), 7.54-7.38 (m, 6H), 7.38-7.32 (m, 2H), 5.31 (t, J=8.0 Hz, 1H), 4.63 (s, 1H), 4.60-4.47 (m, 4H), 4.37 (d, J=15.4 Hz, 1H), 4.18 (s, 1H), 3.97-3.78 (m, 6H), 3.72-3.54 (m, 5H), 3.40 (dd, J=10.8, 7.1 Hz, 1H), 3.29-3.24 (m, 2H), 3.18 (t, J=7.1 Hz, 2H), 2.67-2.61 (m, 2H), 2.48 (s, 3H), 2.34-2.14 (m, 5H), 2.08 (ddd, J=13.3, 9.2, 4.5 Hz, 1H), 1.66-1.57 (m, 2H), 1.50 (q, J=7.3 Hz, 2H), 1.38-1.30 (m, 2H), 1.17 (d, J=7.1 Hz, 3H), 1.03 (s, 9H). HRMS (m/z) for C$_{52}$H$_{70}$ClN$_{10}$O$_7$S$^+$ [M+H]$^+$: molecular weight calculated 1013.4833, found 1013.4847.

Example 7

Synthesis of XF038-162A

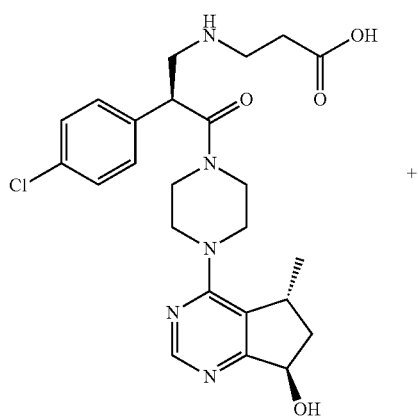

Intermediate 2

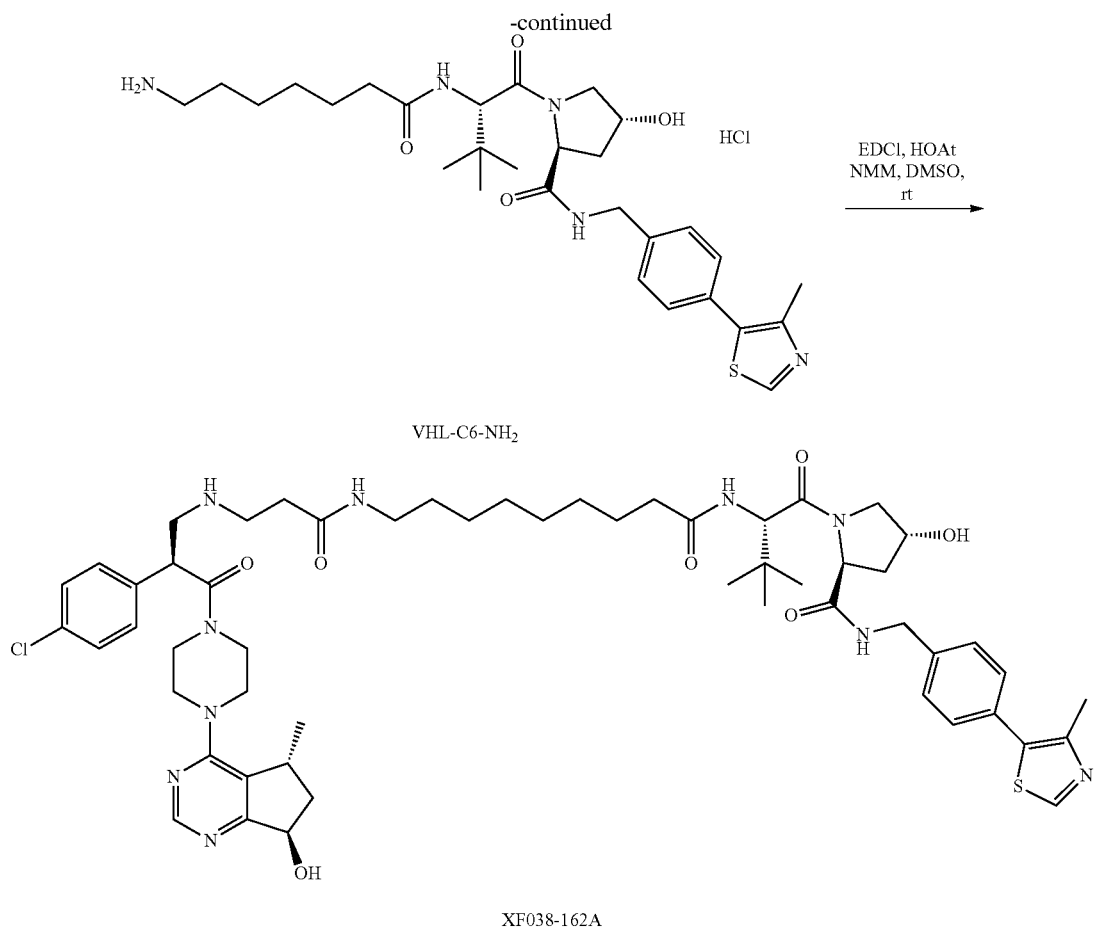

VHL-C6-NH₂

XF038-162A

XF038-162A was synthesized following the standard procedure for preparing XF038-157A from intermediate 2 (12 mg, 0.02 mmol), VHL-C6-NH₂ (11.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-162A was obtained as white solid in TFA salt form (8.6 mg, 42%). ¹H NMR (600 MHz, CD₃OD) δ 8.95 (s, 1H), 8.58 (s, 1H), 7.54-7.38 (m, 6H), 7.36 (t, J=6.6 Hz, 2H), 5.38-5.26 (m, 1H), 4.64 (s, 1H), 4.61-4.48 (m, 4H), 4.37 (d, J=15.6 Hz, 1H), 4.18 (s, 1H), 3.86 (dd, J=58.9, 15.4 Hz, 6H), 3.73-3.53 (m, 5H), 3.41 (s, 1H), 3.27 (d, J=6.0 Hz, 2H), 3.23-3.10 (m, 2H), 2.72-2.57 (m, 2H), 2.48 (s, 3H), 2.33-2.17 (m, 5H), 2.10 (s, 1H), 1.66-1.58 (m, 2H), 1.53-1.46 (m, 2H), 1.39-1.31 (m, 4H), 1.17 (d, J=7.5 Hz, 3H), 1.03 (s, 9H). HRMS (m/z) for $C_{53}H_{72}ClN_{10}O_7S^+$ [M+H]⁺: molecular weight calculated 1027.4989, found 1027.4983.

Example 8

Synthesis of XF038-164A

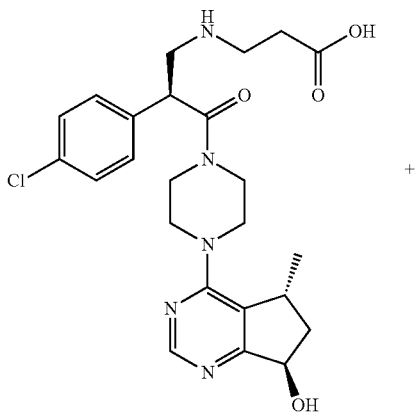

Intermediate 2

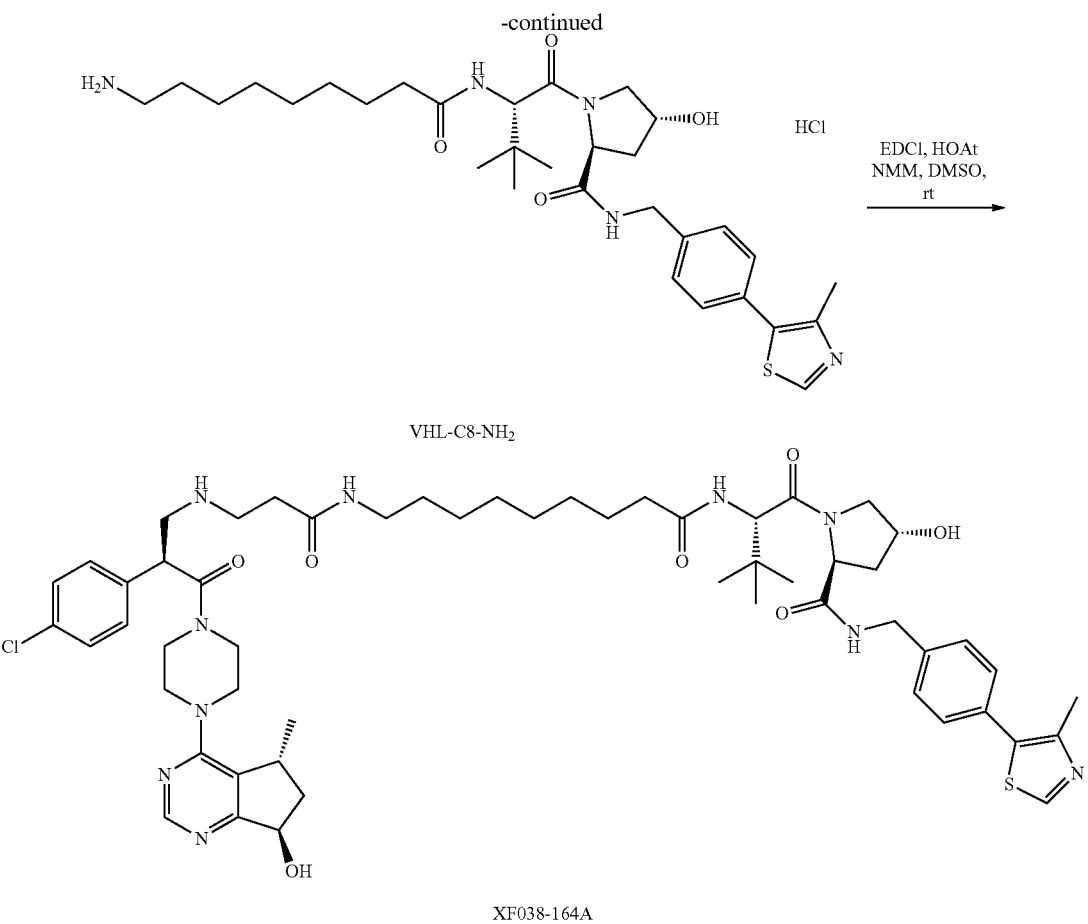

VHL-C8-NH₂

XF038-164A

XF038-164A was synthesized following the standard procedure for preparing XF038-157A from intermediate 2 (12 mg, 0.02 mmol), VHL-C8-NH₂ (12.4 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-164A was obtained as white solid in TFA salt form (9.9 mg, 47%). ¹H NMR (600 MHz, CD₃OD) δ 8.96 (s, 1H), 8.58 (d, J=3.7 Hz, 1H), 7.55-7.39 (m, 6H), 7.39-7.32 (m, 2H), 5.31 (t, J=8.0 Hz, 1H), 4.63 (s, 1H), 4.60-4.48 (m, 4H), 4.36 (d, J=15.5 Hz, 1H), 4.18 (s, 1H), 3.97-3.78 (m, 6H), 3.73-3.60 (m, 5H), 3.40 (t, J=8.9 Hz, 1H), 3.29-3.23 (m, 2H), 3.17 (dd, J=7.8, 6.3 Hz, 2H), 2.67-2.61 (m, 2H), 2.48 (s, 3H), 2.34-2.14 (m, 5H), 2.08 (s, 1H), 1.59 (d, J=7.0 Hz, 2H), 1.48 (d, J=7.1 Hz, 2H), 1.35-1.29 (m, 8H), 1.18 (d, J=7.0 Hz, 3H), 1.03 (s, 9H). HRMS (m/z) for $C_{55}H_{76}ClN_{10}O_{7}S^{+}$ [M+H]⁺: molecular weight calculated 1055.5302, found 1055.5303.

Example 9

Synthesis of XF038-165A

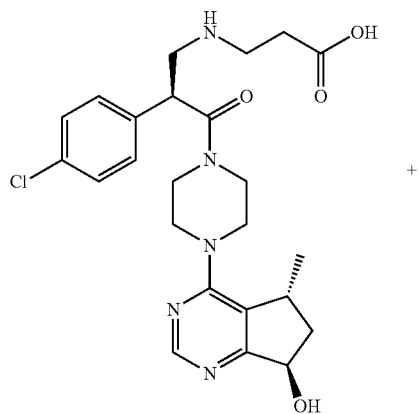

Intermediate 2

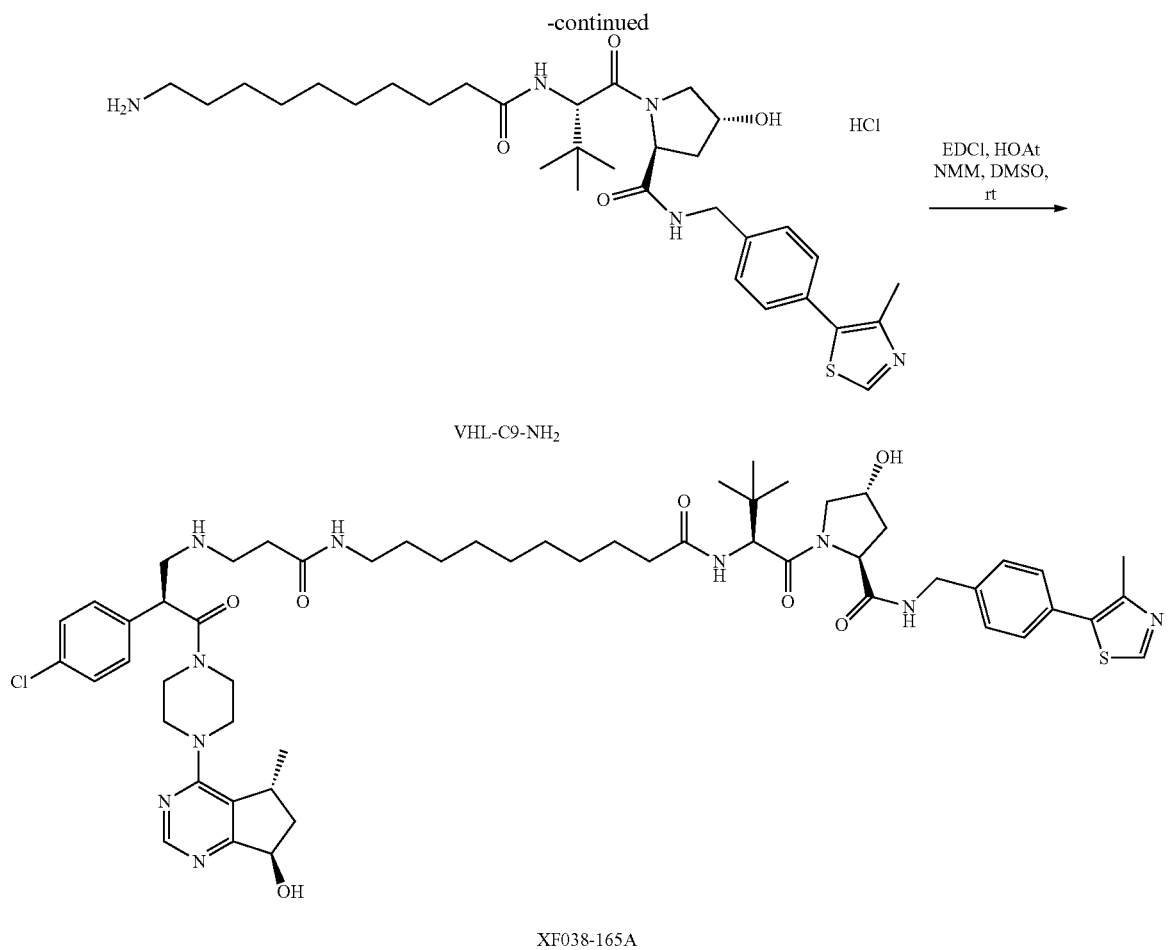

XF038-165A was synthesized following the standard procedure for preparing XF038-157A from intermediate 2 (12 mg, 0.02 mmol), VHL-C9-NH₂ (12.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF038-165A was obtained as white solid in TFA salt form (2.8 mg, 13%). ¹H NMR (600 MHz, CD₃OD) δ 8.93 (s, 1H), 8.58 (s, 1H), 7.44 (d, J=25.3 Hz, 6H), 7.36 (d, J=8.5 Hz, 2H), 5.31 (d, J=8.2 Hz, 1H), 4.63 (s, 1H), 4.61-4.43 (m, 4H), 4.36 (d, J=15.3 Hz, 1H), 4.19 (s, 1H), 4.03-3.78 (m, 6H), 3.76-3.56 (m, 5H), 3.49-3.39 (m, 1H), 3.17 (d, J=7.7 Hz, 2H), 3.03-2.95 (m, 1H), 2.91-2.83 (m, 1H), 2.65 (d, J=8.9 Hz, 2H), 2.47 (s, 3H), 2.36-2.14 (m, 5H), 2.13-2.06 (m, 1H), 1.69-1.56 (m, 2H), 1.56-1.46 (m, 2H), 1.41-1.25 (m, 10H), 1.18 (d, J=7.0 Hz, 3H), 1.04 (s, 9H). HRMS (m/z) for C₅₆H₇₈ClN₁₀O₇S⁺ [M+H]⁺: molecular weight calculated 1069.5459, found 1069.5464.

Example 10

Synthesis of XF038-166A

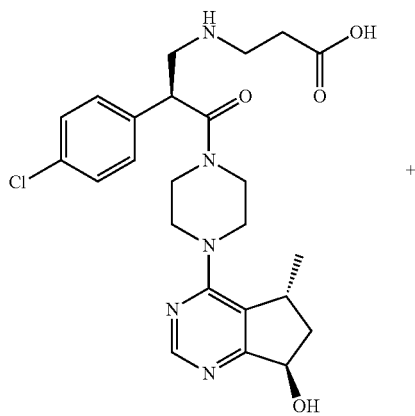

Intermediate 2

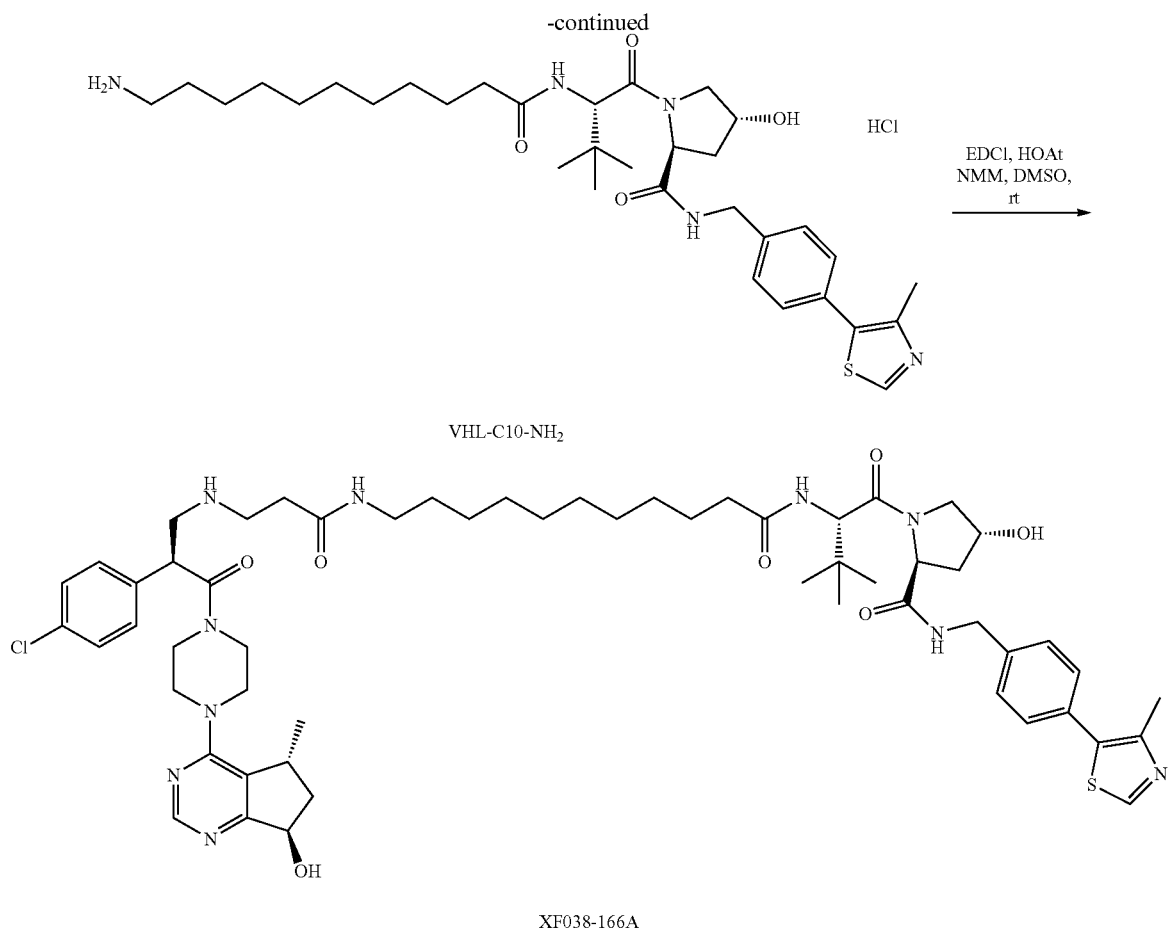

VHL-C10-NH₂

XF038-166A

XF038-166A was synthesized following the standard procedure for preparing XF038-157A from intermediate 2 (12 mg, 0.02 mmol), VHL-C10-NH₂ (13.0 mg, 0.02 mmol, 1.0 equiv), EDCI (5.8 mg, 0.03 mmol, 1.5 equiv), HOAt (4.1 mg, 0.03 mmol, 1.5 equiv), and NMM) (6.1 mg, 0.06 mmol, 3.0 equiv) in DMSO (1 mL). XF038-166A was obtained as white solid in TFA salt form (11.3 mg, 52%). ¹H NMR (600 MHz, CD₃OD) δ 8.96 (s, 1H), 8.58 (d, J=3.9 Hz, 1H), 7.53-7.38 (m, 6H), 7.38-7.28 (m, 2H), 5.31 (t, J=8.0 Hz, 1H), 4.63 (s, 1H), 4.60-4.44 (m, 4H), 4.36 (d, J=15.5 Hz, 1H), 4.18 (s, 1H), 3.97-3.78 (m, 6H), 3.72-3.59 (m, 5H), 3.45-3.36 (m, 1H), 3.29-3.24 (m, 2H), 3.17 (t, J=7.1 Hz, 2H), 2.67-2.62 (m, 2H), 2.48 (s, 3H), 2.34-2.16 (m, 5H), 2.12-2.04 (m, 1H), 1.60 (dt, J=15.2, 7.4 Hz, 2H), 1.49 (t, J=7.0 Hz, 2H), 1.36-1.26 (m, 12H), 1.18 (d, J=6.9 Hz, 3H), 1.03 (s, 9H). HRMS (m/z) for C₅₇H₈₀ClN₁₀O₇S⁺ [M+H]⁺: molecular weight calculated 1083.5615, found 1083.5617.

Example 11

Synthesis of XF042-162

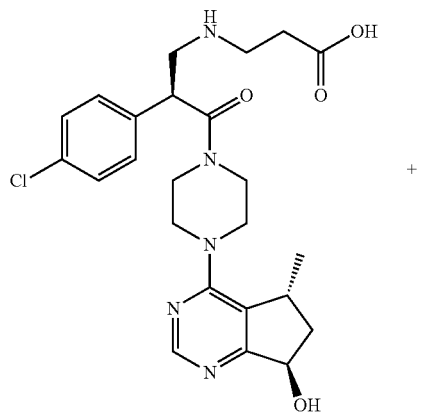

Intermediate 2

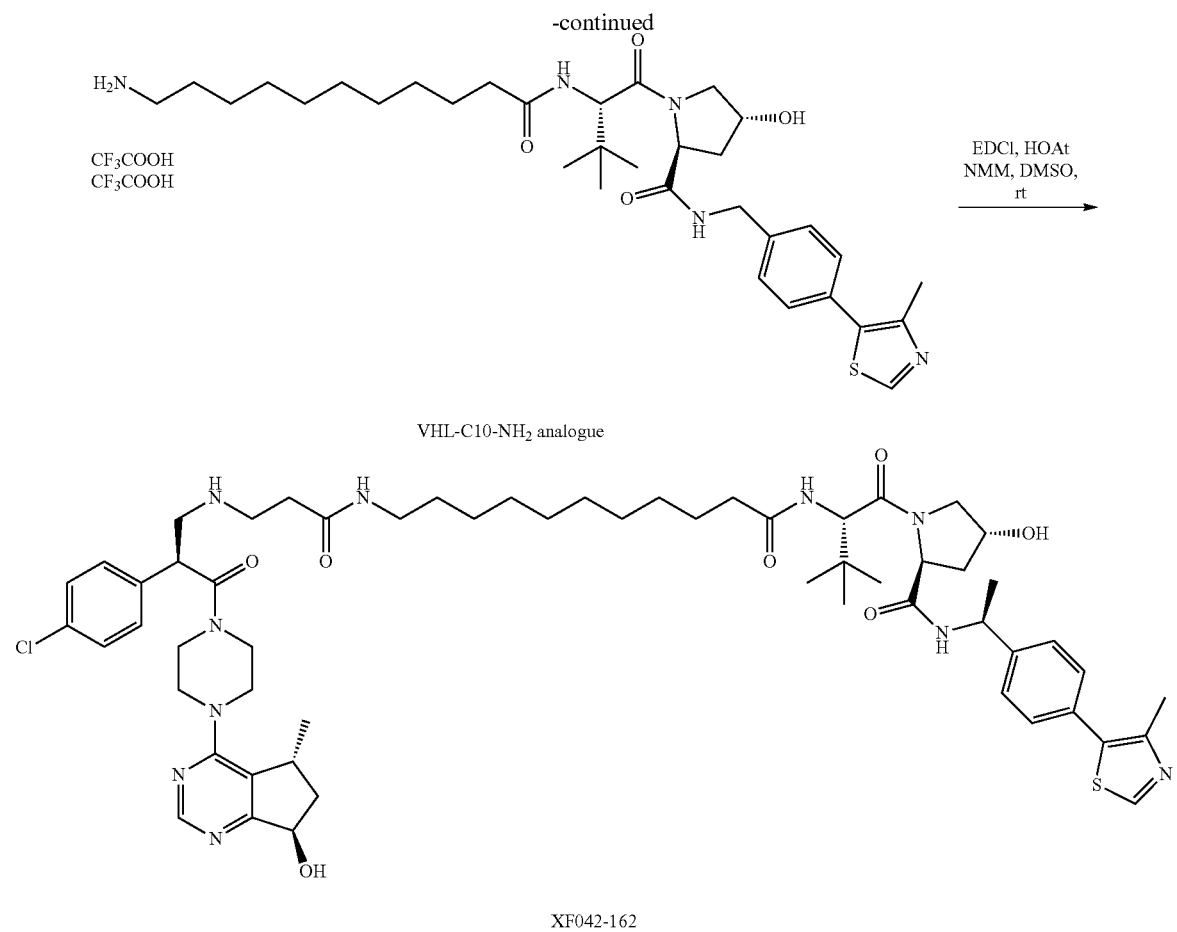

VHL-C10-NH₂ analogue

XF042-162

XF042-162 was synthesized following the standard procedure for preparing XF038-157A from intermediate 2 (6.01 mg, 0.01 mmol), VHL-C10-NH₂ analog (7.4 mg, 0.01 mmol, 1.0 equiv), EDCI (2.9 mg, 0.015 mmol, 1.5 equiv), HOAt (2.1 mg, 0.015 mmol, 1.5 equiv), and NMM (3.1 mg, 0.03 mmol, 3.0 equiv) in DMSO (1 mL). XF042-162 was obtained as white solid in TFA salt form (6.5 mg, 59%). ¹H NMR (600 MHz, CD₃OD) δ 8.87 (s, 1H), 8.52 (s, 1H), 7.43 (dt, J=15.8, 8.5 Hz, 6H), 7.37 (dd, J=8.6, 6.8 Hz, 2H), 5.19 (t, J=7.5 Hz, 1H), 5.00 (q, J=7.0 Hz, 1H), 4.62 (s, 1H), 4.59-4.50 (m, 2H), 4.43 (s, 1H), 4.13-4.03 (m, 1H), 4.02-3.90 (m, 1H), 3.91-3.70 (m, 7H), 3.62 (t, J=11.0 Hz, 4H), 3.59-3.51 (m, 1H), 3.43-3.37 (m, 1H), 3.26 (dd, J=12.6, 3.9 Hz, 1H), 3.17 (t, J=7.2 Hz, 2H), 2.65 (t, J=6.0 Hz, 2H), 2.47 (s, 3H), 2.29 (td, J=16.3, 15.4, 8.2 Hz, 1H), 2.26-2.14 (m, 3H), 1.95 (ddd, J=13.3, 9.1, 4.5 Hz, 1H), 1.50 (d, J=7.0 Hz, 3H), 1.31 (s, 16H), 1.15 (d, J=7.0 Hz, 3H), 1.04 (s, 9H). HRMS (m/z) for $C_{58}H_{82}ClN_{10}O_7S^+$ [M+H]⁺: molecular weight calculated 1097.5772, found 1083.5767.

Example 12

Synthesis of XF042-171

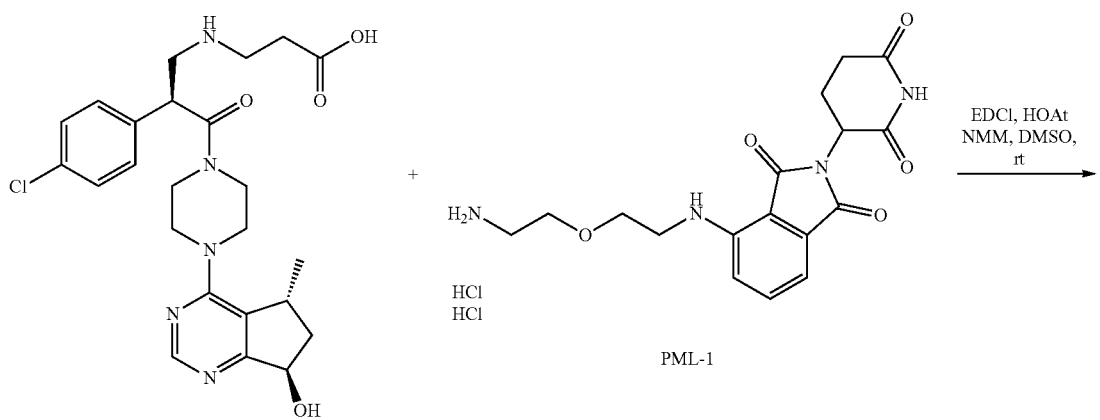

Intermediate 2      PML-1

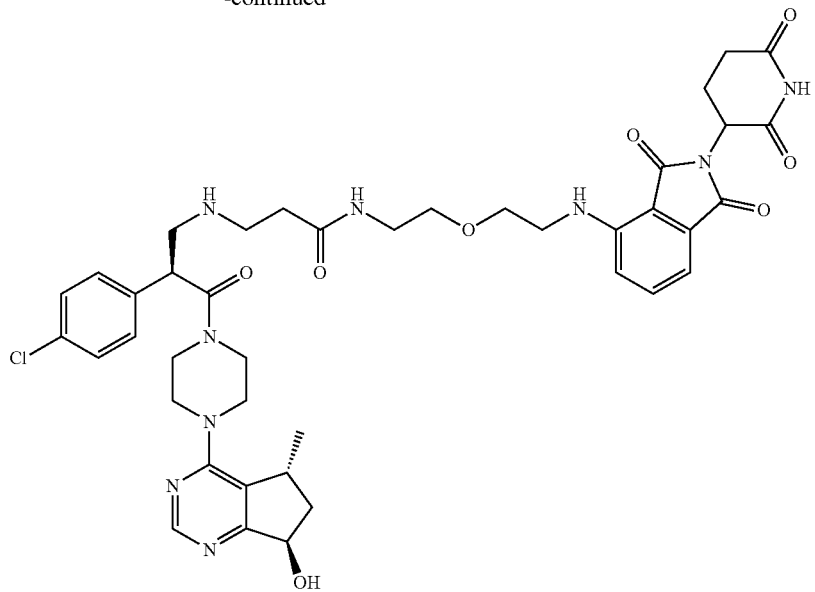

XF042-171

XF042-171 was synthesized following the standard procedure for preparing XF038-157A from intermediate 2 (6.0 mg, 0.01 mmol), PML-1 (4.8 mg, 0.01 mmol, 1.0 equiv), EDCI (2.0 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-171 was obtained as yellow solid in TFA salt form (2.1 mg, 25%). $^1$H NMR (600 MHz, CD$_3$OD) δ 8.56 (s, 1H), 7.57 (t, J=8.4 Hz, 1H), 7.43 (d, J=6.5 Hz, 2H), 7.34 (d, J=8.2 Hz, 2H), 7.16-6.96 (m, 2H), 5.29 (t, J=7.8 Hz, 1H), 5.07 (d, J=12.1 Hz, 1H), 4.49 (s, 1H), 4.22-3.93 (m, 3H), 3.92-3.75 (m, 4H), 3.71 (s, 2H), 3.67-3.53 (m, 5H), 3.50 (s, 2H), 3.46-3.33 (m, 3H), 3.27-3.14 (m, 2H), 2.87 (t, J=14.8 Hz, 1H), 2.79-2.62 (m, 4H), 2.31-2.22 (m, 1H), 2.22-2.05 (m, 2H), 1.16 (d, J=6.9 Hz, 3H). HRMS (m/z) for $C_{41}H_{49}ClN_9O_8^+$ [M+H]$^+$: molecular weight calculated 830.3387, found 830.3385.

Example 13

Synthesis of XF048-7

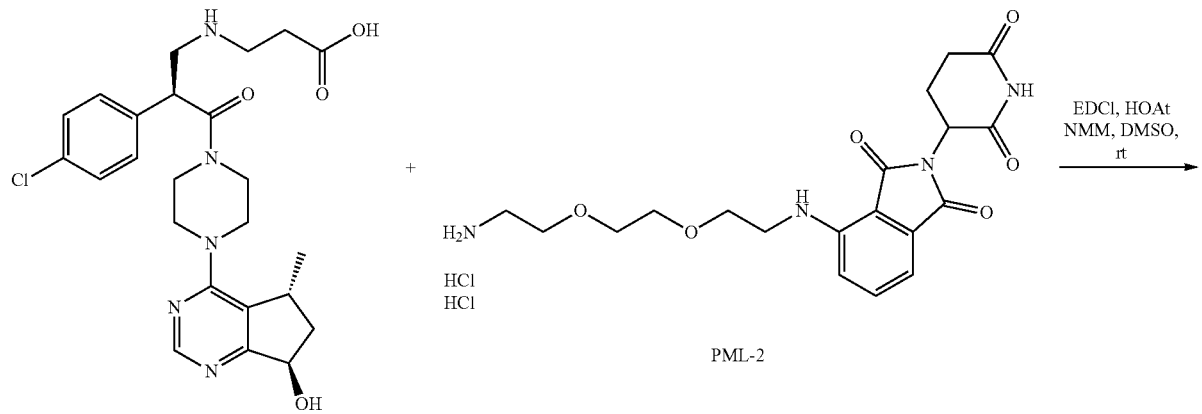

Intermediate 2

PML-2

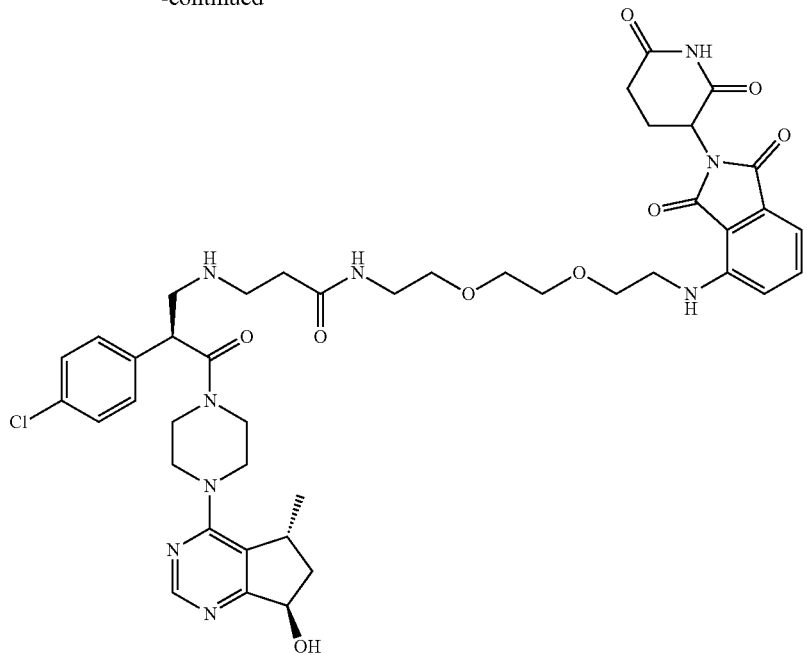

XF048-7

XF048-7 was synthesized following the standard procedure for preparing XF038-157A from intermediate 2 (6.0 mg, 0.01 mmol), PML-2 (5.0 mg, 0.01 mmol, 1.0 equiv), EDCI (3.0 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF048-7 was obtained as yellow solid in TFA salt form (5.8 mg, 64%). $^1$H NMR (600 MHz, CD$_3$OD) δ 8.57 (s, 1H), 7.59-7.53 (m, 1H), 7.45 (dd, J=8.5, 1.8 Hz, 2H), 7.39-7.29 (m, 2H), 7.13-7.03 (m, 2H), 5.30 (t, J=7.9 Hz, 1H), 5.07 (dd, J=12.7, 5.5 Hz, 1H), 4.58-4.45 (m, 1H), 4.20-3.97 (m, 2H), 3.96-3.77 (m, 4H), 3.74-3.70 (m, 2H), 3.71-3.58 (m, 8H), 3.56 (t, J=5.5 Hz, 2H), 3.51 (t, J=5.2 Hz, 2H), 3.43-3.33 (m, 3H), 3.29-3.22 (m, 2H), 2.88 (ddd, J=17.7, 13.8, 5.3 Hz, 1H), 2.80-2.67 (m, 2H), 2.67-2.60 (m, 2H), 2.28 (dd, J=12.8, 7.5 Hz, 1H), 2.22-2.08 (m, 2H), 1.23-1.12 (m, 3H). HRMS (m/z) for C$_{43}$H$_{53}$ClN$_9$O$_9^+$ [M+H]$^+$: molecular weight calculated 874.3649, found 874.3650.

Example 14

Synthesis of XF048-8

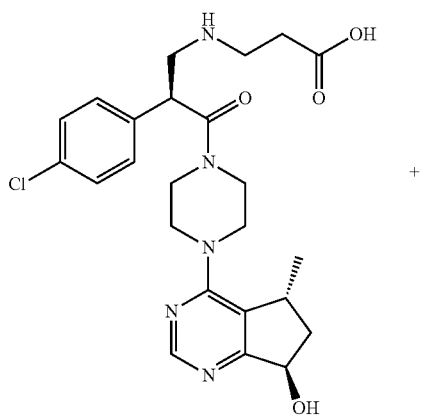

Intermediate 2

+

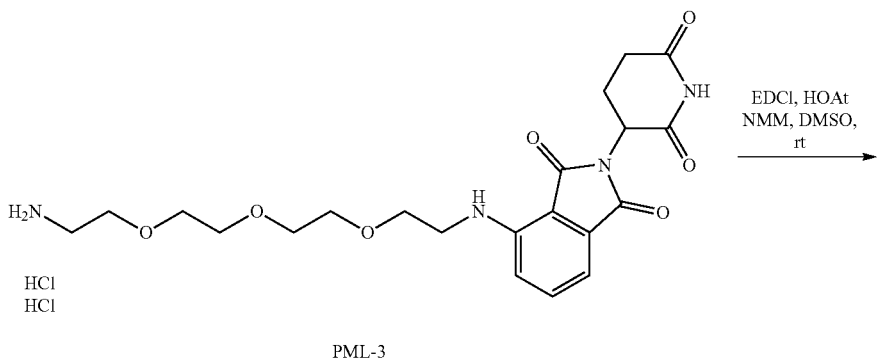

PML-3

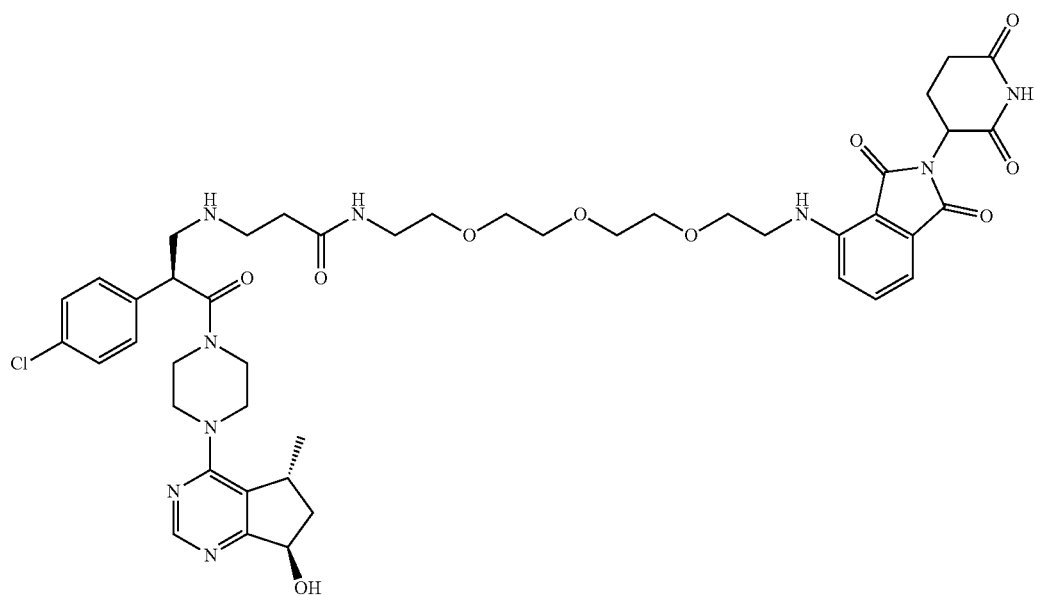

XF048-8

XF048-8 was synthesized following the standard procedure for preparing XF038-157A from intermediate 2 (6.1 mg, 0.01 mmol), PML-3 (5.4 mg, 0.01 mmol, 1.0 equiv), EDCI (3.0 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF048-8 was obtained as yellow solid in TFA salt form (4.7 mg, 50%). $^1$H NMR (600 MHz, CD$_3$OD) δ 8.57 (s, 1H), 7.56 (ddd, J=8.5, 7.0, 1.3 Hz, 1H), 7.49-7.41 (m, 2H), 7.39-7.29 (m, 2H), 7.15-6.99 (m, 2H), 5.30 (t, J=7.9 Hz, 1H), 5.07 (dd, J=12.9, 5.4 Hz, 1H), 4.56-4.48 (m, 1H), 4.16 (s, 1H), 4.05 (s, 1H), 3.95-3.78 (m, 4H), 3.72 (t, J=5.1 Hz, 2H), 3.70-3.55 (m, 12H), 3.56-3.48 (m, 4H), 3.43-3.37 (m, 1H), 3.35 (q, J=3.9, 2.6 Hz, 2H), 3.29-3.20 (m, 2H), 2.92-2.83 (m, 1H), 2.80-2.68 (m, 2H), 2.68-2.61 (m, 2H), 2.29 (dd, J=12.8, 7.5 Hz, 1H), 2.21-2.09 (m, 2H), 1.17 (d, J=7.0 Hz, 3H). HRMS (m/z) for C$_{45}$H$_{57}$ClN$_9$O$_{10}{}^+$ [M+H]$^+$: molecular weight calculated 918.3911, found 918.3916.

Example 15
Synthesis of XF038-176A
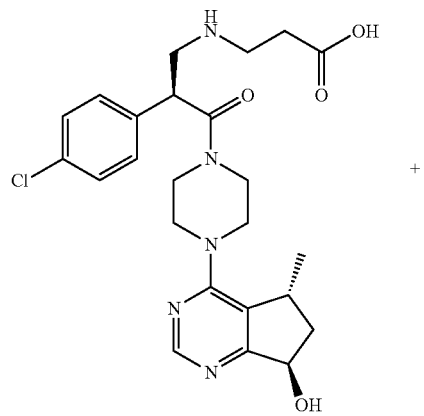
Intermediate 2
+
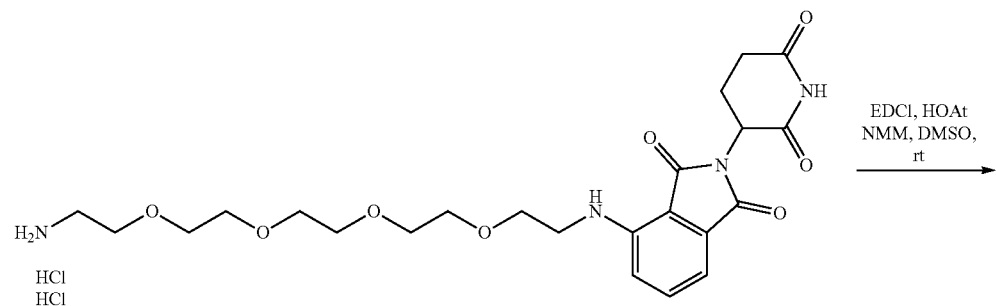
PML-4
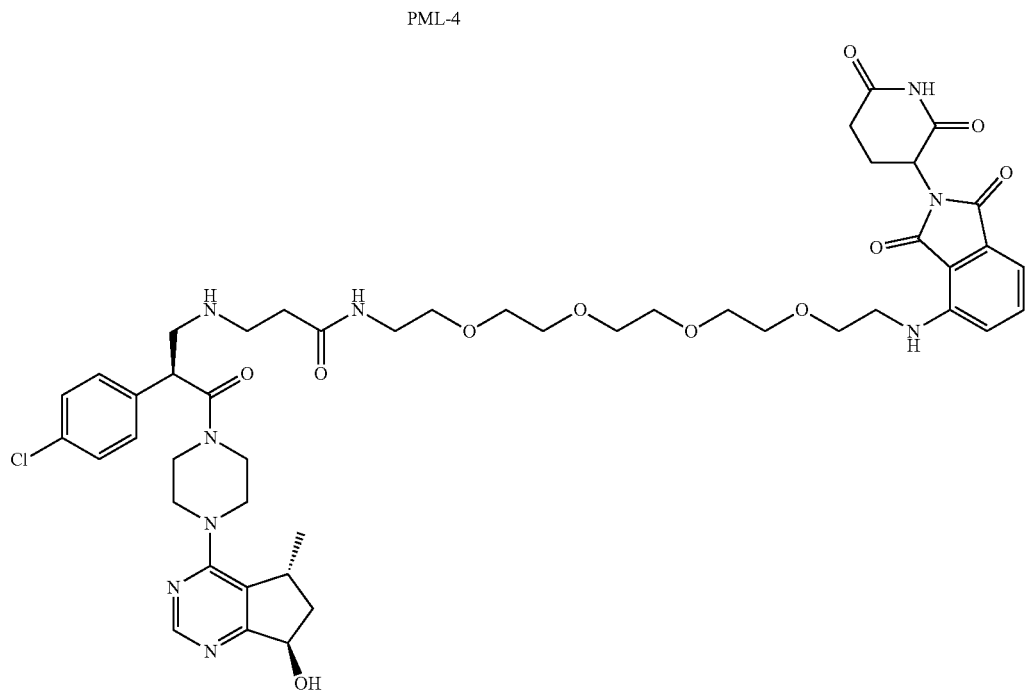
XF038-176A XF038-176A was synthesized following the standard procedure for preparing XF038-157A from intermediate 2 (9.9 mg, 0.0165 mmol), PML-4 (9.3 mg, 0.0165 mmol, 1.0 equiv), EDCI (4.8 mg, 0.025 mmol, 1.5 equiv), HOAt (3.4 mg, 0.025 mmol, 1.5 equiv), and NMM (5.1 mg, 0.05 mmol, 3.0 equiv) in DMSO (1 mL). XF038-176A was obtained as yellow solid in TFA salt form (3.5 mg, 22%). $^1$H NMR (600 MHz, CD$_3$OD) δ 8.57 (s, 1H), 7.56 (tt, J=9.9, 7.1, 2.8 Hz, 1H), 7.49-7.41 (m, 1H), 7.37-7.24 (m, 3H), 7.10 (d, J=8.6 Hz, 1H), 7.06 (d, J=7.1 Hz, 1H), 5.29 (s, 1H), 5.13-5.00 (m, 1H), 4.58-4.42 (m, 1H), 4.16 (s, 1H), 4.03 (s, 1H), 3.95-3.74 (m, 4H), 3.72 (t, J=5.2 Hz, 2H), 3.70-3.54 (m, 14H), 3.52 (dq, J=10.3, 5.4 Hz, 4H), 3.44-3.32 (m, 4H), 3.30-3.22 (m, 3H), 2.93-2.80 (m, 1H), 2.79-2.68 (m, 2H), 2.68-2.59 (m, 2H), 2.34-2.25 (m, 1H), 2.22-2.08 (m, 2H), 1.17 (d, J=7.0 Hz, 3H). HRMS (m/z) for $C_{47}H_{61}ClN_9O_{11}^+$ [M+H]$^+$: molecular weight calculated 962.4174, found 962.4167.

Example 16

Synthesis of XF038-177A

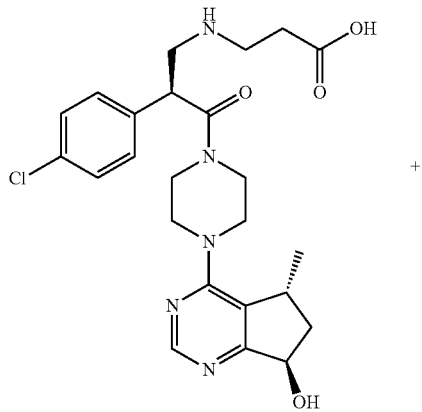

Intermediate 2

+

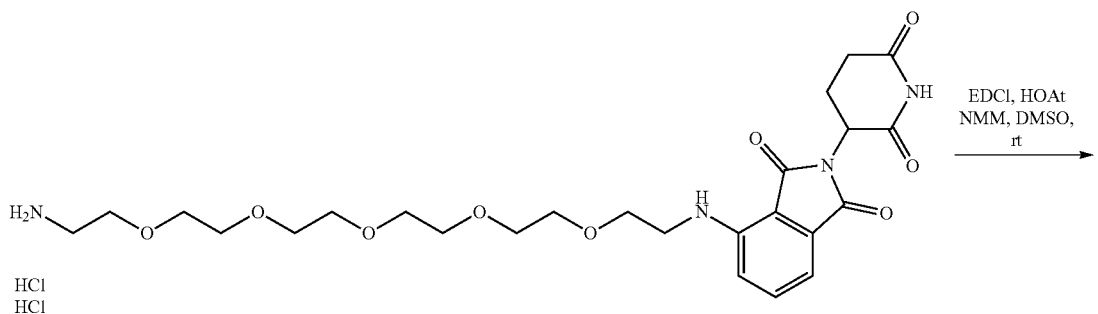

PML-5

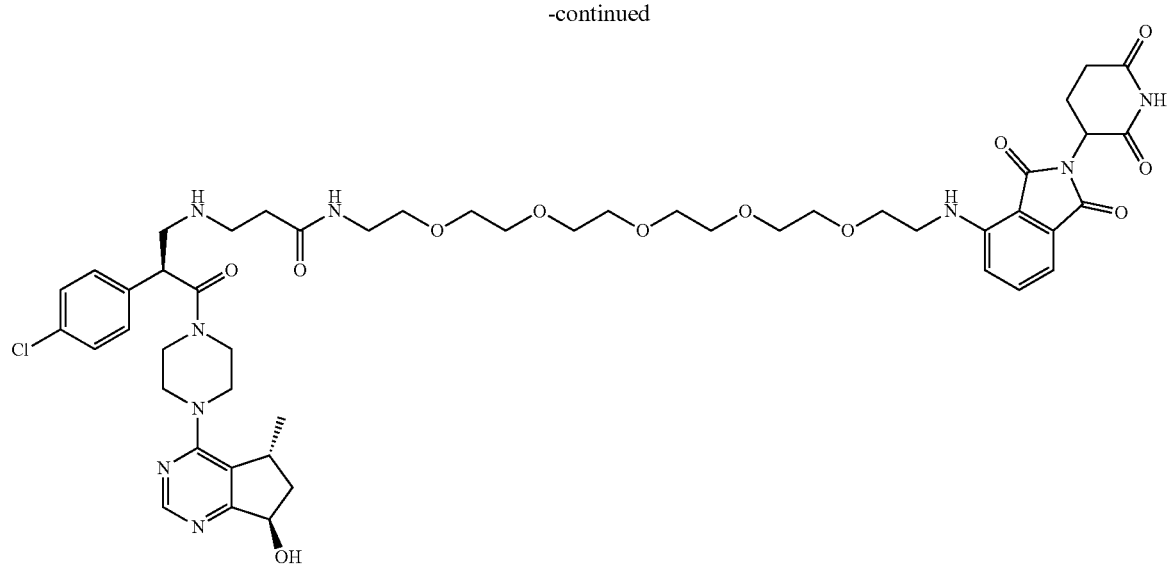

XF038-177A

XF038-177A was synthesized following the standard procedure for preparing XF038-157A from intermediate 2 (9.9 mg, 0.0165 mmol), PML-5 (10.0 mg, 0.0165 mmol, 1.0 equiv), EDCI (4.8 mg, 0.025 mmol, 1.5 equiv), HOAt (3.4 mg, 0.025 mmol, 1.5 equiv), and NMM (5.1 mg, 0.05 mmol, 3.0 equiv) in DMSO (1 mL). XF038-177A was obtained as yellow solid in TFA salt form (5.0 mg, 30%). $^1$H NMR (600 MHz, CD$_3$OD) δ 8.58 (d, J=3.6 Hz, 1H), 7.56 (dd, J=8.6, 7.0 Hz, 1H), 7.49-7.42 (m, 1H), 7.39-7.22 (m, 3H), 7.10 (d, J=8.5 Hz, 1H), 7.05 (d, J=7.1 Hz, 1H), 5.30 (t, J=8.0 Hz, 1H), 5.07 (ddd, J=12.9, 5.5, 2.1 Hz, 1H), 4.56-4.44 (m, 1H), 4.16 (s, 1H), 4.11-3.97 (m, 1H), 3.96-3.77 (m, 4H), 3.72 (t, J=5.2 Hz, 2H), 3.70-3.55 (m, 18H), 3.52 (dq, J=14.4, 5.3 Hz, 4H), 3.43-3.32 (m, 4H), 3.30-3.22 (m, 3H), 2.94-2.82 (m, 1H), 2.79-2.69 (m, 2H), 2.67 (dd, J=10.2, 4.0 Hz, 2H), 2.34-2.23 (m, 1H), 2.22-2.06 (m, 2H), 1.17 (d, J=7.0 Hz, 3H). HRMS (m/z) for C$_{49}$H$_{65}$ClN$_9$O$_{12}$$^+$ [M+H]$^+$: molecular weight calculated 1006.4436, found 1006.4449.

Example 17

Synthesis of XF042-164

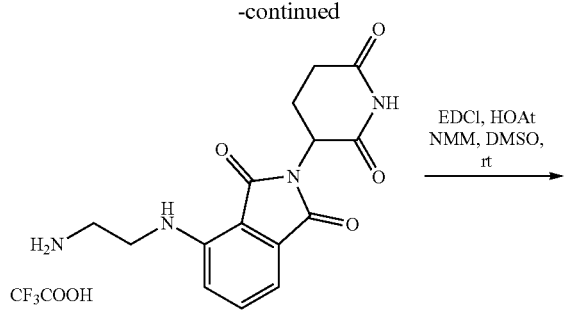

Intermediate 2

+

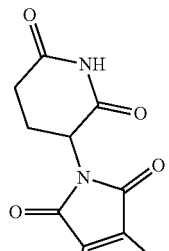

PML-13

→ EDCl, HOAt NMM, DMSO, rt →

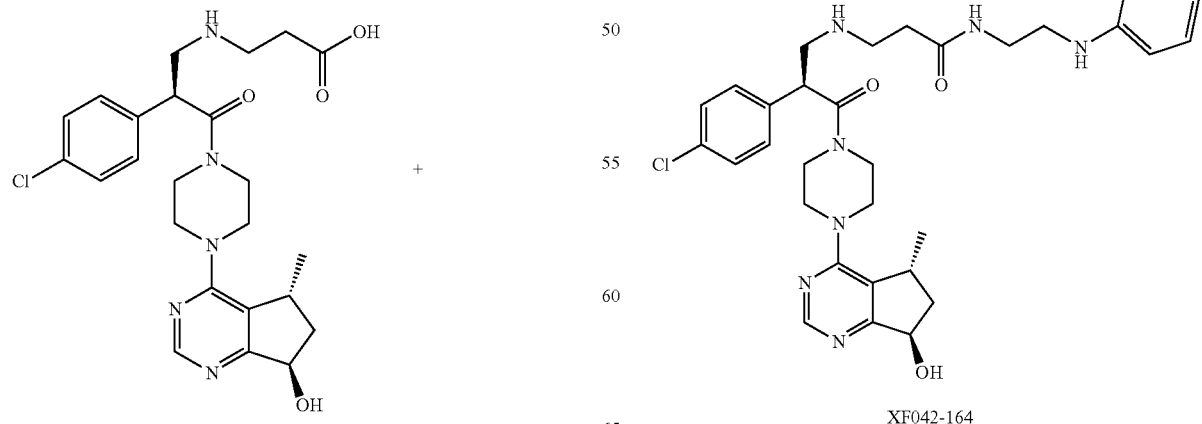

XF042-164

XF042-164 was synthesized following the standard procedure for preparing XF038-157A from intermediate 2 (6.1 mg, 0.01 mmol), PML-13 (4.3 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-164 was obtained as yellow solid in TFA salt form (5.8 mg, 74%). $^1$H NMR (600 MHz, CD$_3$OD) δ 8.55 (s, 1H), 7.62-7.54 (m, 1H), 7.39 (ddd, J=46.1, 8.2, 3.3 Hz, 4H), 7.13 (d, J=8.6 Hz, 1H), 7.05 (dd, J=7.0, 2.3 Hz, 1H), 5.26 (t, J=7.7 Hz, 1H), 5.08 (dt, J=12.3, 5.9 Hz, 1H), 4.57 (d, J=9.1 Hz, 1H), 4.06 (s, 2H), 3.85 (t, J=14.7 Hz, 3H), 3.76-3.56 (m, 4H), 3.56-3.40 (m, 4H), 3.39-3.32 (m, 2H), 3.29-3.24 (m, 2H), 2.92-2.79 (m, 1H), 2.73 (t, J=18.1 Hz, 2H), 2.66 (t, J=5.6 Hz, 2H), 2.25 (t, J=10.2 Hz, 1H), 2.20-2.08 (m, 2H), 1.14 (dd, J=7.0, 1.7 Hz, 3H). HRMS (m/z) for C$_{39}$H$_{45}$ClN$_9$O$_7{}^+$ [M+H]$^+$: molecular weight calculated 786.3125, found 786.3130.

Example 18

Synthesis of XF042-165

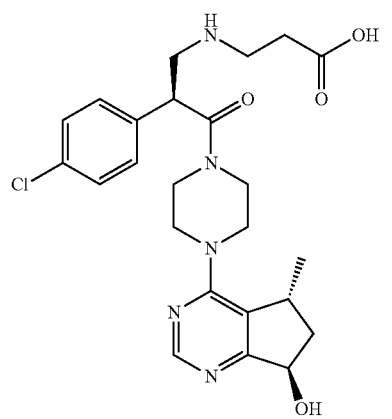

Intermediate 2

+

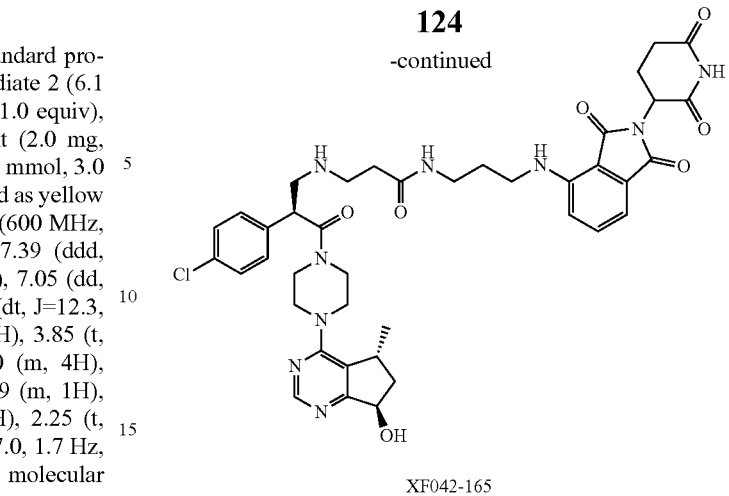

XF042-165

XF042-165 was synthesized following the standard procedure for preparing XF038-157A from intermediate 2 (6.1 mg, 0.01 mmol), PML-14 (4.4 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-165 was obtained as yellow solid in TFA salt form (7.8 mg, 97%). $^1$H NMR (600 MHz, CD$_3$OD) δ 8.51 (s, 1H), 7.55 (q, J=7.0, 6.6 Hz, 1H), 7.44 (d, J=8.3 Hz, 2H), 7.35 (d, J=8.2 Hz, 2H), 7.05 (td, J=8.0, 6.9, 3.6 Hz, 2H), 5.20 (t, J=7.6 Hz, 1H), 5.13-5.02 (m, 1H), 4.61-4.48 (m, 1H), 4.11-3.89 (m, 2H), 3.90-3.67 (m, 4H), 3.68-3.46 (m, 4H), 3.41 (t, J=6.5 Hz, 2H), 3.39-3.31 (m, 3H), 3.28-3.21 (m, 2H), 2.91-2.81 (m, 1H), 2.81-2.55 (m, 4H), 2.28-2.02 (m, 3H), 1.85 (t, J=6.6 Hz, 2H), 1.11 (d, J=7.0 Hz, 3H). HRMS (m/z) for C$_{40}$H$_{47}$ClN$_9$O$_7{}^+$ [M+H]$^+$: molecular weight calculated 800.3281, found 800.3284.

Example 19

Synthesis of XF042-166

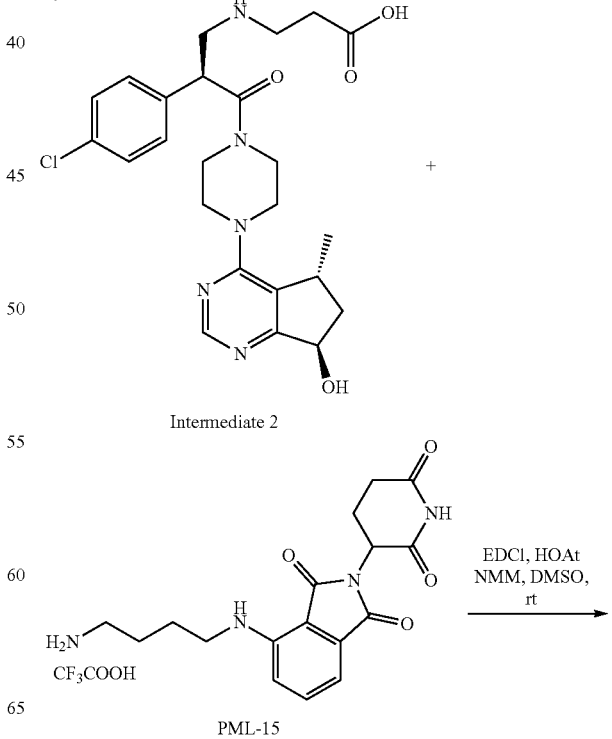

Intermediate 2

+

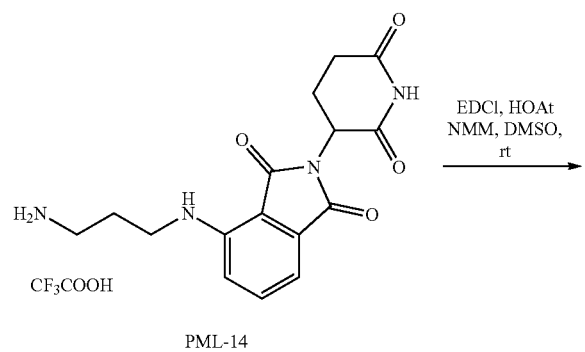

PML-14

PML-15

-continued

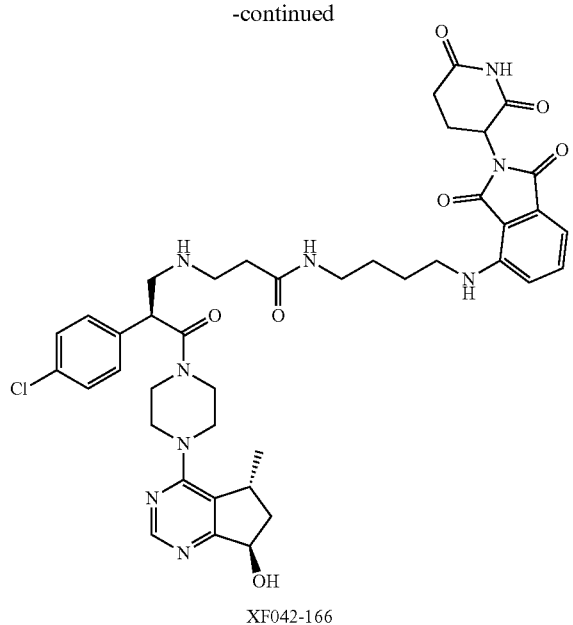

XF042-166

XF042-166 was synthesized following the standard procedure for preparing XF038-157A from intermediate 2 (6.1 mg, 0.01 mmol), PML-15 (4.6 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-166 was obtained as yellow solid in TFA salt form (5.7 mg, 70%). $^1$H NMR (600 MHz, CD$_3$OD) δ 8.53 (s, 1H), 7.56 (t, J=7.8 Hz, 1H), 7.44 (d, J=8.4 Hz, 2H), 7.35 (dd, J=8.4, 4.1 Hz, 2H), 7.05 (t, J=9.5 Hz, 2H), 5.23 (s, 1H), 5.10-5.02 (m, 1H), 4.52 (s, 1H), 4.07 (d, J=11.6 Hz, 1H), 4.03-3.89 (m, 1H), 3.89-3.71 (m, 4H), 3.71-3.50 (m, 4H), 3.42-3.33 (m, 3H), 3.26 (d, J=15.5 Hz, 4H), 2.91-2.80 (m, 1H), 2.80-2.56 (m, 4H), 2.30-2.02 (m, 3H), 1.79-1.55 (m, 4H), 1.14 (d, J=6.8 Hz, 3H). HRMS (m/z) for $C_{41}H_{49}ClN_9O_7^+$ [M+H]$^+$: molecular weight calculated 814.3438, found 814.3443.

Example 20

Synthesis of XF042-167

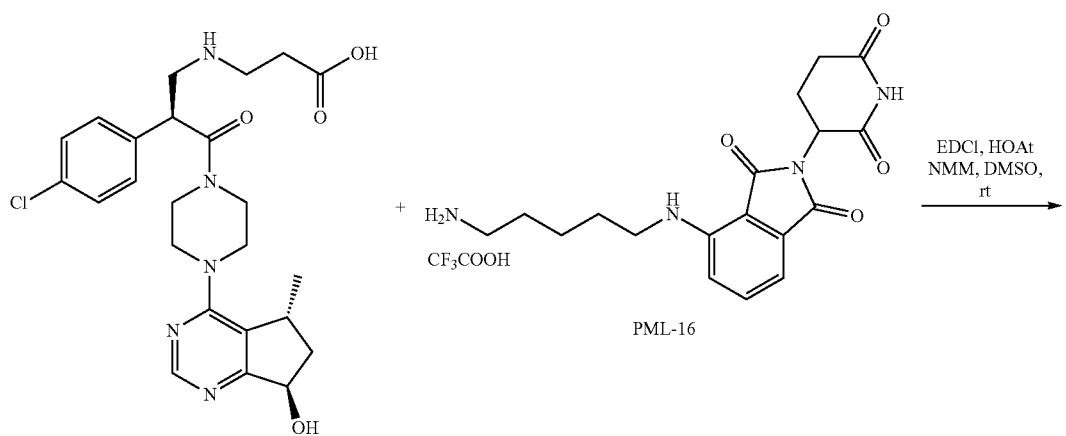

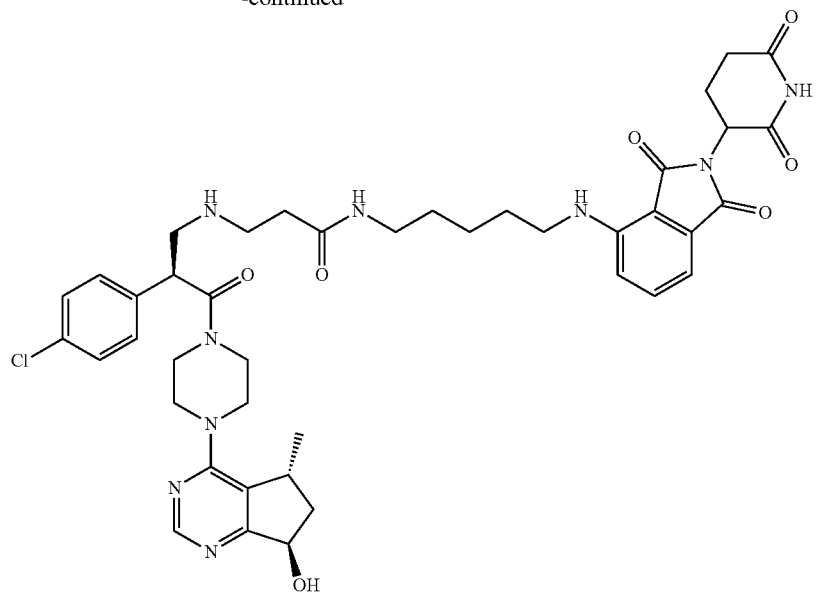

XF042-167

XF042-167 was synthesized following the standard procedure for preparing XF038-157A from intermediate 2 (6.1 mg, 0.01 mmol), PML-16 (4.7 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-167 was obtained as yellow solid in TFA salt form (4.7 mg, 57%). $^1$H NMR (600 MHz, CD$_3$OD) δ 8.54 (s, 1H), 7.55 (t, J=7.8 Hz, 1H), 7.44 (d, J=8.1 Hz, 2H), 7.35 (dd, J=8.4, 2.8 Hz, 2H), 7.04 (t, J=7.8 Hz, 2H), 5.25 (s, 1H), 5.13-5.00 (m, 1H), 4.58-4.45 (m, 1H), 4.16-3.91 (m, 2H), 3.91-3.72 (m, 4H), 3.70-3.54 (m, 4H), 3.35 (q, J=9.8, 6.8 Hz, 4H), 3.28-3.17 (m, 3H), 2.91-2.82 (m, 1H), 2.79-2.68 (m, 2H), 2.65 (d, J=6.2 Hz, 2H), 2.28-2.21 (m, 1H), 2.21-2.14 (m, 1H), 2.13-2.07 (m, 1H), 1.73-1.65 (m, 2H), 1.57 (t, J=7.5 Hz, 2H), 1.46 (d, J=7.7 Hz, 2H), 1.22-1.07 (m, 3H). HRMS (m/z) for C$_{42}$H$_{51}$ClN$_9$O$_7{}^+$ [M+H]$^+$: molecular weight calculated 828.3594, found 828.3597.

Example 21

Synthesis of XF042-168

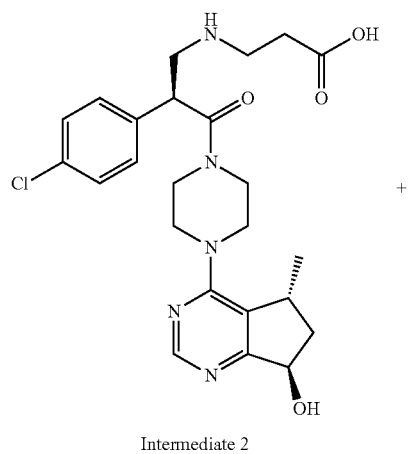

Intermediate 2

+

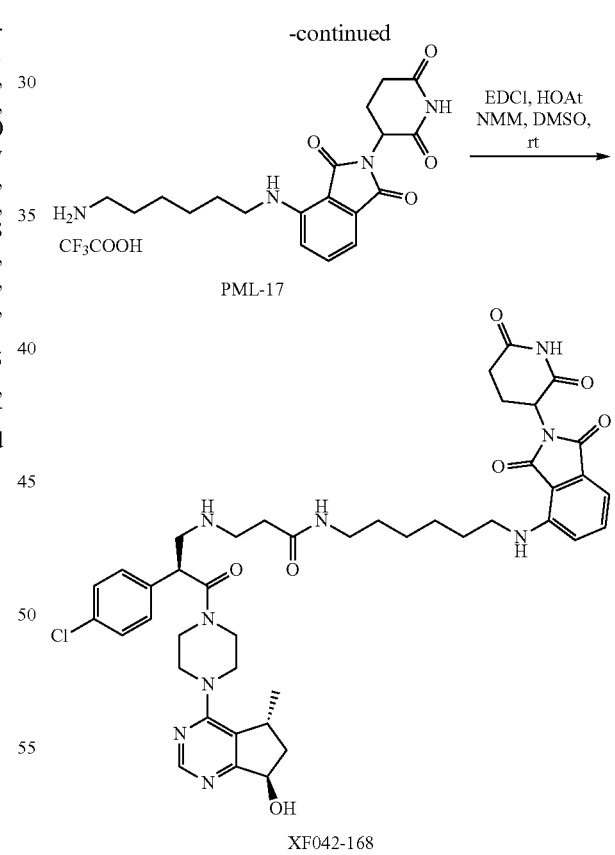

XF042-168

XF042-168 was synthesized following the standard procedure for preparing XF038-157A from intermediate 2 (6.1 mg, 0.01 mmol), PML-17 (4.9 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-168 was obtained as yellow solid in TFA salt form (4.7 mg, 57%). $^1$H NMR (600 MHz, CD₃OD) δ 8.55 (s, 1H), 7.55 (dd, J=8.6, 7.1 Hz, 1H), 7.45 (d, J=8.0 Hz, 2H), 7.39-7.27 (m, 2H), 7.04 (t, J=7.2 Hz, 2H), 5.28 (t, J=7.8 Hz, 1H), 5.05 (dd, J=12.8, 5.5 Hz, 1H), 4.56-4.48 (m, 1H), 4.14 (s, 1H), 4.09-3.97 (m, 1H), 3.92-3.73 (m, 4H), 3.70-3.56 (m, 4H), 3.42-3.32 (m, 4H), 3.28-3.23 (m, 1H), 3.19 (t, J=7.0 Hz, 2H), 2.90-2.81 (m, 1H), 2.77-2.68 (m, 2H), 2.68-2.60 (m, 2H), 2.27 (dd, J=12.9, 7.4 Hz, 1H), 2.21-2.13 (m, 1H), 2.13-2.06 (m, 1H), 1.68 (p, J=7.2 Hz, 2H), 1.53 (p, J=7.2 Hz, 2H), 1.49-1.43 (m, 2H), 1.40 (d, J=7.2 Hz, 2H), 1.16 (d, J=7.0 Hz, 3H). HRMS (m/z) for $C_{43}H_{53}ClN_9O_7^+$ [M+H]⁺: molecular weight calculated 842.3751, found 842.3758.
Example 22
Synthesis of XF048-5
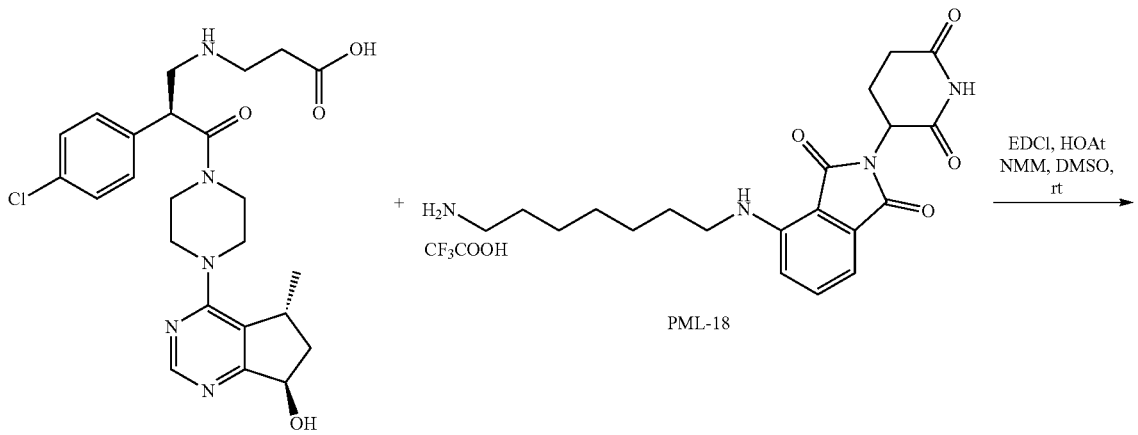
Intermediate 2
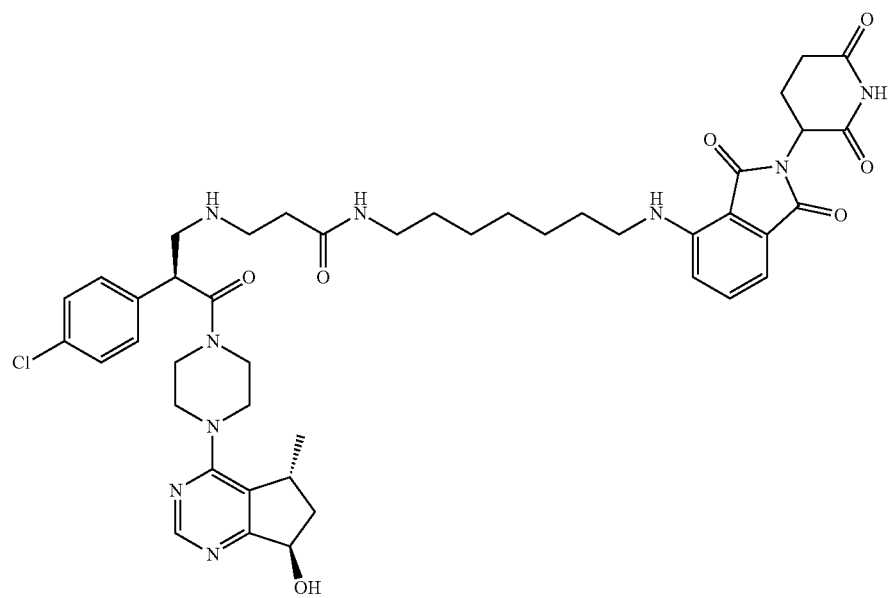
XF048-5

XF048-5 was synthesized following the standard procedure for preparing XF038-157A from intermediate 2 (6.1 mg, 0.01 mmol), PML-18 (5.2 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF048-5 was obtained as yellow solid in TFA salt form (8.8 mg, 98%). $^1$H NMR (600 MHz, CD$_3$OD) δ 8.57 (d, J=4.4 Hz, 1H), 7.55 (dd, J=8.6, 7.1 Hz, 1H), 7.45 (d, J=8.4 Hz, 2H), 7.39-7.29 (m, 2H), 7.04 (dd, J=7.8, 6.1 Hz, 2H), 5.30 (t, J=7.9 Hz, 1H), 5.05 (dd, J=12.8, 5.5 Hz, 1H), 4.52 (dt, J=9.6, 5.0 Hz, 1H), 4.16 (s, 1H), 4.04 (d, J=22.0 Hz, 1H), 3.97-3.76 (m, 4H), 3.71-3.58 (m, 4H), 3.40 (t, J=8.9 Hz, 1H), 3.34 (d, J=6.9 Hz, 2H), 3.29-3.25 (m, 2H), 3.18 (t, J=6.8 Hz, 2H), 2.86 (ddd, J=17.6, 14.0, 5.4 Hz, 1H), 2.79-2.67 (m, 2H), 2.63 (t, J=6.3 Hz, 2H), 2.28 (dd, J=12.7, 7.5 Hz, 1H), 2.17 (dt, J=12.5, 8.1 Hz, 1H), 2.14-2.08 (m, 1H), 1.67 (p, J=7.0 Hz, 2H), 1.50 (p, J=7.2 Hz, 2H), 1.47-1.30 (m, 6H), 1.17 (d, J=6.9 Hz, 3H). HRMS (m/z) for C$_{44}$H$_{55}$ClN$_9$O$_7^+$ [M+H]$^+$: molecular weight calculated 856.3907, found 856.3912.

Example 23

Synthesis of XF042-170

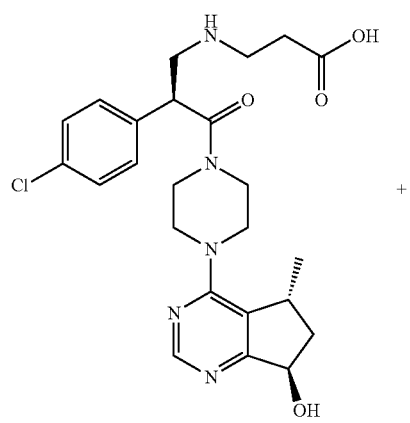

Intermediate 2

+

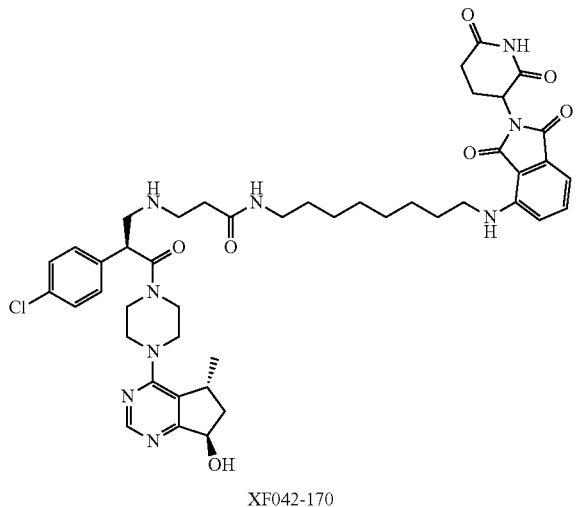

XF042-170

XF042-170 was synthesized following the standard procedure for preparing XF038-157A from intermediate 2 (6.1 mg, 0.01 mmol), PML-19 (5.3 mg, 0.01 mmol, 1.0 equiv), EDCI (2.9 mg, 0.015 mmol, 1.5 equiv), HOAt (2.0 mg, 0.015 mmol, 1.5 equiv), and NMM (3.0 mg, 0.03 mmol, 3.0 equiv) in DMSO (1 mL). XF042-170 was obtained as yellow solid in TFA salt form (2.8 mg, 32%). $^1$H NMR (600 MHz, CD$_3$OD) δ 8.56 (s, 1H), 7.55 (dd, J=8.6, 7.0 Hz, 1H), 7.45 (d, J=8.2 Hz, 2H), 7.41-7.29 (m, 2H), 7.04 (dd, J=7.8, 3.6 Hz, 2H), 5.28 (t, J=7.8 Hz, 1H), 5.05 (dd, J=12.8, 5.5 Hz, 1H), 4.52 (dd, J=9.3, 4.1 Hz, 1H), 4.15 (s, 1H), 4.10-3.97 (m, 1H), 3.94-3.74 (m, 4H), 3.74-3.50 (m, 4H), 3.44-3.32 (m, 4H), 3.28-3.24 (m, 1H), 3.17 (t, J=7.2 Hz, 2H), 2.86 (ddd, J=18.5, 13.8, 5.4 Hz, 1H), 2.78-2.67 (m, 2H), 2.63 (t, J=6.2 Hz, 2H), 2.27 (dd, J=12.9, 7.4 Hz, 1H), 2.21-2.14 (m, 1H), 2.14-2.06 (m, 1H), 1.67 (p, J=7.0 Hz, 2H), 1.53-1.25 (m, 10H), 1.16 (d, J=7.0 Hz, 3H). HRMS (m/z) for C$_{45}$H$_{57}$ClN$_9$O$_7^+$ [M+H]$^+$: molecular weight calculated 870.4064, found 870.4062.

Example 24

Synthesis of Intermediate 3

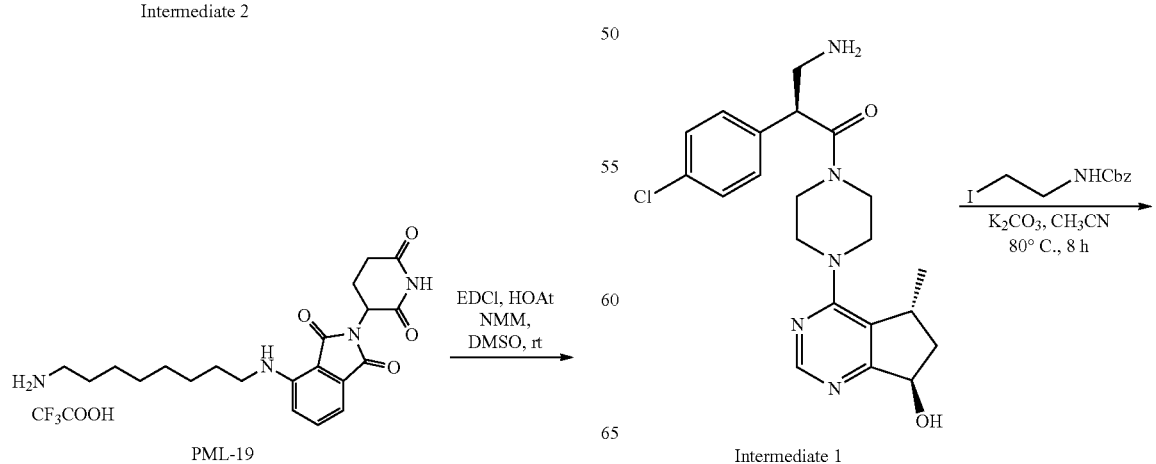

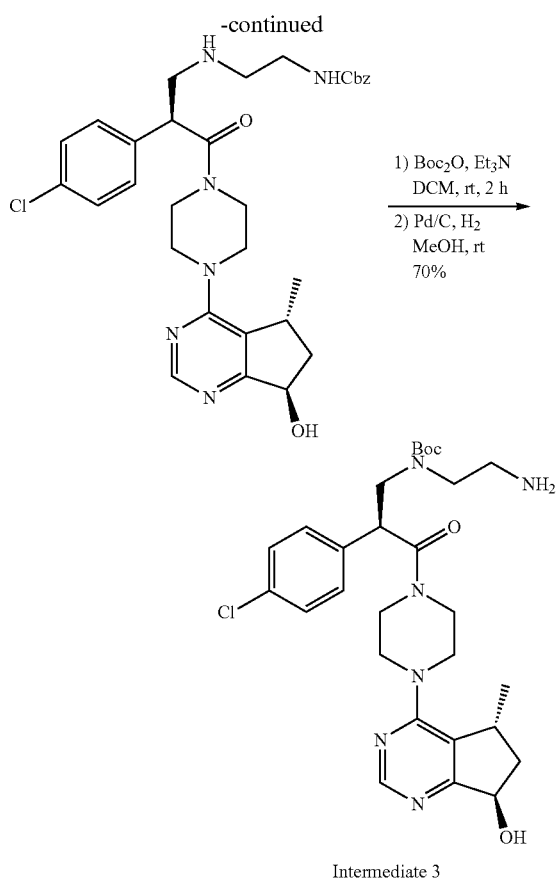

Intermediate 3

To a solution of intermediate 1 (467 mg, 1.12 mmol, 1.1 equiv) in CH₃CN was added potassium carbonate (706 mg, 5 mmol, 5 equiv). After the resulting suspension was stirred at 80° C. for 15 min, benzyl (2-iodoethyl)carbamate (305 mg, 1.0 mmol) was added. The reaction was stirred at 80° C. for 8 h, before the reaction was filtered, and the filtrate was concentrated. The resulting residue was purified by preparative HPLC to afford the desired product as white solid (201 mg, yield 30%). The white solid (201 mg, 0.34 mmol) was dissolved in DCM (5 mL). To the resulting solution was added Triethylamine (92 μL, 0.68 mmol, 2 equiv) and Di-tert-butyl dicarbonate (89 mg, 0.4 mmol, 1.2 equiv). The reaction was stirred at rt for 2 h, before the solvent was removed. The resulting residue was purified by silica gel column (MeOH/DCM=1:9). The desired product was obtained (160 mg, 68% yield). After this product was dissolved in methanol (6 mL), 10% palladium on carbon was added. This reaction was stirred under H₂ for 4 h, before it was filtered. After the filtrate was concentrated, the resulting residue was purified by preparative HPLC to afford the desired product as white solid in TFA salt form (91 mg, yield 71%). ¹H NMR (600 MHz, CD₃OD) δ 8.58 (d, J=3.7 Hz, 1H), 7.44-7.35 (m, 2H), 7.32 (s, 2H), 5.31 (t, J=8.0 Hz, 1H), 4.32 (s, 1H), 4.21 (s, 1H), 3.98 (d, J=8.2 Hz, 1H), 3.85 (s, 2H), 3.79-3.65 (m, 6H), 3.57 (d, J=13.4 Hz, 2H), 3.51-3.41 (m, 2H), 3.03 (s, 1H), 2.29 (ddd, J=12.7, 7.3, 1.1 Hz, 1H), 2.18 (dtd, J=10.7, 7.6, 7.0, 2.9 Hz, 1H), 1.41 (s, 9H), 1.17 (d, J=7.0 Hz, 3H). HRMS (m/z) for $C_{28}H_{40}ClN_6O_4^+$ [M+H]⁺: molecular weight calculated 559.2794, found 559.2792.

Example 25

Synthesis of XF048-1

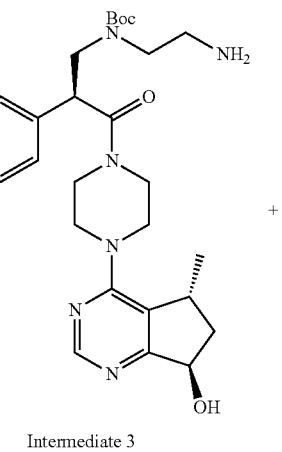

Intermediate 3

+

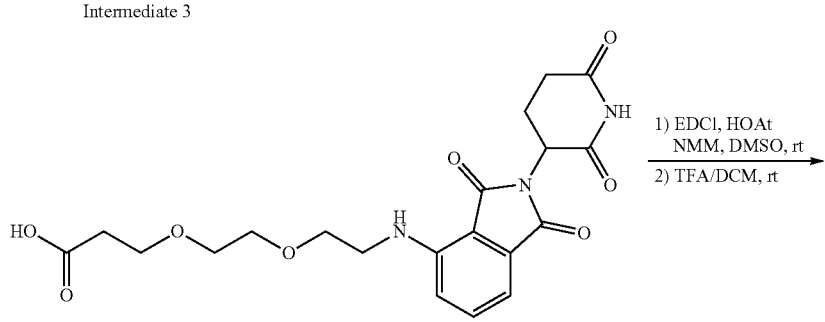

PML-21

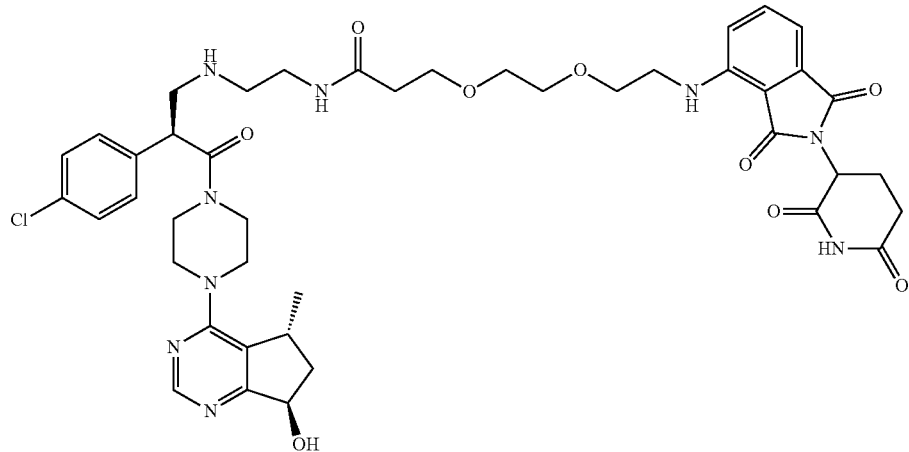

XF048-1

XF048-1 was synthesized following the standard procedure for preparing XF038-157A from intermediate 3 (7.8 mg, 0.012 mmol), PML-21 (5.2 mg, 0.012 mmol, 1.0 equiv), EDCI (3.5 mg, 0.018 mmol, 1.5 equiv), HOAt (2.5 mg, 0.018 mmol, 1.5 equiv), and NMM (3.6 mg, 0.036 mmol, 3.0 equiv) in DMSO (1 mL). Yellow solid in TFA salt form was obtained (8.0 mg, 68%). After this solid was dissolved in DCM (1 mL), TFA (1 mL) was added. The reaction was stirred at rt for 30 min, before the solvent was evaporated. The resulting residue was purified by preparative HPLC (10%-100% methanol/0.1% TFA in H$_2$O) to afford XF048-1 as yellow solid in TFA salt form (9.6 mg, 95%). $^1$H NMR (600 MHz, CD$_3$OD) δ 8.56 (d, J=1.5 Hz, 1H), 7.56 (dd, J=8.6, 7.1 Hz, 1H), 7.49-7.39 (m, 2H), 7.34 (dd, J=8.5, 3.5 Hz, 2H), 7.08 (dd, J=19.9, 7.8 Hz, 2H), 5.30 (t, J=7.9 Hz, 1H), 5.13-5.00 (m, 1H), 4.47 (dd, J=8.8, 4.3 Hz, 1H), 4.16 (s, 1H), 3.95-3.85 (m, 2H), 3.82 (s, 2H), 3.74 (dt, J=15.1, 5.5 Hz, 4H), 3.67-3.58 (m, 8H), 3.53-3.44 (m, 4H), 3.44-3.37 (m, 1H), 3.17 (t, J=5.7 Hz, 2H), 2.91-2.82 (m, 1H), 2.78-2.63 (m, 3H), 2.48 (t, J=5.9 Hz, 2H), 2.28 (dd, J=12.9, 7.4 Hz, 1H), 2.20-2.07 (m, 2H), 1.16 (d, J=6.9 Hz, 3H). HRMS (m/z) for C$_{43}$H$_{53}$ClN$_9$O$_9$$^+$ [M+H]$^+$: molecular weight calculated 874.3649, found 874.3638.

Example 26

Synthesis of XF048-2

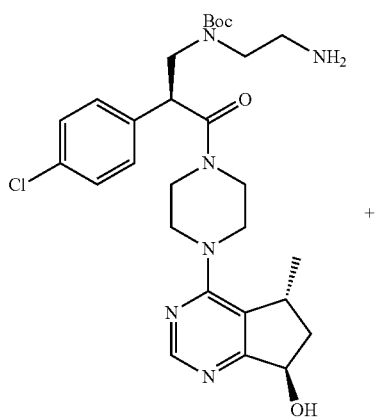

Intermediate 3

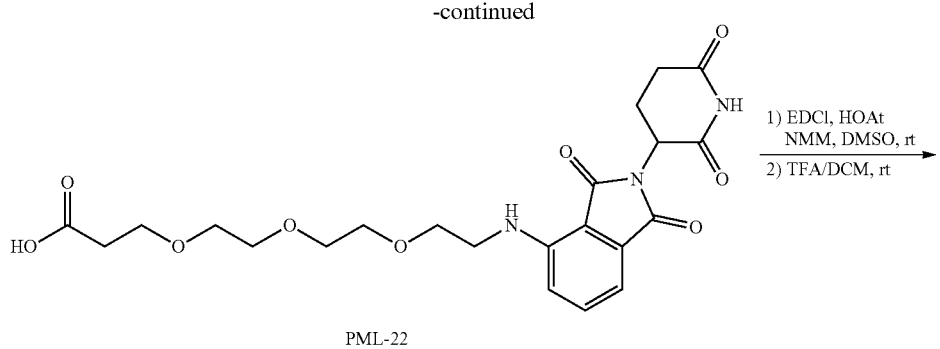

PML-22

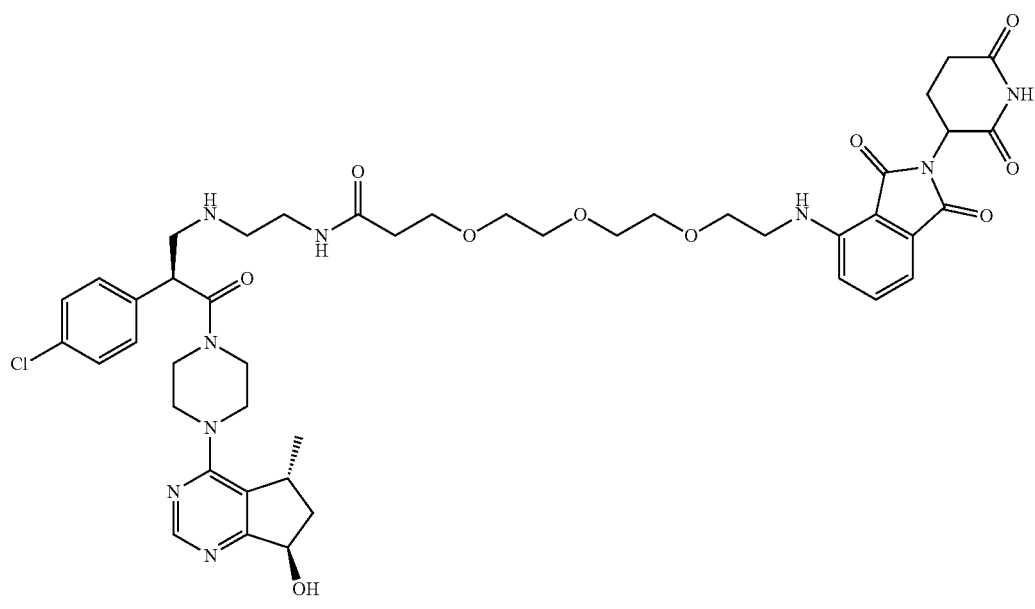

XF048-2

XF048-2 was synthesized following the standard procedure for preparing XF048-1 from intermediate 3 (7.8 mg, 0.012 mmol), PML-22 (5.7 mg, 0.012 mmol, 1.0 equiv), EDCI (3.5 mg, 0.018 mmol, 1.5 equiv), HOAt (2.5 mg, 0.018 mmol, 1.5 equiv), and NMM (3.6 mg, 0.036 mmol, 3.0 equiv) in DMSO (1 mL). Yellow solid in TFA salt form was obtained (11.5 mg, 94%). After this solid was dissolved in DCM (1 mL), TFA (1 mL) was added. The reaction was stirred at rt for 30 min, before the solvent was evaporated. The resulting residue was purified by preparative HPLC (10%-100% methanol/0.1% TFA in H$_2$O) to afford XF048-2 as yellow solid in TFA salt form (8.3 mg, 82%). $^1$H NMR (600 MHz, CD$_3$OD) δ 8.56 (s, 1H), 7.66-7.51 (m, 1H), 7.51-7.41 (m, 2H), 7.41-7.29 (m, 2H), 7.07 (dd, J=20.2, 8.0 Hz, 2H), 5.41-5.22 (m, 1H), 5.17-5.00 (m, 1H), 4.47 (dd, J=9.2, 4.7 Hz, 1H), 4.17 (s, 1H), 4.01-3.78 (m, 4H), 3.79-3.56 (m, 16H), 3.50 (p, J=8.8, 7.6 Hz, 4H), 3.41 (d, J=8.6 Hz, 2H), 3.26-3.15 (m, 2H), 2.86 (d, J=15.4 Hz, 1H), 2.82-2.63 (m, 2H), 2.55-2.43 (m, 2H), 2.28 (dd, J=12.8, 7.5 Hz, 1H), 2.24-2.05 (m, 2H), 1.16 (d, J=7.1 Hz, 3H). HRMS (m/z) for C$_{45}$H$_{57}$ClN$_9$O$_{10}{}^+$ [M+H]$^+$: molecular weight calculated 918.3911, found 918.3914.

Example 27

Synthesis of XF048-3

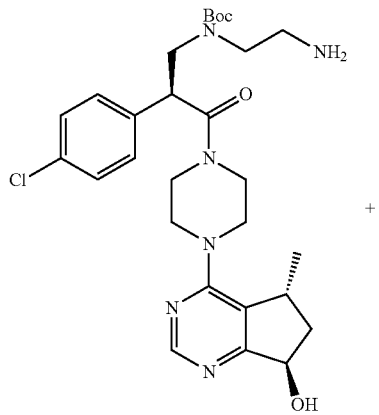
Intermediate 3

+

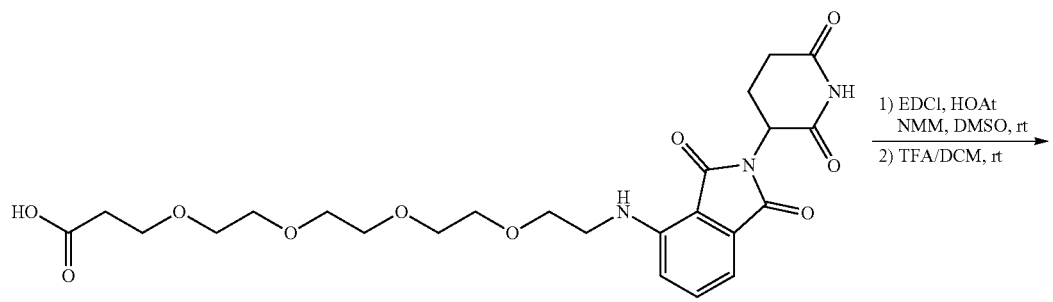
PML-23

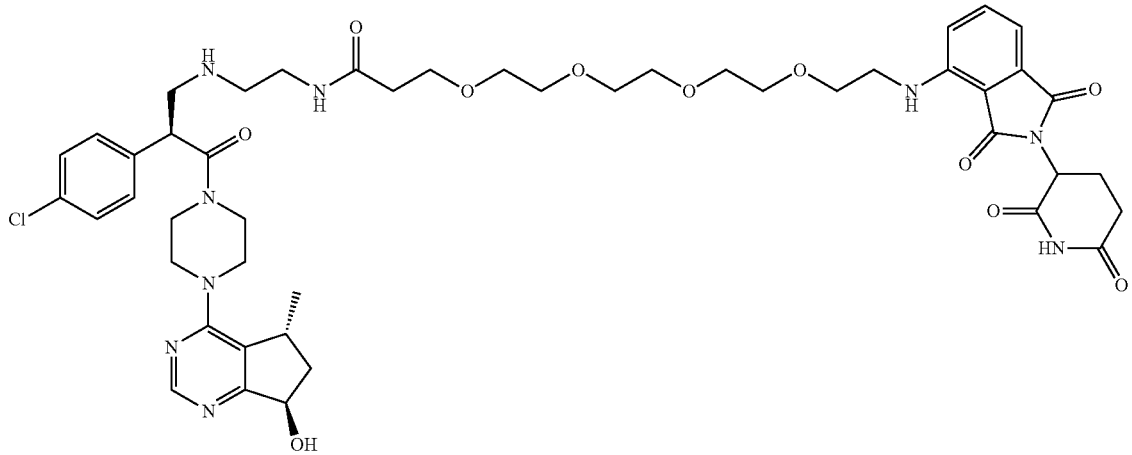
XF048-3

XF048-3 was synthesized following the standard procedure or preparing XF04-1 from intermediate 3 (7.8 mg, 0.012 mmol), PML-23 (6.3 mg, 0.012 mmol, 1.0 equiv), EDCI (3.5 mg, 0.018 mmol, 1.5 equiv), HOAt (2.5 mg, 0.018 mmol, 1.5 equiv), and NMM (3.6 mg, 0.036 mmol, 3.0 equiv) in DMSO (1 mL). Yellow solid in TFA salt form was obtained (9.9 mg, 78%). After this solid was dissolved in DCM (1 mL), TFA (1 mL) was added. The reaction was stirred at rt for 30 min, before the solvent was evaporated. The resulting residue was purified by preparative HPLC (10%-100% methanol/0.1% TFA in $H_2O$) to afford XF048-3 as yellow solid in TFA salt form (6.9 mg, 80%). $^1$H NMR (600 MHz, $CD_3OD$) δ 8.57 (t, J=1.6 Hz, 1H), 7.62-7.51 (m, 1H), 7.48-7.39 (m, 2H), 7.34 (ddd, J=8.5, 4.0, 1.9 Hz, 2H), 7.15-7.00 (m, 2H), 5.30 (t, J=7.9 Hz, 1H), 5.13-5.02 (m, 1H), 4.44 (d, J=8.6 Hz, 1H), 4.17 (s, 1H), 3.96-3.82 (m, 3H), 3.82-3.69 (m, 5H), 3.69-3.52 (m, 16H), 3.52-3.44 (m, 3H), 3.42 (d, J=6.4 Hz, 1H), 3.37-3.32 (m, 1H), 3.26 (d, J=5.9 Hz, 1H), 3.21 (d, J=5.8 Hz, 2H), 2.91-2.83 (m, 1H), 2.80-2.64 (m, 2H), 2.47 (t, J=6.8 Hz, 2H), 2.29 (dd, J=12.8, 7.5 Hz, 1H), 2.21-2.07 (m, 2H), 1.16 (d, J=6.9 Hz, 3H). HRMS (m/z) for $C_{47}H_{61}ClN_9O_{11}^+$ [M+H]$^+$: molecular weight calculated 962.4174, found 962.4154.

Example 28

Synthesis of XF048-4

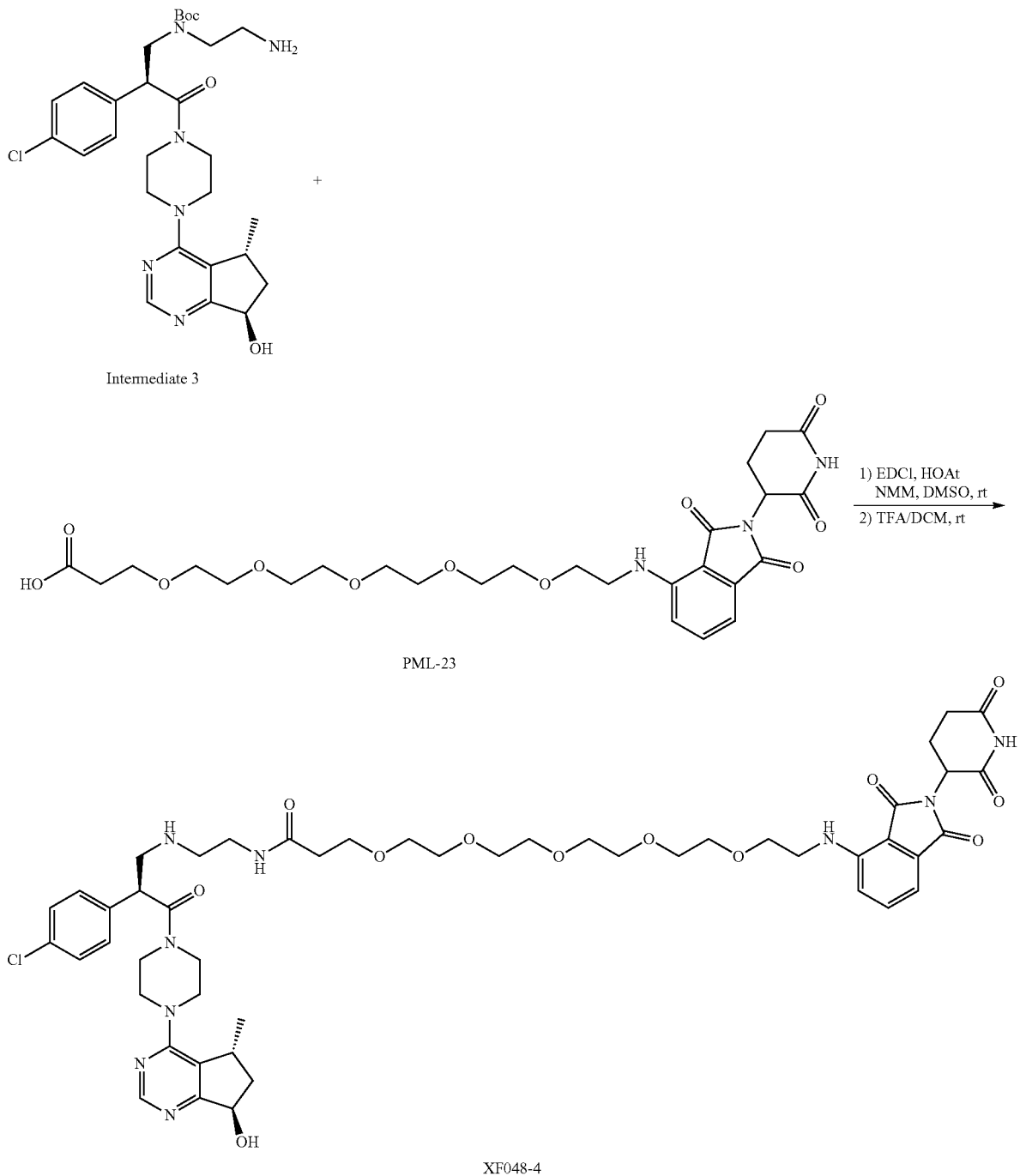

Intermediate 3

PML-23

XF048-4

XF048-4 was synthesized following the standard procedure for preparing XF048-1 from intermediate 3 (7.8 mg, 0.012 mmol), PML-23 (6.6 mg, 0.012 mmol, 1.0 equiv), EDCI (3.5 mg, 0.018 mmol, 1.5 equiv), HOAt (2.5 mg, 0.018 mmol, 1.5 equiv), and NMM (3.6 mg, 0.036 mmol, 3.0 equiv) in DMSO (1 mL). Yellow solid in TFA salt form was obtained (3.0 mg, 23%). After this solid was dissolved in DCM (1 mL), TFA (1 mL) was added. The reaction was stirred at rt for 30 min, before the solvent was evaporated. The resulting residue was purified by preparative HPLC (10%-100% methanol/0.1% TFA in $H_2O$) to afford XF048-4 as yellow solid in TFA salt form (1.2 mg, 38%). $^1$H NMR (600 MHz, $CD_3OD$) δ 8.56 (s, 1H), 7.59-7.53 (m, 1H), 7.45 (dd, J=8.5, 2.9 Hz, 2H), 7.35 (dd, J=8.5, 3.2 Hz, 2H), 7.08 (dd, J=18.9, 7.8 Hz, 2H), 5.29 (t, J=7.9 Hz, 1H), 5.07 (dd, J=12.8, 5.5 Hz, 1H), 4.42 (dd, J=8.9, 4.3 Hz, 1H), 4.17 (s, 1H), 3.95-3.82 (m, 3H), 3.80-3.69 (m, 5H), 3.68-3.51 (m, 21H), 3.49 (t, J=5.2 Hz, 3H), 3.42 (s, 1H), 3.39-3.34 (m, 1H), 3.22 (t, J=5.6 Hz, 2H), 2.91-2.83 (m, 1H), 2.78-2.69 (m, 2H), 2.48 (t, J=5.2 Hz, 2H), 2.28 (dd, J=12.8, 7.5 Hz, 1H), 2.20-2.15 (m, 1H), 2.15-2.09 (m, 1H), 1.16 (d, J=6.9 Hz, 3H). HRMS (m/z) for $C_{49}H_{65}ClN_9O_{11}^+$ $[M+H]^+$: molecular weight calculated 1006.4436, found 1006.4441.

Example 29

Synthesis of Intermediate 6

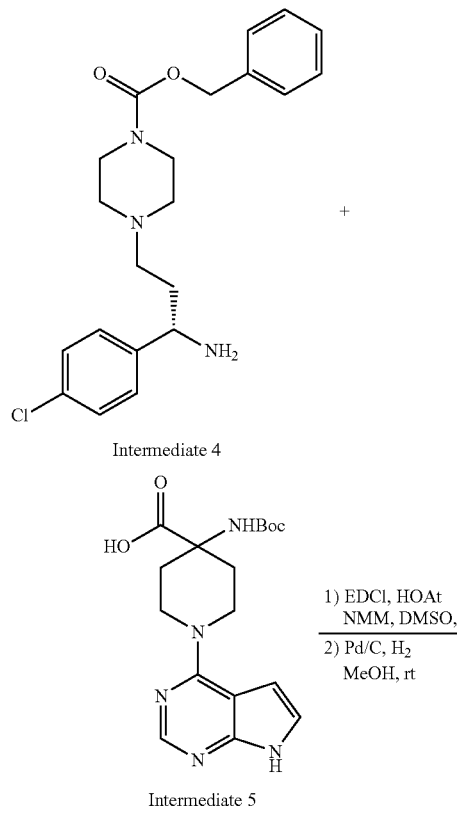

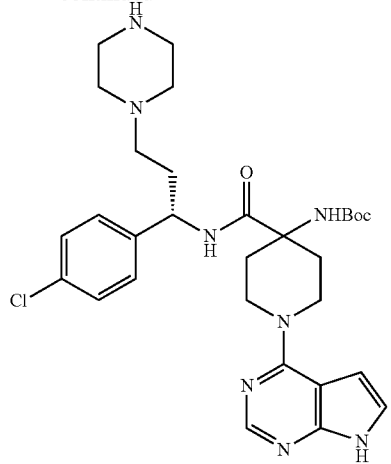

Intermediate 6

To a solution of Intermediate 4 (210 mg, 0.54 mmol) and Intermediate 5 (195 mg, 0.54 mmol, 1.0 equiv) (Addie et al.), in DMSO (5 mL) were added EDCI (159 mg, 0.81 mmol, 1.5 equiv), HOAt (110 mg, 0.81 mmol, 1.5 equiv), and NMM (164 mg, 1.61 mmol, 3.0 equiv). After being stirred overnight at room temperature, the resulting mixture was purified by reverse phase column (0%-100% methanol/ 0.1% TFA in $H_2O$) to afford the desired product as white solid in TFA salt form (416 mg, 99%). After this product was dissolved in methanol (6 mL), 10% palladium on carbon was added. After this reaction was stirred under $H_2$ for 4 h, it was filtered through a pad of celite. The filtrate was concentrated. The resulting residue was purified by reverse phase column (0%-100% methanol/0.1% TFA in $H_2O$) to afford the Intermediate 6 as white solid in TFA salt form (172 mg, yield 51%). $^1$H NMR (600 MHz, $CD_3OD$) δ 8.47-8.31 (m, 1H), 8.28 (s, 1H), 7.35 (dt, J=16.0, 5.8 Hz, 4H), 6.93 (s, 1H), 5.15-5.00 (m, 1H), 4.46-4.19 (m, 2H), 3.91-3.75 (m, 2H), 3.60-3.33 (m, 6H), 3.18-2.76 (m, 4H), 2.46-2.07 (m, 6H), 1.44 (s, 9H). HRMS (m/z) for $C_{30}H_{42}ClN_8O_3^+$ $[M+H]^+$: calculated 597.3063, found 597.3079.

Example 30

Synthesis of XF050-5

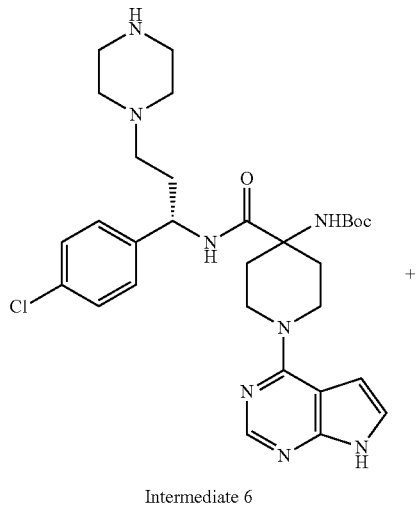

Intermediate 6

-continued

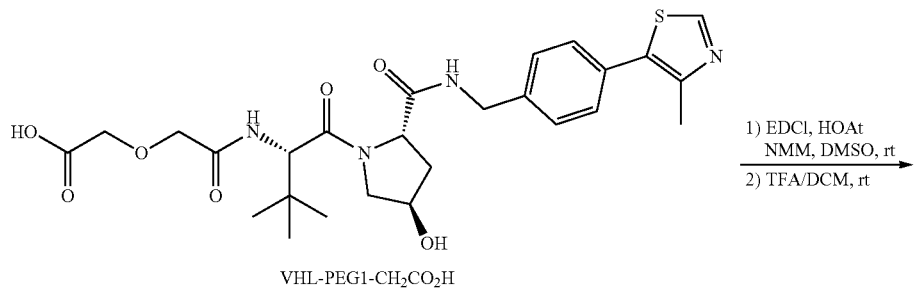

VHL-PEG1-CH2CO2H

1) EDCl, HOAt
NMM, DMSO, rt
2) TFA/DCM, rt

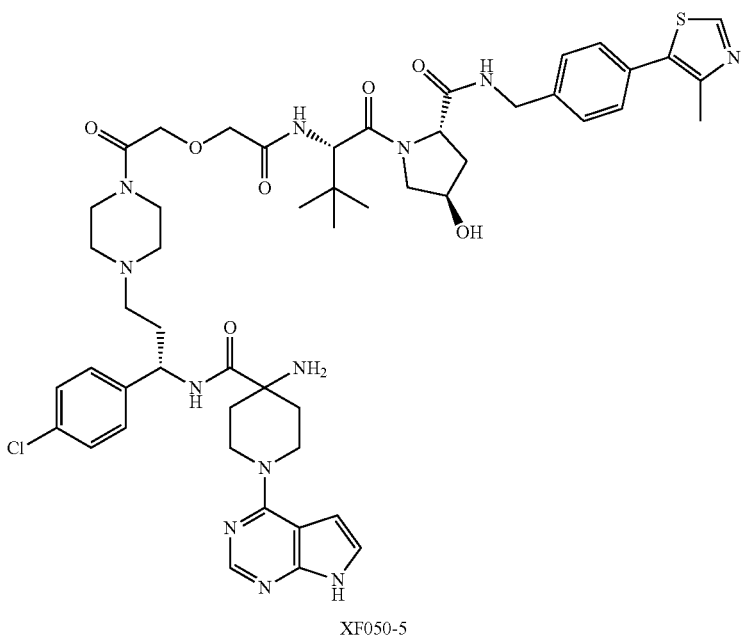

XF050-5

XF050-5 was synthesized following the standard procedure for preparing XF038-157A from intermediate 6 (15.9 mg, 0.022 mmol), VHL-PEG1-CH2CO2H (12.2 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H2O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H2O) to afford XF050-5 as white solid in TFA salt form (19.4 mg, 86%). $^1$H NMR (600 MHz, CD$_3$OD) δ 8.98 (s, 1H), 8.39 (s, 1H), 7.47-7.43 (m, 2H), 7.41 (d, J=8.3 Hz, 2H), 7.39 (d, J=3.7 Hz, 1H), 7.37-7.31 (m, 4H), 6.94 (d, J=3.7 Hz, 1H), 5.00 (dd, J=9.3, 5.8 Hz, 1H), 4.67 (s, 1H), 4.66-4.61 (m, 2H), 4.58-4.53 (m, 1H), 4.53-4.46 (m, 2H), 4.42-4.34 (m, 4H), 4.17-4.03 (m, 3H), 3.92-3.78 (m, 5H), 3.27 (dd, J=12.2, 4.4 Hz, 2H), 3.14 (td, J=12.1, 5.3 Hz, 2H), 2.72-2.58 (m, 3H), 2.47 (s, 3H), 2.39-2.14 (m, 5H), 2.12-2.00 (m, 3H), 1.04 (s, 9H). HRMS (m/z) for $C_{51}H_{66}ClN_{12}O_7S^+$ [M+H]$^+$: calculated 1025.4581, found 1025.4590.

Example 31

Synthesis of XF050-6

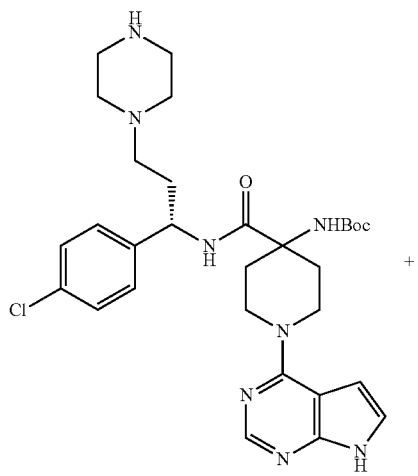

Intermediate 6

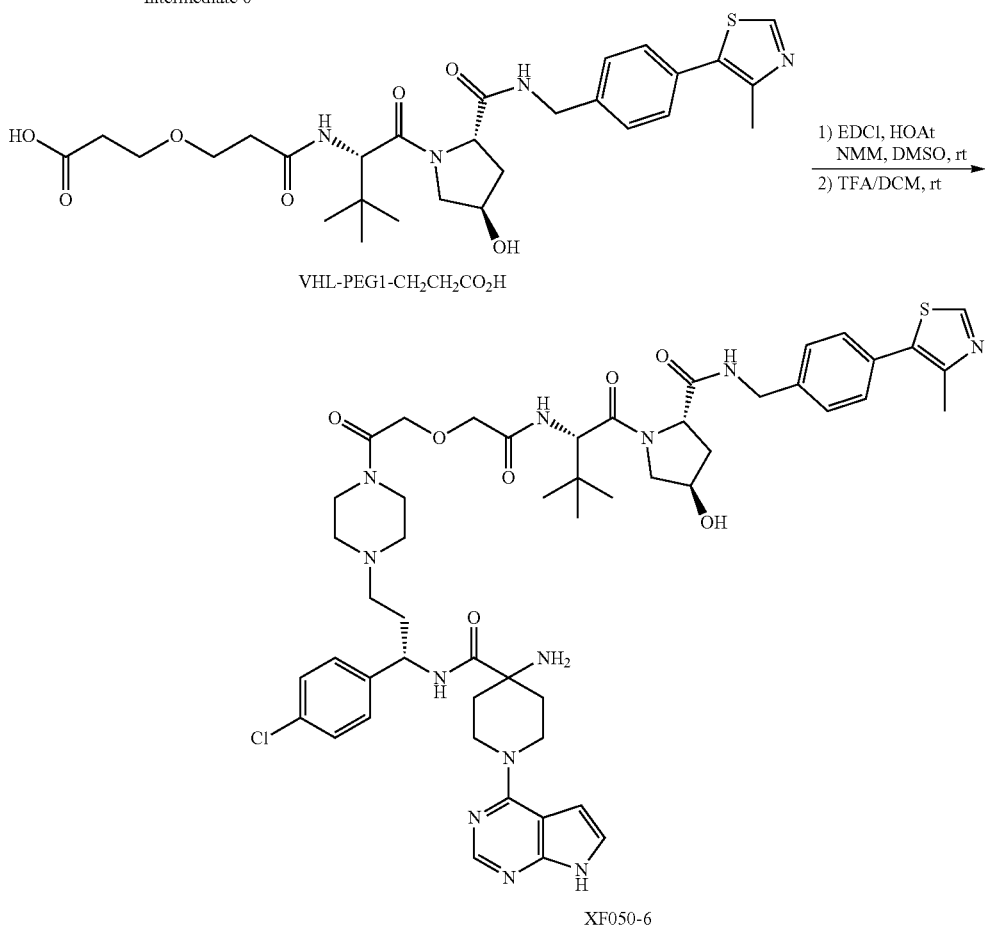

XF050-6 was synthesized following the standard procedure for preparing XF050-5 from intermediate 6 (15.9 mg, 0.022 mmol), VHL-PEG1-CH$_2$CH$_2$CO$_2$H (12.7 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-6 as white solid in TFA salt form (11.9 mg, 52%). ¹H NMR (600 MHz, CD₃OD) δ 8.95 (s, 1H), 8.39 (s, 1H), 7.47-7.30 (m, 9H), 6.94 (d, J=3.8 Hz, 1H), 5.01 (dd, J=9.2, 5.9 Hz, 1H), 4.70-4.60 (m, 4H), 4.53 (dd, J=9.4, 7.5 Hz, 1H), 4.49-4.36 (m, 4H), 3.90-3.76 (m, 5H), 3.75-3.66 (m, 5H), 3.26 (dd, J=12.2, 4.5 Hz, 2H), 3.18-3.09 (m, 2H), 2.71-2.57 (m, 4H), 2.50 (t, J=5.9 Hz, 2H), 2.47 (s, 3H), 2.39-2.13 (m, 5H), 2.11-1.98 (m, 3H), 1.02 (s, 9H). HRMS (m/z) for $C_{53}H_{70}ClN_{12}O_7S^+$ [M+H]⁺: calculated 1053.4894, found 1053.4895.
Example 32
Synthesis of XF050-7
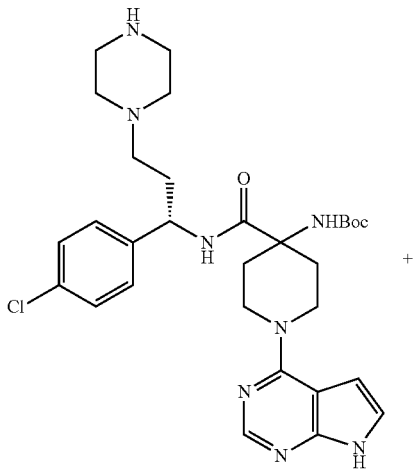
Intermediate 6
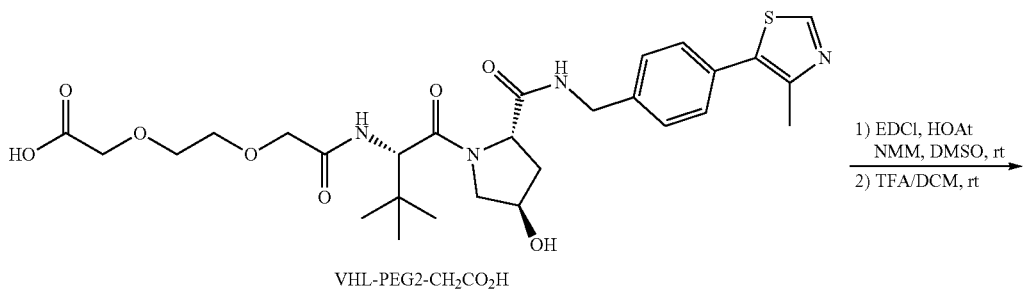
VHL-PEG2-CH₂CO₂H
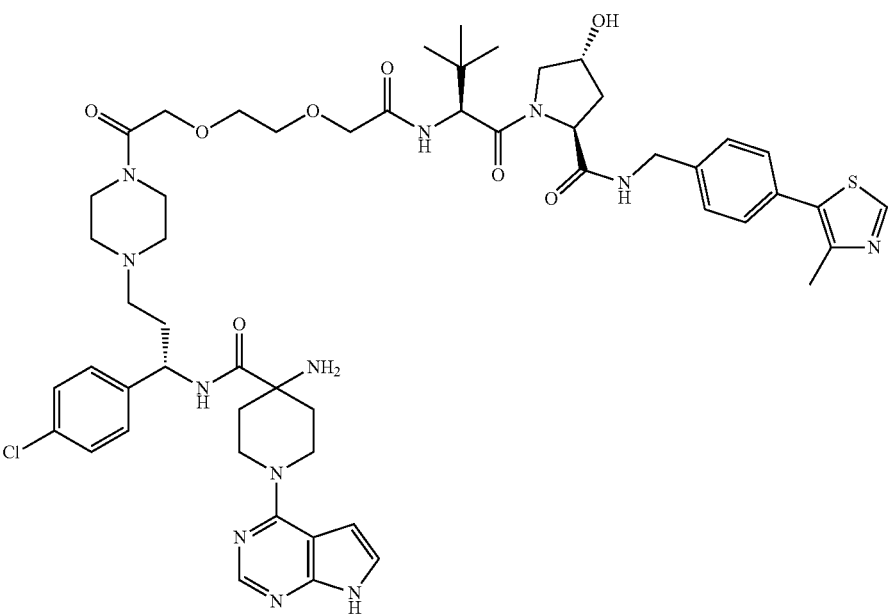
XF050-7

XF050-7 was synthesized following the standard procedure for preparing XF050-5 from intermediate 6 (15.9 mg, 0.022 mmol), VHL-PEG2-CH$_2$CO$_2$H (13.0 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-7 as white solid in TFA salt form (21.1 mg, 89%). $^1$H NMR (600 MHz, CD$_3$OD) δ 9.00 (s, 1H), 8.40 (d, J=2.8 Hz, 1H), 7.48-7.29 (m, 9H), 6.94 (d, J=3.6 Hz, 1H), 5.01 (dd, J=9.2, 5.8 Hz, 1H), 4.69 (d, J=2.7 Hz, 1H), 4.66-4.61 (m, 2H), 4.56-4.51 (m, 1H), 4.47 (d, J=17.9 Hz, 2H), 4.41-4.23 (m, 4H), 4.04 (t, J=2.9 Hz, 2H), 3.90-3.78 (m, 5H), 3.75-3.68 (m, 5H), 3.26 (dd, J=12.1, 4.3 Hz, 2H), 3.19-3.10 (m, 2H), 2.72-2.57 (m, 3H), 2.48 (s, 3H), 2.39-2.14 (m, 5H), 2.12-1.97 (m, 3H), 1.02 (s, 9H). HRMS (m/z) for C$_{53}$H$_{70}$ClN$_{12}$O$_8$S$^+$ [M+H]$^+$: calculated 1069.4843, found 1069.4850.

Example 33

Synthesis of XF050-8

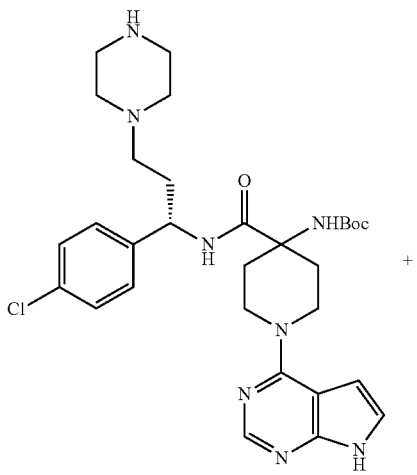

Intermediate 6

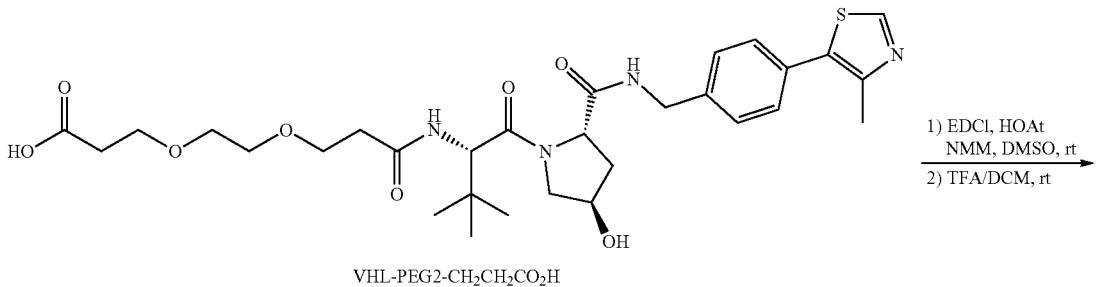

VHL-PEG2-CH$_2$CH$_2$CO$_2$H

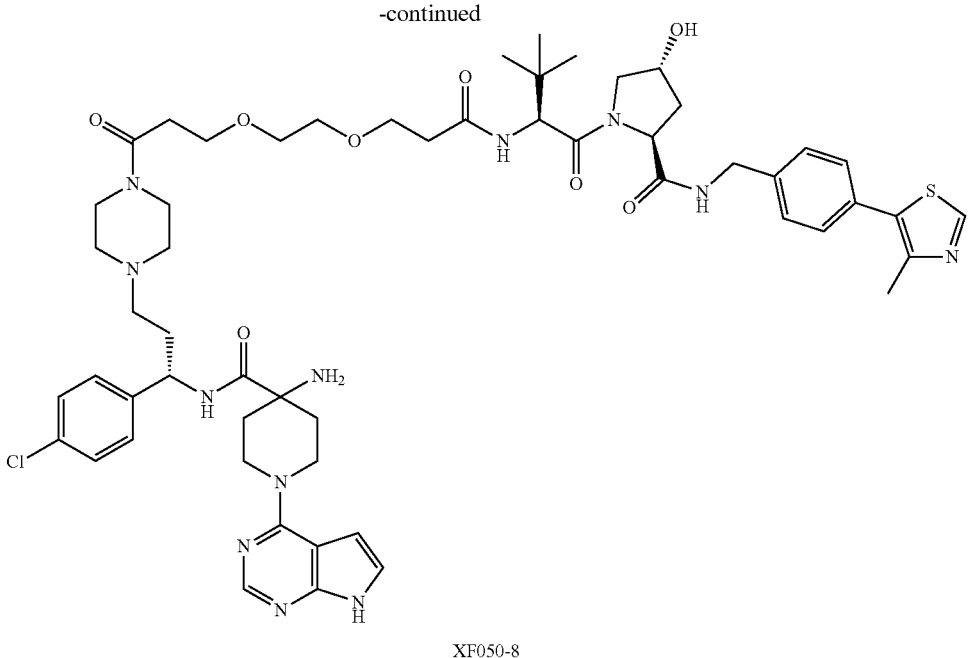

XF050-8

XF050-8 was synthesized following the standard procedure for preparing XF050-5 from intermediate 6 (15.9 mg, 0.022 mmol), VHL-PEG2-CH$_2$CH$_2$CO$_2$H (13.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-8 as white solid in TFA salt form (18.3 mg, 76%). $^1$H NMR (600 MHz, CD$_3$OD) δ 9.00 (s, 1H), 8.39 (s, 1H), 7.49-7.31 (m, 9H), 6.94 (d, J=3.7 Hz, 1H), 5.02 (dd, J=9.2, 5.8 Hz, 1H), 4.64 (s, 4H), 4.59-4.45 (m, 4H), 4.36 (d, J=15.5 Hz, 1H), 3.91-3.77 (m, 5H), 3.75-3.66 (m, 5H), 3.59-3.55 (m, 4H), 3.26 (dd, J=12.3, 4.5 Hz, 2H), 3.13 (td, J=12.1, 5.2 Hz, 2H), 2.74-2.58 (m, 5H), 2.54 (dt, J=15.0, 5.9 Hz, 1H), 2.49-2.42 (m, 4H), 2.40-2.15 (m, 5H), 2.11-2.01 (m, 2H), 1.03 (s, 9H). HRMS (m/z) for C$_{55}$H$_{74}$ClN$_{12}$O$_8$S$^+$ [M+H]$^+$: calculated 1097.5156, found 1097.5160.

Example 34

Synthesis of XF050-9

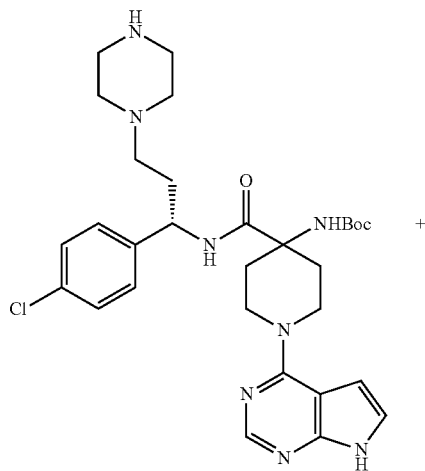

Intermediate 6

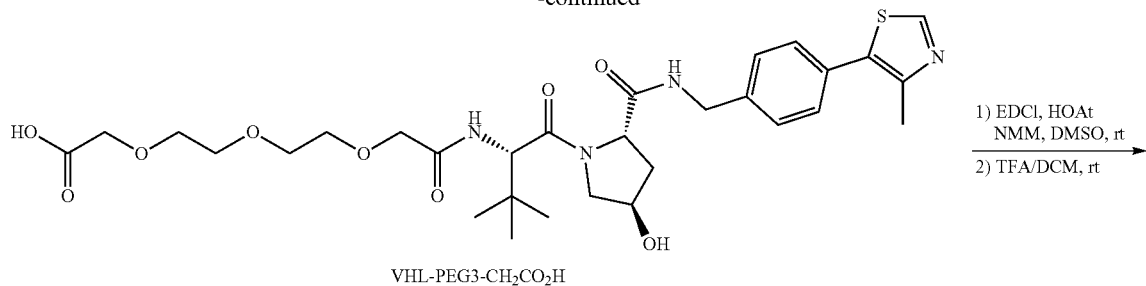

VHL-PEG3-CH₂CO₂H

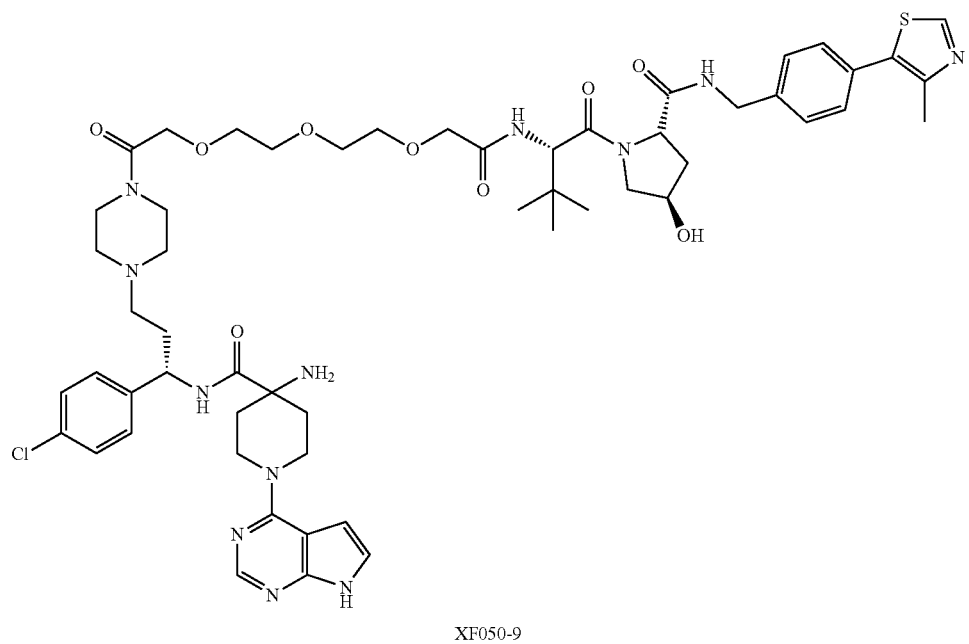

XF050-9

XF050-9 was synthesized following the standard procedure for preparing XF5-5 from intermediate 6 (15.9 mg, 0.022 mmol), VHL-PEG3-CH₂CO₂H (14.0 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H₂O) to afford XF050-9 as white solid in TFA salt form (19.2 mg, 78%). $^1$H NMR (600 MHz, CD$_3$OD) δ 9.01 (d, J=3.0 Hz, 1H), 8.39 (d, J=3.0 Hz, 1H), 7.48-7.30 (m, 9H), 6.95 (d, J=3.7 Hz, 1H), 5.01 (dd, J=9.2, 5.9 Hz, 1H), 4.66 (brs, 4H), 4.57-4.48 (m, 3H), 4.37 (d, J=15.5 Hz, 1H), 4.30-4.17 (m, 2H), 4.04 (s, 2H), 3.93-3.77 (m, 5H), 3.72-3.62 (m, 9H), 3.26 (dd, J=12.2, 4.5 Hz, 2H), 3.12 (td, J=12.1, 5.2 Hz, 2H), 2.73-2.57 (m, 3H), 2.48 (d, J=2.9 Hz, 3H), 2.39-2.15 (m, 5H), 2.13-1.98 (m, 3H), 1.03 (s, 9H). HRMS (m/z) for $C_{55}H_{74}ClN_{12}O_9S^+$ [M+H]$^+$: calculated 1113.5105, found 1113.5120.

Example 35

Synthesis of XF050-10

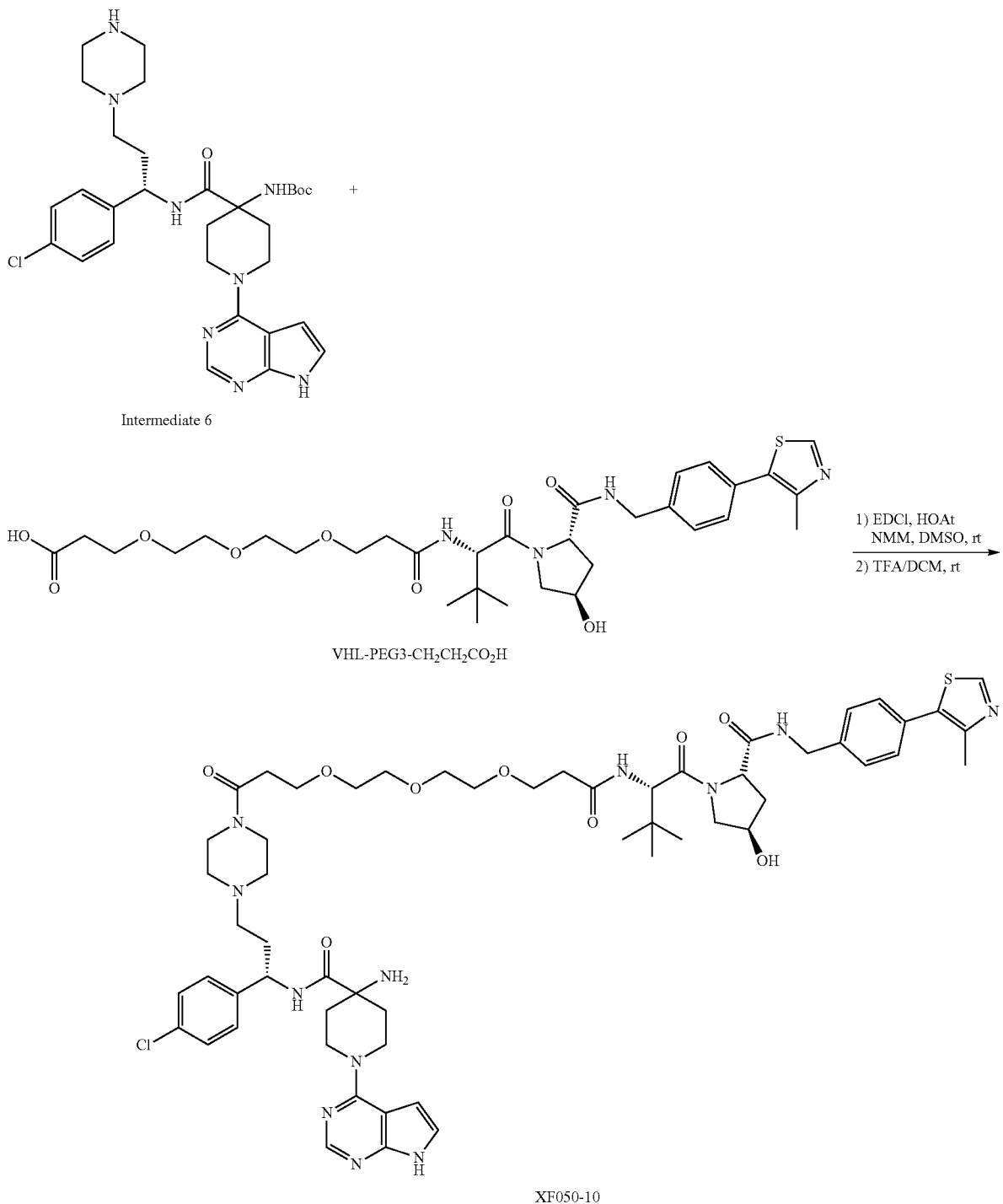

XF050-10 was synthesized following the standard procedure for preparing XF050-5 from intermediate 6 (15.9 mg, 0.022 mmol), VHL-PEG3-CH$_2$CH$_2$CO$_2$H (14.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-10 as white solid in TFA salt form (13.2 mg, 53%). ¹H NMR (600 MHz, CD₃OD) δ 8.99 (s, 1H), 8.40 (s, 1H), 7.51-7.28 (m, 9H), 6.94 (d, J=3.6 Hz, 1H), 5.01 (dd, J=8.9, 6.1 Hz, 1H), 4.74-4.61 (m, 4H), 4.60-4.46 (m, 4H), 4.37 (d, J=15.5 Hz, 1H), 3.91-3.75 (m, 5H), 3.70 (dq, J=16.1, 5.1, 4.1 Hz, 5H), 3.60-3.54 (m, 8H), 3.25 (dd, J=12.2, 4.5 Hz, 2H), 3.11 (td, J=12.1, 5.2 Hz, 2H), 2.73-2.52 (m, 6H), 2.48 (d, J=7.7 Hz, 4H), 2.41-2.14 (m, 5H), 2.12- 2.00 (m, 2H), 1.03 (s, 9H). HRMS (m/z) for $C_{57}H_{78}ClN_{12}O_9S^+$ [M+H]⁺: calculated 1141.5418, found 1141.5438.
Example 36
Synthesis of XF050-11
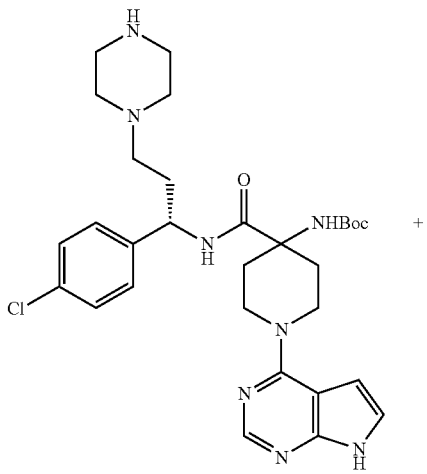
Intermediate 6
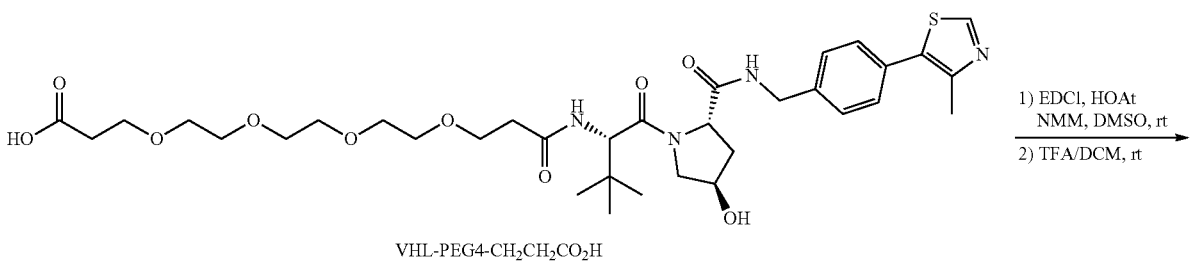
VHL-PEG4-CH₂CH₂CO₂H
1) EDCl, HOAt NMM, DMSO, rt
2) TFA/DCM, rt
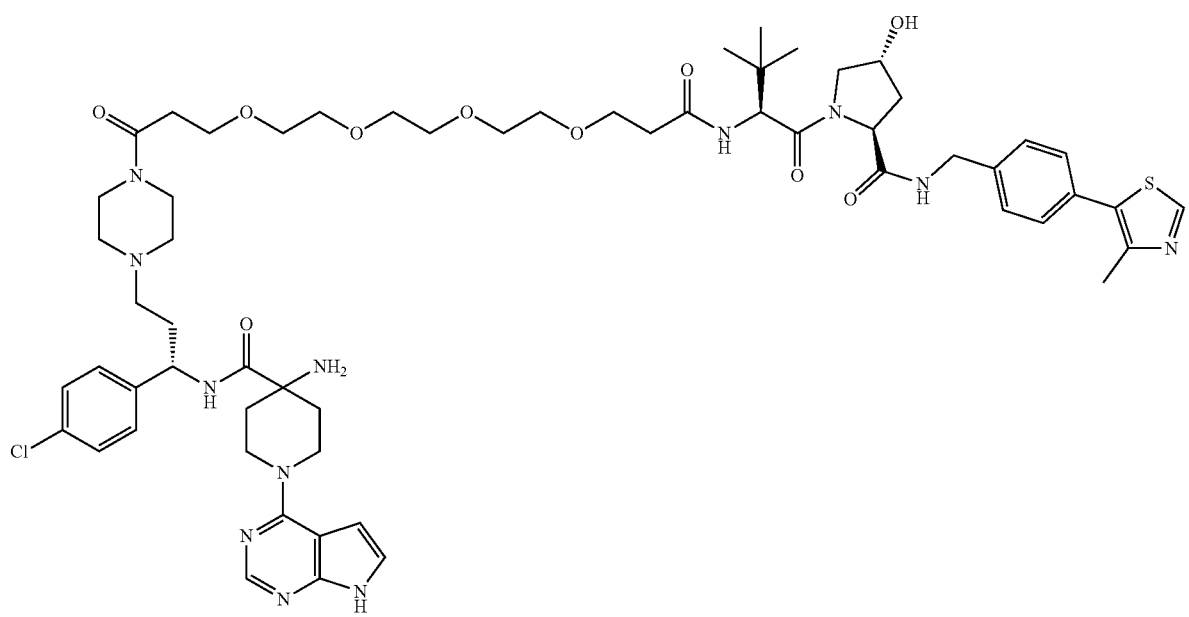
XF050-11

XF050-11 was synthesized following the standard procedure for preparing XF050-5 from intermediate 6 (15.9 mg, 0.022 mmol), VHL-PEG4-CH$_2$CH$_2$CO$_2$H (15.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-11 as white solid in TFA salt form (14.0 mg, 54%). $^1$H NMR (600 MHz, CD$_3$OD) δ 8.95 (s, 1H), 8.39 (s, 1H), 7.51-7.26 (m, 9H), 6.93 (d, J=3.7 Hz, 1H), 5.00 (dd, J=8.8, 6.3 Hz, 1H), 4.70-4.60 (m, 4H), 4.60-4.45 (m, 4H), 4.36 (d, J=15.5 Hz, 1H), 3.90-3.76 (m, 5H), 3.75-3.66 (m, 5H), 3.62-3.51 (m, 12H), 3.26 (td, J=12.4, 4.7 Hz, 2H), 3.10 (td, J=12.1, 5.3 Hz, 2H), 2.72-2.55 (m, 6H), 2.51-2.42 (m, 4H), 2.39-2.14 (m, 5H), 2.11-1.99 (m, 2H), 1.02 (s, 9H). HRMS (m/z) for C$_{59}$H$_{82}$ClN$_{12}$O$_{10}$S$^+$ [M+H]$^+$: calculated 1185.5681, found 1185.5665.

Example 37

Synthesis of XF050-12

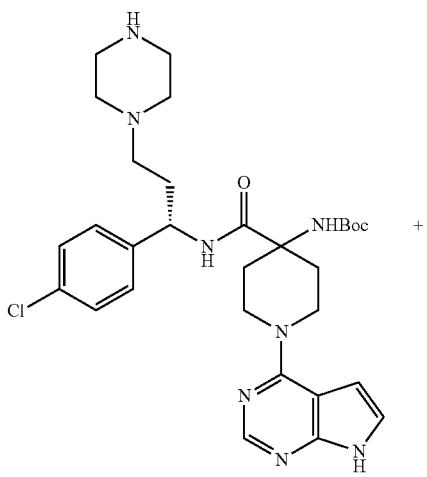

Intermediate 6

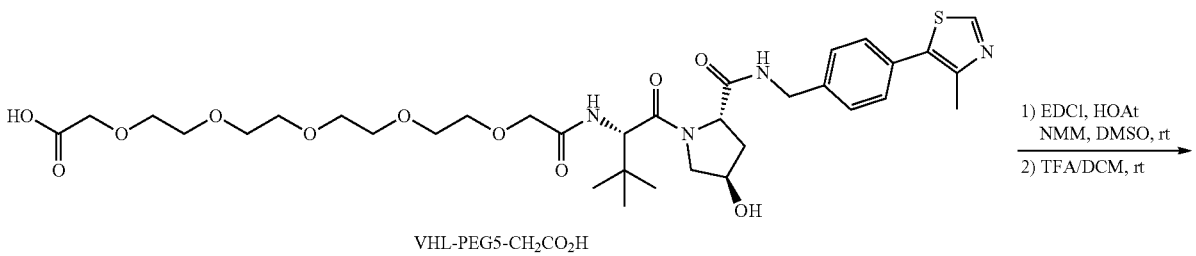

VHL-PEG5-CH$_2$CO$_2$H

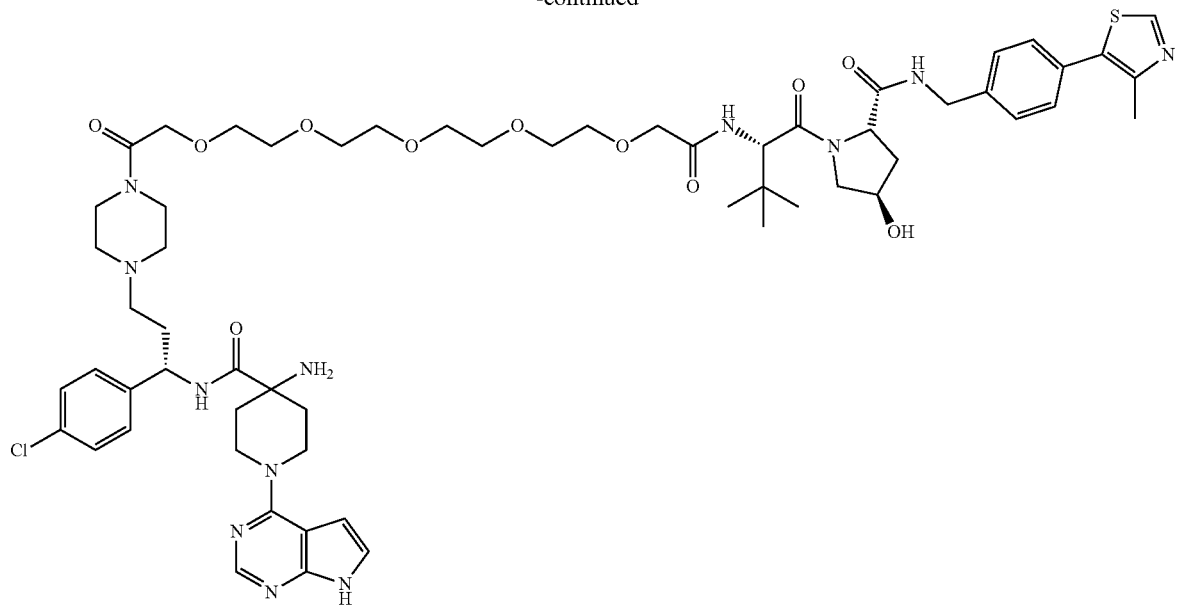

XF050-12

XF050-12 was synthesized following the standard procedure for preparing XF050-5 from intermediate 6 (15.9 mg, 0.022 mmol), VHL-PEG5-CH$_2$CO$_2$H (15.9 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-12 as white solid in TFA salt form (16.3 mg, 62%). $^1$H NMR (600 MHz, CD$_3$OD) δ 8.96 (s, 1H), 8.39 (s, 1H), 7.55-7.17 (m, 9H), 6.93 (d, J=3.7 Hz, 1H), 5.01 (t, J=7.7 Hz, 1H), 4.68-4.46 (m, 8H), 4.36 (d, J=15.5 Hz, 2H), 4.16-4.02 (m, 3H), 3.93-3.82 (m, 4H), 3.78 (dd, J=10.9, 3.8 Hz, 1H), 3.68-3.54 (m, 16H), 3.29-3.20 (m, 2H), 3.17-3.09 (m, 2H), 2.74-2.57 (m, 3H), 2.47 (s, 3H), 2.41-2.13 (m, 5H), 2.12-1.99 (m, 3H), 1.04 (s, 9H). HRMS (m/z) for C$_{59}$H$_{82}$ClN$_{12}$O$_{11}$S$^+$ [M+H]$^+$: calculated 1201.5630, found 1201.5651.

Example 38

Synthesis of XF050-13

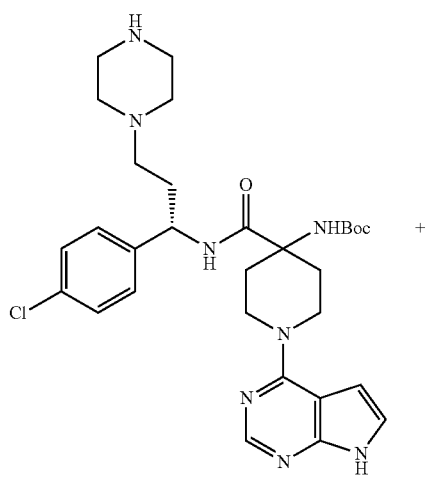

Intermediate 6

-continued

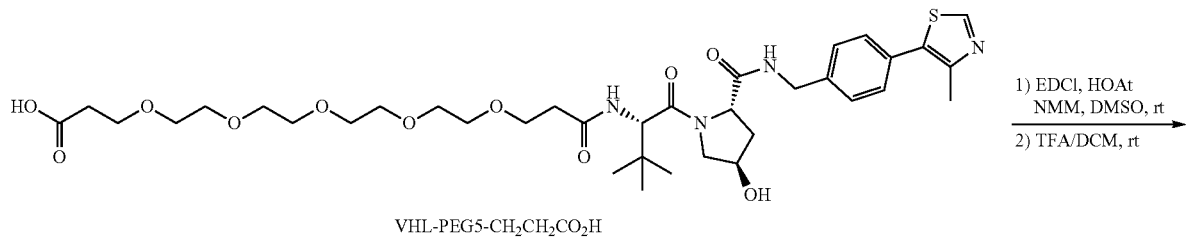

VHL-PEG5-CH₂CH₂CO₂H

1) EDCl, HOAt NMM, DMSO, rt
2) TFA/DCM, rt

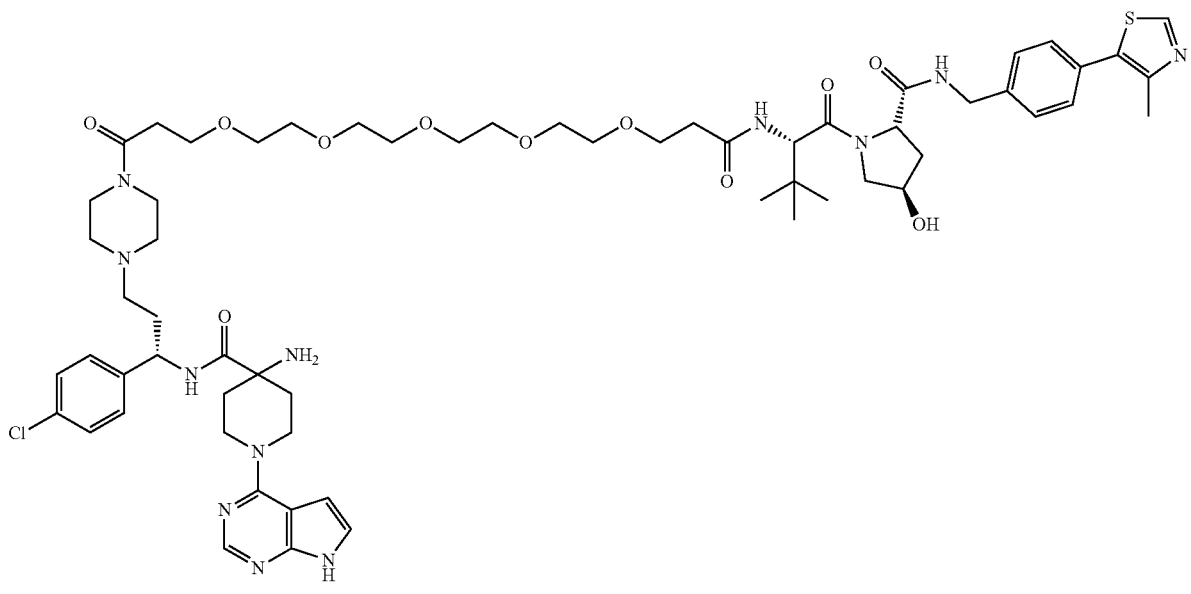

XF050-13

XF050-13 was synthesized following the standard procedure for preparing XF050-5 from intermediate 6 (15.9 mg, 0.022 mmol), VHL-PEG5-CH₂CH₂CO₂H (16.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H₂O) to afford XF050-13 as white solid in TFA salt form (17.3 mg, 64%). $^1$H NMR (600 MHz, CD$_3$OD) δ 9.00 (s, 1H), 8.40 (s, 1H), 7.53-7.28 (m, 9H), 6.94 (d, J=3.7 Hz, 1H), 5.00 (dd, J=8.9, 6.3 Hz, 1H), 4.70-4.60 (m, 4H), 4.60-4.46 (m, 4H), 4.36 (d, J=15.5 Hz, 1H), 3.91-3.76 (m, 5H), 3.76-3.67 (m, 5H), 3.65-3.49 (m, 16H), 3.26 (dd, J=12.3, 4.5 Hz, 2H), 3.11 (td, J=12.2, 5.4 Hz, 2H), 2.72-2.54 (m, 6H), 2.52-2.43 (m, 4H), 2.40-2.13 (m, 5H), 2.12-1.99 (m, 2H), 1.02 (s, 9H). HRMS (m/z) for $C_{61}H_{86}ClN_{12}O_{11}S^+$ [M+H]$^+$: calculated 1229.5943, found 1229.5950.

Example 39
Synthesis of XF050-14
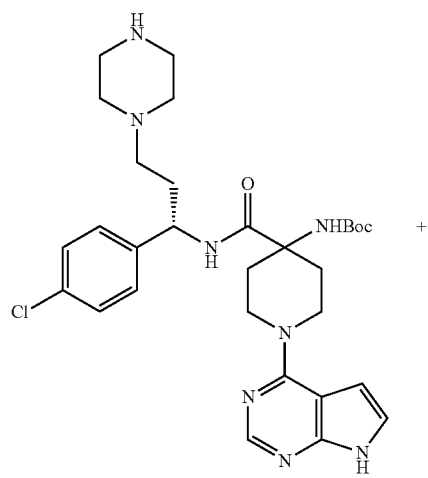
Intermediate 6
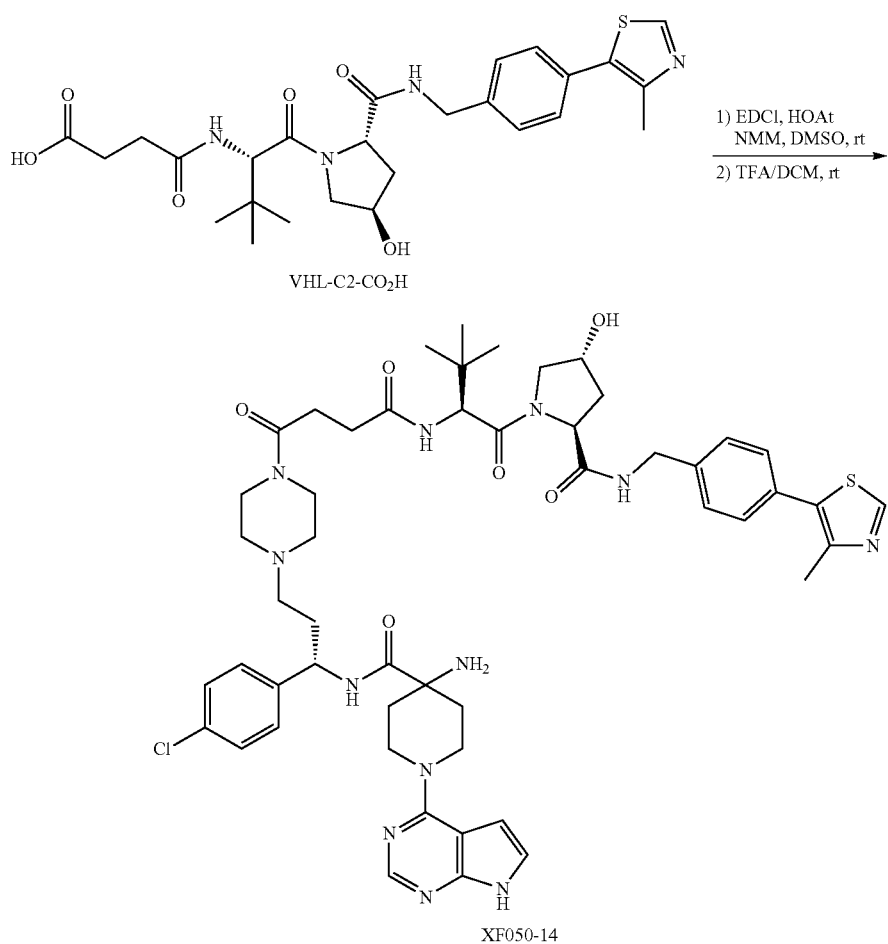

XF050-14 was synthesized following the standard procedure for preparing XF050-5 from intermediate 6 (15.9 mg, 0.022 mmol), VHL-C2-CO$_2$H (11.7 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-14 as white solid in TFA salt form (19.9 mg, 90%). $^1$H NMR (600 MHz, CD$_3$OD) δ 8.99 (s, 1H), 8.40 (s, 1H), 7.52-7.25 (m, 9H), 6.95 (d, J=3.8 Hz, 1H), 5.01 (dd, J=9.2, 5.9 Hz, 1H), 4.71-4.60 (m, 3H), 4.60-4.45 (m, 5H), 4.37 (d, J=15.6 Hz, 1H), 3.92-3.74 (m, 5H), 3.27 (dd, J=12.3, 4.4 Hz, 2H), 3.13 (td, J=12.2, 5.2 Hz, 2H), 2.74-2.52 (m, 7H), 2.48 (s, 3H), 2.41-2.13 (m, 5H), 2.13-1.98 (m, 3H), 1.02 (s, 9H). HRMS (m/z) for C$_{51}$H$_{66}$ClN$_{12}$O$_6$S$^+$ [M+H]$^+$: calculated 1009.4632, found 1009.4638.

Example 40

Synthesis of XF050-15

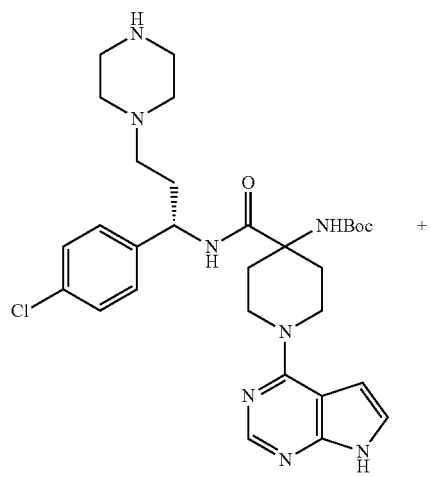

Intermediate 6

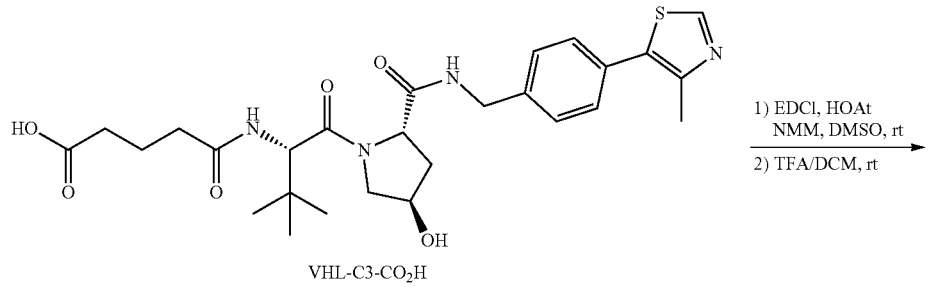

VHL-C3-CO$_2$H

1) EDCI, HOAt NMM, DMSO, rt
2) TFA/DCM, rt

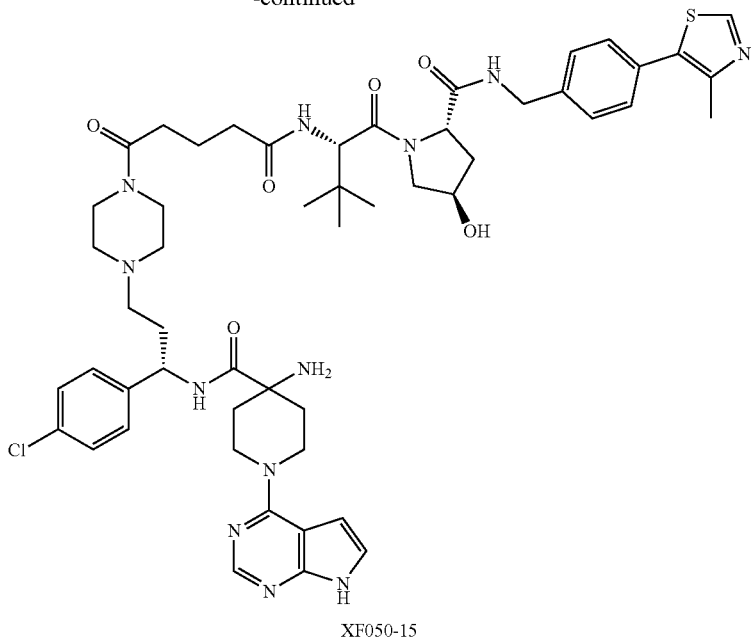

XF050-15

XF050-15 was synthesized following the standard procedure for preparing XF050-5 from intermediate 6 (15.9 mg, 0.022 mmol), VHL-C3-CO$_2$H (12.0 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-15 as white solid in TFA salt form (13.9 mg, 62%). $^1$H NMR (600 MHz, CD$_3$OD) δ 9.00 (s, 1H), 8.40 (s, 1H), 7.51-7.26 (m, 9H), 6.95 (dd, J=3.7, 1.7 Hz, 1H), 5.00 (dd, J=9.2, 5.9 Hz, 1H), 4.70-4.61 (m, 3H), 4.60-4.45 (m, 5H), 4.37 (d, J=15.4 Hz, 1H), 3.94-3.75 (m, 5H), 3.26 (dd, J=12.2, 4.3 Hz, 2H), 3.12 (td, J=12.1, 5.2 Hz, 2H), 2.72-2.57 (m, 3H), 2.48 (d, J=1.5 Hz, 3H), 2.45-2.38 (m, 2H), 2.38-2.12 (m, 8H), 2.12-1.98 (m, 2H), 1.88 (p, J=7.3 Hz, 2H), 1.03 (d, J=1.7 Hz, 9H). HRMS (m/z) for C$_{52}$H$_{68}$ClN$_{12}$O$_6$S$^+$ [M+H]$^+$: calculated 1023.4789, found 1023.4794.

Example 41

Synthesis of XF050-16

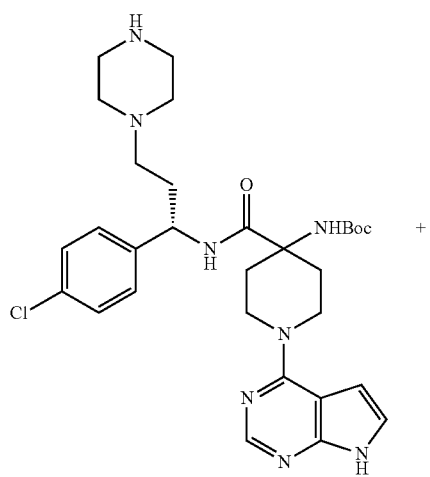

Intermediate 6

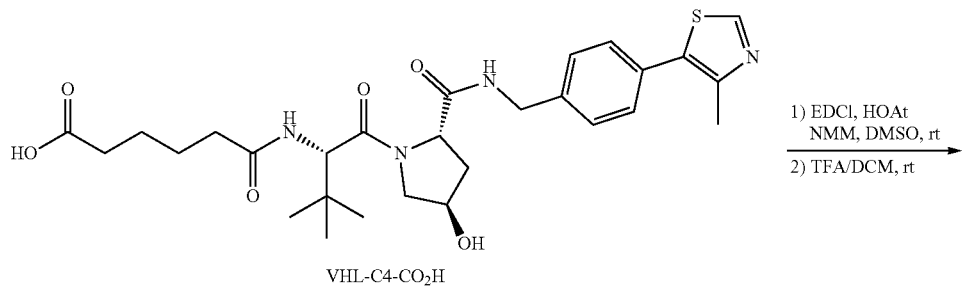

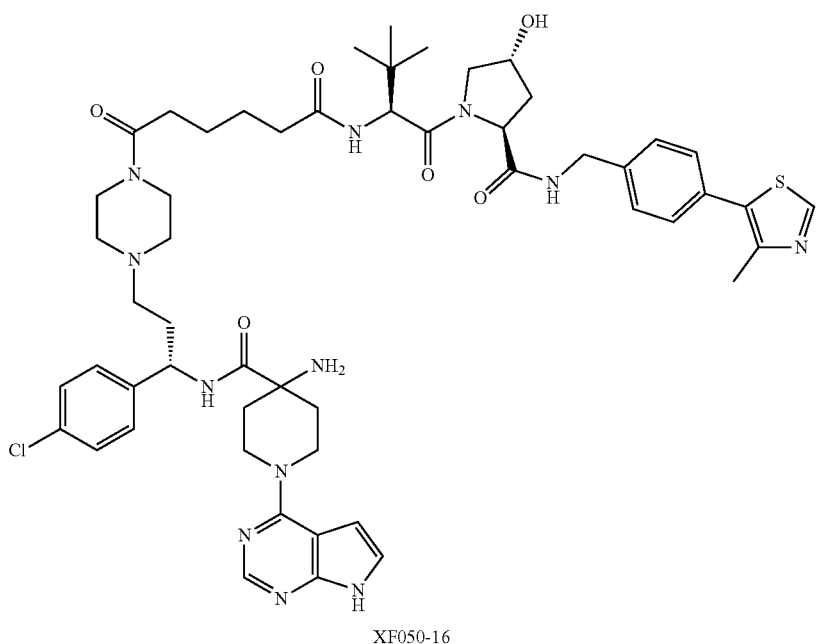

XF050-16

XF050-16 was synthesized following the standard procedure for preparing XF050-5 from intermediate 6 (15.9 mg, 0.022 mmol), VHL-C4-CO₂H (12.3 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%- 100% methanol/0.1% TFA in H₂O) to afford XF050-16 as white solid in TFA salt form (14.0 mg, 61%). $^1$H NMR (600 MHz, CD$_3$OD) δ 9.00 (s, 1H), 8.39 (s, 1H), 7.53-7.22 (m, 9H), 6.95 (d, J=3.7 Hz, 1H), 5.00 (dd, J=9.2, 5.9 Hz, 1H), 4.69-4.59 (m, 4H), 4.59-4.44 (m, 4H), 4.36 (d, J=15.5 Hz, 1H), 3.91-3.76 (m, 5H), 3.26 (dd, J=12.3, 4.4 Hz, 2H), 3.13 (td, J=12.1, 5.2 Hz, 2H), 2.73-2.57 (m, 3H), 2.48 (s, 3H), 2.43 (td, J=7.1, 4.8 Hz, 2H), 2.40-2.13 (m, 8H), 2.11-2.01 (m, 2H), 1.68-1.57 (m, 4H), 1.03 (s, 9H). HRMS (m/z) for C$_{53}$H$_{70}$ClN$_{12}$O$_6$S$^+$ [M+H]$^+$: calculated 1037.4945, found 1037.4923.

Example 42

Synthesis of XF050-17

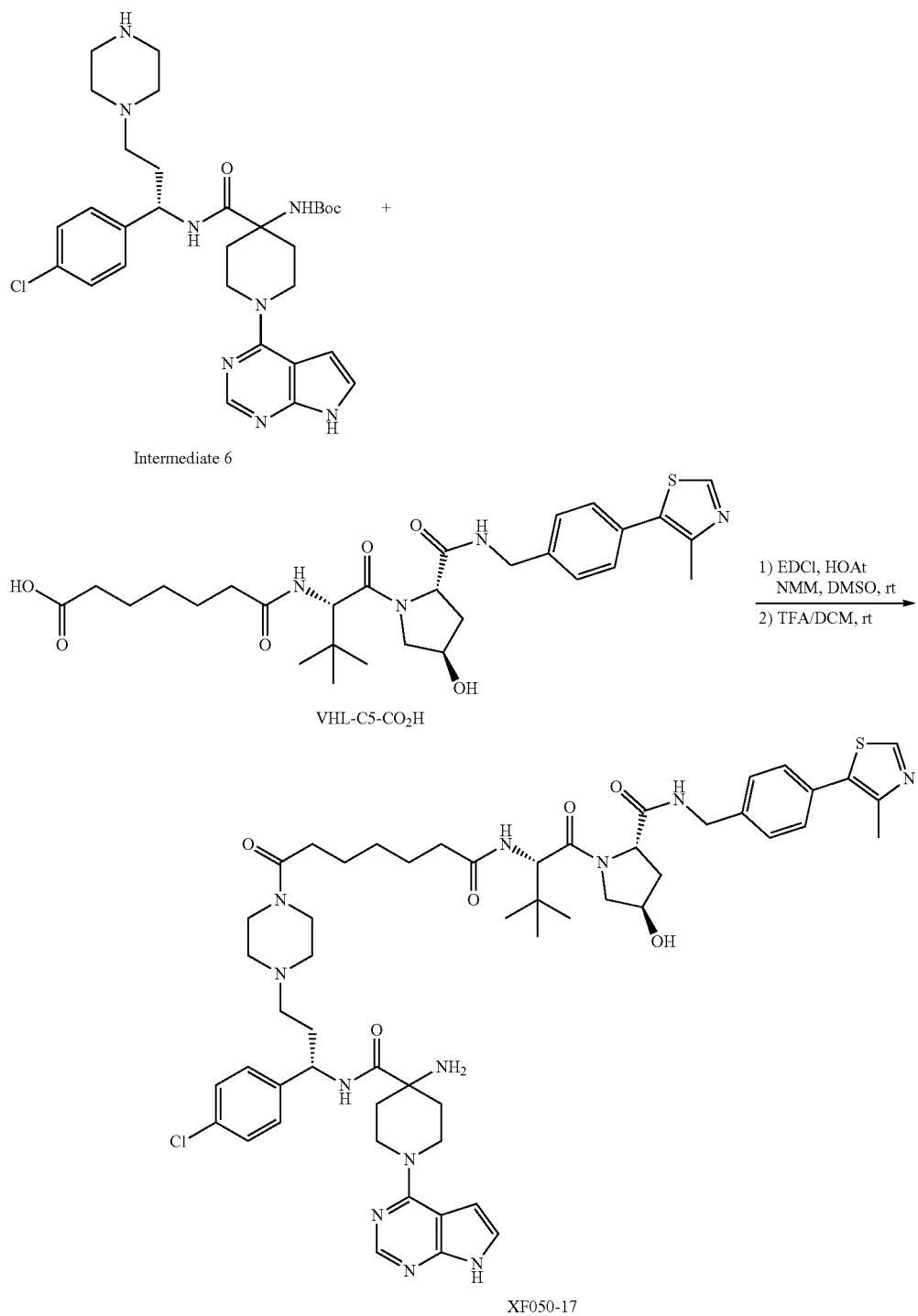

XF050-17 was synthesized following the standard procedure for preparing XF050-5 from intermediate 6 (15.9 mg, 0.022 mmol), VHL-C5-CO$_2$H (12.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-17 as white solid in TFA salt form (16.3 mg, 70%). ¹H NMR (600 MHz, CD₃OD) δ 9.04 (s, 1H), 8.40 (s, 1H), 7.55-7.25 (m, 9H), 6.95 (d, J=3.7 Hz, 1H), 5.01 (dd, J=9.3, 5.8 Hz, 1H), 4.64 (d, J=18.7 Hz, 4H), 4.58-4.45 (m, 4H), 4.37 (d, J=15.5 Hz, 1H), 3.93-3.77 (m, 5H), 3.27 (dd, J=12.3, 4.5 Hz, 2H), 3.14 (td, J=12.2, 5.2 Hz, 2H), 2.74-2.55 (m, 3H), 2.48 (s, 3H), 2.41 (t, J=7.5 Hz, 2H), 2.39-2.14 (m, 8H), 2.12-2.00 (m, 2H), 1.66-1.56 (m, 4H), 1.41-1.29 (m, 2H), 1.02 (s, 9H). HRMS (m/z) for $C_{54}H_{72}ClN_{12}O_6S^+$ [M+H]⁺: calculated 1051.5102, found 1051.5094.
Example 43
Synthesis of XF050-18
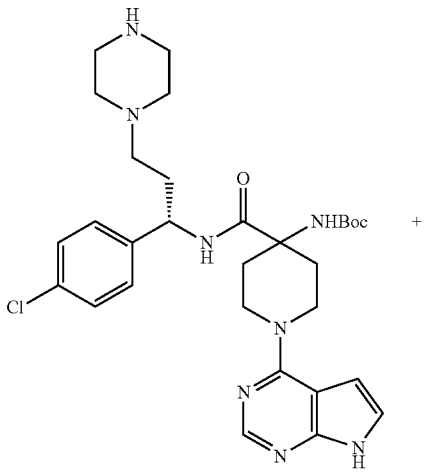
Intermediate 6
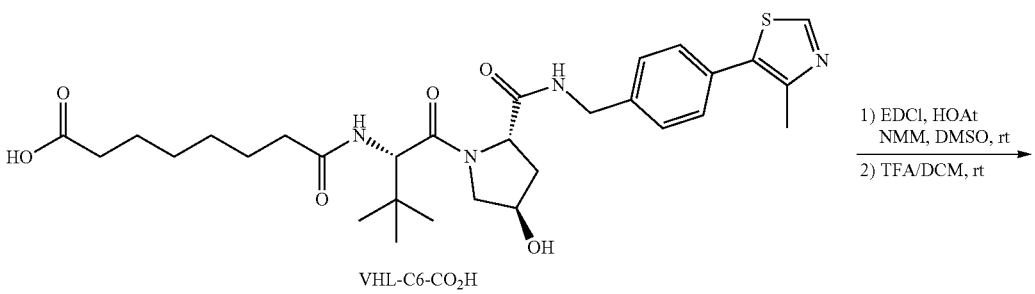
VHL-C6-CO₂H
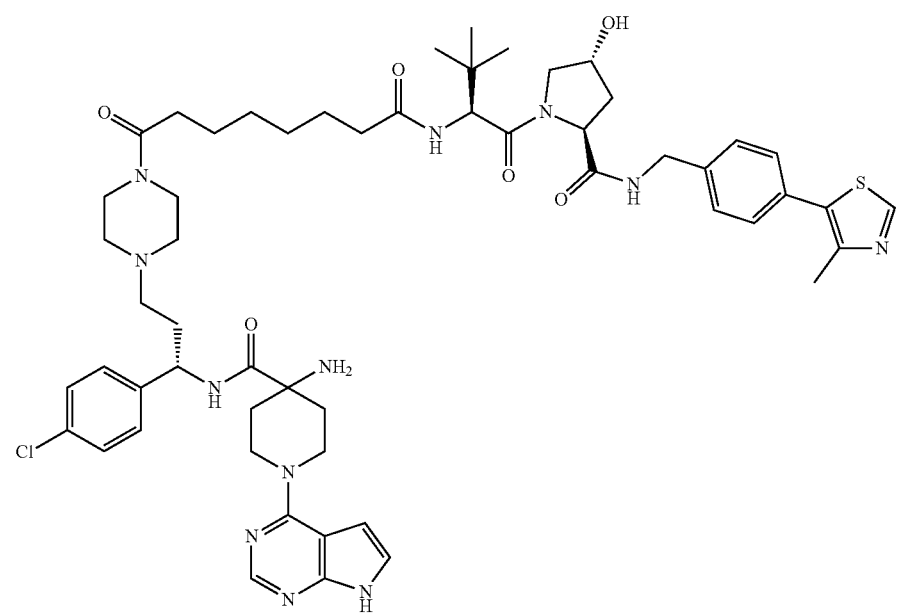
XF050-18

XF050-18 was synthesized following the standard procedure for preparing XF050-5 from intermediate 6 (15.9 mg, 0.022 mmol), VHL-C6-CO$_2$H (12.9 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-18 as white solid in TFA salt form (11.9 mg, 51%). $^1$H NMR (600 MHz, CD$_3$OD) δ 8.97 (s, 1H), 8.39 (s, 1H), 7.53-7.19 (m, 9H), 6.94 (d, J=3.8 Hz, 1H), 5.01 (dd, J=9.2, 5.9 Hz, 1H), 4.71-4.61 (m, 4H), 4.59-4.45 (m, 4H), 4.36 (d, J=15.4 Hz, 1H), 3.92-3.76 (m, 5H), 3.26 (dd, J=12.3, 4.5 Hz, 2H), 3.13 (td, J=12.2, 5.3 Hz, 2H), 2.73-2.55 (m, 3H), 2.48 (s, 3H), 2.40 (t, J=7.6 Hz, 3H), 2.37-2.14 (m, 7H), 2.11-2.00 (m, 2H), 1.64-1.55 (m, 4H), 1.35 (dd, J=7.5, 4.0 Hz, 4H), 1.03 (s, 9H). HRMS (m/z) for C$_{55}$H$_{74}$ClN$_{12}$O$_6$S$^+$ [M+H]$^+$: calculated 1065.5258, found 1065.5272.

Example 44

Synthesis of XF050-19

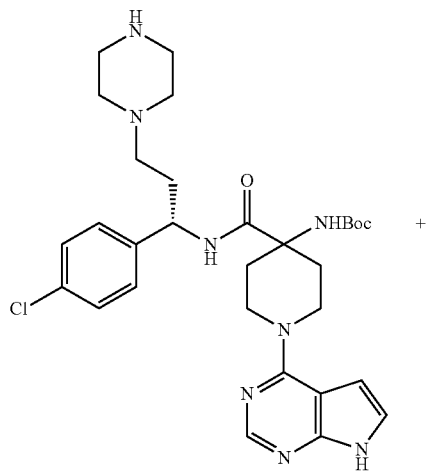

Intermediate 6

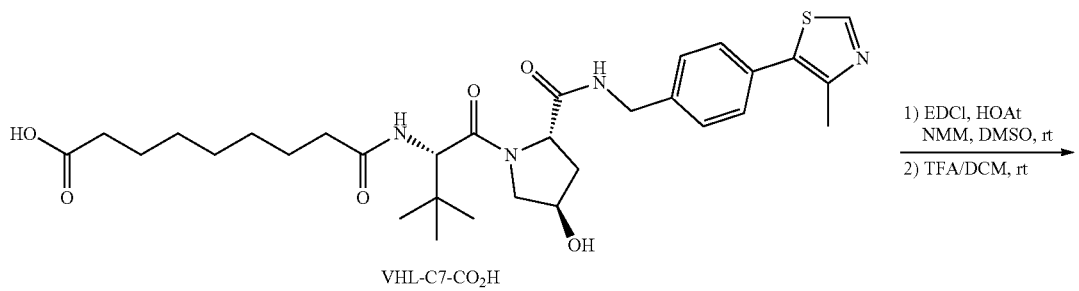

VHL-C7-CO$_2$H

1) EDCl, HOAt NMM, DMSO, rt
2) TFA/DCM, rt

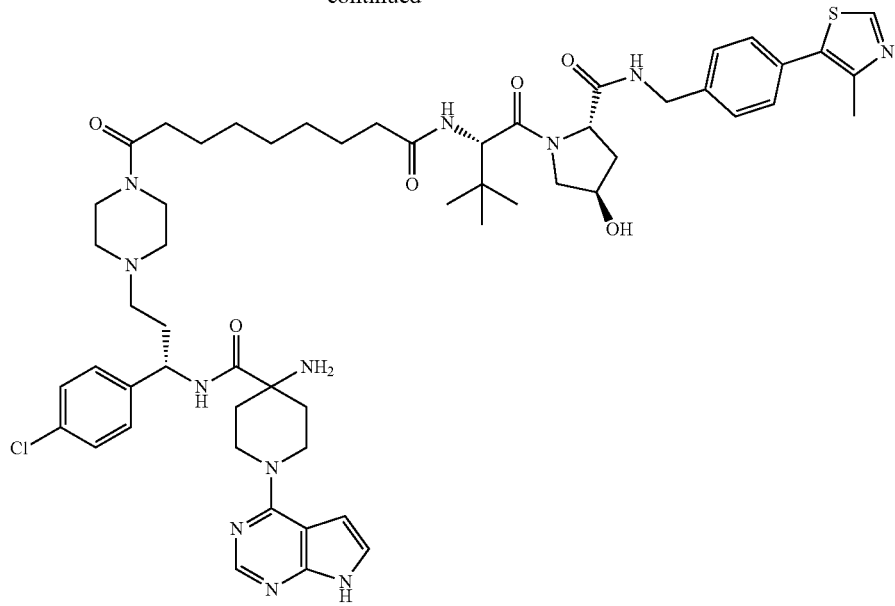

XF050-19

XF050-19 was synthesized following the standard procedure for preparing XF050-5 from intermediate 6 (15.9 mg, 0.022 mmol), VHL-C7-CO$_2$H (13.2 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-19 as white solid in TFA salt form (10.4 mg, 44%). $^1$H NMR (600 MHz, CD$_3$OD) δ 8.98 (s, 1H), 8.40 (d, J=1.9 Hz, 1H), 7.56-7.25 (m, 9H), 6.95 (dd, J=3.7, 1.9 Hz, 1H), 5.01 (dd, J=9.3, 5.8 Hz, 1H), 4.70-4.61 (m, 4H), 4.59-4.47 (m, 4H), 4.36 (d, J=15.5 Hz, 1H), 3.92-3.78 (m, 5H), 3.26 (dd, J=12.3, 4.3 Hz, 2H), 3.13 (td, J=12.0, 5.0 Hz, 2H), 2.73-2.58 (m, 3H), 2.48 (s, 3H), 2.43-2.37 (m, 3H), 2.37-2.14 (m, 7H), 2.11-2.00 (m, 2H), 1.65-1.54 (m, 4H), 1.34 (s, 6H), 1.03 (d, J=1.9 Hz, 9H). HRMS (m/z) for C$_{56}$H$_{76}$ClN$_{12}$O$_6$S$^+$ [M+H]$^+$: calculated 1079.5415, found 1079.5414.

Example 45

Synthesis of XF050-20

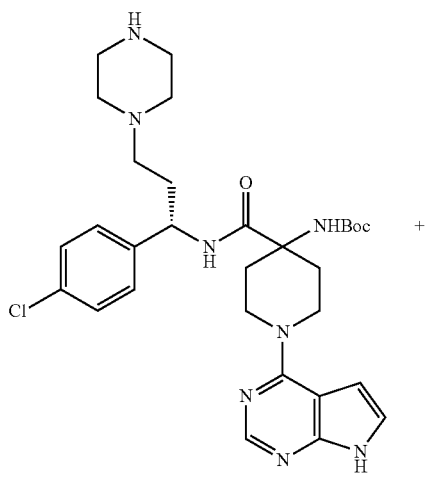

Intermediate 6

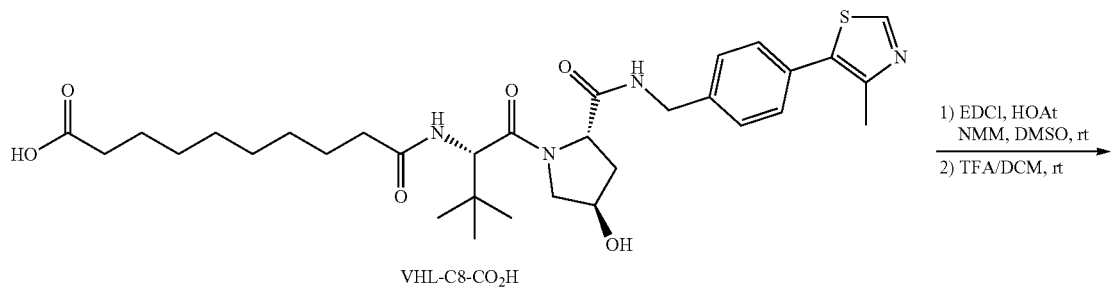

VHL-C8-CO₂H

1) EDCl, HOAt NMM, DMSO, rt
2) TFA/DCM, rt

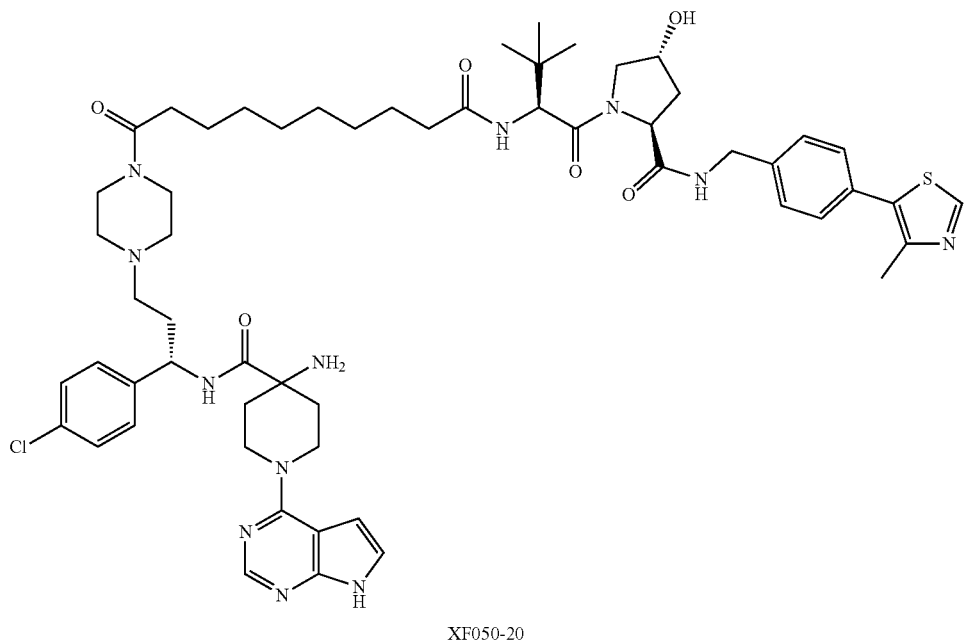

XF050-20

XF050-20 was synthesized following the standard procedure for preparing XF050-5 from intermediate 6 (15.9 mg, 0.022 mmol), VHL-C8-CO₂H (13.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H₂O) to afford XF050-20 as white solid in TFA salt form (13.6 mg, 60%). $^1$H NMR (600 MHz, CD$_3$OD) δ 9.00 (s, 1H), 8.40 (s, 1H), 7.53-7.22 (m, 9H), 6.95 (d, J=3.8 Hz, 1H), 5.01 (dd, J=9.3, 5.8 Hz, 1H), 4.71-4.61 (m, 4H), 4.59-4.46 (m, 4H), 4.36 (d, J=15.5 Hz, 1H), 3.93-3.76 (m, 5H), 3.26 (dd, J=12.3, 4.4 Hz, 2H), 3.13 (td, J=12.2, 5.1 Hz, 2H), 2.73-2.57 (m, 3H), 2.48 (s, 3H), 2.40 (t, J=7.6 Hz, 3H), 2.37-2.14 (m, 7H), 2.11-2.00 (m, 2H), 1.63-1.53 (m, 4H), 1.32 (s, 8H), 1.03 (s, 9H). HRMS (m/z) for C$_{57}$H$_{78}$ClN$_{12}$O$_6$S$^+$ [M+H]$^+$: calculated 1093.5571, found 1093.5561.

Example 46
Synthesis of XF050-21
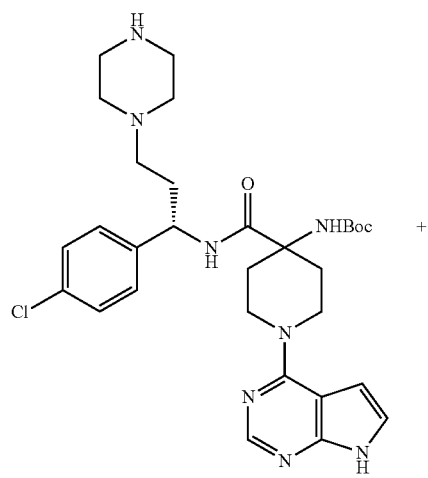
Intermediate 6
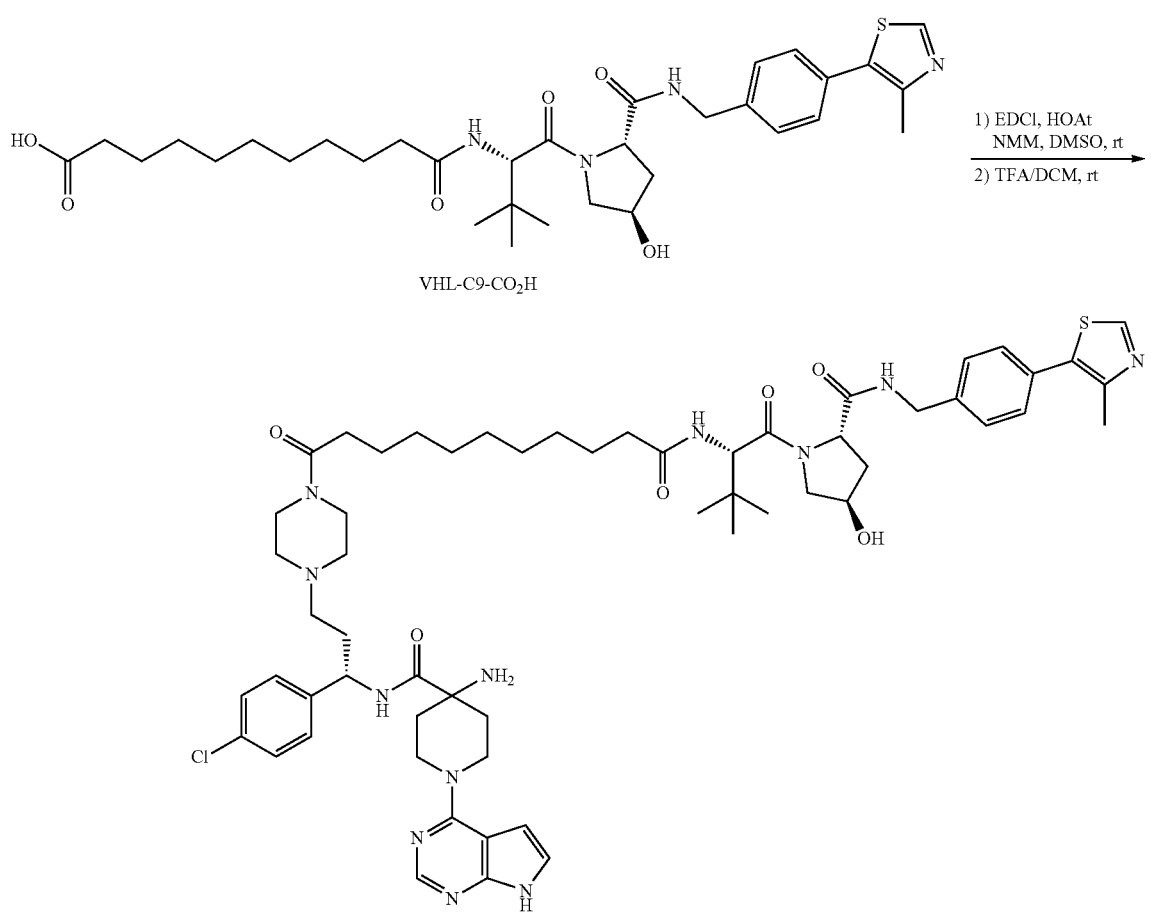
XF050-21

XF050-21 was synthesized following the standard procedure for preparing XF050-5 from intermediate 6 (15.9 mg, 0.022 mmol), VHL-C9-CO$_2$H (13.8 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). White solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-21 as white solid in TFA salt form (16.0 mg, 66%). $^1$H NMR (600 MHz, CD$_3$OD) δ 8.97 (s, 1H), 8.39 (s, 1H), 7.53-7.25 (m, 9H), 6.94 (d, J=3.8 Hz, 1H), 5.01 (dd, J=9.4, 5.8 Hz, 1H), 4.69-4.59 (m, 4H), 4.59-4.47 (m, 4H), 4.36 (d, J=15.5 Hz, 1H), 3.93-3.78 (m, 5H), 3.26 (dd, J=12.3, 4.5 Hz, 2H), 3.14 (td, J=12.2, 5.1 Hz, 2H), 2.74-2.57 (m, 3H), 2.48 (s, 3H), 2.40 (t, J=7.6 Hz, 3H), 2.37-2.15 (m, 7H), 2.11-2.00 (m, 2H), 1.58 (td, J=10.8, 8.0, 4.1 Hz, 4H), 1.31 (s, 10H), 1.03 (s, 9H). HRMS (m/z) for C$_{58}$H$_{80}$ClN$_{12}$O$_6$S$^+$ [M+H]$^+$: calculated 1107.5928, found 1107.5926.

Example 47

Synthesis of XF050-22

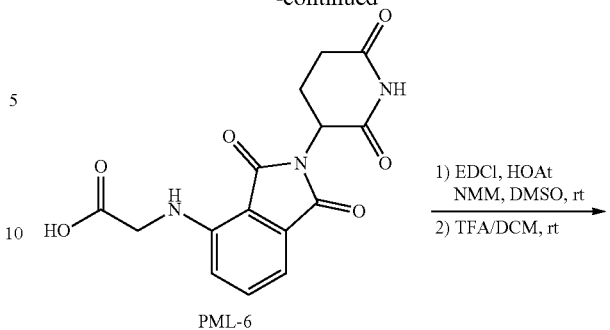

PML-6

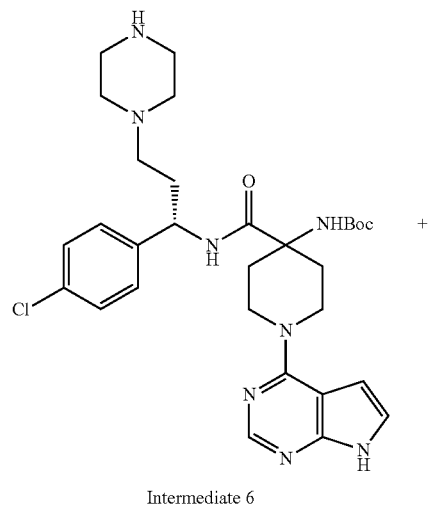

Intermediate 6

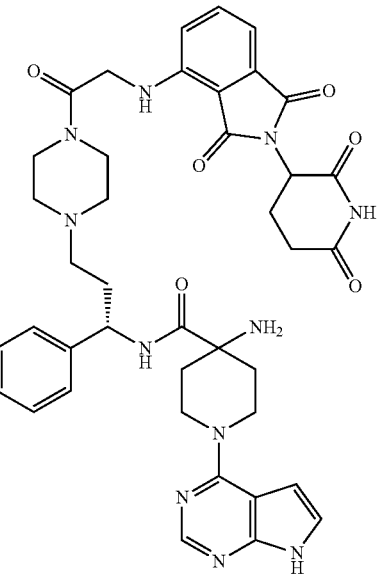

XF050-22

XF050-22 was synthesized following the standard procedure for preparing XF050-5 from intermediate 6 (15.9 mg, 0.022 mmol), PML-6 (7.3 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-22 as yellow solid in TFA salt form (2.9 mg, 16%). $^1$H NMR (600 MHz, CD$_3$OD) δ 8.36 (s, 1H), 7.55 (t, J=7.8 Hz, 1H), 7.44 (dd, J=8.5, 7.0 Hz, 1H), 7.36 (dd, J=12.3, 2.7 Hz, 3H), 7.10 (d, J=7.2 Hz, 1H), 7.04 (d, J=7.0 Hz, 1H), 6.99 (dd, J=8.4, 3.6 Hz, 1H), 6.89 (d, J=3.7 Hz, 1H), 5.10-4.99 (m, 2H), 4.75-4.64 (m, 2H), 4.24 (s, 2H), 3.76 (q, J=12.1 Hz, 4H), 3.44-3.32 (m, 2H), 3.28-3.22 (m, 2H), 3.12 (td, J=12.2, 5.2 Hz, 2H), 2.90-2.80 (m, 2H), 2.78-2.51 (m, 5H), 2.40-2.24 (m, 2H), 2.17-2.06 (m, 2H), 2.04-1.96 (m, 1H). HRMS (m/z) for C$_{40}$H$_{45}$ClN$_{11}$O$_6$$^+$ [M+H]$^+$: calculated 810.3237, found 810.3246.

Example 48

Synthesis of XF050-23

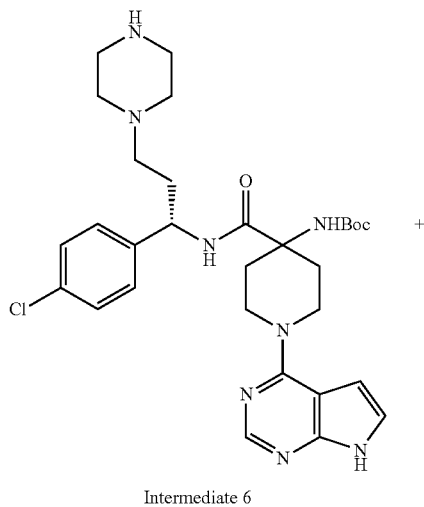

Intermediate 6

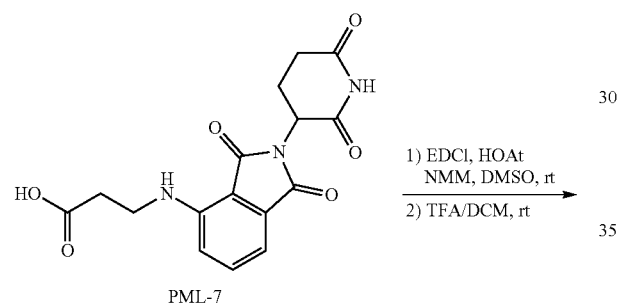

PML-7

XF050-23 was synthesized following the standard procedure for preparing XF050-5 from intermediate 6 (15.9 mg, 0.022 mmol), PML-7 (7.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-23 as yellow solid in TFA salt form (16.2 mg, 89%). $^1$H NMR (600 MHz, CD$_3$OD) δ 8.38 (s, 1H), 7.56 (dd, J=8.5, 7.2 Hz, 1H), 7.39-7.31 (m, 5H), 7.11 (d, J=8.6 Hz, 1H), 7.05 (d, J=7.1 Hz, 1H), 6.93 (d, J=3.7 Hz, 1H), 5.07-4.97 (m, 2H), 4.64 (s, 2H), 3.84 (q, J=12.2 Hz, 4H), 3.68-3.63 (m, 4H), 3.26-3.15 (m, 2H), 3.08 (td, J=11.9, 4.9 Hz, 2H), 2.90-2.79 (m, 2H), 2.77-2.71 (m, 3H), 2.71-2.58 (m, 3H), 2.37-1.98 (m, 6H). HRMS (m/z) for C$_{41}$H$_{47}$ClN$_{11}$O$_6$$^+$ [M+H]$^+$: calculated 824.3394, found 824.3394.

Example 49

Synthesis of XF050-24

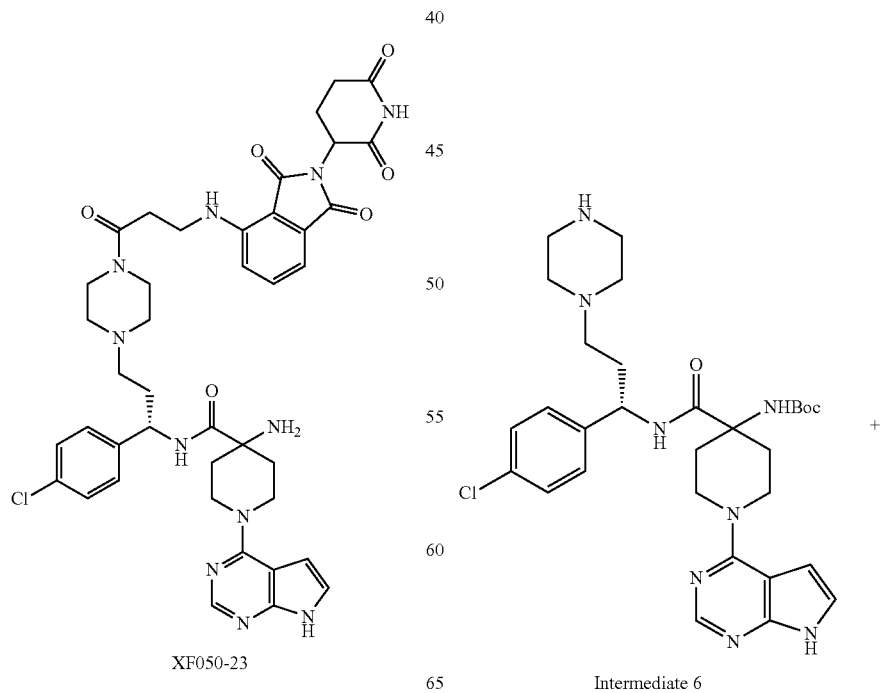

XF050-23

Intermediate 6

Example 50

Synthesis of XF050-25

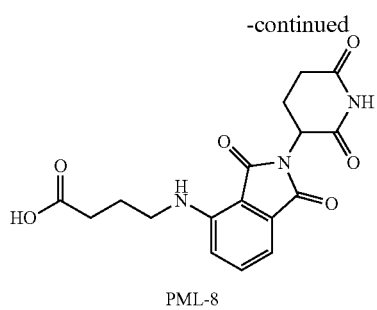
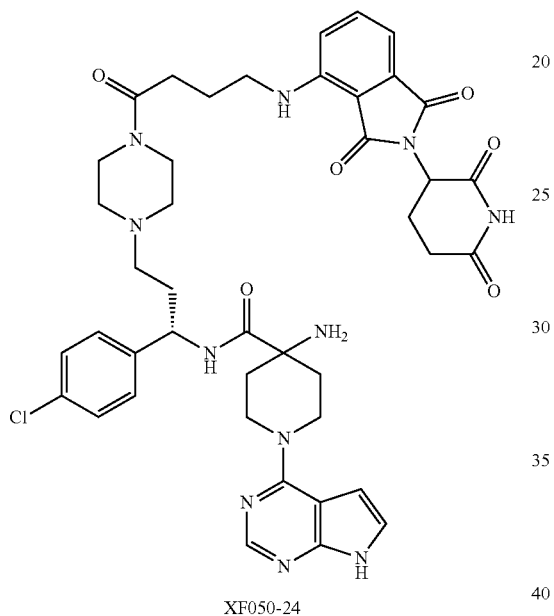

XF050-24 was synthesized following the standard procedure for preparing XF050-5 from intermediate 6 (15.9 mg, 0.022 mmol), PML-8 (7.9 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-24 as yellow solid in TFA salt form (12.5 mg, 68%). $^1$H NMR (600 MHz, CD$_3$OD) δ 8.39 (s, 1H), 7.54 (dd, J=8.5, 7.2 Hz, 1H), 7.37 (dd, J=17.5, 3.5 Hz, 5H), 7.10 (d, J=8.6 Hz, 1H), 7.04 (d, J=7.1 Hz, 1H), 6.94 (d, J=3.7 Hz, 1H), 5.05 (dd, J=12.8, 5.5 Hz, 1H), 5.00 (dd, J=9.2, 5.9 Hz, 1H), 4.70-4.60 (m, 2H), 3.84 (dd, J=13.8, 10.5 Hz, 4H), 3.39 (t, J=6.7 Hz, 4H), 3.23 (t, J=12.2 Hz, 2H), 3.08 (ddd, J=17.1, 11.5, 4.9 Hz, 2H), 2.93-2.79 (m, 2H), 2.78-2.57 (m, 5H), 2.53 (t, J=6.9 Hz, 2H), 2.34 (d, J=11.8 Hz, 1H), 2.26 (dd, J=12.3, 6.2 Hz, 1H), 2.17 (d, J=14.9 Hz, 1H), 2.10 (ddd, J=10.5, 5.5, 3.0 Hz, 1H), 2.04 (d, J=14.7 Hz, 1H), 1.99-1.94 (m, 2H). HRMS (m/z) for C$_{42}$H$_{49}$ClN$_{11}$O$_6$$^+$ [M+H]$^+$: calculated 838.3550, found 838.3552.

XF050-25 was synthesized following the standard procedure for preparing XF050-5 from intermediate 6 (15.9 mg, 0.022 mmol), PML-9 (8.2 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-25 as yellow solid in TFA salt form (9.6 mg, 51%). $^1$H NMR (600 MHz, CD$_3$OD) δ 8.38 (s, 1H), 7.54 (dd, J=8.4, 7.2 Hz, 1H), 7.36 (dd, J=6.5, 3.5 Hz, 5H), 7.07-7.00 (m, 2H), 6.91 (d, J=3.7 Hz, 1H), 5.05 (ddd, J=12.8, 5.5, 2.0 Hz, 1H), 5.00 (dd, J=9.2, 5.9 Hz, 1H), 4.71-4.61 (m, 2H), 3.82 (q, J=12.0 Hz, 4H), 3.36 (d, J=5.8 Hz, 4H), 3.24 (td, J=12.3, 4.5 Hz, 2H), 3.10 (td, J=11.9, 4.9 Hz, 2H), 2.85 (dddd, J=19.5, 14.1, 5.3, 2.2 Hz, 2H), 2.78-2.55 (m, 5H), 2.48 (s, 2H), 2.38-2.29 (m, 1H), 2.25 (tt, J=12.2, 5.5 Hz, 1H), 2.19-2.06 (m, 2H), 2.02 (d, J=14.6 Hz, 1H), 1.75-1.67 (m, 4H). HRMS (m/z) for C$_{43}$H$_{51}$ClN$_{11}$O$_6^+$ [M+H]$^+$: calculated 852.3707, found 852.3710.

Example 51

Synthesis of XF050-26

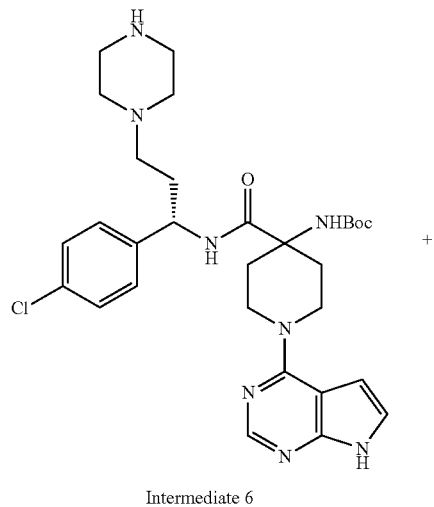

Intermediate 6

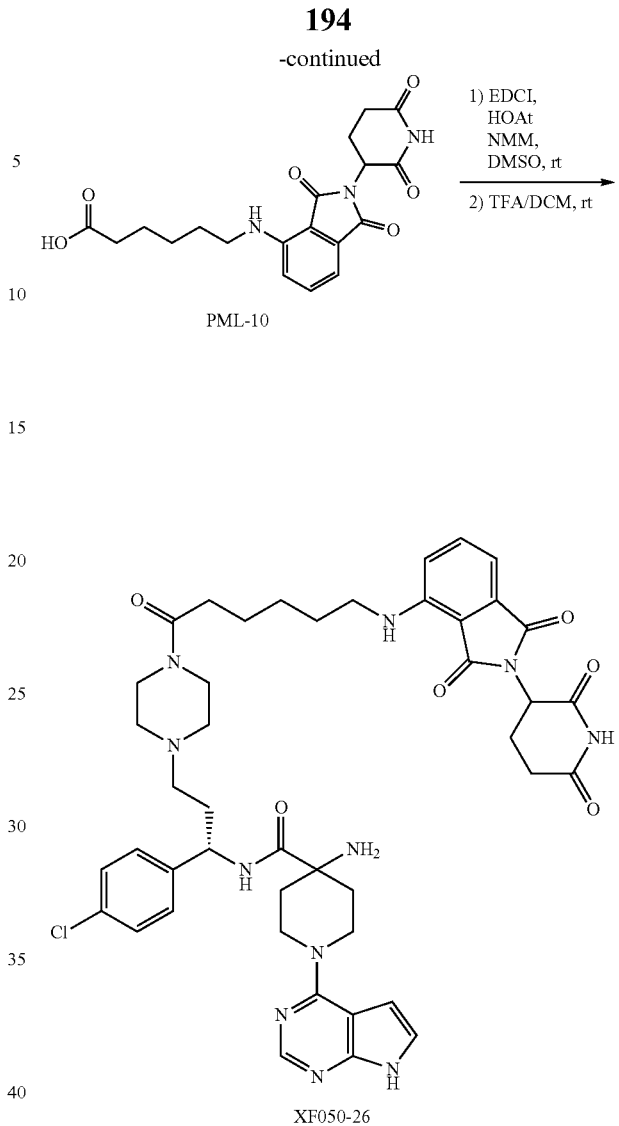

XF050-26 was synthesized following the standard procedure for preparing XF050-5 from intermediate 6 (15.9 mg, 0.022 mmol), PML-10 (8.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-26 as yellow solid in TFA salt form (13.9 mg, 73%). $^1$H NMR (600 MHz, CD$_3$OD) δ 8.39 (s, 1H), 7.59-7.48 (m, 1H), 7.43-7.24 (m, 5H), 7.03 (dd, J=7.8, 5.8 Hz, 2H), 6.93 (d, J=3.7 Hz, 1H), 5.09-4.96 (m, 2H), 4.70-4.57 (m, 2H), 3.85 (q, J=12.1 Hz, 4H), 3.33 (t, J=6.8 Hz, 4H), 3.29-3.22 (m, 2H), 3.11 (td, J=12.2, 5.1 Hz, 2H), 2.92-2.79 (m, 2H), 2.78-2.57 (m, 5H), 2.43 (t, J=7.4 Hz, 2H), 2.38-2.30 (m, 1H), 2.26 (tt, J=12.1, 5.5 Hz, 1H), 2.17 (d, J=14.7 Hz, 1H), 2.13-2.07 (m, 1H), 2.07-1.99 (m, 1H), 1.73-1.61 (m, 4H), 1.46 (tt, J=9.9, 6.4 Hz, 2H). HRMS (m/z) for C$_{44}$H$_{53}$ClN$_{11}$O$_6^+$ [M+H]$^+$: calculated 866.3863, found 866.3859.

Example 52

Synthesis of XF050-27

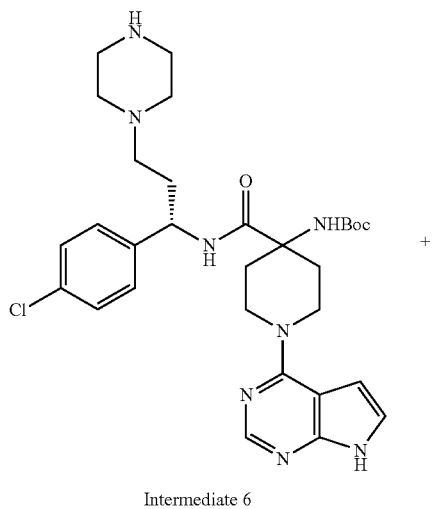

Intermediate 6

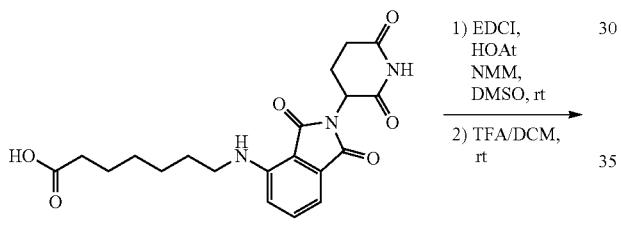

PML-11

XF050-27 was synthesized following the standard procedure for preparing XF050-5 from intermediate 6 (15.9 mg, 0.022 mmol), PML-11 (8.8 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/ 0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H₂O) to afford XF050-27 as yellow solid in TFA salt form (14.5 mg, 75%). $^1$H NMR (600 MHz, CD$_3$OD) δ 8.39 (s, 1H), 7.54 (dd, J=8.6, 7.1 Hz, 1H), 7.40-7.30 (m, 5H), 7.03 (t, J=7.3 Hz, 2H), 6.94 (d, J=3.7 Hz, 1H), 5.08-4.96 (m, 2H), 4.65 (d, J=13.8 Hz, 2H), 3.85 (q, J=12.1 Hz, 4H), 3.36-3.30 (m, 4H), 3.27 (td, J=12.4, 4.5 Hz, 2H), 3.12 (td, J=12.1, 5.1 Hz, 2H), 2.91-2.78 (m, 2H), 2.77-2.59 (m, 5H), 2.41 (d, J=1.6 Hz, 2H), 2.37-2.31 (m, 1H), 2.26 (d, 1H), 2.17 (d, J=15.0 Hz, 1H), 2.14-2.07 (m, 1H), 2.07-1.98 (m, 1H), 1.64 (dp, J=37.0, 7.2 Hz, 4H), 1.49-1.35 (m, 4H). HRMS (m/z) for $C_{45}H_{55}ClN_{11}O_6^+$ [M+H]$^+$: calculated 880.4020, found 880.4026.

Example 53

Synthesis of XF050-28

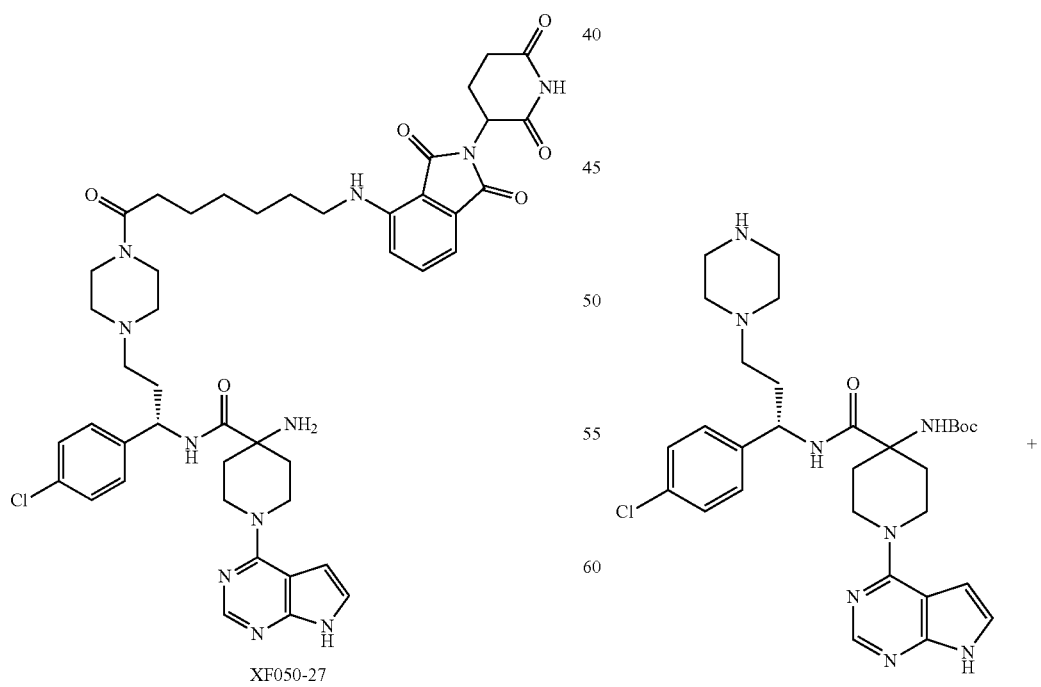

XF050-27

Intermediate 6

197
-continued

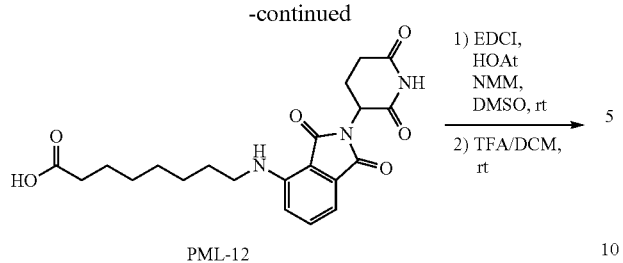

PML-12

1) EDCI, HOAt, NMM, DMSO, rt
2) TFA/DCM, rt

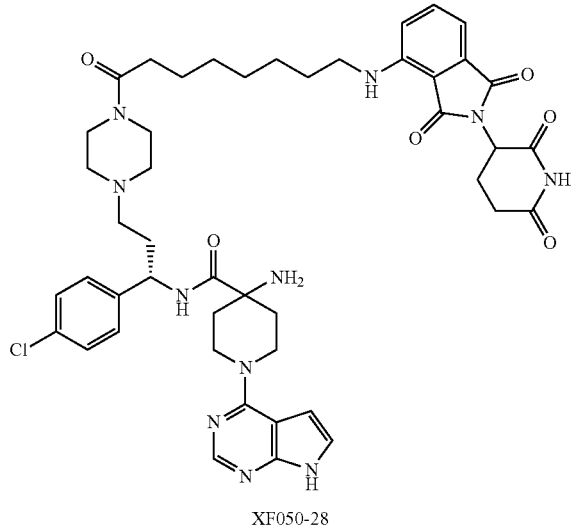

XF050-28

XF050-28 was synthesized following the standard procedure for preparing XF050-5 from intermediate 6 (15.9 mg, 0.022 mmol), PML-12 (9.1 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-28 as yellow solid in TFA salt form (15.5 mg, 78%). $^1$H NMR (600 MHz, CD$_3$OD) δ 8.39 (s, 1H), 7.54 (dd, J=8.6, 7.1 Hz, 1H), 7.39-7.32 (m, 5H), 7.03 (dd, J=7.8, 4.3 Hz, 2H), 6.94 (d, J=3.7 Hz, 1H), 5.08-4.97 (m, 2H), 4.68-4.62 (m, 2H), 3.84 (q, J=12.2 Hz, 4H), 3.35-3.31 (m, 4H), 3.28-3.24 (m, 2H), 3.12 (td, J=12.2, 5.2 Hz, 2H), 2.85 (ddd, J=17.6, 13.9, 5.4 Hz, 2H), 2.78-2.56 (m, 5H), 2.39 (t, J=7.5 Hz, 2H), 2.34 (t, J=10.4 Hz, 1H), 2.26 (tt, J=12.1, 5.5 Hz, 1H), 2.17 (d, J=14.8 Hz, 1H), 2.10 (ddt, J=13.1, 5.6, 2.8 Hz, 1H), 2.03 (d, J=14.6 Hz, 1H), 1.66 (p, J=7.1 Hz, 2H), 1.58 (p, J=7.5 Hz, 2H), 1.47-1.33 (m, 6H). HRMS (m/z) for C$_{46}$H$_{57}$ClN$_{11}$O$_6^+$ [M+H]$^+$: calculated 894.4176, found 894.4192.

198
Example 54

Synthesis of XF050-29

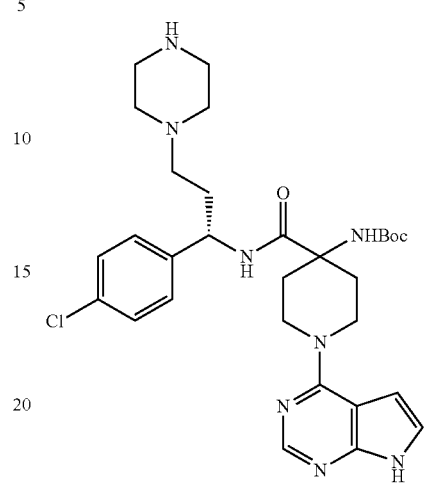

Intermediate 6

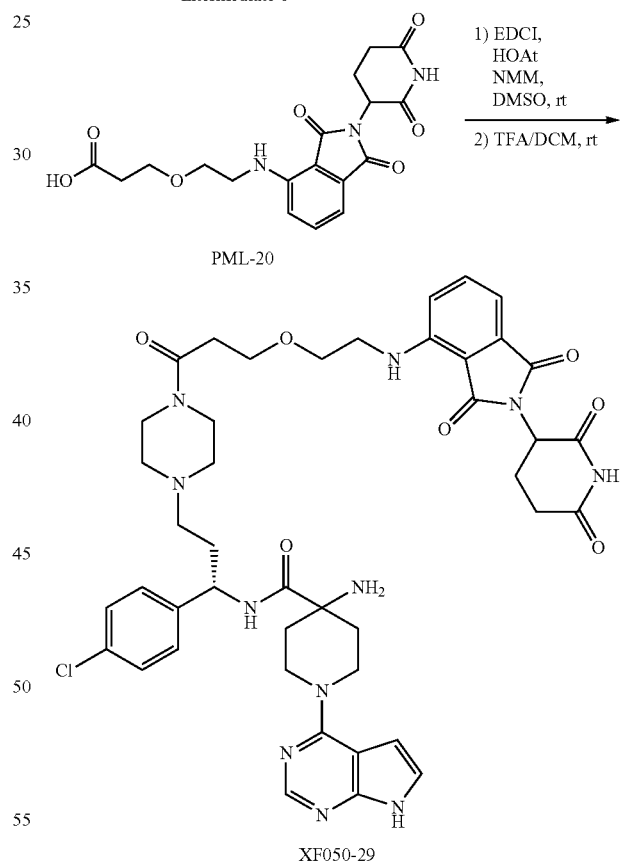

PML-20

1) EDCI, HOAt, NMM, DMSO, rt
2) TFA/DCM, rt

XF050-29

XF050-29 was synthesized following the standard procedure for preparing XF050-5 from intermediate 6 (15.9 mg, 0.022 mmol), PML-20 (8.6 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-29 as yellow solid in TFA salt form (16.7 mg, 87%). $^1$H NMR (600 MHz, CD$_3$OD) δ 8.39 (s, 1H), 7.57 (ddd, J=8.6, 7.1, 3.9 Hz, 1H), 7.37 (dd, J=3.9, 1.1 Hz, 1H), 7.34-7.28 (m, 4H), 7.10-7.03 (m, 2H), 6.93 (dd, J=3.7, 1.5 Hz, 1H), 5.04 (ddd, J=12.7, 5.5, 2.3 Hz, 1H), 4.68-4.59 (m, 3H), 3.91-3.74 (m, 6H), 3.70 (tt, J=4.7, 2.2 Hz, 3H), 3.48 (td, J=4.9, 4.3, 2.3 Hz, 3H), 3.15 (td, J=15.0, 13.5, 8.3 Hz, 2H), 2.95 (dq, J=12.2, 5.7 Hz, 2H), 2.88-2.78 (m, 2H), 2.77-2.54 (m, 6H), 2.32-2.06 (m, 5H), 2.02 (d, J=14.6 Hz, 1H). HRMS (m/z) for C$_{43}$H$_{51}$ClN$_{11}$O$_7^+$ [M+H]$^+$: calculated 868.3656, found 868.3661.

Example 55

Synthesis of XF050-30

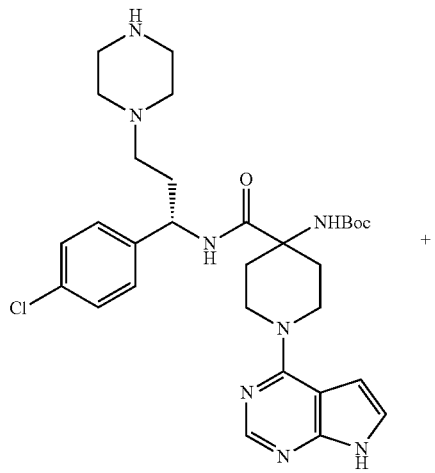

Intermediate 6

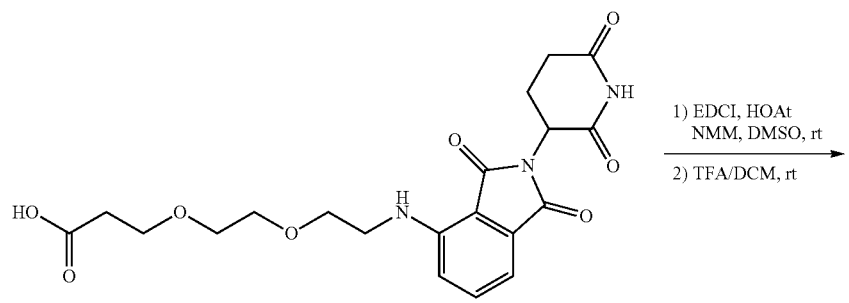

PML-21

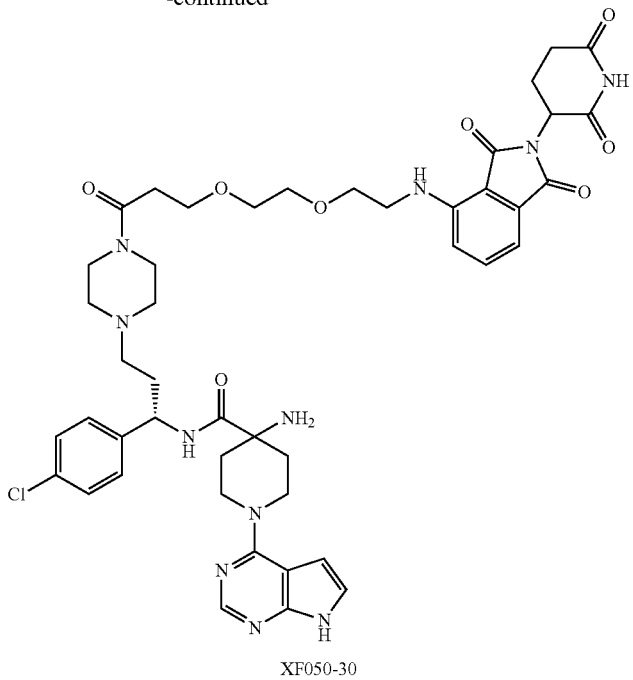

XF050-30

XF050-30 was synthesized following the standard procedure for preparing XF050-5 from intermediate 6 (15.9 mg, 0.022 mmol), PML-21 (9.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-30 as yellow solid in TFA salt form (15.8 mg, 79%). $^1$H NMR (600 MHz, CD$_3$OD) δ 8.38 (s, 1H), 7.54 (ddt, J=8.6, 7.1, 1.4 Hz, 1H), 7.37 (dd, J=3.8, 1.3 Hz, 1H), 7.34-7.28 (m, 4H), 7.08 (d, J=8.5 Hz, 1H), 7.04 (dd, J=7.0, 2.7 Hz, 1H), 6.92 (dd, J=3.8, 1.6 Hz, 1H), 5.05 (ddd, J=12.6, 5.4, 3.8 Hz, 1H), 4.96 (dt, J=9.6, 3.9 Hz, 1H), 4.68-4.54 (m, 3H), 3.89-3.80 (m, 3H), 3.73 (td, J=6.0, 1.7 Hz, 2H), 3.68 (td, J=5.2, 2.3 Hz, 2H), 3.65-3.54 (m, 5H), 3.46 (t, J=5.1 Hz, 3H), 3.22 (td, J=12.3, 4.4 Hz, 2H), 3.10-3.01 (m, 2H), 2.84 (ddt, J=17.7, 13.8, 4.6 Hz, 2H), 2.77-2.57 (m, 6H), 2.35-2.07 (m, 5H), 2.02 (d, J=14.7 Hz, 1H). HRMS (m/z) for C$_{45}$H$_{55}$ClN$_{11}$O$_8^+$ [M+H]$^+$: calculated 912.3918, found 912.3902.

Example 56

Synthesis of XF050-31

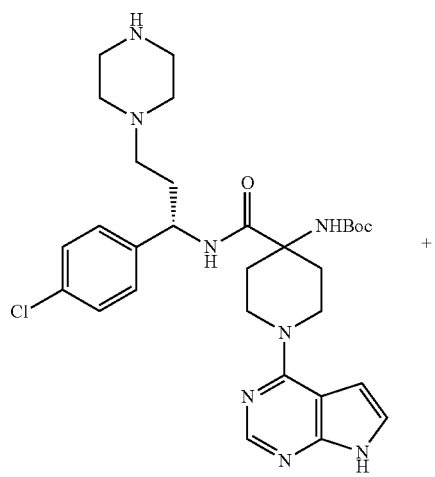

Intermediate 6

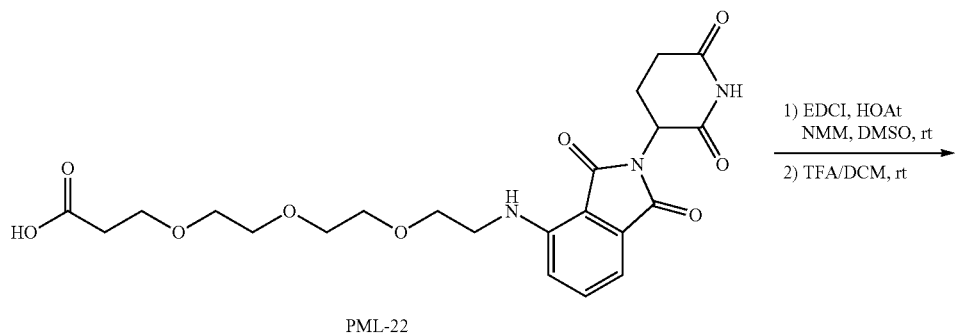

PML-22

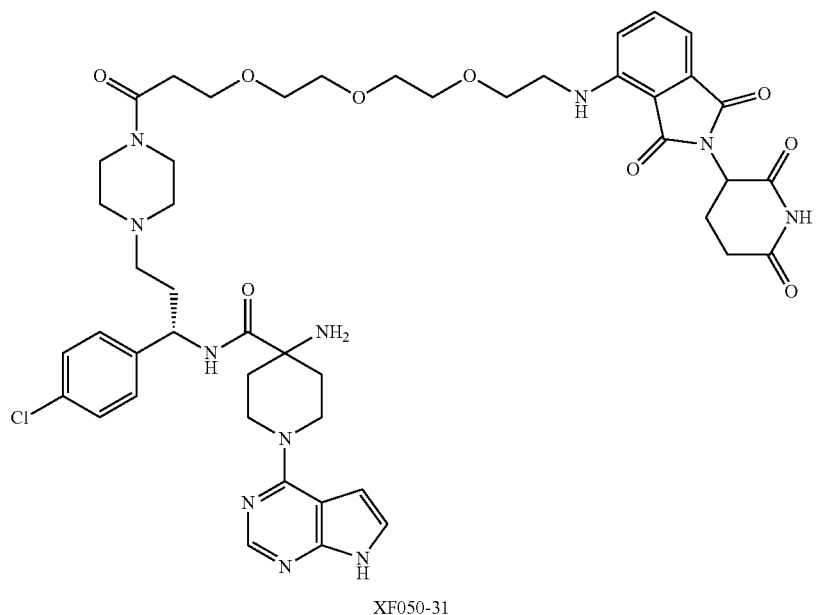

XF050-31

XF050-31 was synthesized following the standard procedure for preparing XF050-5 from intermediate 6 (15.9 mg, 0.022 mmol), PML-22 (10.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in H$_2$O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H$_2$O) to afford XF050-31 as yellow solid in TFA salt form (16.2 mg, 77%). $^1$H NMR (600 MHz, CD$_3$OD) δ 8.38 (s, 1H), 7.54 (ddd, J=8.6, 7.1, 1.5 Hz, 1H), 7.39-7.28 (m, 5H), 7.07 (d, J=8.6 Hz, 1H), 7.04 (s, 1H), 6.92 (dd, J=3.7, 1.6 Hz, 1H), 5.05 (ddd, J=12.6, 5.4, 1.5 Hz, 1H), 4.99 (ddd, J=9.4, 6.2, 3.8 Hz, 1H), 4.67-4.53 (m, 3H), 3.91-3.80 (m, 3H), 3.73-3.67 (m, 4H), 3.64-3.53 (m, 8H), 3.53-3.44 (m, 4H), 3.25 (t, J=12.8 Hz, 2H), 3.09 (td, J=11.9, 5.7 Hz, 2H), 2.91-2.80 (m, 2H), 2.77-2.57 (m, 7H), 2.37-2.23 (m, 2H), 2.20-2.07 (m, 2H), 2.03 (d, J=14.7 Hz, 1H). HRMS (m/z) for C$_{47}$H$_{59}$ClN$_{11}$O$_9$$^+$ [M+H]$^+$: calculated 956.4180, found 956.4183.

Example 57
Synthesis of XF050-32
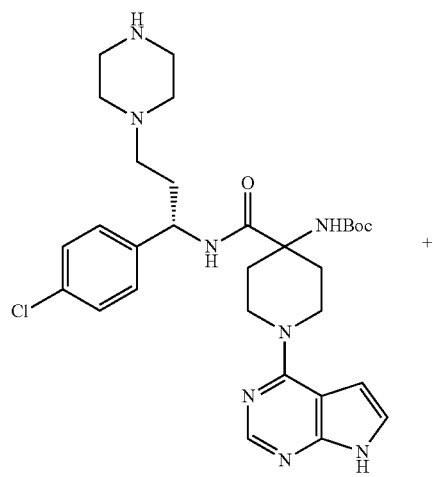
Intermediate 6
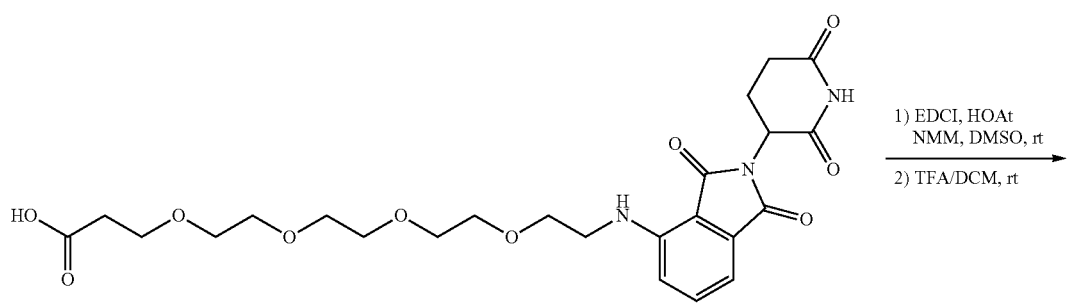
PML-23
1) EDCI, HOAt NMM, DMSO, rt
2) TFA/DCM, rt
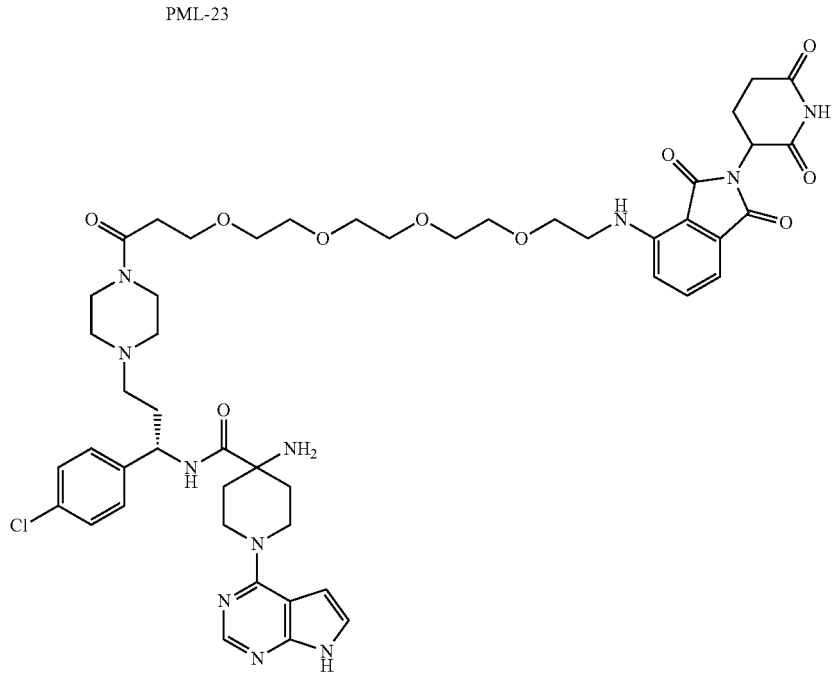
XF050-32

XF050-32 was synthesized following the standard procedure for preparing XF050-5 from intermediate 6 (15.9 mg, 0.022 mmol), PML-23 (11.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/0.1% TFA in $H_2O$). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in $H_2O$) to afford XF050-32 as yellow solid in TFA salt form (12.8 mg, 58%). $^1$H NMR (600 MHz, $CD_3OD$) δ 8.38 (s, 1H), 7.54 (ddd, J=8.6, 7.1, 1.5 Hz, 1H), 7.38-7.31 (m, 5H), 7.08 (d, J=8.5 Hz, 1H), 7.04 (dd, J=7.1, 2.1 Hz, 1H), 6.92 (dd, J=3.8, 1.3 Hz, 1H), 5.05 (dd, J=12.8, 5.5 Hz, 1H), 5.02-4.96 (m, 1H), 4.68-4.57 (m, 3H), 3.85 (dt, J=15.4, 9.3 Hz, 3H), 3.73-3.68 (m, 4H), 3.62 (ttt, J=5.6, 3.6, 1.9 Hz, 4H), 3.59-3.53 (m, 9H), 3.49 (t, J=5.2 Hz, 3H), 3.25 (td, J=12.1, 4.3 Hz, 2H), 3.09 (td, J=12.1, 5.4 Hz, 2H), 2.89-2.80 (t, 2H), 2.77-2.56 (m, 7H), 2.38-2.24 (m, 2H), 2.19-2.08 (m, 2H), 2.03 (d, J=14.7 Hz, 1H). HRMS (m/z) for $C_{49}H_{63}ClN_{11}O_{10}^+$ [M+H]$^+$: calculated 1000.4442, found 1000.4462.

Example 58

Synthesis of XF050-33

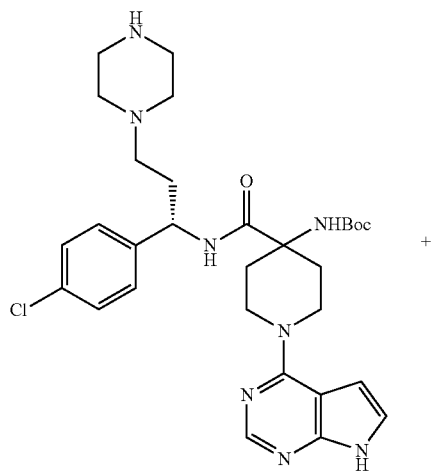

Intermediate 6

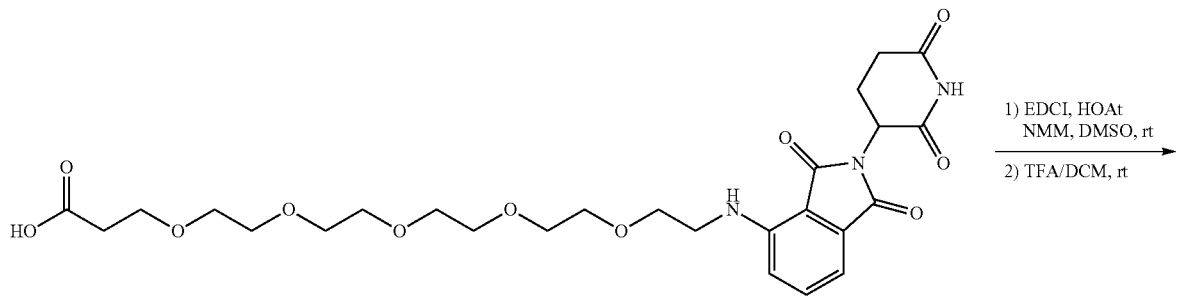

PML-24

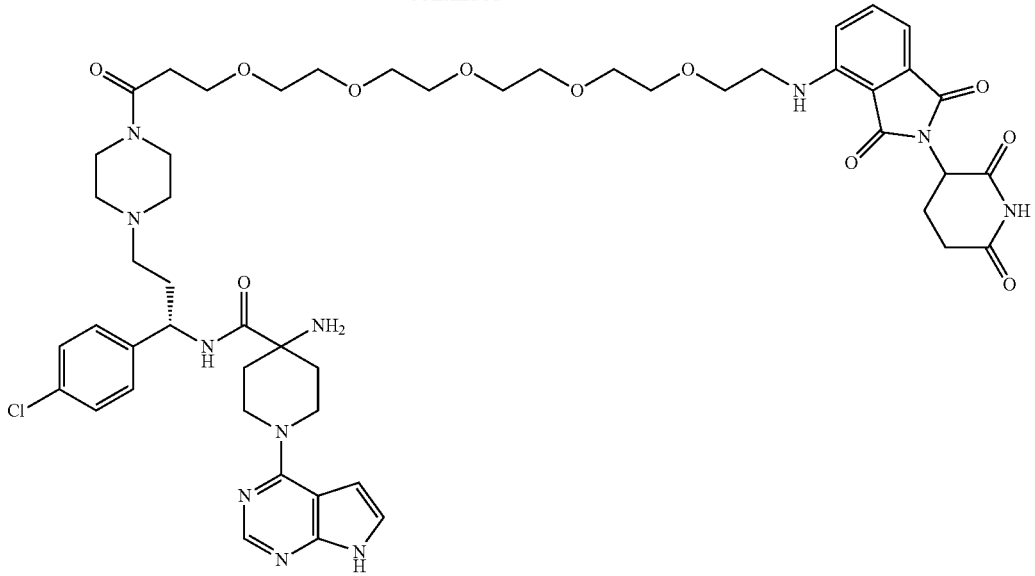

XF050-33

XF050-33 was synthesized following the standard procedure for preparing XF050-5 from intermediate 6 (15.9 mg, 0.022 mmol), PML-24 (12.5 mg, 0.022 mmol, 1.0 equiv), EDCI (6.5 mg, 0.033 mmol, 1.5 equiv), HOAt (4.5 mg, 0.033 mmol, 1.5 equiv), and NMM (6.7 mg, 0.066 mmol, 3.0 equiv) in DMSO (1 mL). Yellow solid in TFA salt form was isolated by preparative HPLC (10%-100% methanol/ 0.1% TFA in H₂O). After this solid was dissolved in DCM (1 mL), TFA (1 mL) was added. The reaction was stirred at rt for 2 h, before the solvent was evaporated. The resulting residue was purified by preparative HPLC (10%-100% methanol/0.1% TFA in H₂O) to afford XF050-33 as yellow solid in TFA salt form (5.0 mg, 22%). $^1$H NMR (600 MHz, CD$_3$OD) 8.37 (s, 1H), 7.55 (ddd, J=8.4, 7.2, 0.9 Hz, 1H), 7.38-7.31 (m, 5H), 7.08 (d, J=8.6 Hz, 1H), 7.05 (dd, J=7.1, 1.3 Hz, 1H), 6.89 (d, J=3.7 Hz, 1H), 5.05 (dd, J=12.8, 5.5 Hz, 1H), 5.02-4.97 (m, 1H), 4.71-4.59 (m, 3H), 3.84-3.75 (m, 3H), 3.71 (t, J=5.3 Hz, 4H), 3.66-3.58 (m, 7H), 3.58-3.51 (m, 10H), 3.49 (t, J=5.2 Hz, 3H), 3.24 (td, J=12.0, 4.2 Hz, 2H), 3.08 (td, J=12.1, 5.4 Hz, 2H), 2.90-2.80 (m, 2H), 2.78-2.55 (m, 7H), 2.37-2.22 (m, 2H), 2.16-2.07 (m, 2H), 2.01 (d, J=14.6 Hz, 1H). HRMS (m/z) for C$_{51}$H$_{67}$ClN$_{11}$O$_{11}$$^+$ [M+H]$^+$: calculated 1044.4705, found 1044.4711.

Example 59

Synthesis of XF050-98

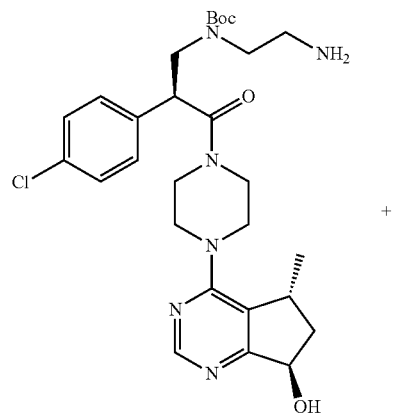

Intermediate 3

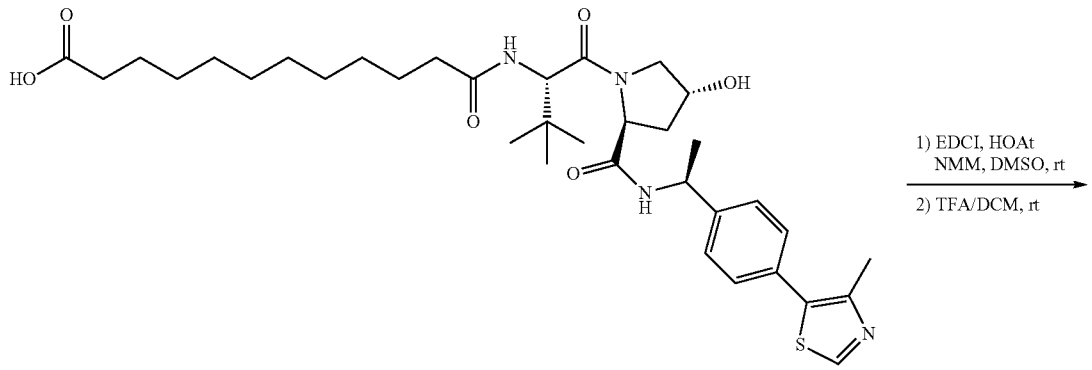

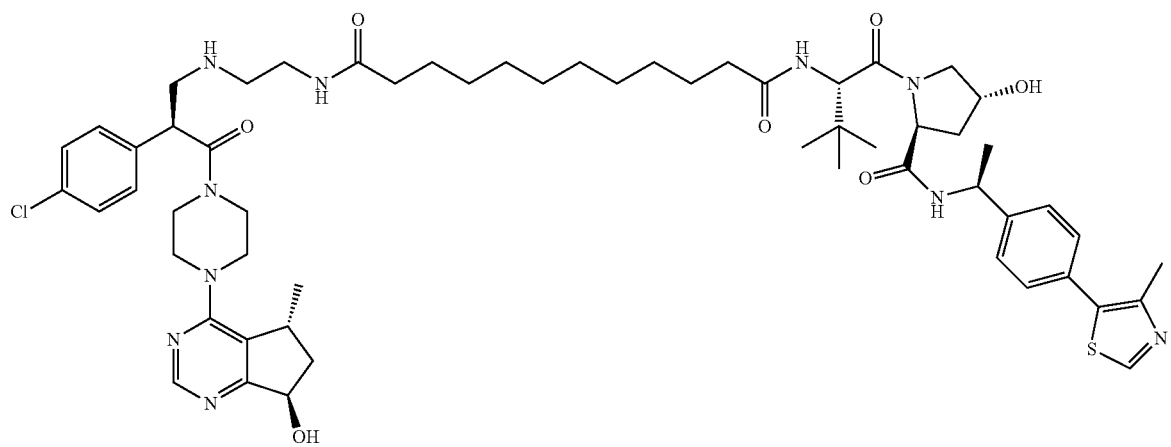

XF050-98

To a solution of Intermediate 3 (11.2 mg, 0.02 mmol) in DMSO (1 mL) were added 12-(((S)-1-((2S,4R)-4-hydroxy-2-(((S)-1-(4-(4-methylthiazol-5-yl)phenyl)ethyl)carbamoyl) pyrrolidin-1-yl)-3,3-dimethyl-1-oxobutan-2-yl)amino)-12-oxododecanoic acid (13.1 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirred overnight at room temperature, the resulting mixture was purified by preparative HPLC (10%-100% methanol/0.1% TFA in H$_2$O) to afford the corresponding product. This product was dissolved in DCM (1 mL), before the reaction mixture was treated with TFA (1 mL) for 30 min. After the solvent was evaporated, the residue was purified by preparative HPLC (10%-100% methanol/0.1% TFA in H$_2$O) to afford XF050-98 as white solid in TFA salt form (17.4 mg, 79%). $^1$H NMR (600 MHz, CD$_3$OD) δ 8.98 (s, 1H), 8.58 (s, 1H), 7.49-7.41 (m, 6H), 7.36 (dd, J=8.5, 1.8 Hz, 2H), 5.31 (t, J=8.0 Hz, 1H), 5.00 (q, J=7.0 Hz, 1H), 4.62 (s, 1H), 4.59-4.50 (m, 2H), 4.43 (dp, J=4.3, 1.9 Hz, 1H), 4.18 (d, J=13.7 Hz, 1H), 4.13-3.99 (m, 1H), 3.93 (ddt, J=12.8, 9.8, 4.9 Hz, 2H), 3.90-3.78 (m, 3H), 3.75 (dd, J=11.0, 4.0 Hz, 1H), 3.73-3.59 (m, 4H), 3.51-3.46 (m, 2H), 3.46-3.36 (m, 1H), 3.35-3.27 (m, 2H), 3.19 (t, J=5.7 Hz, 2H), 2.48 (s, 3H), 2.36-2.14 (m, 5H), 1.95 (ddd, J=13.3, 9.0, 4.6 Hz, 1H), 1.67-1.53 (m, 4H), 1.50 (d, J=7.0 Hz, 3H), 1.31 (d, J=4.9 Hz, 12H), 1.19 (d, J=21.4, 7.0 Hz, 3H), 1.04 (s, 9H). HRMS (m/z) for C$_{58}$H$_{82}$ClN$_{10}$O$_7$S$^+$ [M+H]$^+$: calculated 1097.5772, found 1097.5768.

Example 60

Synthesis of XF050-137

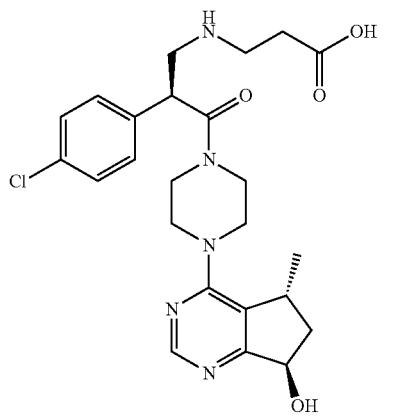

Intermediate 2

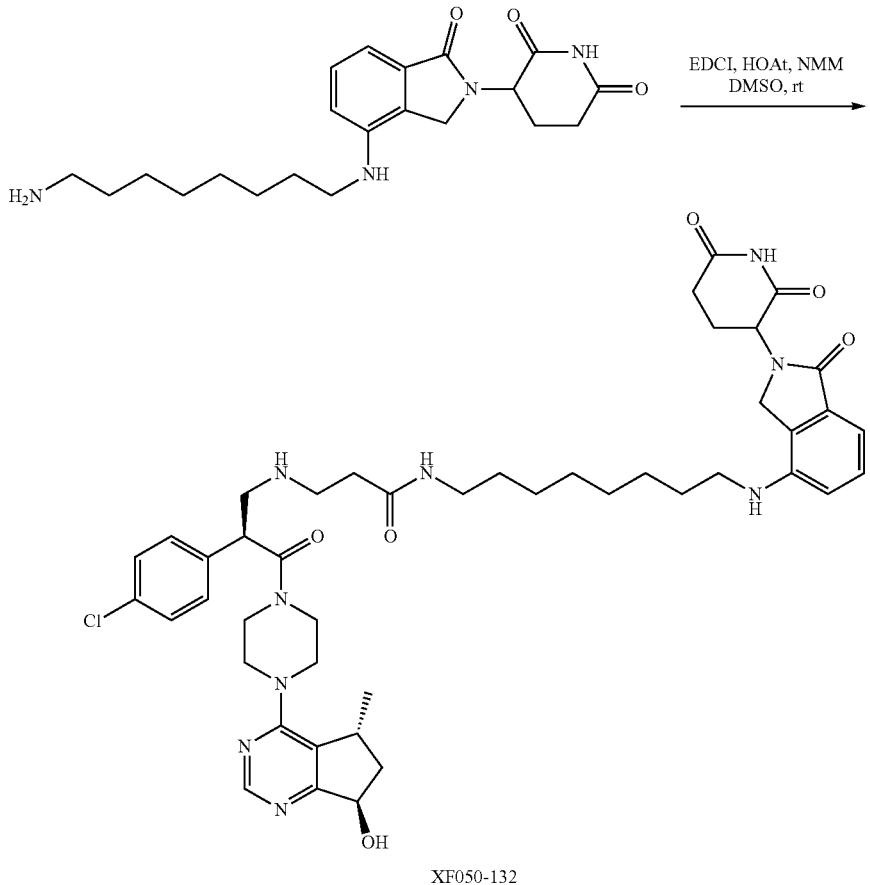

XF050-132

To a solution of Intermediate 2 (12.2 mg, 0.025 mmol) in DMSO (1 mL) were added 3-(4-((8-aminooctyl)amino)-1-oxoisoindolin-2-yl)piperidine-2,6-dione (9.7 mg, 0.025 mmol, 1.0 equiv), EDCI (1-ethyl-3-(3-dimethylaminopropyl)carbodiimide) (7.4 mg, 0.038 mmol, 1.5 equiv), HOAt (1-hydroxy-7-azabenzo-triazole) (5.2 mg, 0.038 mmol, 1.5 equiv), and NMM (N-Methylmorpholine) (7.7 mg, 0.076 mmol, 3.0 equiv). After being stirred overnight at room temperature, the resulting mixture was purified by preparative HPLC (10%-100% methanol/0.1% TFA in $H_2O$) to afford the XF050-132 as white solid in TFA salt form (8.8 mg, 41%). $^1$H NMR (600 MHz, $CD_3OD$) δ 8.57 (s, 1H), 7.51-7.42 (m, 2H), 7.38-7.33 (m, 2H), 7.27 (ddd, J=8.9, 6.9, 1.3 Hz, 1H), 7.21-7.12 (m, 1H), 7.00-6.90 (m, 1H), 5.30 (t, J=7.9 Hz, 1H), 5.13 (dd, J=13.4, 5.1 Hz, 1H), 4.57-4.48 (m, 1H), 4.36 (dd, J=16.7, 1.1 Hz, 1H), 4.27 (d, J=16.7 Hz, 1H), 4.19-4.12 (m, 1H), 3.97-3.46 (m, 8H), 3.44-3.23 (m, 6H), 3.21-3.10 (m, 2H), 3.02-2.81 (m, 2H), 2.68-2.59 (m, 2H), 2.46 (qd, J=13.1, 5.1 Hz, 1H), 2.32-2.24 (m, 1H), 2.21-2.10 (m, 2H), 1.56-1.43 (m, 4H), 1.39-1.24 (m, 8H), 1.24-1.08 (m, 3H). HRMS (m/z) for $C_{45}H_{59}ClN_9O_6^+$ [M+H]$^+$: calculated 856.4271, found 856.4277.

Example 61

Synthesis of XF050-133

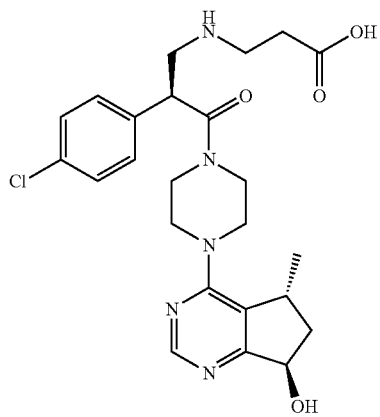

Intermediate 2

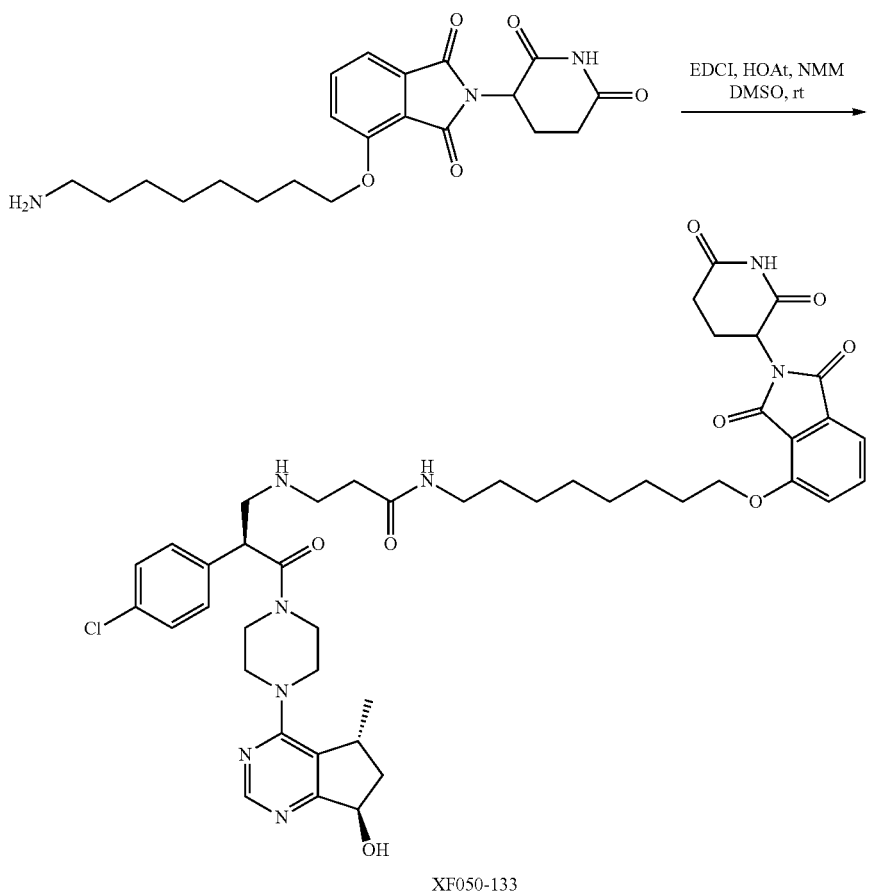

XF050-133 was synthesized following the standard procedure for preparing XF050-132 from intermediate 2 (12.2 mg, 0.025 mmol), 4-((8-aminooctyl)oxy)-2-(2,6-dioxopiperidin-3-yl)isoindoline-1,3-dione (10 mg, 0.025 mmol, 1.0 equiv), EDCI (7.4 mg, 0.038 mmol, 1.5 equiv), HOAt (5.2 mg, 0.038 mmol, 1.5 equiv), and NMM (7.7 mg, 0.06 mmol, 3.0 equiv) in DMSO (1 mL). XF050-133 was obtained as white solid in TFA salt form (10.2 mg, 47%). $^1$H NMR (600 MHz, CD$_3$OD) δ 8.57 (d, J=2.2 Hz, 1H), 7.81-7.74 (m, 1H), 7.49-7.38 (m, 4H), 7.38-7.33 (m, 2H), 5.30 (t, J=8.0 Hz, 1H), 5.10 (dd, J=12.8, 5.5 Hz, 1H), 4.61-4.49 (m, 1H), 4.25-4.13 (m, 3H), 3.98-3.76 (m, 3H), 3.73-3.58 (m, 4H), 3.43-3.36 (m, 1H), 3.35-3.28 (m, 2H), 3.21-3.16 (m, 2H), 2.96-2.82 (m, 1H), 2.79-2.67 (m, 2H), 2.64 (t, J=6.2 Hz, 2H), 2.31-2.24 (m, 1H), 2.23-2.03 (m, 2H), 1.86-1.81 (m, 2H), 1.59-1.45 (m, 4H), 1.46-1.33 (m, 8H), 1.17 (d, J=7.0 Hz, 3H). HRMS (m/z) for C$_{45}$H$_{56}$ClN$_8$O$_8{}^+$ [M+H]$^+$: calculated 871.3904, found 871.3938.

Example 62

Synthesis of XF050-134

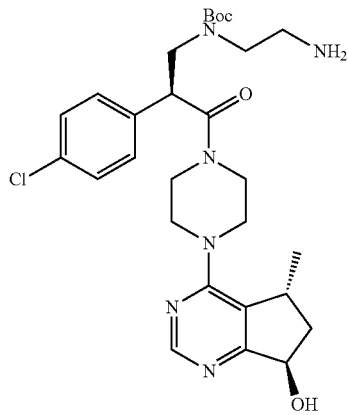

Intermediate 3

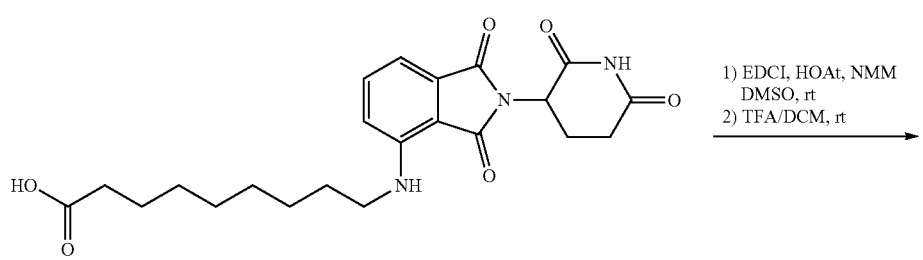

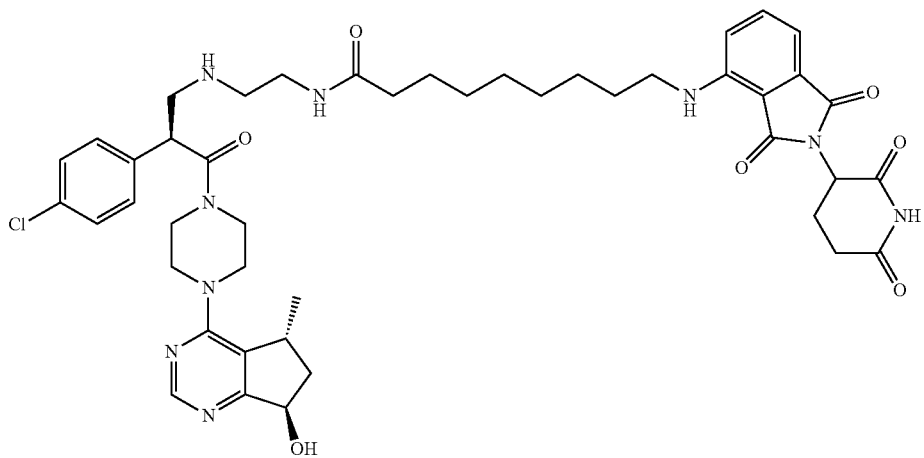

XF050-134

XF050-134 was synthesized following the standard procedure for preparing XF050-98 from intermediate 3 (19.2 mg, 0.034 mmol), 9-((2-(2,6-dioxopiperidin-3-yl)-1,3-dioxoisoindolin-4-yl)amino)nonanoic acid (14.7 mg, 0.034 mmol, 1.0 equiv), EDCI (10 mg, 0.051 mmol, 1.5 equiv), HOAt (7 mg, 0.051 mmol, 1.5 equiv), and NMM (10.1 mg, 0.1 mmol, 3.0 equiv) in DMSO (1 mL). XF050-134 was obtained as yellow solid in TFA salt form (22.1 mg, 74%).

$^1$H NMR (600 MHz, CD$_3$OD) δ 8.57 (d, J=3.9 Hz, 1H), 7.58-7.32 (m, 5H), 7.12-6.90 (m, 2H), 5.30 (t, J=7.9 Hz, 1H), 5.06 (ddd, J=12.9, 5.6, 3.4 Hz, 1H), 4.64-4.52 (m, 1H), 4.24-3.31 (m, 15H), 3.24-3.15 (m, 2H), 2.94-2.79 (m, 2H), 2.76-2.57 (m, 1H), 2.34-2.02 (m, 5H), 1.71-1.49 (m, 4H), 1.41-1.27 (m, 8H), 1.16 (d, J=7.0 Hz, 3H). HRMS (m/z) for C$_{45}$H$_{57}$ClN$_9$O$_7^+$ [M+H]$^+$: calculated 870.4064, found 870.4056.

Example 63

Synthesis of XF050-93

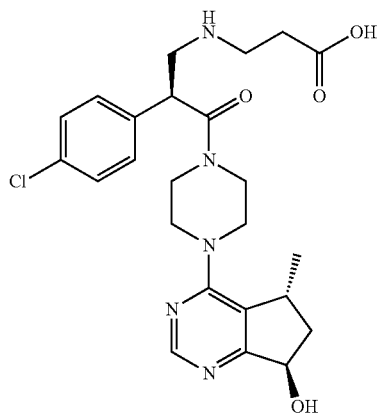

Intermediate 2

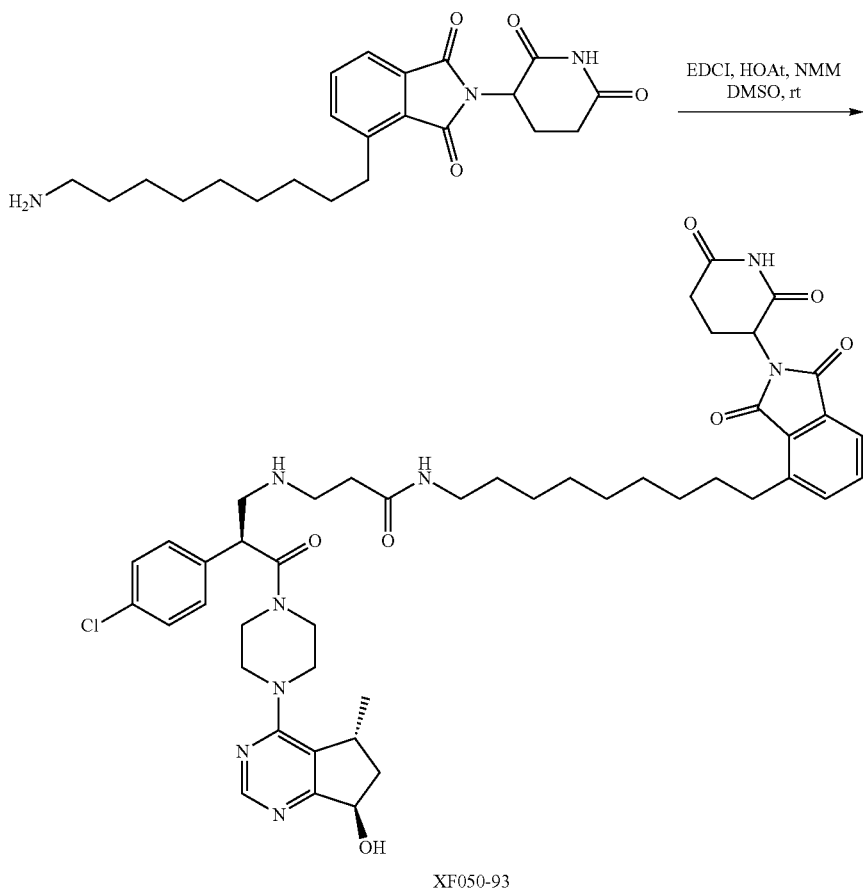

XF050-93

XF056-93 was synthesized following the standard procedure for preparing XF050-132 from intermediate 2 (9.7 mg, 0.02 mmol), 4-(9-aminononyl)-2-(2,6-dioxopiperidin-3-yl)isoindoline-1,3-dione (8 mg, 0.025 mmol, 1.0 equiv), EDCI (5.8 mg, 0.038 mmol, 1.5 equiv), HOAt (4.1 mg, 0.038 mmol, 1.5 equiv), and NMM (6.1 mg, 0.06 mmol, 3.0 equiv) in DMSO (1 mL). XF056-93 was obtained as white solid in TFA salt form (11.2 mg, 64%). $^1$H NMR (600 MHz, CD$_3$OD) δ 8.57 (d, J=4.1 Hz, 1H), 7.74-7.68 (m, 2H), 7.65-7.59 (m, 1H), 7.47-7.42 (m, 2H), 7.36 (dd, J=8.4, 1.2 Hz, 2H), 5.31 (t, J=8.0 Hz, 1H), 5.13 (ddd, J=12.8, 5.5, 2.7 Hz, 1H), 4.54 (dd, J=9.4, 4.1 Hz, 1H), 4.17-4.10 (m, 1H), 3.95-3.86 (m, 2H), 3.82 (s, 1H), 3.71-3.59 (m, 3H), 3.47-3.23 (m, 6H), 3.16 (t, J=7.2 Hz, 2H), 3.12-3.06 (m, 2H), 2.94-2.84 (m, 1H), 2.80-2.69 (m, 2H), 2.67-2.62 (m, 2H), 2.29 (dd, J=12.8, 7.5 Hz, 1H), 2.21-2.11 (m, 2H), 1.65 (q, J=7.5 Hz, 2H), 1.48 (t, J=7.1 Hz, 2H), 1.36 (s, 5H), 1.30 (d, J=3.4 Hz, 5H), 1.17 (d, J=7.0 Hz, 3H). HRMS (m/z) for $C_{46}H_{58}ClN_8O_7^+$ [M+H]$^+$: calculated 869.4112, found 869.4123.
Example 64
Synthesis of XF050-143
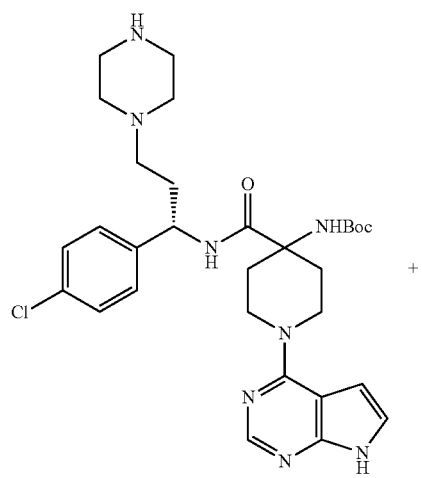
Intermediate 6
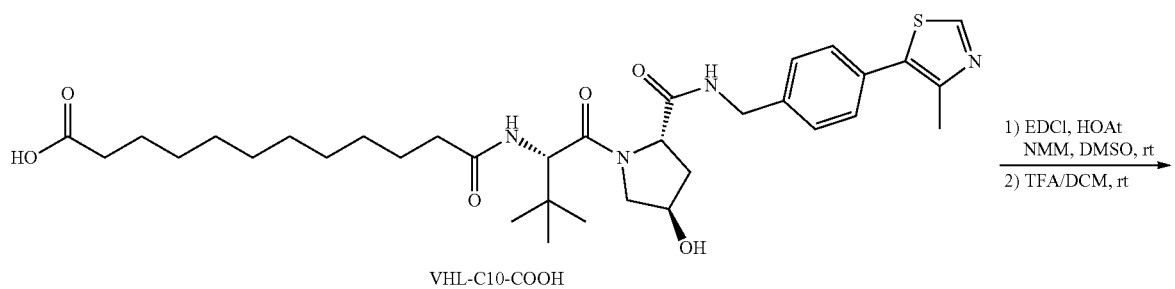
VHL-C10-COOH
1) EDCl, HOAt NMM, DMSO, rt
2) TFA/DCM, rt
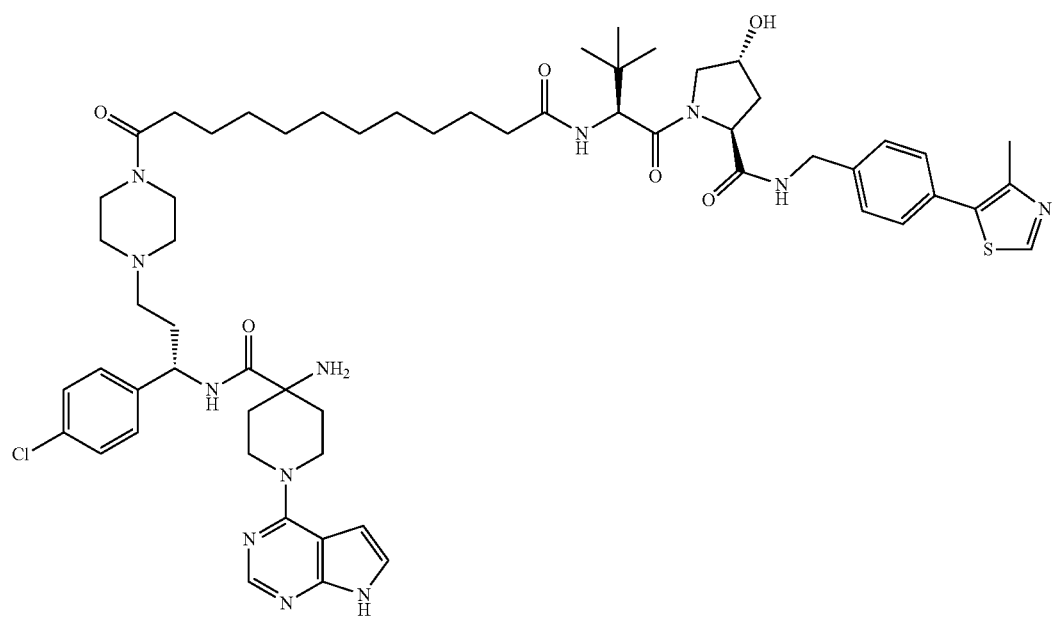
XF050-143

XF050-143 was synthesized following the standard procedure for preparing XF050-5 from intermediate 6 (14.2 mg, 0.02 mmol), VHL-C10-COOH (12.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF050-143 was obtained as white solid in TFA salt form (13.5 mg, 60%). $^1$H NMR (600 MHz, CD$_3$OD) δ 8.93 (s, 1H), 8.39 (s, 1H), 7.57-7.29 (m, 9H), 6.93 (d, J=3.7 Hz, 1H), 5.01 (dd, J=9.3, 5.8 Hz, 1H), 4.64 (d, J=12.5 Hz, 3H), 4.60-4.47 (m, 3H), 4.35 (d, J=15.4 Hz, 1H), 3.95-3.75 (m, 4H), 3.30-3.24 (m, 9H), 3.13 (td, J=12.2, 5.1 Hz, 1H), 2.68 (ddd, J=15.2, 10.9, 4.7 Hz, 1H), 2.61 (ddd, J=15.0, 10.8, 4.6 Hz, 1H), 2.47 (s, 3H), 2.43-2.32 (m, 4H), 2.32-2.14 (m, 4H), 2.12-2.00 (m, 2H), 1.58 (dp, J=14.4, 7.3, 6.6 Hz, 4H), 1.38-1.25 (m, 12H), 1.03 (s, 9H). HRMS (m/z) for C$_{59}$H$_{82}$ClN$_{12}$O$_6$S$^+$ [M+H]$^+$: calculated 1121.5884, found 1121.5898.

Example 65

Synthesis of XF050-144

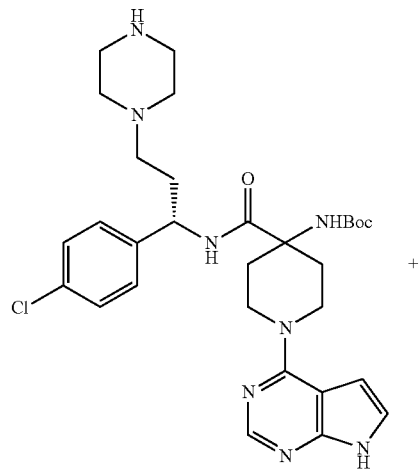

Intermediate 6

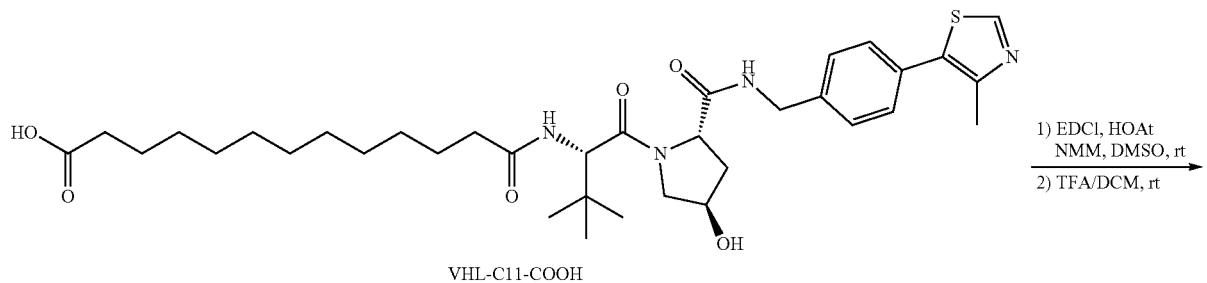

VHL-C11-COOH

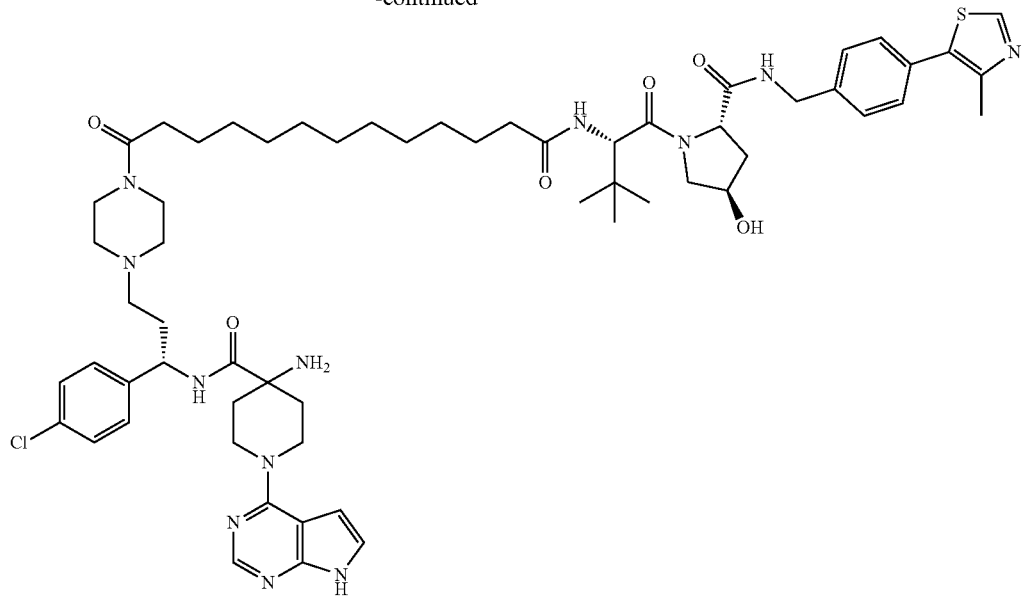

XF050-144

XF050-144 was synthesized following the standard procedure for preparing XF050-5 from intermediate 6 (14.2 mg, 0.02 mmol), VHL-C11-COOH (13.1 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF050-144 was obtained as white solid in TFA salt form (15 mg, 66%). $^1$H NMR (600 MHz, CD$_3$OD) δ 9.06-8.86 (m, 1H), 8.41-8.34 (m, 1H), 7.57-7.27 (m, 9H), 6.94 (q, J=3.9 Hz, 1H), 5.00 (td, J=8.9, 5.1 Hz, 1H), 4.71-4.64 (m, 3H), 4.63-4.46 (m, 3H), 4.35 (dd, J=15.5, 7.0 Hz, 1H), 3.95-3.76 (m, 4H), 3.61-2.89 (m, 10H), 2.65-1.95 (m, 15H), 1.58 (dh, J=15.0, 7.3 Hz, 4H), 1.30 (dd, J=13.9, 6.9 Hz, 14H), 1.09-0.89 (m, 9H). HRMS (m/z) for C$_{60}$H$_{84}$ClN$_{12}$O$_6$S$^+$ [M+H]$^+$: calculated 1135.6041, found 1135.6034.

Example 66

Synthesis of XF050-145

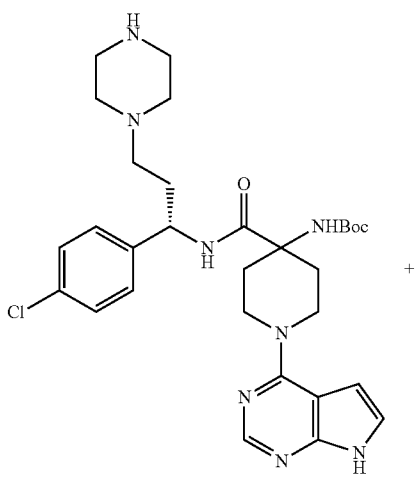

Intermediate 6

-continued

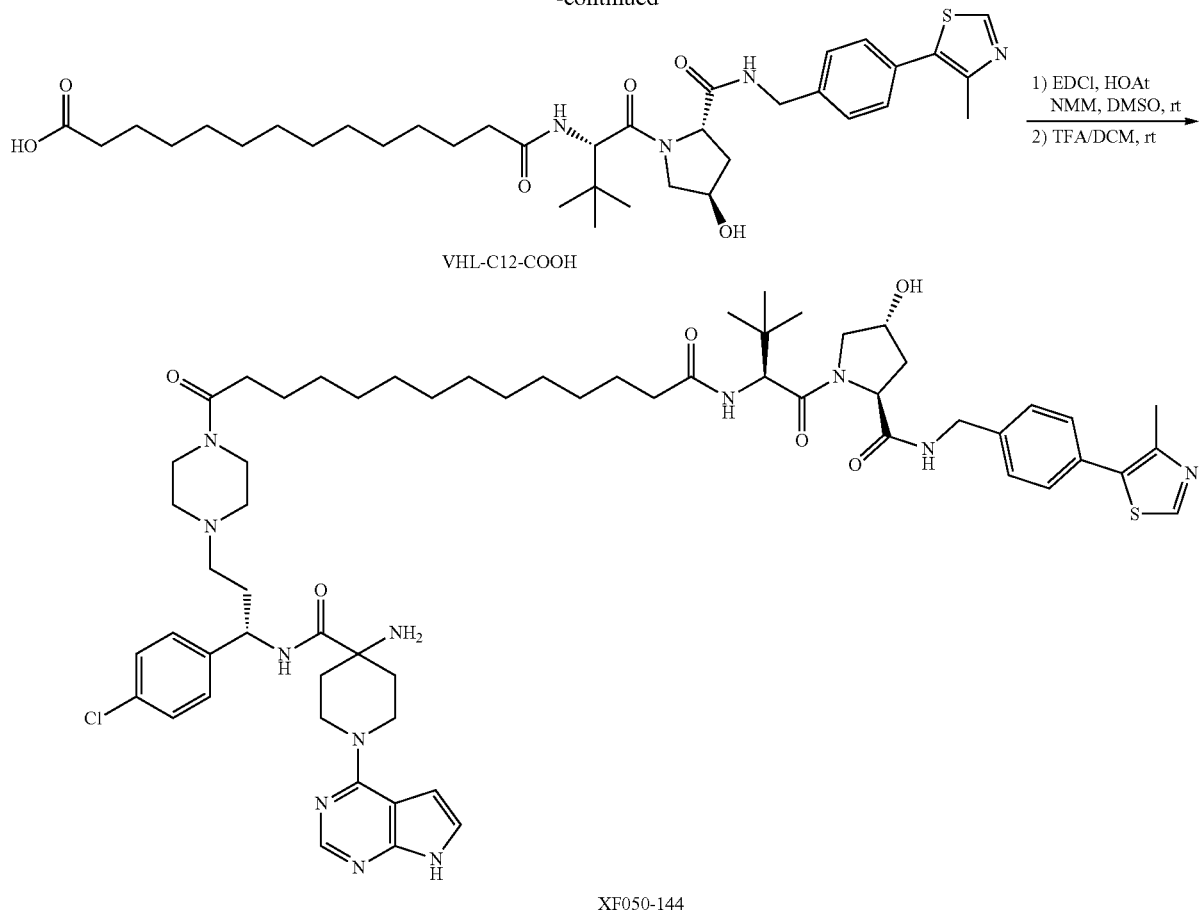

VHL-C12-COOH

1) EDCl, HOAt NMM, DMSO, rt
2) TFA/DCM, rt

XF050-144

XF050-145 was synthesized following the standard procedure for preparing XF050-5 from intermediate 6 (14.2 mg, 0.02 mmol), VHL-C12-COOH (13.4 mg, 0.02 mmol, 1.0 equiv), DCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF050-145 was obtained as white solid in TFA salt form (20.2 mg, 88%). $^1$H NMR (600 MHz, CD$_3$OD) δ 9.04 (s, 1H), 8.40 (s, 1H), 7.55-7.24 (m, 9H), 7.07-6.84 (m, 1H), 5.01 (dd, J=9.3, 5.8 Hz, 1H), 4.71-4.63 (m, 3H), 4.63-4.43 (m, 3H), 4.36 (d, J=15.5 Hz, 1H), 3.95-3.77 (m, 4H), 3.61-2.95 (m, 10H), 2.66 (dddd, J=44.2, 15.0, 10.8, 4.6 Hz, 2H), 2.49 (s, 3H), 2.45-2.14 (m, 8H), 2.12-1.97 (m, 2H), 1.63-1.53 (m, 4H), 1.39-1.19 (m, 16H), 1.03 (s, 9H). HRMS (m/z) for C$_{61}$H$_{86}$ClN$_{12}$O$_6$S$^+$ [M+H]$^+$: calculated 1149.6197, found 1149.6176.

Example 67

Synthesis of XF050-167

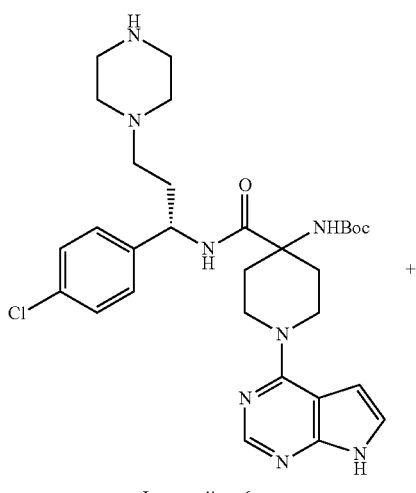

Intermediate 6

+

-continued

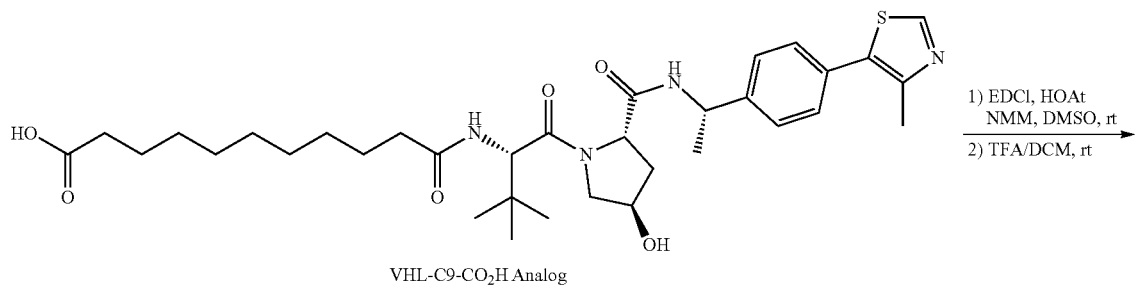

VHL-C9-CO₂H Analog

1) EDCl, HOAt NMM, DMSO, rt
2) TFA/DCM, rt

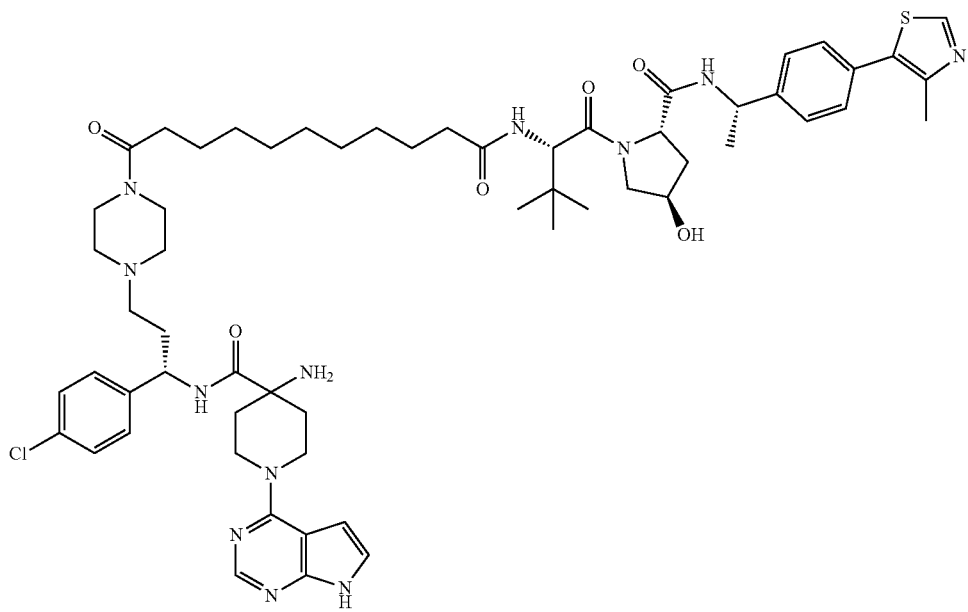

XF050-167

XF050-167 was synthesized following the standard procedure for preparing XF050-5 from intermediate 6 (23.5 mg, 0.033 mmol), VHL-C9-COOH Analog (21.2 mg, 0.033 mmol, 1.0 equiv), DCI (9.6 mg, 0.05 mmol, 1.5 equiv), HOAt (6.8 mg, 0.05 mmol, 1.5 equiv), and NMM (10.1 mg, 0.1 mmol, 3.0 equiv) in DMSO (1 mL). XF050-167 was obtained as white solid in TFA salt form (22.4 mg, 61%). ¹H NMR (600 MHz, CD₃OD) δ 8.95 (d, J=6.3 Hz, 1H), 8.39 (s, 1H), 7.47-7.40 (m, 4H), 7.40-7.30 (m, 5H), 6.94 (d, J=3.8 Hz, 1H), 5.08-4.95 (m, 1H), 4.69-4.63 (m, 3H), 4.61-4.52 (m, 1H), 4.46-4.35 (m, 1H), 3.98-3.81 (m, 4H), 3.74 (dd, J=11.0, 4.0 Hz, 1H), 3.64-2.91 (m, 10H), 2.69 (ddd, J=15.1, 10.9, 4.7 Hz, 1H), 2.62 (ddd, J=15.1, 10.8, 4.7 Hz, 1H), 2.48 (s, 3H), 2.44-2.13 (m, 8H), 2.04 (dq, J=14.7, 3.2, 2.2 Hz, 1H), 1.95 (ddd, J=13.3, 9.1, 4.5 Hz, 1H), 1.66-1.53 (m, 4H), 1.50 (d, J=7.0 Hz, 3H), 1.41-1.23 (m, 10H), 1.04 (s, 9H). HRMS (m/z) for $C_{59}H_{82}ClN_{12}O_6S^+$ [M+H]⁺: calculated 1121.5884, found 1121.5869.

Example 68

Synthesis of XF056-33

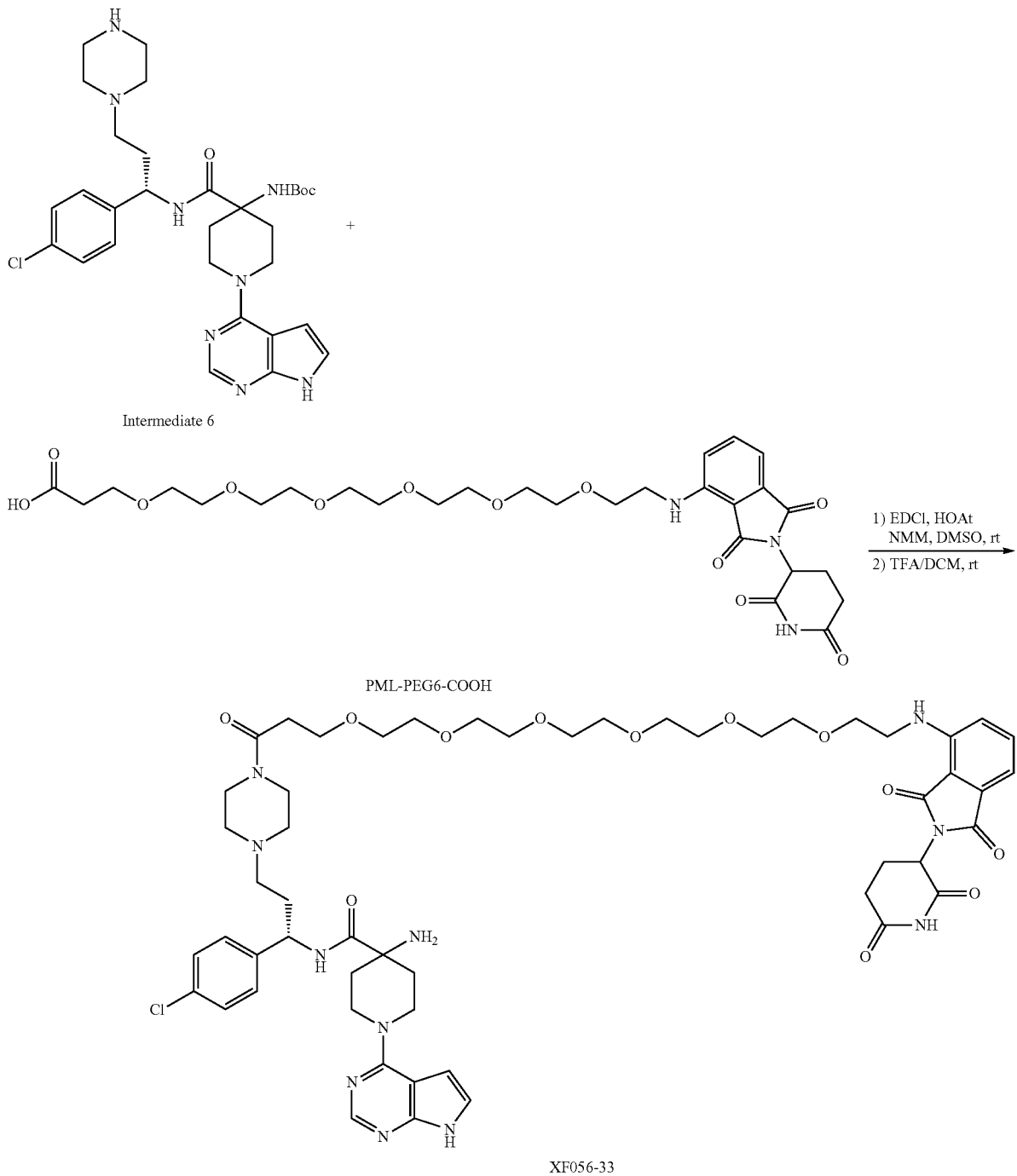

XF056-33 was synthesized following the standard procedure for preparing XF050-5 from intermediate 6 (12 mg, 0.02 mmol), PML-PEG6-COOH (12.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-33 was obtained as yellow solid in TFA salt form (10.3 mg, 47%). $^1$H NMR (600 MHz, CD$_3$OD) δ 8.38 (s, 1H), 7.61-7.51 (m, 1H), 7.44-7.28 (m, 4H), 7.07 (dd, J=20.2, 7.8 Hz, 2H), 6.92 (d, J=3.6 Hz, 1H), 5.09-4.98 (m, 2H), 4.65 (d, J=12.4 Hz, 2H), 3.91-3.79 (m, 2H), 3.79-3.69 (m, 4H), 3.69-3.48 (m, 23H), 3.41-3.07 (m, 10H), 2.87 (t, J=14.8 Hz, 1H), 2.80-2.53 (m, 5H), 2.41-2.24 (m, 3H), 2.15 (dd, J=29.7, 13.5 Hz, 2H), 2.04 (d, J=14.7 Hz, 1H). HRMS (m/z) for C$_{53}$H$_{71}$ClN$_{11}$O$_{12}{}^+$ [M+H]$^+$: calculated 1088.4967, found 1088.4974.

Example 69

Synthesis of XF056-34

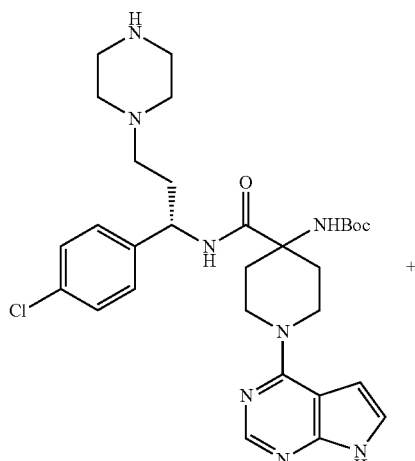

Intermediate 6

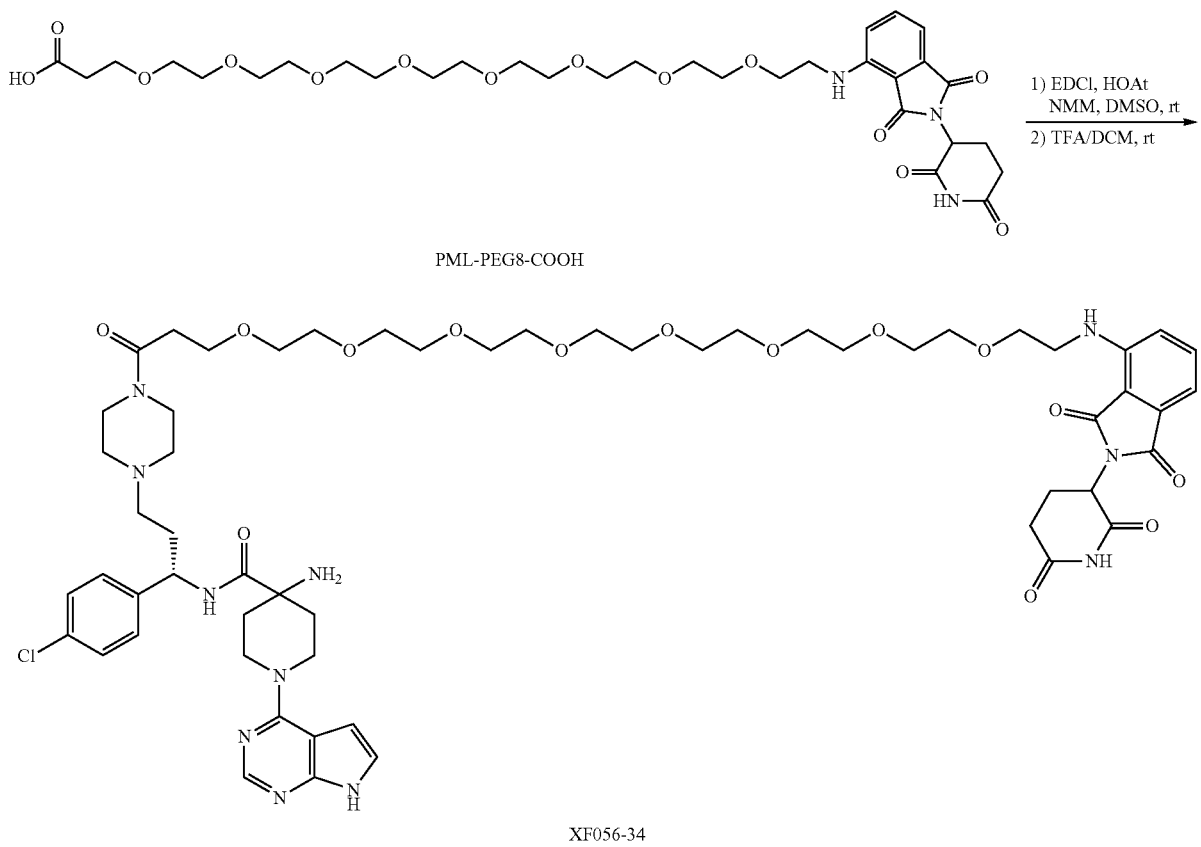

XF056-34 was synthesized following the standard procedure for preparing XF050-5 from intermediate 6 (12.2 mg, 0.02 mmol), PML-PEG8-COOH (14.1 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-34 was obtained as yellow solid in TFA salt form (16.1 mg, 68%). $^1$H NMR (600 MHz, CD$_3$OD) δ 8.39 (s, 1H), 7.54 (t, J=7.8 Hz, 1H), 7.41-7.26 (m, 4H), 7.06 (dd, J=21.5, 7.8 Hz, 2H), 6.93 (d, J=3.7 Hz, 1H), 5.13-5.01 (m, 2H), 4.61 (d, J=14.1 Hz, 2H), 3.94-3.79 (m, 2H), 3.80-3.37 (m, 36H), 3.36-3.00 (m, 10H), 2.91-2.83 (m, 1H), 2.79-2.53 (m, 5H), 2.40-2.26 (m, 2H), 2.22-2.00 (m, 3H). HRMS (m/z) for $C_{57}H_{79}ClN_{11}O_{14}^+$ [M+H]$^+$: calculated 1176.5491, found 1176.5475.

Example 70

Synthesis of XF056-35

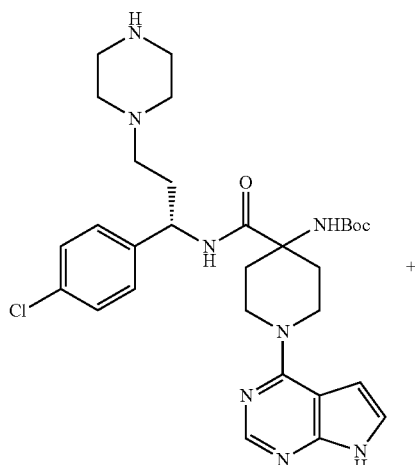

Intermediate 6

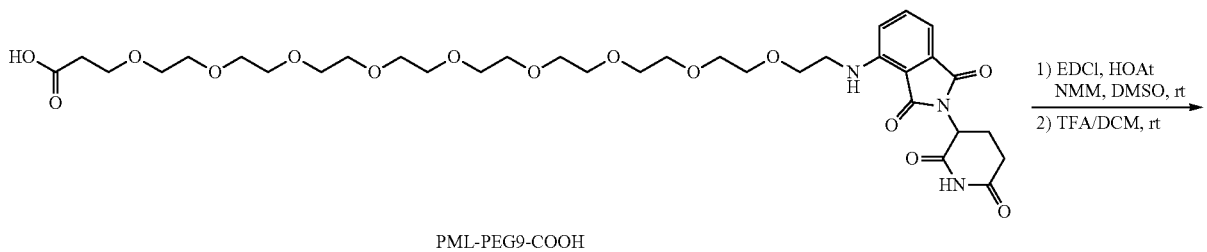

PML-PEG9-COOH

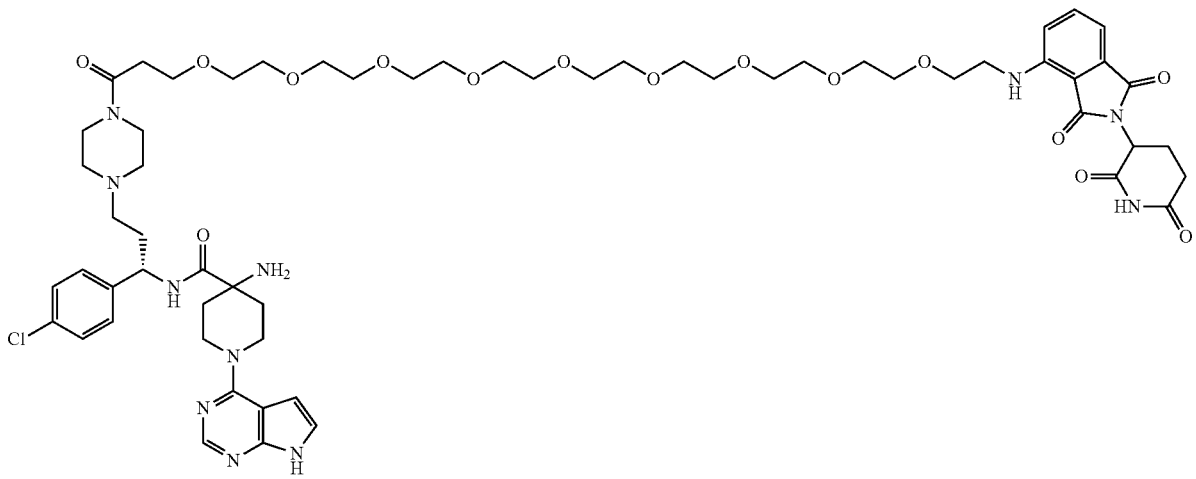

XF056-35

XF056-35 was synthesized following the standard procedure for preparing XF050-5 from intermediate 6 (12.2 mg, 0.034 mmol), PML-PEG9-COOH (14.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.1 mmol, 3.0 equiv) in DMSO (1 mL). XF056-35 was obtained as yellow solid in TFA salt form (15.9 mg, 65%). $^1$H NMR (600 MHz, CD$_3$OD) δ 8.40 (s, 1H), 7.56 (t, J=7.8 Hz, 1H), 7.46-7.30 (m, 4H), 7.08 (dd, J=22.3, 7.9 Hz, 2H), 6.94 (d, J=3.6 Hz, 1H), 5.15-4.98 (m, 2H), 4.64 (d, J=14.3 Hz, 2H), 3.87 (q, J=10.9 Hz, 2H), 3.81-3.39 (m, 40H), 3.39-2.96 (m, 10H), 2.87 (td, J=16.2, 14.3, 5.3 Hz, 1H), 2.81-2.57 (m, 5H), 2.41-2.24 (m, 2H), 2.24-1.97 (m, 3H). HRMS (m/z) for $C_{59}H_{83}ClN_{11}O_{15}^+$ [M+H]$^+$: calculated 1220.5753, found 1220.5767.

Example 71

Synthesis of XF056-36

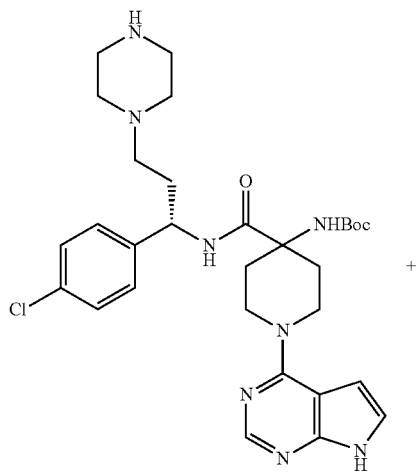
Intermediate 6

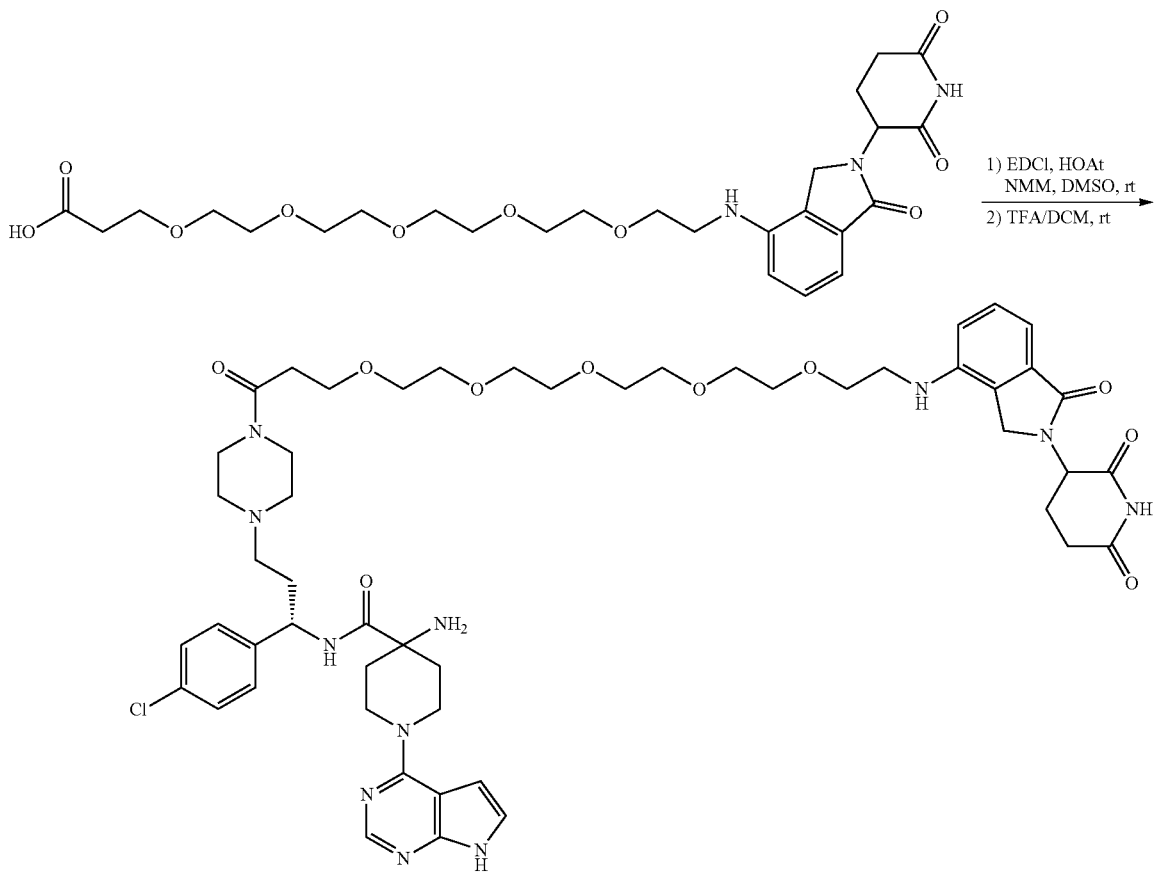
XF056-36

XF056-36 was synthesized following the standard procedure for preparing XF050-5 from intermediate 6 (12.2 mg, 0.02 mmol), 1-((2-(2,6-dioxopiperidin-3-yl)-1-oxoisoindolin-4-yl)amino)-3,6,9,12,15-pentaoxaoctadecan-18-oic acid (14.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-36 was obtained as yellow solid in TFA salt form (16.1 mg, 78%). $^1$H NMR (600 MHz, CD$_3$OD) δ 8.39 (d, J=8.9 Hz, 1H), 7.41-7.32 (m, 6H), 7.00-6.97 (m, 1H), 6.96-6.92 (m, 1H), 5.18 (d, J=13.2 Hz, 1H), 5.05-4.98 (m, 1H), 4.65 (s, 2H), 4.37 (d, J=16.8 Hz, 1H), 4.27 (dd, J=16.8, 3.3 Hz, 1H), 4.07-3.92 (m, 2H), 3.92-3.80 (m, 2H), 3.79-3.68 (m, 2H), 3.67-3.36 (m, 20H), 3.38-3.04 (m, 10H), 3.02-2.80 (m, 2H), 2.67 (dd, J=31.5, 17.7 Hz, 4H), 2.53-2.42 (m, 1H), 2.33 (s, 2H), 2.18 (d, J=14.2 Hz, 1H), 2.10-1.99 (m, 1H). HRMS (m/z) for $C_{51}H_{69}ClN_{11}O_{10}^+$ [M+H]$^+$: calculated 1030.4912, found 1030.4945.
Example 72
Synthesis of XF056-37
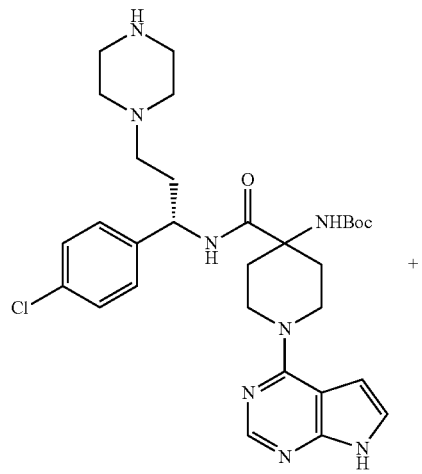
Intermediate 6
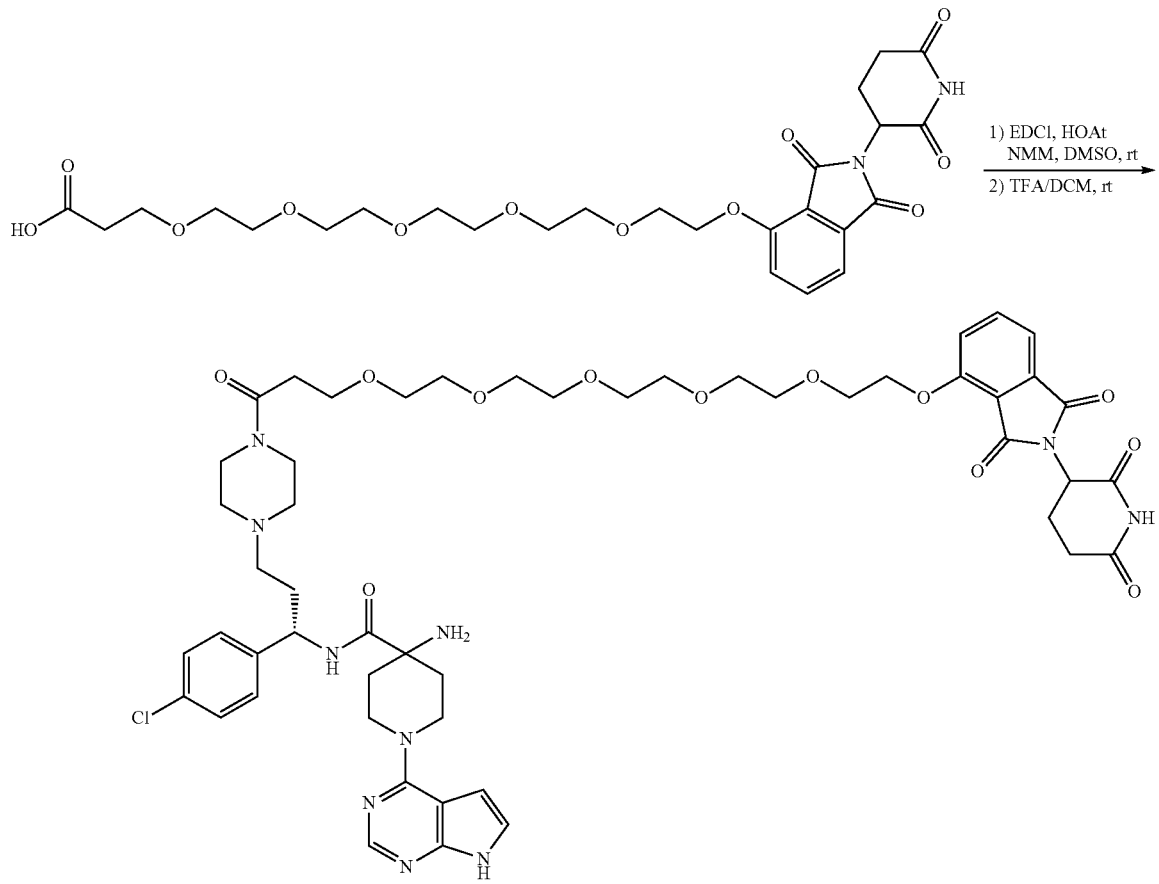
XF056-37

XF056-37 was synthesized following the standard procedure for preparing XF050-5 from intermediate 6 (12.2 mg, 0.034 mmol), 1-((2-(2,6-dioxopiperidin-3-yl)-1,3-dioxoisoindolin-4-yl)oxy)-3,6,9,12,15-pentaoxaoctadecan-18-oic acid (11.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-37 was obtained as yellow solid in TFA salt form (13.4 mg, 64%). $^1$H NMR (600 MHz, CD$_3$OD) δ 8.39 (s, 1H), 7.78 (t, J=7.5 Hz, 1H), 7.47 (d, J=8.2 Hz, 2H), 7.36 (q, J=8.4 Hz, 4H), 6.92 (d, J=3.6 Hz, 1H), 5.11 (dd, J=12.8, 5.4 Hz, 1H), 5.01 (d, J=8.2 Hz, 1H), 4.79-4.60 (m, 2H), 4.38 (s, 2H), 3.92 (d, J=4.5 Hz, 2H), 3.88-3.78 (m, 2H), 3.78-3.69 (m, 4H), 3.60 (q, J=17.4, 13.4 Hz, 16H), 3.37-3.02 (m, 10H), 2.88 (t, J=15.1 Hz, 1H), 2.81-2.54 (m, 5H), 2.43-2.25 (m, 2H), 2.22-2.10 (m, 2H), 2.04 (d, J=14.6 Hz, 1H). HRMS (m/z) for C$_{51}$H$_{66}$ClN$_{10}$O$_{12}{}^+$ [M+H]$^+$: calculated 1045.4545, found 1045.4534.

Example 73

Synthesis of XF056-73

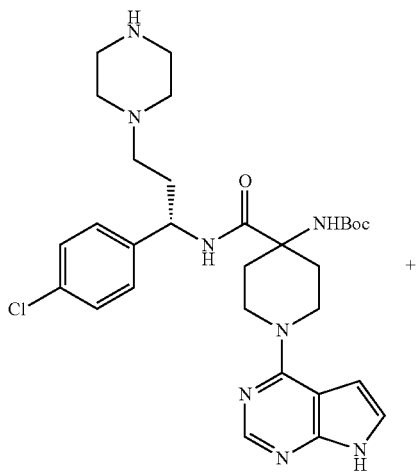

Intermediate 6

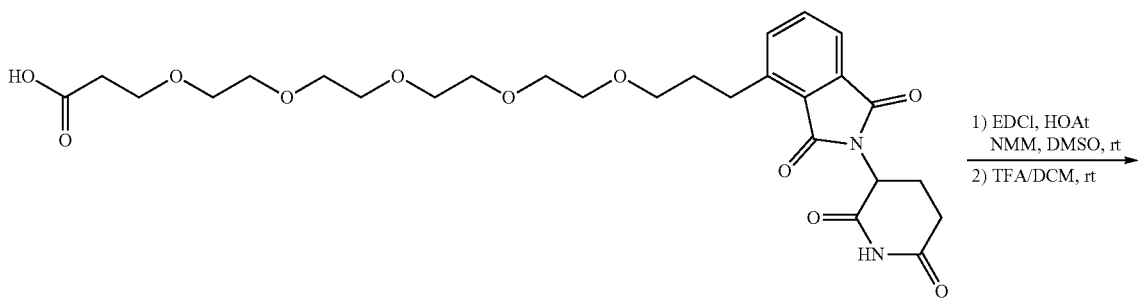

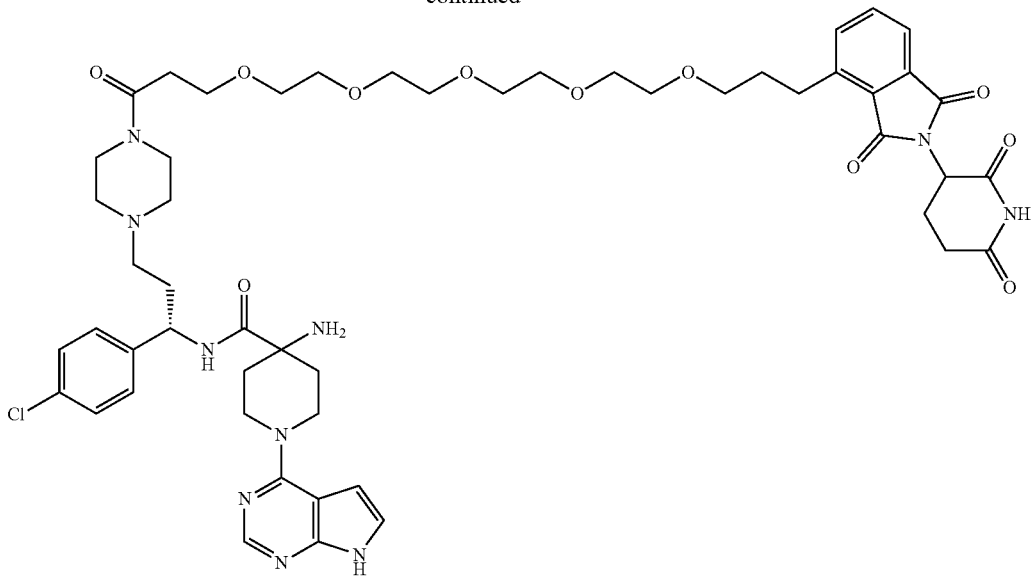

XF056-73

XF056-73 was synthesized following the standard procedure for preparing XF050-5 from intermediate 6 (12.7 mg, 0.02 mmol), 19-(2-(2,6-dioxopiperidin-3-yl)-1,3-dioxoisoindolin-4-yl)-4,7,10,13,16-pentaoxanonadecanoic acid (11.4 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF056-73 was obtained as yellow solid in TFA salt form (12.1 mg, 58%). $^1$H NMR (600 MHz, CD$_3$OD) δ 8.40 (s, 1H), 7.80-7.71 (m, 2H), 7.66 (dd, J=6.1, 2.8 Hz, 1H), 7.45-7.26 (m, 4H), 6.95 (d, J=3.6 Hz, 1H), 5.13 (dd, J=12.8, 5.4 Hz, 1H), 5.02 (t, J=7.7 Hz, 1H), 4.66 (s, 2H), 3.86 (q, J=11.8 Hz, 2H), 3.73 (t, J=6.1 Hz, 2H), 3.59 (dt, J=17.2, 4.5 Hz, 17H), 3.51 (t, J=6.4 Hz, 2H), 3.36-3.24 (m, 9H), 3.23-3.06 (m, 3H), 2.94-2.84 (m, 1H), 2.81-2.55 (m, 5H), 2.42-2.25 (m, 2H), 2.16 (t, J=17.3 Hz, 2H), 2.04 (d, J=14.8 Hz, 1H), 1.94 (p, J=6.8 Hz, 2H). HRMS (m/z) for C$_{52}$H$_{68}$ClN$_{10}$O$_{11}$$^+$ [M+H]$^+$: calculated 1043.4752, found 1043.4746.

Example 74

Synthesis of XF061-10

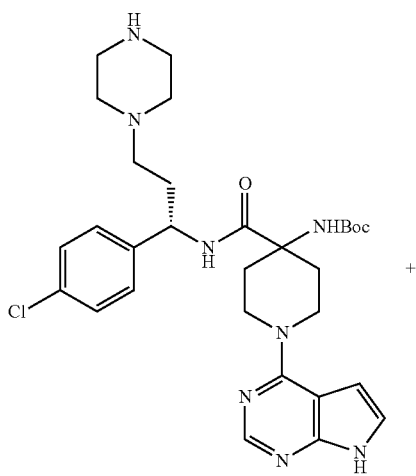

Intermediate 6

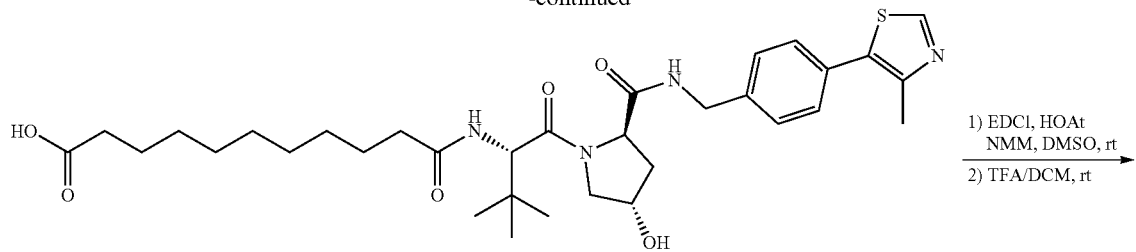

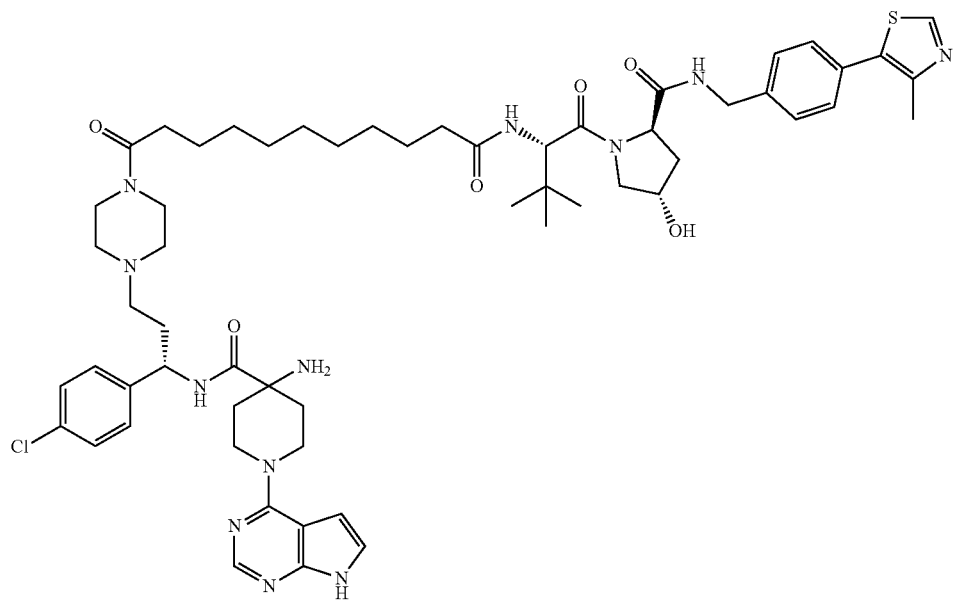

XF061-10

XF061-10 was synthesized following the standard procedure for preparing XF050-5 from intermediate 6 (12.1 mg, 0.02 mmol), 11-(((S)-1-((2R,4S)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (12.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF061-10 was obtained as white solid in TFA salt form (9.3 mg, 42%). $^1$H NMR (600 MHz, CD$_3$OD) δ 8.94 (s, 1H), 8.39 (s, 1H), 7.50-7.42 (m, 2H), 7.42-7.32 (m, 7H), 6.94 (d, J=3.7 Hz, 1H), 5.01 (dd, J=9.3, 5.9 Hz, 1H), 4.67 (dd, J=14.4, 8.6 Hz, 2H), 4.57 (dd, J=8.4, 6.5 Hz, 1H), 4.54-4.45 (m, 2H), 4.43 (s, 1H), 4.35 (d, J=15.6 Hz, 1H), 3.99 (dd, J=10.8, 4.9 Hz, 1H), 3.83 (q, J=10.9 Hz, 2H), 3.76-3.71 (m, 1H), 3.58-2.97 (m, 10H), 2.75-2.55 (m, 2H), 2.49 (s, 3H), 2.37 (q, J=7.0, 6.5 Hz, 3H), 2.32-2.23 (m, 2H), 2.23-2.12 (m, 3H), 2.02 (ddd, J=14.6, 9.1, 5.8 Hz, 2H), 1.59-1.13 (m, 14H), 1.07 (s, 9H). HRMS (m/z) for C$_{58}$H$_{80}$ClN$_{12}$O$_6$S$^+$ [M+H]$^+$: calculated 1107.5728, found 1107.5745.

Example 75

Synthesis of Intermediate 8

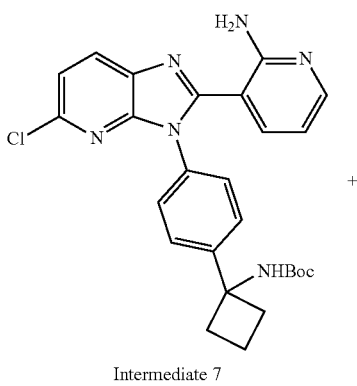

Intermediate 7

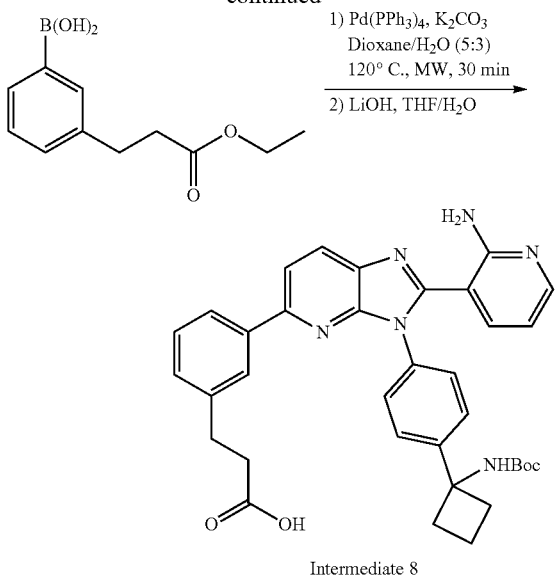

Intermediate 8

To a suspension of Intermediate 7 (Lapierre et al., 2016) (152 mg, 0.31 mmol) and (3-(3-ethoxy-3-oxopropyl)phenyl)boronic acid (137 mg, 0.62 mmol) in 2.5 mL of dioxane and 1.5 mL of H$_2$O was added potassium carbonate (128 mg, 0.93 mmol). The mixture was degassed for 5 min, before the catalyst Pd(PPh$_3$)$_4$ (18 mg, 5 mol %) was added. After the reaction mixture was stirred at 120° C. for 30 min in microwave, the solvent was removed and the mixture was purified by reverse phase C18 column (10%-100% methanol/0.1% TFA in H$_2$O) to afford the desired product as white solid in TFA salt form (206 mg, 97% yield). After this product was dissolved in THF (5 mL) and H$_2$O (2 mL), lithium hydroxide (15 mg, 0.64 mmol) was added. The reaction mixture was stirred at rt overnight. The solvent was removed and the mixture was purified by reverse phase C18 column (10%-100% methanol/0.1% TFA in H$_2$O) to afford the intermediate 8 as white solid in TFA salt form (193 mg, 99% yield). $^1$H NMR (600 MHz, DMSO-d$_6$) δ 8.31 (d, J=8.4 Hz, 1H), 8.05 (dd, J=5.8, 1.7 Hz, 1H), 8.01 (d, J=8.5 Hz, 1H), 7.87 (d, J=1.7 Hz, 1H), 7.84 (dt, J=7.7, 1.5 Hz, 1H), 7.64-7.57 (m, 3H), 7.57-7.51 (m, 4H), 7.50-7.45 (m, 1H), 2.87 (t, J=7.7 Hz, 2H), 2.57 (t, J=7.7 Hz, 2H), 2.07-1.91 (m, 1H), 1.84-1.77 (m, 1H), 1.33 (s, 9H), 1.13-1.08 (m, 4H). ESI-MS (m/z) [M+H]$^+$: 605.2878.

Example 76

Synthesis of XF067-1

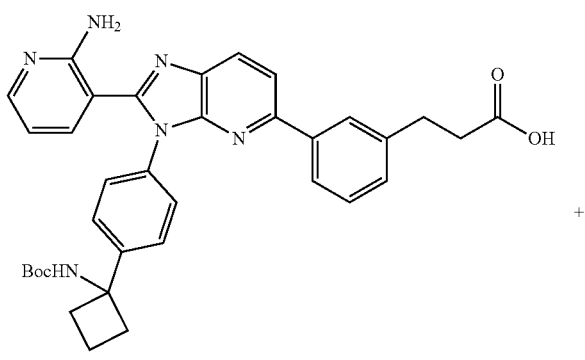

Intermediate 8

+

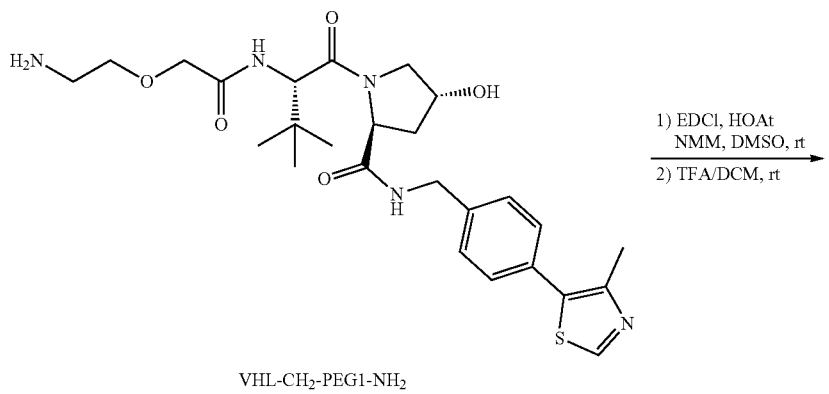

VHL-CH$_2$-PEG1-NH$_2$

-continued

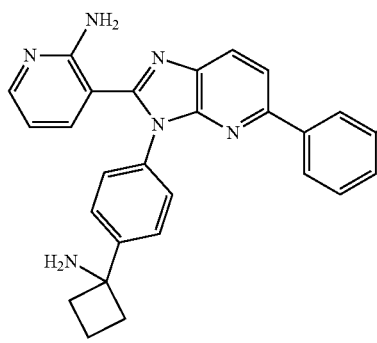
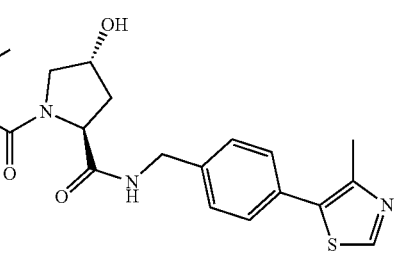

XF067-1

To a solution of Intermediate 8 (12 mg, 0.02 mmol) in DMSO (1 mL) were added VHL-PEG1-NH$_2$ (11.4 mg, 0.02 mmol, 1.0 equiv), EDCI (1-ethyl-3-(3-dimethylaminopropyl)carbodiimide) (5.8 mg, 0.03 mmol, 1.5 equiv), HOAt (1-hydroxy-7-azabenzo-triazole) (4.1 mg, 0.03 mmol, 1.5 equiv), and NMM (N-Methylmorpholine) (6.1 mg, 0.06 mmol, 3.0 equiv). After being stirred overnight at rt, the resulting mixture was purified by preparative HPLC (10%-100% methanol/0.1% TFA in H$_2$O) to afford the corresponding product. After this product was dissolved in DCM (1 mL), the reaction mixture was treated with TFA (1 mL) for 30 min. After the solvent was evaporated, the residue was purified by preparative HPLC (10%-100% methanol/0.1% TFA in H$_2$O) to afford XF067-1 as white solid in TFA salt form (7.8 mg, 38%). $^1$H NMR (800 MHz, CD$_3$OD) δ 8.88 (s, 1H), 8.30 (d, J=8.3 Hz, 1H), 8.03 (d, J=17.2 Hz, 1H), 7.99 (d, J=8.3 Hz, 1H), 7.91-7.78 (m, 5H), 7.72 (d, J=8.0 Hz, 2H), 7.42 (d, J=7.9 Hz, 2H), 7.38 (d, J=7.8 Hz, 2H), 7.33 (t, J=7.7 Hz, 1H), 7.27 (d, J=7.6 Hz, 1H), 6.83 (s, 1H), 4.70 (s, 1H), 4.60 (t, J=8.3 Hz, 1H), 4.56-4.47 (m, 2H), 4.32 (d, J=15.4 Hz, 1H), 3.93-3.86 (m, 2H), 3.86-3.78 (m, 2H), 3.48 (dd, J=10.1, 5.3 Hz, 1H), 3.40 (dt, J=9.7, 5.2 Hz, 1H), 3.35-3.29 (m, 2H), 3.00 (t, J=7.6 Hz, 2H), 2.91 (dt, J=14.3, 8.4 Hz, 2H), 2.71 (q, J=11.7, 10.2 Hz, 2H), 2.58 (t, J=7.6 Hz, 2H), 2.44 (s, 3H), 2.42-2.30 (m, 1H), 2.26 (dd, J=13.2, 7.6 Hz, 1H), 2.15-2.03 (m, 2H), 1.03 (s, 9H). ESI-MS (m/z) [M+H]$^+$: 1018.4762.

Example 77

Synthesis of XF067-2

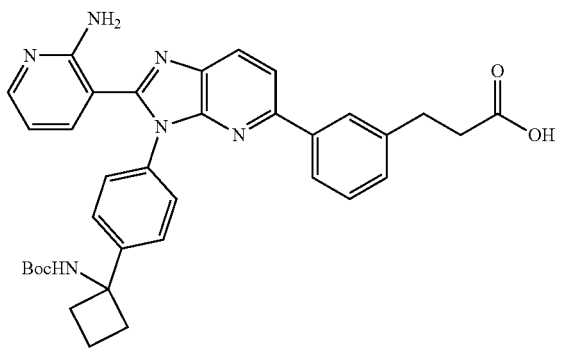

Intermediate 8

+

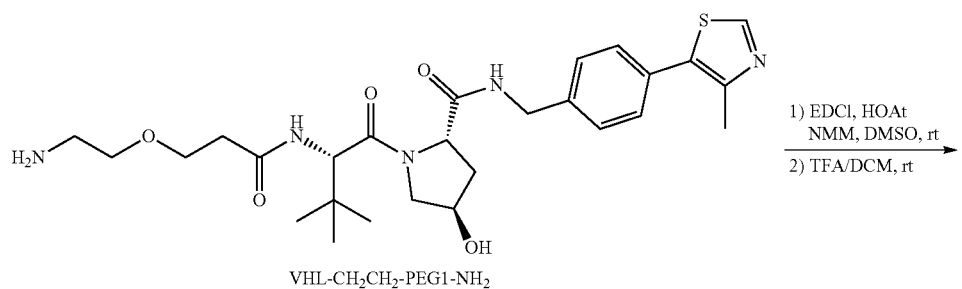

VHL-CH$_2$CH$_2$-PEG1-NH$_2$

1) EDCl, HOAt NMM, DMSO, rt
2) TFA/DCM, rt

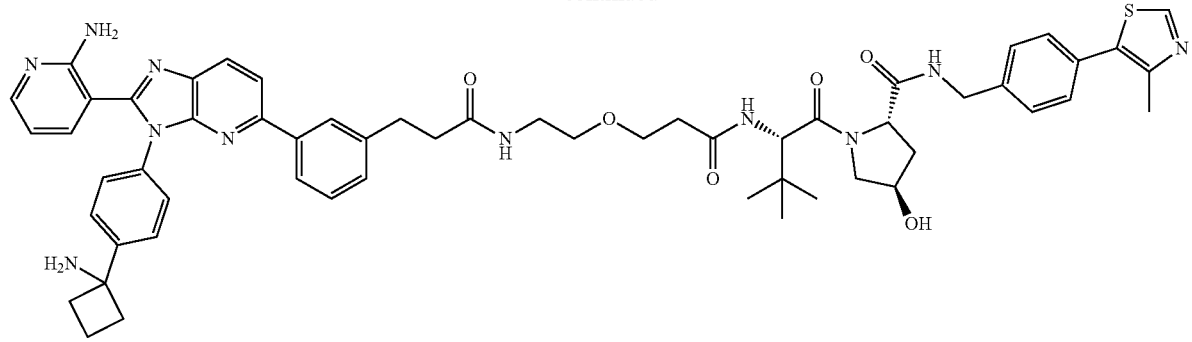

XF067-2

XF067-2 was synthesized following the standard procedure for preparing XF067-1 from intermediate 8 (12 mg, 0.02 mmol), VHL-CH$_2$CH$_2$PEG1-NH$_2$ (15.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-2 was obtained as white solid in TFA salt form (14.6 mg, 71%). $^1$H NMR (800 MHz, CD$_3$OD) δ 8.96 (s, 1H), 8.31 (dd, J=8.5, 4.3 Hz, 1H), 8.05-7.97 (m, 2H), 7.91-7.85 (m, 2H), 7.84 (d, J=7.6 Hz, 1H), 7.81 (d, J=8.0 Hz, 2H), 7.72 (d, J=8.1 Hz, 2H), 7.42 (d, J=7.9 Hz, 2H), 7.37 (dd, J=23.2, 7.8 Hz, 3H), 7.29 (d, J=7.5 Hz, 1H), 6.84 (t, J=6.9 Hz, 1H), 4.64 (s, 1H), 4.63-4.54 (m, 1H), 4.52-4.44 (m, 2H), 4.33 (d, J=15.4 Hz, 1H), 3.88 (d, J=10.9 Hz, 1H), 3.79 (dd, J=11.2, 4.0 Hz, 1H), 3.53 (dq, J=9.8, 4.7, 4.1 Hz, 1H), 3.48 (dt, J=10.1, 5.5 Hz, 1H), 3.38 (ddt, J=26.6, 10.1, 5.3 Hz, 2H), 3.30 (t, J=5.3 Hz, 2H), 2.98 (t, J=7.6 Hz, 2H), 2.91 (tt, J=9.1, 5.8 Hz, 2H), 2.77-2.67 (m, 2H), 2.56 (t, J=7.6 Hz, 2H), 2.47 (s, 3H), 2.41-2.31 (m, 3H), 2.24 (dd, J=13.3, 7.6 Hz, 1H), 2.08 (ddt, J=12.2, 7.9, 3.9 Hz, 2H), 1.01 (s, 9H). ESI-MS (m/z) [M+H]$^+$: 1032.4912.

Example 78

Synthesis of XF067-3

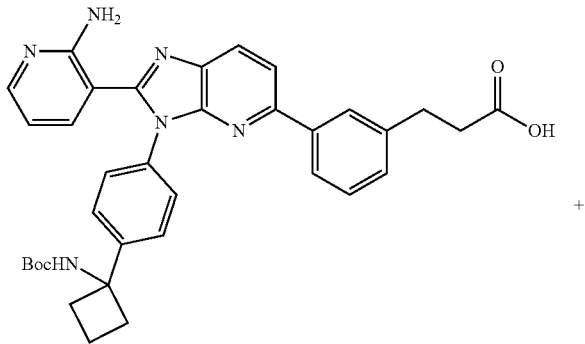

Intermediate 8

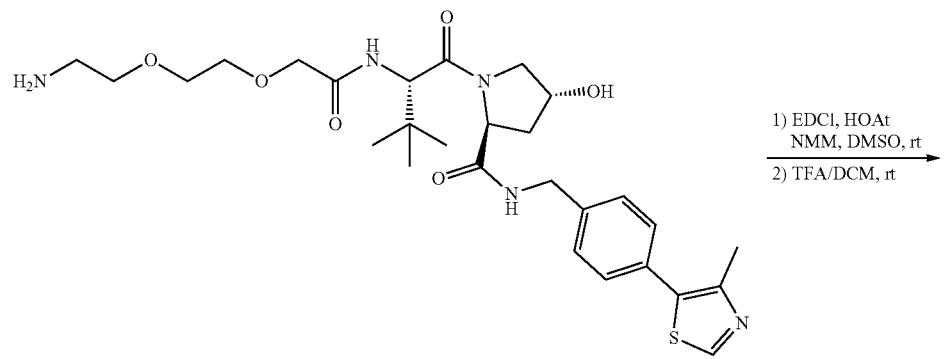

VHL-CH$_2$-PEG2-NH$_2$

1) EDCl, HOAt NMM, DMSO, rt
2) TFA/DCM, rt

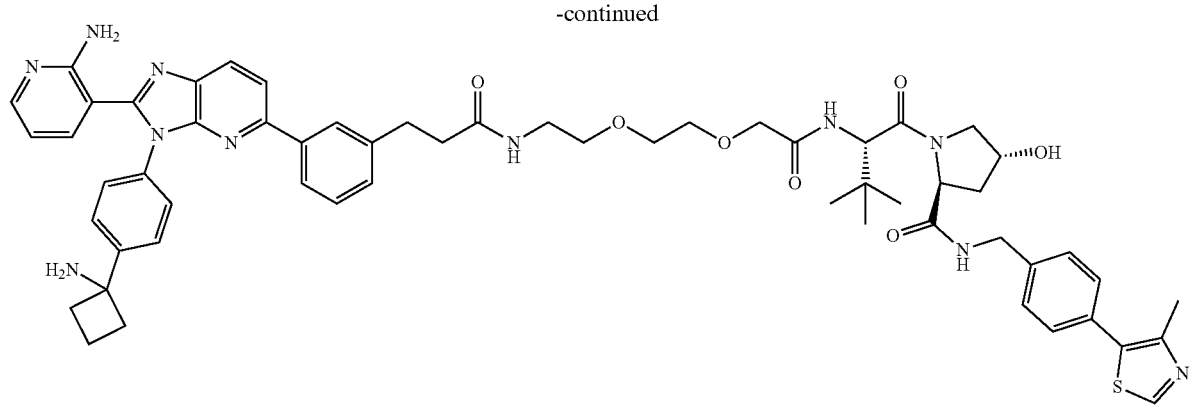
XF067-3

XF067-3 was synthesized following the standard procedure for preparing XF067-1 from intermediate 8 (12 mg, 0.02 mmol), VHL-CH₂PEG2-NH₂ (12.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-3 was obtained as white solid in TFA salt form (10.5 mg, 49%). $^1$H NMR (800 MHz, CD$_3$OD) δ 8.94 (s, 1H), 8.31 (dd, J=8.3, 3.7 Hz, 1H), 8.02 (dd, J=18.9, 7.4 Hz, 2H), 7.93-7.86 (m, 2H), 7.82 (dd, J=20.7, 8.0 Hz, 3H), 7.72 (d, J=8.0 Hz, 2H), 7.49-7.32 (m, 5H), 7.28 (d, J=7.7 Hz, 1H), 6.84 (t, J=6.8 Hz, 1H), 4.73 (s, 1H), 4.62-4.56 (m, 1H), 4.54-4.45 (m, 2H), 4.40-4.32 (m, 1H), 4.01-3.93 (m, 1H), 3.93-3.86 (m, 2H), 3.82 (dd, J=11.2, 4.1 Hz, 1H), 3.66-3.54 (m, 2H), 3.52-3.36 (m, 5H), 3.25 (ddd, J=14.2, 7.3, 3.8 Hz, 1H), 3.02-2.95 (m, 2H), 2.90 (dd, J=12.7, 7.3 Hz, 2H), 2.75-2.69 (m, 2H), 2.59 (dt, J=15.1, 7.8 Hz, 1H), 2.53 (dt, J=14.2, 7.5 Hz, 1H), 2.47 (s, 3H), 2.34 (td, J=11.1, 6.7 Hz, 1H), 2.25 (dd, J=13.4, 7.7 Hz, 1H), 2.09 (ddt, J=25.6, 11.5, 4.7 Hz, 2H), 1.02 (s, 9H). ESI-MS (m/z) [M+H]$^+$: 1062.5023.

Example 79

Synthesis of XF067-4

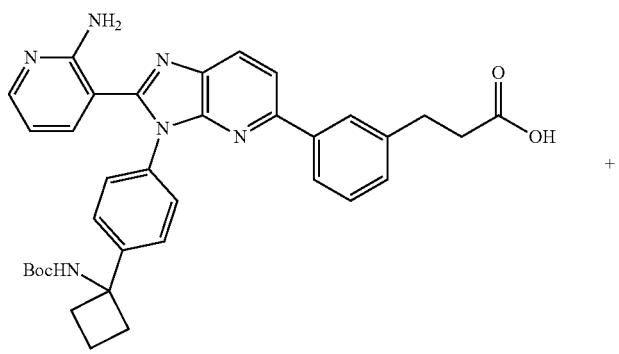
Intermediate 8

+

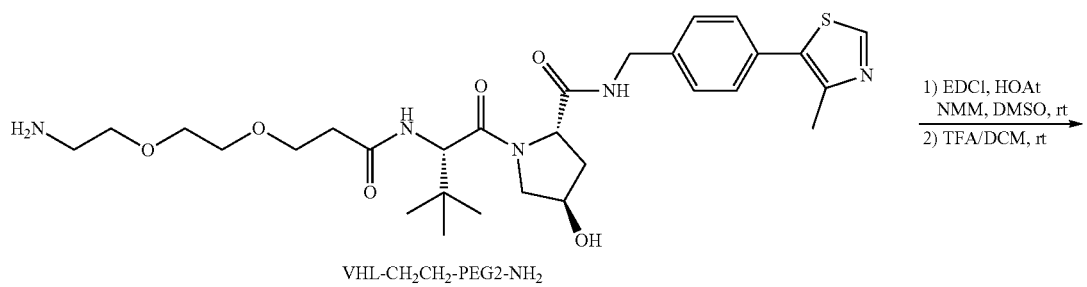
VHL-CH₂CH₂-PEG2-NH₂

1) EDCI, HOAt
NMM, DMSO, rt
2) TFA/DCM, rt

-continued

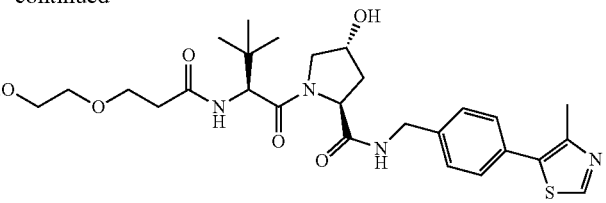

XF067-4

XF067-4 was synthesized following the standard procedure for preparing XF067-1 from intermediate 8 (12 mg, 0.02 mmol), VHL-CH₂CH₂PEG2-NH₂ (16.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-4 was obtained as white solid in TFA salt form (12.6 mg, 58%). ¹H NMR (800 MHz, CD₃OD) δ 8.95 (d, J=7.0 Hz, 1H), 8.31 (d, J=8.4 Hz, 1H), 8.03 (t, J=6.4 Hz, 2H), 7.92-7.86 (m, 2H), 7.83 (dd, J=20.3, 7.9 Hz, 3H), 7.73 (d, J=8.0 Hz, 2H), 7.48-7.38 (m, 4H), 7.40-7.33 (m, 1H), 7.29 (d, J=7.6 Hz, 1H), 6.84 (t, J=7.0 Hz, 1H), 4.65 (s, 1H), 4.61-4.56 (m, 1H), 4.56-4.49 (m, 2H), 4.40-4.34 (m, 1H), 3.89 (d, J=10.9 Hz, 1H), 3.80 (dd, J=11.1, 4.1 Hz, 1H), 3.72-3.62 (m, 2H), 3.52 (t, J=4.5 Hz, 2H), 3.47 (t, J=5.1 Hz, 2H), 3.40 (t, J=5.4 Hz, 2H), 3.29 (t, J=5.4 Hz, 2H), 2.99 (t, J=7.6 Hz, 2H), 2.91 (ddd, J=14.6, 9.0, 5.8 Hz, 2H), 2.72 (ddd, J=13.3, 9.0, 5.9 Hz, 2H), 2.53 (s, 3H), 2.49-2.42 (m, 4H), 2.36-2.30 (m, 1H), 2.23 (dd, J=13.4, 7.6 Hz, 1H), 2.12-2.03 (m, 2H), 1.03 (s, 9H). ESI-MS (m/z) [M+H]⁺: 1076.5164.

Example 80

Synthesis of XF067-5

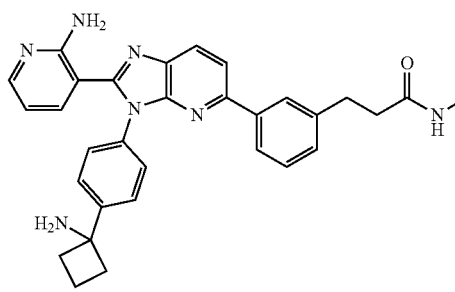

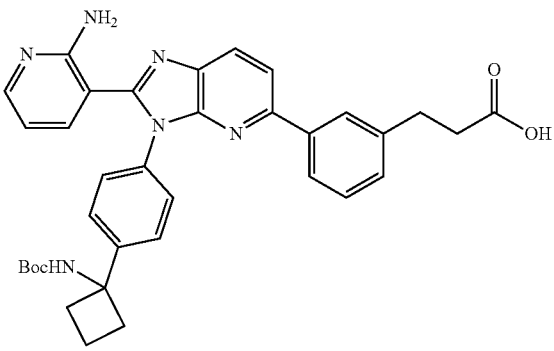

Intermediate 8

+

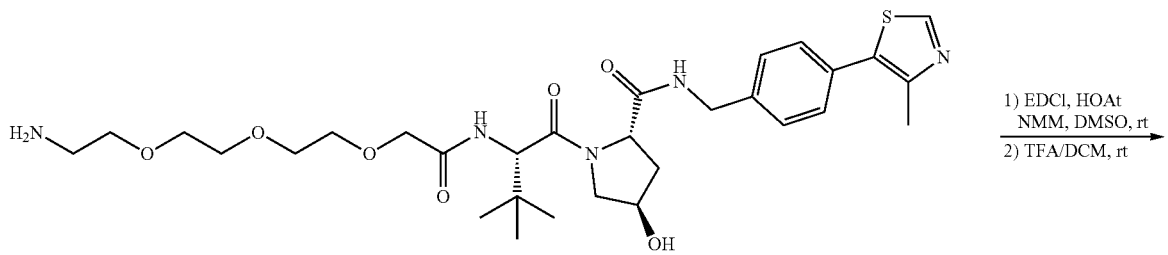

VHL-CH₂-PEG3-NH₂

1) EDCl, HOAt
   NMM, DMSO, rt
2) TFA/DCM, rt

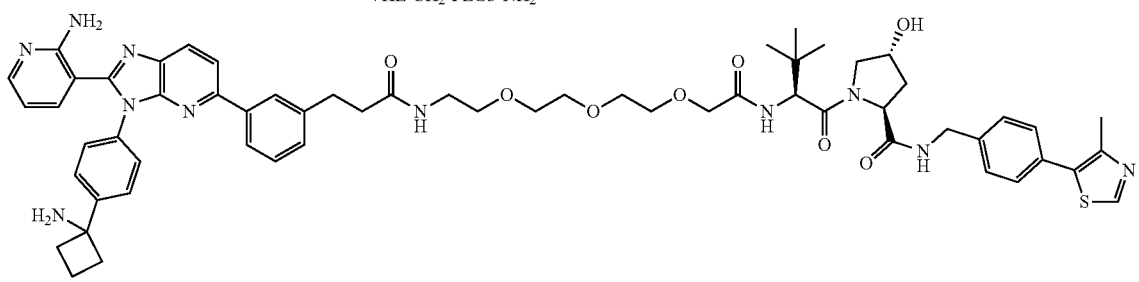

XF067-5

XF067-5 was synthesized following the standard procedure for preparing XF067-1 from intermediate 8 (12 mg, 0.02 mmol), VHL-CH$_2$PEG3-NH$_2$ (16.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-5 was obtained as white solid in TFA salt form (16.4 mg, 74%). $^1$H NMR (800 MHz, CD$_3$OD) δ 8.93 (s, 1H), 8.31 (d, J=8.3 Hz, 1H), 8.03 (t, J=6.9 Hz, 2H), 7.91 (s, 1H), 7.88 (d, J=7.8 Hz, 1H), 7.83 (dd, J=19.6, 7.8 Hz, 3H), 7.73 (d, J=5.3 Hz, 2H), 7.46 (d, J=8.1 Hz, 2H), 7.41 (d, J=7.9 Hz, 2H), 7.37 (t, J=7.7 Hz, 1H), 7.29 (d, J=7.5 Hz, 1H), 6.84 (t, J=6.9 Hz, 1H), 4.70 (s, 1H), 4.59 (t, J=8.6 Hz, 1H), 4.52 (d, J=4.3 Hz, 2H), 4.37 (d, J=15.4 Hz, 1H), 4.06-3.96 (m, 4H), 3.88 (d, J=11.0 Hz, 1H), 3.81 (dd, J=11.2, 4.0 Hz, 1H), 3.69-3.62 (m, 4H), 3.57 (q, J=4.5 Hz, 2H), 3.47 (t, J=4.7 Hz, 2H), 3.38 (t, J=5.5 Hz, 2H), 3.27 (t, J=5.4 Hz, 2H), 2.99 (t, J=7.6 Hz, 2H), 2.91 (dt, J=14.3, 8.7 Hz, 2H), 2.76-2.68 (m, 2H), 2.53 (t, J=7.6 Hz, 2H), 2.47 (s, 3H), 2.38-2.29 (m, 1H), 2.25 (dd, J=12.8, 7.9 Hz, 1H), 2.14-2.04 (m, 2H), 1.04 (s, 9H). ESI-MS (m/z) [M+H]$^+$: 1106.5268.

Example 81

Synthesis of XF067-6

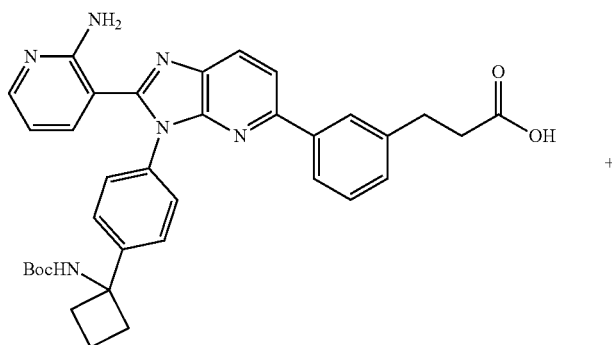

Intermediate 8

+

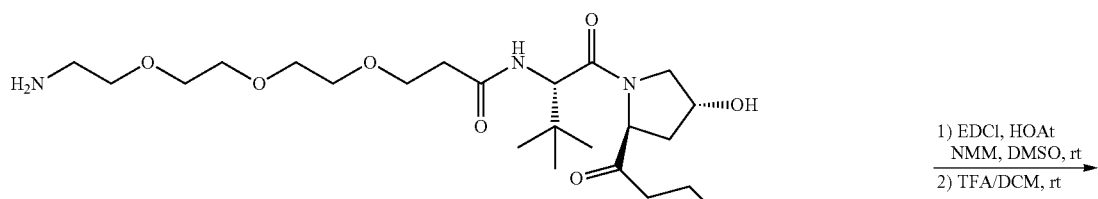

VHL-CH$_2$CH$_2$-PEG3-NH$_2$

1) EDCl, HOAt
NMM, DMSO, rt
2) TFA/DCM, rt

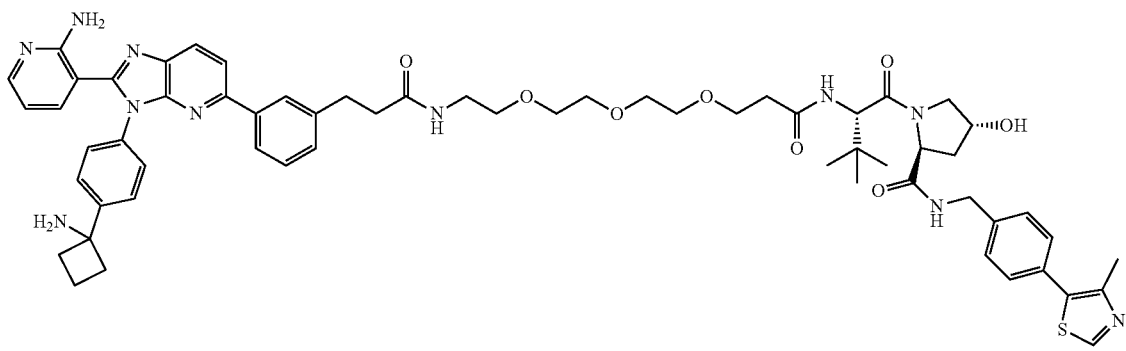

XF067-6

XF067-6 was synthesized following the standard procedure for preparing XF067-1 from intermediate 8 (12 mg, 0.02 mmol), VHL-CH$_2$CH$_2$PEG3-NH$_2$ (17.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-6 was obtained as white solid in TFA salt form (12.2 mg, 54%). $^1$H NMR (800 MHz, CD$_3$OD) δ 8.95 (s, 1H), 8.32 (d, J=8.4 Hz, 1H), 8.04 (t, J=6.5 Hz, 2H), 7.92 (s, 1H), 7.88 (d, J=7.8 Hz, 1H), 7.85 (d, J=7.6 Hz, 1H), 7.82 (d, J=8.0 Hz, 2H), 7.73 (d, J=8.0 Hz, 2H), 7.47 (d, J=7.8 Hz, 2H), 7.42 (d, J=7.8 Hz, 2H), 7.37 (t, J=7.7 Hz, 1H), 7.30 (d, J=7.5 Hz, 1H), 6.84 (t, J=6.9 Hz, 1H), 4.65 (s, 1H), 4.58 (t, J=8.5 Hz, 1H), 4.54 (d, J=15.4 Hz, 1H), 4.52-4.50 (m, 1H), 4.40-4.34 (m, 1H), 3.90 (d, J=10.9 Hz, 1H), 3.81 (dd, J=11.1, 4.1 Hz, 1H), 3.74-3.66 (m, 2H), 3.63-3.55 (m, 4H), 3.53 (t, J=4.7 Hz, 2H), 3.44 (t, J=4.7 Hz, 2H), 3.39 (d, J=5.4 Hz, 2H), 3.28 (t, J=5.5 Hz, 2H), 3.00 (t, J=7.6 Hz, 2H), 2.91 (dt, J=14.4, 8.6 Hz, 2H), 2.72 (ddd, J=13.7, 9.1, 6.0 Hz, 2H), 2.60-2.51 (m, 3H), 2.51-2.43 (m, 4H), 2.37-2.32 (m, 1H), 2.24 (dd, J=13.4, 7.6 Hz, 1H), 2.09 (dtd, J=15.6, 11.0, 10.1, 5.2 Hz, 2H), 1.04 (s, 9H). ESI-MS (m/z) [M+H]$^+$: 1120.5423.

Example 82

Synthesis of XF067-7

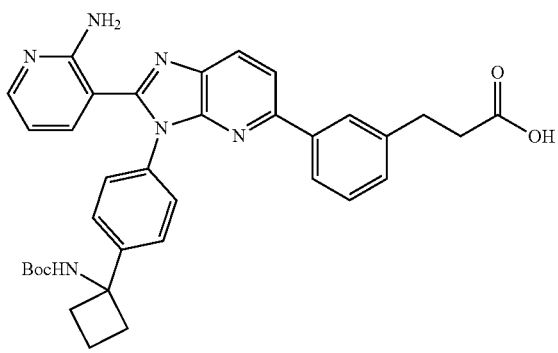

Intermediate 8

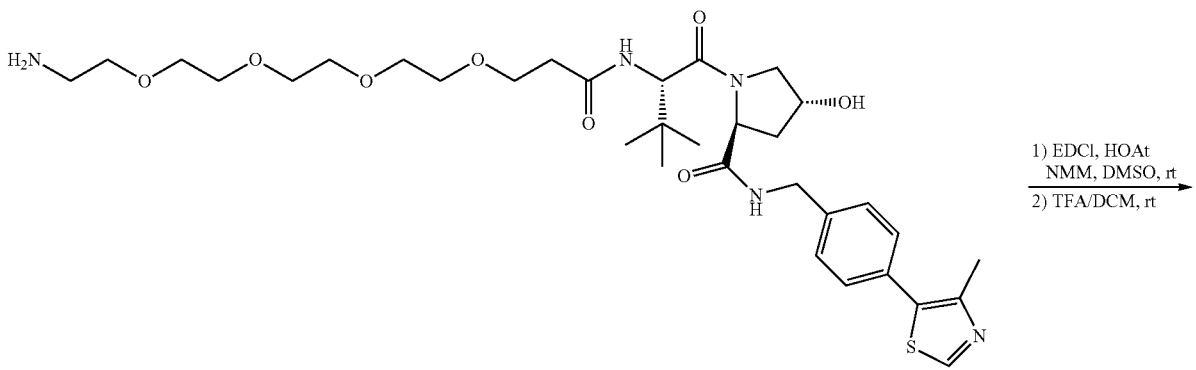

VHL-CH$_2$CH$_2$-PEG4-NH$_2$

1) EDCI, HOAt NMM, DMSO, rt
2) TFA/DCM, rt

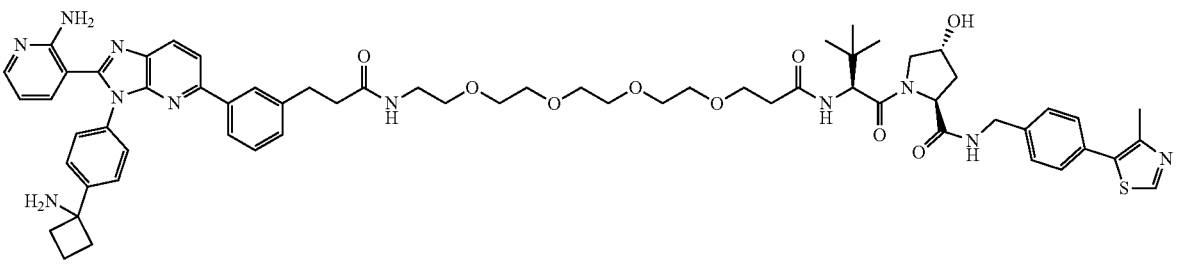

XF067-7

XF067-7 was synthesized following the standard procedure for preparing XF067-1 from intermediate 8 (12 mg, 0.02 mmol), VHL-CH$_2$CH$_2$PEG4-NH$_2$ (14.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-7 was obtained as white solid in TFA salt form (12.2 mg, 52%). $^1$H NMR (800 MHz, CD$_3$OD) δ 8.92 (s, 1H), 8.31 (d, J=8.3 Hz, 1H), 8.08-8.00 (m, 2H), 7.92 (s, 1H), 7.89 (d, J=7.8 Hz, 1H), 7.83 (dd, J=12.6, 7.9 Hz, 3H), 7.73 (d, J=8.0 Hz, 2H), 7.47 (d, J=7.9 Hz, 2H), 7.42 (d, J=7.9 Hz, 2H), 7.37 (t, J=7.7 Hz, 1H), 7.30 (d, J=7.6 Hz, 1H), 6.83 (t, J=6.9 Hz, 1H), 4.65 (s, 1H), 4.62-4.47 (m, 3H), 4.37 (d, J=15.4 Hz, 1H), 3.90 (d, J=10.9 Hz, 1H), 3.81 (dd, J=11.1, 4.1 Hz, 1H), 3.70 (ddq, J=28.0, 10.3, 5.4 Hz, 2H), 3.64-3.55 (m, 8H), 3.52 (t, J=4.6 Hz, 2H), 3.44 (t, J=4.7 Hz, 2H), 3.39 (t, J=5.5 Hz, 2H), 3.28 (t, J=5.4 Hz, 2H), 3.00 (t, J=7.6 Hz, 2H), 2.95-2.87 (m, 2H), 2.77-2.68 (m, 2H), 2.59-2.51 (m, 3H), 2.51-2.44 (m, 4H), 2.33 (dd, J=13.4, 8.2 Hz, 1H), 2.24 (dd, J=13.2, 7.7 Hz, 1H), 2.12-2.04 (m, 2H), 1.04 (s, 9H). ESI-MS (m/z) [M+H]$^+$: 1164.5673.

Example 83

Synthesis of XF067-8

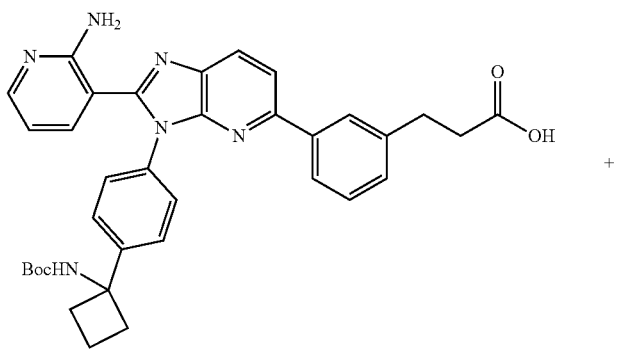

Intermediate 8

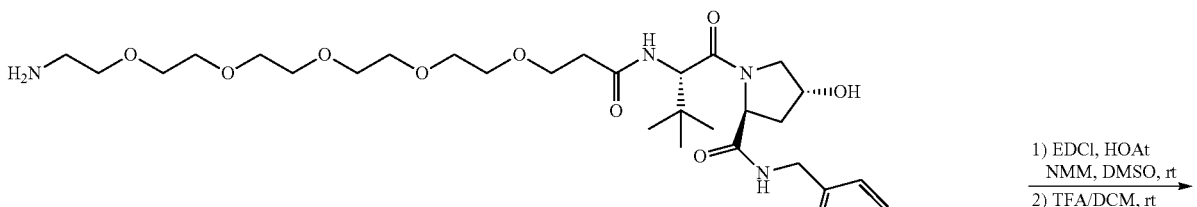

VHL-CH$_2$CH$_2$-PEG5-NH$_2$

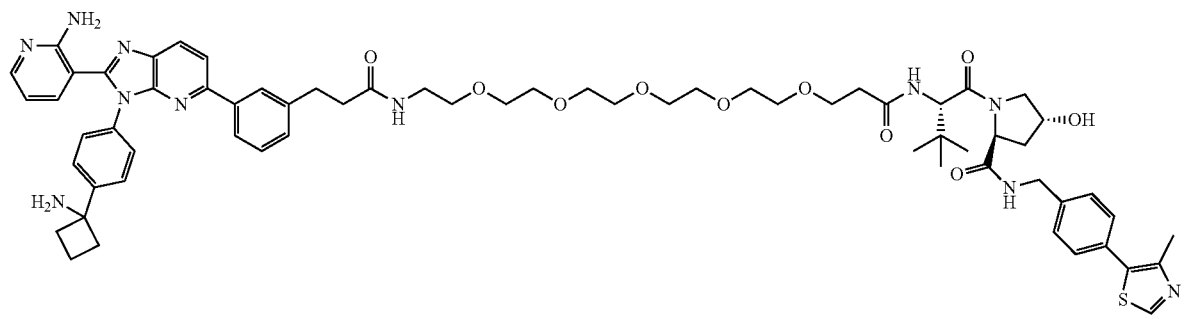

XF067-8

XF067-8 was synthesized following the standard procedure for preparing XF067-1 from intermediate 8 (12 mg, 0.02 mmol), VHL-CH$_2$CH$_2$PEG5-NH$_2$ (18.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-8 was obtained as white solid in TFA salt form (13.9 mg, 58%). $^1$H NMR (800 MHz, CD$_3$OD) δ 8.91 (s, 1H), 8.32 (d, J=8.4 Hz, 1H), 8.04 (d, J=8.0 Hz, 2H), 7.92 (s, 1H), 7.89 (d, J=7.8 Hz, 1H), 7.83 (dd, J=12.5, 7.9 Hz, 3H), 7.73 (d, J=8.0 Hz, 2H), 7.48 (d, J=7.8 Hz, 2H), 7.42 (d, J=7.8 Hz, 2H), 7.38 (t, J=7.7 Hz, 1H), 7.30 (d, J=7.5 Hz, 1H), 6.83 (t, J=6.9 Hz, 1H), 4.66 (s, 1H), 4.63-4.53 (m, 2H), 4.51 (s, 1H), 4.37 (d, J=15.4 Hz, 1H), 3.90 (d, J=10.9 Hz, 1H), 3.81 (dd, J=11.1, 4.1 Hz, 1H), 3.72 (dtt, J=21.3, 10.3, 5.4 Hz, 2H), 3.59 (ddt, J=15.3, 10.8, 4.4 Hz, 12H), 3.52 (t, J=4.6 Hz, 2H), 3.44 (t, J=4.6 Hz, 2H), 3.39 (t, J=5.5 Hz, 2H), 3.27 (t, J=5.5 Hz, 2H), 3.00 (t, J=7.6 Hz, 2H), 2.95-2.88 (m, 2H), 2.78-2.69 (m, 2H), 2.60-2.51 (m, 3H), 2.51-2.41 (m, 4H), 2.34 (dq, J=13.7, 7.8, 5.9 Hz, 1H), 2.24 (dd, J=13.1, 7.7 Hz, 1H), 2.13-2.03 (m, 2H), 1.04 (s, 9H). ESI-MS (m/z) [M+H]$^+$: 1208.5948.

Example 84

Synthesis of XF067-9

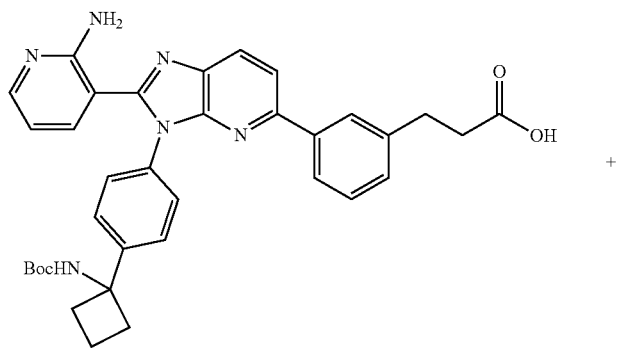

Intermediate 8

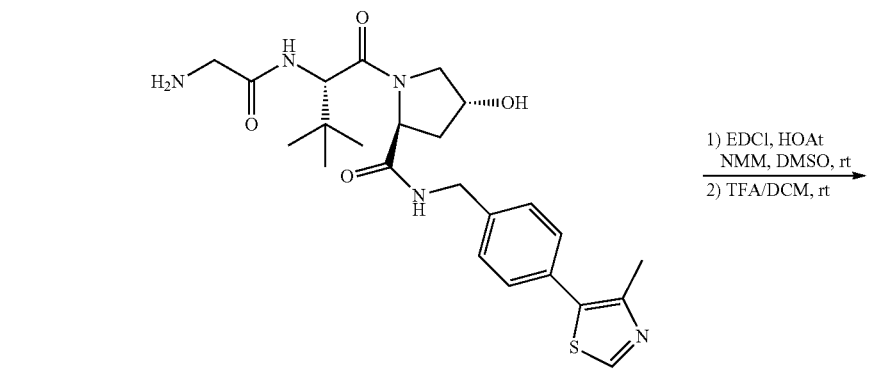

VHL-C1-NH$_2$

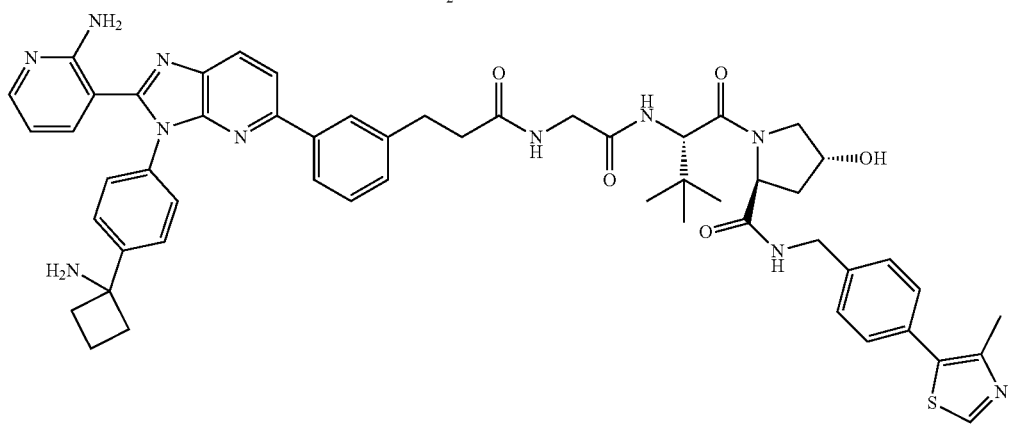

XF067-9

XF067-9 was synthesized following the standard procedure for preparing XF067-1 from intermediate 8 (12 mg, 0.02 mmol), VHL-C1-NH$_2$ (14.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-9 was obtained as white solid in TFA salt form (11.7 mg, 60%). $^1$H NMR (800 MHz, CD$_3$OD) δ 8.88 (s, 1H), 8.30 (d, J=8.4 Hz, 1H), 8.07-7.98 (m, 2H), 7.92 (s, 1H), 7.87 (d, J=7.8 Hz, 1H), 7.83-7.80 (m, 3H), 7.73 (s, 2H), 7.48 (d, J=7.9 Hz, 2H), 7.41 (d, J=7.8 Hz, 2H), 7.36 (t, J=7.6 Hz, 1H), 7.31 (d, J=7.5 Hz, 1H), 6.83 (t, J=6.9 Hz, 1H), 4.64 (s, 1H), 4.61-4.53 (m, 2H), 4.52 (d, J=4.4 Hz, 1H), 4.36 (d, J=15.4 Hz, 1H), 3.89-3.79 (m, 4H), 3.03 (t, J=7.8 Hz, 2H), 2.91 (tt, J=9.3, 5.6 Hz, 2H), 2.72 (dq, J=14.3, 9.3, 7.6 Hz, 2H), 2.63 (t, J=7.8 Hz, 2H), 2.46 (s, 3H), 2.34 (dd, J=10.8, 6.3 Hz, 1H), 2.25 (dd, J=13.3, 7.6 Hz, 1H), 2.16-2.02 (m, 2H), 1.03 (s, 9H). ESI-MS (m/z) [M+H]$^+$: 974.4486.

Example 85

Synthesis of XF067-10

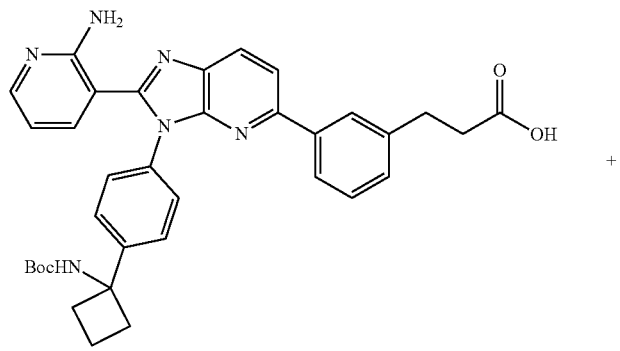

Intermediate 8

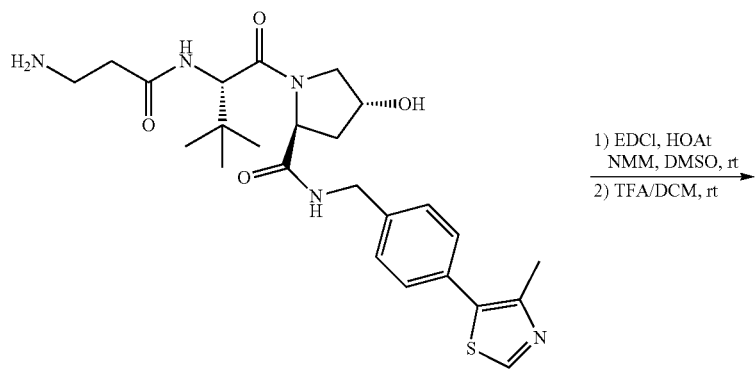

VHL-C2-NH$_2$

1) EDCl, HOAt NMM, DMSO, rt
2) TFA/DCM, rt

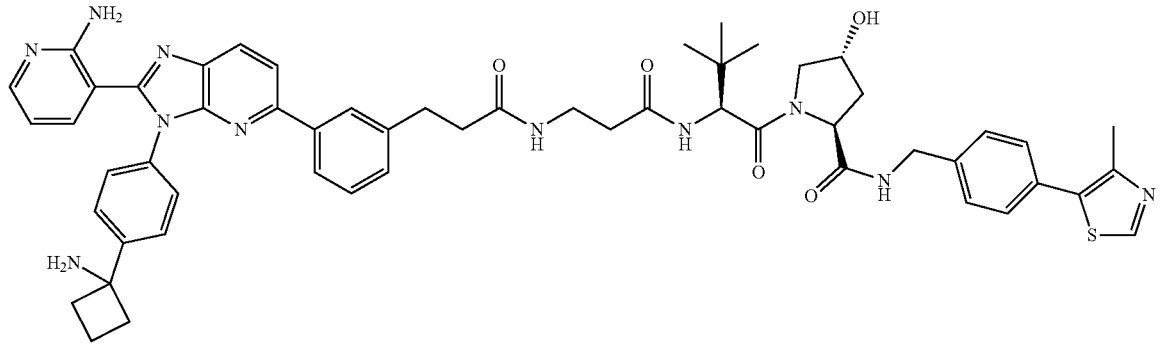

XF067-10

XF067-10 was synthesized following the standard procedure for preparing XF067-1 from intermediate 8 (12 mg, 0.02 mmol), VHL-C2-NH$_2$ (14.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-10 was obtained as white solid in TFA salt form (13.5 mg, 68%). $^1$H NMR (800 MHz, CD$_3$OD) δ 8.93 (s, 1H), 8.30 (d, J=8.4 Hz, 1H), 8.02 (dd, J=11.7, 7.3 Hz, 2H), 7.94-7.79 (m, 5H), 7.72 (d, J=8.0 Hz, 2H), 7.45 (d, J=7.9 Hz, 2H), 7.40 (d, J=7.9 Hz, 2H), 7.38-7.35 (m, 1H), 7.29 (d, J=7.6 Hz, 1H), 6.84 (t, J=6.9 Hz, 1H), 4.61-4.46 (m, 4H), 4.35 (d, J=15.4 Hz, 1H), 3.91 (d, J=10.9 Hz, 1H), 3.80 (dd, J=11.1, 4.1 Hz, 1H), 3.42-3.35 (m, 2H), 2.99 (t, J=7.6 Hz, 2H), 2.95-2.88 (m, 2H), 2.76-2.64 (m, 2H), 2.51 (t, J=7.6 Hz, 2H), 2.47 (s, 3H), 2.40-2.28 (m, 3H), 2.23 (dd, J=13.3, 7.5 Hz, 1H), 2.09 (tdd, J=17.2, 10.8, 6.6 Hz, 2H), 1.01 (s, 9H). ESI-MS (m/z) [M+H]$^+$: 988.4638.

Example 86

Synthesis of XF067-11

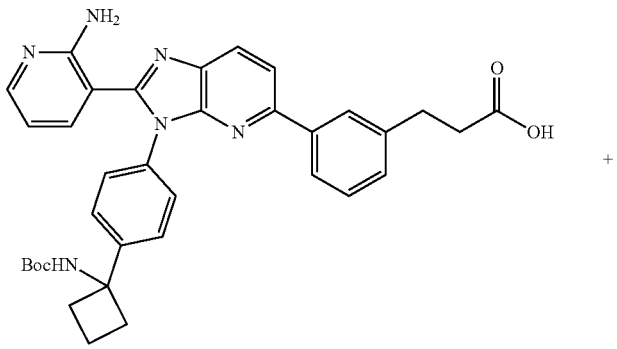

Intermediate 8

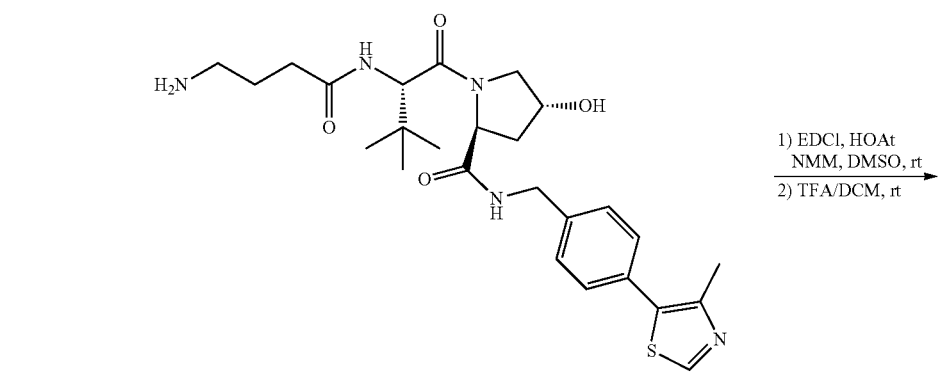

VHL-C3-NH$_2$

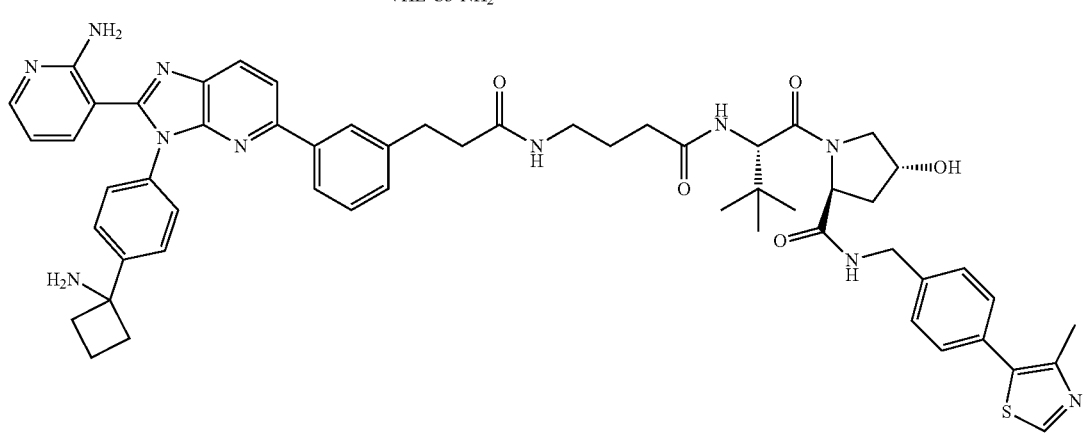

XF067-11

XF067-11 was synthesized following the standard procedure for preparing XF067-1 from intermediate 8 (12 mg, 0.02 mmol), VHL-C3-NH$_2$ (14.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-11 was obtained as white solid in TFA salt form (13.8 mg, 69%). $^1$H NMR (800 MHz, CD$_3$OD) δ 8.94 (s, 1H), 8.31 (d, J=8.4 Hz, 1H), 8.03 (dd, J=11.1, 7.1 Hz, 2H), 7.92 (s, 1H), 7.88 (d, J=7.8 Hz, 1H), 7.85 (d, J=7.7 Hz, 1H), 7.81 (d, J=8.1 Hz, 2H), 7.73 (d, J=8.1 Hz, 2H), 7.48 (d, J=7.8 Hz, 2H), 7.42 (d, J=7.9 Hz, 2H), 7.37 (q, J=7.9 Hz, 1H), 7.30 (d, J=7.7 Hz, 1H), 6.84 (t, J=7.0 Hz, 1H), 4.60-4.56 (m, 2H), 4.55 (s, 1H), 4.52 (d, J=3.2 Hz, 1H), 4.37 (d, J=15.4 Hz, 1H), 3.90 (d, J=10.9 Hz, 1H), 3.81 (dd, J=11.1, 4.1 Hz, 1H), 3.16-3.10 (m, 2H), 3.02-2.98 (m, 2H), 2.94-2.89 (m, 2H), 2.72 (td, J=14.3, 11.7, 7.2 Hz, 2H), 2.53 (t, J=7.5 Hz, 2H), 2.48 (s, 3H), 2.39-2.29 (m, 1H), 2.28-2.21 (m, 1H), 2.17-2.02 (m, 4H), 1.73-1.64 (m, 2H), 1.03 (s, 9H). ESI-MS (m/z) [M+H]$^+$: 1002.4804.

Example 87

Synthesis of XF067-12

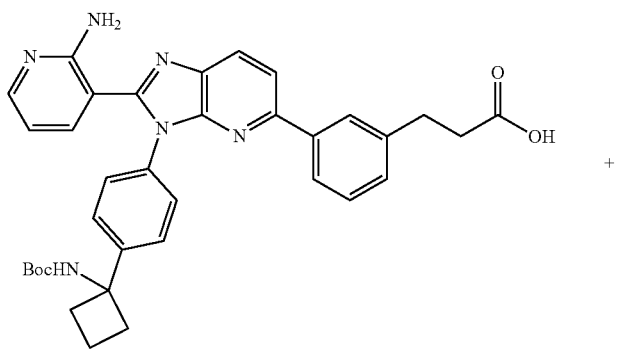

Intermediate 8

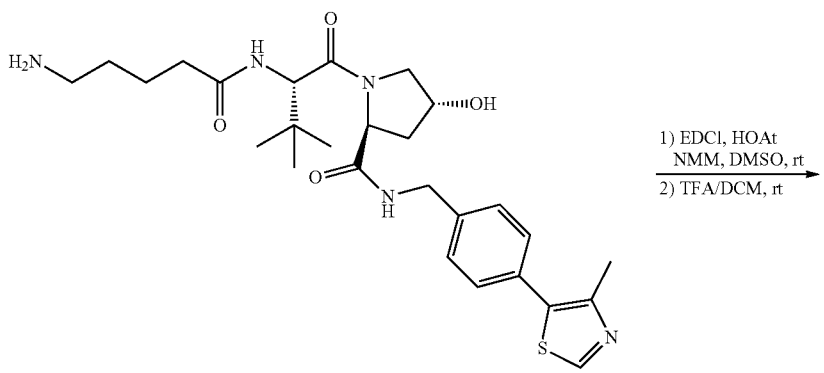

VHL-C4-NH$_2$

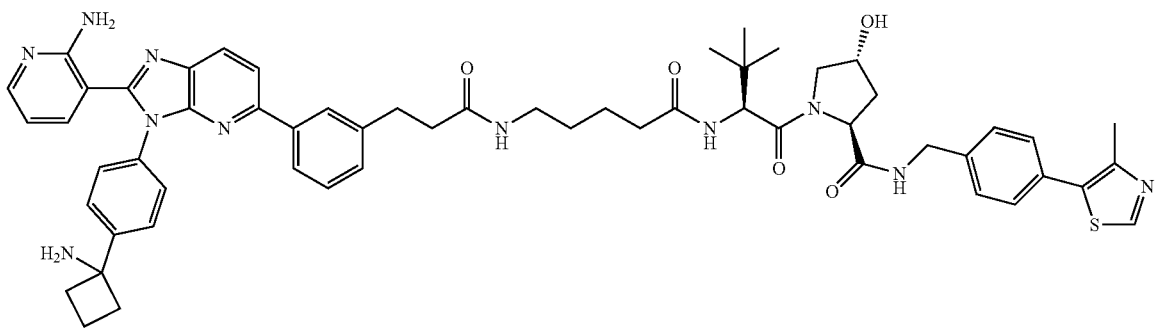

XF067-12

XF067-12 was synthesized following the standard procedure for preparing XF067-1 from intermediate 8 (12 mg, 0.02 mmol), VHL-C4-NH₂ (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-12 was obtained as white solid in TFA salt form (15.5 mg, 76%). ¹H NMR (800 MHz, CD₃OD) δ 8.93 (s, 1H), 8.32 (d, J=8.4 Hz, 1H), 8.03 (dd, J=8.4, 4.5 Hz, 2H), 7.92 (s, 1H), 7.88 (d, J=8.0 Hz, 1H), 7.85 (d, J=7.5 Hz, 1H), 7.81 (d, J=8.0 Hz, 2H), 7.77-7.67 (m, 2H), 7.47 (d, J=7.8 Hz, 2H), 7.44-7.33 (m, 3H), 7.32-7.25 (m, 1H), 6.84 (t, J=7.0 Hz, 1H), 4.60 (s, 1H), 4.60-4.49 (m, 3H), 4.37 (d, J=15.4 Hz, 1H), 3.90 (d, J=10.9 Hz, 1H), 3.81 (dd, J=11.1, 4.1 Hz, 1H), 3.11 (t, J=6.9 Hz, 2H), 3.00 (t, J=7.5 Hz, 2H), 2.92 (dt, J=14.5, 8.6 Hz, 2H), 2.72 (dt, J=13.2, 8.0 Hz, 2H), 2.56-2.50 (m, 2H), 2.48 (s, 3H), 2.37-2.30 (m, 1H), 2.26-2.21 (m, 1H), 2.19-2.14 (m, 1H), 2.13-2.05 (m, 2H), 1.50-1.41 (m, 2H), 1.40-1.32 (m, 2H), 1.03 (s, 9H). ESI-MS (m/z) [M+H]⁺: 1016.4976.

Example 88

Synthesis of XF067-13

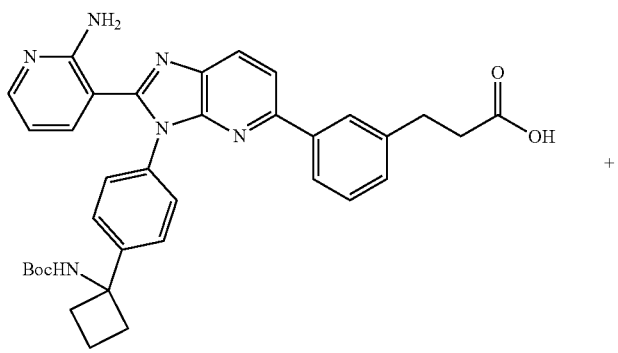

Intermediate 8

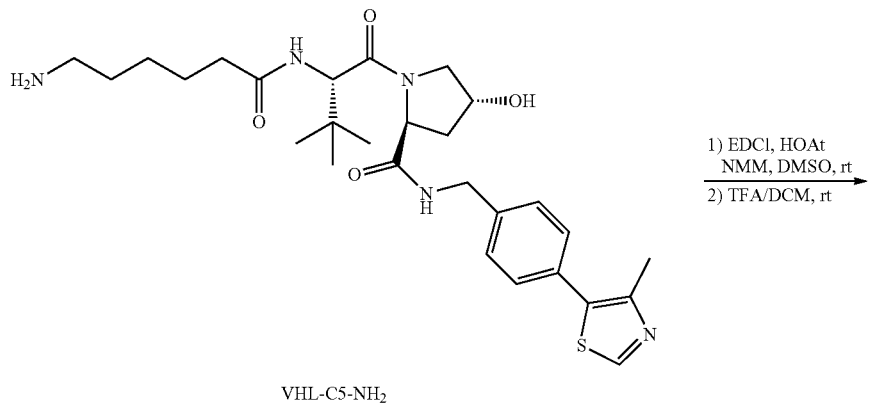

VHL-C5-NH₂

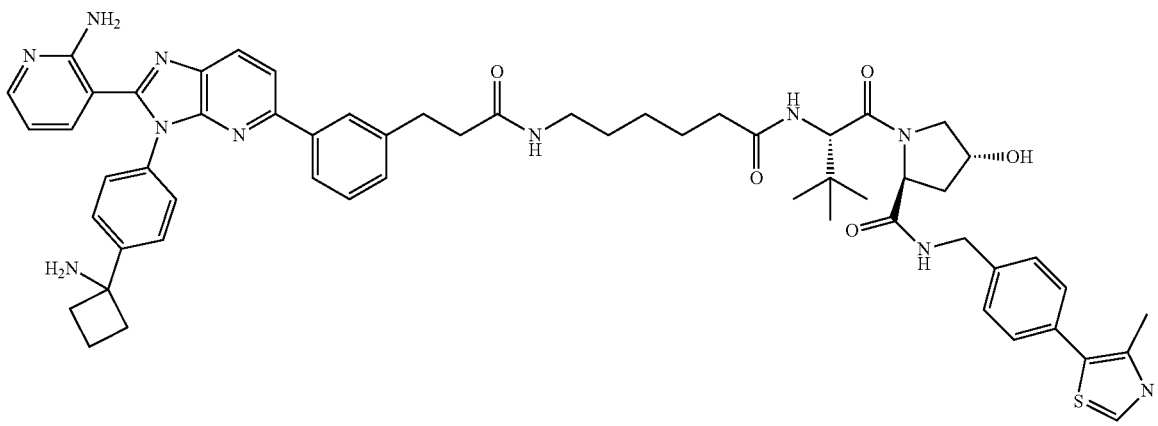

XF067-13

XF067-13 was synthesized following the standard procedure or preparing XF067-1 from intermediate 8 (12 mg, 0.02 mmol), VHL-C5-NH$_2$ (11.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-13 was obtained as white solid in TFA salt form (13.6 mg, 66%). $^1$H NMR (800 MHz, CD$_3$OD) δ 8.97 (s, 1H), 8.31 (d, J=8.4 Hz, 1H), 8.03 (t, J=6.8 Hz, 2H), 7.92 (s, 1H), 7.88 (dd, J=18.0, 7.8 Hz, 2H), 7.83-7.79 (m, 2H), 7.74 (d, J=8.1 Hz, 2H), 7.48 (d, J=7.8 Hz, 2H), 7.43 (d, J=7.8 Hz, 2H), 7.38 (t, J=7.7 Hz, 1H), 7.30 (d, J=7.6 Hz, 1H), 6.85 (t, J=7.0 Hz, 1H), 4.62 (s, 1H), 4.61-4.57 (m, 1H), 4.55 (d, J=15.4 Hz, 1H), 4.52 (s, 1H), 4.38 (d, J=15.4 Hz, 1H), 3.91 (d, J=10.9 Hz, 1H), 3.81 (dd, J=11.1, 4.1 Hz, 1H), 3.09 (td, J=7.5, 2.5 Hz, 2H), 2.99 (t, J=7.5 Hz, 2H), 2.92 (ddd, J=14.7, 11.9, 7.2 Hz, 2H), 2.77-2.69 (m, 2H), 2.52 (d, J=7.5 Hz, 2H), 2.48 (s, 3H), 2.39-2.30 (m, 1H), 2.24 (dd, J=13.4, 7.6 Hz, 1H), 2.19-2.16 (m, 1H), 2.15-2.01 (m, 3H), 1.46 (dp, J=15.1, 7.1 Hz, 2H), 1.35 (p, J=7.5 Hz, 2H), 1.20-1.14 (m, 2H), 1.03 (s, 9H). ESI-MS (m/z) [M+H]$^+$: 1030.5111.

Example 89

Synthesis of XF067-14

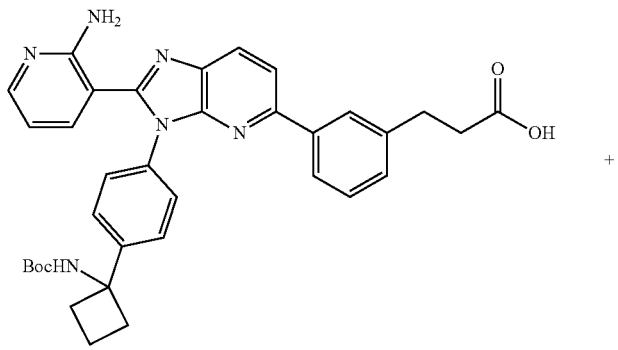

Intermediate 8

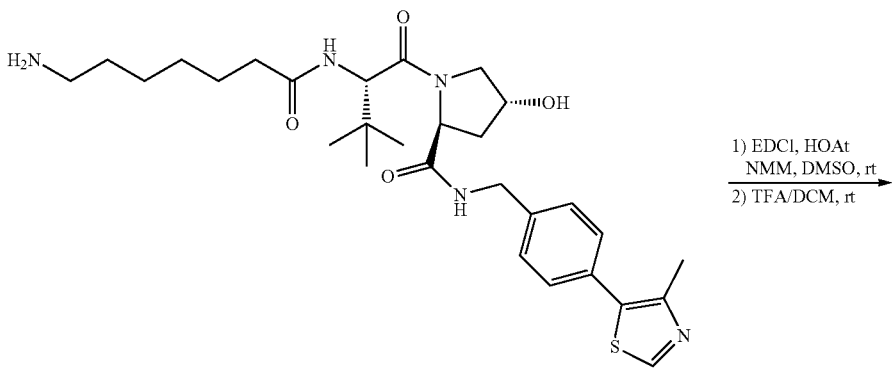

VHL-C6-NH$_2$

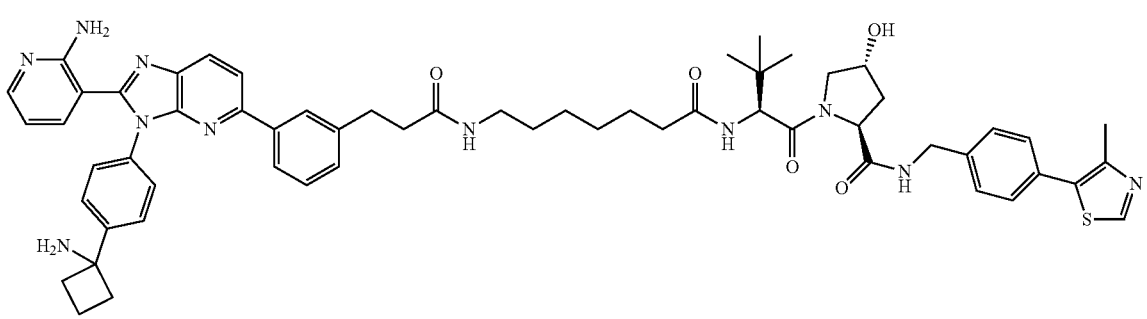

XF067-14

XF067-14 was synthesized following the standard procedure for preparing XF067-1 from intermediate 8 (12 mg, 0.02 mmol), VHL-C6-NH$_2$ (11.8 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-14 was obtained as white solid in TFA salt form (8.4 mg, 40%). $^1$H NMR (800 MHz, CD$_3$OD) δ 8.95 (s, 1H), 8.32 (d, J=8.3 Hz, 1H), 8.04 (q, J=3.7 Hz, 2H), 7.93-7.87 (m, 2H), 7.86 (d, J=7.6 Hz, 1H), 7.82 (d, J=8.0 Hz, 2H), 7.74 (d, J=8.0 Hz, 2H), 7.48 (d, J=7.8 Hz, 2H), 7.43 (d, J=7.8 Hz, 2H), 7.41-7.35 (m, 1H), 7.29 (d, J=7.5 Hz, 1H), 6.85 (t, J=6.9 Hz, 1H), 4.63 (s, 1H), 4.60 (t, J=8.0 Hz, 1H), 4.57-4.49 (m, 2H), 4.38 (d, J=15.4 Hz, 1H), 3.92 (d, J=10.9 Hz, 1H), 3.82 (dd, J=11.1, 4.1 Hz, 1H), 3.08 (t, J=7.1 Hz, 2H), 2.99 (t, J=7.5 Hz, 2H), 2.92 (dt, J=14.6, 8.3 Hz, 2H), 2.76-2.67 (m, 2H), 2.52 (d, J=7.5 Hz, 2H), 2.48 (s, 3H), 2.34 (tq, J=16.4, 10.0, 7.7 Hz, 1H), 2.28-2.03 (m, 5H), 1.53-1.44 (m, 2H), 1.34 (p, J=7.1 Hz, 2H), 1.21-1.12 (m, 4H), 1.04 (s, 9H). ESI-MS (m/z) [M+H]$^+$: 1044.5284.

Example 90

Synthesis of XF067-15

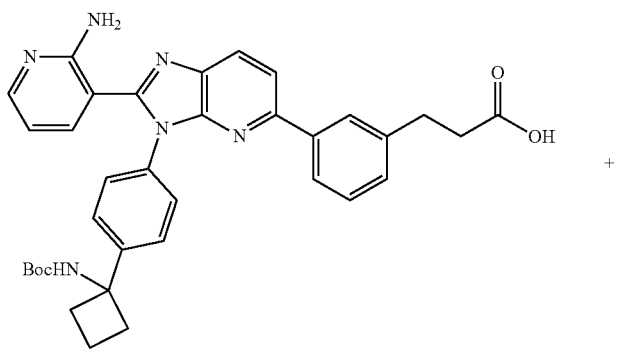

Intermediate 8

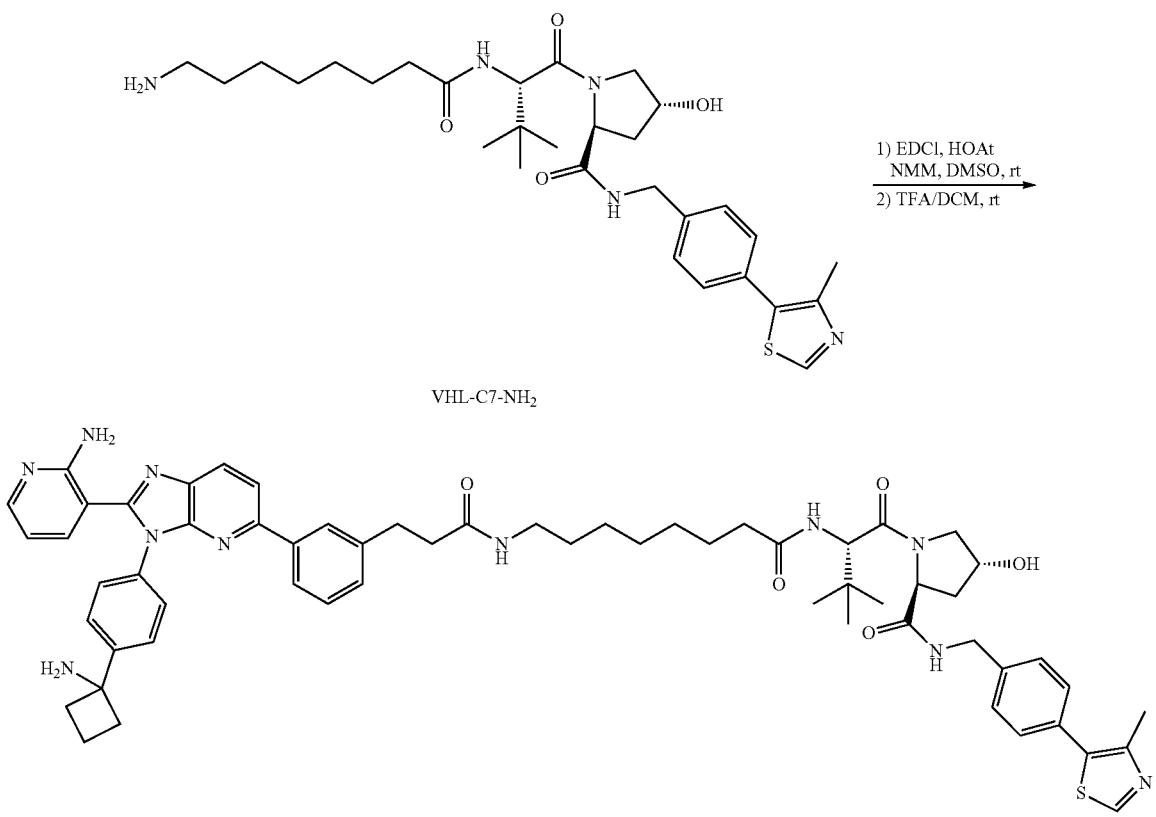

XF067-15

XF067-15 was synthesized following the standard procedure for preparing XF067-1 from intermediate 8 (12 mg, 0.02 mmol), VHL-C7-NH₂ (16 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-15 was obtained as white solid in TFA salt form (9.6 mg, 45%). ¹H NMR (800 MHz, CD₃OD) δ 8.96 (s, 1H), 8.32 (d, J=8.3 Hz, 1H), 8.07-8.00 (m, 2H), 7.92 (s, 1H), 7.89 (d, J=7.8 Hz, 1H), 7.86 (d, J=7.6 Hz, 1H), 7.82 (d, J=8.0 Hz, 2H), 7.73 (d, J=8.1 Hz, 2H), 7.48 (d, J=7.8 Hz, 2H), 7.43 (d, J=7.8 Hz, 2H), 7.37 (t, J=7.7 Hz, 1H), 7.29 (d, J=7.6 Hz, 1H), 6.84 (t, J=6.9 Hz, 1H), 4.64 (s, 1H), 4.59 (t, J=8.3 Hz, 1H), 4.56 (d, J=15.4 Hz, 1H), 4.52 (d, J=4.2 Hz, 1H), 4.38 (d, J=15.4 Hz, 1H), 3.91 (d, J=11.0 Hz, 1H), 3.82 (dd, J=11.1, 4.1 Hz, 1H), 3.08 (q, J=6.7 Hz, 2H), 2.99 (t, J=7.4 Hz, 2H), 2.92 (tt, J=9.3, 5.8 Hz, 2H), 2.75-2.68 (m, 2H), 2.52 (t, J=7.4 Hz, 2H), 2.49 (s, 3H), 2.37-2.31 (m, 1H), 2.28-2.21 (m, 2H), 2.18 (dt, J=14.6, 7.5 Hz, 1H), 2.14-2.04 (m, 2H), 1.57-1.45 (m, 2H), 1.33 (p, J=7.1 Hz, 2H), 1.24-1.09 (m, 6H), 1.04 (s, 9H). ESI-MS (m/z) [M+H]⁺: 1058.5425.

Example 91

Synthesis of XF067-16

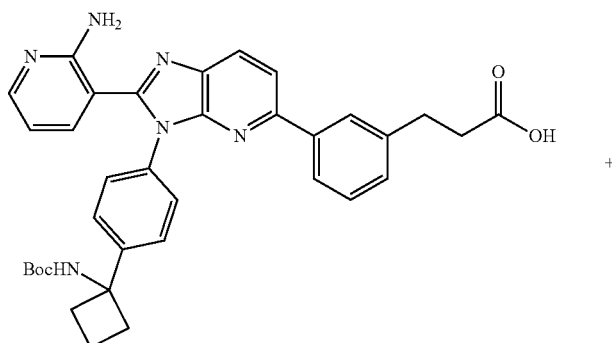

Intermediate 8

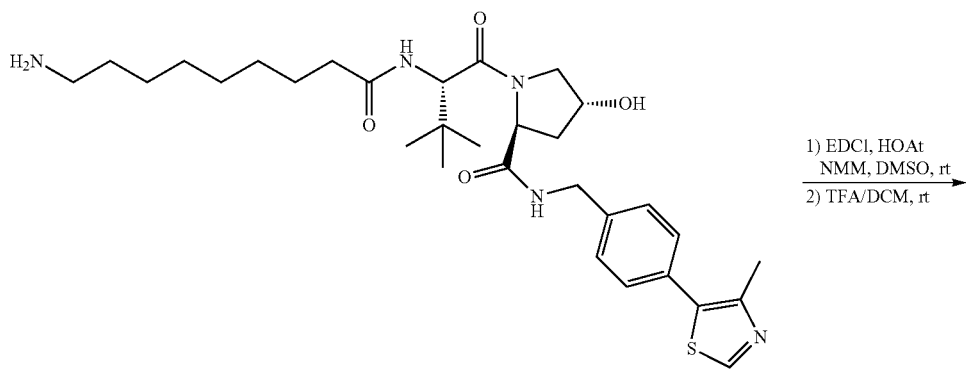

VHL-C8-NH₂

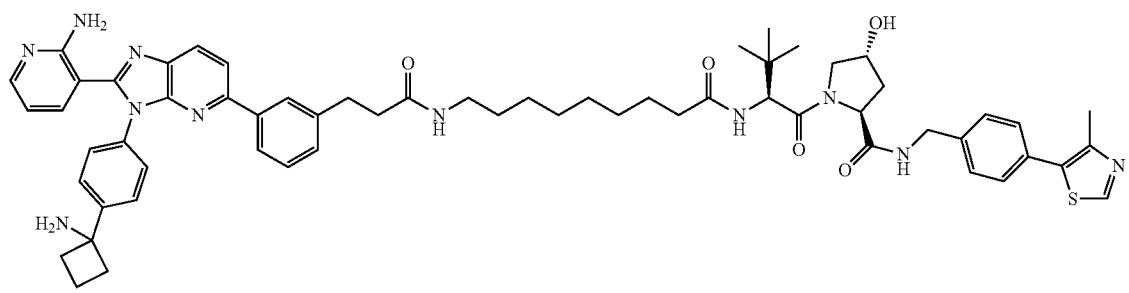

XF067-16

XF067-16 was synthesized following the standard procedure for preparing XF067-1 from intermediate 8 (12 mg, 0.02 mmol), VHL-C8-NH₂ (12.4 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-16 was obtained as white solid in TFA salt form (8.6 mg, 40%). ¹H NMR (800 MHz, CD₃OD) δ 8.92 (s, 1H), 8.32 (d, J=8.4 Hz, 1H), 8.07-8.00 (m, 2H), 7.92 (s, 1H), 7.89 (d, J=7.7 Hz, 1H), 7.83 (dd, J=14.8, 7.8 Hz, 3H), 7.77-7.69 (m, 2H), 7.48 (d, J=7.8 Hz, 2H), 7.43 (d, J=7.8 Hz, 2H), 7.37 (t, J=7.7 Hz, 1H), 7.29 (d, J=7.6 Hz, 1H), 6.83 (t, J=6.9 Hz, 1H), 4.65 (s, 1H), 4.60 (t, J=8.1 Hz, 1H), 4.57-4.50 (m, 2H), 4.38 (d, J=15.4 Hz, 1H), 3.92 (d, J=10.9 Hz, 1H), 3.82 (dd, J=11.1, 4.1 Hz, 1H), 3.08 (t, J=7.1 Hz, 2H), 2.99 (t, J=7.4 Hz, 2H), 2.92 (dt, J=14.6, 6.1 Hz, 2H), 2.76-2.67 (m, 2H), 2.52 (t, J=7.6 Hz, 2H), 2.48 (s, 3H), 2.34 (tqd, J=10.8, 6.8, 3.3 Hz, 1H), 2.23 (ddq, J=29.7, 14.6, 7.3 Hz, 3H), 2.10 (dddd, J=23.5, 17.8, 10.5, 5.8 Hz, 2H), 1.54 (qq, J=13.9, 7.0 Hz, 2H), 1.32 (dp, J=13.9, 7.1 Hz, 2H), 1.27-1.09 (m, 8H), 1.05 (s, 9H). ESI-MS (m/z) [M+H]⁺: 1072.5598.

Example 92

Synthesis of XF067-17

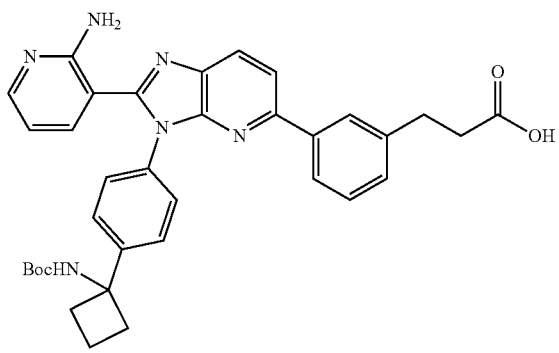

Intermediate 8

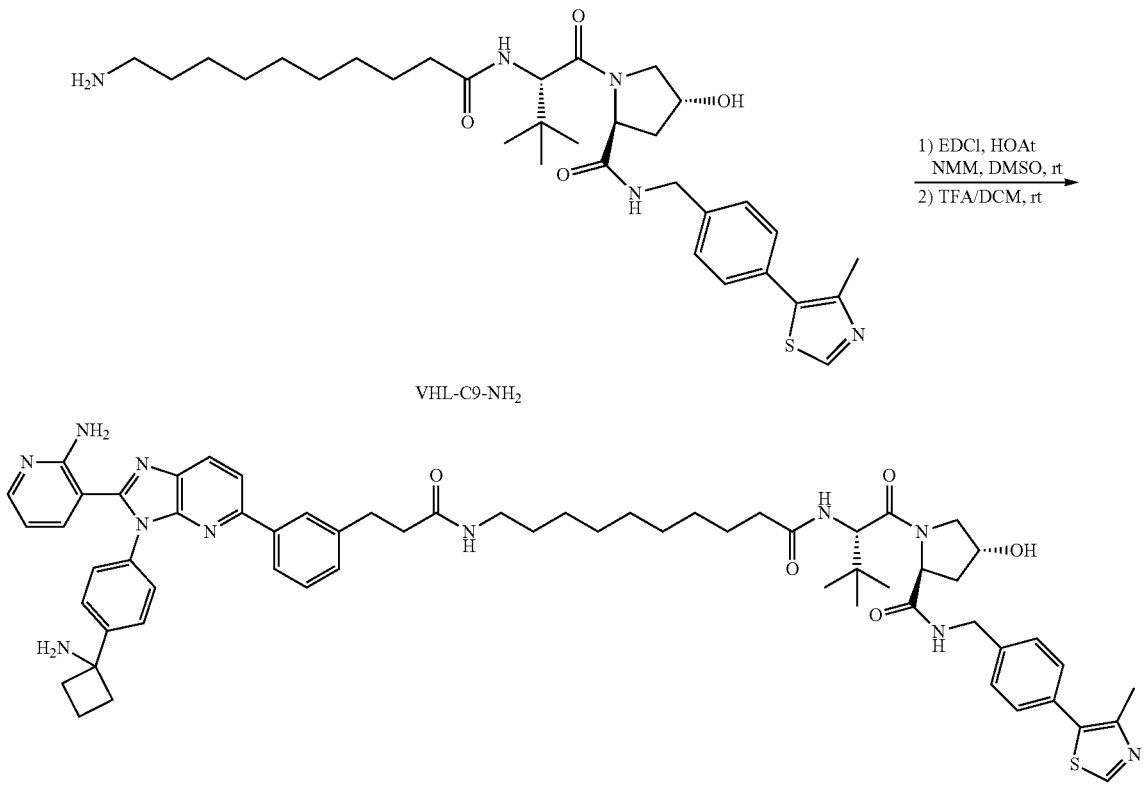

XF067-17 was synthesized following the standard procedure for preparing XF067-1 from intermediate 8 (12 mg, 0.02 mmol), VHL-C9-NH$_2$ (16.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-17 was obtained as white solid in TFA salt form (7.3 mg, 34%). $^1$H NMR (800 MHz, CD$_3$OD) δ 8.92 (s, 1H), 8.32 (d, J=8.3 Hz, 1H), 8.09-8.00 (m, 2H), 7.92 (s, 1H), 7.89 (d, J=7.8 Hz, 1H), 7.82 (t, J=7.9 Hz, 3H), 7.73 (d, J=8.1 Hz, 2H), 7.48 (d, J=7.8 Hz, 2H), 7.43 (d, J=7.9 Hz, 2H), 7.37 (t, J=7.7 Hz, 1H), 7.30 (d, J=7.4 Hz, 1H), 6.83 (t, J=6.9 Hz, 1H), 4.65 (s, 1H), 4.62-4.51 (m, 3H), 4.38 (d, J=15.4 Hz, 1H), 3.92 (d, J=10.9 Hz, 1H), 3.83 (dd, J=11.1, 4.1 Hz, 1H), 3.08 (t, J=7.1 Hz, 2H), 2.99 (t, J=7.5 Hz, 2H), 2.92 (q, J=9.8, 7.7 Hz, 2H), 2.72 (dt, J=14.0, 8.5 Hz, 2H), 2.54-2.46 (m, 5H), 2.38-2.31 (m, 1H), 2.30-2.18 (m, 3H), 2.15-2.02 (m, 2H), 1.56 (ddq, J=20.4, 13.5, 6.8 Hz, 2H), 1.32 (t, J=7.1 Hz, 2H), 1.29-1.23 (m, 2H), 1.23-1.19 (m, 2H), 1.18-1.14 (m, 2H), 1.14-1.11 (m, 4H), 1.06 (s, 9H). ESI-MS (m/z) [M+H]$^+$: 1086.5721.

Example 93

Synthesis of XFF067-18

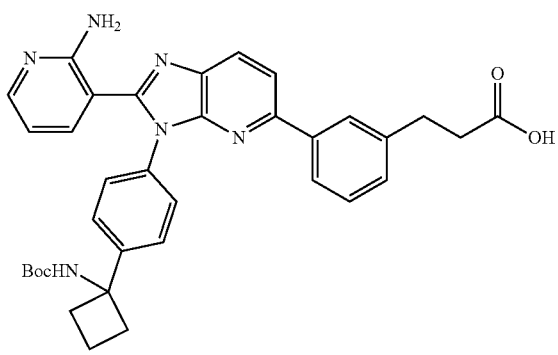

Intermediate 8

+

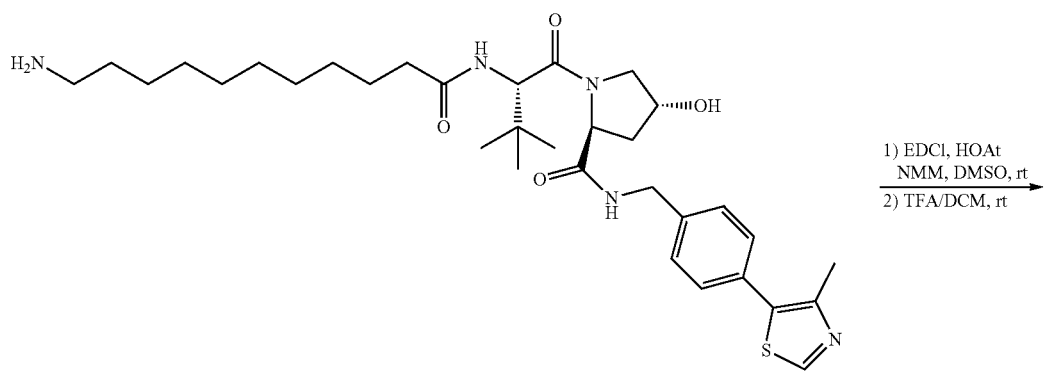

VHL-C10-NH$_2$

1) EDCI, HOAt NMM, DMSO, rt
2) TFA/DCM, rt

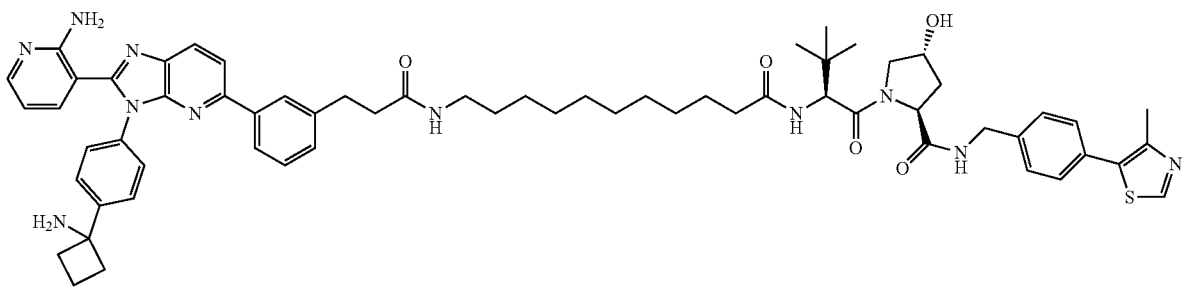

XF067-18

XF067-18 was synthesized following the standard procedure for preparing XF067-1 from intermediate 8 (12 mg, 0.02 mmol), VHL-C10-NH$_2$ (16.5 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-18 was obtained as white solid in TFA salt form (8.7 mg, 37%). $^1$H NMR (800 MHz, CD$_3$OD) δ 8.92 (s, 1H), 8.31 (d, J=8.3 Hz, 1H), 8.05-8.01 (m, 2H), 7.93 (s, 1H), 7.89 (d, J=7.7 Hz, 1H), 7.82 (t, J=6.9 Hz, 3H), 7.75-7.68 (m, 2H), 7.48 (d, J=7.9 Hz, 2H), 7.43 (d, J=7.9 Hz, 2H), 7.37 (t, J=7.6 Hz, 1H), 7.30 (d, J=7.4 Hz, 1H), 6.83 (t, J=6.9 Hz, 1H), 4.65 (s, 1H), 4.62-4.58 (m, 1H), 4.56 (d, J=15.5 Hz, 1H), 4.52 (d, J=3.8 Hz, 1H), 4.41-4.35 (m, 1H), 3.92 (d, J=10.9 Hz, 1H), 3.85-3.79 (m, 1H), 3.08 (t, J=7.1 Hz, 2H), 3.00 (t, J=7.5 Hz, 2H), 2.92 (tt, J=9.4, 5.6 Hz, 2H), 2.77-2.68 (m, 2H), 2.52 (t, J=7.5 Hz, 2H), 2.49 (s, 3H), 2.35 (tt, J=10.8, 5.8 Hz, 1H), 2.29 (dt, J=14.9, 7.7 Hz, 1H), 2.24 (dt, J=14.8, 7.8 Hz, 2H), 2.14-2.02 (m, 2H), 1.64-1.52 (m, 2H), 1.37-1.23 (m, 6H), 1.22-1.10 (m, 8H), 1.05 (s, 9H). ESI-MS (m/z) [M+H]$^+$: 1110.5912.

Example 94

Synthesis of XF067-19

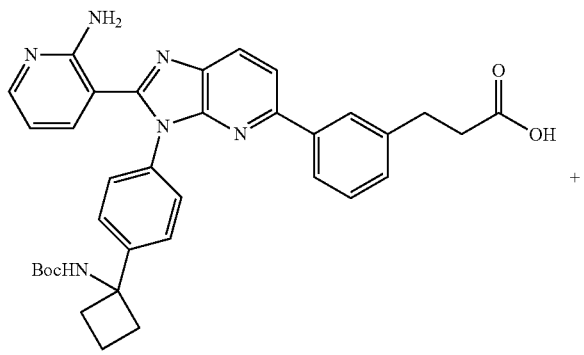

Intermediate 8

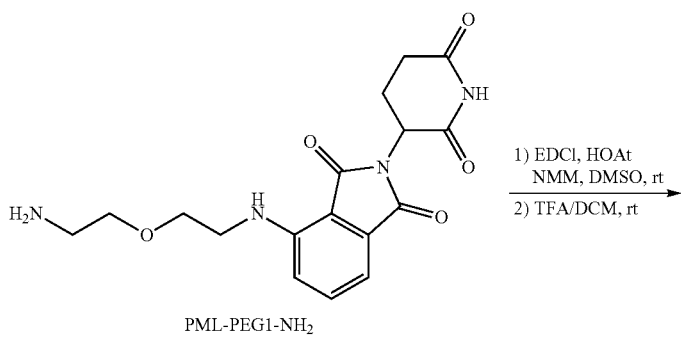

PML-PEG1-NH$_2$

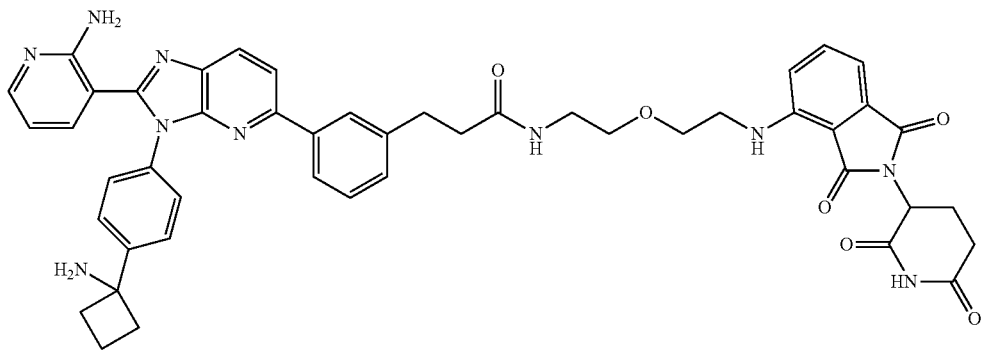

XF067-19

XF067-19 was synthesized following the standard procedure for preparing XF067-1 from intermediate 8 (12 mg, 0.02 mmol), PML-PEG1-NH$_2$ (9.4 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-19 was obtained as yellow solid in TFA salt form (10.9 mg, 64%). $^1$H NMR (800 MHz, CD$_3$OD) δ 8.22 (d, J=8.4 Hz, 1H), 8.03 (d, J=6.2 Hz, 1H), 8.02-7.96 (m, 1H), 7.92 (s, 1H), 7.86 (d, J=7.8 Hz, 1H), 7.79 (t, J=8.0 Hz, 3H), 7.77-7.67 (m, 2H), 7.45 (t, J=7.8 Hz, 1H), 7.32 (q, J=7.8 Hz, 1H), 7.27 (d, J=7.5 Hz, 1H), 6.98-6.93 (m, 1H), 6.88 (d, J=8.5 Hz, 1H), 6.82 (t, J=7.0 Hz, 1H), 4.93 (dd, J=21.3, 10.7, 7.4, 3.5 Hz, 1H), 3.48-3.37 (m, 3H), 3.35-3.32 (m, 1H), 3.33-3.23 (m, 2H), 3.27-3.25 (m, 2H), 3.01 (h, J=6.8 Hz, 2H), 2.90 (dt, J=14.1, 8.1 Hz, 2H), 2.70 (ddd, J=18.2, 13.5, 6.6 Hz, 3H), 2.67-2.53 (m, 4H), 2.32 (ddd, J=16.4, 10.8, 6.3 Hz, 1H), 2.07 (dp, J=16.5, 7.9 Hz, 1H), 1.96 (dd, J=12.5, 6.4 Hz, 1H). ESI-MS (m/z) [M+H]$^+$: 847.3668.

Example 95

Synthesis of XF067-20

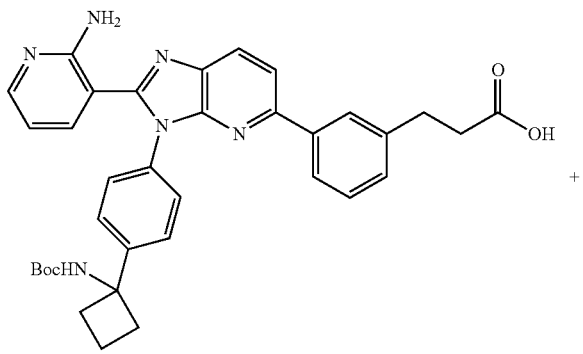

Intermediate 8

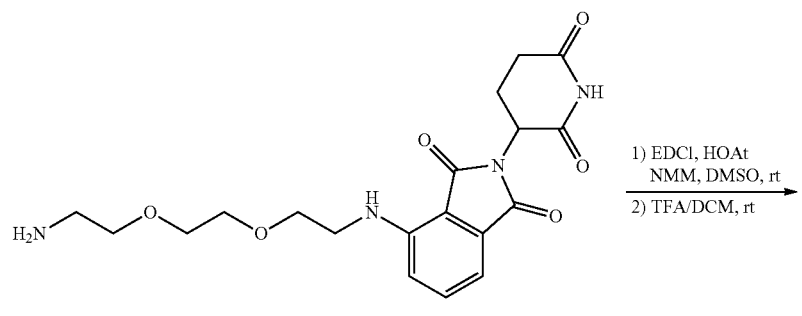

PML-PEG2-NH$_2$

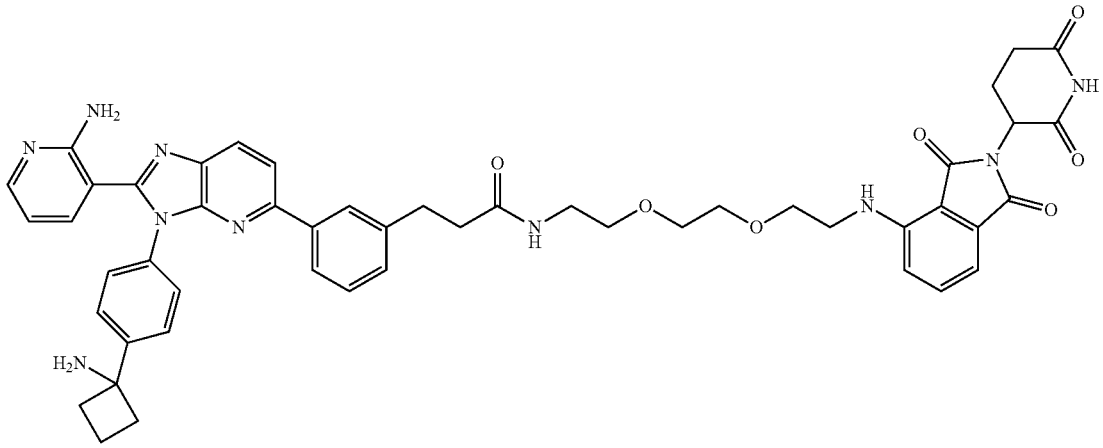

XF067-20

XF067-20 was synthesized following the standard procedure for preparing XF067-1 from intermediate 8 (12 mg, 0.02 mmol), PML-PEG2-NH₂ (10.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-20 was obtained as yellow solid in TFA salt form (13.4 mg, 75%). ¹H NMR (800 MHz, CD₃OD) δ 8.28 (d, J=8.4 Hz, 1H), 8.01 (dd, J=14.4, 7.2 Hz, 2H), 7.92-7.85 (m, 2H), 7.80 (t, J=7.8 Hz, 3H), 7.71 (d, J=8.0 Hz, 2H), 7.46 (t, J=7.8 Hz, 1H), 7.35 (t, J=7.7 Hz, 1H), 7.27 (d, J=7.5 Hz, 1H), 6.98 (t, J=8.3 Hz, 2H), 6.81 (t, J=6.9 Hz, 1H), 5.01 (dd, J=12.8, 5.4 Hz, 1H), 3.64 (t, J=5.2 Hz, 2H), 3.55 (t, J=4.4 Hz, 2H), 3.48 (t, J=4.5 Hz, 2H), 3.41 (dt, J=10.5, 5.4 Hz, 4H), 3.30 (q, J=5.8 Hz, 2H), 2.98 (t, J=7.5 Hz, 2H), 2.94-2.87 (m, 2H), 2.81 (ddd, J=18.1, 13.7, 5.3 Hz, 1H), 2.75-2.67 (m, 3H), 2.68-2.62 (m, 1H), 2.52 (t, J=7.5 Hz, 2H), 2.33 (qt, J=10.5, 6.4 Hz, 1H), 2.06 (ddq, J=18.7, 12.1, 6.9, 6.1 Hz, 2H). ESI-MS (m/z) [M+H]⁺: 891.3945.

Example 96

Synthesis of XF067-21

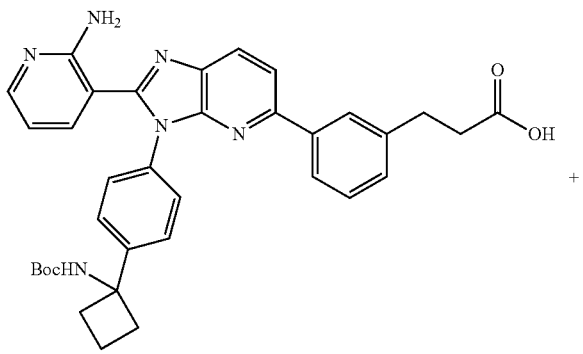

Intermediate 8

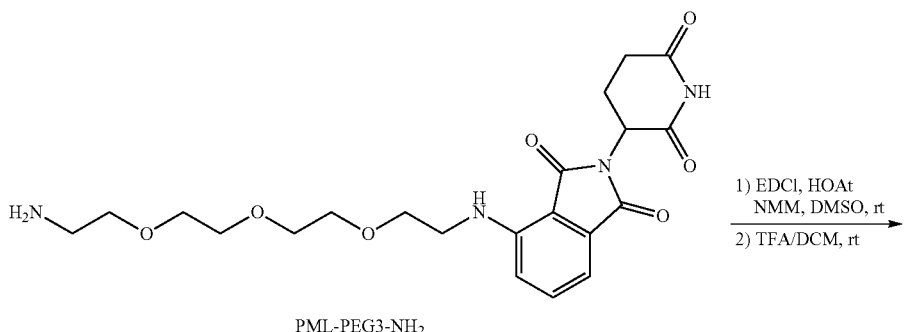

PML-PEG3-NH₂

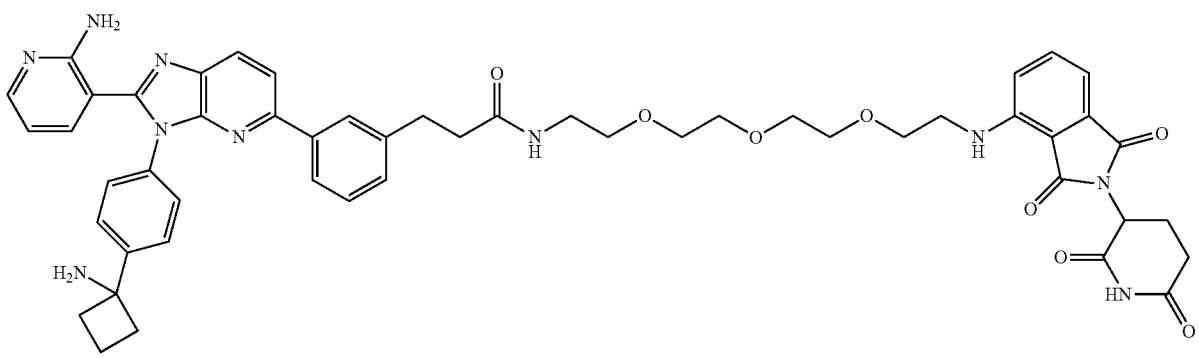

XF067-21

XF067-21 was synthesized following the standard procedure for preparing XF067-1 from intermediate 8 (12 mg, 0.02 mmol), PML-PEG3-NH$_2$ (11.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-21 was obtained as yellow solid in TFA salt form (11.9 mg, 64%). $^1$H NMR (800 MHz, CD$_3$OD) δ 8.28 (d, J=8.4 Hz, 1H), 8.02 (dd, J=14.8, 7.2 Hz, 2H), 7.90 (s, 1H), 7.87 (d, J=7.8 Hz, 1H), 7.81 (d, J=7.9 Hz, 3H), 7.71 (d, J=8.0 Hz, 2H), 7.47 (t, J=7.8 Hz, 1H), 7.36 (t, J=7.7 Hz, 1H), 7.28 (d, J=7.6 Hz, 1H), 7.07-6.94 (m, 2H), 6.81 (t, J=6.9 Hz, 1H), 5.01 (dd, J=12.7, 5.3 Hz, 1H), 3.66 (t, J=5.2 Hz, 2H), 3.62 (p, J=4.5, 3.8 Hz, 4H), 3.55 (t, J=4.5 Hz, 2H), 3.46 (t, J=4.5 Hz, 2H), 3.41 (dt, J=21.3, 5.3 Hz, 4H), 3.27 (t, J=5.4 Hz, 2H), 2.99 (t, J=7.6 Hz, 2H), 2.94-2.87 (m, 2H), 2.82 (ddd, J=18.2, 13.7, 5.3 Hz, 1H), 2.74-2.62 (m, 4H), 2.54 (t, J=7.6 Hz, 2H), 2.34 (qd, J=10.4, 5.3 Hz, 1H), 2.07 (ddt, J=17.7, 11.6, 6.9 Hz, 2H). ESI-MS (m/z) [M+H]$^+$: 935.4187.

Example 97

Synthesis of XF067-22

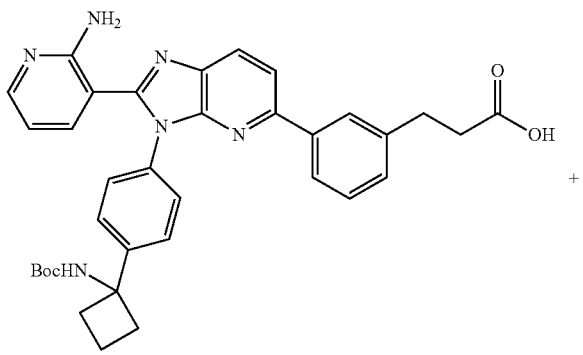

Intermediate 8

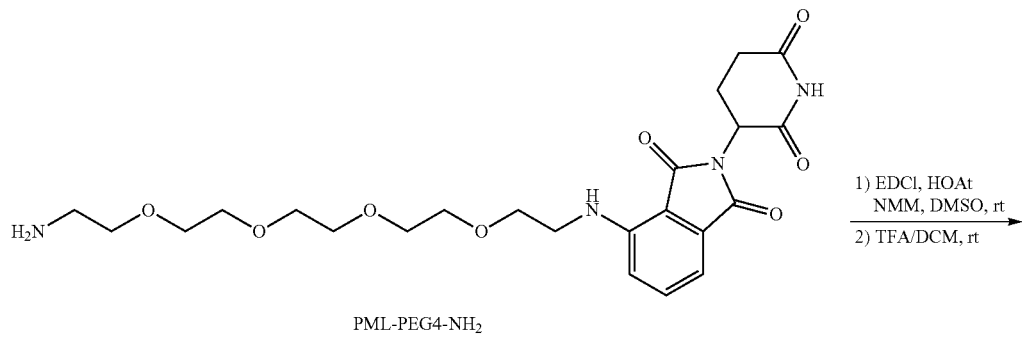

PML-PEG4-NH$_2$

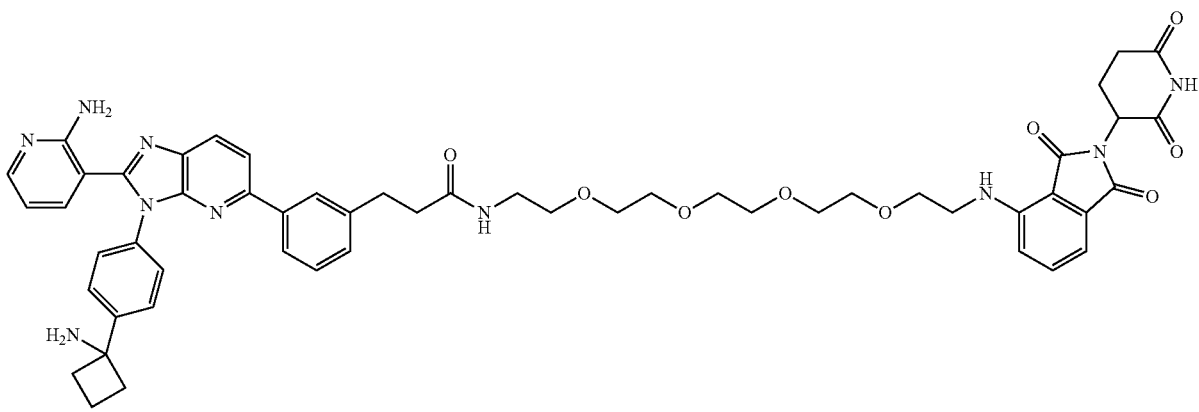

XF067-22

XF067-22 was synthesized following the standard procedure or preparing XF067-1 from intermediate 8 (12 mg, 0.02 mmol), PML-PEG4-NH$_2$ (11.3 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-22 was obtained as yellow solid in TFA salt form (9.5 mg, 49%). $^1$H NMR (800 MHz, CD$_3$OD) δ 8.29 (s, 1H), 8.02 (d, J=8.0 Hz, 2H), 7.91 (s, 1H), 7.87 (d, J=7.9 Hz, 1H), 7.79 (d, J=8.0 Hz, 2H), 7.71 (t, J=11.1 Hz, 3H), 7.49 (t, J=7.9 Hz, 1H), 7.37 (t, J=7.8 Hz, 1H), 7.29 (d, J=7.6 Hz, 1H), 7.04-6.99 (m, 2H), 6.76 (s, 1H), 5.01 (dd, J=12.6, 5.3 Hz, 1H), 3.71-3.59 (m, 8H), 3.59-3.56 (m, 2H), 3.52 (t, J=4.6 Hz, 2H), 3.43 (q, J=4.9 Hz, 4H), 3.38 (t, J=5.4 Hz, 2H), 3.27 (t, J=5.4 Hz, 2H), 2.99 (t, J=7.6 Hz, 2H), 2.91 (dd, J=13.1, 7.1 Hz, 2H), 2.86-2.78 (m, 1H), 2.73-2.65 (m, 4H), 2.54 (t, J=7.6 Hz, 2H), 2.33 (d, J=10.2 Hz, 1H), 2.10-2.03 (m, 2H). ESI-MS (m/z) [M+H]$^+$: 979.4463.

Example 98

Synthesis of XF067-23

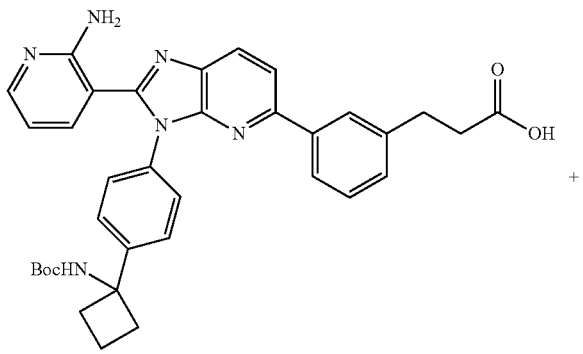

Intermediate 8

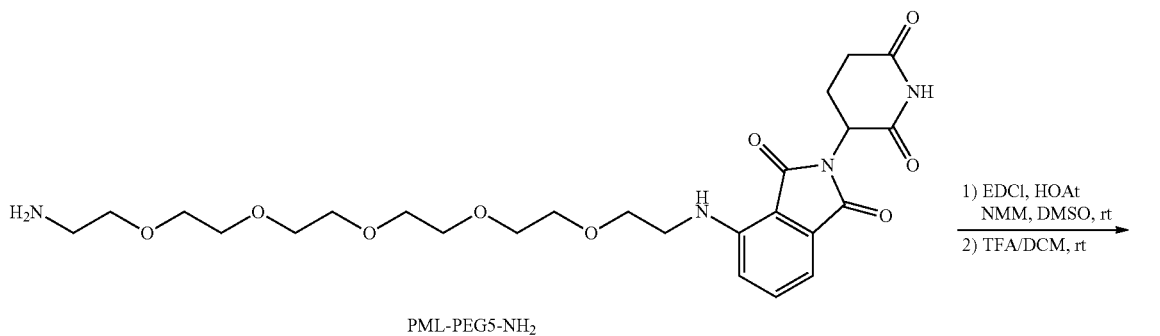

PML-PEG5-NH$_2$

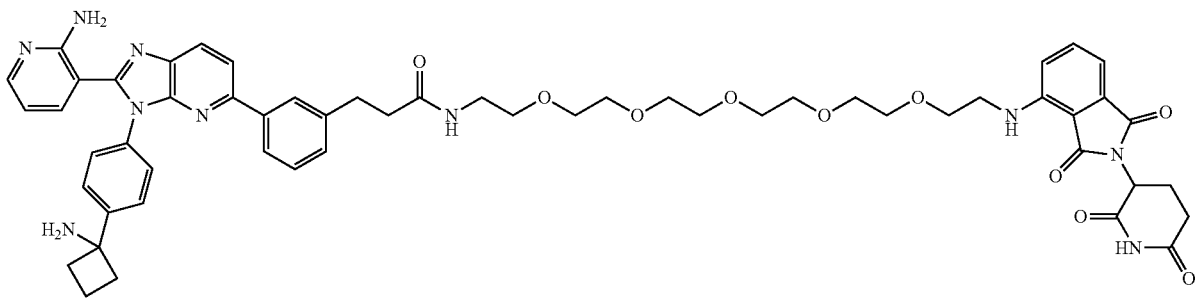

XF067-23

XF067-23 was synthesized following the standard procedure or preparing XF607-1 from intermediate 8 (12 mg, 0.02 mmol), PML-PEG5-NH$_2$ (12.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-23 was obtained as yellow solid in TFA salt form (11.3 mg, 55%). $^1$H NMR (800 MHz, CD$_3$OD) δ 8.30 (d, J=8.3 Hz, 1H), 8.08-7.97 (m, 2H), 7.91 (s, 1H), 7.88 (d, J=7.8 Hz, 1H), 7.81 (d, J=8.3 Hz, 3H), 7.72 (d, J=8.0 Hz, 2H), 7.50 (t, J=7.8 Hz, 1H), 7.37 (t, J=7.7 Hz, 1H), 7.29 (d, J=7.5 Hz, 1H), 7.02 (dd, J=17.2, 7.9 Hz, 2H), 6.82 (t, J=6.9 Hz, 1H), 5.02 (dd, J=12.6, 5.4 Hz, 1H), 3.68 (t, J=5.1 Hz, 2H), 3.66-3.54 (m, 12H), 3.52 (q, J=4.6 Hz, 2H), 3.44 (dt, J=9.4, 4.8 Hz, 4H), 3.38 (t, J=5.4 Hz, 2H), 3.26 (t, J=5.4 Hz, 2H), 2.99 (t, J=7.5 Hz, 2H), 2.91 (dq, J=14.4, 8.5, 7.2 Hz, 2H), 2.82 (ddd, J=18.0, 13.6, 5.3 Hz, 1H), 2.75-2.64 (m, 4H), 2.54 (t, J=7.6 Hz, 2H), 2.34 (tt, J=12.1, 6.4 Hz, 1H), 2.08 (dq, J=12.6, 7.5, 6.6 Hz, 2H). ESI-MS (m/z) [M+H]$^+$: 1023.4738.

Example 99

Synthesis of XF067-24

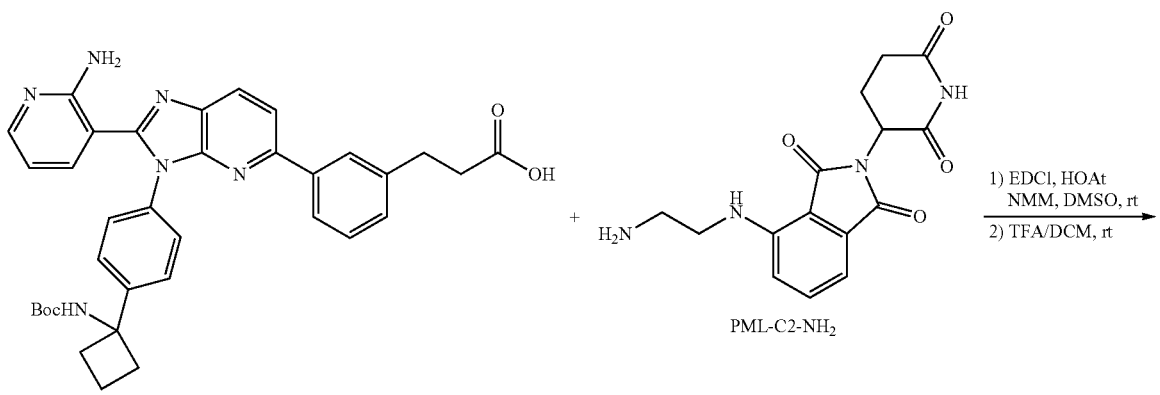

Intermediate 8

PML-C2-NH$_2$

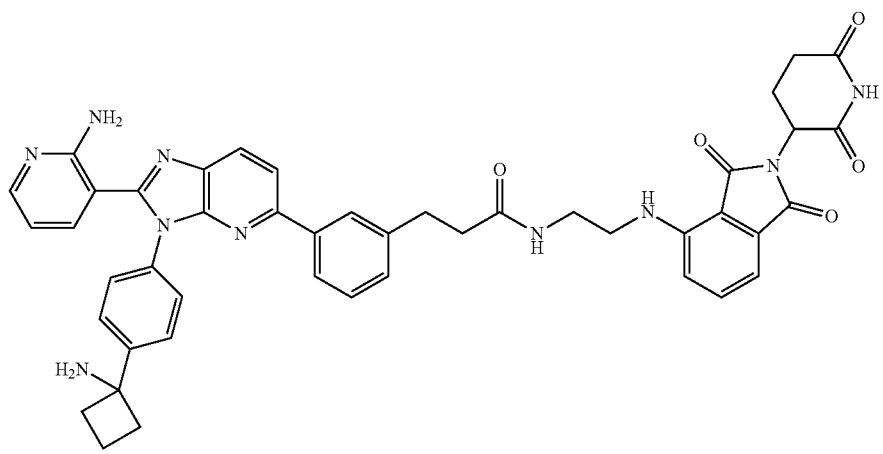

XF067-24

XF067-24 was synthesized following the standard procedure or preparing XF067-1 from intermediate 8 (12 mg, 0.02 mmol), PML-C2-NH₂ (8.6 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-24 was obtained as yellow solid in TFA salt form (10.5 mg, 65%). ¹H NMR (800 MHz, CD₃OD) δ 8.22 (d, J=8.4 Hz, 1H), 8.03 (d, J=6.2 Hz, 1H), 7.99-7.93 (m, 1H), 7.91 (s, 1H), 7.85 (d, J=7.8 Hz, 1H), 7.80 (t, J=7.1 Hz, 3H), 7.66 (d, J=8.0 Hz, 2H), 7.38-7.33 (m, 1H), 7.31-7.25 (m, 2H), 6.92-6.87 (m, 1H), 6.82 (t, J=6.9 Hz, 1H), 6.70 (d, J=8.5 Hz, 1H), 5.01 (dd, J=12.7, 5.4 Hz, 1H), 3.27 (hept, J=6.5, 5.8 Hz, 2H), 3.16-3.10 (m, 2H), 3.01 (t, J=7.2 Hz, 2H), 2.92 (dt, J=11.1, 7.2 Hz, 2H), 2.82 (ddd, J=18.2, 13.7, 5.3 Hz, 1H), 2.75-2.63 (m, 4H), 2.53 (t, J=7.3 Hz, 2H), 2.33 (qt, J=10.6, 6.3 Hz, 1H), 2.07 (dq, J=13.7, 7.8, 6.7 Hz, 2H). ESI-MS (m/z) [M+H]⁺: 803.3417.

Example 100

Synthesis of XF067-25

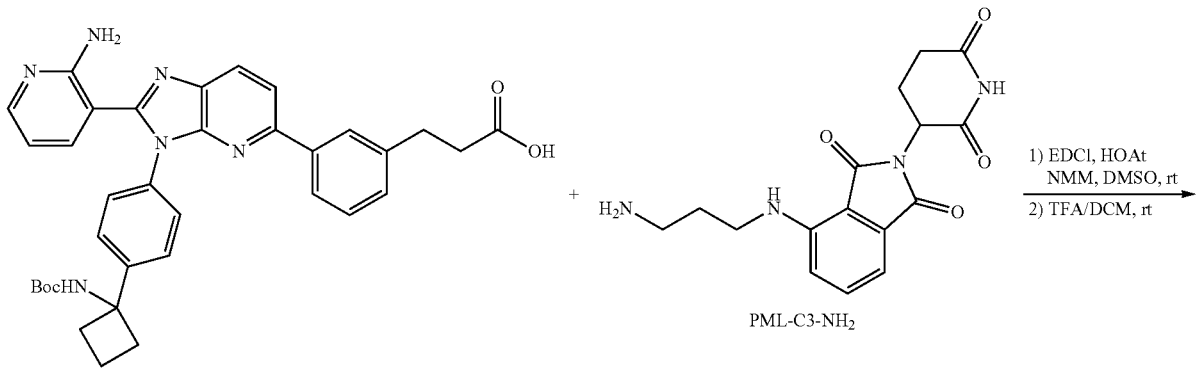

Intermediate 8    PML-C3-NH₂

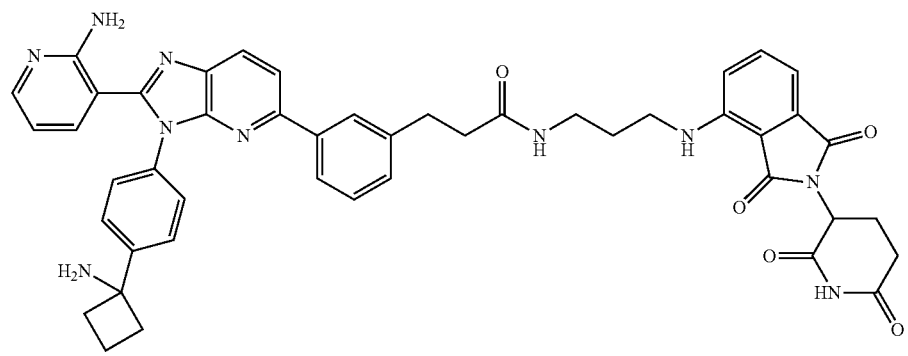

XF067-25

XF067-25 was synthesized following the standard procedure for preparing XF067-1 from intermediate 8 (12 mg, 0.02 mmol), PML-C3-NH₂ (8.9 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-25 was obtained as yellow solid in TFA salt form (16.3 mg, 99%). ¹H NMR (800 MHz, CD₃OD) δ 8.20 (d, J=8.4 Hz, 1H), 8.03 (d, J=6.2 Hz, 1H), 7.93 (s, 1H), 7.92-7.86 (m, 1H), 7.80 (dq, J=19.8, 7.5, 6.0 Hz, 4H), 7.68 (d, J=8.0 Hz, 2H), 7.39 (t, J=7.7 Hz, 1H), 7.35-7.28 (m, 2H), 6.87 (d, J=7.1 Hz, 1H), 6.83 (q, J=6.6 Hz, 1H), 6.62 (d, J=8.5 Hz, 1H), 5.00 (dd, J=12.8, 5.5 Hz, 1H), 3.18 (pt, J=12.8, 6.6 Hz, 2H), 3.03 (t, J=7.1 Hz, 2H), 2.92 (dt, J=14.5, 8.2 Hz, 2H), 2.87-2.79 (m, 3H), 2.77-2.66 (m, 4H), 2.56 (t, J=7.0 Hz, 2H), 2.34 (dtd, J=16.2, 10.3, 6.5 Hz, 1H), 2.13 (dt, J=12.6, 6.2 Hz, 1H), 2.07 (dq, J=16.4, 8.3 Hz, 1H), 1.54 (p, J=6.8 Hz, 2H). ESI-MS (m/z) [M+H]⁺: 817.3578.

Example 101

Synthesis of XF067-26

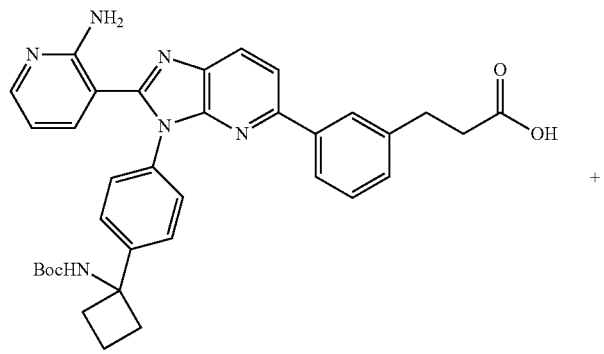

Intermediate 8

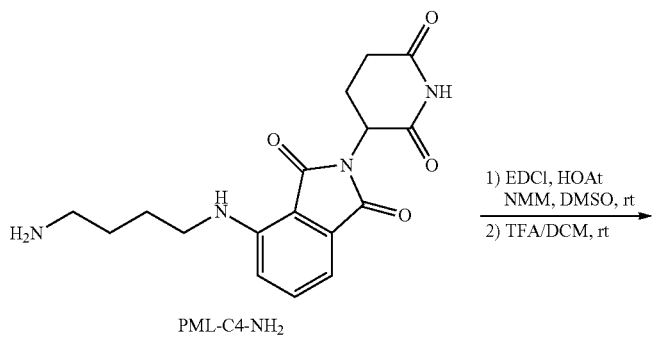

PML-C4-NH₂

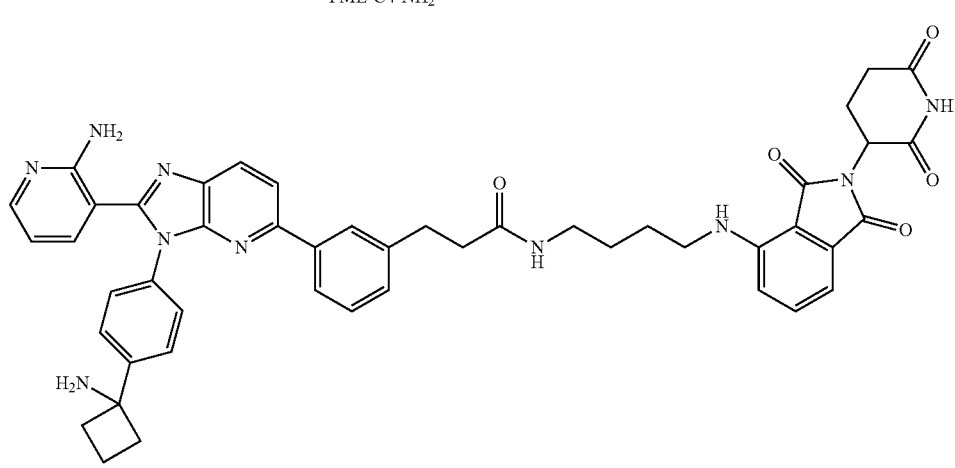

XF067-26

XF067-26 was synthesized following the standard procedure for preparing XF067-1 from intermediate 8 (12 mg, 0.02 mmol), PML-C4-NH₂ (9.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-26 was obtained as yellow solid in TFA salt form (10.5 mg, 63%). ¹H NMR (800 MHz, CD₃OD) δ 8.23 (d, J=8.3 Hz, 1H), 8.02 (d, J=6.3 Hz, 1H), 7.97 (d, J=8.3 Hz, 1H), 7.90-7.85 (m, 2H), 7.78 (dd, J=21.0, 7.8 Hz, 3H), 7.66 (d, J=8.0 Hz, 2H), 7.38 (t, J=7.7 Hz, 2H), 7.31 (d, J=7.6 Hz, 1H), 6.97-6.91 (m, 1H), 6.82 (q, J=9.2, 6.9 Hz, 1H), 6.67 (d, J=8.4 Hz, 1H), 5.09-5.03 (m, 1H), 3.10 (t, J=6.6 Hz, 2H), 3.01 (t, J=7.1 Hz, 2H), 2.94-2.83 (m, 5H), 2.80-2.67 (m, 4H), 2.54 (t, J=7.1 Hz, 2H), 2.33 (qt, J=10.3, 6.4 Hz, 1H), 2.13 (dt, J=12.6, 5.8 Hz, 1H), 2.06 (dq, J=14.0, 8.4 Hz, 1H), 1.32 (dq, J=11.4, 6.6 Hz, 2H), 1.24 (q, J=7.6 Hz, 2H). ESI-MS (m/z) [M+H]⁺: 831.3721.

Example 102

Synthesis of XF067-27

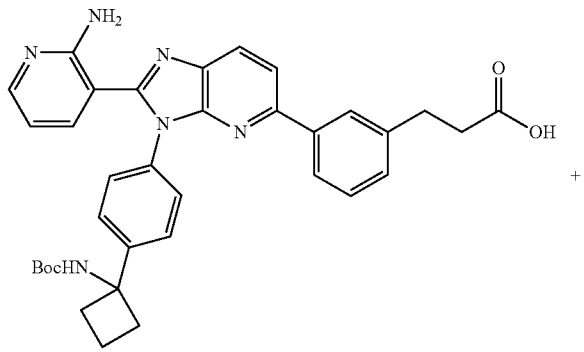

Intermediate 8

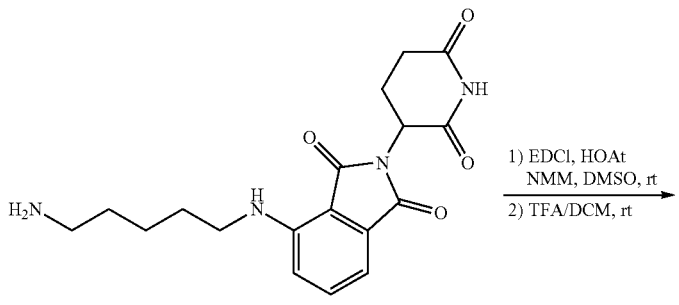

PML-C5-NH₂

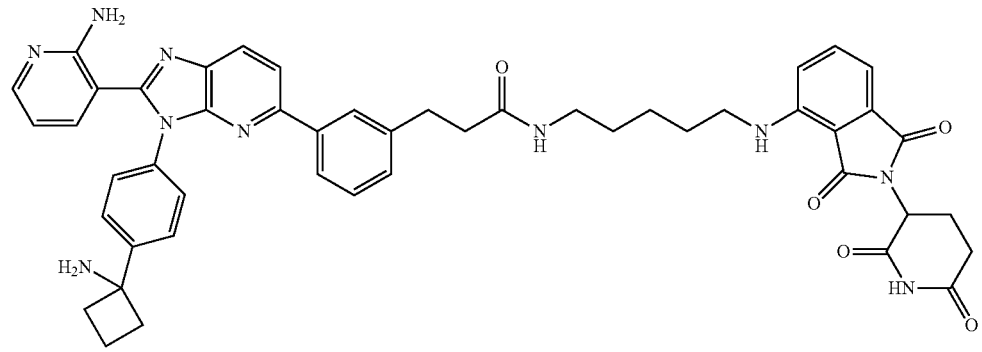

XF067-27

XF067-27 was synthesized following the standard procedure for preparing XF067-1 from intermediate 8 (12 mg, 0.02 mmol), PML-C5-NH$_2$ (9.7 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-27 was obtained as yellow solid in TFA salt form (11.1 mg, 66%). $^1$H NMR (800 MHz, CD$_3$OD) δ 8.27 (d, J=8.4 Hz, 1H), 8.01 (dd, J=10.1, 7.0 Hz, 2H), 7.94-7.88 (m, 2H), 7.79 (d, J=8.1 Hz, 2H), 7.71 (d, J=7.7 Hz, 1H), 7.65 (d, J=8.1 Hz, 2H), 7.41 (t, J=7.7 Hz, 1H), 7.38 (t, J=7.7 Hz, 1H), 7.31 (d, J=7.6 Hz, 1H), 6.94-6.88 (m, 1H), 6.79 (t, J=7.0 Hz, 1H), 6.76 (d, J=8.5 Hz, 1H), 5.02 (dd, J=12.7, 5.4 Hz, 1H), 3.11 (td, J=7.2, 2.3 Hz, 2H), 3.01 (t, J=7.2 Hz, 2H), 2.97 (t, J=7.3 Hz, 2H), 2.93-2.87 (m, 2H), 2.86-2.79 (m, 1H), 2.77-2.64 (m, 4H), 2.54 (t, J=7.2 Hz, 2H), 2.33 (dq, J=11.8, 6.1, 5.2 Hz, 1H), 2.07 (tt, J=13.3, 6.0 Hz, 2H), 1.38-1.29 (m, 4H), 1.11 (q, J=7.8 Hz, 2H). ESI-MS (m/z) [M+H]$^+$: 845.3867.

Example 103

Synthesis of XF067-28

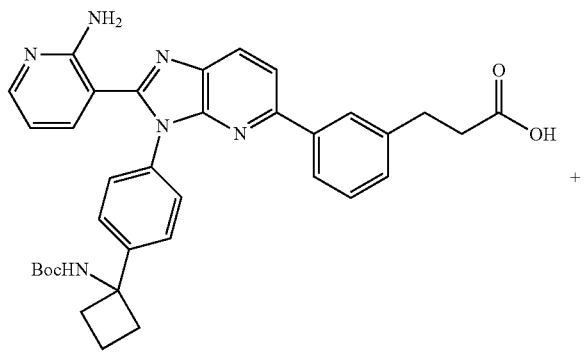

Intermediate 8

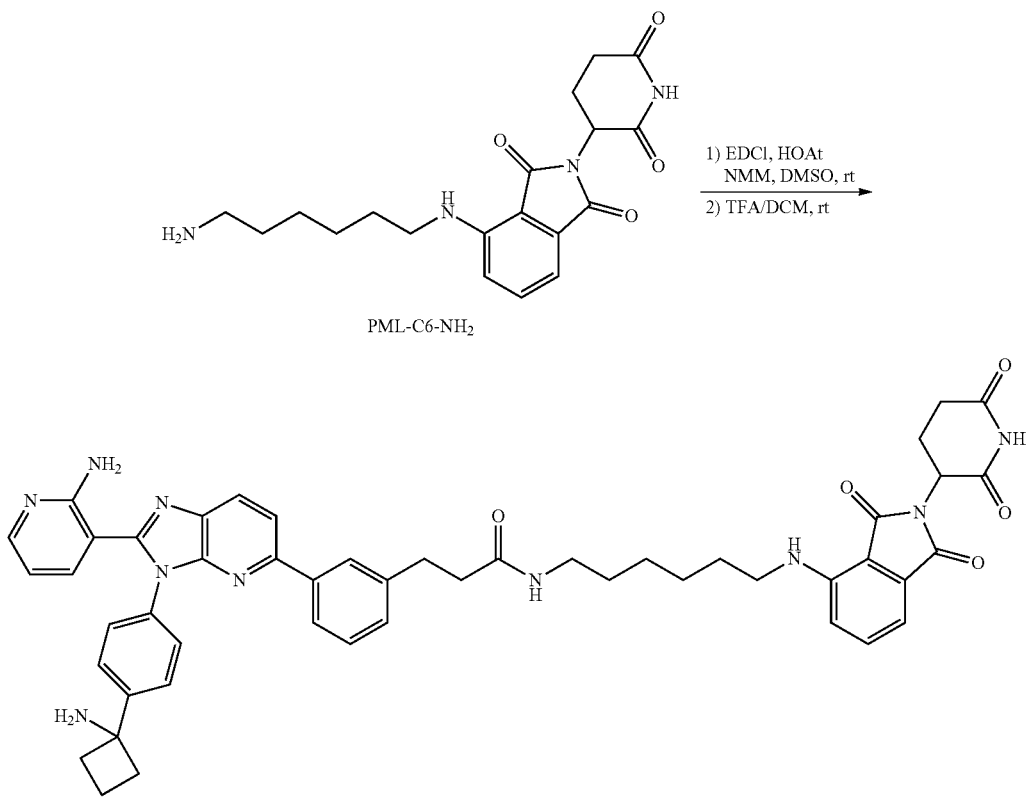

XF067-28

XF067-28 was synthesized following the standard procedure for preparing XF067-1 from intermediate 8 (12 mg, 0.02 mmol), PML-C6-NH$_2$ (8.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-28 was obtained as yellow solid in TFA salt form (10.9 mg, 63%). $^1$H NMR (800 MHz, CD$_3$OD) δ 8.28 (d, J=8.3 Hz, 1H), 8.05-7.99 (m, 2H), 7.93-7.88 (m, 2H), 7.80 (d, J=8.0 Hz, 2H), 7.70 (dd, J=27.6, 7.9 Hz, 3H), 7.46 (t, J=7.8 Hz, 1H), 7.37 (t, J=7.7 Hz, 1H), 7.30 (d, J=7.6 Hz, 1H), 6.95 (d, J=7.1 Hz, 1H), 6.86 (d, J=8.5 Hz, 1H), 6.78 (t, J=6.9 Hz, 1H), 5.07 (dd, J=12.6, 5.4 Hz, 1H), 3.09 (t, J=6.8 Hz, 2H), 3.04 (t, J=7.3 Hz, 2H), 3.01 (t, J=7.2 Hz, 2H), 2.94-2.83 (m, 3H), 2.80-2.68 (m, 4H), 2.54 (t, J=7.2 Hz, 2H), 2.33 (qt, J=10.3, 6.4 Hz, 1H), 2.13 (dq, J=12.7, 6.6, 5.5 Hz, 1H), 2.07 (dq, J=13.6, 8.4, 7.8 Hz, 1H), 1.38 (p, J=7.4 Hz, 2H), 1.31 (q, J=7.3 Hz, 2H), 1.18-1.14 (m, 2H), 1.08 (q, J=7.9 Hz, 2H). ESI-MS (m/z) [M+H]$^+$: 859.4043.

Example 104

Synthesis of XF067-29

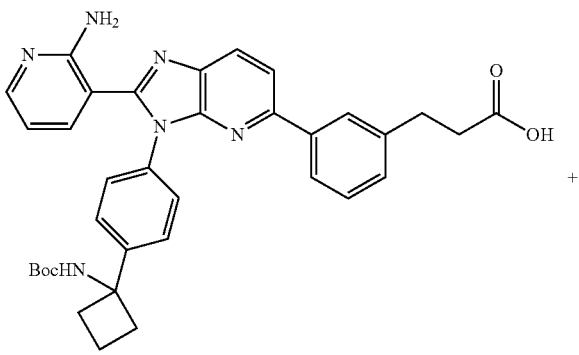

Intermediate 8

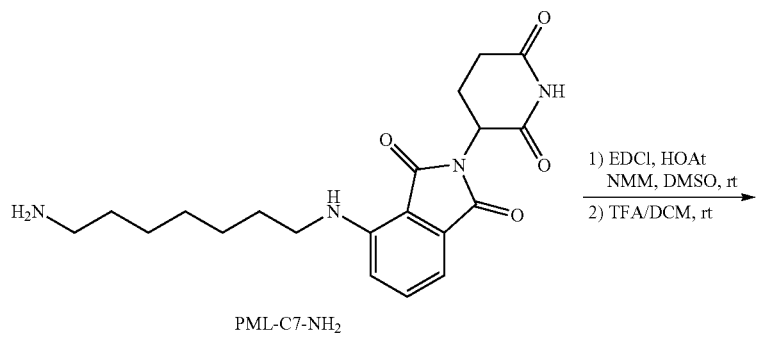

PML-C7-NH$_2$

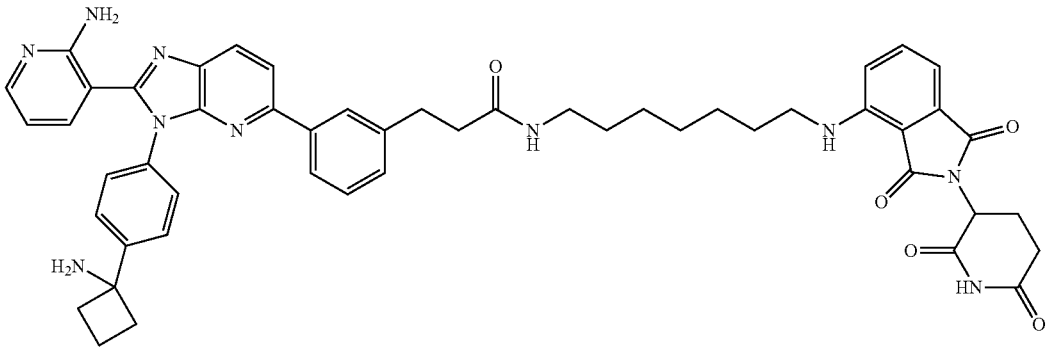

XF067-29

XF067-29 was synthesized following the standard procedure for preparing XF067-1 from intermediate 8 (12 mg, 0.02 mmol), PML-C7-NH$_2$ (10 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-29 was obtained as yellow solid in TFA salt form (15.2 mg, 87%). $^1$H NMR (800 MHz, CD$_3$OD) δ 8.29 (d, J=8.4 Hz, 1H), 8.03 (d, J=8.4 Hz, 1H), 8.00 (d, J=6.3 Hz, 1H), 7.93-7.88 (m, 2H), 7.81 (d, J=8.1 Hz, 2H), 7.74 (d, J=7.6 Hz, 1H), 7.69 (d, J=8.0 Hz, 2H), 7.50 (t, J=7.8 Hz, 1H), 7.37 (t, J=7.6 Hz, 1H), 7.30 (d, J=7.5 Hz, 1H), 7.01-6.96 (m, 1H), 6.92 (d, J=8.5 Hz, 1H), 6.78 (t, J=6.9 Hz, 1H), 5.05 (dd, J=12.7, 5.4 Hz, 1H), 3.14-3.05 (m, 4H), 3.00 (t, J=7.2 Hz, 2H), 2.94-2.82 (m, 3H), 2.78-2.67 (m, 4H), 2.53 (t, J=7.2 Hz, 2H), 2.33 (dtd, J=16.3, 10.4, 6.5 Hz, 1H), 2.13-2.03 (m, 2H), 1.44 (p, J=7.4 Hz, 2H), 1.29 (p, J=7.2 Hz, 2H), 1.19 (p, J=7.3 Hz, 2H), 1.13-1.03 (m, 4H). ESI-MS (m/z) [M+H]$^+$: 873.4186.

Example 105

Synthesis of XF067-30

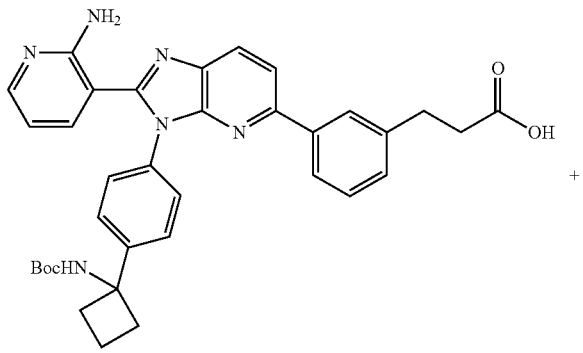

Intermediate 8

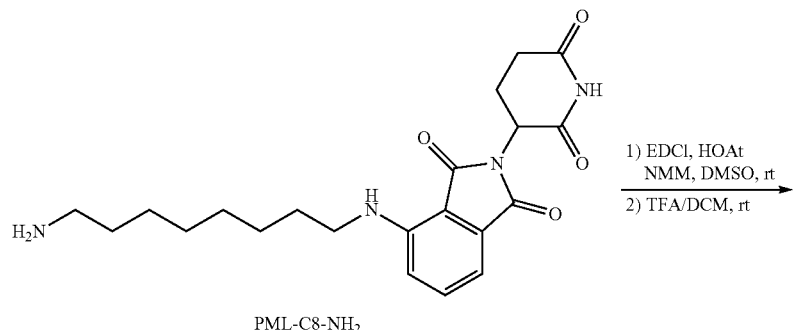

PML-C8-NH$_2$

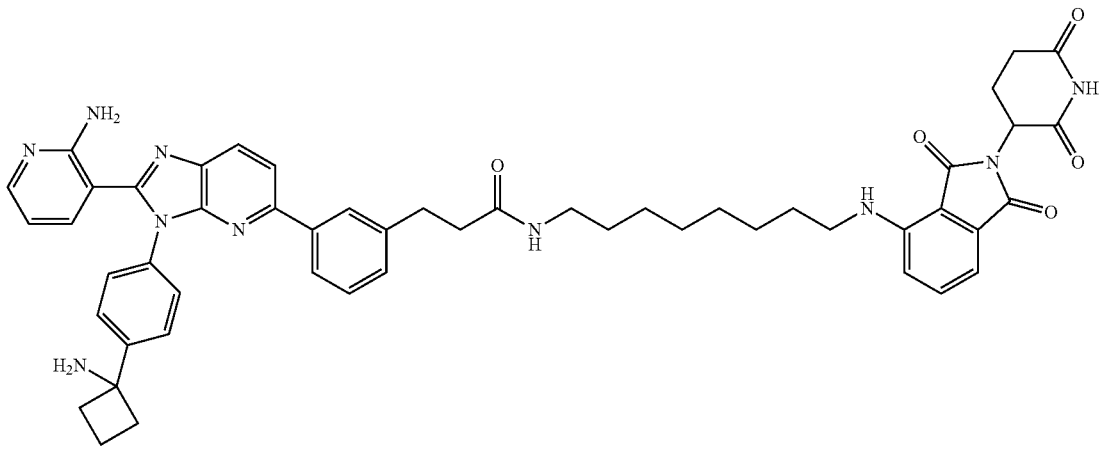

XF067-30

XF067-30 was synthesized following the standard procedure for preparing XF067-1 from intermediate 8 (12 mg, 0.02 mmol), PML-C8-NH$_2$ (10.2 mg, 0.02 mmol, 1.0 equiv), EDCI (5.8 mg, 0.03 mmol, 1.5 equiv), HOAt (4.1 mg, 0.03 mmol, 1.5 equiv), and NMM (6.1 mg, 0.06 mmol, 3.0 equiv) in DMSO (1 mL). XF067-30 was obtained as yellow solid in TFA salt form (11.1 mg, 63%). $^1$H NMR (800 MHz, CD$_3$OD) δ 8.32-8.26 (m, 1H), 8.05-7.98 (m, 2H), 7.92-7.87 (m, 2H), 7.85-7.78 (m, 2H), 7.76 (d, J=7.7 Hz, 1H), 7.70 (d, J=8.1 Hz, 2H), 7.50 (t, J=7.8 Hz, 1H), 7.40-7.33 (m, 1H), 7.30 (d, J=7.6 Hz, 1H), 7.02-6.97 (m, 1H), 6.94 (d, J=8.4 Hz, 1H), 6.79 (t, J=7.0 Hz, 1H), 5.06 (dd, J=12.8, 5.3 Hz, 1H), 3.17 (t, J=7.2 Hz, 2H), 3.09 (t, J=7.0 Hz, 2H), 3.00 (t, J=7.3 Hz, 2H), 2.94-2.82 (m, 3H), 2.79-2.66 (m, 4H), 2.53 (t, J=7.3 Hz, 2H), 2.34 (qt, J=10.4, 6.3 Hz, 1H), 2.13-2.04 (m, 2H), 1.49 (p, J=7.3 Hz, 2H), 1.31 (p, J=7.2 Hz, 2H), 1.26 (q, J=7.4 Hz, 2H), 1.15 (q, J=7.3 Hz, 2H), 1.09 (ddt, J=21.5, 14.5, 7.8 Hz, 4H). ESI-MS (m/z) [M+H]$^+$: 887.4367.

Example 106

Synthesis of Intermediate 9

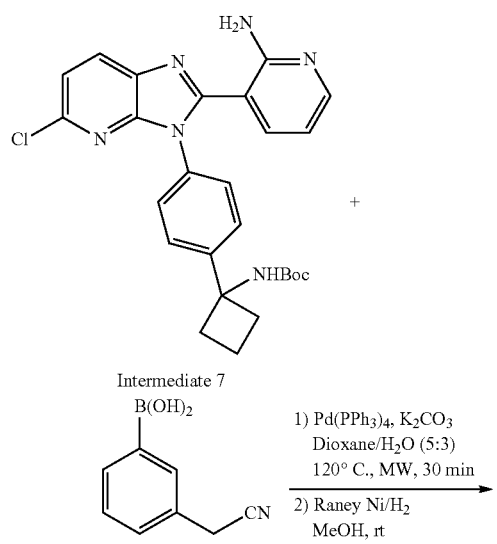

Intermediate 7

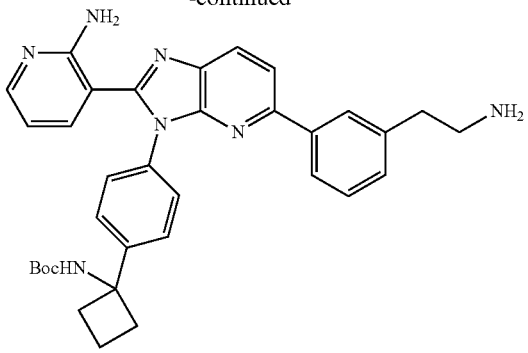

Intermediate 9

To a suspension of Intermediate 7 (156.4 mg, 0.32 mmol) and (3-(cyanomethyl)phenyl)boronic acid (102 mg, 0.64 mmol) in dioxane (2.5 mL) and H$_2$O (1.5 mL) was added potassium carbonate (144 mg, 0.93 mmol). The mixture was degassed for 5 min, before the catalyst Pd(PPh$_3$)$_4$ (19 mg, 5 mol %) was added. After the reaction mixture was stirred at 120° C. for 30 min in microwave, the solvent was removed and the mixture was purified by reverse phase C18 column (10%-100% methanol/0.1% TFA in H$_2$O) to afford the desired product as white solid in TFA salt form (206 mg, 97% yield). After this product was dissolved in 5 mL of methanol, the catalyst Raney nickel and NH$_3$.H$_2$O (a few drops) were added. The reaction was stirred at rt for 1 h, before the mixture was filtered through a pad of Celite. After the filtrate was concentrated, the resulting residue was purified by reverse phase C18 column (10%-100% methanol/0.1% TFA in H$_2$O) to afford the intermediate 9 as yellow solid in TFA salt form (272.5 mg, 43% yield). $^1$H NMR (500 MHz, CD$_3$OD) δ 8.31 (d, J=8.4 Hz, 1H), 8.09-7.93 (m, 5H), 7.81-7.68 (m, 2H), 7.53 (d, J=8.1 Hz, 2H), 7.46 (t, J=7.7 Hz, 1H), 7.36 (dt, J=7.7, 1.4 Hz, 1H), 6.77 (t, J=6.9 Hz, 1H), 3.25 (t, J=7.7 Hz, 2H), 3.06 (t, J=7.7 Hz, 2H), 2.61 (ddd, J=12.2, 6.2, 2.5 Hz, 2H), 2.55 (d, J=13.8 Hz, 2H), 2.20 (s, 1H), 2.00 (s, 1H), 1.56-1.06 (m, 9H). ESI-MS (m/z) [M+H]$^+$: 576.3062.

Example 107

Synthesis of XF067-31

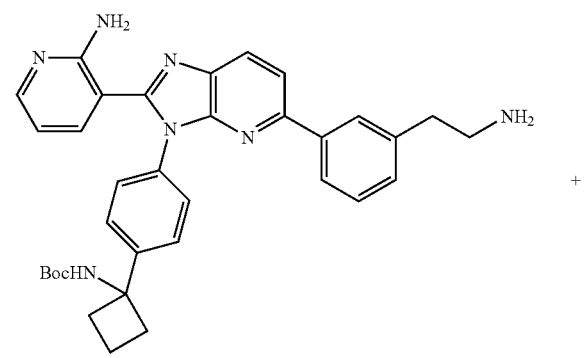

Intermediate 9

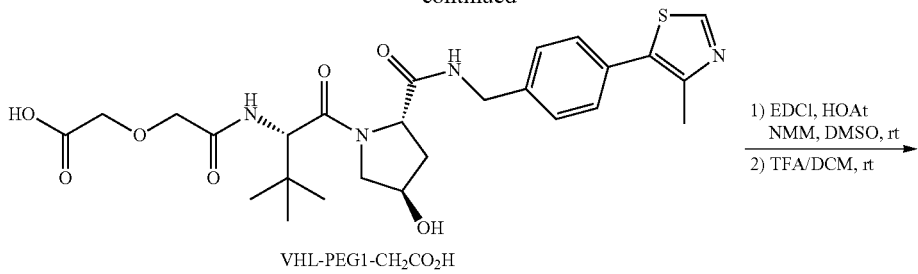

VHL-PEG1-CH2CO2H

1) EDCl, HOAt NMM, DMSO, rt
2) TFA/DCM, rt

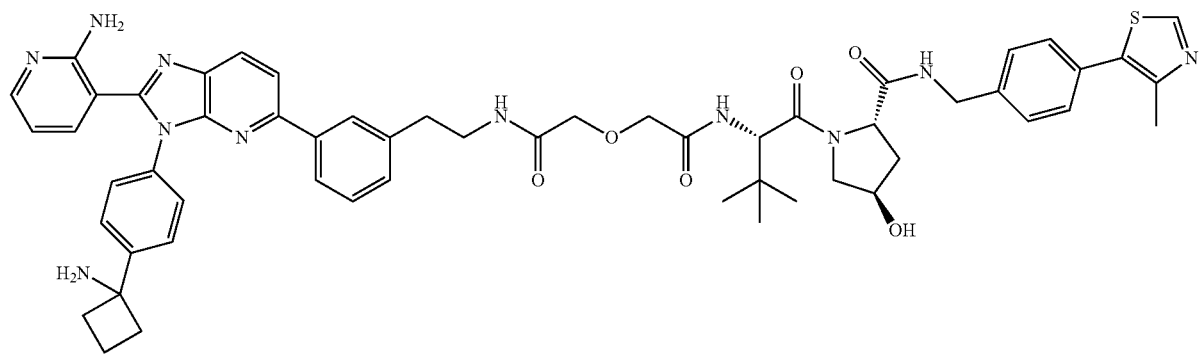

XF067-31

To a solution of Intermediate 9 (9.3 mg, 0.016 mmol) in DMSO (1 mL) were added VHL-PEG1-CH2COOH (8.3 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (4.8 mg, 0.048 mmol, 3.0 equiv). After being stirred overnight at room temperature, the resulting mixture was purified by preparative HPLC (10%-100% methanol/0.1% TFA in H2O) to afford the corresponding product. After this product was dissolved in DCM (1 mL), the reaction mixture was treated with TFA (1 mL) for 30 min. After the solvent was evaporated, the residue was purified by preparative HPLC (10%-100% methanol/0.1% TFA in H2O) to afford XF067-31 as white solid in TFA salt form (7.8 mg, 38%). $^1$H NMR (800 MHz, CD$_3$OD) δ 8.88 (d, J=25.3 Hz, 1H), 8.43-7.64 (m, 10H), 7.61-7.20 (m, 6H), 6.83 (t, J=25.0 Hz, 1H), 4.77-4.27 (m, 5H), 4.20-3.78 (m, 6H), 3.70-3.43 (m, 2H), 2.92 (t, J=21.5 Hz, 6H), 2.56-1.98 (m, 7H), 1.03 (s, 9H). ESI-MS (m/z) [M+H]$^+$: 1004.4613.

Example 108

Synthesis of XF067-32

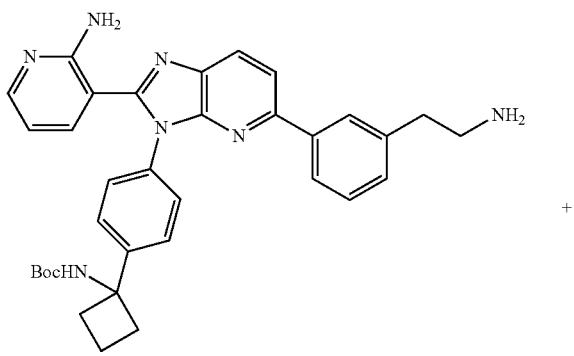

Intermediate 9

+

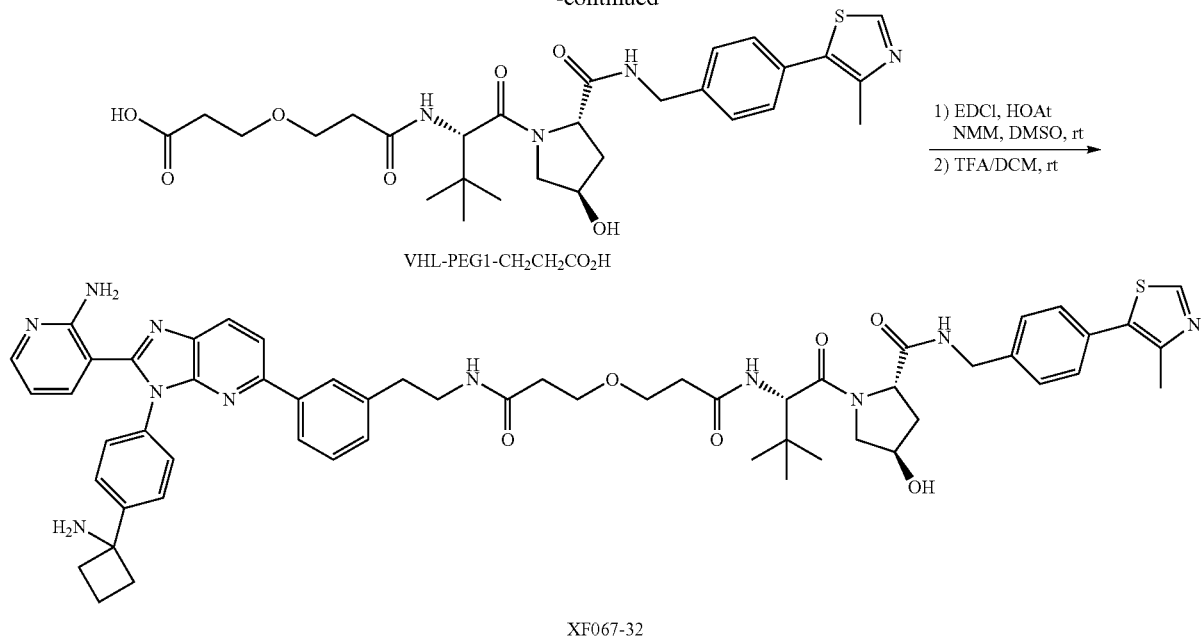

VHL-PEG1-CH$_2$CH$_2$CO$_2$H

XF067-32

XF067-32 was synthesized following the standard procedure or preparing XF067-31 from intermediate 9 (9.3 mg, 0.016 mmol), VHL-PEG1-CH$_2$CH$_2$—CO$_2$H (9.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-32 was obtained as white solid in TFA salt form (9.1 mg, 55%). $^1$H NMR (800 MHz, CD$_3$OD) δ 8.95 (s, 1H), 8.32 (d, J=8.3 Hz, 1H), 8.04 (d, J=8.1 Hz, 2H), 7.96 (s, 1H), 7.88 (dd, J=22.4, 7.7 Hz, 2H), 7.82 (d, J=8.0 Hz, 2H), 7.73 (d, J=8.0 Hz, 2H), 7.48-7.35 (m, 5H), 7.30 (d, J=7.5 Hz, 1H), 6.85 (t, J=6.9 Hz, 1H), 4.64 (s, 1H), 4.58 (t, J=8.4 Hz, 1H), 4.56-4.49 (m, 2H), 4.39-4.34 (m, 1H), 3.89 (d, J=10.9 Hz, 1H), 3.80 (dd, J=11.1, 4.0 Hz, 1H), 3.69-3.63 (m, 3H), 3.60 (dt, J=10.2, 5.7 Hz, 1H), 3.48 (t, J=7.6 Hz, 2H), 2.90 (dt, J=19.6, 7.5 Hz, 4H), 2.73 (dt, J=12.4, 7.7 Hz, 2H), 2.52-2.38 (m, 7H), 2.35 (s, 1H), 2.24 (dd, J=13.3, 7.6 Hz, 1H), 2.09 (dtd, J=12.8, 8.8, 4.4 Hz, 2H), 1.03 (s, 9H). ESI-MS (m/z) for [M+H]$^+$: 1032.4904.

Example 109

Synthesis of XF067-33

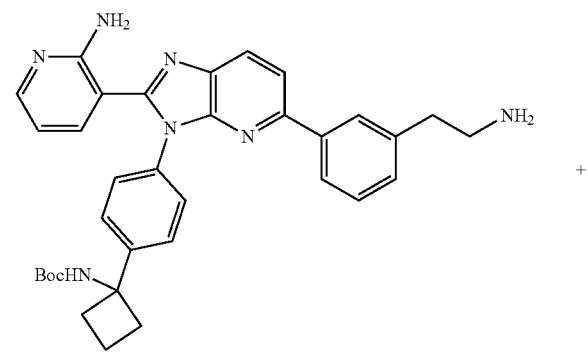

Intermediate 9

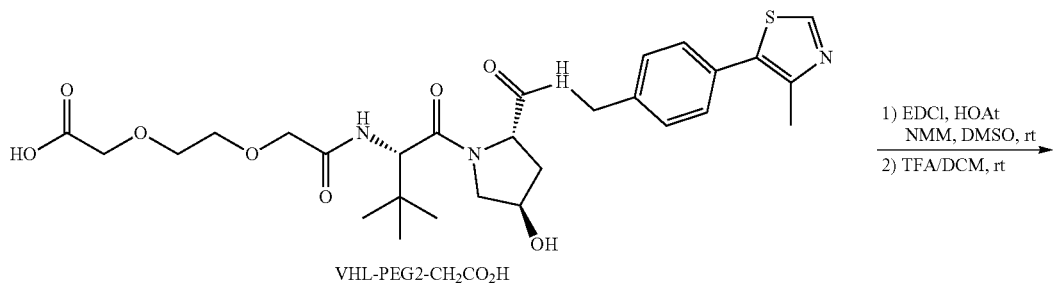

VHL-PEG2-CH$_2$CO$_2$H

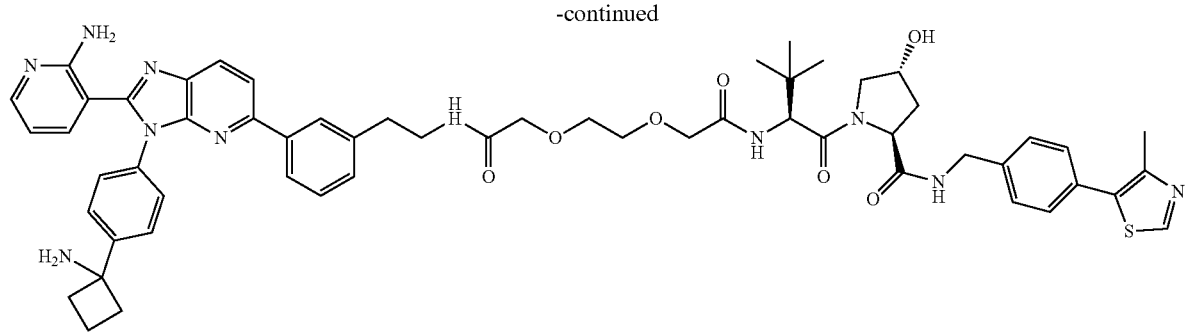

XF067-33

XF067-33 was synthesized following the standard procedure for preparing XF067-31 from intermediate 9 (9.3 mg, 0.016 mmol), VHL-PEG2-CH$_2$—CO$_2$H (9.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-33 was obtained as white solid in TFA salt form (6.2 mg, 37%). $^1$H NMR (800 MHz, CD$_3$OD) δ 8.90 (s, 1H), 8.31 (d, J=8.3 Hz, 1H), 8.07-8.02 (m, 2H), 7.97 (s, 1H), 7.90 (d, J=7.8 Hz, 1H), 7.86 (d, J=7.8 Hz, 1H), 7.82 (d, J=7.9 Hz, 2H), 7.73 (d, J=8.1 Hz, 2H), 7.39-7.35 (m, 5H), 7.31 (d, J=7.5 Hz, 1H), 6.85 (t, J=6.9 Hz, 1H), 4.73 (s, 1H), 4.61 (t, J=8.5 Hz, 1H), 4.53 (s, 1H), 4.41 (d, J=15.3 Hz, 1H), 4.35 (d, J=15.4 Hz, 1H), 4.05-3.88 (m, 6H), 3.86-3.81 (m, 1H), 3.70-3.50 (m, 5H), 2.96-2.86 (m, 4H), 2.75-2.69 (m, 2H), 2.45 (s, 3H), 2.38-2.31 (m, 1H), 2.27 (dd, J=13.0, 7.6 Hz, 1H), 2.12-2.04 (m, 2H), 1.04 (s, 9H). ESI-MS (m/z) [M+H]$^+$: 1048.4877.

Example 110

Synthesis of XF067-34

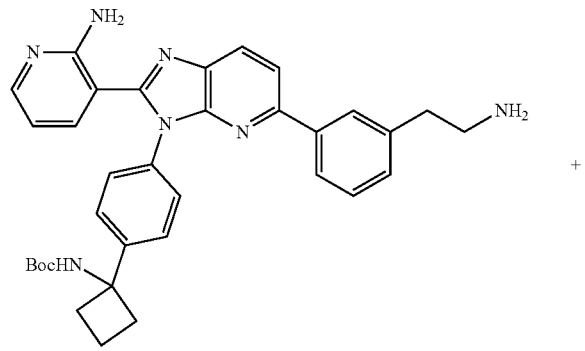

Intermediate 9

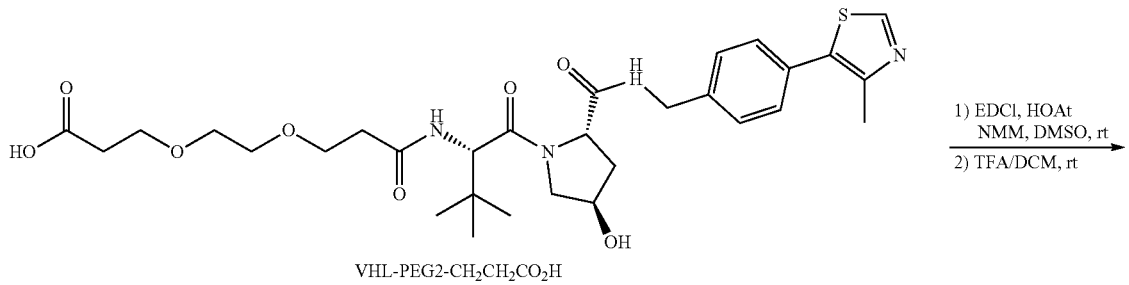

VHL-PEG2-CH$_2$CH$_2$CO$_2$H

1) EDCl, HOAt
   NMM, DMSO, rt
2) TFA/DCM, rt

-continued

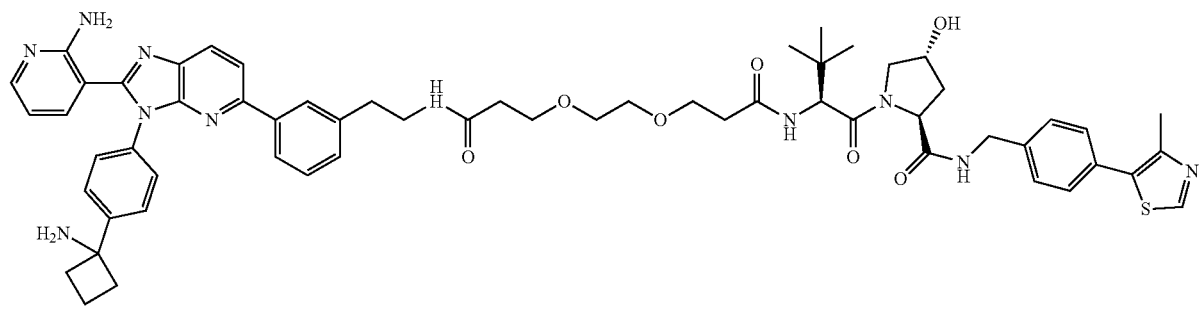

XF067-34

XF067-34 was synthesized following the standard procedure for preparing XF067-31 from intermediate 9 (9.3 mg, 0.016 mmol), VHL-PEG2-CH$_2$CH$_2$—CO$_2$H (9.9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-34 was obtained as white solid in TFA salt form (9.1 mg, 53%). $^1$H NMR (800 MHz, CD$_3$OD) δ 8.94 (s, 1H), 8.32 (d, J=8.3 Hz, 1H), 8.05 (t, J=7.7 Hz, 2H), 7.96 (s, 1H), 7.90 (d, J=7.8 Hz, 1H), 7.86 (d, J=7.6 Hz, 1H), 7.82 (d, J=8.1 Hz, 2H), 7.74 (d, J=8.0 Hz, 2H), 7.47 (d, J=7.9 Hz, 2H), 7.40 (dt, J=26.0, 8.4 Hz, 3H), 7.31 (d, J=7.5 Hz, 1H), 6.85 (t, J=7.0 Hz, 1H), 4.65 (s, 1H), 4.58 (t, J=8.2 Hz, 1H), 4.54 (d, J=15.4 Hz, 1H), 4.50 (s, 1H), 4.37 (d, J=15.4 Hz, 1H), 3.89 (d, J=10.9 Hz, 1H), 3.80 (dd, J=11.1, 4.1 Hz, 1H), 3.68 (dhept, J=11.5, 5.2 Hz, 4H), 3.58-3.51 (m, 4H), 3.48 (t, J=7.5 Hz, 2H), 2.90 (dt, J=24.4, 7.0 Hz, 4H), 2.76-2.70 (m, 2H), 2.53 (dt, J=13.6, 6.8 Hz, 1H), 2.49-2.39 (m, 6H), 2.34 (dd, J=11.3, 6.1 Hz, 1H), 2.23 (dd, J=13.3, 7.6 Hz, 1H), 2.09 (ddt, J=17.0, 12.3, 6.3 Hz, 2H), 1.03 (s, 9H). ESI-MS (m/z) [M+H]$^+$: 1076.5189.

Example 111

Synthesis of XF067-35

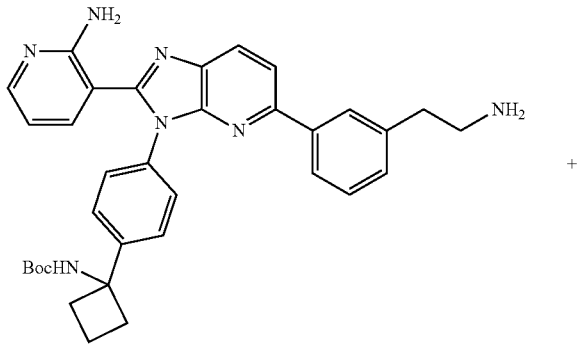

Intermediate 9

+

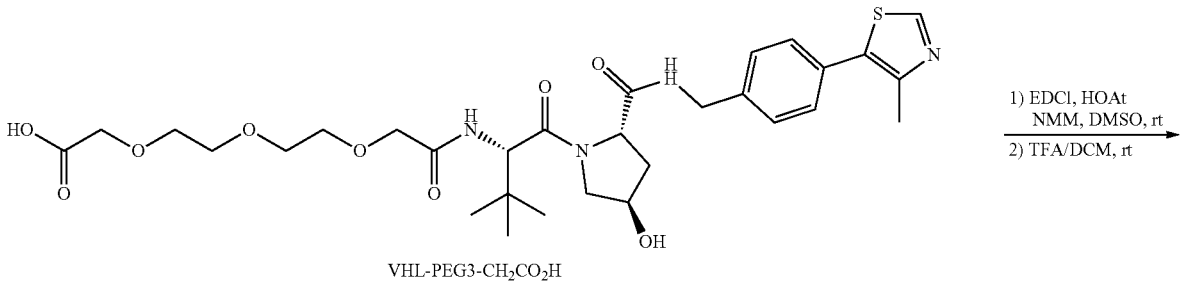

VHL-PEG3-CH$_2$CO$_2$H

1) EDCl, HOAt
NMM, DMSO, rt
2) TFA/DCM, rt

-continued

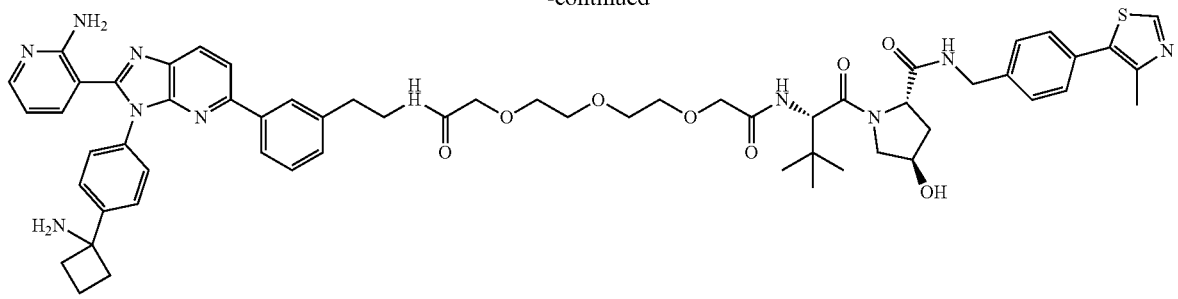

XF067-35

XF067-35 was synthesized following the standard procedure for preparing XF067-31 from intermediate 9 (9.3 mg, 0.016 mmol), VHL-PEG3-CH$_2$—CO$_2$H (10.1 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-35 was obtained as white solid in TFA salt form (6.8 mg, 39%). $^1$H NMR (800 MHz, CD$_3$OD) δ 8.91 (s, 1H), 8.32 (d, J=8.4 Hz, 1H), 8.05 (dd, J=8.3, 4.2 Hz, 2H), 7.99 (s, 1H), 7.91 (d, J=8.0 Hz, 1H), 7.84 (dd, J=29.9, 7.9 Hz, 3H), 7.76-7.69 (m, 2H), 7.45 (d, J=7.9 Hz, 2H), 7.40 (dp, J=15.2, 7.7 Hz, 3H), 7.30 (d, J=7.6 Hz, 1H), 6.84 (s, 1H), 4.70 (s, 1H), 4.62-4.47 (m, 3H), 4.35 (d, J=15.3 Hz, 1H), 4.09-3.84 (m, 5H), 3.80 (dd, J=11.1, 4.0 Hz, 1H), 3.70-3.58 (m, 8H), 3.58-3.47 (m, 2H), 2.91 (dt, J=15.0, 7.1 Hz, 4H), 2.73 (q, J=12.1, 9.9 Hz, 2H), 2.47 (s, 3H), 2.38-2.30 (m, 1H), 2.23 (dd, J=13.3, 7.6 Hz, 1H), 2.13-2.02 (m, 2H), 1.03 (s, 9H). ESI-MS (m/z) [M+H]$^+$: 1092.5135.

Example 112

Synthesis of XF067-36

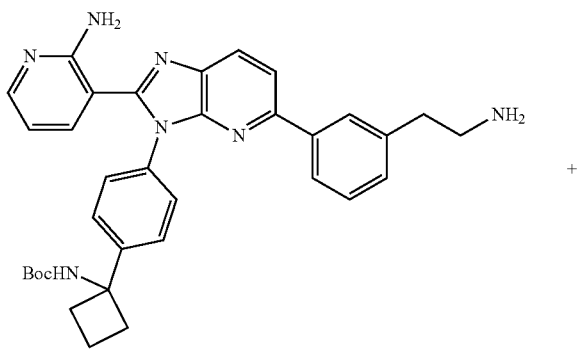

Intermediate 9

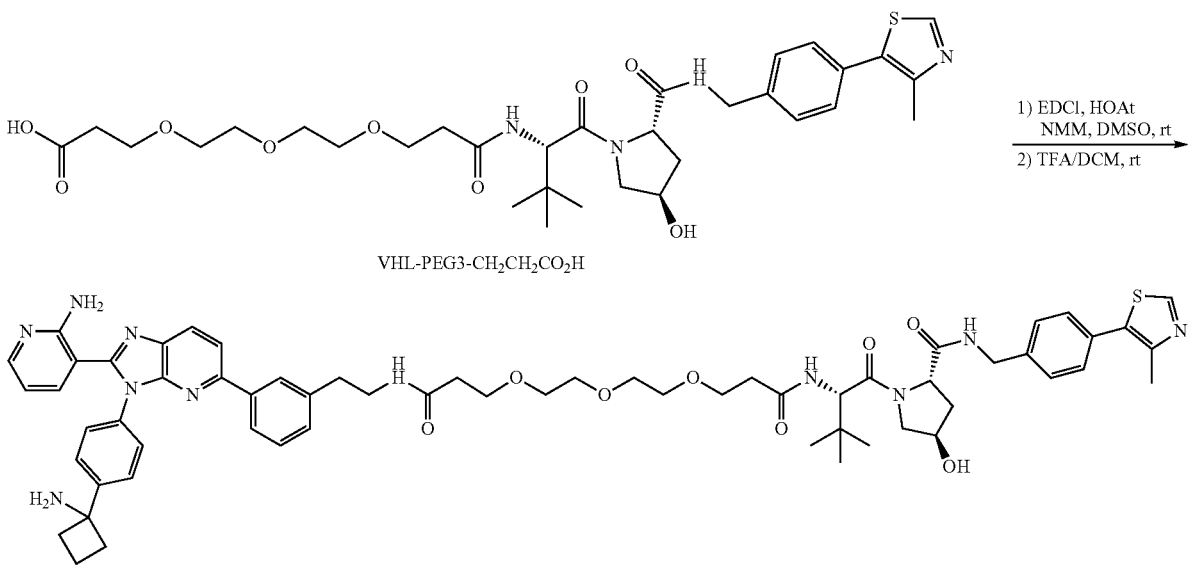

XF067-36

XF067-36 was synthesized following the standard procedure for preparing XF067-31 from intermediate 9 (9.3 mg, 0.016 mmol), VHL-PEG3-CH$_2$CH$_2$—CO$_2$H (10.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-36 was obtained as white solid in TFA salt form (8.3 mg, 46%). $^1$H NMR (800 MHz, CD$_3$OD) δ 8.93 (s, 1H), 8.32 (d, J=8.4 Hz, 1H), 8.05 (t, J=8.1 Hz, 2H), 7.97 (s, 1H), 7.90 (d, J=7.8 Hz, 1H), 7.84 (dd, J=25.3, 7.8 Hz, 3H), 7.74 (d, J=8.0 Hz, 2H), 7.47 (d, J=7.9 Hz, 2H), 7.41 (tt, J=15.4, 6.9 Hz, 3H), 7.31 (d, J=7.5 Hz, 1H), 6.84 (t, J=7.0 Hz, 1H), 4.64 (s, 1H), 4.59-4.47 (m, 3H), 4.37 (d, J=15.4 Hz, 1H), 3.89 (d, J=10.9 Hz, 1H), 3.80 (dd, J=11.1, 4.0 Hz, 1H), 3.74-3.63 (m, 4H), 3.63-3.51 (m, 8H), 3.48 (t, J=7.5 Hz, 2H), 2.94-2.86 (m, 4H), 2.76-2.70 (m, 2H), 2.58-2.51 (m, 1H), 2.49-2.39 (m, 6H), 2.38-2.31 (m, 1H), 2.23 (dd, J=13.1, 7.7 Hz, 1H), 2.12-2.03 (m, 2H), 1.03 (s, 9H). ESI-MS (m/z) [M+H]$^+$: 1120.5442.

Example 113

Synthesis of XF067-37

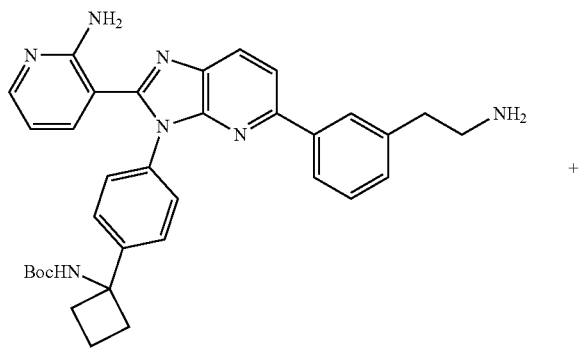

Intermediate 9

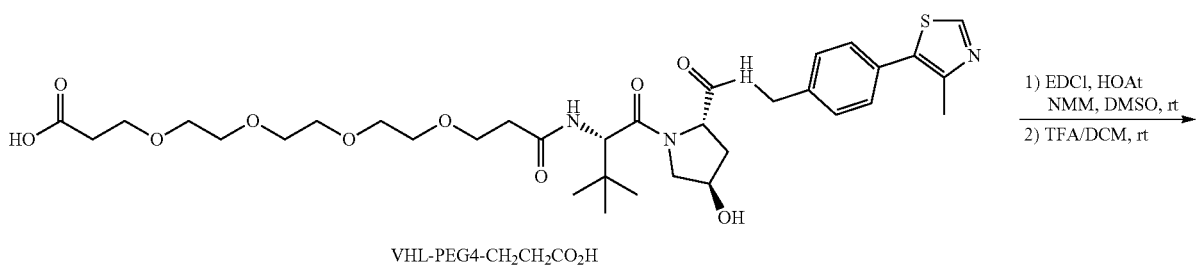

VHL-PEG4-CH$_2$CH$_2$CO$_2$H

1) EDCl, HOAt NMM, DMSO, rt
2) TFA/DCM, rt

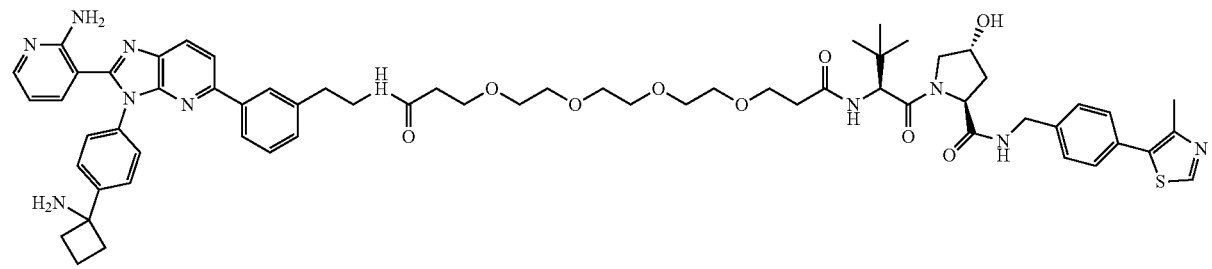

XF067-37

XF067-37 was synthesized following the standard procedure for preparing XF067-31 from intermediate 9 (9.3 mg, 0.016 mmol), VHL-PEG4-CH$_2$CH$_2$—CO$_2$H (11.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-37 was obtained as white solid in TFA salt form (8.4 mg, 45%). $^1$H NMR (800 MHz, CD$_3$OD) δ 8.92 (s, 1H), 8.32 (d, J=8.4 Hz, 1H), 8.05 (dd, J=11.9, 7.2 Hz, 2H), 7.98 (s, 1H), 7.91 (d, J=7.8 Hz, 1H), 7.86 (d, J=7.6 Hz, 1H), 7.82 (d, J=8.0 Hz, 2H), 7.74 (d, J=8.1 Hz, 2H), 7.47 (d, J=7.8 Hz, 2H), 7.45-7.37 (m, 3H), 7.31 (d, J=7.5 Hz, 1H), 6.84 (t, J=7.0 Hz, 1H), 4.64 (s, 1H), 4.59-4.48 (m, 3H), 4.37 (d, J=15.4 Hz, 1H), 3.89 (d, J=10.9 Hz, 1H), 3.81 (dd, J=11.1, 4.0 Hz, 1H), 3.73-3.63 (m, 4H), 3.63-3.50 (m, 12H), 3.48 (t, J=7.5 Hz, 2H), 2.93-2.87 (m, 4H), 2.79-2.68 (m, 2H), 2.57-2.40 (m, 7H), 2.33 (q, J=8.7, 7.0 Hz, 1H), 2.23 (dd, J=13.3, 7.6 Hz, 1H), 2.12-2.04 (m, 2H), 1.03 (s, 9H). ESI-MS (m/z) [M+H]$^+$: 1164.5682.

Example 114

Synthesis of XF067-38

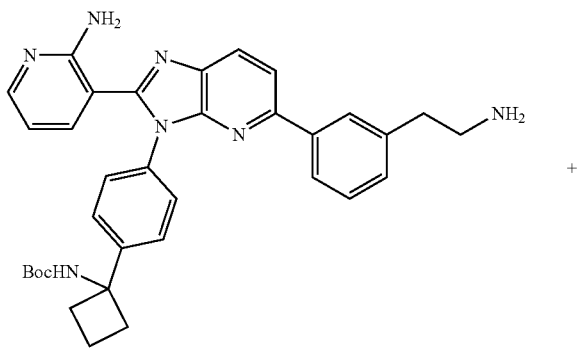

Intermediate 9

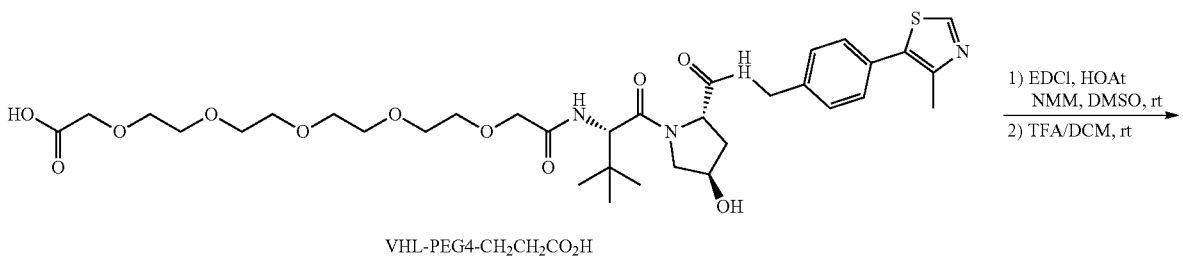

VHL-PEG4-CH$_2$CH$_2$CO$_2$H

1) EDCI, HOAt, NMM, DMSO, rt
2) TFA/DCM, rt

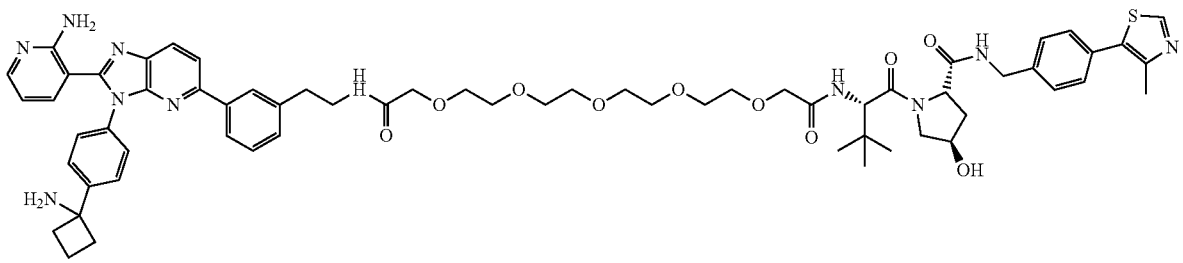

XF067-38

XF067-38 was synthesized following the standard procedure for preparing XF067-31 from intermediate 9 (9.3 mg, 0.016 mmol), VHL-PEG5-CH$_2$—CO$_2$H (11.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-38 was obtained as white solid in TFA salt form (9.7 mg, 51%). $^1$H NMR (800 MHz, CD$_3$OD) δ 8.95 (d, J=13.9 Hz, 1H), 8.32 (d, J=8.3 Hz, 1H), 8.11-7.98 (m, 3H), 7.92 (d, J=7.8 Hz, 1H), 7.88 (d, J=7.8 Hz, 1H), 7.82 (d, J=8.0 Hz, 2H), 7.74 (d, J=7.9 Hz, 2H), 7.49-7.36 (m, 5H), 7.31 (d, J=7.6 Hz, 1H), 6.86 (t, J=7.0 Hz, 1H), 4.69 (s, 1H), 4.62-4.50 (m, 3H), 4.37 (d, J=15.4 Hz, 1H), 4.05-3.91 (m, 4H), 3.88 (d, J=11.2 Hz, 1H), 3.82 (dd, J=11.2, 3.9 Hz, 1H), 3.73-3.50 (m, 18H), 2.91 (d, J=7.7 Hz, 4H), 2.74 (q, J=12.0, 10.3 Hz, 2H), 2.48 (s, 3H), 2.37-2.31 (m, 1H), 2.25 (dd, J=13.4, 7.7 Hz, 1H), 2.14-2.02 (m, 2H), 1.04 (s, 9H). ESI-MS (m/z) [M+H]$^+$: 1180.5672.

Example 115

Synthesis of XF067-39

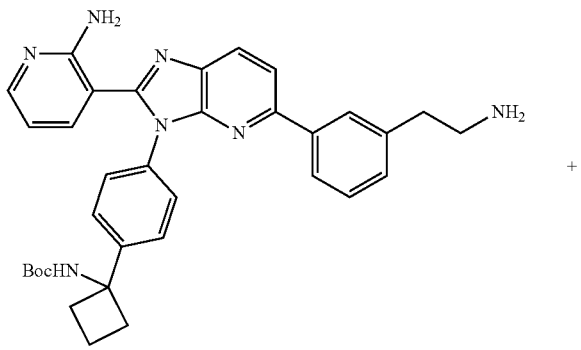

+

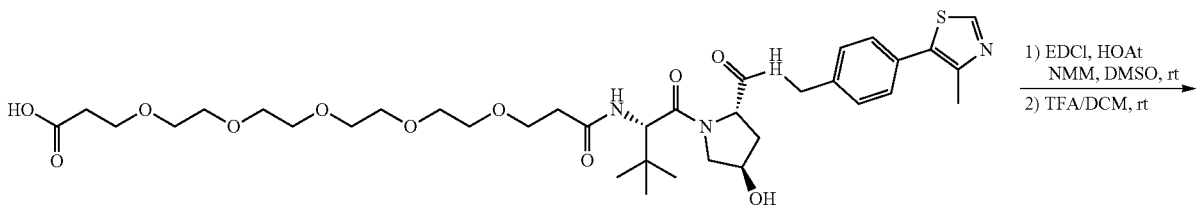

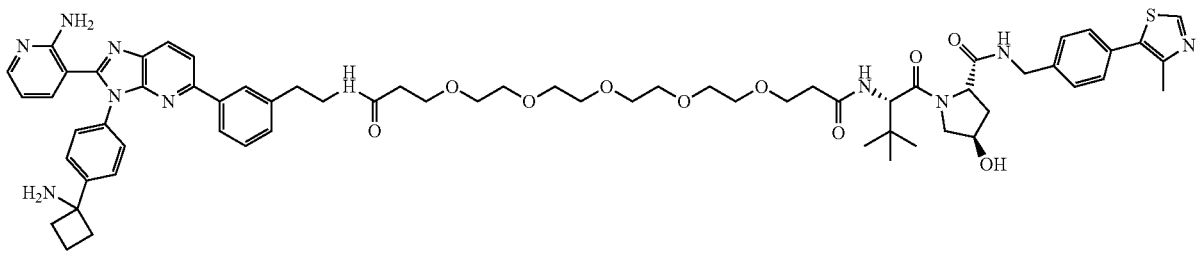

XF067-39

XF067-39 was synthesized following the standard procedure for preparing XF067-31 from intermediate 9 (9.3 mg, 0.016 mmol), VHL-PEG5-CH$_2$CH$_2$—CO$_2$H (12 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-39 was obtained as white solid in TFA salt form (10.6 mg, 55%). $^1$H NMR (800 MHz, CD$_3$OD) δ 8.96 (s, 1H), 8.33 (d, J=8.5 Hz, 1H), 8.05 (dd, J=12.2, 7.2 Hz, 2H), 8.00 (s, 1H), 7.91 (d, J=7.8 Hz, 1H), 7.88 (d, J=7.6 Hz, 1H), 7.83 (d, J=8.1 Hz, 2H), 7.75 (d, J=8.0 Hz, 2H), 7.48 (d, J=7.8 Hz, 2H), 7.42 (d, J=7.9 Hz, 2H), 7.39 (t, J=7.7 Hz, 1H), 7.31 (d, J=7.5 Hz, 1H), 6.85 (t, J=6.9 Hz, 1H), 4.65 (s, 1H), 4.61-4.47 (m, 3H), 4.37 (d, J=15.4 Hz, 1H), 3.89 (d, J=10.9 Hz, 1H), 3.81 (dd, J=11.1, 4.0 Hz, 1H), 3.70-3.62 (m, 4H), 3.62-3.51 (m, 16H), 3.49 (t, J=7.6 Hz, 2H), 2.90 (dt, J=27.1, 6.6 Hz, 4H), 2.74 (q, J=12.4, 10.6 Hz, 2H), 2.57-2.51 (m, 1H), 2.49 (s, 3H), 2.43 (h, J=5.6 Hz, 3H), 2.38-2.30 (m, 1H), 2.24 (dd, J=13.3, 7.7 Hz, 1H), 2.14-2.03 (m, 2H), 1.03 (s, 9H). ESI-MS (m/z) [M+H]$^+$: 1208.5978.

Example 116

Synthesis of XF067-40

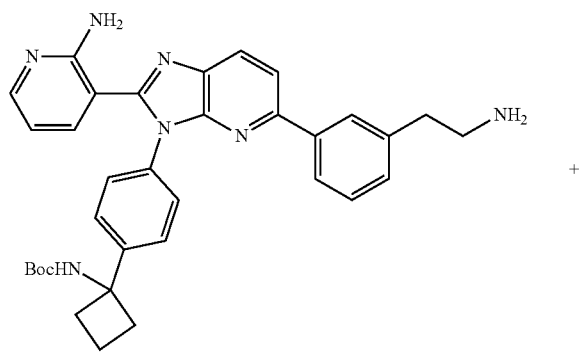

Intermediate 9

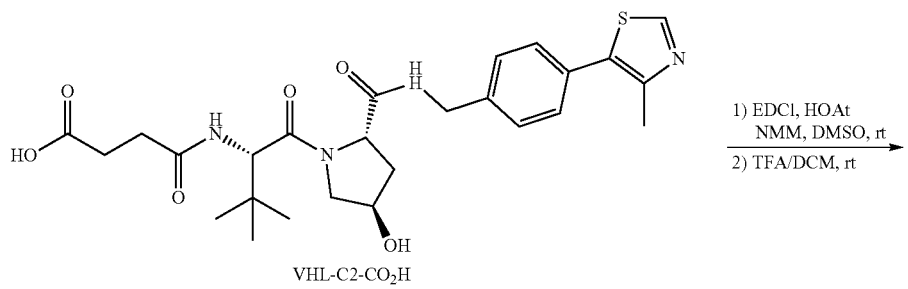

VHL-C2-CO$_2$H

1) EDCI, HOAt NMM, DMSO, rt
2) TFA/DCM, rt

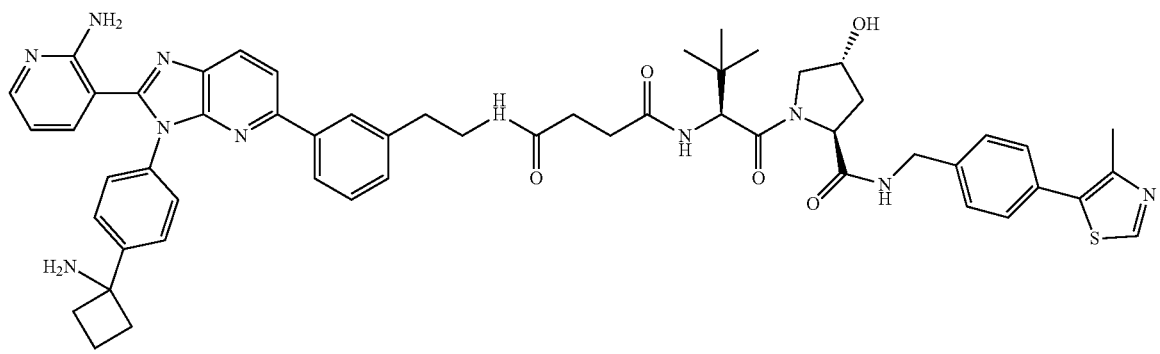

XF067-40

XF067-40 was synthesized following the standard procedure for preparing XF067-31 from intermediate 9 (9.3 mg, 0.016 mmol), VHL-C2-CO₂H (8.5 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-40 was obtained as white solid in TFA salt form (10.6 mg, 67%). ¹H NMR (800 MHz, CD₃OD) δ 8.97 (s, 1H), 8.32 (d, J=8.4 Hz, 1H), 8.04 (t, J=7.8 Hz, 2H), 7.95 (s, 1H), 7.90 (d, J=7.8 Hz, 1H), 7.84 (dd, J=27.5, 7.8 Hz, 3H), 7.73 (d, J=8.1 Hz, 2H), 7.47 (d, J=7.9 Hz, 2H), 7.42 (d, J=7.9 Hz, 2H), 7.41-7.35 (m, 1H), 7.30 (d, J=7.6 Hz, 1H), 6.84 (t, J=6.9 Hz, 1H), 4.64-4.47 (m, 4H), 4.38 (d, J=15.4 Hz, 1H), 3.90 (d, J=10.9 Hz, 1H), 3.85-3.74 (m, 1H), 3.51-3.41 (m, 2H), 2.96-2.85 (m, 4H), 2.77-2.69 (m, 2H), 2.58 (dt, J=14.3, 7.1 Hz, 1H), 2.54-2.41 (m, 6H), 2.39-2.31 (m, 1H), 2.23 (dd, J=13.2, 7.7 Hz, 1H), 2.13-2.03 (m, 2H), 1.07-0.99 (m, 9H). ESI-MS (m/z) [M+H]⁺: 988.4659.

Example 117

Synthesis of XF067-41

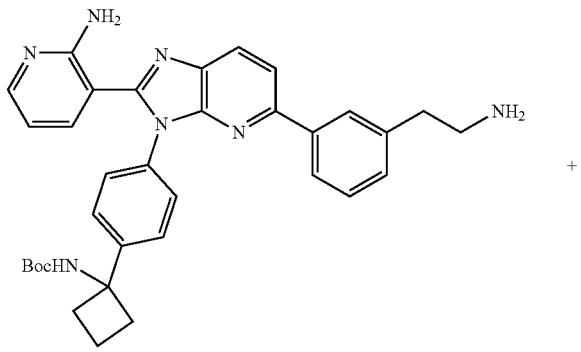

Intermediate 9

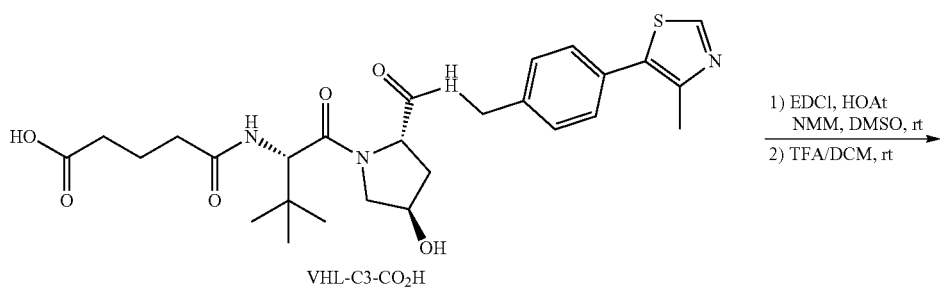

VHL-C3-CO₂H

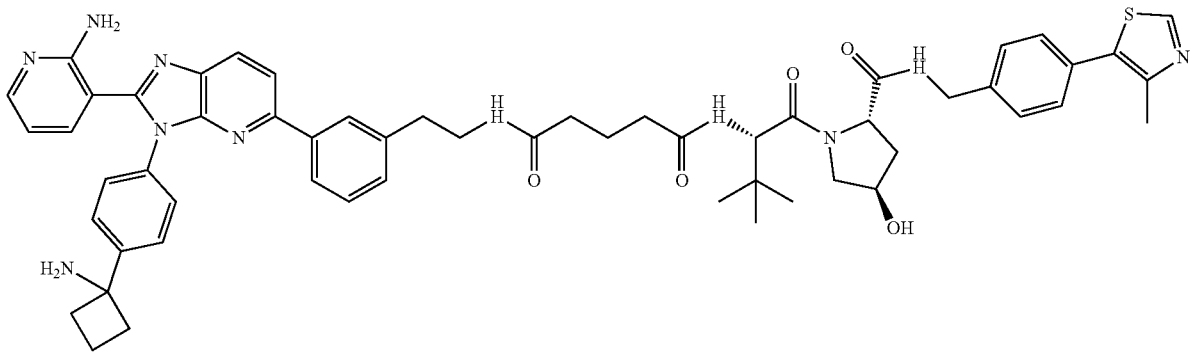

XF067-41

XF067-41 was synthesized following the standard procedure or preparing XF067-31 from intermediate 9 (9.3 mg, 0.016 mmol), VHL-C3-CO$_2$H (8.7 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-41 was obtained as white solid in TFA salt form (8.3 mg, 52%). $^1$H NMR (800 MHz, CD$_3$OD) δ 8.93 (d, J=29.3 Hz, 1H), 8.30 (dd, J=25.1, 8.4 Hz, 1H), 8.04 (t, J=6.3 Hz, 2H), 7.97 (s, 1H), 7.88 (dd, J=23.2, 7.7 Hz, 2H), 7.82 (d, J=8.0 Hz, 2H), 7.74 (d, J=8.0 Hz, 2H), 7.48 (d, J=7.8 Hz, 2H), 7.44-7.36 (m, 3H), 7.29 (d, J=7.5 Hz, 1H), 6.85 (s, 1H), 4.63-4.46 (m, 4H), 4.37 (d, J=15.4 Hz, 1H), 3.92 (d, J=10.9 Hz, 1H), 3.83 (dd, J=11.1, 4.1 Hz, 1H), 3.48 (hept, J=6.9, 6.2 Hz, 2H), 2.91 (dq, J=19.5, 7.9 Hz, 4H), 2.76-2.70 (m, 2H), 2.47 (s, 3H), 2.37 (ddt, J=28.9, 13.6, 5.6 Hz, 1H), 2.29-2.14 (m, 5H), 2.14-2.03 (m, 2H), 1.85 (p, J=7.5 Hz, 2H), 1.03 (s, 9H). ESI-MS (m/z) [M+H]$^+$: 1002.4811.

Example 118

Synthesis of XF067-42

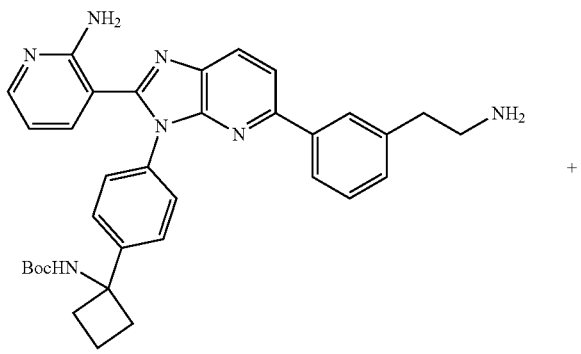

Intermediate 9

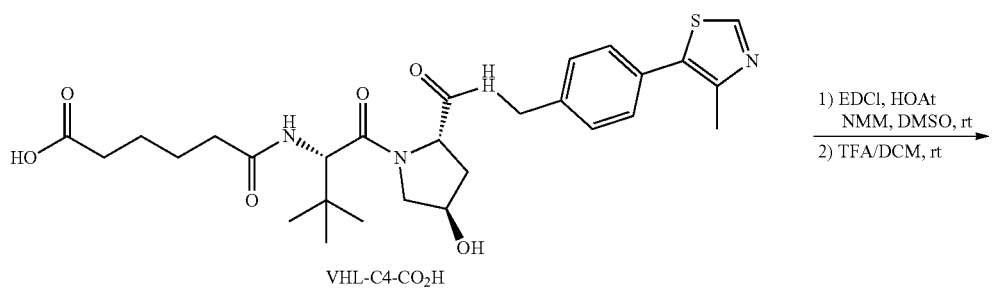

VHL-C4-CO$_2$H

1) EDCl, HOAt
NMM, DMSO, rt
2) TFA/DCM, rt

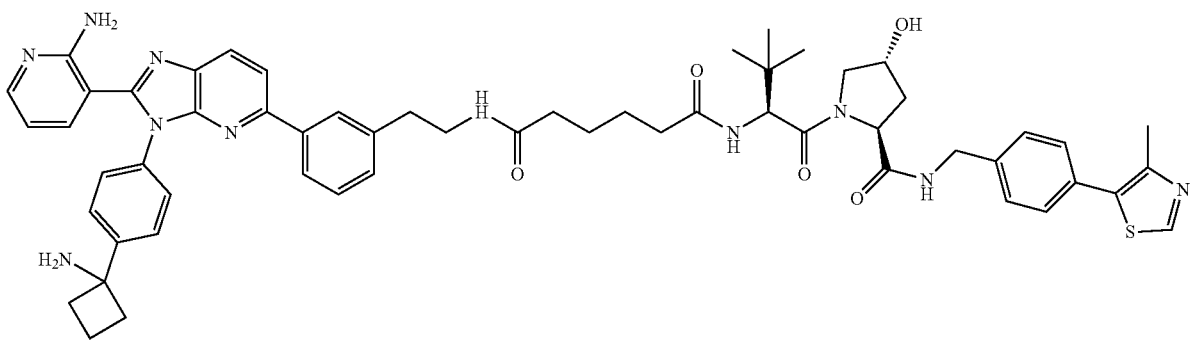

XF067-42

XF067-42 was synthesized following the standard procedure for preparing XF067-31 from intermediate 9 (9.3 mg, 0.016 mmol), VHL-C4-CO₂H (8.9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-42 was obtained as white solid in TFA salt form (6.7 mg, 41%). ¹H NMR (800 MHz, CD₃OD) δ 8.93 (s, 1H), 8.32 (d, J=8.4 Hz, 1H), 8.09-8.00 (m, 2H), 7.96 (s, 1H), 7.90 (d, J=7.8 Hz, 1H), 7.86 (d, J=7.7 Hz, 1H), 7.82 (d, J=8.1 Hz, 2H), 7.74 (d, J=8.1 Hz, 2H), 7.47 (d, J=7.8 Hz, 2H), 7.42 (d, J=7.9 Hz, 2H), 7.39 (q, J=7.9 Hz, 1H), 7.30 (d, J=7.5 Hz, 1H), 6.84 (t, J=6.9 Hz, 1H), 4.63 (s, 1H), 4.61-4.50 (m, 3H), 4.37 (d, J=15.4 Hz, 1H), 3.91 (d, J=10.9 Hz, 1H), 3.82 (dd, J=11.1, 4.1 Hz, 1H), 3.47 (t, J=7.5 Hz, 2H), 2.98-2.83 (m, 4H), 2.77-2.70 (m, 2H), 2.54-2.45 (m, 3H), 2.39-2.30 (m, 1H), 2.28-2.12 (m, 5H), 2.13-2.05 (m, 2H), 1.58 (q, J=9.0 Hz, 4H), 1.04 (s, 9H). ESI-MS (m/z) [M+H]⁺: 1016.4956.

Example 119

Synthesis of XF067-43

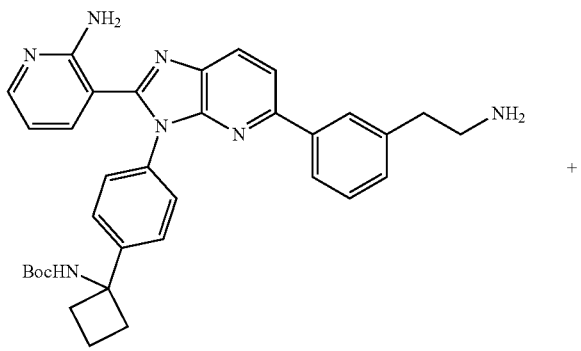

Intermediate 9

+

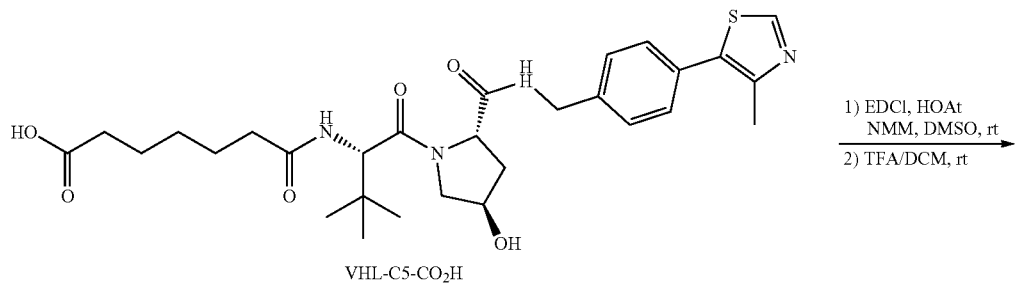

VHL-C5-CO₂H

1) EDCl, HOAt NMM, DMSO, rt
2) TFA/DCM, rt

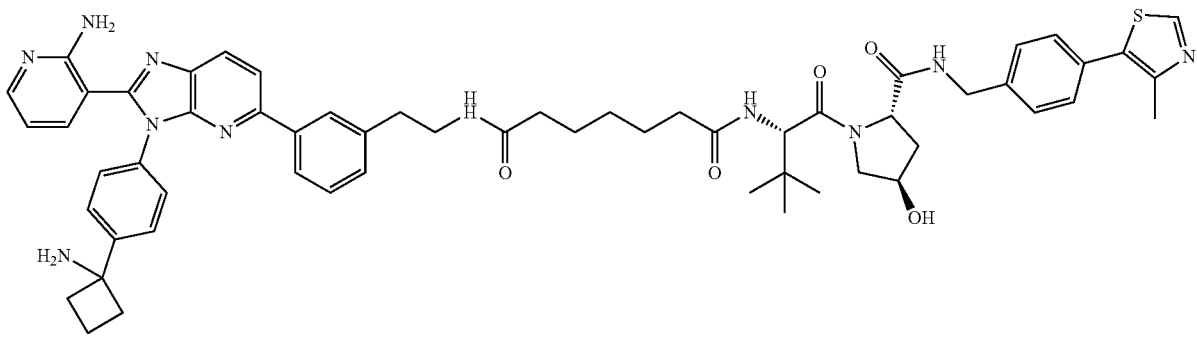

XF067-43

XF067-43 was synthesized following the standard procedure for preparing XF067-31 from intermediate 9 (9.3 mg, 0.016 mmol), VHL-C5-CO₂H (9.2 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-43 was obtained as white solid in TFA salt form (8.6 mg, 52%). ¹H NMR (800 MHz, CD₃OD) δ 8.94 (s, 1H), 8.32 (d, J=8.3 Hz, 1H), 8.09-7.99 (m, 2H), 7.96 (s, 1H), 7.90 (d, J=7.9 Hz, 1H), 7.87 (d, J=7.7 Hz, 1H), 7.82 (d, J=8.1 Hz, 2H), 7.74 (d, J=8.1 Hz, 2H), 7.48 (d, J=7.9 Hz, 2H), 7.43 (d, J=7.9 Hz, 2H), 7.39 (t, J=7.7 Hz, 1H), 7.30 (d, J=7.6 Hz, 1H), 6.85 (t, J=6.9 Hz, 1H), 4.63 (s, 1H), 4.61-4.49 (m, 3H), 4.40-4.34 (m, 1H), 3.91 (d, J=10.9 Hz, 1H), 3.81 (dd, J=11.1, 4.1 Hz, 1H), 3.47 (q, J=7.8 Hz, 2H), 2.91 (dq, J=19.4, 8.3, 7.5 Hz, 4H), 2.72 (dt, J=14.0, 8.4 Hz, 2H), 2.49 (s, 3H), 2.34 (dp, J=21.6, 7.1 Hz, 1H), 2.23 (tt, J=12.3, 5.8 Hz, 2H), 2.16 (dt, J=19.4, 7.4 Hz, 3H), 2.13-2.04 (m, 2H), 1.54 (dp, J=18.7, 7.2 Hz, 4H), 1.27 (p, J=9.1, 8.4 Hz, 2H), 1.04 (s, 9H). ESI-MS (m/z) [M+H]⁺: 1030.5126.

Example 120

Synthesis of XF067-44

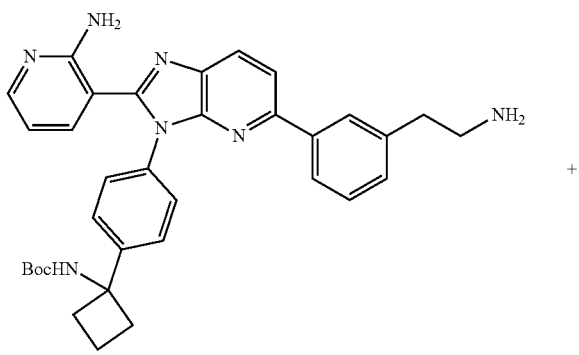

Intermediate 9

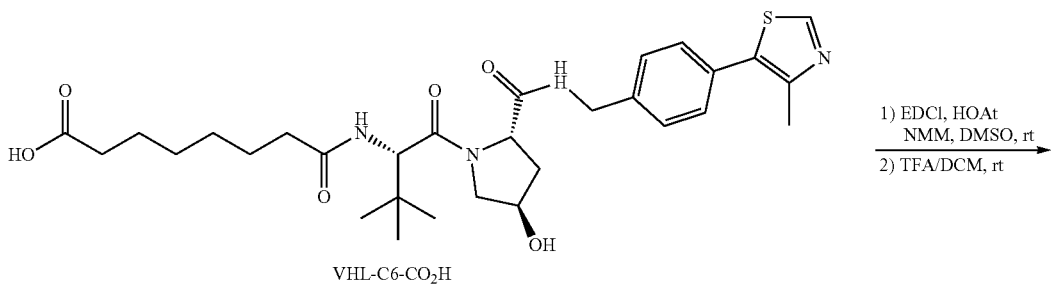

VHL-C6-CO₂H

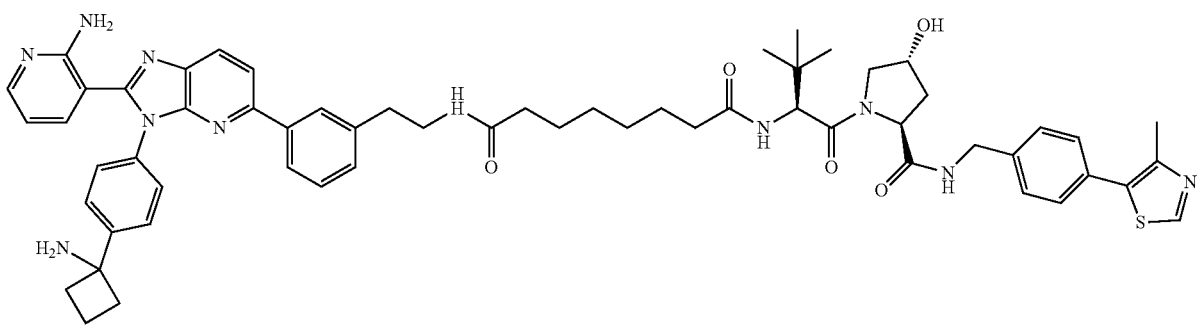

XF067-44

XF067-44 was synthesized following the standard procedure for preparing XF067-31 from intermediate 9 (9.3 mg, 0.016 mmol), VHL-C6-CO$_2$H (9.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-44 was obtained as white solid in TFA salt form (8.4 mg, 50%). $^1$H NMR (800 MHz, CD$_3$OD) δ 8.95 (s, 1H), 8.32 (d, J=8.3 Hz, 1H), 8.04 (h, J=4.3 Hz, 2H), 7.96 (s, 1H), 7.90 (d, J=7.9 Hz, 1H), 7.86 (d, J=7.5 Hz, 1H), 7.82 (d, J=8.1 Hz, 2H), 7.77-7.70 (m, 2H), 7.48 (d, J=7.8 Hz, 2H), 7.43 (d, J=7.8 Hz, 2H), 7.41-7.35 (m, 1H), 7.30 (d, J=7.5 Hz, 1H), 6.85 (t, J=6.9 Hz, 1H), 4.64 (s, 1H), 4.62-4.48 (m, 3H), 4.38 (d, J=15.5 Hz, 1H), 3.92 (d, J=10.9 Hz, 1H), 3.82 (dd, J=11.1, 4.1 Hz, 1H), 3.47 (t, J=7.4 Hz, 2H), 2.89 (dhept, J=16.3, 8.1 Hz, 4H), 2.72 (dt, J=14.1, 8.5 Hz, 2H), 2.53-2.44 (m, 3H), 2.39-2.28 (m, 1H), 2.27-2.03 (m, 7H), 1.59-1.49 (m, 4H), 1.26 (p, J=3.8 Hz, 4H), 1.04 (s, 9H). ESI-MS (m/z) [M+H]$^+$: 1044.5289.

Example 121

Synthesis of XF067-45

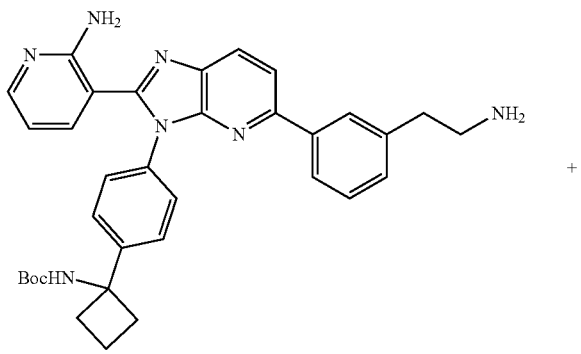

Intermediate 9

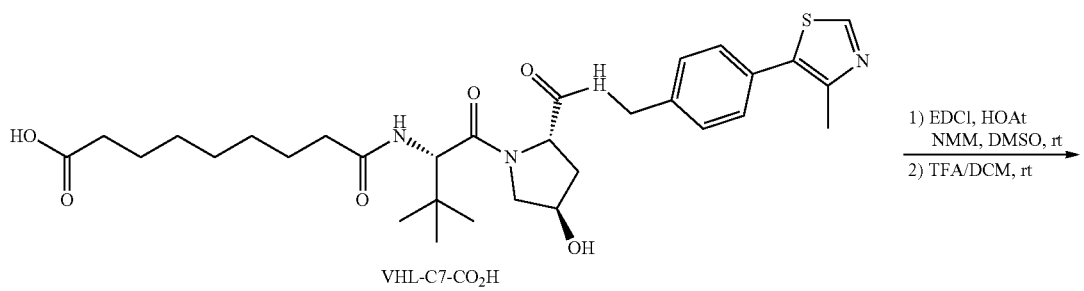

VHL-C7-CO$_2$H

1) EDCI, HOAt NMM, DMSO, rt
2) TFA/DCM, rt

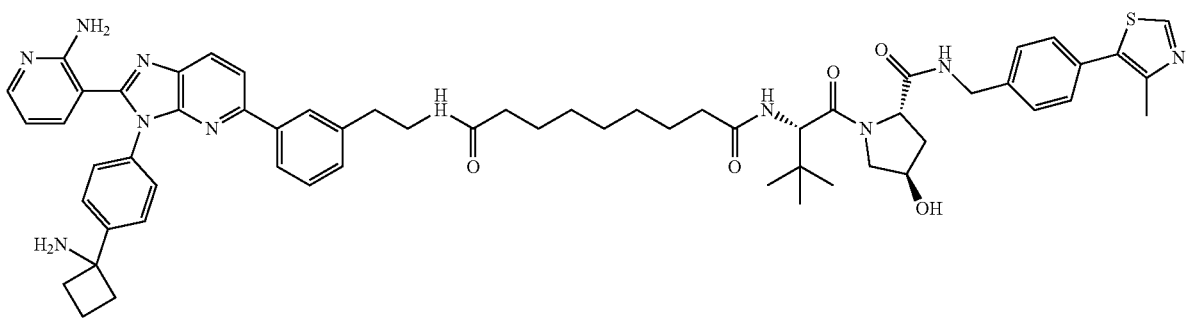

XF067-45

XF067-45 was synthesized following the standard procedure for preparing XF067-31 from intermediate 9 (9.3 mg, 0.016 mmol), VHL-C7-CO₂H (9.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-45 was obtained as white solid in TFA salt form (5.4 mg, 32%). ¹H NMR (800 MHz, CD₃OD) δ 8.93 (s, 1H), 8.32 (d, J=7.4 Hz, 1H), 8.07-7.67 (m, 9H), 7.55-7.22 (m, 6H), 6.84 (s, 1H), 4.70-4.45 (m, 4H), 4.38 (dd, J=15.3, 6.4 Hz, 1H), 3.91 (t, J=8.7 Hz, 1H), 3.82 (p, J=4.2 Hz, 1H), 3.47 (q, J=7.6 Hz, 2H), 2.97-2.84 (m, 4H), 2.72 (dq, J=13.8, 8.0 Hz, 2H), 2.49 (s, 3H), 2.34 (s, 1H), 2.30-2.01 (m, 7H), 1.54 (dd, J=13.8, 7.0 Hz, 4H), 1.32-1.11 (m, 6H), 1.15-0.94 (m, 9H). ESI-MS (m/z) [M+H]⁺: 1058.5451.

Example 122

Synthesis of XF067-46

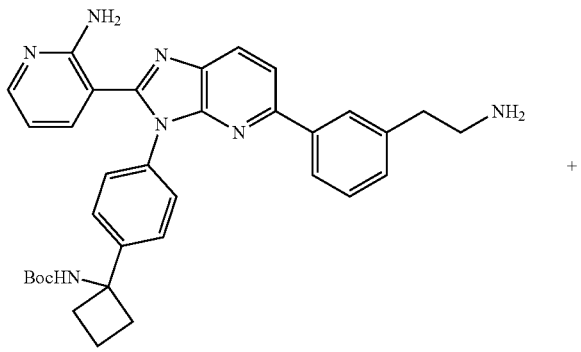

Intermediate 9

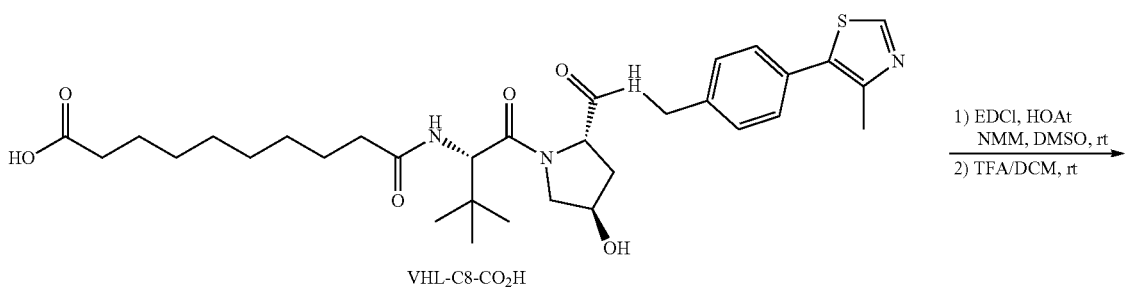

VHL-C8-CO₂H

1) EDCl, HOAt NMM, DMSO, rt
2) TFA/DCM, rt

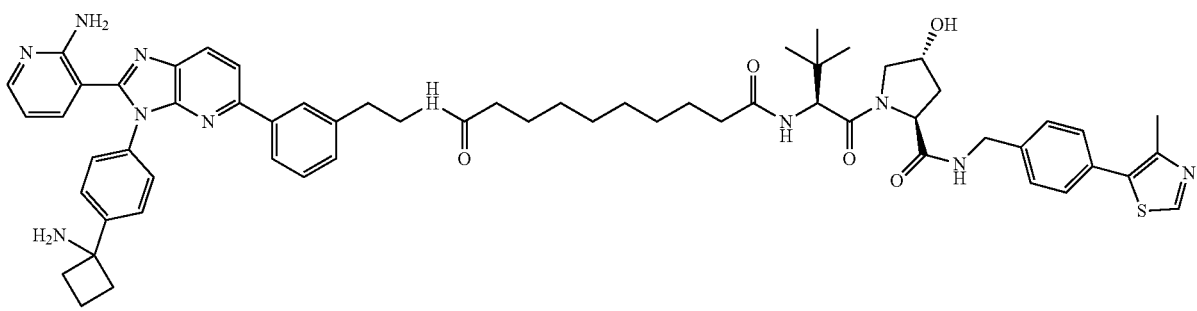

XF067-46

XF067-46 was synthesized following the standard procedure for preparing XF067-31 from intermediate 9 (9.3 mg, 0.016 mmol), VHL-C8-CO₂H (9.8 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-46 was obtained as white solid in TFA salt form (5.3 mg, 31%). $^1$H NMR (800 MHz, CD$_3$OD) δ 8.94 (s, 1H), 8.33 (d, J=8.4 Hz, 1H), 8.05 (dd, J=8.4, 4.7 Hz, 2H), 7.96 (s, 1H), 7.90 (d, J=7.7 Hz, 1H), 7.86 (d, J=7.6 Hz, 1H), 7.82 (d, J=8.0 Hz, 2H), 7.74 (d, J=8.0 Hz, 2H), 7.48 (d, J=7.8 Hz, 2H), 7.43 (d, J=7.8 Hz, 2H), 7.38 (t, J=7.7 Hz, 1H), 7.30 (d, J=7.6 Hz, 1H), 6.84 (s, 1H), 4.68-4.62 (m, 1H), 4.63-4.47 (m, 3H), 4.38 (d, J=15.4 Hz, 1H), 3.92 (d, J=10.9 Hz, 1H), 3.82 (dd, J=11.1, 4.1 Hz, 1H), 3.47 (q, J=7.7 Hz, 2H), 2.94-2.86 (m, 4H), 2.72 (q, J=12.3, 10.3 Hz, 2H), 2.49 (d, J=4.6 Hz, 3H), 2.34 (d, J=10.5 Hz, 1H), 2.25 (ddt, J=36.7, 14.8, 7.5 Hz, 3H), 2.19-2.03 (m, 4H), 1.56 (ddd, J=32.8, 14.0, 7.1 Hz, 4H), 1.23 (s, 8H), 1.05 (s, 9H). ESI-MS (m/z) [M+H]⁺: 1072.5593.

Example 123

Synthesis of XF067-47

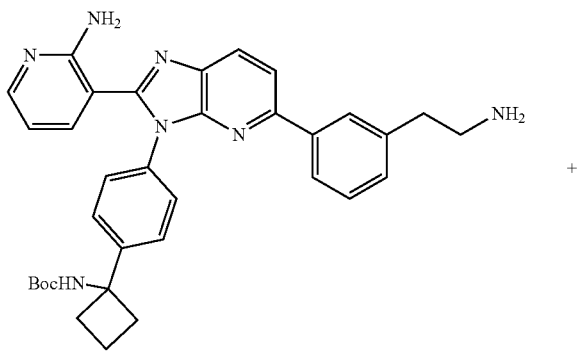

Intermediate 9

+

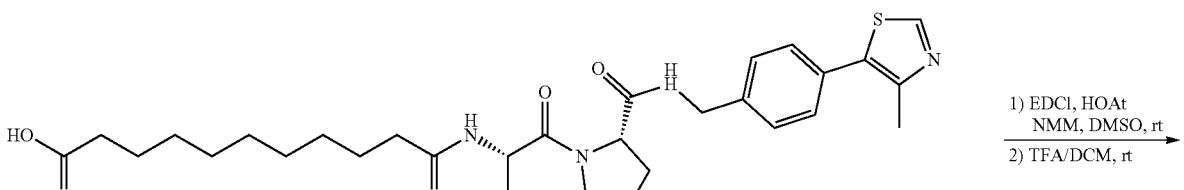

VHLC9-CO₂H

1) EDCl, HOAt NMM, DMSO, rt
2) TFA/DCM, rt

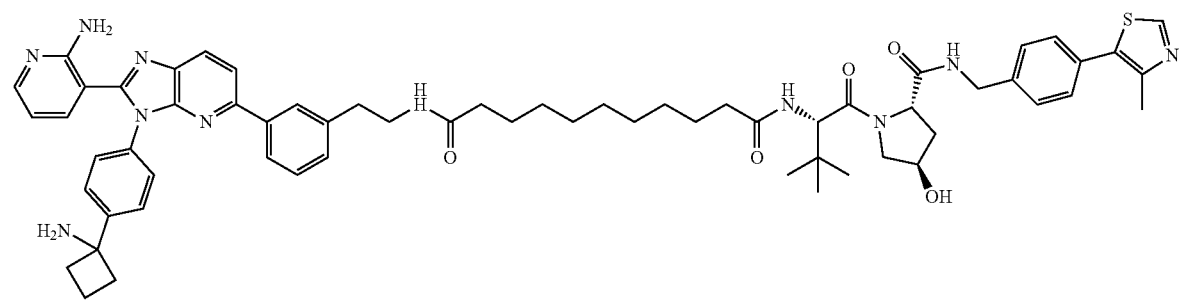

XF067-47 was synthesized following the standard procedure for preparing XF067-31 from intermediate 9 (9.3 mg, 0.016 mmol), VHL-C9-CO₂H (10 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-47 was obtained as white solid in TFA salt form (8.4 mg, 48%). ¹H NMR (800 MHz, CD₃OD) δ 8.92 (s, 1H), 8.32 (d, J=8.0 Hz, 1H), 8.05 (d, J=8.2 Hz, 2H), 7.96 (s, 1H), 7.90 (d, J=7.6 Hz, 1H), 7.82 (t, J=8.4 Hz, 3H), 7.73 (d, J=8.1 Hz, 2H), 7.55-7.35 (m, 5H), 7.30 (d, J=7.4 Hz, 1H), 6.82 (s, 1H), 4.65 (s, 1H), 4.61-4.47 (m, 3H), 4.38 (d, J=15.4 Hz, 1H), 3.92 (d, J=10.7 Hz, 1H), 3.82 (dd, J=11.1, 4.0 Hz, 1H), 3.48 (t, J=7.4 Hz, 2H), 2.98-2.84 (m, 4H), 2.78-2.66 (m, 2H), 2.49 (s, 3H), 2.40-2.20 (m, 5H), 2.20-2.01 (m, 3H), 1.68-1.45 (m, 4H), 1.22 (s, 10H), 1.04 (s, 9H). ESI-MS (m/z) [M+H]⁺: 1086.5765.

Example 124

Synthesis of XF067-48

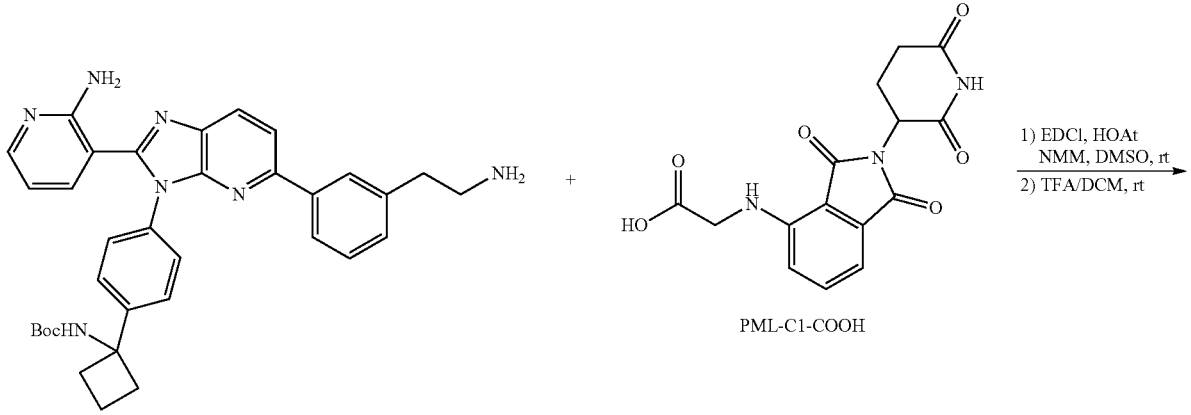

Intermediate 9

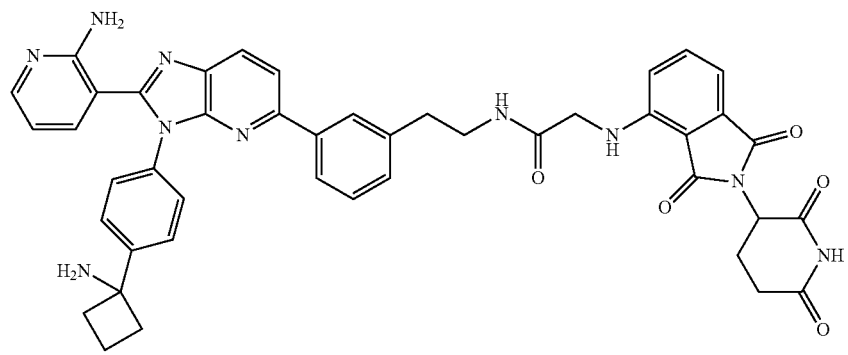

XF067-48

XF067-48 was synthesized following the standard procedure for preparing XF067-31 from intermediate 9 (9.3 mg, 0.016 mmol), PML-C1-CO$_2$H (5.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-48 was obtained as yellow solid in TFA salt form (5.3 mg, 42%). $^1$H NMR (800 MHz, CD$_3$OD) δ 8.28 (d, J=8.4 Hz, 1H), 8.03 (d, J=6.0 Hz, 1H), 7.99 (d, J=8.4 Hz, 1H), 7.88 (d, J=5.7 Hz, 2H), 7.78 (d, J=8.1 Hz, 2H), 7.73 (d, J=7.7 Hz, 1H), 7.67 (d, J=8.0 Hz, 2H), 7.35 (t, J=7.8 Hz, 1H), 7.27-7.20 (m, 2H), 6.86 (d, J=7.2 Hz, 1H), 6.77 (t, J=6.8 Hz, 1H), 6.62 (d, J=8.4 Hz, 1H), 5.06 (dd, J=12.8, 5.5 Hz, 1H), 3.91 (s, 2H), 3.58 (hept, J=6.7 Hz, 2H), 2.94-2.85 (m, 5H), 2.79-2.67 (m, 4H), 2.34-2.30 (m, 1H), 2.16-1.98 (m, 2H). ESI-MS (m/z) [M+H]$^+$: 789.3244.

Example 125

Synthesis of XF067-49

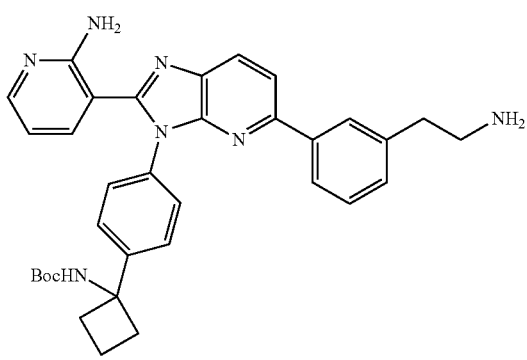

Intermediate 9

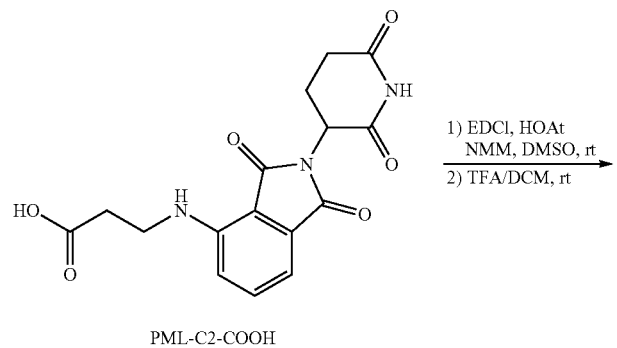

PML-C2-COOH

1) EDCI, HOAt NMM, DMSO, rt
2) TFA/DCM, rt

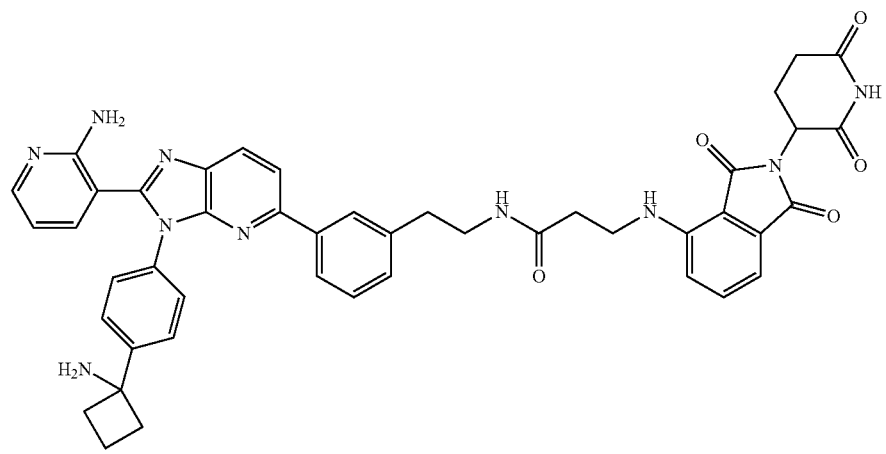

XF067-49

XF067-49 was synthesized following the standard procedure for preparing XF067-31 from intermediate 9 (9.3 mg, 0.016 mmol), PML-C2-CO$_2$H (5.5 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-49 was obtained as yellow solid in TFA salt form (7.4 mg, 58%). $^1$H NMR (800 MHz, CD$_3$OD) δ 8.26 (d, J=8.4 Hz, 1H), 8.05-7.99 (m, 2H), 7.94 (s, 1H), 7.88 (d, J=7.8 Hz, 1H), 7.82-7.78 (m, 3H), 7.68 (d, J=8.0 Hz, 2H), 7.43-7.33 (m, 2H), 7.28 (d, J=7.5 Hz, 1H), 6.97 (d, J=7.1 Hz, 1H), 6.89 (d, J=8.5 Hz, 1H), 6.85-6.76 (m, 1H), 5.01 (dd, J=12.5, 5.3 Hz, 1H), 3.48 (q, J=7.9 Hz, 4H), 2.94-2.88 (m, 2H), 2.87 (t, J=7.3 Hz, 2H), 2.80 (ddd, J=19.2, 14.3, 5.4 Hz, 1H), 2.71 (td, J=14.1, 11.7, 7.2 Hz, 2H), 2.70-2.61 (m, 2H), 2.46 (t, J=6.7 Hz, 2H), 2.37-2.30 (m, 1H), 2.06-2.03 (m, 2H). ESI-MS (m/z) [M+H]$^+$: 803.3419.

Example 126

Synthesis of XF067-50

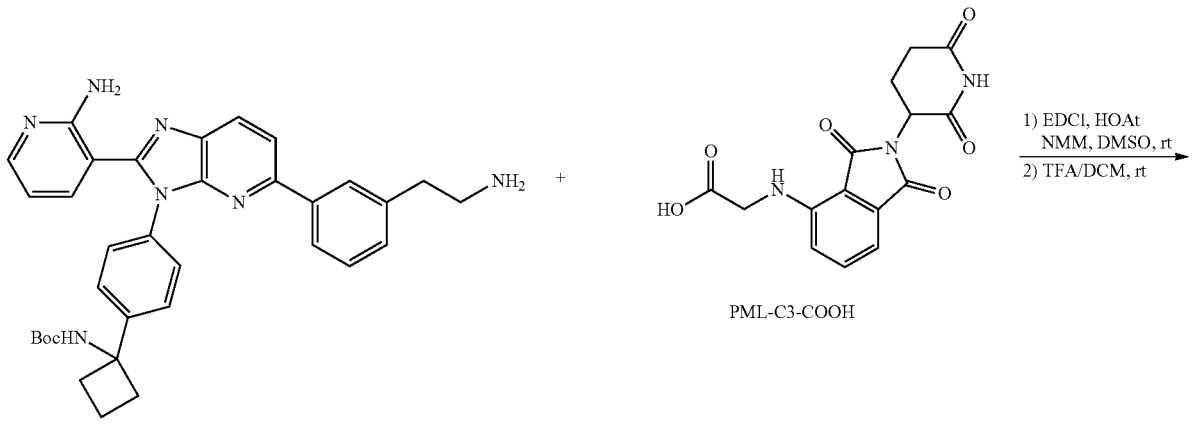

Intermediate 9

PML-C3-COOH

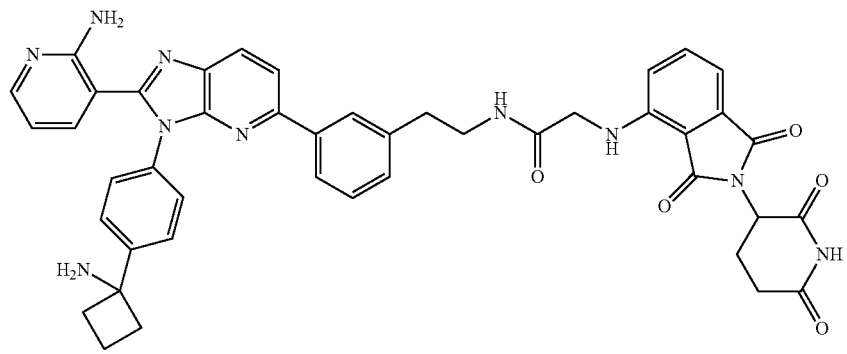

XF067-50

XF06-50 was synthesized following the standard procedure or preparing XF067-31 from intermediate 9 (9.3 mg, 0.016 mmol), PML-C3-CO₂H (5.7 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-50 was obtained as yellow solid in TFA salt form (8.5 mg, 65%). ¹H NMR (800 MHz, CD₃OD) δ 8.24 (d, J=8.4 Hz, 1H), 8.03 (d, J=6.2 Hz, 1H), 8.00-7.95 (m, 2H), 7.85 (d, J=7.8 Hz, 1H), 7.79 (dd, J=14.6, 7.7 Hz, 3H), 7.68 (t, J=6.1 Hz, 2H), 7.37 (dt, J=16.3, 7.7 Hz, 2H), 7.31 (d, J=7.5 Hz, 1H), 6.94-6.87 (m, 1H), 6.82 (t, J=6.9 Hz, 1H), 6.77 (d, J=8.5 Hz, 1H), 4.99 (dt, J=13.5, 6.3 Hz, 1H), 3.53 (p, J=6.7 Hz, 2H), 3.07 (t, J=7.3 Hz, 2H), 2.91 (p, J=8.3, 7.8 Hz, 4H), 2.79 (ddd, J=18.3, 13.8, 5.1 Hz, 1H), 2.76-2.62 (m, 4H), 2.35-2.30 (m, 1H), 2.22 (t, J=7.2 Hz, 2H), 2.06 (s, 2H), 1.79 (p, J=7.3 Hz, 2H). ESI-MS (m/z) [M+H]⁺: 817.3576.

Example 127

Synthesis of XF067-51

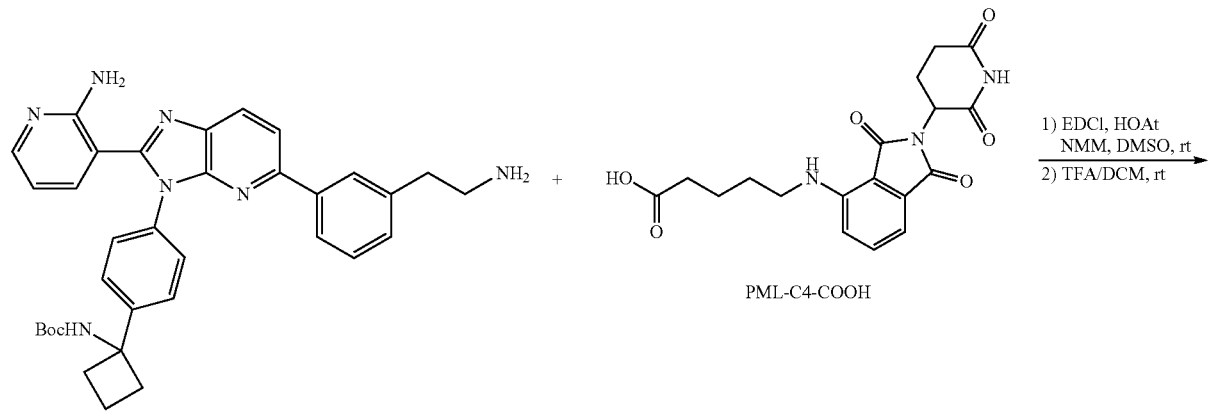

Intermediate 9

PML-C4-COOH

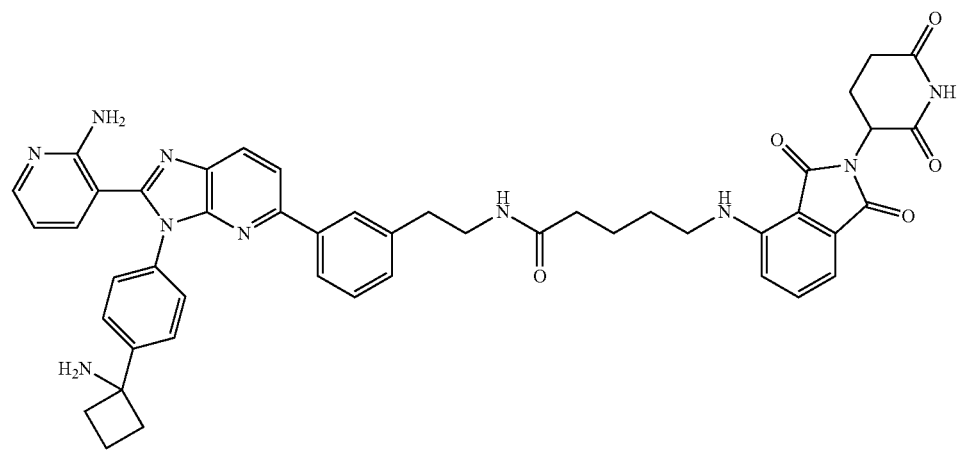

XF067-51

XF067-51 was synthesized following the standard procedure for preparing XF067-31 from intermediate 9 (9.3 mg, 0.016 mmol), PML-C4-CO₂H (6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-51 was obtained as yellow solid in TFA salt form (7.6 mg, 57%). ¹H NMR (800 MHz, CD₃OD) δ 8.25 (d, J=8.4 Hz, 1H), 8.02 (dd, J=24.9, 7.3 Hz, 2H), 7.94 (s, 1H), 7.87 (d, J=7.8 Hz, 1H), 7.79 (dd, J=11.5, 7.6 Hz, 3H), 7.68 (d, J=8.0 Hz, 2H), 7.43 (t, J=7.8 Hz, 1H), 7.38 (t, J=7.7 Hz, 1H), 7.31 (d, J=7.6 Hz, 1H), 6.98-6.93 (m, 1H), 6.81 (dd, J=20.2, 7.7 Hz, 2H), 5.08-5.02 (m, 1H), 3.53 (t, J=7.1 Hz, 2H), 3.06 (t, J=7.1 Hz, 2H), 2.95-2.82 (m, 5H), 2.79-2.68 (m, 4H), 2.33 (tq, J=16.4, 7.0 Hz, 1H), 2.18 (t, J=7.2 Hz, 2H), 2.12 (dd, J=12.5, 5.8 Hz, 1H), 2.10-2.02 (m, 1H), 1.58 (p, J=7.3 Hz, 2H), 1.44 (p, J=7.3 Hz, 2H). ESI-MS (m/z) [M+H]⁺: 831.3715.

Example 128

Synthesis of XF067-52

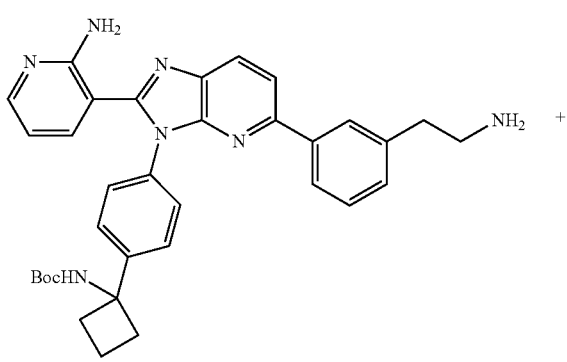

Intermediate 9

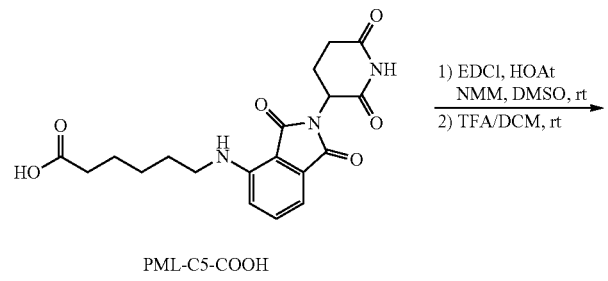

PML-C5-COOH

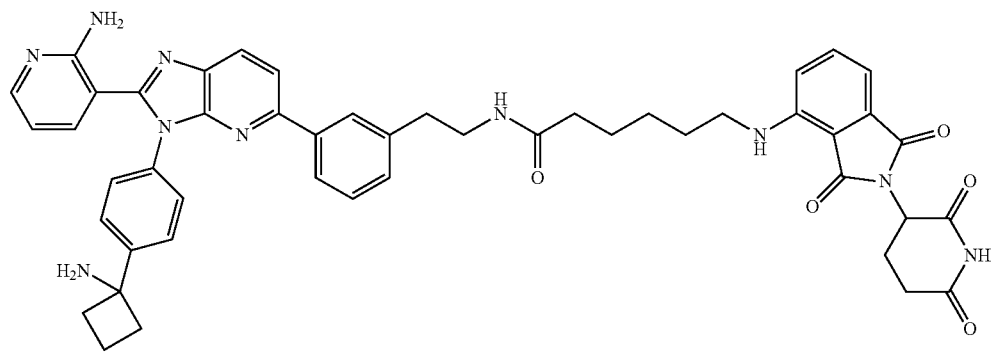

XF067-52

XF067-52 was synthesized following the standard procedure for preparing XF067-31 from intermediate 9 (9.3 mg, 0.016 mmol), PML-C5-CO$_2$H (6.2 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-52 was obtained as yellow solid in TFA salt form (9.2 mg, 68%). $^1$H NMR (800 MHz, CD$_3$OD) δ 8.28 (d, J=8.4 Hz, 1H), 8.03 (dd, J=12.4, 7.3 Hz, 2H), 7.95 (s, 1H), 7.90 (d, J=7.8 Hz, 1H), 7.79 (d, J=8.0 Hz, 2H), 7.75 (d, J=7.6 Hz, 1H), 7.68 (d, J=8.0 Hz, 2H), 7.45 (t, J=7.8 Hz, 1H), 7.39 (t, J=7.7 Hz, 1H), 7.31 (d, J=7.5 Hz, 1H), 6.97-6.91 (m, 1H), 6.84-6.78 (m, 2H), 4.99 (dd, J=12.7, 5.4 Hz, 1H), 3.52 (t, J=7.1 Hz, 2H), 3.07 (t, J=7.2 Hz, 2H), 2.94-2.86 (m, 5H), 2.79 (ddd, J=18.2, 13.6, 5.3 Hz, 1H), 2.74-2.70 (m, 2H), 2.67 (dtd, J=31.0, 13.2, 11.6, 4.3 Hz, 2H), 2.33 (dt, J=11.5, 6.0 Hz, 1H), 2.16 (t, J=7.2 Hz, 2H), 2.10-2.01 (m, 1H), 1.55 (q, J=7.5 Hz, 2H), 1.47 (q, J=7.4 Hz, 2H), 1.27-1.22 (m, 2H). ESI-MS (m/z) [M+H]$^+$: 845.3876.

Example 129

Synthesis of XF067-53

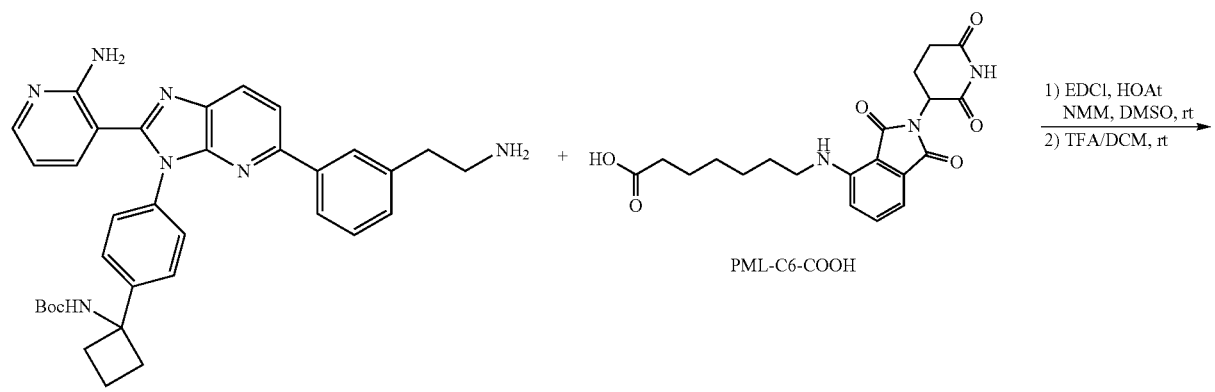

Intermediate 9    PML-C6-COOH

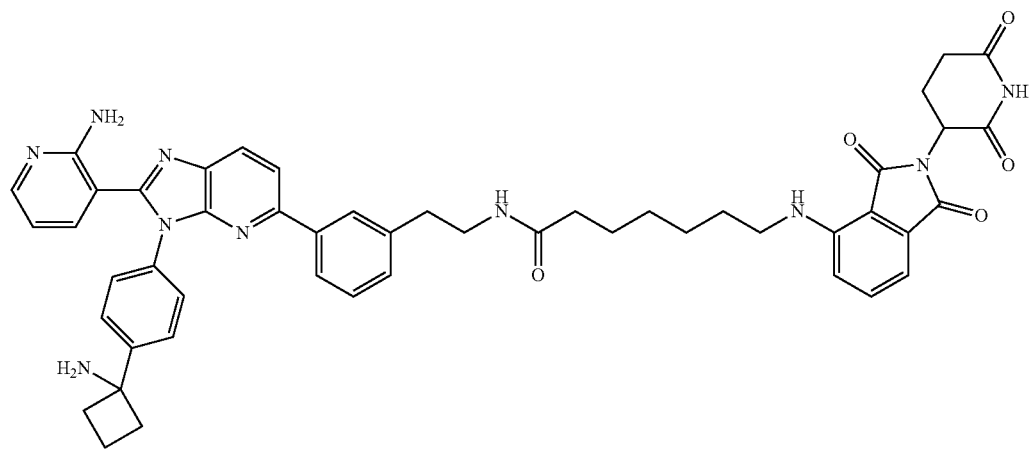

XF067-53

XF067-53 was synthesized following the standard procedure for preparing XF067-31 from intermediate 9 (9.3 mg, 0.016 mmol), PML-C6-CO$_2$H (6.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-53 was obtained as yellow solid in TFA salt form (8.3 mg, 60%). $^1$H NMR (800 MHz, CD$_3$OD) δ 8.29 (d, J=8.4 Hz, 1H), 8.02 (dd, J=12.1, 7.0 Hz, 2H), 7.94 (s, 1H), 7.89 (d, J=7.8 Hz, 1H), 7.80 (d, J=8.0 Hz, 2H), 7.75 (d, J=7.7 Hz, 1H), 7.69 (d, J=8.0 Hz, 2H), 7.47 (t, J=7.8 Hz, 1H), 7.38 (t, J=7.7 Hz, 1H), 7.31 (d, J=7.6 Hz, 1H), 6.96 (d, J=7.1 Hz, 1H), 6.90 (d, J=8.5 Hz, 1H), 6.79 (s, 1H), 5.06 (dd, J=12.6, 5.4 Hz, 1H), 3.52 (t, J=7.1 Hz, 2H), 3.11 (t, J=7.2 Hz, 2H), 2.94-2.83 (m, 5H), 2.78-2.68 (m, 4H), 2.33 (dq, J=16.3, 8.6, 7.9 Hz, 1H), 2.17-2.08 (m, 3H), 2.07-2.05 (m, 1H), 1.53 (q, J=7.5 Hz, 2H), 1.46 (p, J=7.3 Hz, 2H), 1.26 (q, J=7.5 Hz, 2H), 1.21 (q, J=7.7 Hz, 2H). ESI-MS (m/z) [M+H]$^+$: 859.4025.

Example 130

Synthesis of XF067-54

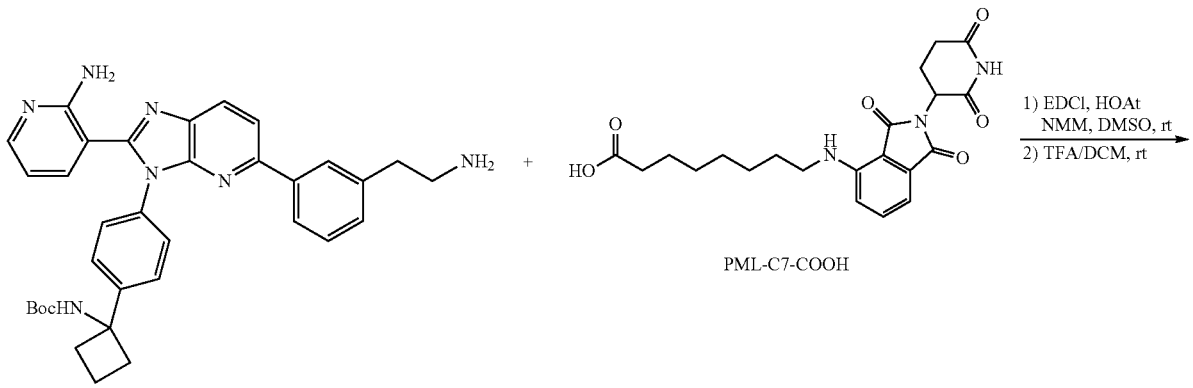

Intermediate 9     PML-C7-COOH

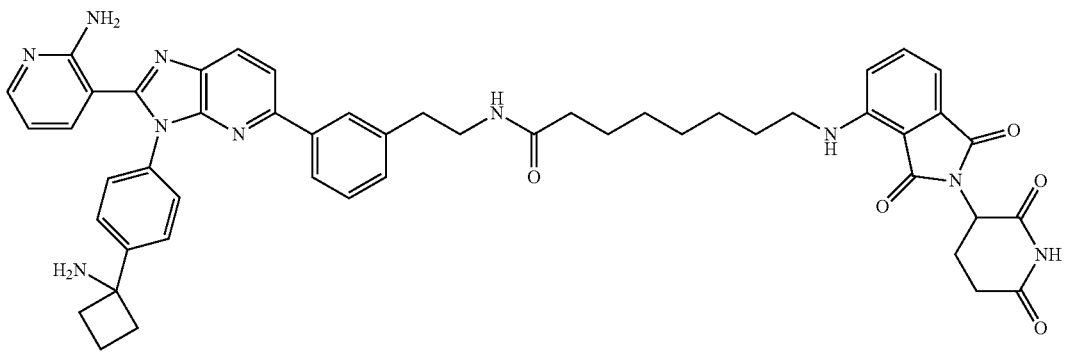

XF067-54

XF067-54 was synthesized following the standard procedure for preparing XF067-31 from intermediate 9 (9.3 mg, 0.016 mmol), PML-C7-CO$_2$H (6.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-54 was obtained as yellow solid in TFA salt form (9.2 mg, 66%). $^1$H NMR (800 MHz, CD$_3$OD) δ 8.31 (d, J=8.3 Hz, 1H), 8.05 (d, J=8.3 Hz, 1H), 8.01 (d, J=6.2 Hz, 1H), 7.94 (s, 1H), 7.91 (d, J=7.8 Hz, 1H), 7.79 (dd, J=26.9, 7.8 Hz, 3H), 7.71 (d, J=8.0 Hz, 2H), 7.50 (t, J=7.8 Hz, 1H), 7.38 (t, J=7.7 Hz, 1H), 7.30 (d, J=7.6 Hz, 1H), 6.99 (t, J=5.9 Hz, 1H), 6.94 (d, J=8.5 Hz, 1H), 6.80 (t, J=6.9 Hz, 1H), 5.07-5.01 (m, 1H), 3.51 (t, J=7.2 Hz, 2H), 3.16 (t, J=7.2 Hz, 2H), 2.91 (h, J=7.5 Hz, 4H), 2.84 (ddd, J=18.0, 13.6, 5.3 Hz, 1H), 2.77-2.66 (m, 4H), 2.34 (tq, J=15.8, 7.4, 7.0 Hz, 1H), 2.14 (t, J=7.4 Hz, 2H), 2.12-2.05 (m, 2H), 1.51 (qt, J=11.1, 5.5 Hz, 4H), 1.26 (q, J=7.4 Hz, 2H), 1.21 (tq, J=11.0, 6.8, 6.0 Hz, 4H). ESI-MS (m/z) [M+H]$^+$: 873.4187.

Example 131

Synthesis of XF067-55

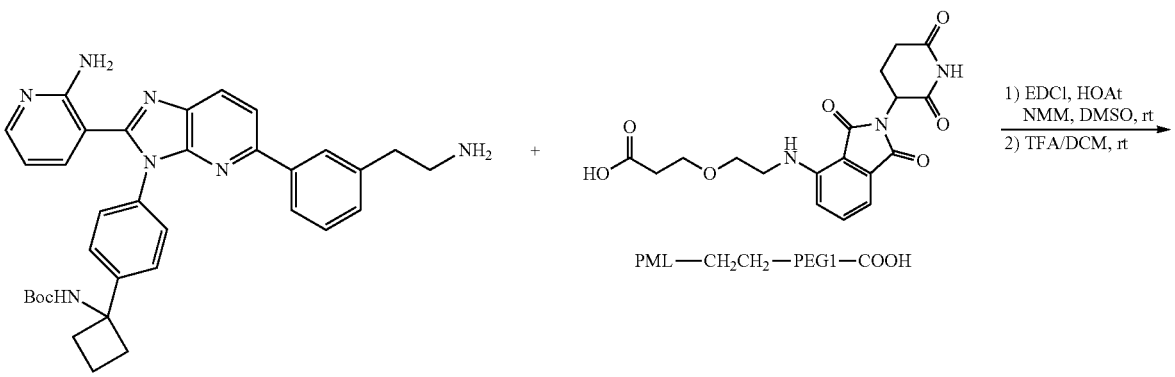

Intermediate 9

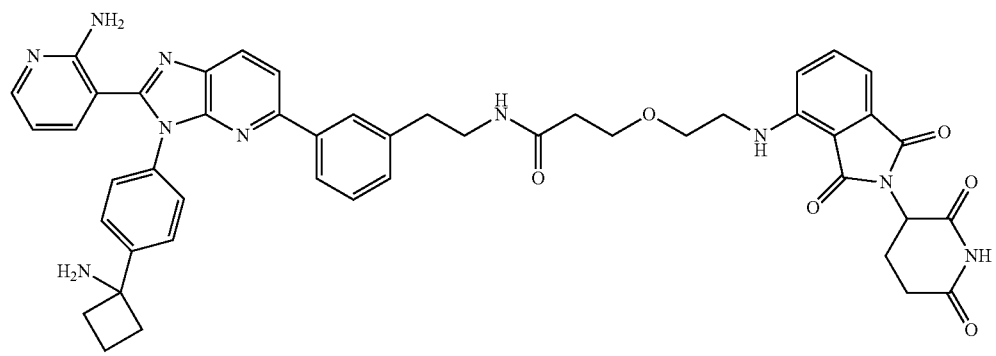

XF067-55

XF067-55 was synthesized following the standard procedure for preparing XF067-31 from intermediate 9 (9.3 mg, 0.016 mmol), PML-CH$_2$CH$_2$-PEG1-CO$_2$H (6.2 mg, 0.016 mmol), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-55 was obtained as yellow solid in TFA salt form (7.7 mg, 57%). $^1$H NMR (800 MHz, CD$_3$OD) δ 8.28 (d, J=8.3 Hz, 1H), 8.02 (dd, J=11.4, 7.2 Hz, 2H), 7.97 (s, 1H), 7.87 (d, J=7.7 Hz, 1H), 7.80 (dd, J=8.0, 5.0 Hz, 3H), 7.70 (d, J=8.0 Hz, 2H), 7.48 (t, J=7.8 Hz, 1H), 7.39-7.33 (m, 1H), 7.28 (d, J=7.5 Hz, 1H), 6.96 (t, J=7.6 Hz, 2H), 6.82 (t, J=6.9 Hz, 1H), 4.88-4.77 (m, 1H), 3.76-3.70 (m, 2H), 3.58 (t, J=5.1 Hz, 2H), 3.49 (t, J=7.5 Hz, 2H), 3.36 (t, J=5.2 Hz, 2H), 2.89 (dt, J=15.1, 11.1 Hz, 5H), 2.73-2.69 (m, 2H), 2.62-2.52 (m, 2H), 2.45 (t, J=5.8 Hz, 2H), 2.37-2.29 (m, 1H), 2.10-2.04 (m, 1H), 1.89 (d, J=12.6 Hz, 1H). ESI-MS (m/z) [M+H]$^+$: 847.3673.

Example 132

Synthesis of XF067-56

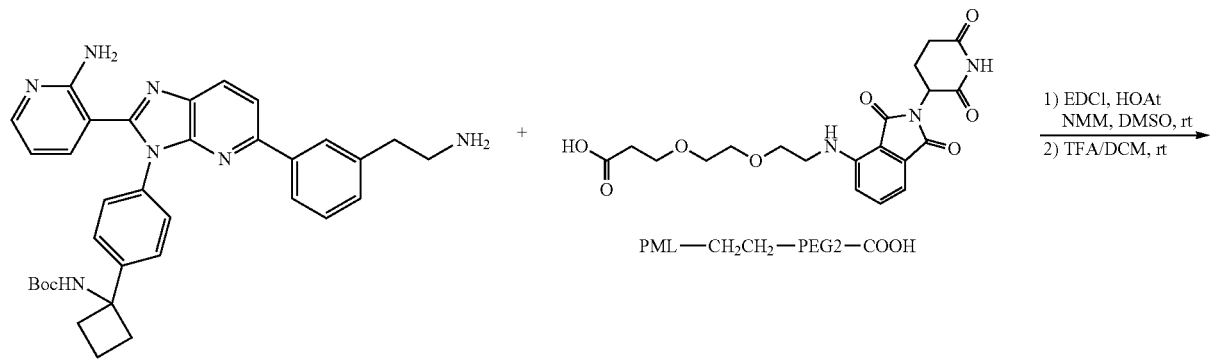

Intermediate 9

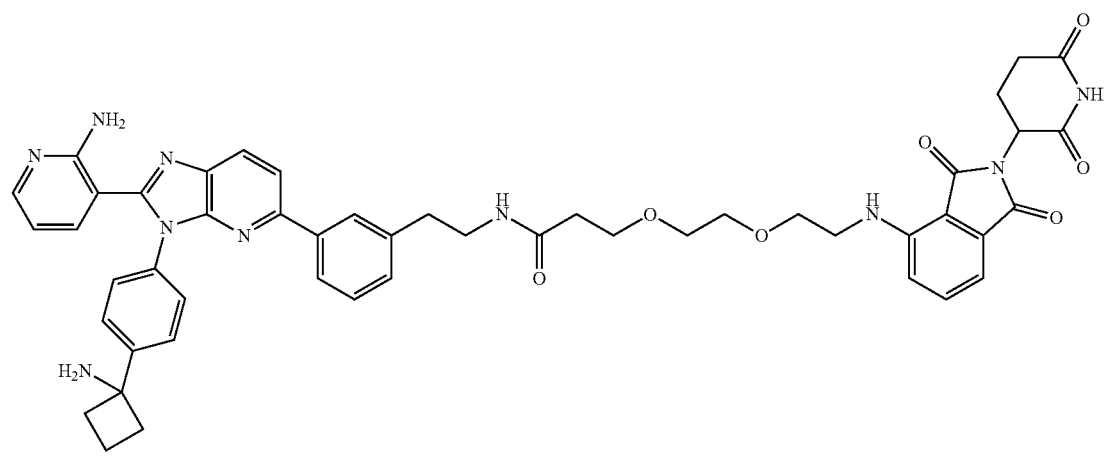

XF067-56

XF067-56 was synthesized following the standard procedure or preparing XF067-31 from intermediate 9 (9.3 mg, 0.016 mmol), PML-CH$_2$CH$_2$-PEG2-CO$_2$H (6.9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-56 was obtained as yellow solid in TFA salt form (8.7 mg, 61%). $^1$H NMR (800 MHz, CD$_3$OD) δ 8.28 (d, J=8.4 Hz, 1H), 8.02 (dd, J=10.4, 6.3 Hz, 2H), 7.93 (s, 1H), 7.88 (d, J=7.8 Hz, 1H), 7.78 (dd, J=26.3, 7.8 Hz, 3H), 7.70 (d, J=8.0 Hz, 2H), 7.43 (t, J=7.8 Hz, 1H), 7.36 (t, J=7.7 Hz, 1H), 7.27 (d, J=7.5 Hz, 1H), 6.98-6.92 (m, 2H), 6.79 (t, J=6.8 Hz, 1H), 4.99 (dq, J=11.7, 6.6, 5.3 Hz, 1H), 3.69 (t, J=5.9 Hz, 2H), 3.63 (t, J=5.2 Hz, 2H), 3.56 (s, 4H), 3.47 (t, J=7.4 Hz, 2H), 3.39 (t, J=5.2 Hz, 2H), 2.89 (dt, J=30.3, 6.5 Hz, 4H), 2.80 (ddd, J=18.3, 13.7, 5.2 Hz, 1H), 2.67 (dddt, J=53.5, 17.7, 13.2, 6.6 Hz, 4H), 2.42 (t, J=5.9 Hz, 2H), 2.36-2.30 (m, 1H), 2.09-2.01 (m, 2H). ESI-MS (m/z) [M+H]$^+$: 891.3945.

Example 133

Synthesis of XF067-57

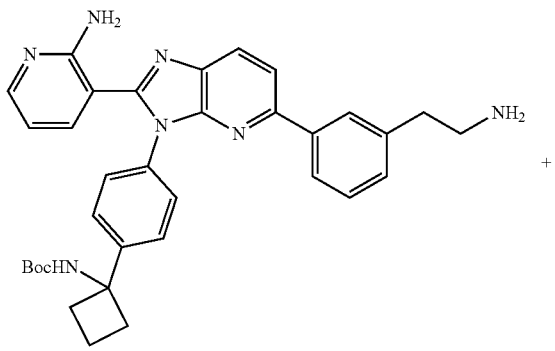

Intermediate 9

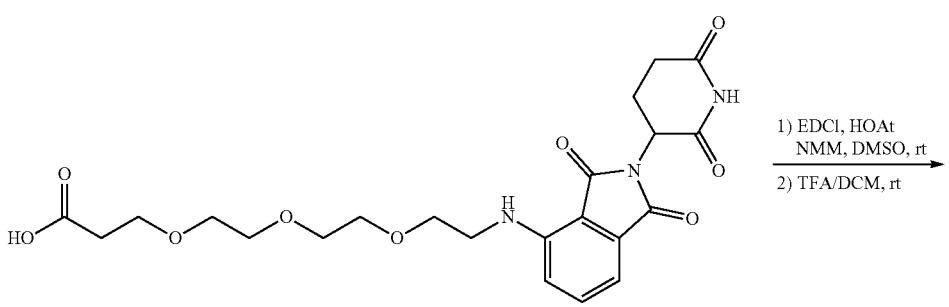

PML-CH$_2$CH$_2$-PEG3-COOH

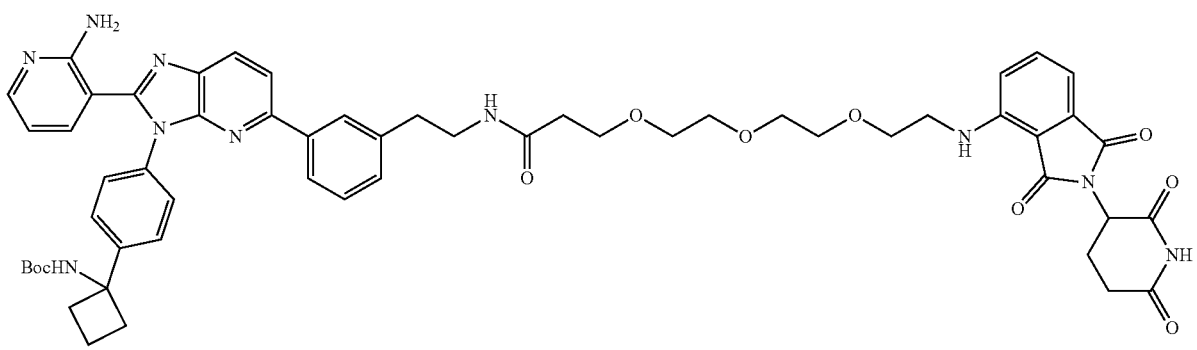

XF067-57

XF067-57 was synthesized following the standard procedure for preparing XF067-31 from intermediate 9 (9.3 mg, 0.016 mmol), PML-CH$_2$CH$_2$-PEG3-CO$_2$H (7.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-57 was obtained as yellow solid in TFA salt form (7.9 mg, 53%). $^1$H NMR (800 MHz, CD$_3$OD) δ 8.29 (d, J=8.4 Hz, 1H), 8.03 (d, J=8.3 Hz, 2H), 7.96 (s, 1H), 7.88 (d, J=7.8 Hz, 1H), 7.79 (dd, J=15.4, 7.7 Hz, 3H), 7.71 (d, J=8.0 Hz, 2H), 7.46 (t, J=7.8 Hz, 1H), 7.37 (t, J=7.7 Hz, 1H), 7.29 (d, J=7.5 Hz, 1H), 6.98 (t, J=7.4 Hz, 2H), 6.80 (s, 1H), 5.01 (dd, J=12.9, 5.3 Hz, 1H), 3.67 (t, J=6.0 Hz, 2H), 3.65 (t, J=5.2 Hz, 2H), 3.62 (s, 4H), 3.58 (t, J=4.5 Hz, 2H), 3.56-3.52 (m, 2H), 3.48 (t, J=7.5 Hz, 2H), 3.40 (t, J=5.2 Hz, 2H), 2.95-2.85 (m, 4H), 2.82 (ddd, J=18.2, 13.7, 5.3 Hz, 1H), 2.75-2.60 (m, 4H), 2.41 (t, J=5.9 Hz, 2H), 2.36-2.30 (m, 1H), 2.11-2.02 (m, 2H). ESI-MS (m/z) [M+H]$^+$: 935.4178.

Example 134

Synthesis of XF067-58

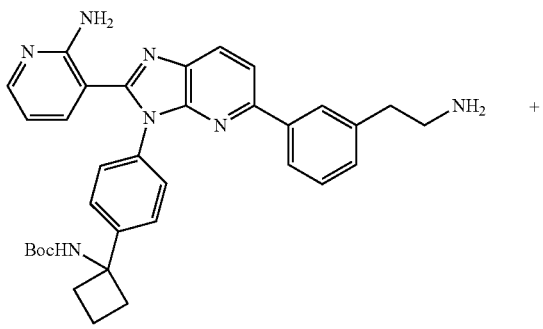

Intermediate 9

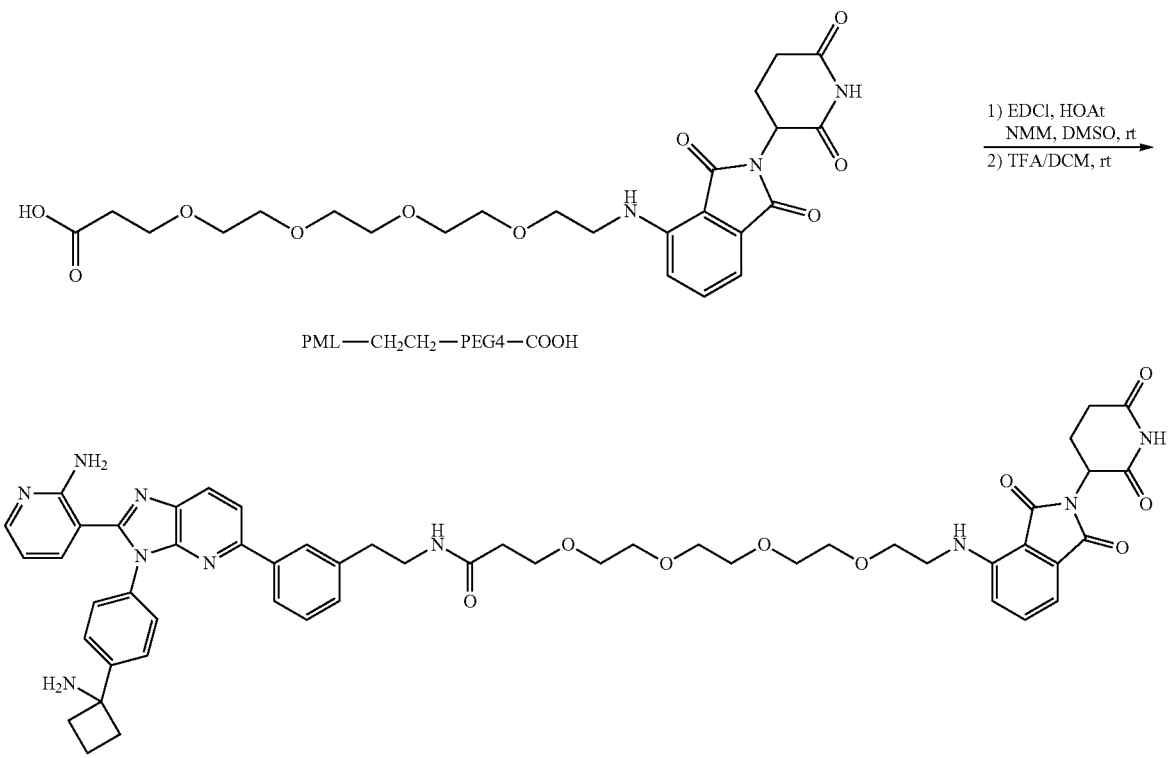

XF067-58 was synthesized following the standard procedure for preparing XF067-31 from intermediate 9 (9.3 mg, 0.016 mmol), PML-CH$_2$CH$_2$-PEG4-CO$_2$H (8.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-58 was obtained as yellow solid in TFA salt form (8 mg, 51%). $^1$H NMR (800 MHz, CD$_3$OD) δ 8.28 (d, J=8.4 Hz, 1H), 8.04 (q, J=6.4, 4.3 Hz, 3H), 7.87 (dd, J=23.8, 7.7 Hz, 2H), 7.83 (d, J=8.0 Hz, 2H), 7.73 (d, J=8.0 Hz, 2H), 7.44-7.34 (m, 2H), 7.28 (d, J=7.5 Hz, 1H), 7.00-6.94 (m, 1H), 6.83 (dd, J=19.1, 7.7 Hz, 2H), 5.01 (dd, J=12.9, 5.4 Hz, 1H), 3.72-3.69 (m, 2H), 3.67-3.60 (m, 6H), 3.62-3.56 (m, 6H), 3.58-3.53 (m, 2H), 3.49 (t, J=7.7 Hz, 2H), 3.28 (dq, J=8.6, 5.1, 4.5 Hz, 2H), 2.92 (dt, J=16.0, 7.7 Hz, 2H), 2.89-2.79 (m, 3H), 2.79-2.63 (m, 4H), 2.45 (t, J=5.8 Hz, 2H), 2.35 (qd, J=10.1, 5.0 Hz, 1H), 2.07 (d, J=14.0 Hz, 2H). ESI-MS (m/z) [M+H]$^+$: 979.4459.

Example 135

Synthesis of XF067-59

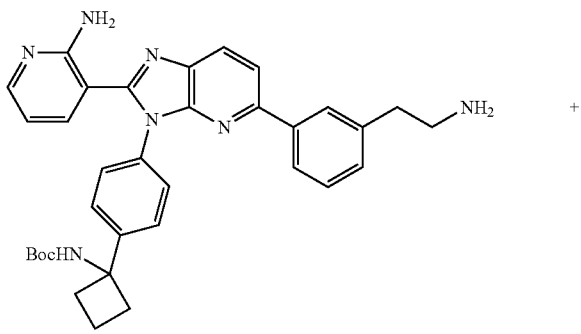

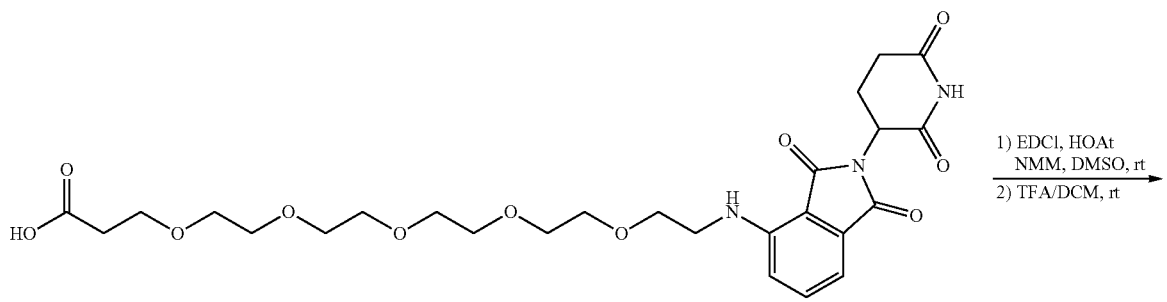

PML—CH$_2$CH$_2$—PEG5—COOH

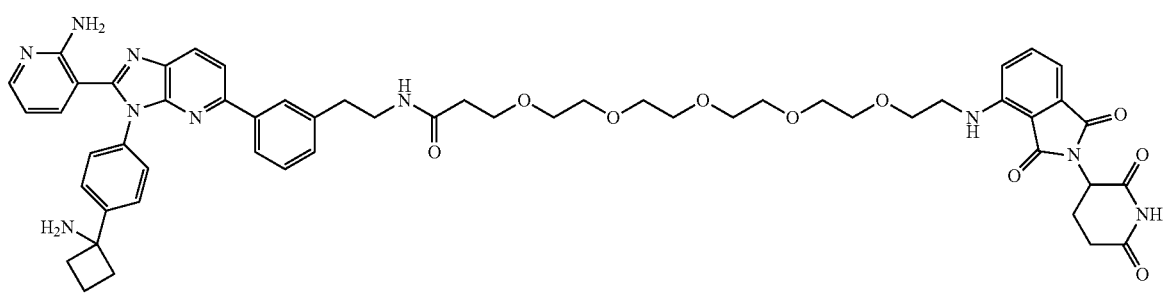

XF067-59

XF067-59 was synthesized following the standard procedure or preparing XF067-31 rom intermediate 9 (9.3 mg, 0.016 mmol), PML-CH$_2$CH$_2$-PEG5-CO$_2$H (9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-59 was obtained as yellow solid in TFA salt form (7.8 mg, 48%). $^1$H NMR (800 MHz, CD$_3$OD) δ 8.30 (d, J=8.3 Hz, 1H), 8.09-7.98 (m, 3H), 7.90 (d, J=7.8 Hz, 1H), 7.84 (dd, J=14.9, 7.9 Hz, 3H), 7.72 (d, J=8.1 Hz, 2H), 7.50 (t, J=7.8 Hz, 1H), 7.41-7.35 (m, 1H), 7.30 (d, J=7.5 Hz, 1H), 7.02 (s, 1H), 6.98 (d, J=8.5 Hz, 1H), 6.84 (s, 1H), 5.02 (dd, J=12.8, 5.2 Hz, 1H), 3.70 (q, J=5.6 Hz, 2H), 3.62-3.55 (m, 14H), 3.55-3.46 (m, 6H), 3.38-3.34 (m, 2H), 2.97-2.86 (m, 4H), 2.83 (ddd, J=18.2, 13.8, 5.6 Hz, 1H), 2.78-2.72 (m, 2H), 2.71 (s, 1H), 2.70-2.63 (m, 1H), 2.44 (t, J=5.8 Hz, 2H), 2.37-2.32 (m, 1H), 2.12-2.03 (m, 2H). ESI-MS (m/z) [M+H]$^+$: 1023.4716.

Example 136

Synthesis of Intermediate 13

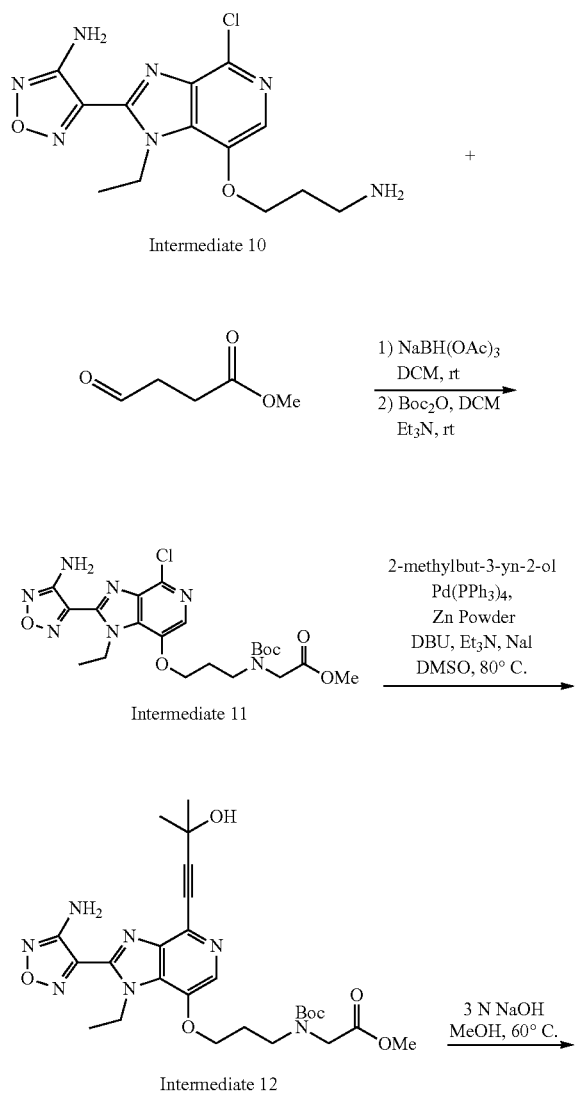

Intermediate 10

Intermediate 11

Intermediate 12

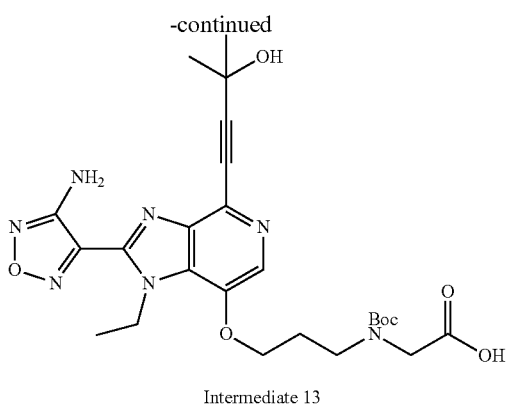

Intermediate 13

The intermediate 10 was synthesized following a known procedure (Heerding et al., 2008). To the suspension of intermediate 10 (119 mg×3, 0.5 mmol) and methyl-4-oxobutanonate (58 mg×3, 0.5 mmol) in 5 mL of DCM was added sodium triacetoxyborohydride (211 mg×3, 1.0 mmol) in three times. Once the reaction mixture became clear solution, saturated NaHCO$_3$ solution was added to quench the reaction. After the organic phase was separated, the aqueous phase was extracted with DCM (10 mL×3). The combined organic layers were dried over Na$_2$SO$_4$, filtered and concentrated. The resulting residue was dissolved in DCM (15 mL). To the resulting solution were added di-tert-butyl decarbonate (272 mg, 1.25 mmol) and triethylamine (188 mg, 1.86 mmol). The reaction was stirred for 30 min, before the reaction mixture was concentrated. The resulting residue was purified by silica gel column (Hexane/EA=1:3) to afford intermediate 11 as yellow solid (178 mg, 53%). ESI m/z 548.8 [M+H]$^+$. Intermediate 11 (178 mg, 0.34 mmol) was dissolved in DMSO (5 mL) in a pressure vessel. To the resulting solution were added 2-methylbut-3-yn-2-ol (371 µL, 4.1 mmol), zinc powder (68 mg, 1.02 mmol), NaI (16 mg, 0.11 mmol), DBU (153 µL, 1.02 mmol), and triethylamine (207 µL, 1.02 mmol). The reaction was degassed for 5 min, before the catalyst Pd(PPh$_3$)$_4$ (40 mg, 10 mol %) was added. The reaction vessel was purged with nitrogen, sealed and heated to 80° C. for 1 h. The reaction was quenched by pouring into saturated NH$_4$Cl. The aqueous layer was extracted with ethyl acetate. The combined organic extracts were dried over Na$_2$SO$_4$, filtered, and concentrated under reduced pressure to give the intermediate 12, which was used in the next step without further purification. The intermediate 12 (146 mg, 0.25 mmol) was dissolved in methanol (5 mL). To the resulting solution was added NaOH (0.5 mL, 3 N). The reaction was heated to 60° C. for 1 h, before the reaction mixture was concentrated. The resulting residue was purified by preparative HPLC (10%-100% methanol/0.1% TFA in H$_2$O) to afford Intermediate 13 as white solid in TFA salt form (128.3 mg, 90%). $^1$H NMR (500 MHz, DMSO-d$_6$) δ 8.15 (s, 1H), 7.03 (s, 2H), 4.93-4.74 (m, 2H), 4.40-4.26 (m, 2H), 3.39 (t, J=7.1 Hz, 2H), 3.22 (t, J=7.2 Hz, 2H), 2.21 (t, J=7.2 Hz, 2H), 2.13-2.02 (m, 2H), 1.82-1.69 (m, 2H), 1.47 (t, J=7.0 Hz, 3H), 1.41-1.30 (m, 15H). ESI-MS (m/z) [M+H]$^+$: 572.3213

Example 137

Synthesis of XF067-84

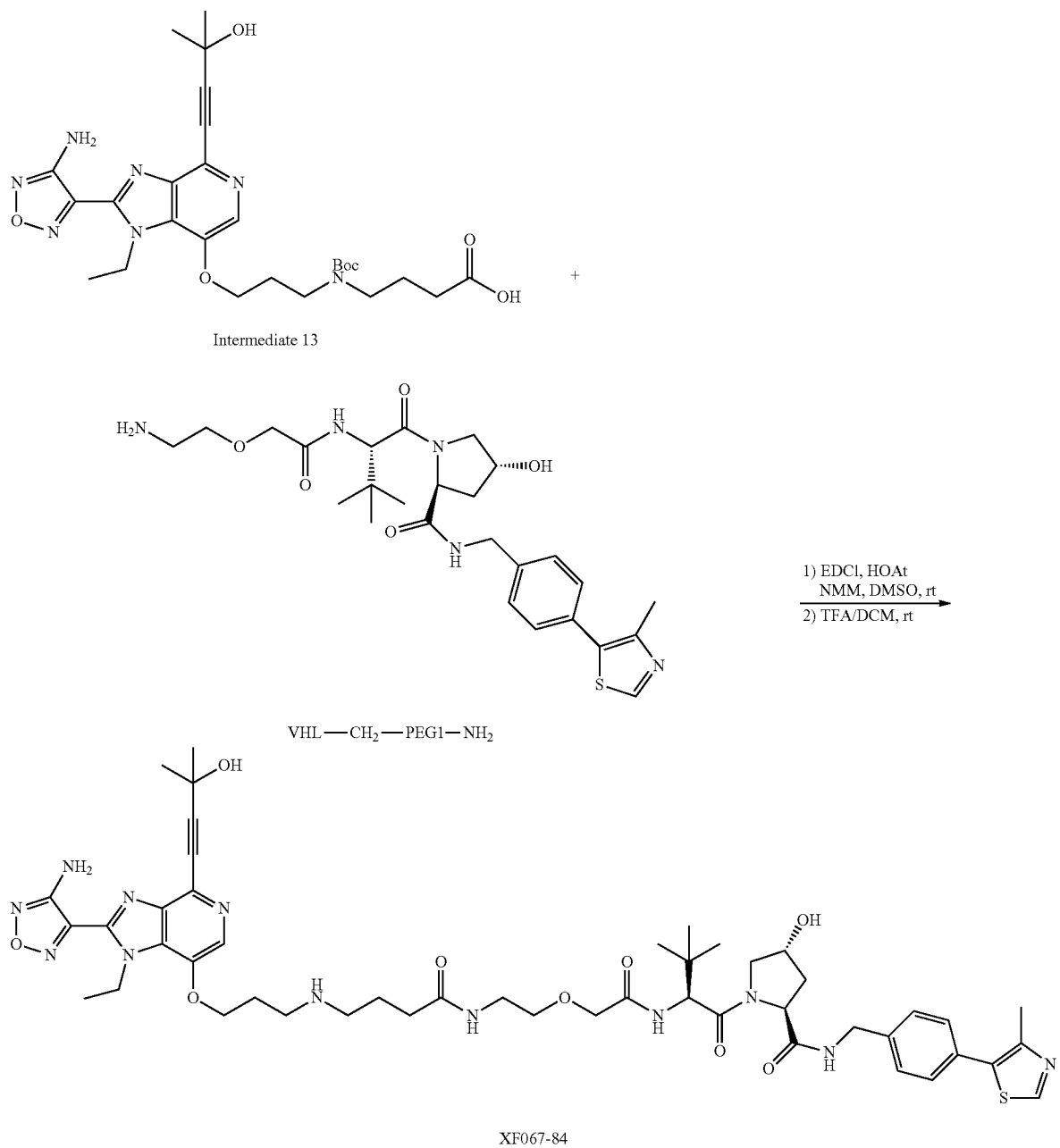

To a solution of Intermediate 13 (9.1 mg, 0.016 mmol) in DMSO (1 mL) were added VHL-CH$_2$-PEG1-NH$_2$ (9.1 mg, 0.016 mmol, 1.0 equiv), EDCI (1-ethyl-3-(3-dimethylaminopropyl)carbodiimide) (4.6 mg, 0.024 mmol, 1.5 equiv), HOAt (1-hydroxy-7-azabenzo-triazole) (3.3 mg, 0.024 mmol, 1.5 equiv), and NMM (N-Methylmorpholine) (4.8 mg, 0.048 mmol, 3.0 equiv). After being stirred overnight at room temperature, the resulting mixture was purified by preparative HPLC (10%-100% methanol/0.1% TFA in H$_2$O) to afford the corresponding product. After this product was dissolved in DCM (1 mL), the reaction mixture was treated with TFA (1 mL) for 30 min. After the solvent was evaporated, the residue was purified by preparative HPLC (10%-100% methanol/0.1% TFA in H$_2$O) to afford XF067-84 as white solid in TFA salt form (6.1 mg, 39%). $^1$H NMR (500 MHz, CD$_3$OD) δ 8.97 (d, J=5.7 Hz, 1H), 8.23 (s, 1H), 7.51-7.34 (m, 4H), 5.05 (q, J=7.0 Hz, 2H), 4.74-4.65 (m, 1H), 4.64-4.28 (m, 6H), 4.13-3.93 (m, 2H), 3.93-3.77 (m, 2H), 3.68-3.49 (m, 2H), 3.43-3.35 (m, 4H), 3.24-3.07 (m, 2H), 2.58-2.33 (m, 7H), 2.27 (dd, J=13.2, 7.6 Hz, 1H), 2.10 (ddd, J=13.5, 9.4, 4.4 Hz, 1H), 2.00 (h, J=7.2 Hz, 2H), 1.69 (s, 6H), 1.58 (t, J=7.0 Hz, 3H), 1.05 (s, 9H). ESI-MS (m/z) [M+H]$^+$: 985.4728.

Example 138
Synthesis of XF067-85
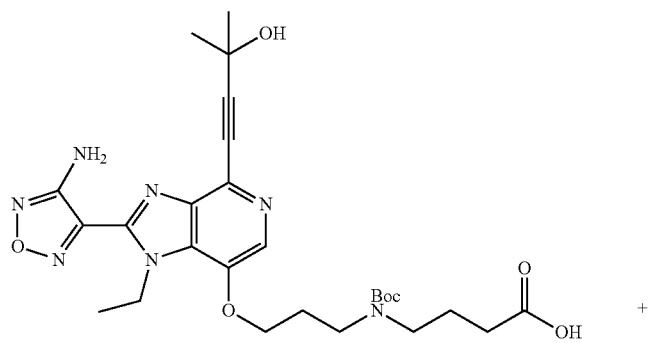
Intermediate 13
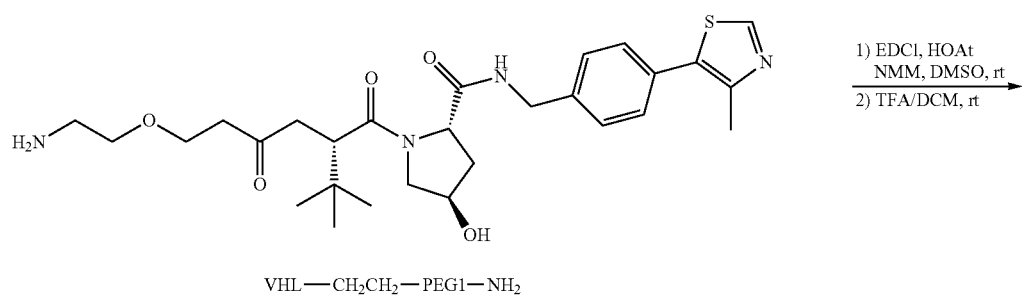
VHL—CH₂CH₂—PEG1—NH₂
1) EDCl, HOAt
   NMM, DMSO, rt
2) TFA/DCM, rt
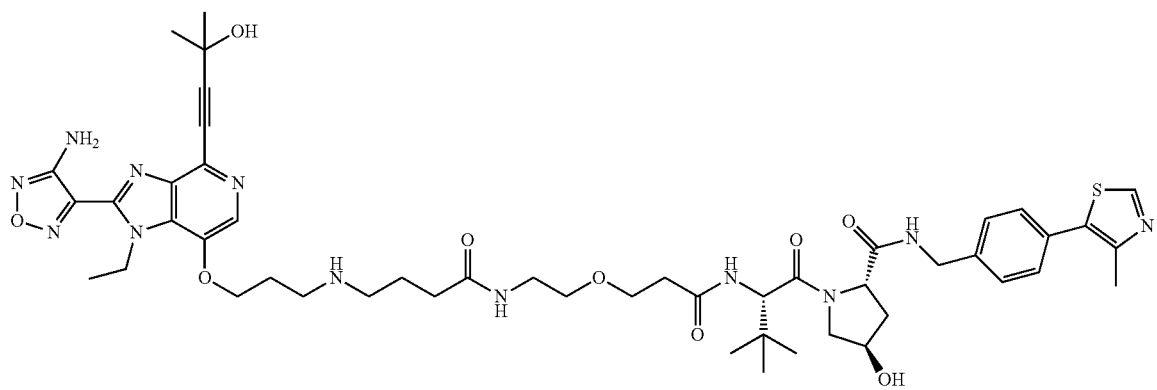
XF067-85

XF067-85 was synthesized following the standard procedure for preparing XF067-84 from intermediate 13 (9.1 mg, 0.016 mmol), VHL-CH$_2$CH$_2$-PEG1-NH$_2$ (12.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-85 was obtained as white solid in TFA salt form (11.8 mg, 74%). $^1$H NMR (500 MHz, CD$_3$OD) δ 8.97 (s, 1H), 8.24 (s, 1H), 7.55-7.32 (m, 4H), 5.05 (q, J=7.1 Hz, 2H), 4.71-4.63 (m, 1H), 4.64-4.48 (m, 5H), 4.41 (d, J=15.4 Hz, 1H), 3.96-3.80 (m, 2H), 3.71 (tt, J=10.5, 4.8 Hz, 2H), 3.50 (t, J=5.4 Hz, 2H), 3.38-3.33 (m, 4H), 3.16 (t, J=7.0 Hz, 2H), 2.56-2.36 (m, 9H), 2.26 (ddt, J=13.2, 7.7, 1.9 Hz, 1H), 2.10 (ddd, J=13.3, 9.2, 4.4 Hz, 1H), 1.98 (p, J=6.8 Hz, 2H), 1.69 (s, 6H), 1.58 (t, J=7.1 Hz, 3H), 1.05 (s, 9H). ESI-MS (m/z) [M+H]$^+$: 999.4875.

Example 139

Synthesis of XF067-86

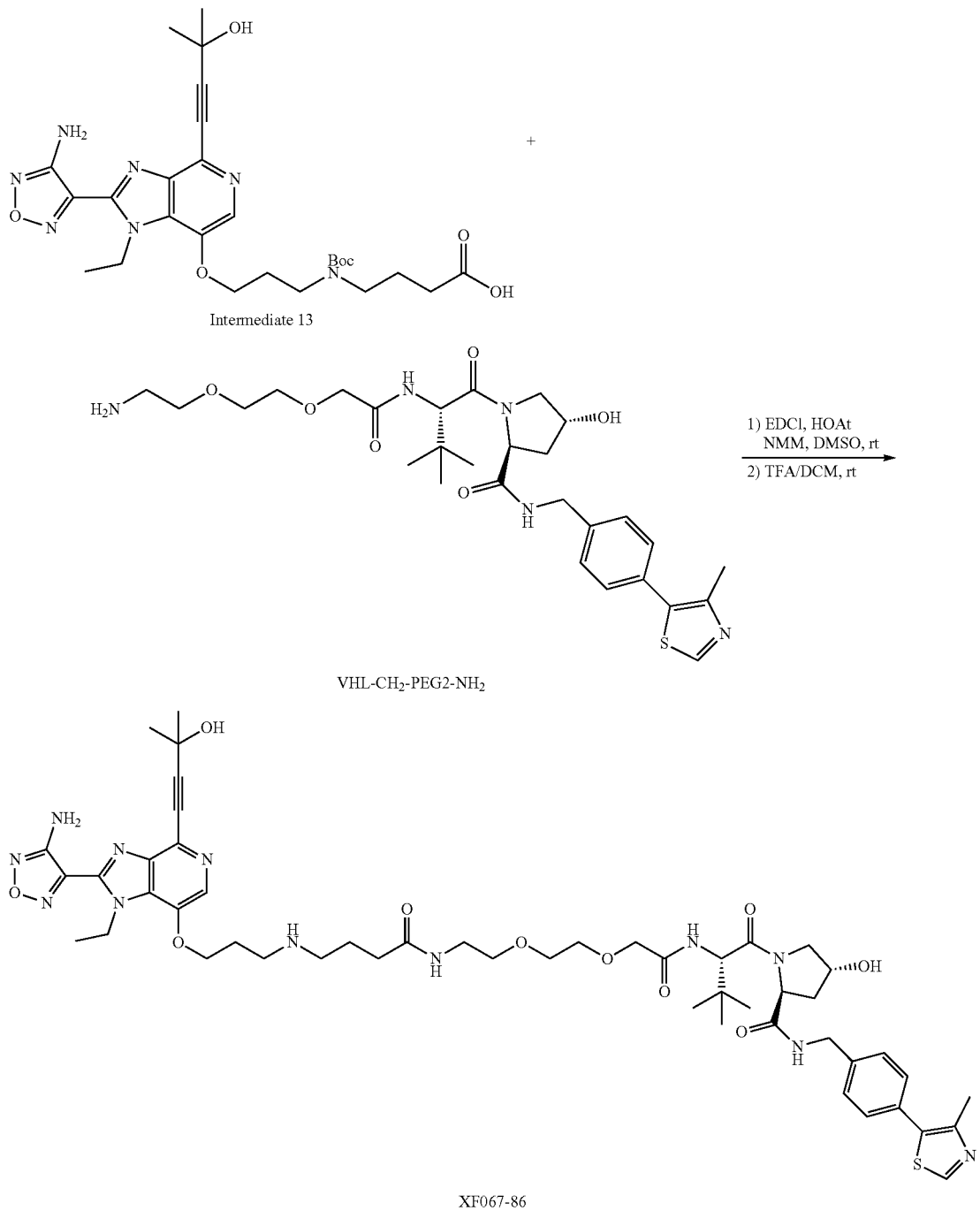

XF067-86

XF067-86 was synthesized following the standard procedure for preparing XF067-84 from intermediate 13 (9.1 mg, 0.016 mmol), VHL-CH$_2$-PEG2-NH$_2$ (9.8 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-86 was obtained as white solid in TFA salt form (10.6 mg, 64%). $^1$H NMR (500 MHz, CD$_3$OD) δ 9.01 (d, J=2.9 Hz, 1H), 8.26 (d, J=3.0 Hz, 1H), 7.53-7.44 (m, 4H), 5.06 (q, J=7.0 Hz, 2H), 4.95-4.71 (m, 1H), 4.64-4.31 (m, 6H), 4.03-4.01 (m, 2H), 3.94-3.78 (m, 2H), 3.80-3.58 (m, 4H), 3.56-3.48 (m, 2H), 3.46-3.26 (m, 4H), 3.22-3.08 (m, 2H), 2.59-2.35 (m, 7H), 2.36-2.23 (m, 1H), 2.19-2.06 (m, 1H), 2.03-1.93 (m, 2H), 1.70 (s, 6H), 1.59 (t, J=7.0 Hz, 3H), 1.06 (s, 9H). ESI-MS (m/z) [M+H]$^+$: 1029.4983.

Example 140

Synthesis of XF067-87

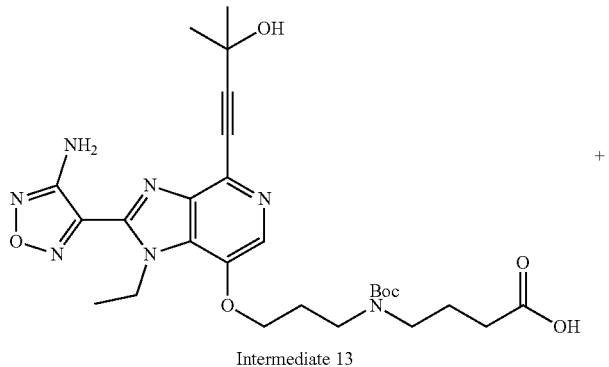

Intermediate 13

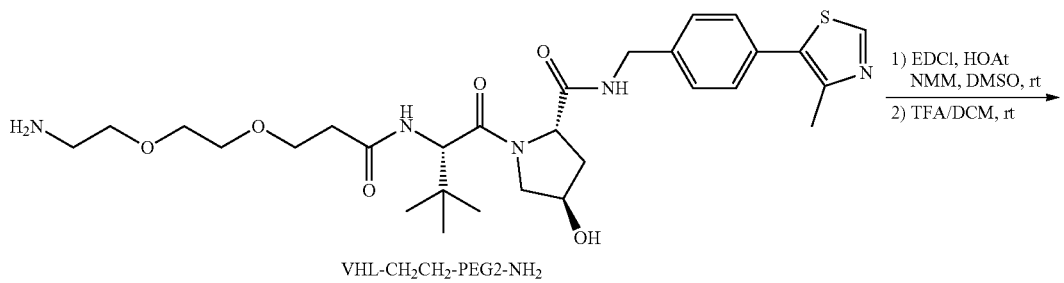

VHL-CH$_2$CH$_2$-PEG2-NH$_2$

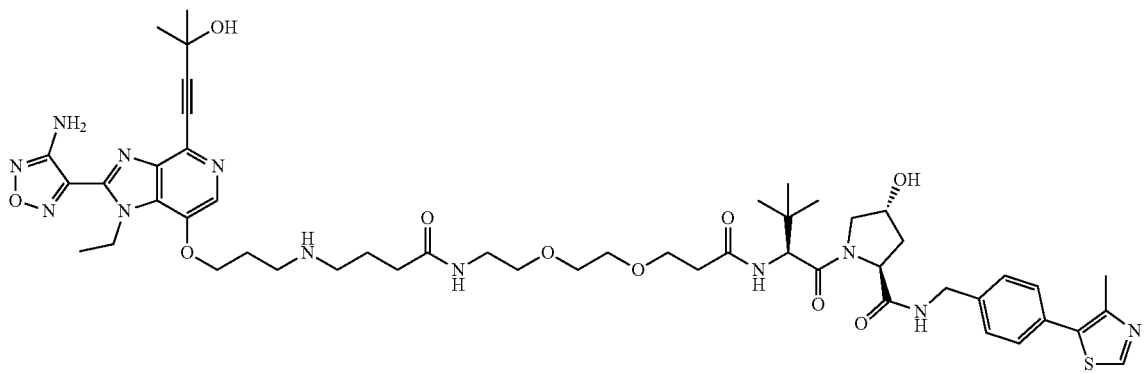

XF067-87

XF067-87 was synthesized following the standard procedure for preparing XF067-84 from intermediate 13 (9.1 mg, 0.016 mmol), VHL-CH$_2$CH$_2$-PEG2-NH$_2$ (13.1 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-87 was obtained as white solid in TFA salt form (6.4 mg, 38%). $^1$H NMR (500 MHz, CD$_3$OD) δ 9.01 (s, 1H), 8.26 (s, 1H), 7.54-7.36 (m, 4H), 5.07 (q, J=7.1 Hz, 2H), 4.67 (d, J=6.2 Hz, 1H), 4.64-4.47 (m, 5H), 4.39 (d, J=15.4 Hz, 1H), 3.91 (d, J=11.0 Hz, 1H), 3.82 (dd, J=11.0, 3.9 Hz, 1H), 3.80-3.69 (m, 2H), 3.66-3.56 (m, 4H), 3.50 (t, J=5.4 Hz, 2H), 3.36-3.31 (m, 4H), 3.17 (t, J=7.0 Hz, 2H), 2.59 (ddd, J=15.0, 7.3, 5.2 Hz, 1H), 2.55-2.34 (m, 8H), 2.24 (ddt, J=13.3, 7.6, 2.0 Hz, 1H), 2.10 (ddd, J=13.3, 9.1, 4.5 Hz, 1H), 1.99 (p, J=6.9 Hz, 2H), 1.70 (s, 6H), 1.59 (t, J=7.1 Hz, 3H), 1.05 (s, 9H). ESI-MS (m/z) [M+H]$^+$: 1043.5145.

Example 141

Synthesis of XF067-88

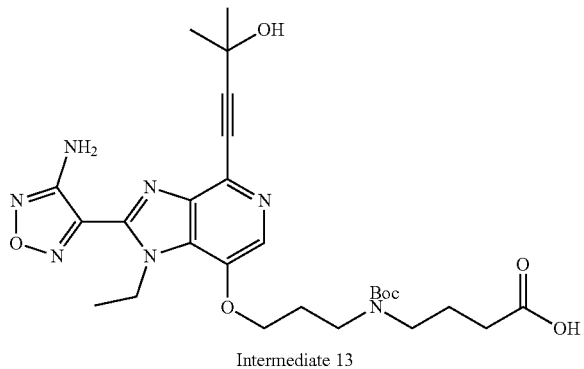

Intermediate 13

+

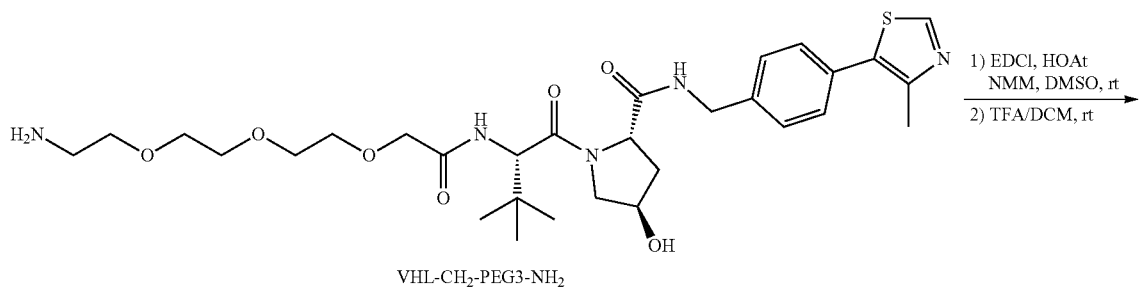

VHL-CH$_2$-PEG3-NH$_2$

1) EDCl, HOAt NMM, DMSO, rt
2) TFA/DCM, rt

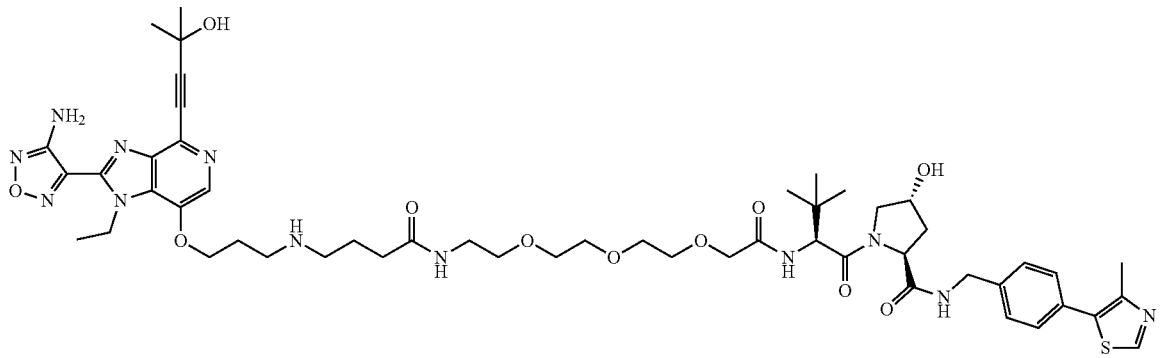

XF067-88

XF067-88 was synthesized following the standard procedure for preparing XF067-84 from intermediate 13 (9.1 mg, 0.016 mmol), VHL-CH$_2$—PEG3-NH$_2$ (13.5 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-88 was obtained as white solid in TFA salt form (8.1 mg, 47%). $^1$H NMR (500 MHz, CD$_3$OD) δ 9.00 (s, 1H), 8.25 (s, 1H), 7.49-7.41 (m, 4H), 5.06 (q, J=6.9 Hz, 2H), 4.75-4.64 (m, 1H), 4.64-4.45 (m, 5H), 4.48-4.30 (m, 1H), 4.15-3.97 (m, 2H), 3.93-3.78 (m, 2H), 3.78-3.57 (m, 8H), 3.49 (t, J=5.4 Hz, 2H), 3.34-3.24 (m, 4H), 3.17 (d, J=7.1, 2.4 Hz, 2H), 2.54-2.33 (m, 7H), 2.33-2.21 (m, 1H), 2.17-2.05 (m, 1H), 2.04-1.92 (m, 2H), 1.75-1.63 (m, 6H), 1.59 (t, J=7.1 Hz, 3H), 1.06 (s, 9H). ESI-MS (m/z) [M+H]$^+$: 1073.5231.

Example 142

Synthesis of XF067-89

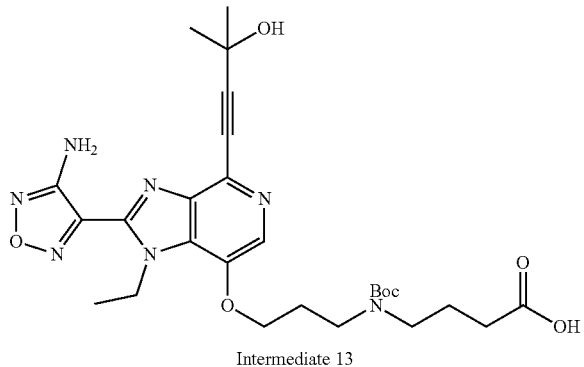

Intermediate 13

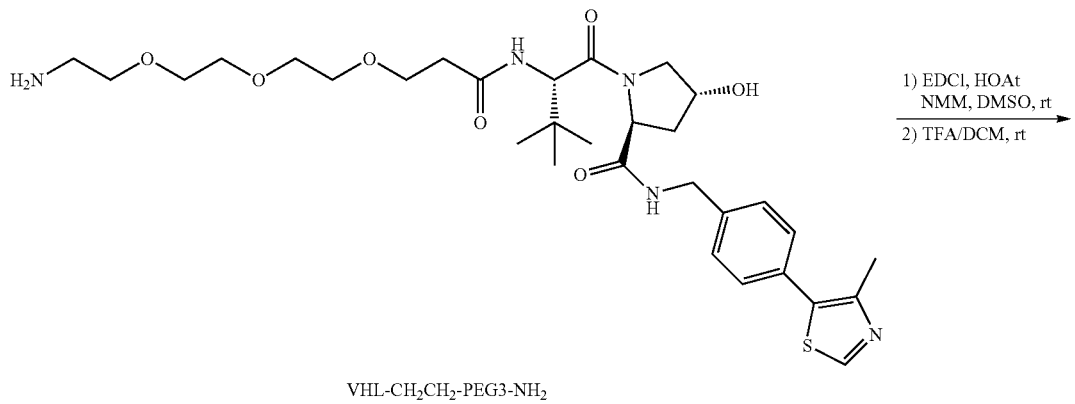

VHL-CH$_2$CH$_2$-PEG3-NH$_2$

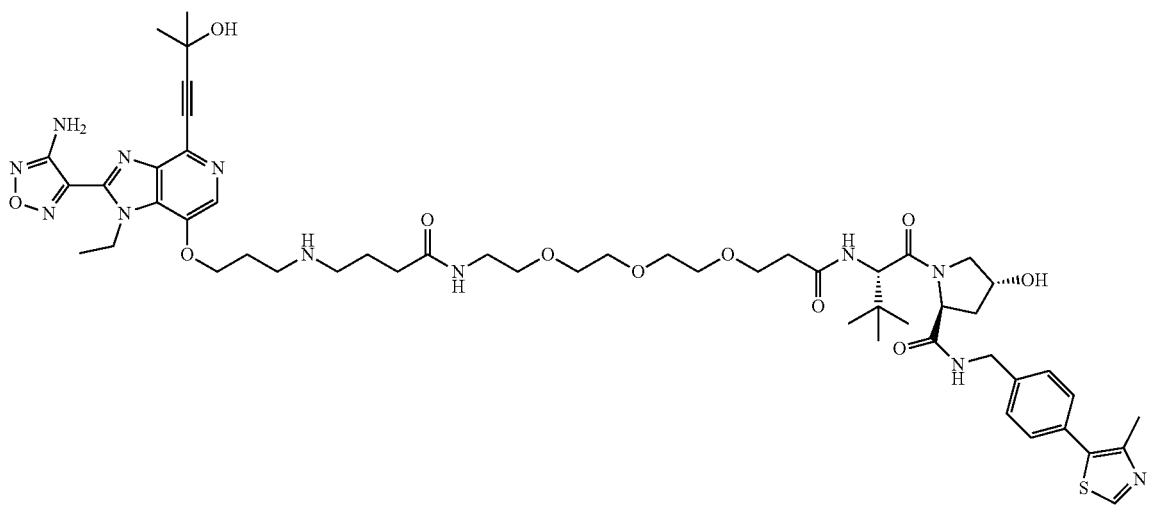

XF067-89

XF067-89 was synthesized following the standard procedure for preparing XF067-84 from intermediate 13 (9.1 mg, 0.016 mmol), VHL-CH₂CH₂-PEG3-NH₂ (13.8 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-89 was obtained as white solid in TFA salt form (10.7 mg, 61%). ¹H NMR (500 MHz, CD₃OD) δ 9.02 (s, 1H), 8.27 (s, 1H), 7.59-7.33 (m, 4H), 5.07 (q, J=7.2 Hz, 2H), 4.73-4.62 (m, 1H), 4.62-4.47 (m, 5H), 4.39 (dd, J=15.6, 2.6 Hz, 1H), 3.94-3.87 (m, 1H), 3.87-3.66 (m, 3H), 3.70-3.54 (m, 8H), 3.50 (t, J=5.4 Hz, 2H), 3.37-3.30 (m, 4H), 3.17 (t, J=7.0 Hz, 2H), 2.60 (ddd, J=15.0, 7.5, 5.2 Hz, 1H), 2.52-2.30 (m, 8H), 2.24 (ddt, J=13.3, 7.7, 2.1 Hz, 1H), 2.10 (ddd, J=13.3, 9.2, 4.4 Hz, 1H), 2.00 (p, J=6.8 Hz, 2H), 1.70 (s, 6H), 1.60 (t, J=7.1 Hz, 3H), 1.06 (s, 9H). ESI-MS [M+H]⁺: 1087.5383.

Example 143

Synthesis of XF067-90

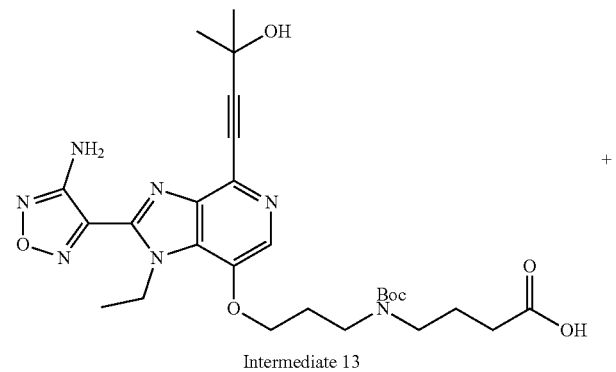

Intermediate 13

+

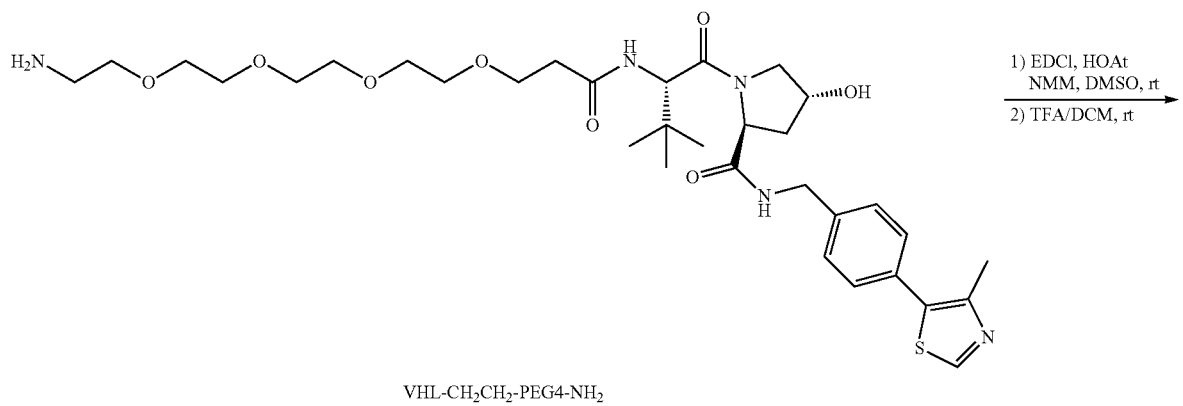

VHL-CH₂CH₂-PEG4-NH₂

1) EDCI, HOAt NMM, DMSO, rt
2) TFA/DCM, rt

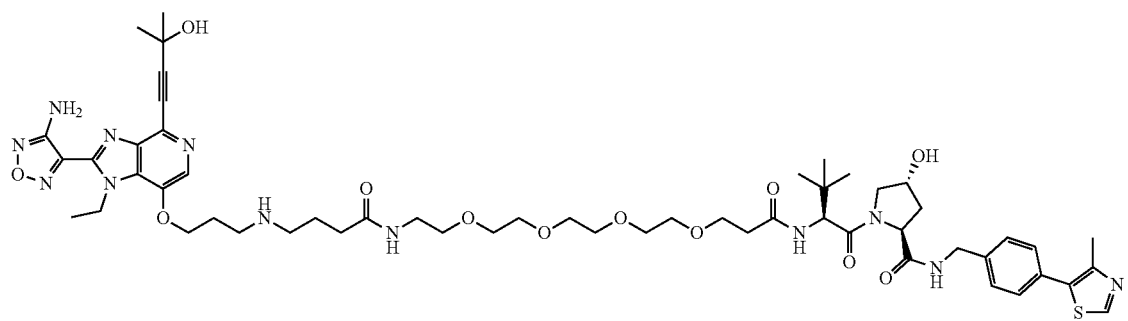

XF067-90

XF067-90 was synthesized following the standard procedure or preparing XF067-84 from intermediate 13 (9.1 mg, 0.016 mmol), VHL-CH$_2$CH$_2$—PEG4-NH$_2$ (11.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-90 was obtained as white solid in TFA salt form (12.6 mg, 70%). $^1$H NMR (500 MHz, CD$_3$OD) δ 9.02 (s, 1H), 8.27 (s, 1H), 7.56-7.33 (m, 4H), 5.07 (q, J=7.1 Hz, 2H), 4.65 (s, 1H), 4.62-4.46 (m, 5H), 4.38 (d, J=15.5 Hz, 1H), 3.90 (d, J=11.0 Hz, 1H), 3.82 (dd, J=11.0, 3.9 Hz, 1H), 3.74 (dq, J=9.7, 4.8, 4.2 Hz, 2H), 3.67-3.55 (m, 12H), 3.51 (t, J=5.4 Hz, 2H), 3.40-3.32 (m, 4H), 3.17 (t, J=7.1 Hz, 2H), 2.60 (ddd, J=15.0, 7.3, 5.3 Hz, 1H), 2.55-2.29 (m, 8H), 2.24 (ddt, J=13.2, 7.7, 2.0 Hz, 1H), 2.10 (ddd, J=13.3, 9.1, 4.5 Hz, 1H), 2.00 (td, J=13.7, 12.3, 5.5 Hz, 2H), 1.70 (s, 6H), 1.60 (t, J=7.1 Hz, 3H), 1.05 (s, 9H). ESI-MS (m/z) for [M+H]$^+$: 1131.5653.

Example 144

Synthesis of XF067-91

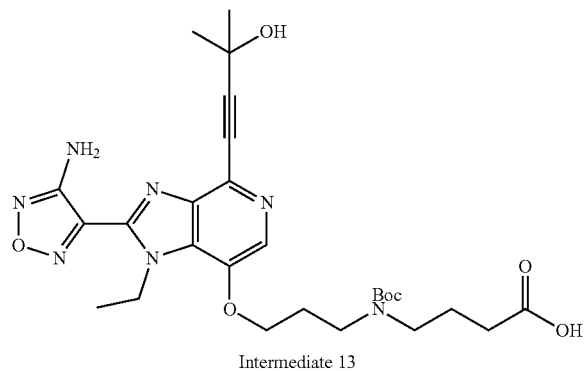

Intermediate 13

+

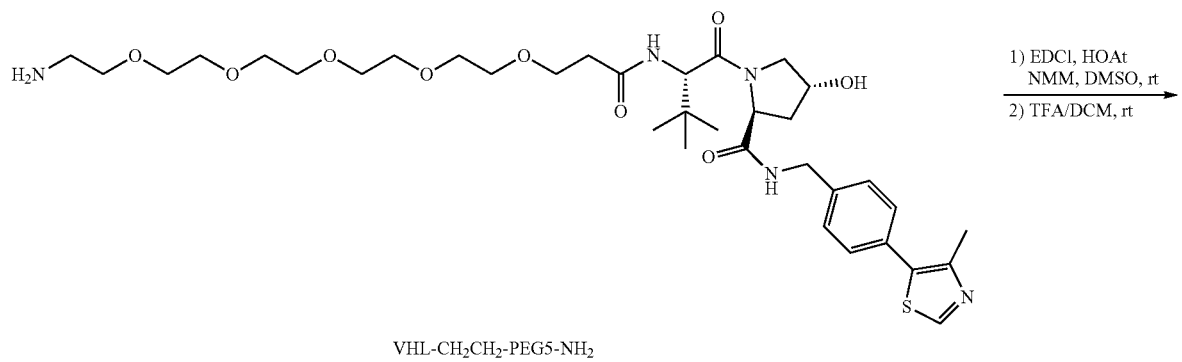

VHL-CH$_2$CH$_2$-PEG5-NH$_2$

1) EDCl, HOAt NMM, DMSO, rt
2) TFA/DCM, rt

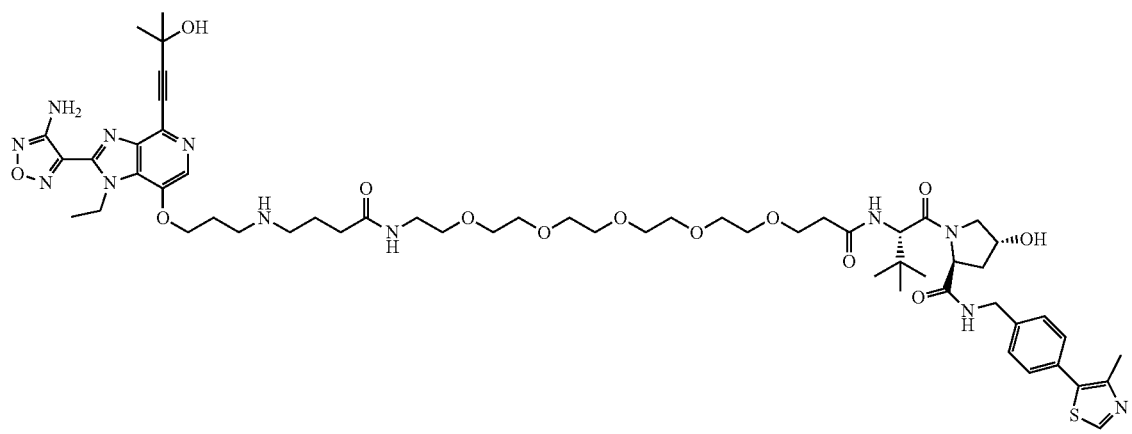

XF067-91

XF067-91 was synthesized following the standard procedure for preparing XF067-84 from intermediate 13 (9.1 mg, 0.016 mmol), VHL-CH$_2$CH$_2$-PEG5-NH$_2$ (15.2 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-91 was obtained as white solid in TFA salt form (9.4 mg, 50%). $^1$H NMR (500 MHz, CD$_3$OD) δ 8.99 (s, 1H), 8.25 (s, 1H), 7.53-7.36 (m, 4H), 5.07 (q, J=7.1 Hz, 2H), 4.66 (s, 1H), 4.61-4.47 (m, 5H), 4.38 (d, J=15.5 Hz, 1H), 3.90 (d, J=11.1 Hz, 1H), 3.86-3.70 (m, 3H), 3.66-3.56 (m, 16H), 3.50 (t, J=5.4 Hz, 2H), 3.36-3.28 (m, 4H), 3.18 (t, J=7.0 Hz, 2H), 2.60 (ddd, J=14.8, 7.4, 5.1 Hz, 1H), 2.52-2.32 (m, 8H), 2.24 (ddt, J=11.7, 7.7, 1.9 Hz, 1H), 2.15-2.02 (m, 1H), 1.99 (q, J=6.8 Hz, 2H), 1.69 (s, 6H), 1.59 (t, J=7.1 Hz, 3H), 1.06 (s, 9H). ESI-MS (m/z) for [M+H]$^+$: 1175.5911.

Example 145

Synthesis of XF067-92

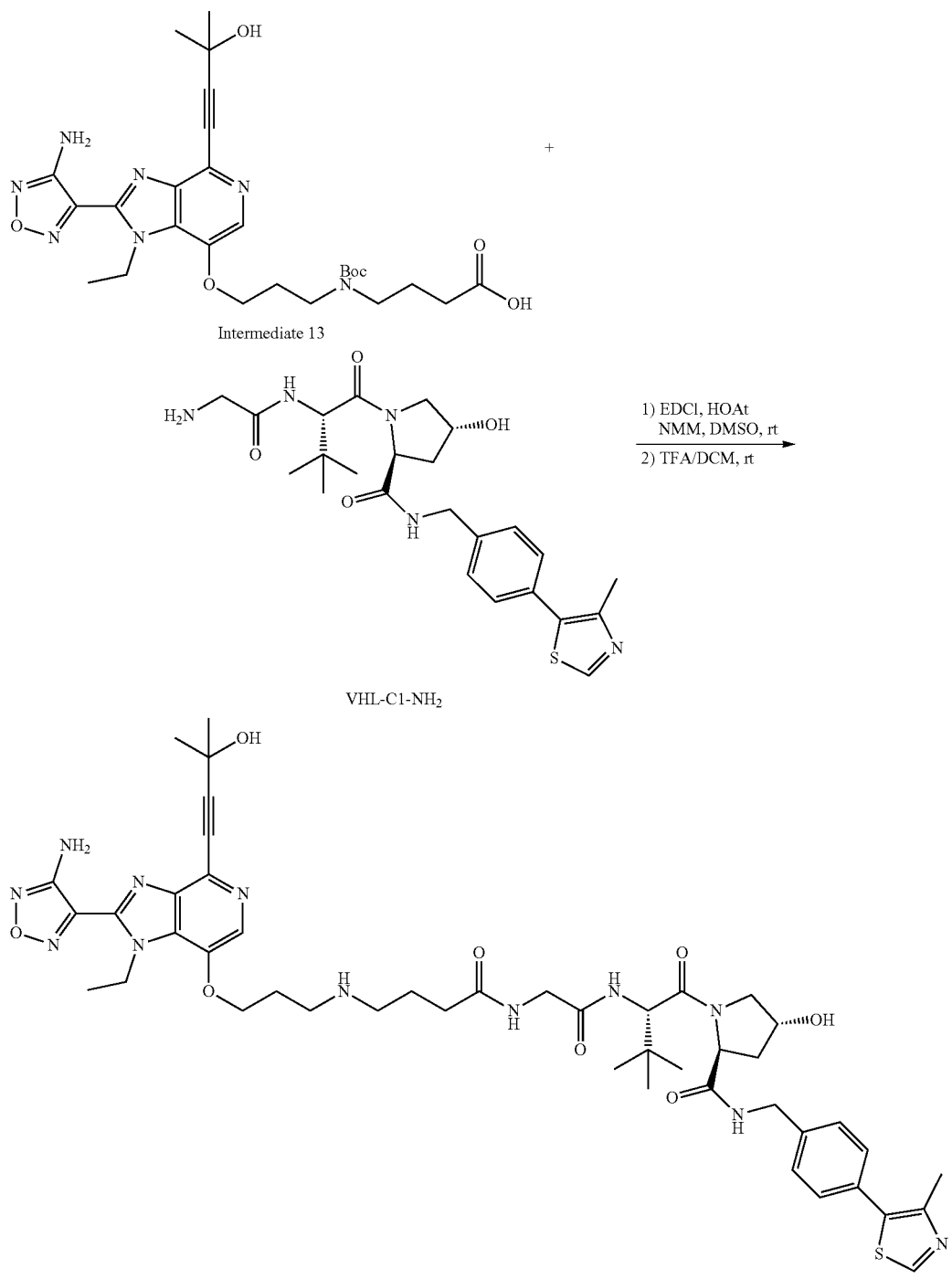

XF067-92 was synthesized following the standard procedure for preparing XF067-84 from intermediate 13 (9.1 mg, 0.016 mmol), VHL-C1-NH₂ (11.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-92 was obtained as white solid in TFA salt form (9.3 mg, 62%). ¹H NMR (500 MHz, CD₃OD) δ 9.01 (d, J=6.5 Hz, 1H), 8.25 (d, J=6.2 Hz, 1H), 7.56-7.39 (m, 4H), 5.06 (dd, J=12.7, 5.7 Hz, 2H), 4.83-4.31 (m, 7H), 4.08-3.78 (m, 4H), 3.46-3.35 (m, 2H), 3.21 (q, J=7.2, 5.9 Hz, 2H), 2.80-2.29 (m, 7H), 2.33-2.18 (m, 1H), 2.18-1.90 (m, 3H), 1.70 (s, 6H), 1.64-1.51 (m, 3H), 1.06 (d, J=10.6 Hz, 9H). ESI-MS (m/z) for [M+H]⁺: 941.4458.

Example 146

Synthesis of XF067-93

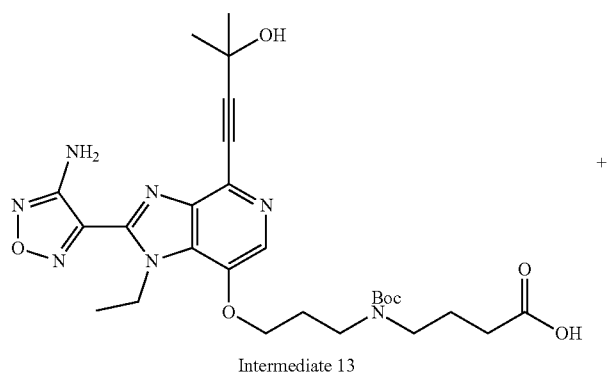
Intermediate 13

+

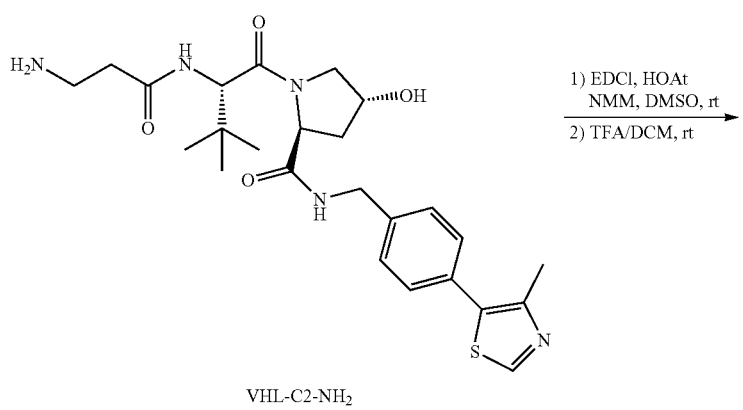
VHL-C2-NH₂

1) EDCl, HOAt
   NMM, DMSO, rt
2) TFA/DCM, rt

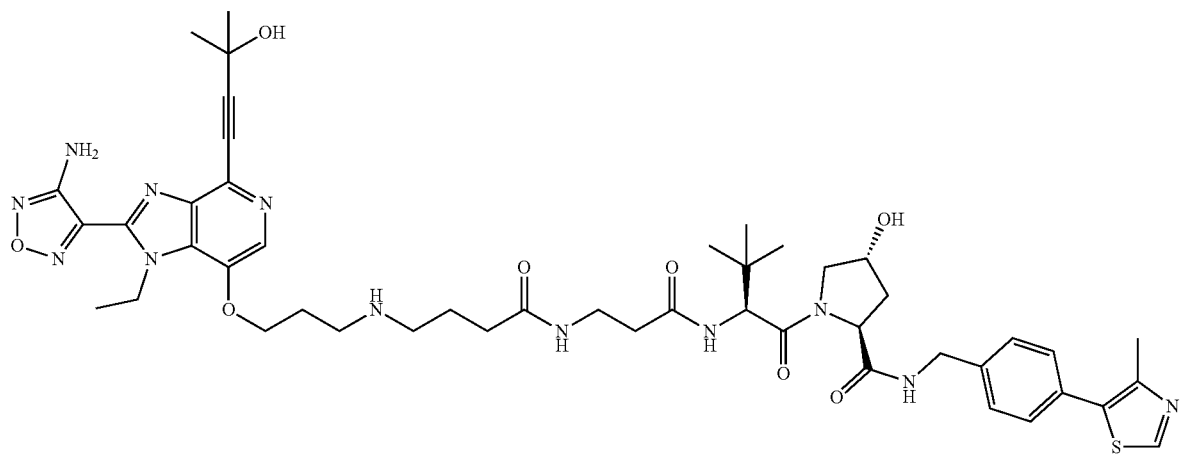
XF067-93

XF067-93 was synthesized following the standard procedure for preparing XF067-84 from intermediate 13 (9.1 mg, 0.016 mmol), VHL-C2-NH$_2$ (11.7 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-93 was obtained as white solid in TFA salt form (12.9 mg, 84%). $^1$H NMR (500 MHz, CD$_3$OD) δ 9.02 (s, 1H), 8.26 (s, 1H), 7.51-7.28 (m, 4H), 5.07 (q, J=7.0 Hz, 2H), 4.62 (s, 1H), 4.59-4.47 (m, 5H), 4.40 (d, J=15.5 Hz, 1H), 3.95 (d, J=11.0 Hz, 1H), 3.82 (dd, J=11.0, 3.9 Hz, 1H), 3.47-3.33 (m, 4H), 3.17 (t, J=7.2 Hz, 2H), 2.57-2.33 (m, 9H), 2.26 (dd, J=13.3, 7.6 Hz, 1H), 2.11 (ddd, J=13.4, 9.3, 4.3 Hz, 1H), 1.99 (p, J=6.8 Hz, 2H), 1.70 (s, 6H), 1.60 (t, J=7.1 Hz, 3H), 1.05 (s, 9H). ESI-MS (m/z) [M+H]$^+$: 955.4613.

Example 147

Synthesis of XF067-94

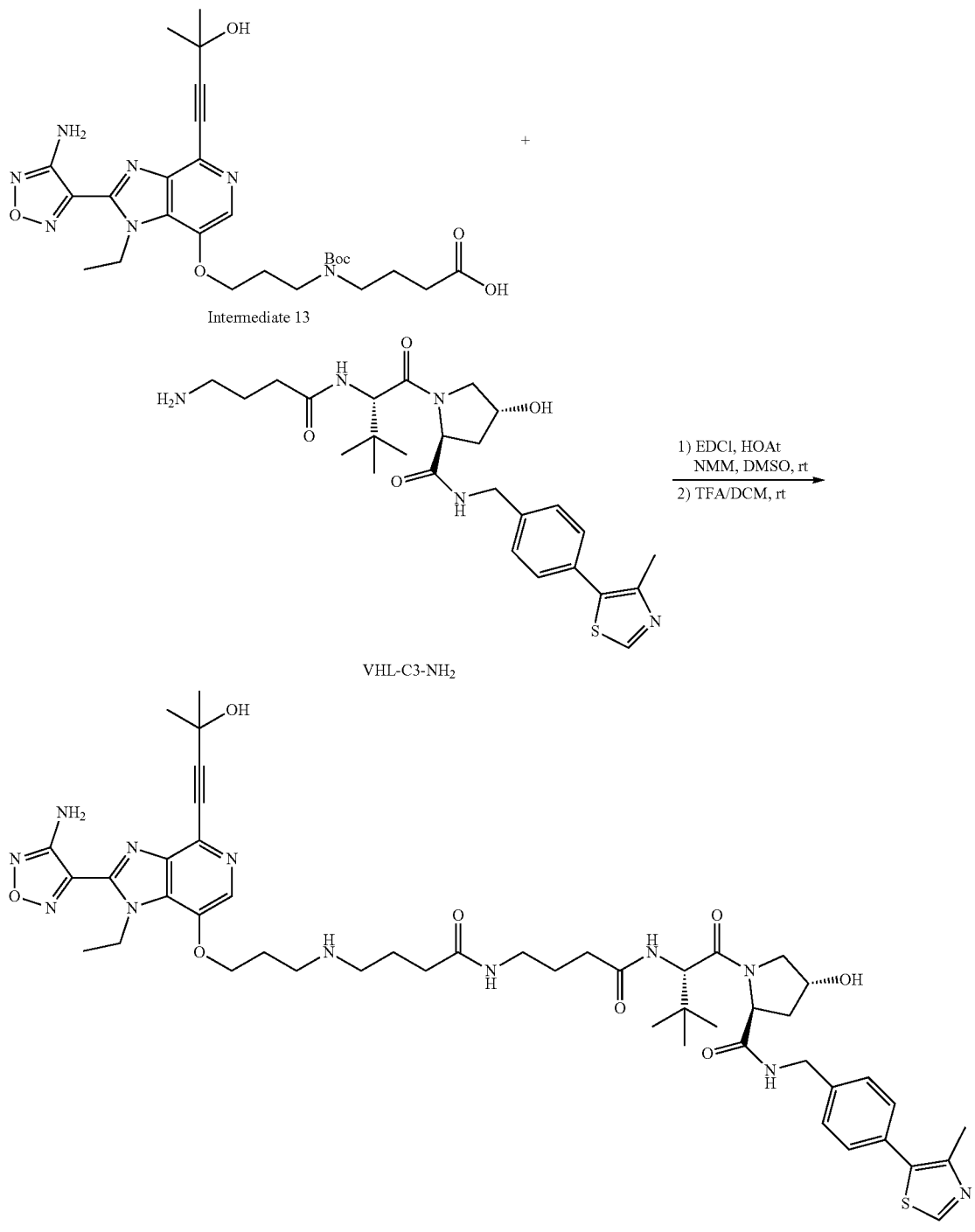

XF067-94 was synthesized following the standard procedure for preparing XF067-84 from intermediate 13 (9.1 mg, 0.016 mmol), VHL-C3-NH$_2$ (11.9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-94 was obtained as white solid in TFA salt form (9.3 mg, 60%). $^1$H NMR (500 MHz, CD$_3$OD) δ 9.02 (s, 1H), 8.27 (s, 1H), 7.58-7.34 (m, 4H), 5.07 (q, J=7.3, 6.3 Hz, 2H), 4.75-4.48 (m, 6H), 4.40 (dd, J=15.5, 4.9 Hz, 1H), 3.96-3.77 (m, 2H), 3.40-3.32 (m, 4H), 3.18 (q, J=7.2, 6.4 Hz, 2H), 2.63-2.19 (m, 10H), 2.11 (ddd, J=13.3, 9.2, 4.6 Hz, 1H), 2.00 (p, J=6.6 Hz, 2H), 1.85-1.64 (m, 8H), 1.60 (t, J=7.0 Hz, 3H), 1.06 (d, J=4.6 Hz, 9H). ESI-MS (m/z) for [M+H]$^+$: 969.4754.

Example 148

Synthesis of XF067-95

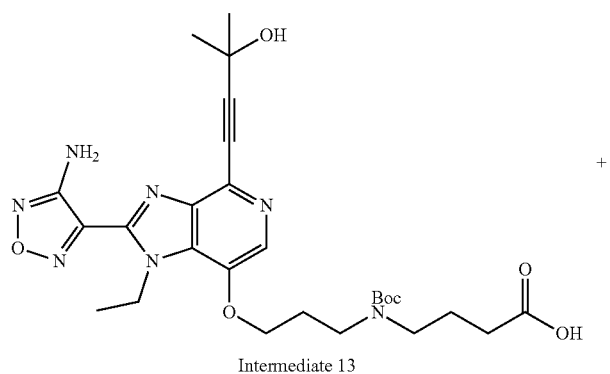

Intermediate 13

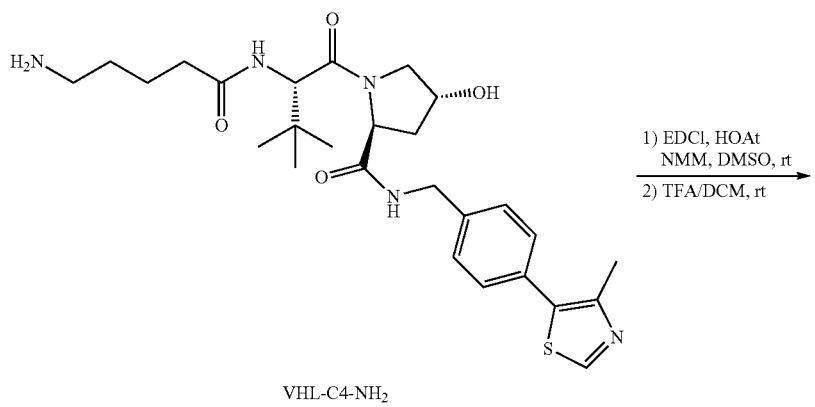

VHL-C4-NH$_2$

1) EDCl, HOAt NMM, DMSO, rt
2) TFA/DCM, rt

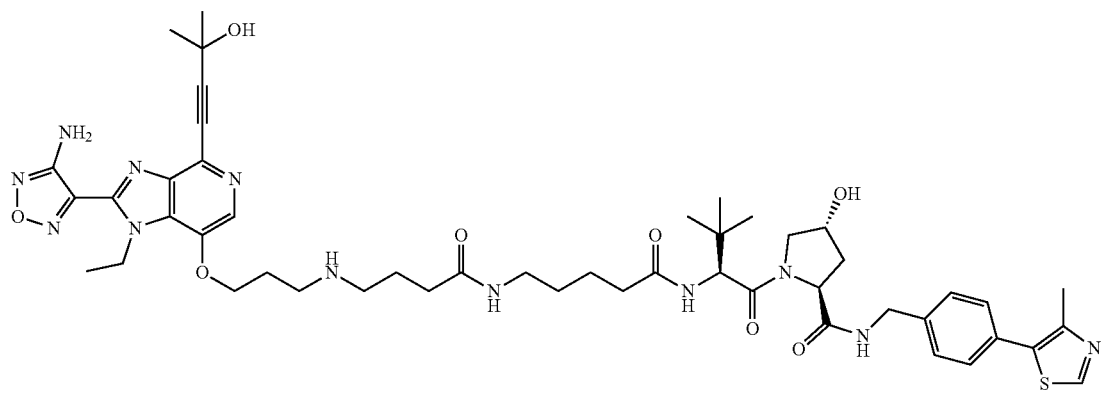

XF067-95

XF067-95 was synthesized following the standard procedure for preparing XF067-84 from intermediate 13 (9.1 mg, 0.016 mmol), VHL-C4-NH$_2$ (9.1 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-95 was obtained as white solid in TFA salt form (6.7 mg, 43%). $^1$H NMR (500 MHz, CD$_3$OD) δ 8.98 (s, 1H), 8.24 (s, 1H), 7.52-7.37 (m, 4H), 5.06 (q, J=7.1 Hz, 2H), 4.63 (s, 1H), 4.55 (ddt, J=17.1, 10.3, 6.2 Hz, 5H), 4.39 (d, J=15.4 Hz, 1H), 3.91 (d, J=11.0 Hz, 1H), 3.82 (dd, J=11.0, 4.0 Hz, 1H), 3.41-3.26 (m, 2H), 3.22-3.04 (m, 4H), 2.51-2.35 (m, 7H), 2.35-2.18 (m, 3H), 2.17-2.05 (m, 1H), 1.99 (p, J=6.9 Hz, 2H), 1.69 (s, 6H), 1.65-1.40 (m, 7H), 1.04 (s, 9H). ESI-MS (m/z) [M+H]$^+$: 983.4927.

Example 149

Synthesis of XF067-96

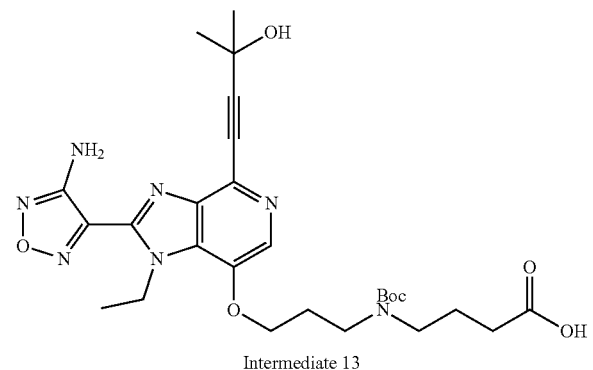

Intermediate 13

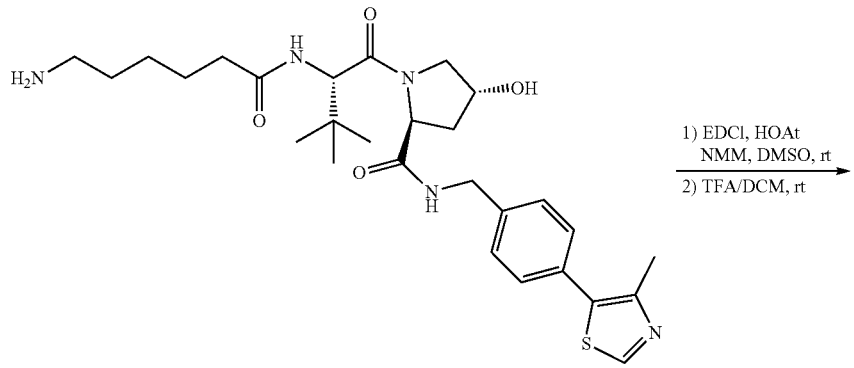

VHL-C5-NH$_2$

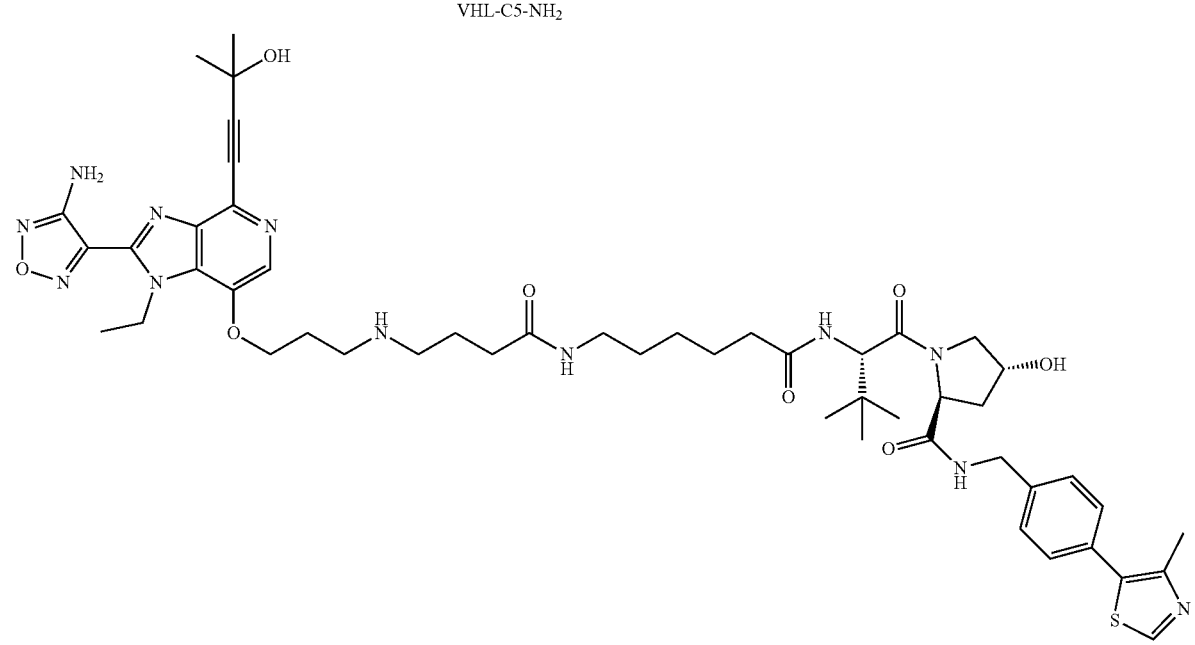

XF067-96

XF067-96 was synthesized following the standard procedure for preparing XF067-84 from intermediate 13 (9.1 mg, 0.016 mmol), VHL-C5-NH$_2$ (9.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-96 was obtained as white solid in TFA salt form (6.7 mg, 42%). $^1$H NMR (500 MHz, CD$_3$OD) δ 8.97 (s, 1H), 8.23 (s, 1H), 7.54-7.35 (m, 4H), 5.06 (q, J=7.0 Hz, 2H), 4.64 (s, 1H), 4.61-4.47 (m, 5H), 4.38 (d, J=15.5 Hz, 1H), 3.92 (d, J=11.0 Hz, 1H), 3.83 (dd, J=10.9, 3.9 Hz, 1H), 3.39-3.32 (m, 2H), 3.17 (t, J=7.0 Hz, 2H), 3.08 (t, J=7.1 Hz, 2H), 2.50 (s, 3H), 2.48-2.35 (m, 4H), 2.34-2.20 (m, 3H), 2.11 (ddd, J=13.3, 9.1, 4.5 Hz, 1H), 1.99 (p, J=6.9 Hz, 2H), 1.69 (s, 6H), 1.65-1.54 (m, 5H), 1.48 (p, J=7.3 Hz, 2H), 1.39-1.25 (m, 2H), 1.05 (s, 9H). ESI-MS (m/z) for [M+H]$^+$: 997.5079.

Example 150

Synthesis of XF067-97

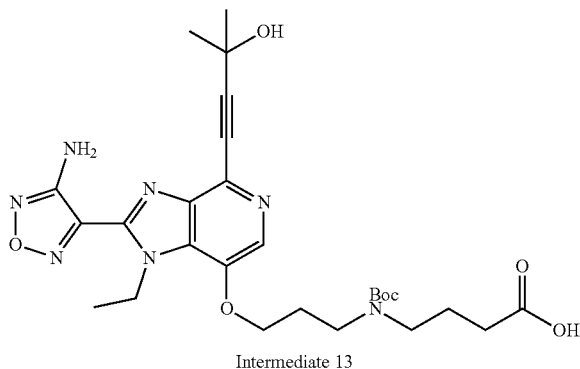

Intermediate 13

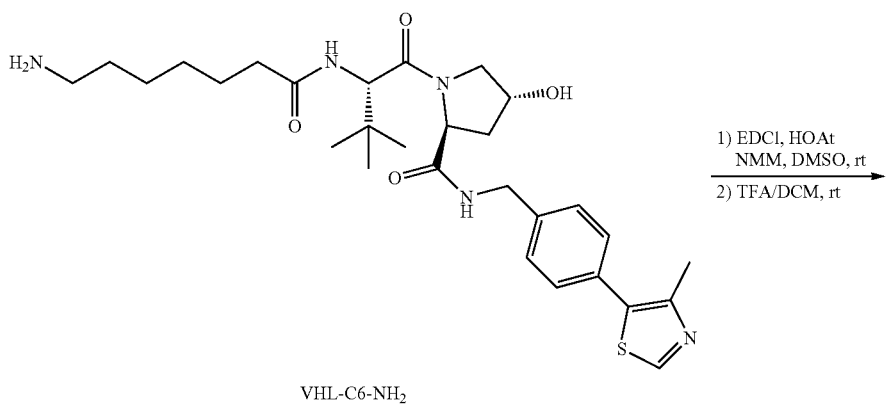

VHL-C6-NH$_2$

1) EDCl, HOAt
   NMM, DMSO, rt
2) TFA/DCM, rt

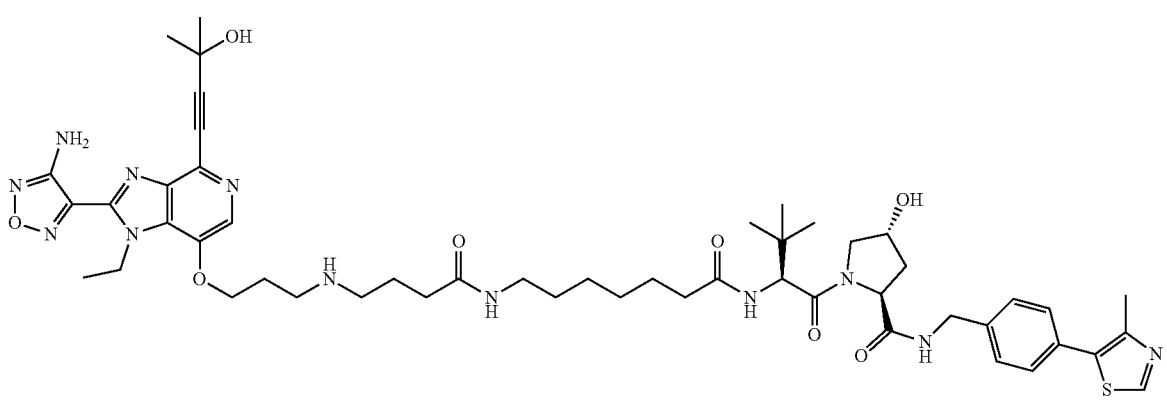

XF067-97

XF067-97 was synthesized following the standard procedure for preparing XF067-84 from intermediate 13 (9.1 mg, 0.016 mmol), VHL-C6-NH₂ (9.5 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-97 was obtained as white solid in TFA salt form (13.9 mg, 86%). $^1$H NMR (500 MHz, CD$_3$OD) δ 9.11-8.85 (m, 1H), 8.25 (s, 1H), 7.58-7.32 (m, 4H), 5.07 (tt, J=9.3, 4.8 Hz, 2H), 4.72-4.48 (m, 6H), 4.39 (dd, J=15.4, 3.3 Hz, 1H), 3.92 (d, J=10.7 Hz, 1H), 3.83 (d, J=10.9, 3.6 Hz, 1H), 3.33-3.27 (m, 2H), 3.22-3.14 (m, 2H), 3.11-2.95 (m, 2H), 2.57-2.17 (m, 10H), 2.11 (ddt, J=13.2, 8.9, 3.9 Hz, 1H), 2.00 (dtt, J=12.8, 8.9, 4.6 Hz, 2H), 1.73-1.51 (m, 9H), 1.51-1.41 (m, 2H), 1.41-1.23 (m, 6H), 1.05 (s, 9H). ESI-MS (m/z) for [M+H]$^+$: 1011.5239.

Example 151

Synthesis of XF067-98

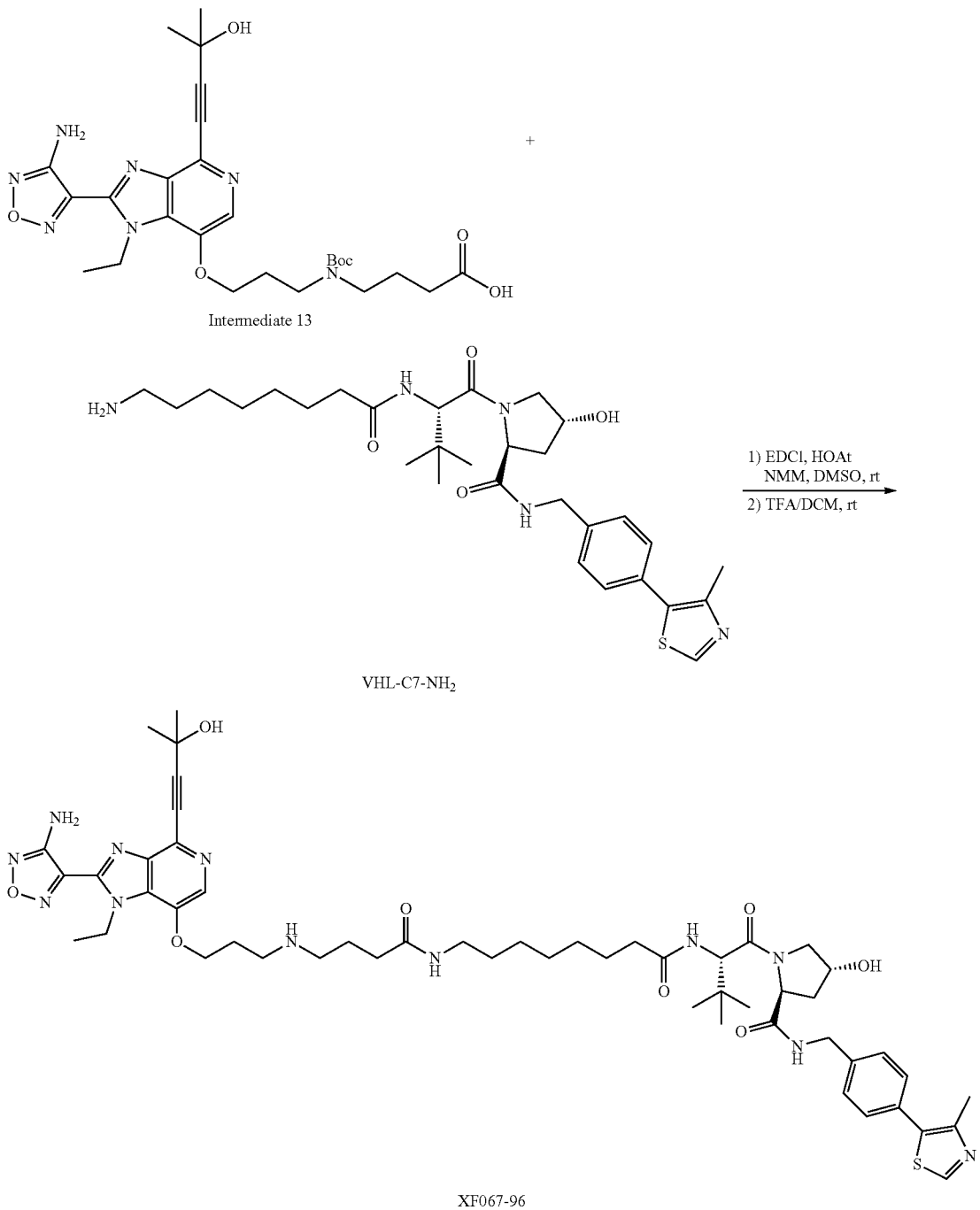

Intermediate 13

VHL-C7-NH₂

1) EDCl, HOAt NMM, DMSO, rt
2) TFA/DCM, rt

XF067-96

XF067-98 was synthesized following the standard procedure for preparing XF067-84 from intermediate 13 (9.1 mg, 0.016 mmol), VHL-C7-NH$_2$ (12.8 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-98 was obtained as white solid in TFA salt form (8.6 mg, 52%). $^1$H NMR (500 MHz, CD$_3$OD) δ 8.97 (s, 1H), 8.22 (s, 1H), 7.57-7.19 (m, 4H), 5.14-4.97 (m, 2H), 4.67-4.43 (m, 6H), 4.38 (dd, J=15.5, 2.6 Hz, 1H), 3.92 (d, J=11.0 Hz, 1H), 3.82 (dd, J=11.0, 3.9 Hz, 1H), 3.32 (d, J=2.2 Hz, 2H), 3.17 (td, J=7.0, 2.6 Hz, 2H), 3.06 (td, J=7.1, 2.6 Hz, 2H), 2.54-2.35 (m, 8H), 2.34-2.18 (m, 2H), 2.13-2.06 (m, 1H), 2.04-1.93 (m, 2H), 1.77-1.52 (m, 9H), 1.44 (p, J=7.2 Hz, 2H), 1.39-1.12 (m, 8H), 1.05 (s, 9H). ESI-MS (m/z) [M+H]$^+$: 1025.5387.

Example 152

Synthesis of XF067-99

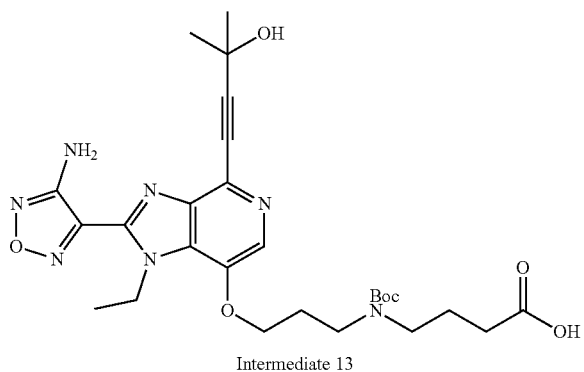

Intermediate 13

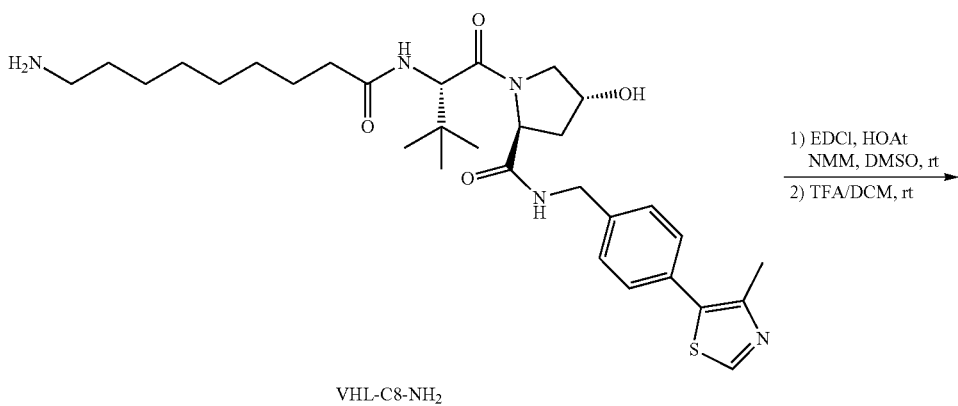

VHL-C8-NH$_2$

1) EDCI, HOAt
   NMM, DMSO, rt
2) TFA/DCM, rt

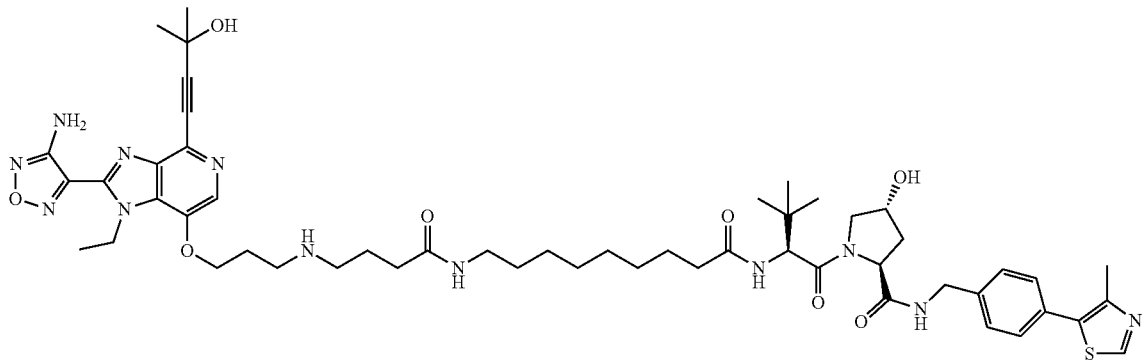

XF067-99

XF067-99 was synthesized following the standard procedure for preparing XF067-84 from intermediate 13 (9.1 mg, 0.016 mmol), VHL-C8-NH$_2$ (10 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-99 was obtained as white solid in TFA salt form (7 mg, 42%). $^1$H NMR (500 MHz, CD$_3$OD) δ 8.95 (s, 1H), 8.21 (s, 1H), 7.54-7.31 (m, 4H), 5.06 (q, J=7.1 Hz, 2H), 4.65 (s, 1H), 4.62-4.48 (m, 5H), 4.38 (d, J=15.5 Hz, 1H), 3.92 (d, J=11.0 Hz, 1H), 3.83 (dd, J=11.0, 3.9 Hz, 1H), 3.37-3.29 (m, J=2.8 Hz, 2H), 3.17 (t, J=6.9 Hz, 2H), 3.05 (t, J=7.1 Hz, 2H), 2.52-2.37 (m, 7H), 2.34-2.19 (m, 3H), 2.15-2.04 (m, 1H), 1.98 (p, J=6.7 Hz, 2H), 1.69 (s, 6H), 1.65-1.54 (m, 3H), 1.43 (p, J=7.1 Hz, 2H), 1.30 (d, J=13.7 Hz, 10H), 1.05 (s, 9H). ESI-MS (m/z) [M+H]$^+$: 1039.5534.

Example 153

Synthesis of XF067-100

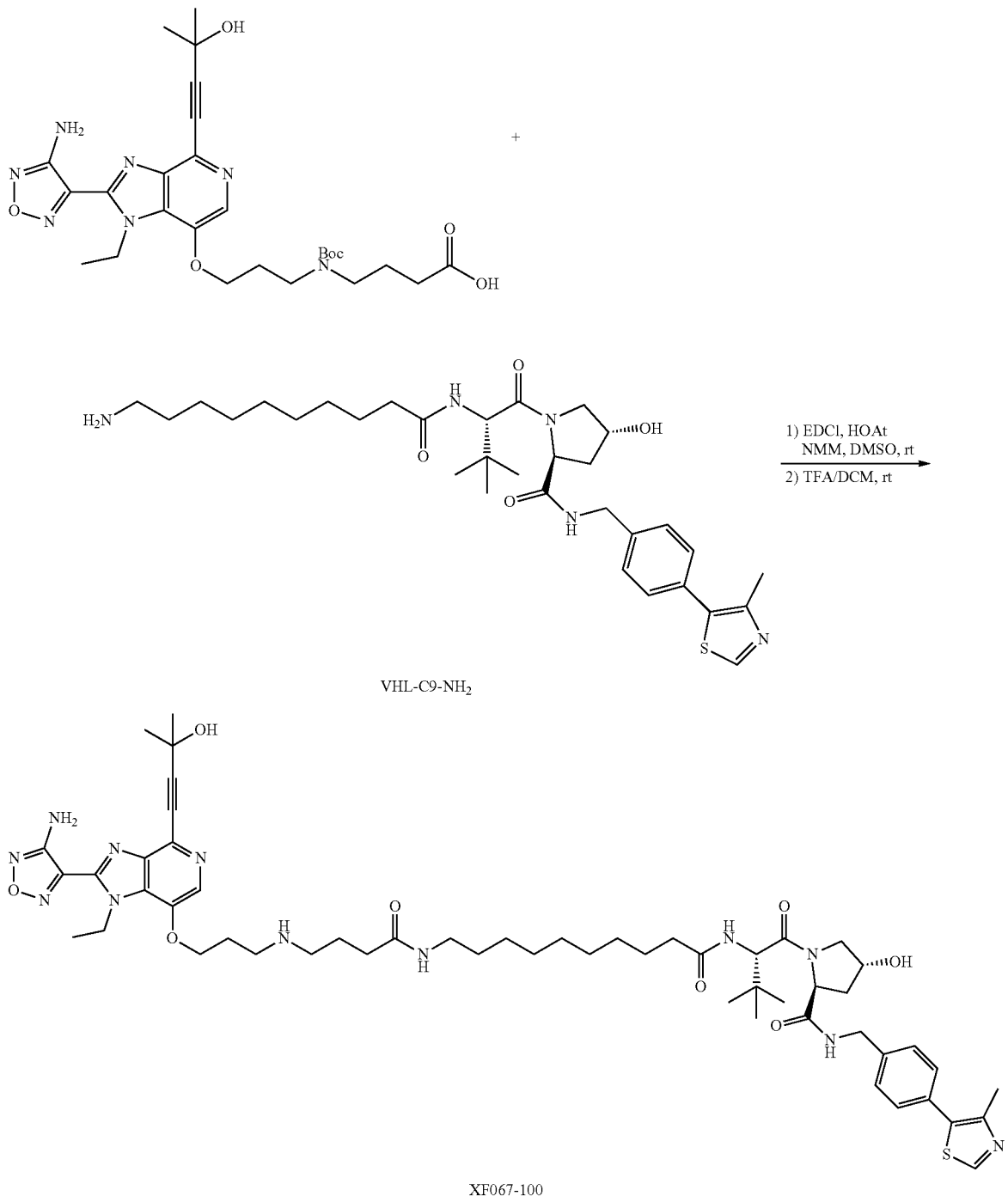

XF067-100

XF067-100 was synthesized following the standard procedure for preparing XF067-84 from intermediate 13 (9.1 mg, 0.016 mmol), VHL-C9-NH$_2$ (13.2 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-100 was obtained as white solid in TFA salt form (3.9 mg, 23%). $^1$H NMR (500 MHz, CD$_3$OD) δ 8.92 (d, J=4.5 Hz, 1H), 8.17 (d, J=5.8 Hz, 1H), 7.62-7.29 (m, 4H), 5.15-5.00 (m, 2H), 4.65 (d, J=2.5 Hz, 1H), 4.63-4.46 (m, 5H), 4.42-4.29 (m, 1H), 3.92 (d, J=11.0 Hz, 1H), 3.83 (dd, J=11.0, 3.9 Hz, 1H), 3.35-3.29 (m, 2H), 3.17 (dd, J=7.8, 5.9 Hz, 2H), 3.05 (td, J=7.3, 3.5 Hz, 2H), 2.58-2.18 (m, 10H), 2.11 (ddd, J=13.2, 9.0, 4.5 Hz, 1H), 2.04-1.89 (m, 2H), 1.76-1.50 (m, 9H), 1.42 (t, J=7.0 Hz, 2H), 1.38-1.12 (m, 12H), 1.05 (s, 9H). ESI-MS (m/z) [M+H]$^+$: 1053.5711.

Example 154

Synthesis of XF067-101

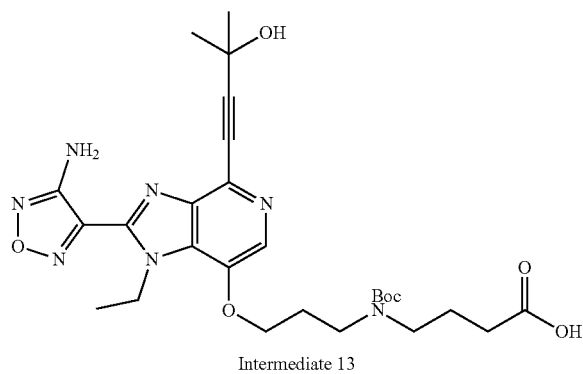

Intermediate 13

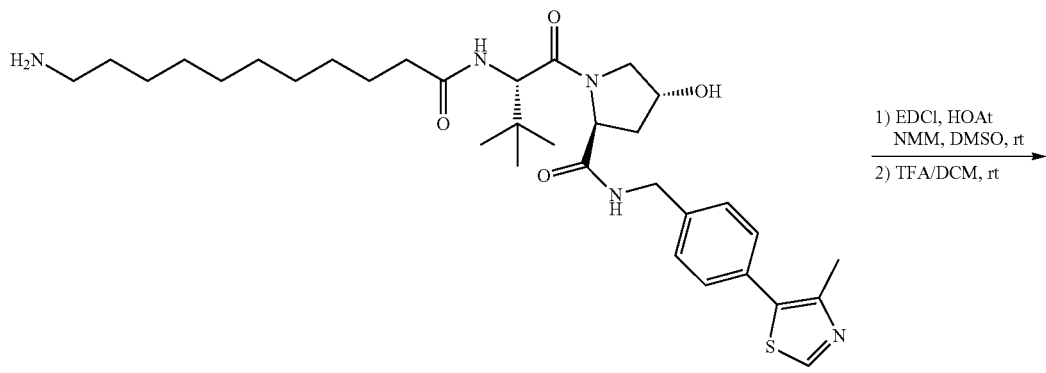

VHL-C10-NH$_2$

1) EDCl, HOAt NMM, DMSO, rt
2) TFA/DCM, rt

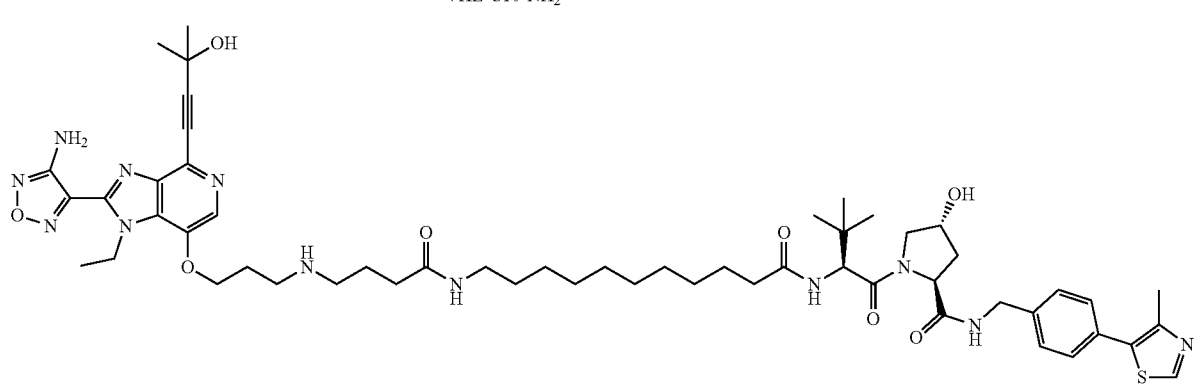

XF067-101

XF067-101 was synthesized following the standard procedure for preparing XF067-84 from intermediate 13 (9.1 mg, 0.016 mmol), VHL-C10-NH₂ (10.4 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-101 was obtained as white solid in TFA salt form (4.8 mg, 26%). ¹H NMR (500 MHz, CD₃OD) δ 8.96 (d, J=2.6 Hz, 1H), 8.22 (d, J=2.5 Hz, 1H), 7.58-7.32 (m, 4H), 5.13-5.00 (m, 2H), 4.65 (s, 1H), 4.63-4.50 (m, 5H), 4.37 (dd, J=15.4, 2.8 Hz, 1H), 3.92 (d, J=11.0 Hz, 1H), 3.83 (dd, J=11.0, 3.9 Hz, 1H), 3.33-3.30 (m, 2H), 3.21-3.14 (m, 2H), 3.06 (dd, J=9.4, 4.5 Hz, 2H), 2.54-2.38 (m, 7H), 2.36-2.20 (m, 3H), 2.11 (ddd, J=13.3, 9.1, 4.5 Hz, 1H), 2.06-1.91 (m, 2H), 1.75-1.57 (m, 9H), 1.43 (t, J=7.1 Hz, 2H), 1.39-1.22 (m, 14H), 1.05 (s, 9H). ESI-MS (m/z) [M+H]⁺: 1067.5853.

Example 155

Synthesis of XF067-102

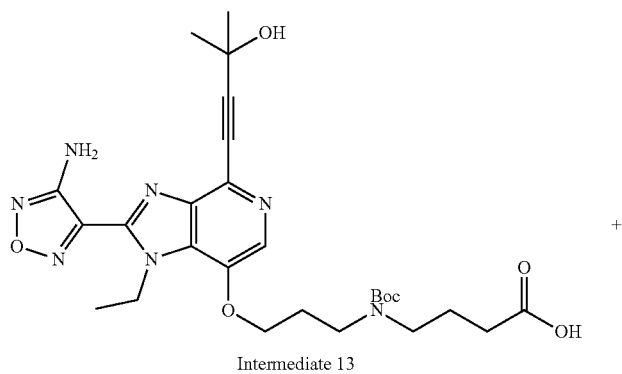

Intermediate 13

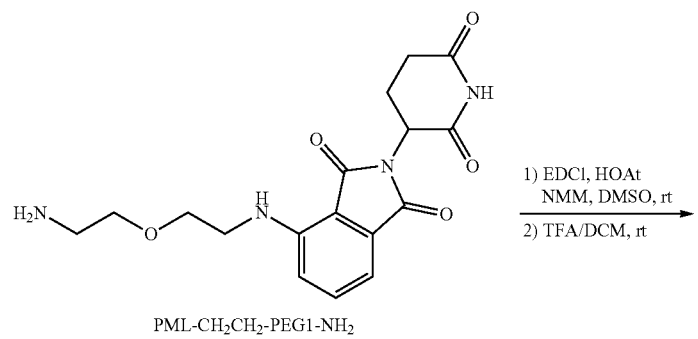

PML-CH₂CH₂-PEG1-NH₂

1) EDCl, HOAt NMM, DMSO, rt
2) TFA/DCM, rt

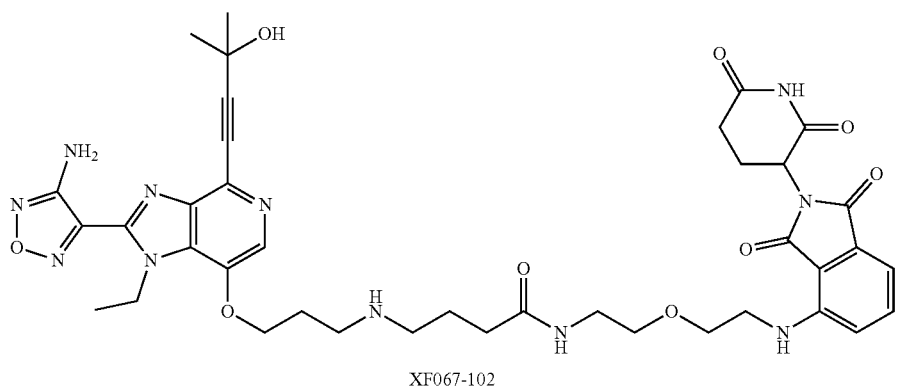

XF067-102

XF067-102 was synthesized following the standard procedure for preparing XF067-84 from intermediate 13 (9.1 mg, 0.016 mmol), PML-CH$_2$CH$_2$-PEG1-NH$_2$ (7.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-102 was obtained as yellow solid in TFA salt form (9.6 mg, 26%). $^1$H NMR (500 MHz, CD$_3$OD) δ 8.17 (s, 1H), 7.50 (dd, J=8.6, 7.1 Hz, 1H), 7.01 (t, J=8.2 Hz, 2H), 5.06 (dd, J=12.7, 5.5 Hz, 1H), 4.99 (q, J=7.1 Hz, 2H), 4.50 (t, J=5.8 Hz, 2H), 3.66 (t, J=5.1 Hz, 2H), 3.52 (t, J=5.3 Hz, 2H), 3.44 (t, J=5.1 Hz, 2H), 3.40-3.26 (m, 4H), 3.14 (t, J=6.8 Hz, 2H), 2.88 (ddd, J=17.3, 13.8, 5.3 Hz, 1H), 2.81-2.63 (m, 2H), 2.48 (t, J=6.4 Hz, 2H), 2.39-2.35 (m, 2H), 2.13 (dtd, J=13.2, 5.3, 2.5 Hz, 1H), 1.97 (p, J=6.7 Hz, 2H), 1.69 (s, 6H), 1.53 (t, J=7.1 Hz, 3H). ESI-MS (m/z) [M+H]$^+$: 814.3611.

Example 156

Synthesis of XF067-103

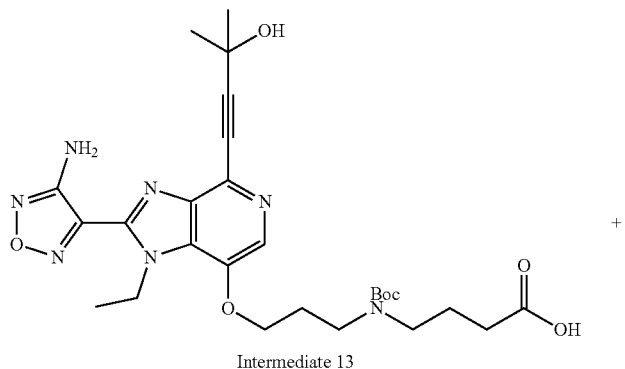

Intermediate 13

+

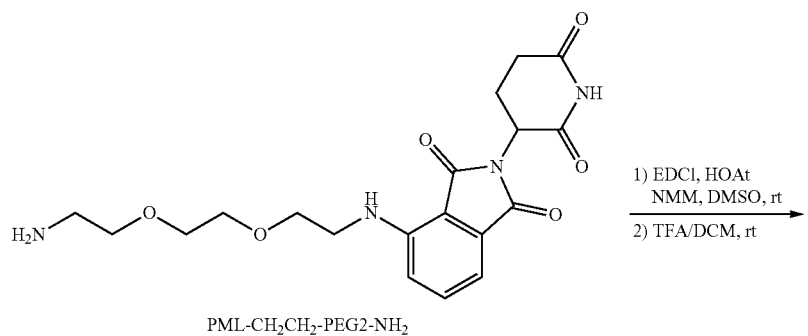

PML-CH$_2$CH$_2$-PEG2-NH$_2$

1) EDCl, HOAt NMM, DMSO, rt
2) TFA/DCM, rt

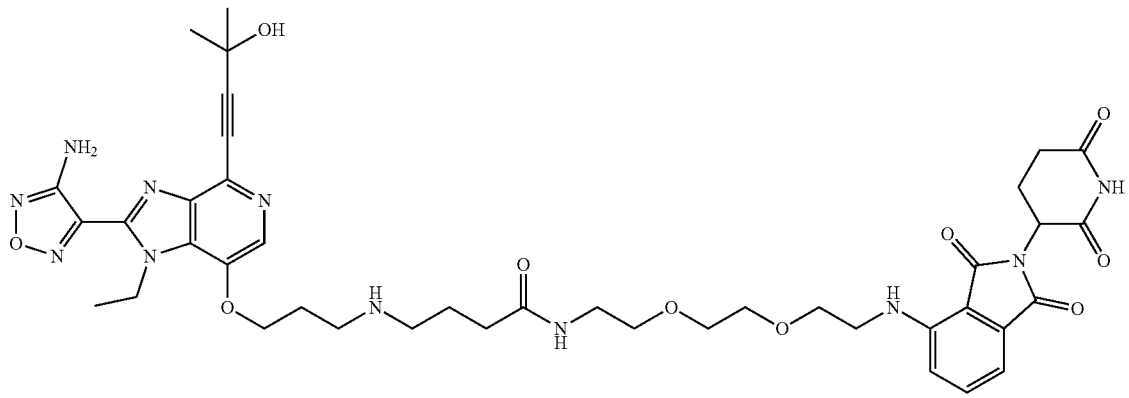

XF067-103

XF067-103 was synthesized following the standard procedure for preparing XF067-84 from intermediate 13 (9.1 mg, 0.016 mmol), PML-CH$_2$CH$_2$-PEG2-NH$_2$ (8.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-103 was obtained as yellow solid in TFA salt form (7.8 mg, 57%). $^1$H NMR (500 MHz, CD$_3$OD) δ 8.16 (s, 1H), 7.53 (dd, J=8.5, 7.1 Hz, 1H), 7.05 (dd, J=15.6, 7.8 Hz, 2H), 5.09-4.97 (m, 3H), 4.51 (t, J=5.9 Hz, 2H), 3.73 (t, J=5.2 Hz, 2H), 3.70-3.60 (m, 4H), 3.55-3.46 (m, 4H), 3.34-3.24 (m, 4H), 3.14 (t, J=7.0 Hz, 2H), 2.87 (ddd, J=17.6, 14.0, 5.3 Hz, 1H), 2.80-2.64 (m, 2H), 2.46-2.34 (m, 4H), 2.13 (dtd, J=13.1, 5.7, 2.9 Hz, 1H), 1.97 (p, J=6.8 Hz, 2H), 1.69 (s, 6H), 1.56 (t, J=7.1 Hz, 3H). ESI-MS (m/z) [M+H]$^+$: 858.3879.

Example 157

Synthesis of XF067-104

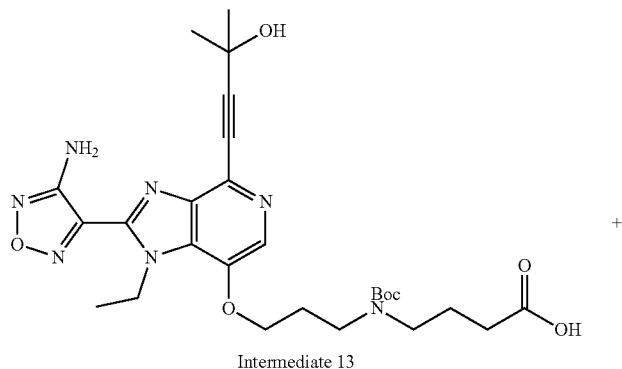

Intermediate 13

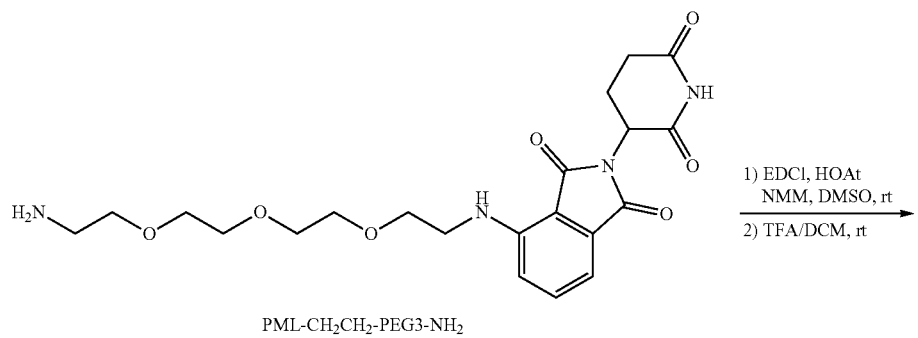

PML-CH$_2$CH$_2$-PEG3-NH$_2$

1) EDCl, HOAt NMM, DMSO, rt
2) TFA/DCM, rt

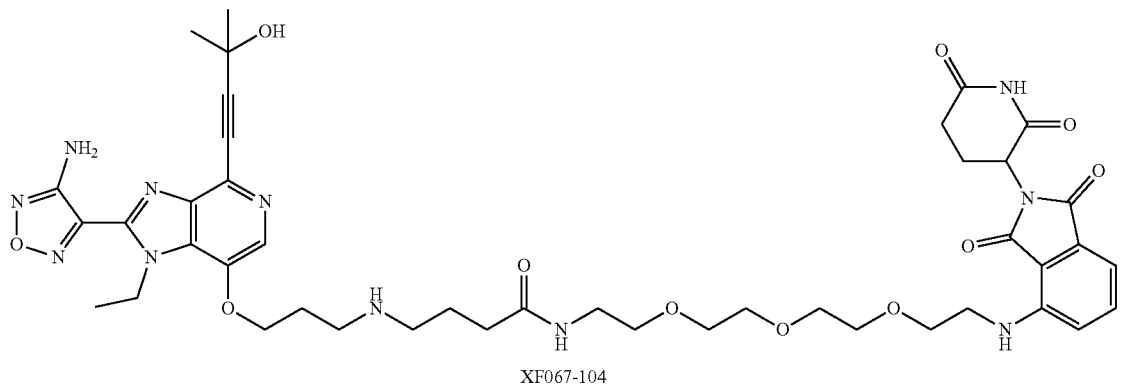

XF067-104

XF067-104 was synthesized following the standard procedure for preparing XF067-84 from intermediate 13 (9.1 mg, 0.016 mmol), PML-CH$_2$CH$_2$-PEG3-NH$_2$ (9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-104 was obtained as yellow solid in TFA salt form (11.3 mg, 78%). $^1$H NMR (500 MHz, CD$_3$OD) δ 8.23 (s, 1H), 7.51 (dd, J=8.6, 7.1 Hz, 1H), 7.02 (dd, J=19.2, 7.8 Hz, 2H), 5.09-4.99 (m, 3H), 4.52 (t, J=5.9 Hz, 2H), 3.73 (t, J=5.2 Hz, 2H), 3.68 (s, 4H), 3.69-3.63 (m, 2H), 3.66-3.55 (m, 2H), 3.49 (dt, J=7.7, 5.3 Hz, 4H), 3.37-3.25 (m, 4H), 3.15 (t, J=7.0 Hz, 2H), 2.88 (ddd, J=17.6, 14.0, 5.3 Hz, 1H), 2.82-2.65 (m, 2H), 2.47-2.38 (m, 4H), 2.13 (dtd, J=13.1, 5.7, 2.9 Hz, 1H), 1.98 (p, J=6.9 Hz, 2H), 1.70 (s, 6H), 1.57 (t, J=7.1 Hz, 3H). ESI-MS (m/z) [M+H]$^+$: 902.4134.

Example 158

Synthesis of XF067-105

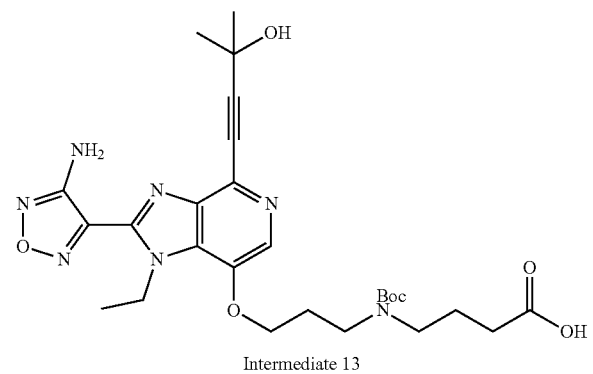

Intermediate 13

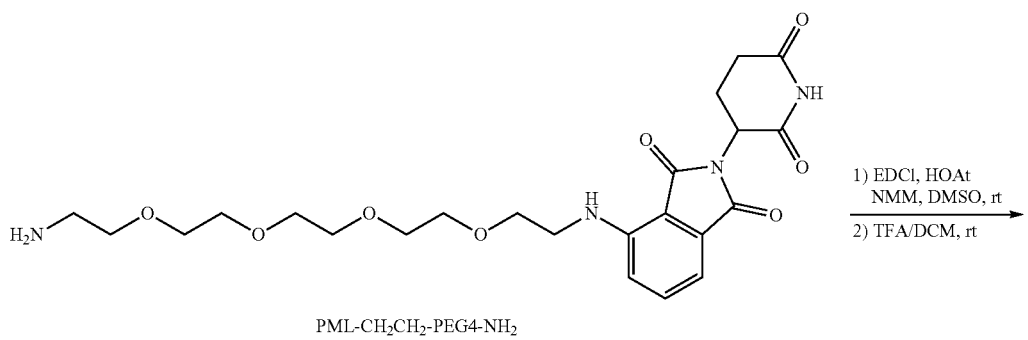

PML-CH$_2$CH$_2$-PEG4-NH$_2$

1) EDCI, HOAt NMM, DMSO, rt
2) TFA/DCM, rt

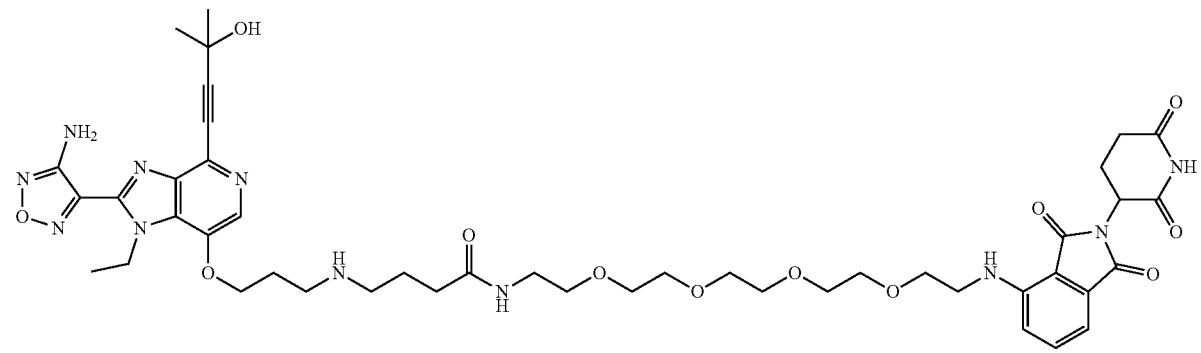

XF067-105

XF067-105 was synthesized following the standard procedure for preparing XF067-84 from intermediate 13 (9.1 mg, 0.016 mmol), PML-CH$_2$CH$_2$—PEG4-NH$_2$ (9 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-105 was obtained as yellow solid in TFA salt form (5.2 mg, 34%). $^1$H NMR (500 MHz, CD$_3$OD) δ 8.19 (s, 1H), 7.52 (dd, J=8.6, 7.1 Hz, 1H), 7.04 (dd, J=19.6, 7.8 Hz, 2H), 5.09-4.98 (m, 3H), 4.51 (t, J=5.8 Hz, 2H), 3.73 (t, J=5.2 Hz, 2H), 3.70-3.60 (m, 10H), 3.58 (dd, J=6.1, 3.4 Hz, 2H), 3.49 (t, J=5.3 Hz, 4H), 3.34-3.25 (m, 4H), 3.16 (t, J=7.0 Hz, 2H), 2.88 (ddd, J=17.5, 14.0, 5.3 Hz, 1H), 2.81-2.65 (m, 2H), 2.46 (t, J=6.5 Hz, 2H), 2.41-2.37 (m, 2H), 2.17-2.10 (m, 1H), 1.98 (p, J=6.9 Hz, 2H), 1.69 (s, 6H), 1.57 (t, J=7.1 Hz, 3H). ESI-MS (m/z) [M+H]$^+$: 946.4412.

Example 159

Synthesis of XF067-106

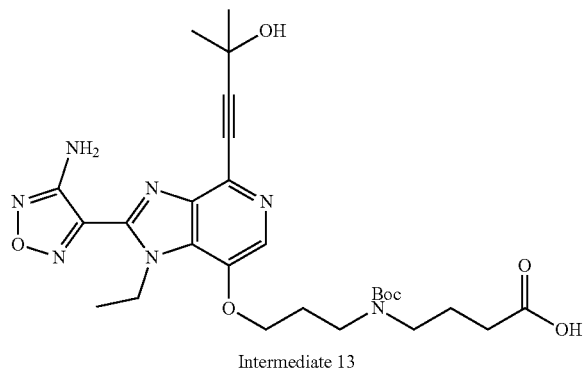

Intermediate 13

+

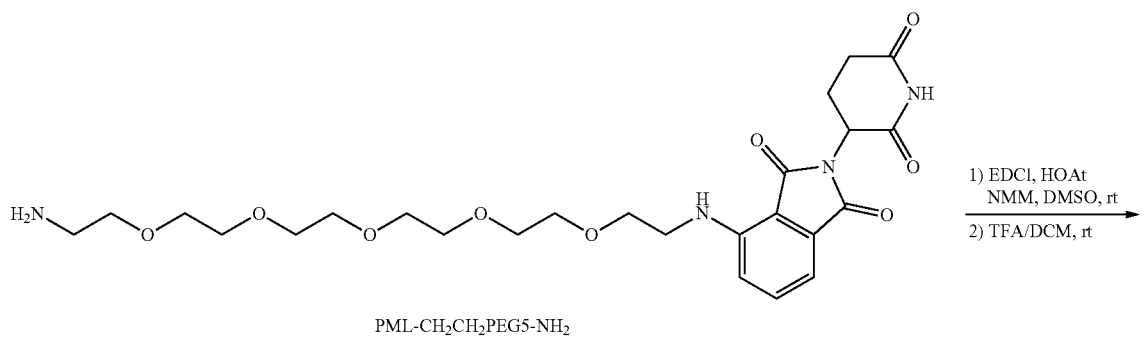

PML-CH$_2$CH$_2$PEG5-NH$_2$

1) EDCl, HOAt NMM, DMSO, rt
2) TFA/DCM, rt

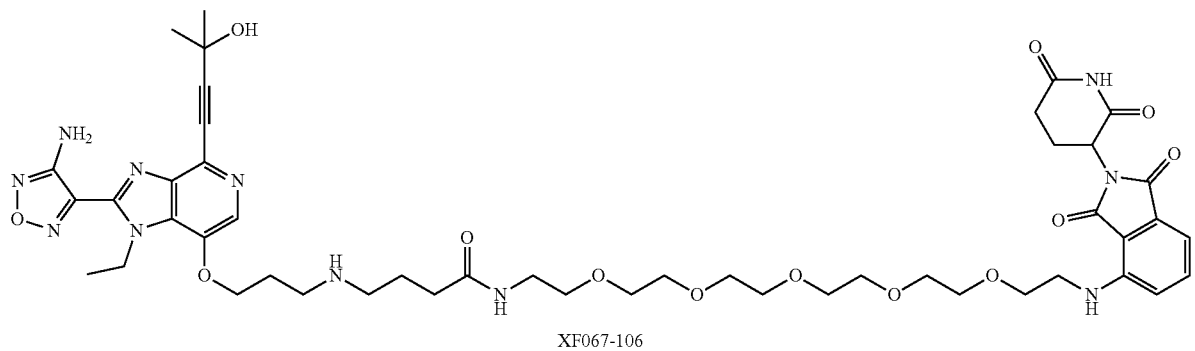

XF067-106

XF067-106 was synthesized following the standard procedure for preparing XF067-84 from intermediate 13 (9.1 mg, 0.016 mmol), PML-CH$_2$CH$_2$-PEG5-NH$_2$ (9.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-106 was obtained as yellow solid in TFA salt form (12.8 mg, 81%). $^1$H NMR (500 MHz, CD$_3$OD) δ 8.24 (d, J=3.6 Hz, 1H), 7.60-7.45 (m, 1H), 7.04 (ddd, J=19.7, 8.0, 3.7 Hz, 2H), 5.05 (td, J=8.7, 7.4, 3.8 Hz, 3H), 4.54 (q, J=5.8, 5.0 Hz, 2H), 3.82-3.56 (m, 18H), 3.49 (q, J=5.3 Hz, 4H), 3.37-3.27 (m, 4H), 3.23-3.15 (m, 2H), 2.93-2.82 (m, 1H), 2.83-2.72 (m, 2H), 2.47-2.37 (m, 4H), 2.13 (dtd, J=13.0, 5.7, 2.9 Hz, 1H), 1.99 (p, J=6.8, 5.6 Hz, 2H), 1.70 (d, J=3.7 Hz, 6H), 1.62-1.53 (m, 3H). ESI-MS (m/z) [M+H]$^+$: 990.4668.

Example 160

Synthesis of XF067-107

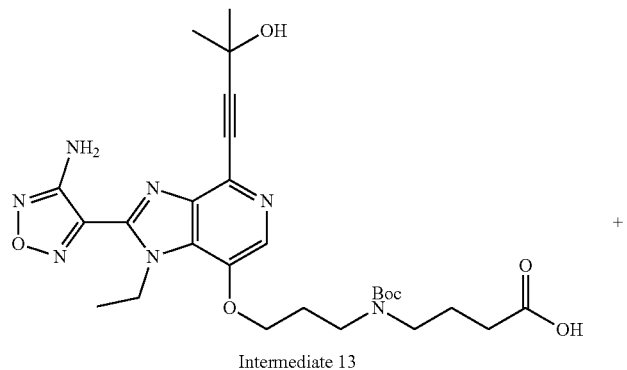

Intermediate 13

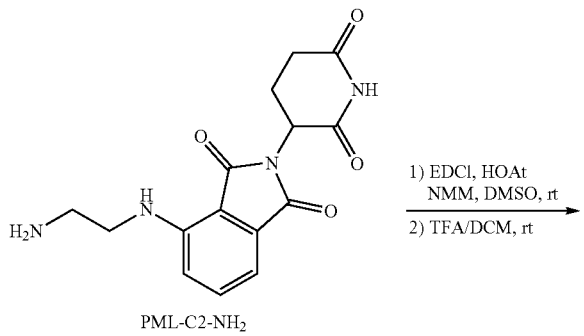

PML-C2-NH$_2$

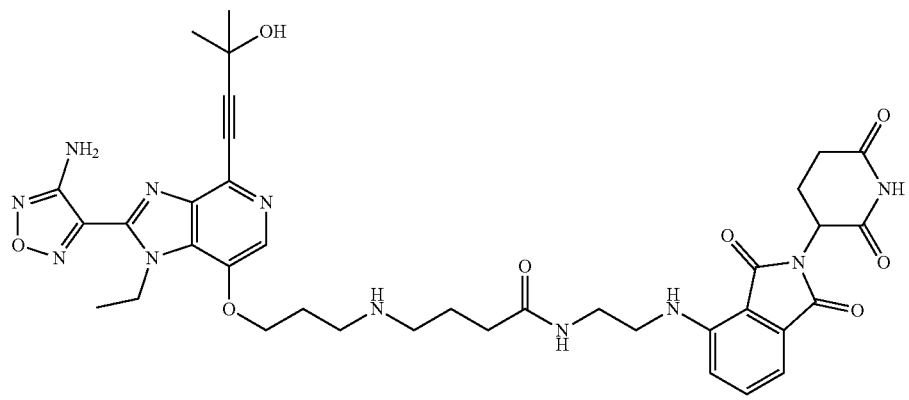

XF067-107

XF067-107 was synthesized following the standard procedure for preparing XF067-84 from intermediate 13 (9.1 mg, 0.016 mmol), PML-C2-NH$_2$ (7 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-107 was obtained as yellow solid in TFA salt form (12.1 mg, 98%). $^1$H NMR (500 MHz, CD$_3$OD) δ 8.26 (d, J=13.2 Hz, 1H), 7.55-7.44 (m, 1H), 7.02 (dd, J=14.2, 7.8 Hz, 2H), 5.09-4.98 (m, 3H), 4.62-4.51 (m, 2H), 3.36-3.32 (m, 6H), 3.15 (t, J=6.6 Hz, 2H), 2.87 (ddd, J=17.2, 13.8, 5.3 Hz, 1H), 2.81-2.62 (m, 2H), 2.51-2.43 (m, 2H), 2.39 (tq, J=12.7, 6.8 Hz, 2H), 2.13 (dtd, J=13.2, 5.4, 2.6 Hz, 1H), 2.01-1.94 (m, 2H), 1.69 (s, 6H), 1.64-1.52 (m, 3H). ESI-MS (m/z) [M+H]$^+$: 770.3356.

Example 161

Synthesis of XF067-108

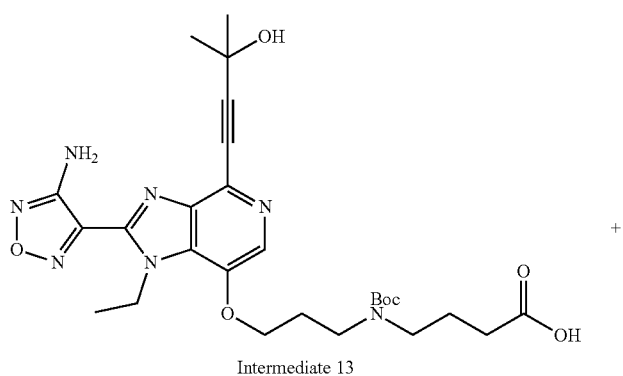

Intermediate 13

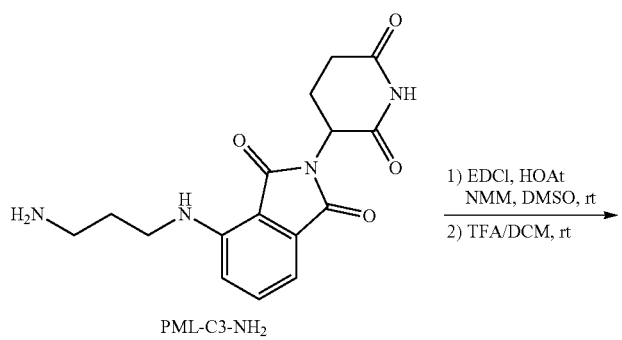

PML-C3-NH$_2$

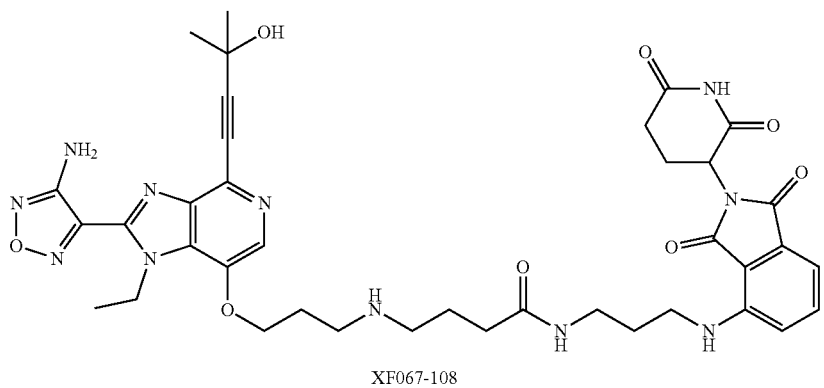

XF067-108

XF067-108 was synthesized following the standard procedure for preparing XF067-84 from intermediate 13 (9.1 mg, 0.016 mmol), PML-C3-NH$_2$ (7.1 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-108 was obtained as yellow solid in TFA salt form (11.7 mg, 93%). $^1$H NMR (500 MHz, CD$_3$OD) δ 8.25 (s, 1H), 7.51 (dd, J=8.6, 7.1 Hz, 1H), 6.99 (dd, J=7.8, 4.6 Hz, 2H), 5.08-4.98 (m, 3H), 4.54 (t, J=5.8 Hz, 2H), 3.39-3.29 (m, 4H), 3.31-3.22 (m, 2H), 3.18 (t, J=6.6 Hz, 2H), 2.87 (ddd, J=17.5, 14.0, 5.4 Hz, 1H), 2.80-2.64 (m, 2H), 2.51 (t, J=6.4 Hz, 2H), 2.45-2.38 (m, 2H), 2.12 (ddt, J=13.1, 5.4, 2.8 Hz, 1H), 2.00 (q, J=6.5 Hz, 2H), 1.77 (q, J=6.4 Hz, 2H), 1.70 (s, 6H), 1.56 (t, J=7.1 Hz, 3H). ESI-MS (m/z) [M+H]$^+$: 784.3534.

Example 162

Synthesis of XF067-109

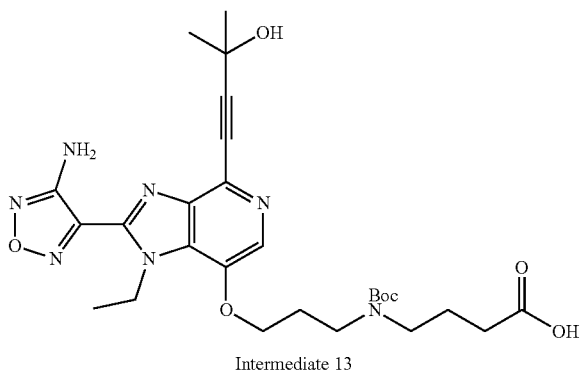

Intermediate 13

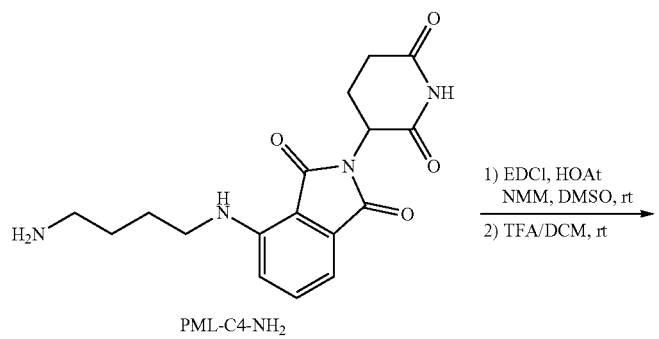

PML-C4-NH$_2$

1) EDCI, HOAt NMM, DMSO, rt
2) TFA/DCM, rt

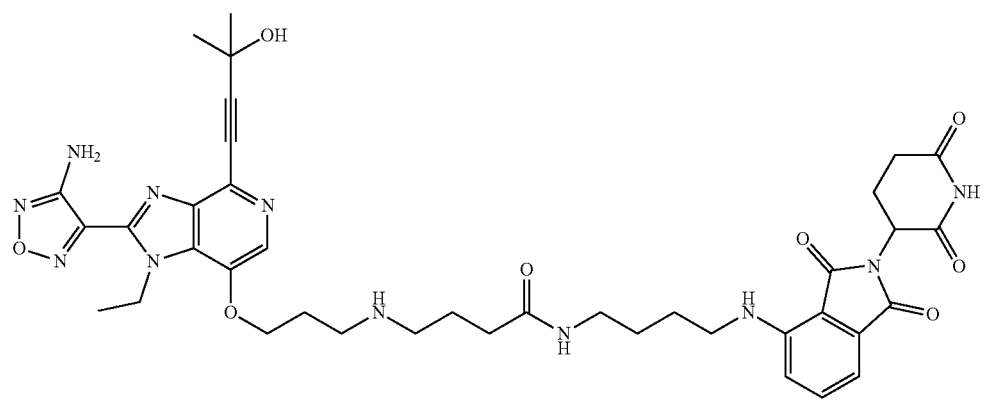

XF067-109

XF067-109 was synthesized following the standard procedure for preparing XF067-84 from intermediate 13 (9.1 mg, 0.016 mmol), PML-C4-NH₂ (7.3 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-109 was obtained as yellow solid in TFA salt form (9.6 mg, 75%). ¹H NMR (500 MHz, CD₃OD) δ 8.25 (s, 1H), 7.51 (t, J=7.8 Hz, 1H), 7.03-6.96 (m, 2H), 5.04 (q, J=7.1, 6.3 Hz, 3H), 4.54 (t, J=5.8 Hz, 2H), 3.47-3.01 (m, 8H), 2.93-2.62 (m, 3H), 2.59-2.31 (m, 4H), 2.18-2.07 (m, 1H), 1.99 (p, J=6.4 Hz, 2H), 1.82-1.45 (m, 13H). ESI-MS (m/z) [M+H]⁺: 798.3667.

Example 163

Synthesis of XF067-110

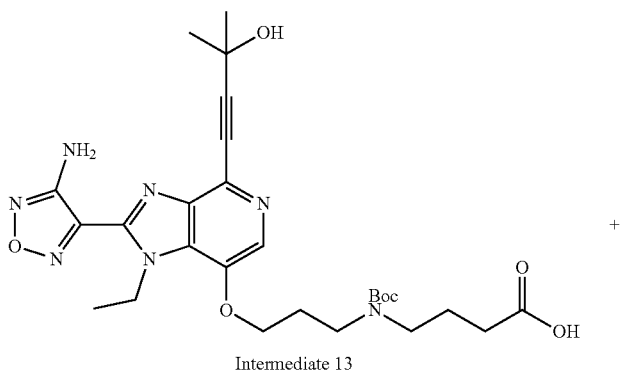

Intermediate 13

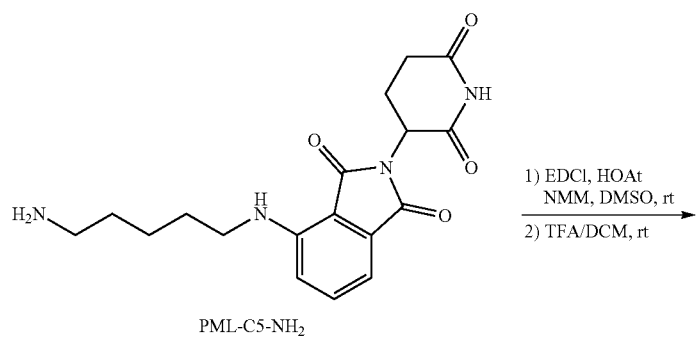

PML-C5-NH₂

1) EDCl, HOAt NMM, DMSO, rt
2) TFA/DCM, rt

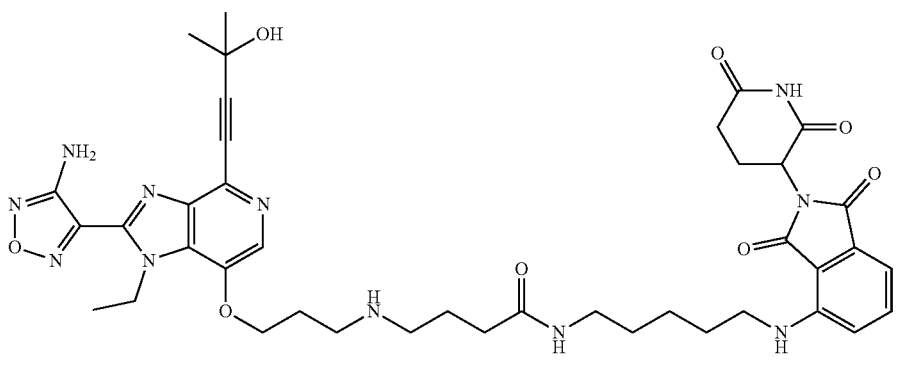

XF067-110

XF067-110 was synthesized following the standard procedure for preparing XF067-84 from intermediate 13 (9.1 mg, 0.016 mmol), PML-C5-NH$_2$ (7.6 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-110 was obtained as yellow solid in TFA salt form (10.6 mg, 82%). $^1$H NMR (500 MHz, CD$_3$OD) δ 8.18 (s, 1H), 7.49 (dd, J=8.5, 7.1 Hz, 1H), 6.98 (dd, J=7.8, 6.4 Hz, 2H), 5.08-4.96 (m, 3H), 4.51 (t, J=5.8 Hz, 2H), 3.34-3.23 (m, 3H), 3.20-3.07 (m, 4H), 2.88 (ddd, J=17.0, 13.7, 5.2 Hz, 1H), 2.81-2.64 (m, 2H), 2.47 (t, J=6.5 Hz, 2H), 2.39 (p, J=6.4 Hz, 2H), 2.18-2.08 (m, 1H), 1.98 (p, J=6.7 Hz, 2H), 1.69 (s, 6H), 1.69-1.60 (m, 2H), 1.58-1.47 (m, 5H), 1.40 (qd, J=8.5, 5.6 Hz, 2H). ESI-MS (m/z) [M+H]$^+$: 812.3854.

Example 164

Synthesis of XF067-111

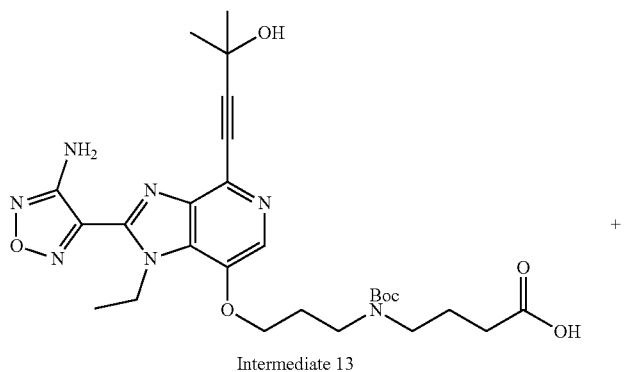

Intermediate 13

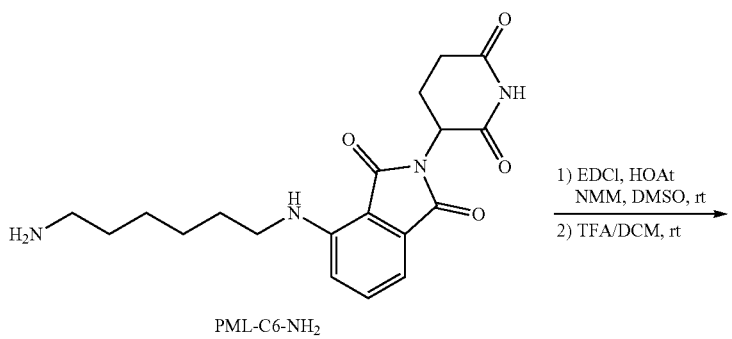

PML-C6-NH$_2$

1) EDCl, HOAt NMM, DMSO, rt
2) TFA/DCM, rt

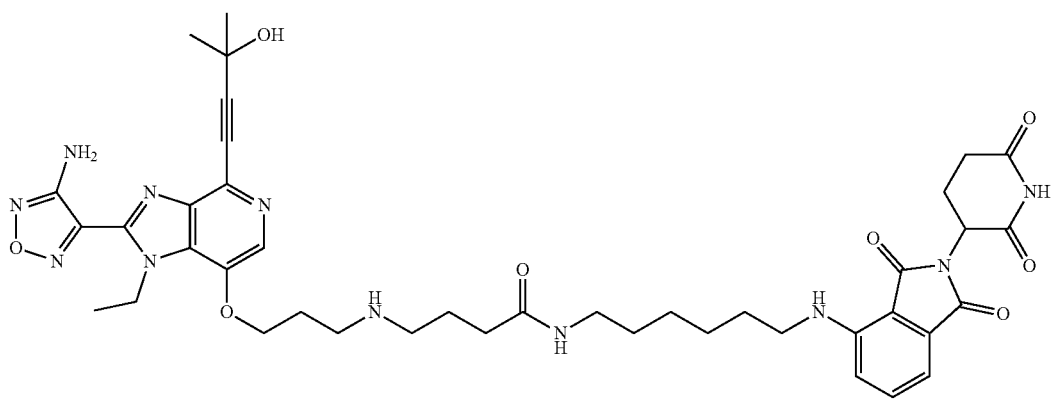

XF067-111

XF067-111 was synthesized following the standard procedure for preparing XF067-84 from intermediate 13 (9.1 mg, 0.016 mmol), PML-C6-NH₂ (6.5 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-111 was obtained as yellow solid in TFA salt form (11.9 mg, 90%). ¹H NMR (500 MHz, CD₃OD) δ 8.24 (s, 1H), 7.60-7.48 (m, 1H), 7.15-6.86 (m, 2H), 5.04 (dt, J=12.3, 5.2 Hz, 3H), 4.54 (q, J=5.8, 4.9 Hz, 2H), 3.14 (dt, J=25.1, 7.0 Hz, 8H), 2.98-2.67 (m, 3H), 2.43 (dq, J=19.2, 7.8, 6.4 Hz, 4H), 2.19-2.10 (m, 1H), 1.99 (p, J=6.7 Hz, 2H), 1.83-1.15 (m, 17H). ESI-MS (m/z) [M+H]⁺: 826.3987.

Example 165

Synthesis of XF067-112

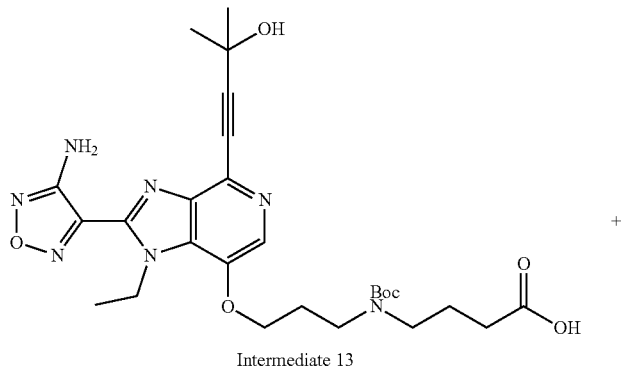

Intermediate 13

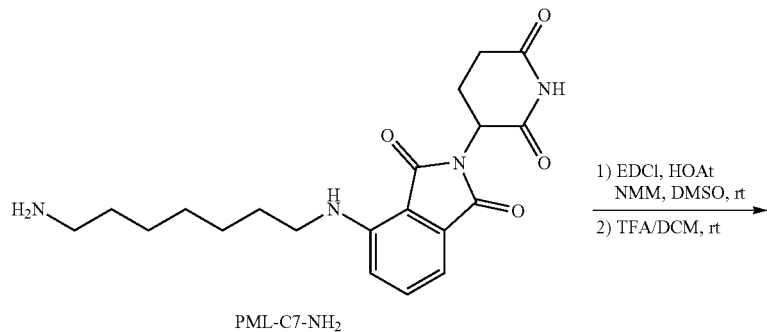

PML-C7-NH₂

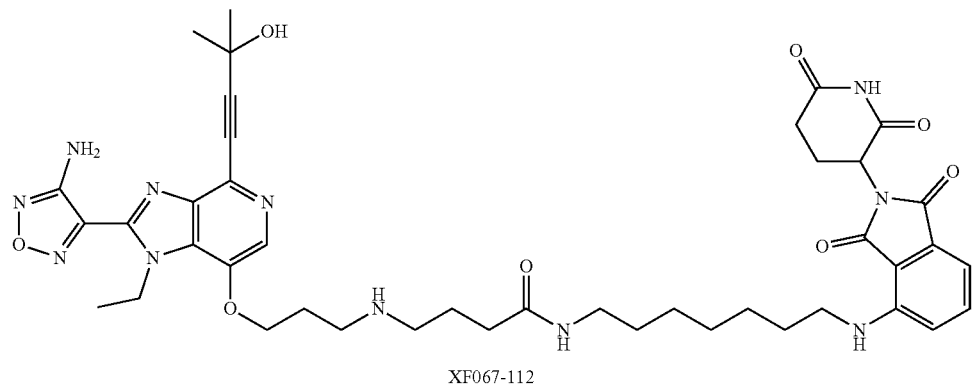

XF067-112

XF067-112 was synthesized following the standard procedure for preparing XF067-84 from intermediate 13 (9.1 mg, 0.016 mmol), PML-C7-NH₂ (8 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-112 was obtained as yellow solid in TFA salt form (12.5 mg, 93%). ¹H NMR (500 MHz, CD₃OD) δ 8.22 (s, 1H), 7.53 (ddd, J=8.5, 7.2, 2.0 Hz, 1H), 7.01 (td, J=6.9, 2.2 Hz, 2H), 5.09-5.00 (m, 3H), 4.53 (t, J=5.9 Hz, 2H), 3.39-3.27 (m, 4H), 3.16 (t, J=6.9 Hz, 2H), 3.09 (t, J=7.1 Hz, 2H), 2.93-2.82 (m, 1H), 2.81-2.66 (m, 2H), 2.43 (dt, J=20.7, 6.9 Hz, 4H), 2.12 (dtd, J=13.0, 5.6, 2.8 Hz, 1H), 1.99 (p, J=6.9 Hz, 2H), 1.72-1.62 (m, 8H), 1.58 (t, J=7.1 Hz, 3H), 1.49-1.29 (m, 8H). ESI-MS (m/z) [M+H]⁺: 840.4157.

Example 166

Synthesis of XF067-113

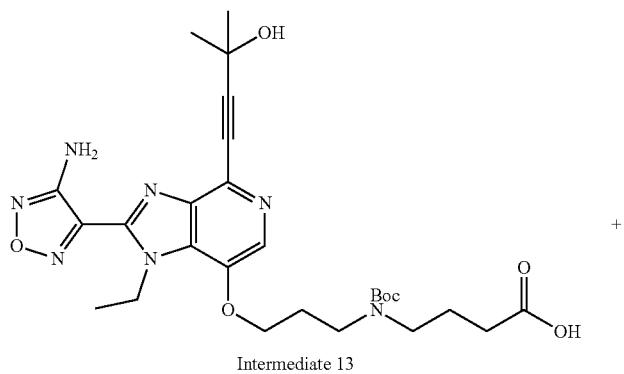

Intermediate 13

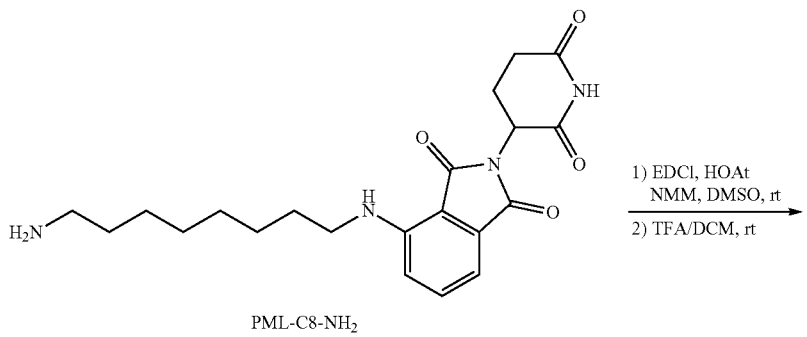

PML-C8-NH₂

1) EDCI, HOAt NMM, DMSO, rt
2) TFA/DCM, rt

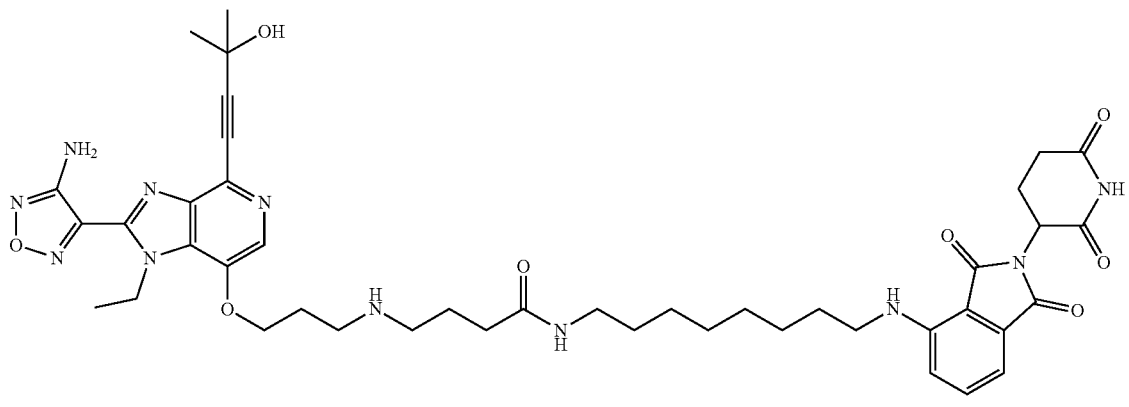

XF067-113

XF067-113 was synthesized following the standard procedure for preparing XF067-84 from intermediate 13 (9.1 mg, 0.016 mmol), PML-C8-NH$_2$ (8.2 mg, 0.016 mmol, 1.0 equiv), EDCI (4.6 mg, 0.024 mmol, 1.5 equiv), HOAt (3.3 mg, 0.024 mmol, 1.5 equiv), and NMM (4.8 mg, 0.048 mmol, 3.0 equiv) in DMSO (1 mL). XF067-113 was obtained as yellow solid in TFA salt form (12.6 mg, 98%). $^1$H NMR (500 MHz, CD$_3$OD) δ 8.25 (d, J=2.8 Hz, 1H), 7.54 (ddd, J=8.5, 7.1, 2.3 Hz, 1H), 7.02 (dd, J=7.8, 3.0 Hz, 2H), 5.10-5.01 (m, 3H), 4.54 (t, J=5.8 Hz, 2H), 3.34-3.27 (m, 4H), 3.17 (td, J=7.3, 2.6 Hz, 2H), 3.09-3.07 (m, 2H), 2.92-2.82 (m, 1H), 2.81-2.66 (m, 2H), 2.48-2.36 (m, 4H), 2.12 (dtd, J=13.1, 5.6, 2.8 Hz, 1H), 2.03-1.92 (m, 2H), 1.75-1.62 (m, 8H), 1.65-1.55 (m, 3H), 1.49-1.25 (m, 10H). ESI-MS (m/z) [M+H]$^+$: 854.4313.

Compounds synthesized in the Examples above are set forth in Table 1, below.

In Table 1, the left portion of the structure of the AKT disruptors/degraders binds to AKT (as, e.g., GSK690693 (Heerding et al., 2008), GSK2110183 (Dumble et al., 2014), GSK2141795 (Dumble et al., 2014), AZD5363 (Addie et al., 2013), GDC0068 (Blake et al., 2012), MK-2206 (Hirai et al., 2010), and ARQ-092 (Yu et al., 2015) do), and the right portion of the structure recruits the ubiquitination machinery to AKT, which induces poly-ubiquitination and degradation of AKT at the proteasome.

TABLE 1

| Compound ID | Structure | Chemical Name |
|---|---|---|
| XF038-157A | 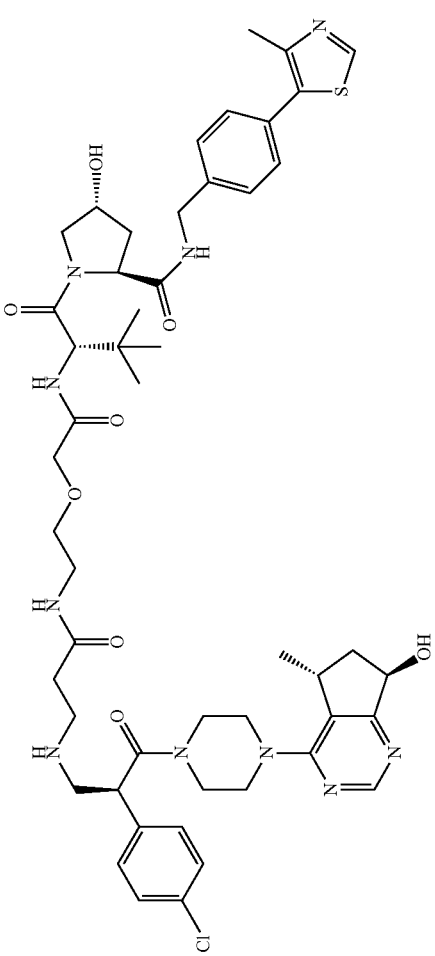 | (2S,4R)-1-((2S,15S)-2-(tert-butyl)-15-(4-chlorophenyl)-16-(4-((5R,7R)-7-hydroxy-5-methyl-6,7-dihydro-5H-cyclopenta[d]pyrimidin-4-yl)piperazin-1-yl)-4,10,16-trioxo-6-oxa-3,9,13-triazahexadecanoyl)-4-hydroxy-N-(4-(4-methylthiazol-5-yl)benzyl)pyrrolidine-2-carboxamide |
| XF038-158A | 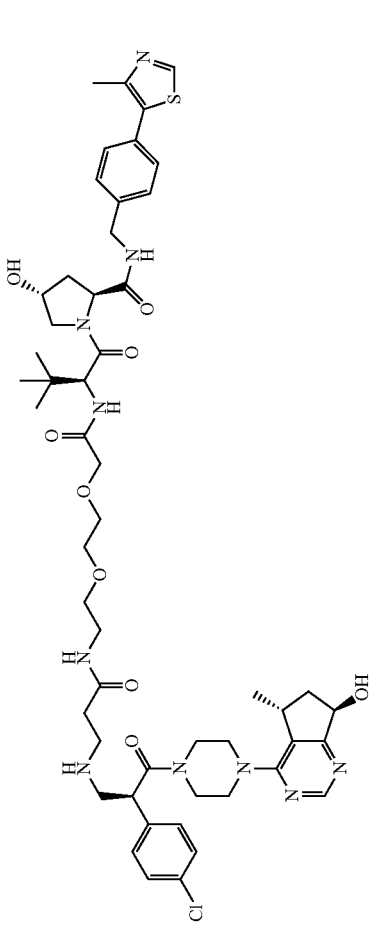 | (2S,4R)-1-((2S,18S)-2-(tert-butyl)-18-(4-chlorophenyl)-19-(4-((5R,7R)-7-hydroxy-5-methyl-6,7-dihydro-5H-cyclopenta[d]pyrimidin-4-yl)piperazin-1-yl)-4,13,19-trioxo-6,9-dioxa-3,12,16-triazanonadecanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF038-159A | 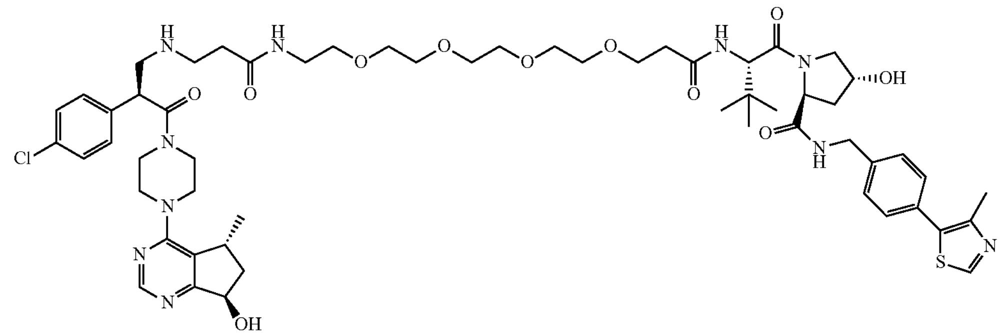 [SMILES: Cc1ncsc1-c1ccc(CNC(=O)[C@@H]2C[C@@H](O)CN2C(=O)[C@@H](NC(=O)CCOCCOCCOCCOCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((2S,25S)-2-(tert-butyl)-25-(4-chlorophenyl)-26-(4-((5R,7R)-7-hydroxy-5-methyl-6,7-dihydro-5H-cyclopenta[d]pyrimidin-4-yl)piperazin-1-yl)-4,20,26-trioxo-7,10,13,16-tetraoxa-3,19,23-triazahexacosanoyl)-4-hydroxy-N-(4-(4-methylthiazol-5-yl)benzyl)pyrrolidine-2-carboxamide |
| XF038-160A | 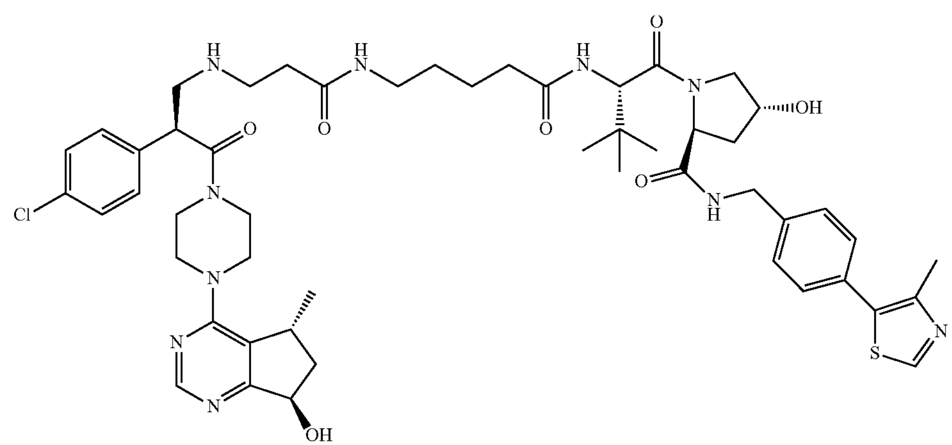 [SMILES: Cc1ncsc1-c1ccc(CNC(=O)[C@@H]2C[C@@H](O)CN2C(=O)[C@@H](NC(=O)CCCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((S)-2-(5-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)propanamido)pentanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF038-161A | 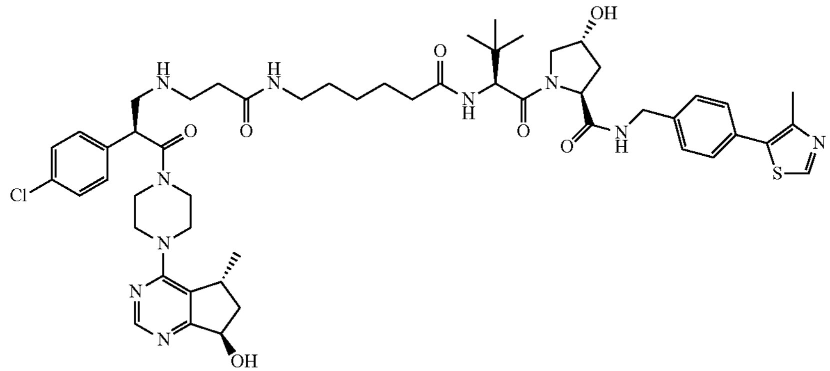 [SMILES: Cc1ncsc1-c1ccc(CNC(=O)[C@@H]2C[C@@H](O)CN2C(=O)[C@@H](NC(=O)CCCCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((S)-2-(6-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)hexanamido)-3,3-dimethylbutanoyl)-4-hydroxy-N-(4-(4-methylthiazol-5-yl)benzyl)pyrrolidine-2-carboxamide |
| XF038-162A | 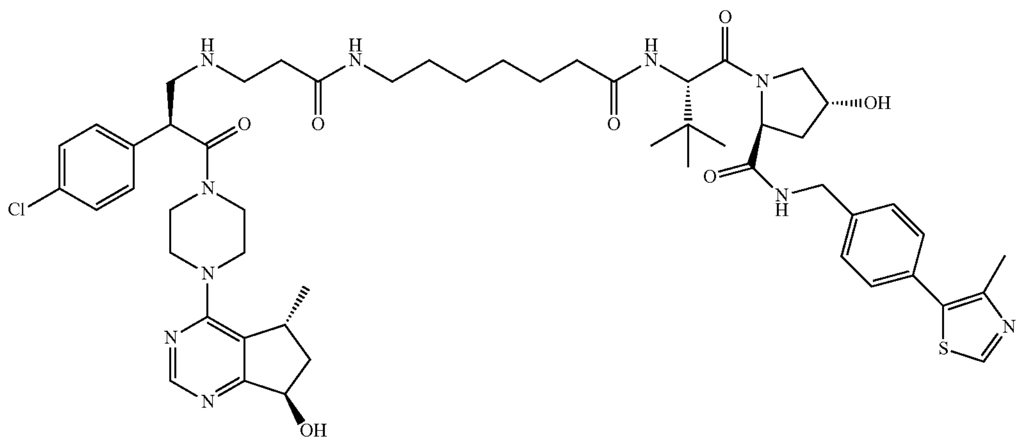 [SMILES: Cc1ncsc1-c1ccc(CNC(=O)[C@@H]2C[C@@H](O)CN2C(=O)[C@@H](NC(=O)CCCCCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((S)-2-(7-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)heptanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF038-164A | 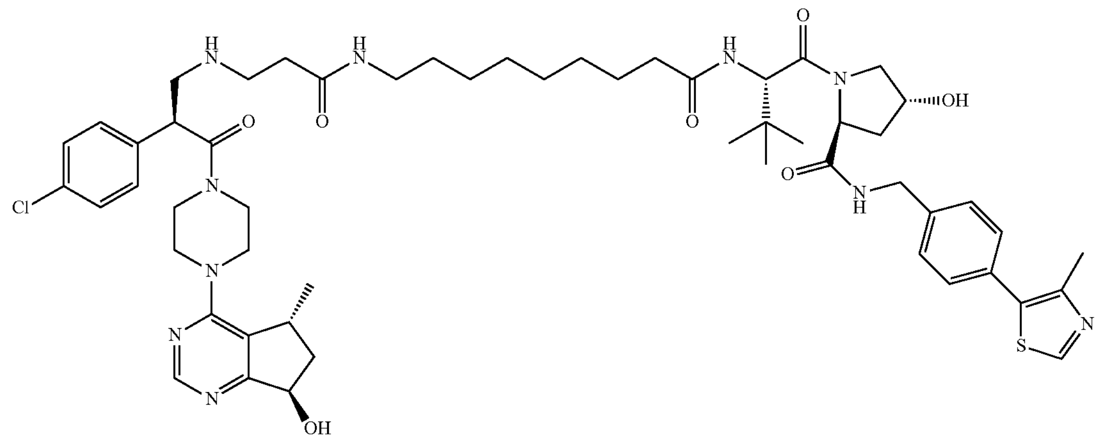 [SMILES: Cc1ncsc1-c1ccc(CNC(=O)[C@@H]2C[C@@H](O)CN2C(=O)[C@@H](NC(=O)CCCCCCCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((S)-2-(9-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)nonanamido)-3,3-dimethylbutanoyl)-4-hydroxy-N-(4-(4-methylthiazol-5-yl)benzyl)pyrrolidine-2-carboxamide |
| XF038-165A | 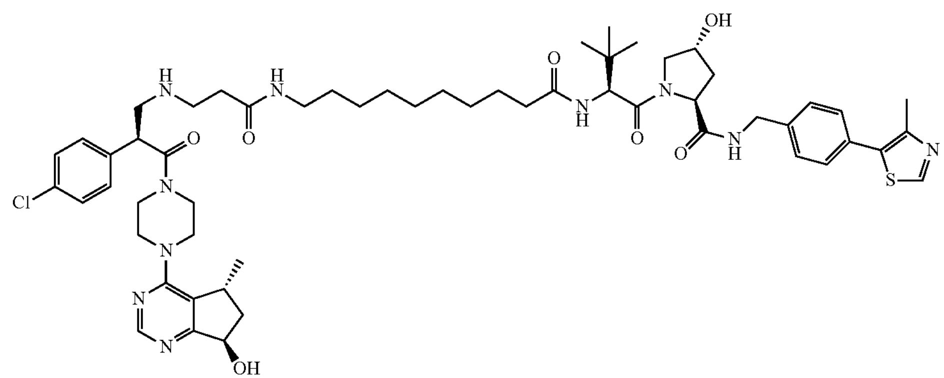 [SMILES: Cc1ncsc1-c1ccc(CNC(=O)[C@@H]2C[C@@H](O)CN2C(=O)[C@@H](NC(=O)CCCCCCCCCNC(=O)CCNC[C@@H](C(=O)N2CCN(c3ncnc4c3[C@H](C)C[C@H]4O)CC2)c2ccc(Cl)cc2)C(C)(C)C)cc1] | (2S,4R)-1-((S)-2-(10-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)decanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF038-166A | 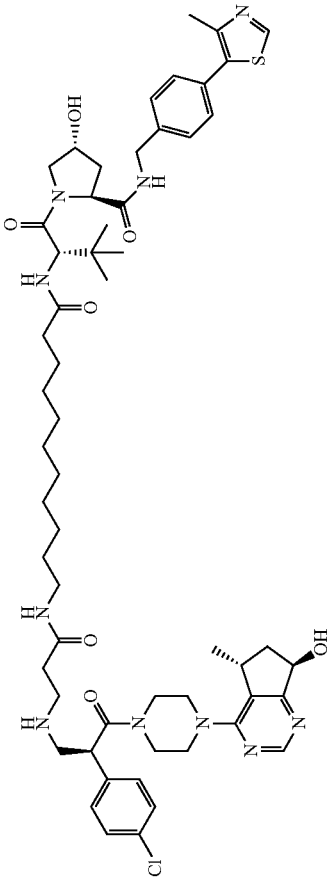 | (2S,4R)-1-((S)-2-(11-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)propanamido)undecanamido)-3,3-dimethylbutanoyl)-4-hydroxy-N-(4-(4-methylthiazol-5-yl)benzyl)pyrrolidine-2-carboxamide |
| XF042-162 | 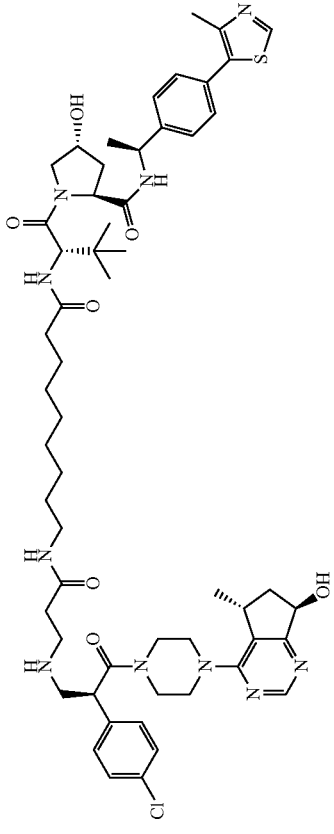 | (2S,4R)-1-((S)-2-(11-(3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)propanamido)undecanamido)-3,3-dimethylbutanoyl)-4-hydroxy-N-((S)-1-(4-(4-methylthiazol-5-yl)phenyl)ethyl)pyrrolidine-2-carboxamide |

TABLE 1-continued
| Compound ID | Structure | Chemical Name |
|---|---|---|
| XF042-171 | 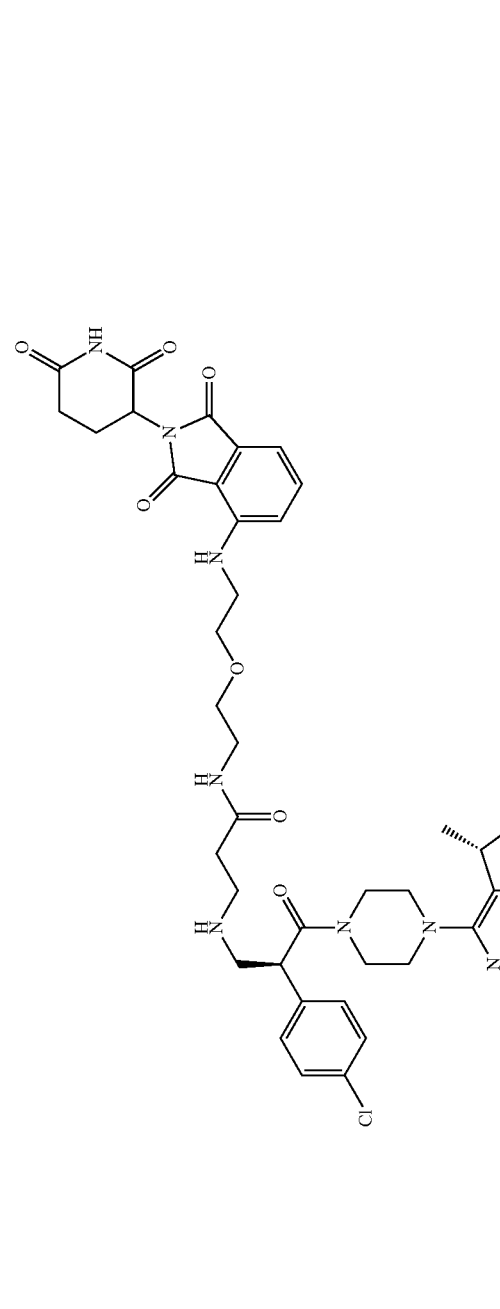 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(2-(2-((2-(2,6-dioxopiperidin-3-yl)-1,3-dioxoisoindolin-4-yl)amino)ethoxy)ethyl)propanamide |

TABLE 1-continued

| Compound ID | Structure | Chemical Name |
|---|---|---|
| XF048-7 | 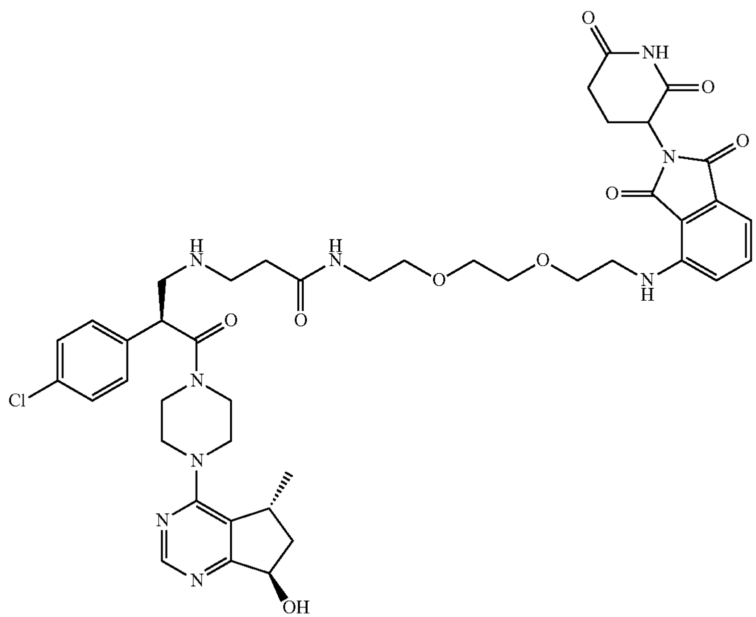 [SMILES: C[C@@H]1C[C@@H](O)c2ncnc(N3CCN(C(=O)[C@H](CNCCC(=O)NCCOCCOCCNc4cccc5c4C(=O)N(C4CCC(=O)NC4=O)C5=O)c4ccc(Cl)cc4)CC3)c21] | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(2-(2-((2-(2,6-dioxopiperidin-3-yl)-1,3-dioxoisoindolin-4-yl)amino)ethoxy)ethoxy)ethyl) propanamide |

| Compound ID | Structure | Chemical Name |
|---|---|---|
| XF048-8 | 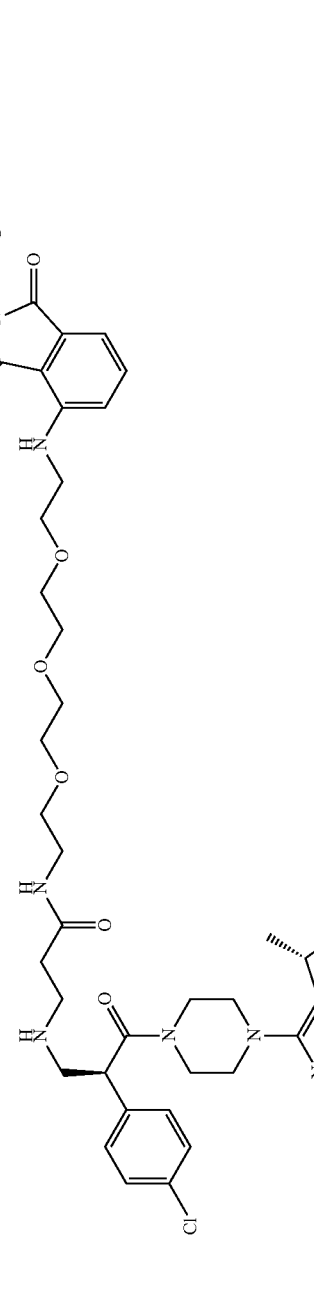 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(2-(2-(2-(2-(2,6-dioxopiperidin-3-yl)-1,3-dioxoisoindolin-4-yl)amino)ethoxy)ethoxy)ethoxy)ethyl)propanamide |

TABLE 1-continued

| Compound ID | Structure | Chemical Name |
|---|---|---|
| XF038-176A | 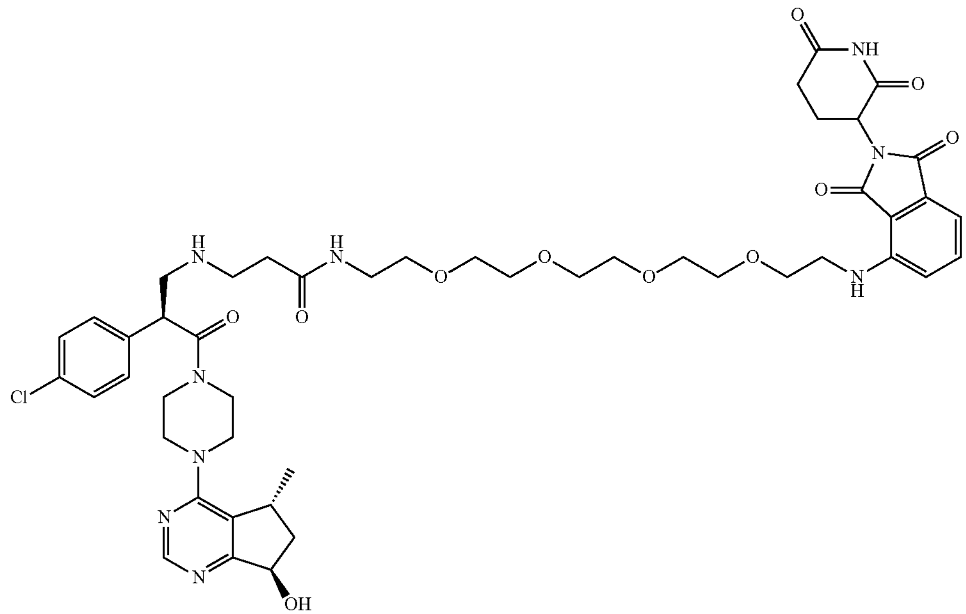 [SMILES: C[C@@H]1C[C@@H](O)c2ncnc(N3CCN(C(=O)[C@H](CNCCC(=O)NCCOCCOCCOCCOCCNc4cccc5c4C(=O)N(C4CCC(=O)NC4=O)C5=O)c4ccc(Cl)cc4)CC3)c21] | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(14-((2-(2,6-dioxopiperidin-3-yl)-1,3-dioxoisoindolin-4-yl)amino)-3,6,9,12-tetraoxatetradecyl)propanamide |
| XF038-177A | 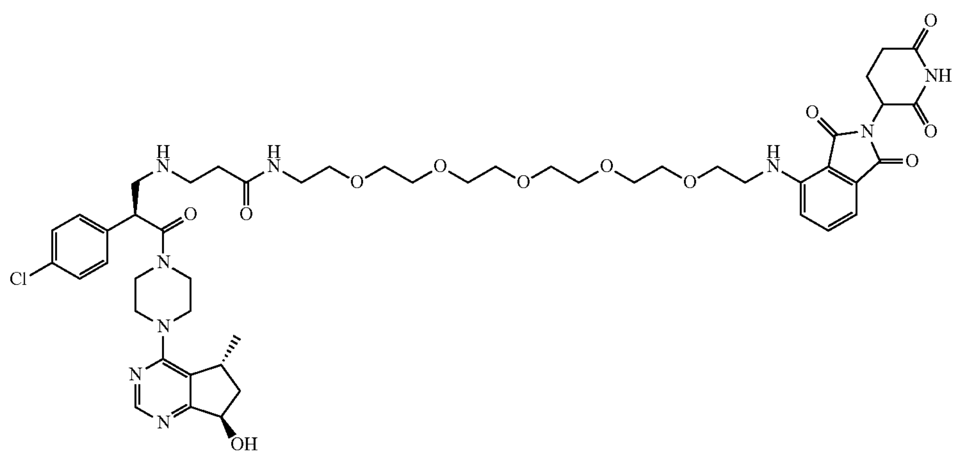 [SMILES: C[C@@H]1C[C@@H](O)c2ncnc(N3CCN(C(=O)[C@H](CNCCC(=O)NCCOCCOCCOCCOCCOCCNc4cccc5c4C(=O)N(C4CCC(=O)NC4=O)C5=O)c4ccc(Cl)cc4)CC3)c21] | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(17-((2-(2,6-dioxopiperidin-3-yl)-1,3-dioxoisoindolin-4-yl)amino)-3,6,9,12,15-pentaoxaheptadecyl)propanamide |

TABLE 1-continued
| Compound ID | Structure | Chemical Name |
|---|---|---|
| XF042-164 | 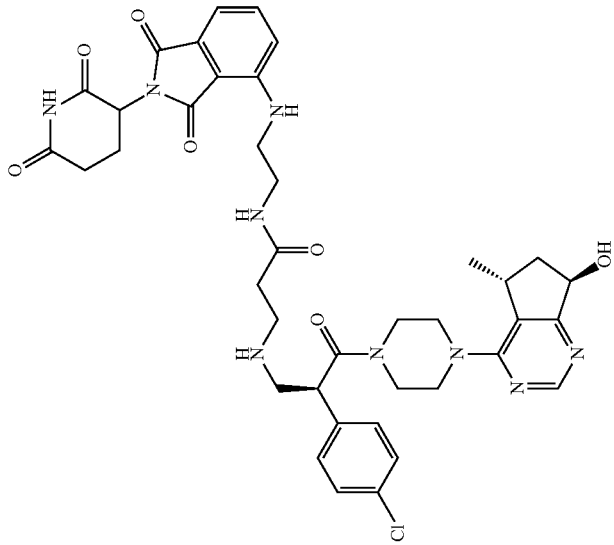 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(2-((2-(2,6-dioxopiperidin-3-yl)-1,3-dioxoisoindolin-4-yl)amino)ethyl)propanamide |

TABLE 1-continued
| Compound ID | Structure | Chemical Name |
|---|---|---|
| XF042-165 | 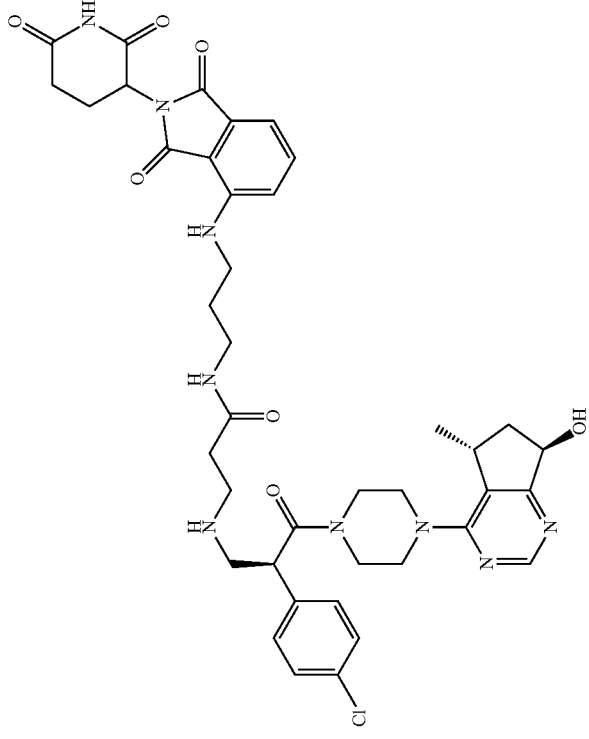 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(3-((2-(2,6-dioxopiperidin-3-yl)-1,3-dioxoisoindolin-4-yl)amino)propyl)propanamide |

TABLE 1-continued
| Compound ID | Structure | Chemical Name |
|---|---|---|
| XF042-166 | 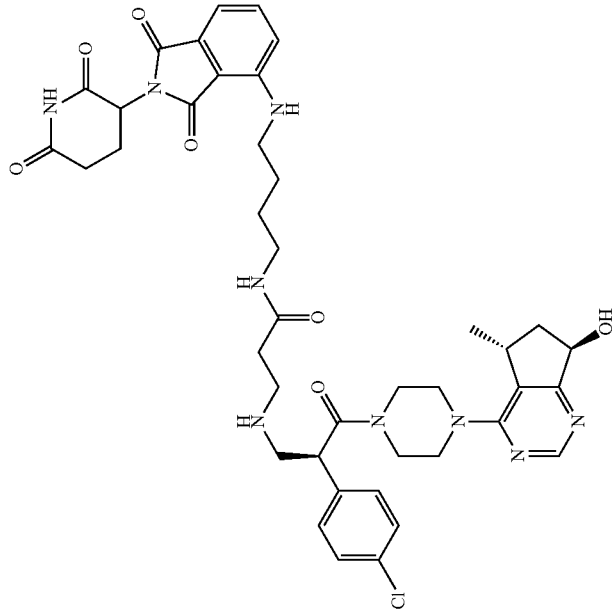 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(4-((2-(2,6-dioxopiperidin-3-yl)-1,3-dioxoisoindolin-4-yl)amino)butyl)propanamide |

TABLE 1-continued

| Compound ID | Structure | Chemical Name |
|---|---|---|
| XF042-167 | 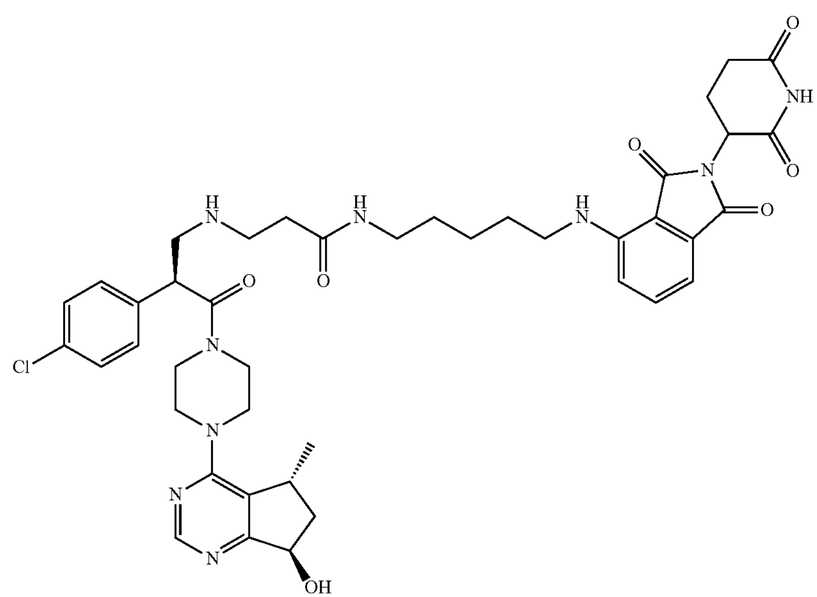 [SMILES: C[C@@H]1C[C@@H](O)c2ncnc(N3CCN(C(=O)[C@H](CNCCC(=O)NCCCCCNc4cccc5c4C(=O)N(C4CCC(=O)NC4=O)C5=O)c4ccc(Cl)cc4)CC3)c21] | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(5-((2-(2,6-dioxopiperidin-3-yl)-1,3-dioxoisoindolin-4-yl)amino)pentyl)propanamide |

TABLE 1-continued
| Compound ID | Structure | Chemical Name |
|---|---|---|
| XF042-168 | 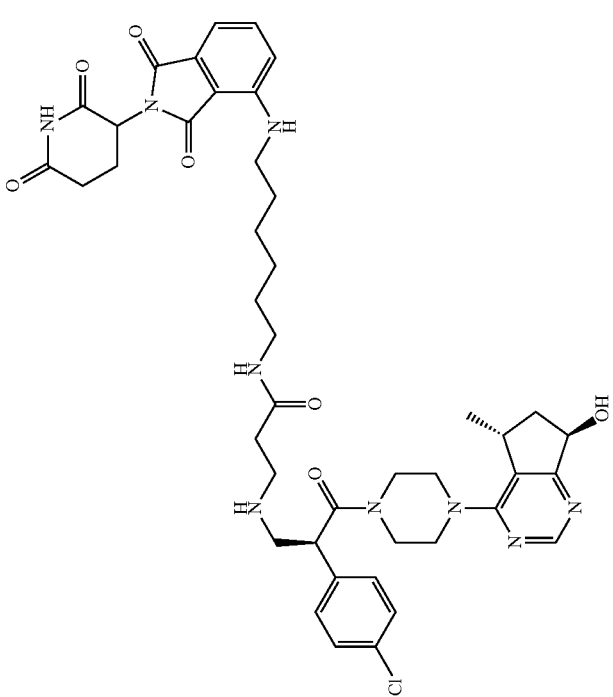 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(6-((2-(2,6-dioxopiperidin-3-yl)-1,3-dioxoisoindolin-4-yl)amino)hexyl)propanamide |

TABLE 1-continued
| Compound ID | Structure | Chemical Name |
|---|---|---|
| XF048-5 | 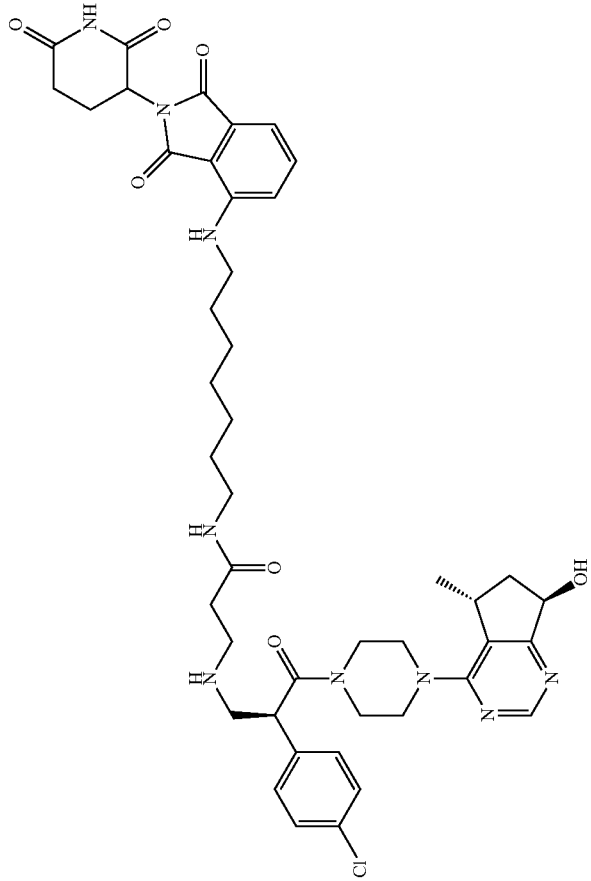 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(7-((2-(2,6-dioxopiperidin-3-yl)-1,3-dioxoisoindolin-4-yl)amino)heptyl)propanamide |

| Compound ID | Structure | Chemical Name |
|---|---|---|
| XF042-170 | 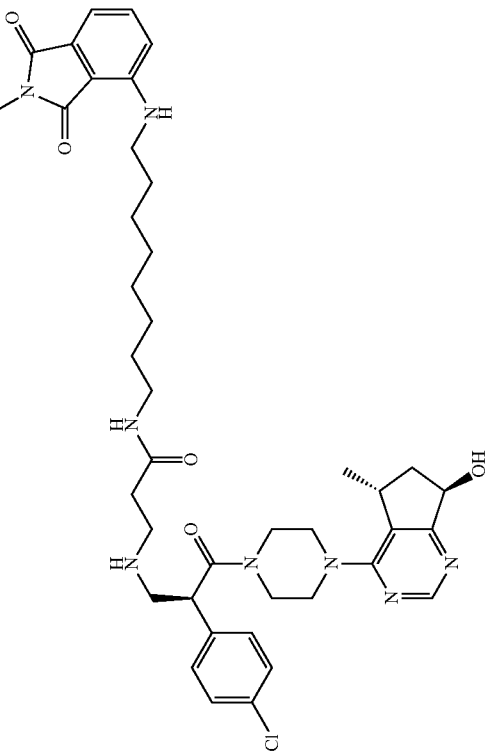 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(8-((2-(2,6-dioxopiperidin-3-yl)-1,3-dioxoisoindolin-4-yl)amino)octyl)propanamide |
| XF048-1 | 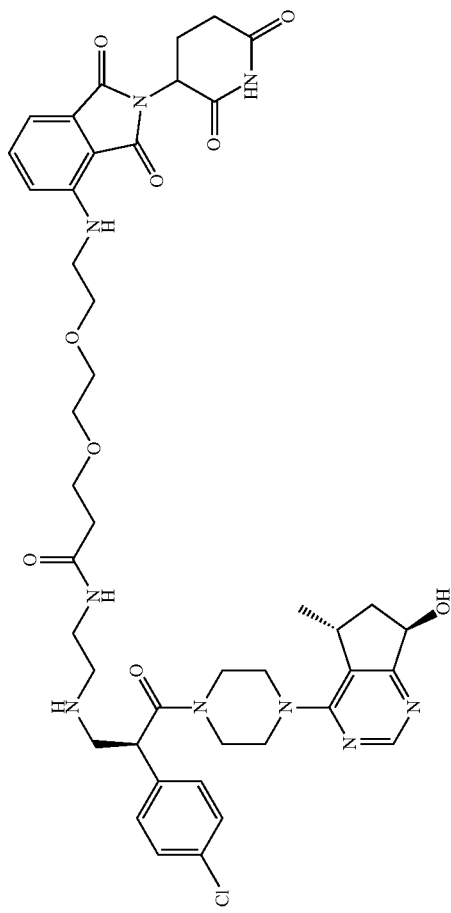 | N-(2-(((N)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-3-(2-(2-(2,6-dioxopiperidin-3-yl)-1,3-dioxoisoindolin-4-yl)amino)ethoxy)ethoxy)propanamide |

TABLE 1-continued

| Compound ID | Structure | Chemical Name |
|---|---|---|
| XF048-2 | 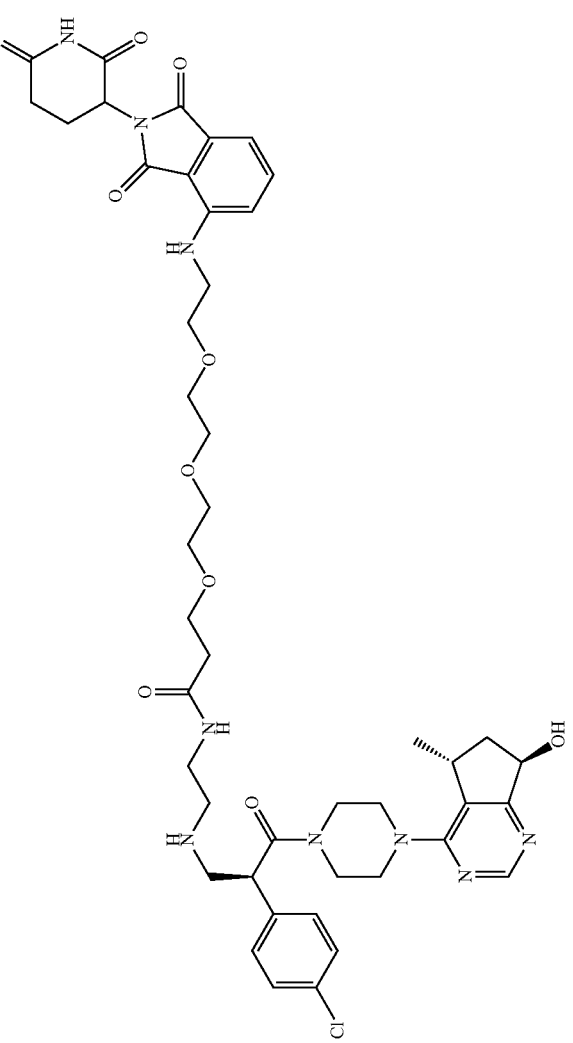 | N-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-3-(2-(2-((2-(2,6-dioxopiperidin-3-yl)-1,3-dioxoisoindolin-4-yl)amino)ethoxy)ethoxy)propanamide |
| XF048-3 | 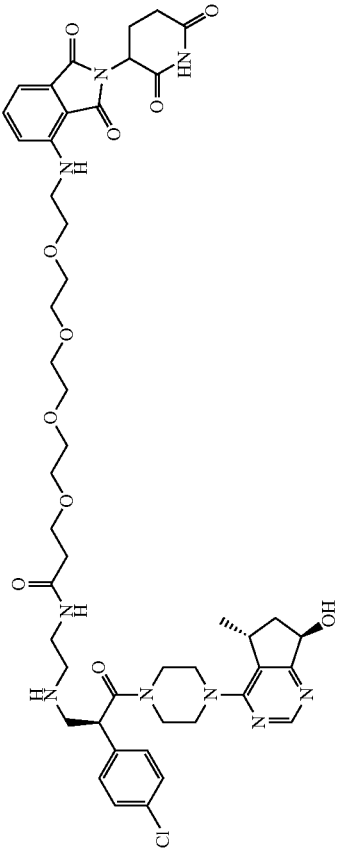 | N-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-1-((2-(2,6-dioxopiperidin-3-yl)-1,3-dioxoisoindolin-4-yl)amino)-3,6,9,12-tetraoxapentadecan-15-amide |

TABLE 1-continued

| Compound ID | Structure | Chemical Name |
|---|---|---|
| XF048-4 | 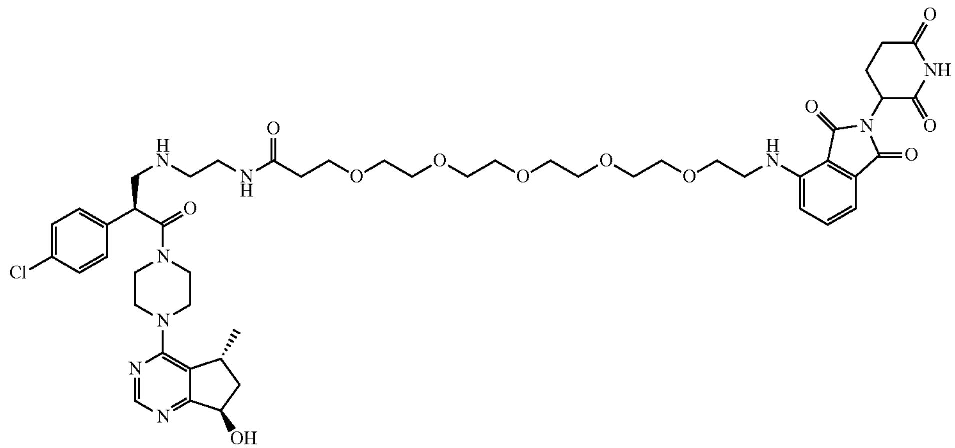 [SMILES: C[C@@H]1C[C@@H](O)c2ncnc(N3CCN(C(=O)[C@H](CNCCNC(=O)CCOCCOCCOCCOCCOCCNc4cccc5c4C(=O)N(C4CCC(=O)NC4=O)C5=O)c4ccc(Cl)cc4)CC3)c21] | N-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-1-((2-(2,6-dioxopiperidin-3-yl)-1,3-dioxoisoindolin-4-yl)amino)-3,6,9,12,15-pentaoxaoctadecan-18-amide |
| XF050-5 | 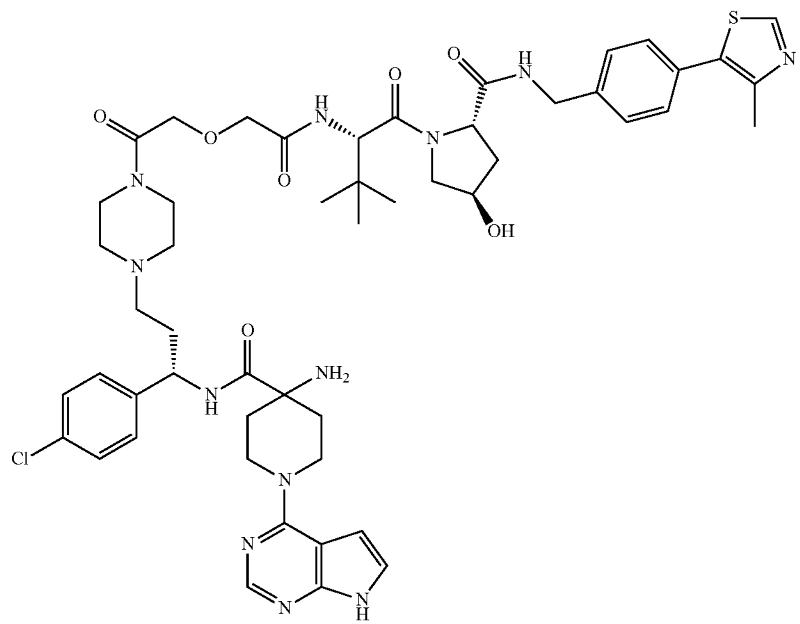 [SMILES: Cc1ncsc1-c1ccc(CNC(=O)[C@@H]2C[C@@H](O)CN2C(=O)[C@@H](NC(=O)COCC(=O)N2CCN(CC[C@H](NC(=O)C3(N)CCN(c4ncnc5[nH]ccc45)CC3)c3ccc(Cl)cc3)CC2)C(C)(C)C)cc1] | 4-amino-N-((S)-1-(4-chlorophenyl)-3-(4-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-6 | 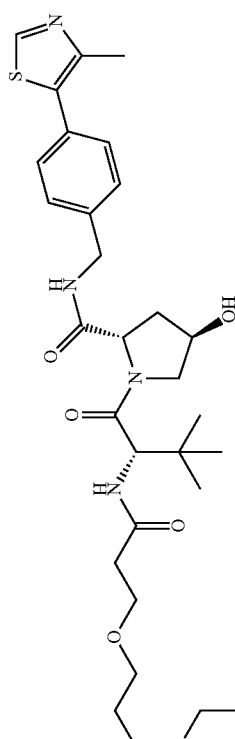 | 4-amino-N-((S)-1-(4-chlorophenyl)-3-(4-(3-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-7 | 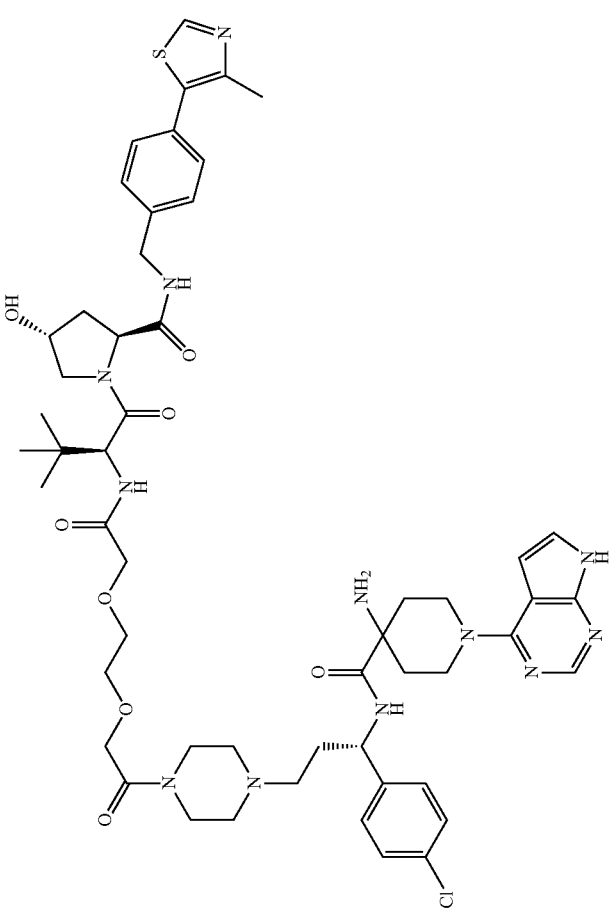 | 4-amino-N-((S)-1-(4-chlorophenyl)-3-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-8 | 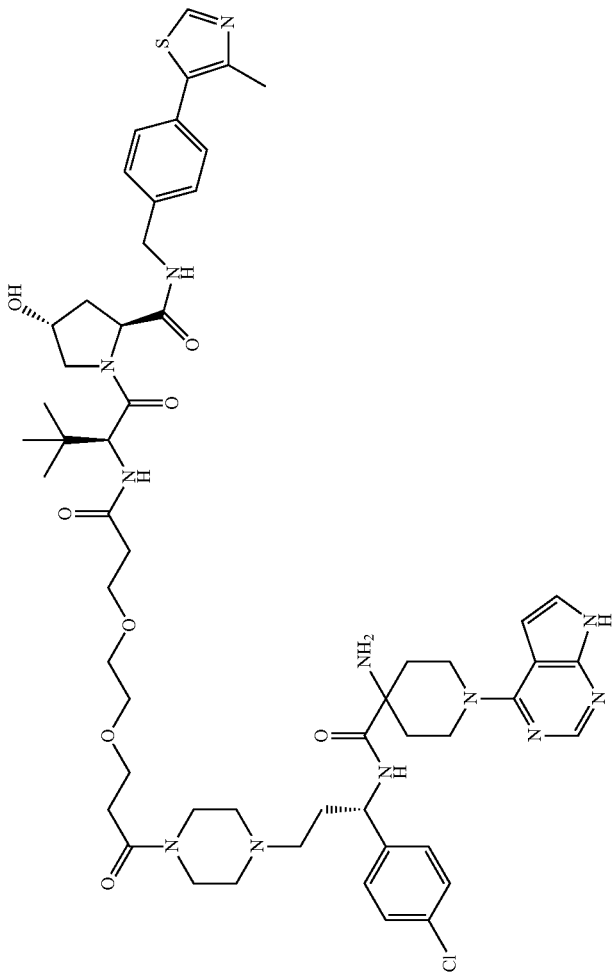 | 4-amino-N-((S)-1-(4-chlorophenyl)-3-(4-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-9 | 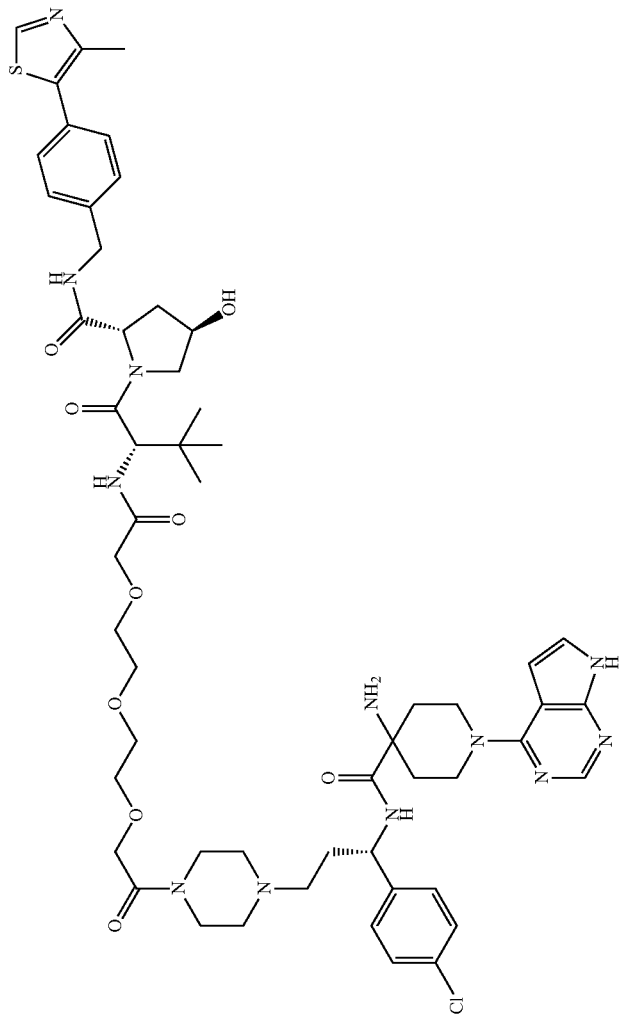 | 4-amino-N-((S)-1-(4-chlorophenyl)-3-(4-((S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-10 | 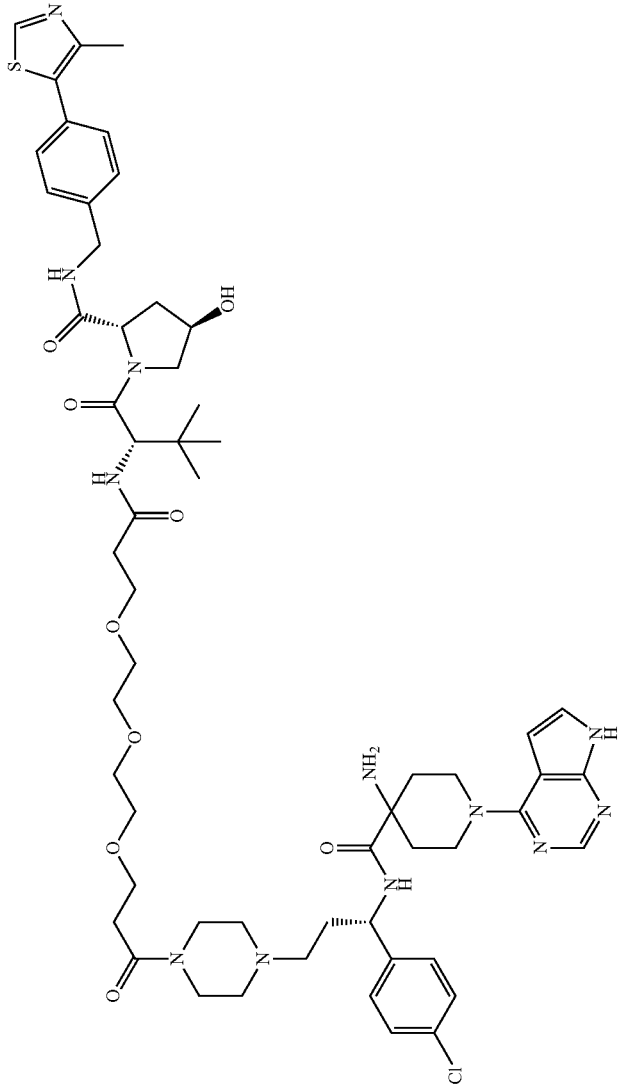 | 4-amino-N-((S)-1-(4-chlorophenyl)-3-(4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)propyl)-1-(7H-pyrrolo[2,3-d]pyrimidin-4-yl)piperidine-4-carboxamide |

TABLE 1-continued

| Compound ID | Structure | Chemical Name |
|---|---|---|
| XF050-11 | 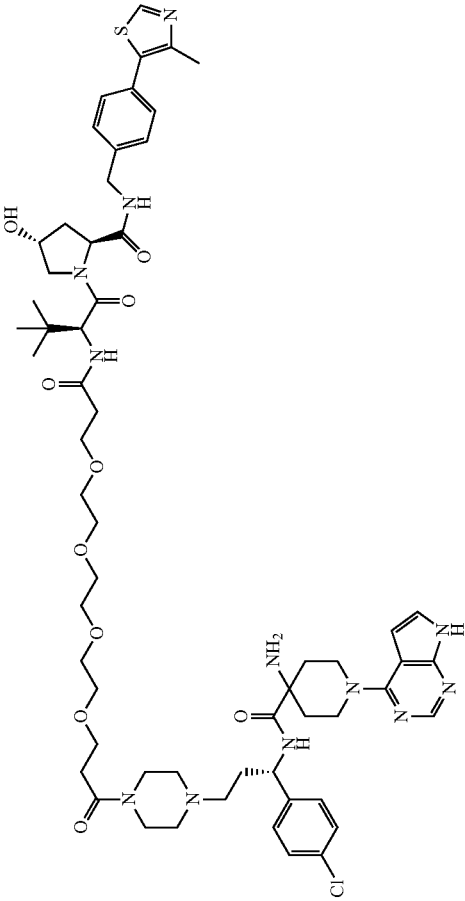 | 4-amino-N-((S)-1-(4-chlorophenyl)-3-(4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)propyl)-1-(7H-pyrrolo[2,3-d]pyrimidin-4-yl)piperidine-4-carboxamide |
| XF050-12 | 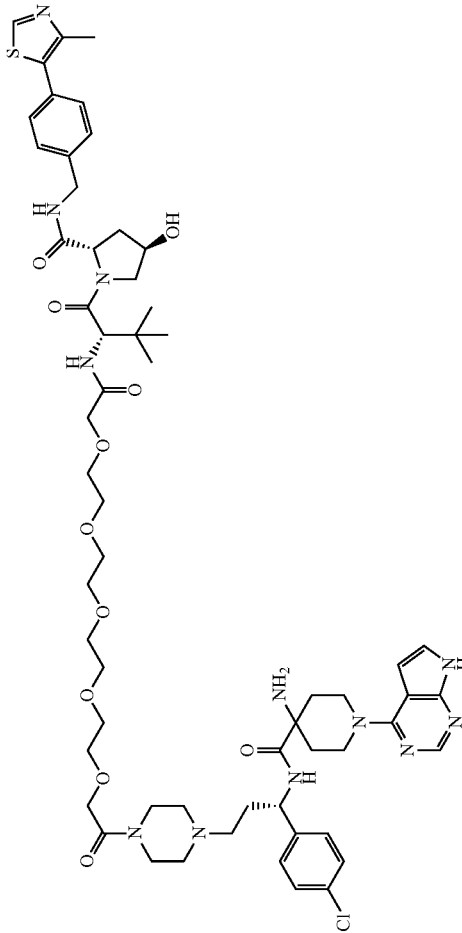 | 4-amino-N-((S)-1-(4-chlorophenyl)-3-(4-((S)-19-((2S,4R)-4-hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoyl)piperazin-1-yl)propyl)-1-(7H-pyrrolo[2,3-d]pyrimidin-4-yl)piperidine-4-carboxamide |

TABLE 1-continued

| Compound ID | Structure | Chemical Name |
|---|---|---|
| XF050-13 | 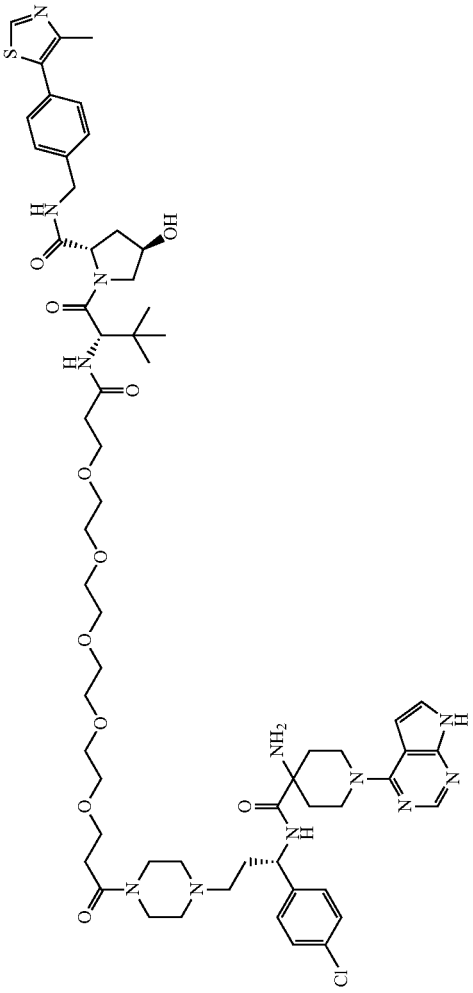 | 4-amino-N-((S)-1-(4-chlorophenyl)-3-(4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)propyl)-1-(7H-pyrrolo[2,3-d]pyrimidin-4-yl)piperidine-4-carboxamide |
| XF050-14 | 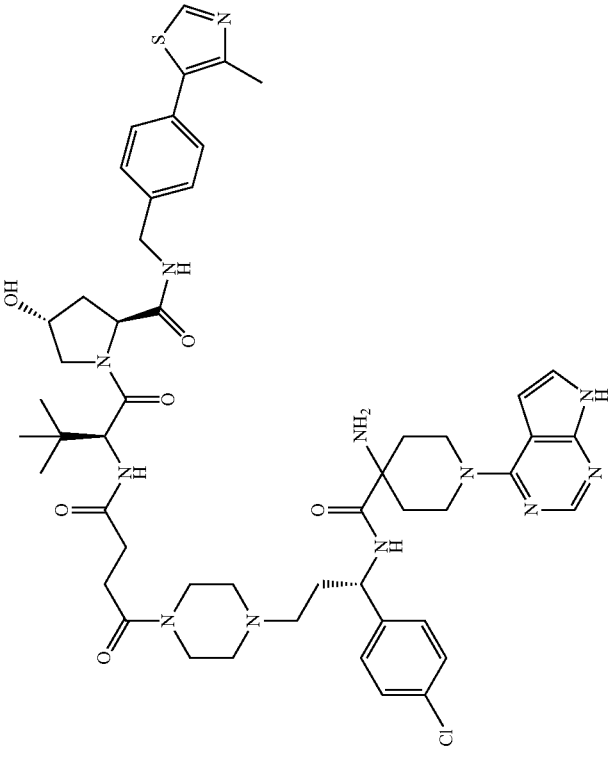 | 4-amino-N-((S)-1-(4-chlorophenyl)-3-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-15 | 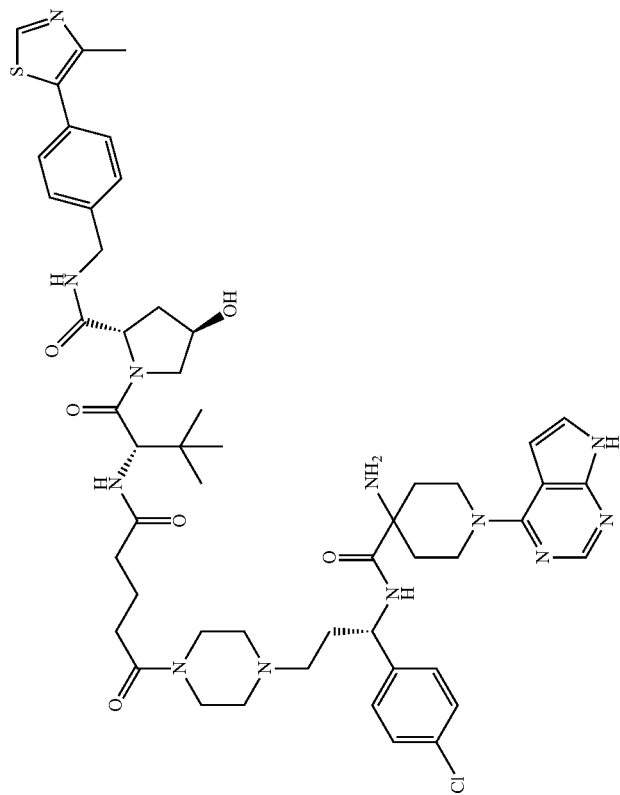 | 4-amino-N-((S)-1-(4-chlorophenyl)-3-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
| --- | --- | --- |
| XF050-16 | 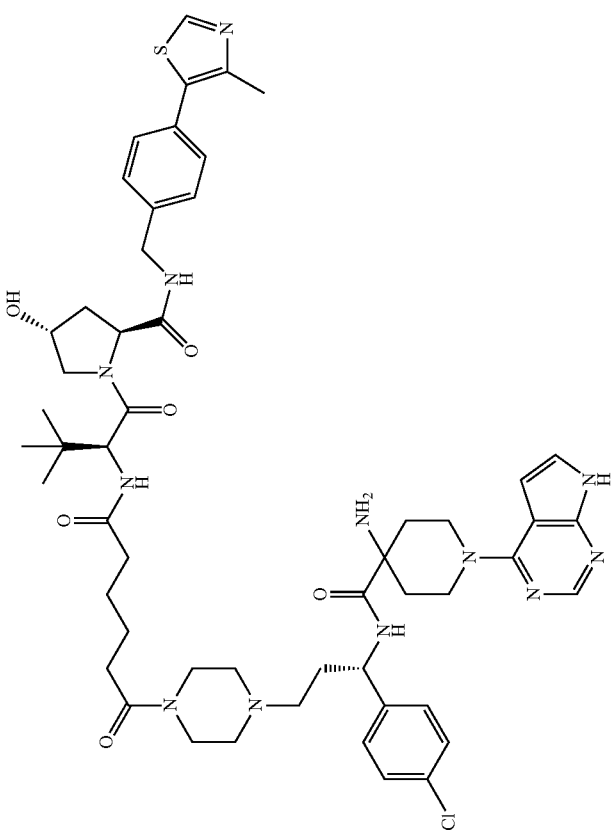 | 4-amino-N-((S)-1-(4-chlorophenyl)-3-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-17 | 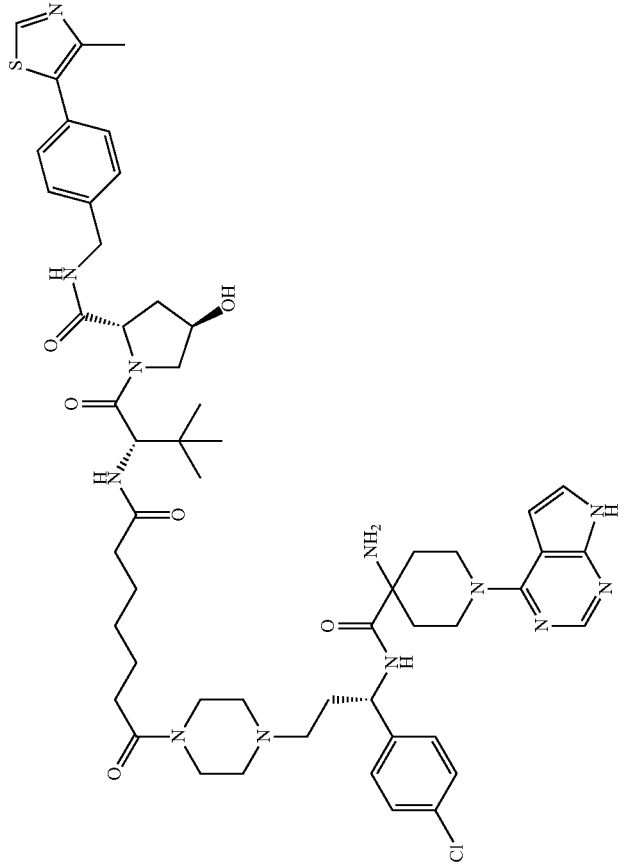 | 4-amino-N-((S)-1-(4-chlorophenyl)-3-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-18 | 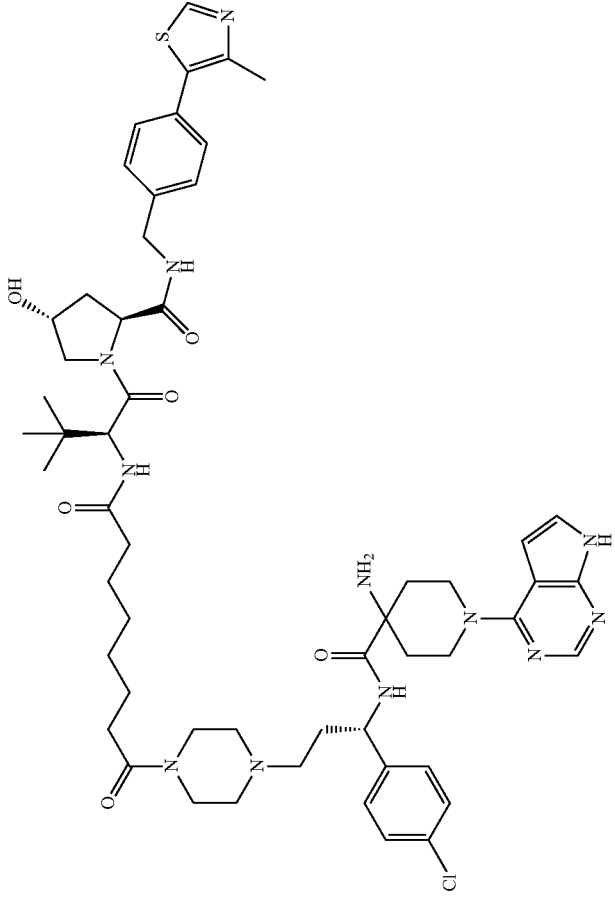 | 4-amino-N-((S)-1-(4-chlorophenyl)-3-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-19 | 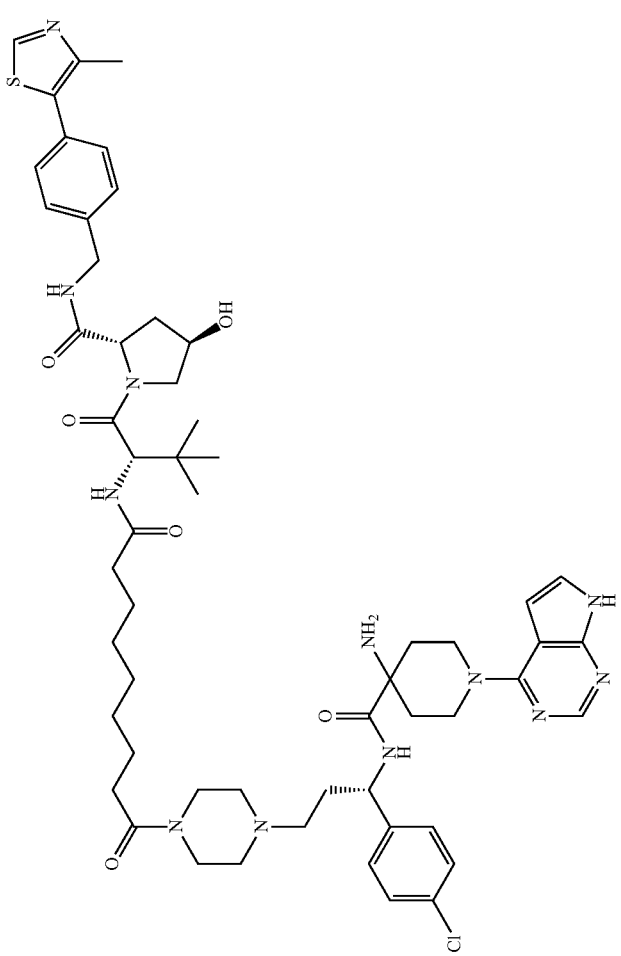 | 4-amino-N-((S)-1-(4-chlorophenyl)-3-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-20 | 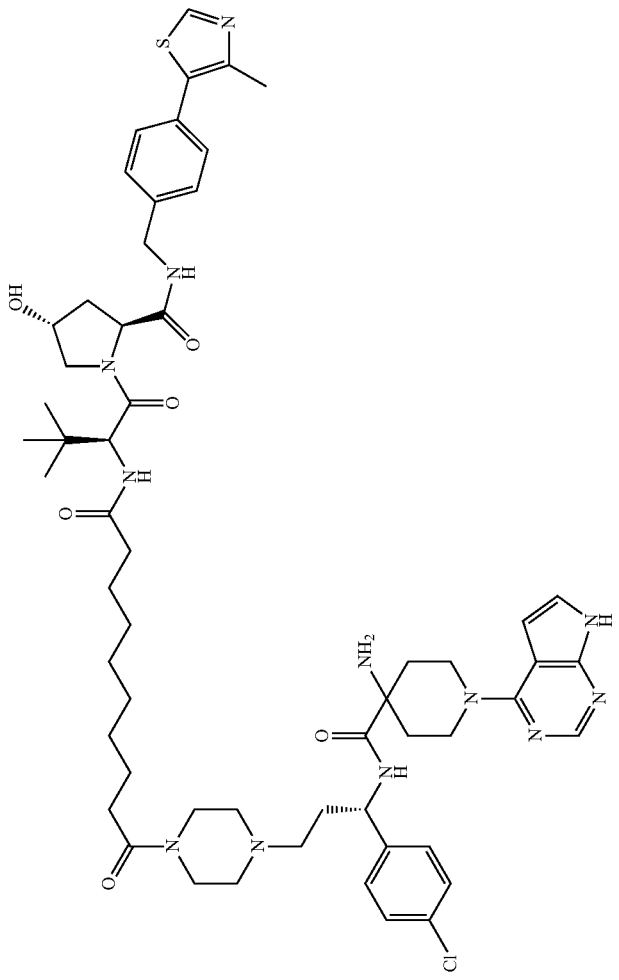 | 4-amino-N-((S)-1-(4-chlorophenyl)-3-(4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-21 | 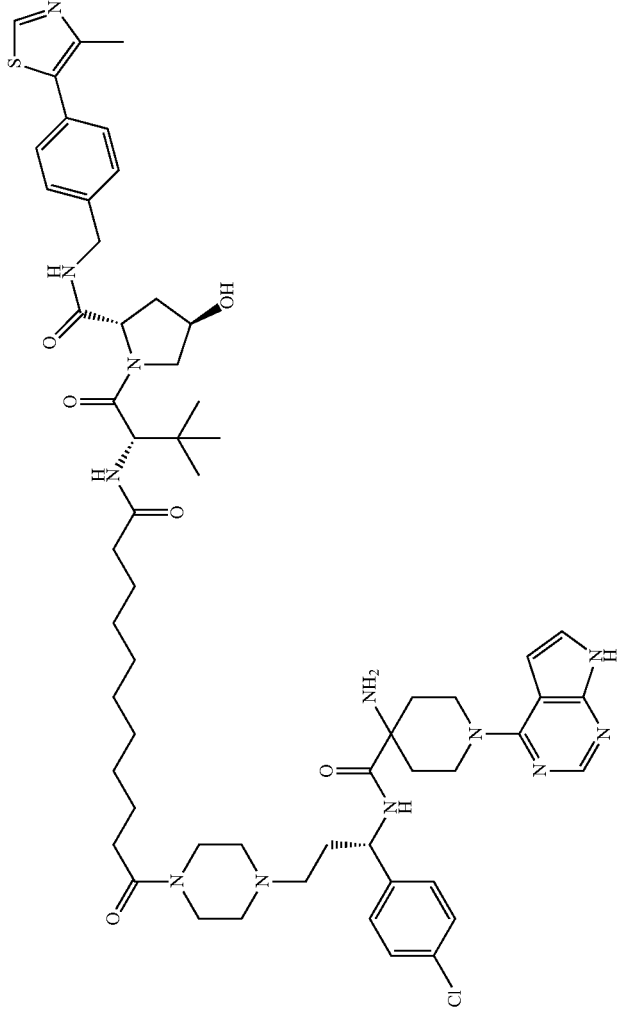 | 4-amino-N-((S)-1-(4-chlorophenyl)-3-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-22 | 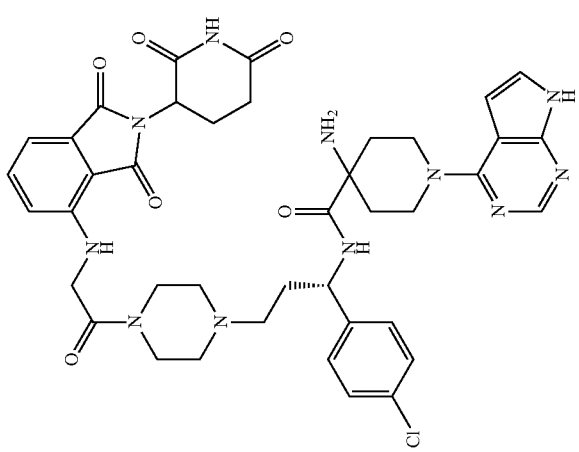 | 4-amino-N-((1S)-1-(4-chlorophenyl)-3-(4-(2-(2,6-dioxopiperidin-3-yl)-1,3-dioxoisoindolin-4-yl)glycyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-23 | 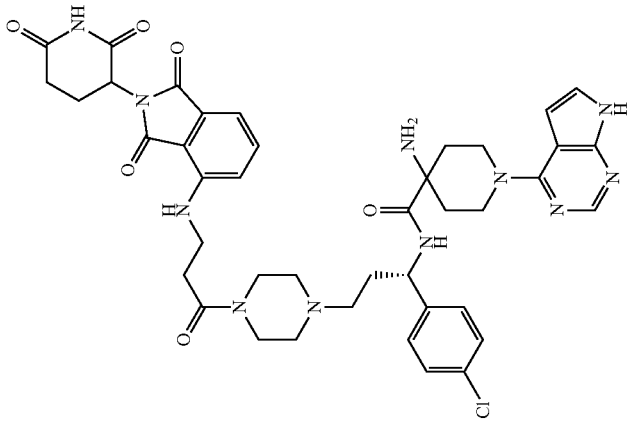 | 4-amino-N-((1S)-1-(4-chlorophenyl)-3-(4-(3-((2-(2,6-dioxopiperidin-3-yl)-1,3-dioxoisoindolin-4-yl)amino)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-24 | 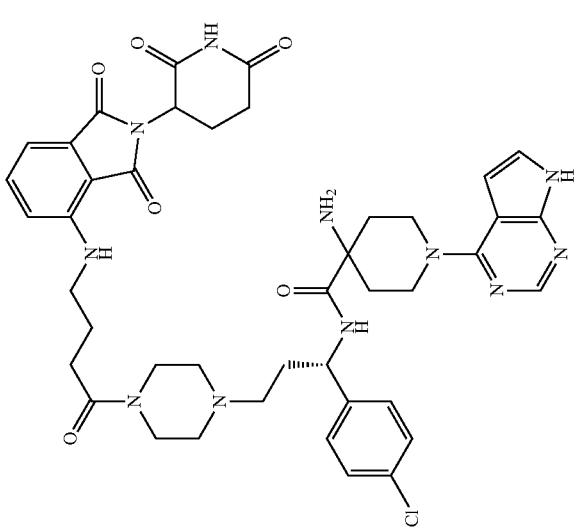 | 4-amino-N-((1S)-1-(4-chlorophenyl)-3-(4-(4-((2-(2,6-dioxopiperidin-3-yl)-1,3-dioxoisoindolin-4-yl)amino)butanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-25 | 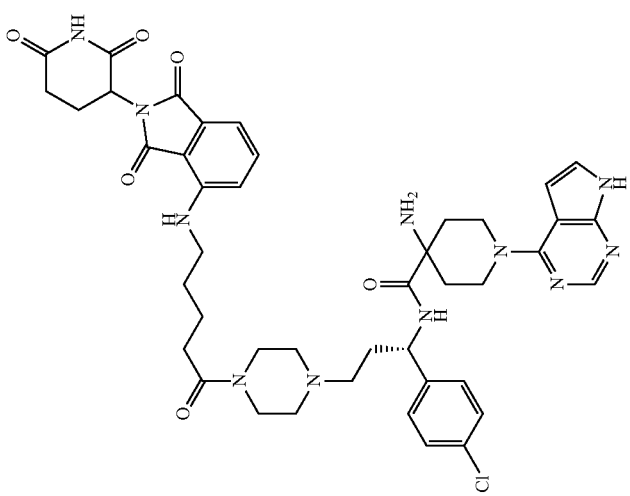 | 4-amino-N-((1S)-1-(4-chlorophenyl)-3-(4-(5-((2-(2,6-dioxopiperidin-3-yl)-1,3-dioxoisoindolin-4-yl)amino)pentanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-26 | 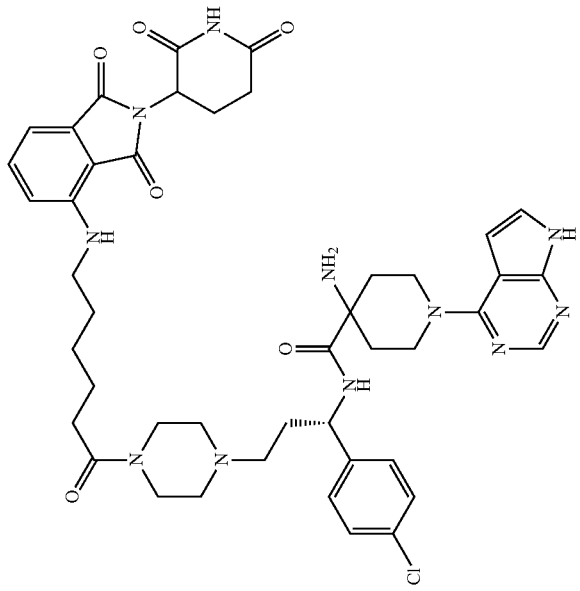 | 4-amino-N-((1S)-1-(4-chlorophenyl)-3-(4-(6-((2-(2,6-dioxopiperidin-3-yl)-1,3-dioxoisoindolin-4-yl)amino)hexanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-27 | 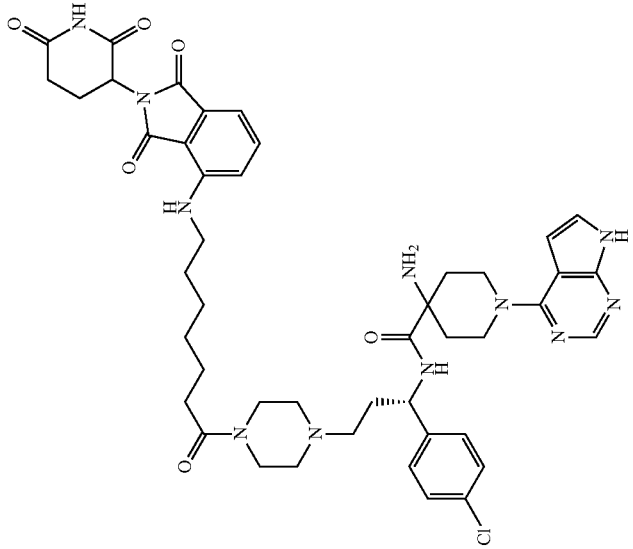 | 4-amino-N-((1S)-1-(4-chlorophenyl)-3-(4-(7-((2-(2,6-dioxopiperidin-3-yl)-1,3-dioxoisoindolin-4-yl)amino)heptanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-28 | 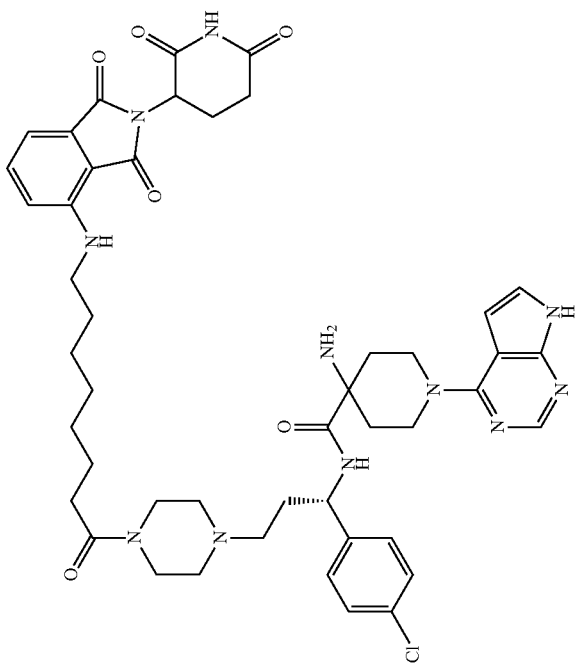 | 4-amino-N-((1S)-1-(4-chlorophenyl)-3-(4-(8-((2-(2,6-dioxopiperidin-3-yl)-1,3-dioxoisoindolin-4-yl)amino)octanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-29 | 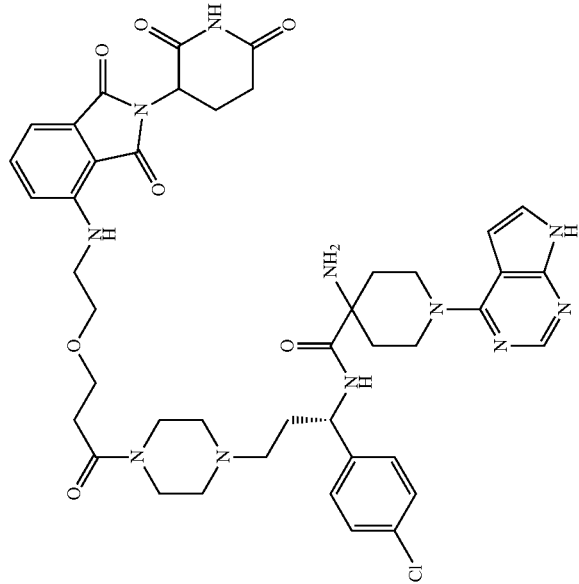 | 4-amino-N-((1S)-1-(4-chlorophenyl)-3-(4-(3-(2-((2-(2,6-dioxopiperidin-3-yl)-1,3-dioxoisoindolin-4-yl)amino)ethoxy)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-30 | 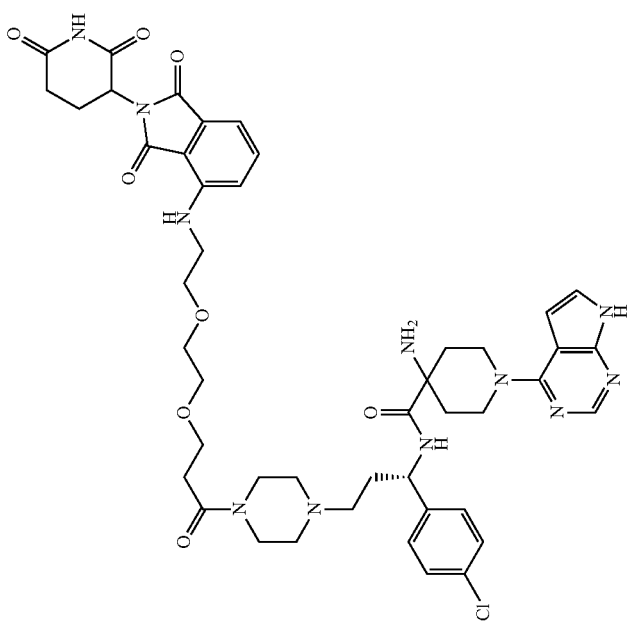 | 4-amino-N-((1S)-1-(4-chlorophenyl)-3-(4-(3-(2-(2-(2-(2,6-dioxopiperidin-3-yl)-1,3-dioxoisoindolin-4-yl)amino)ethoxy)ethoxy)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-31 | 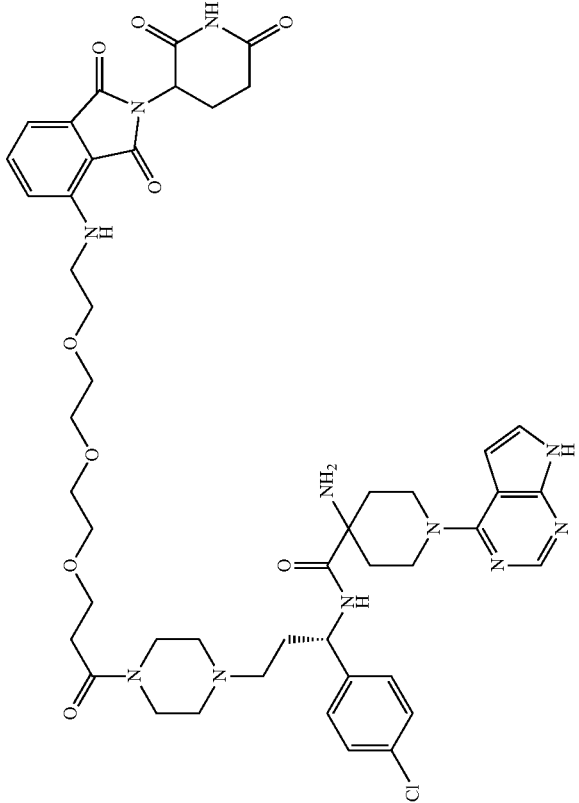 | 4-amino-N-((1S)-1-(4-chlorophenyl)-3-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-32 | 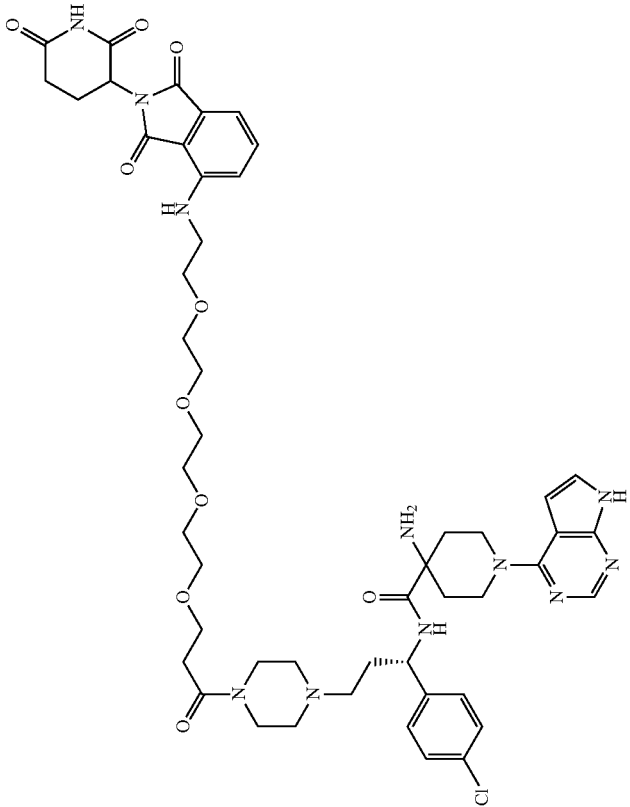 | 4-amino-N-((1S)-1-(4-chlorophenyl)-3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propyl)-1-(7H-pyrrolo[2,3-d]pyrimidin-4-yl)piperidine-4-carboxamide |

TABLE 1-continued

| Compound ID | Structure | Chemical Name |
|---|---|---|
| XF050-33 | 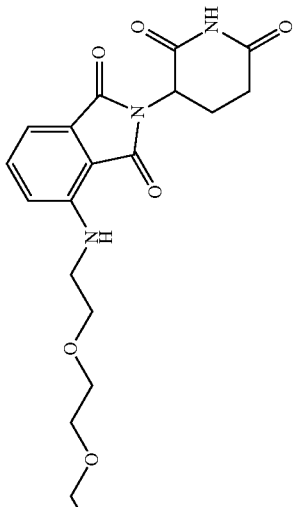 | 4-amino-N-((1S)-1-(4-chlorophenyl)-3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propyl)-1-(7H-pyrrolo[2,3-d]pyrimidin-4-yl)piperidine-4-carboxamide |
| XF050-98 | 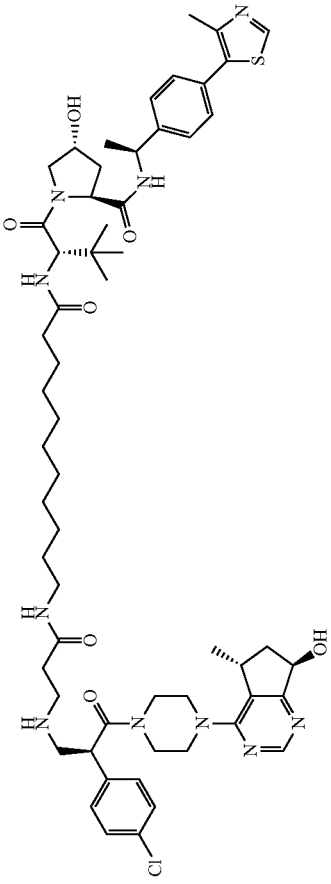 | N¹-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-N¹²-(((S)-((2S,4R)-4-hydroxy-2-((((S)-1-(4-(4-methylthiazol-5-yl)phenyl)ethyl)carbamoyl)pyrrolidin-1-yl)-3,3-dimethyl-1-oxobutan-2-yl)dodecanediamide |

TABLE 1-continued
| Compound ID | Structure | Chemical Name |
|---|---|---|
| XF050-132 | 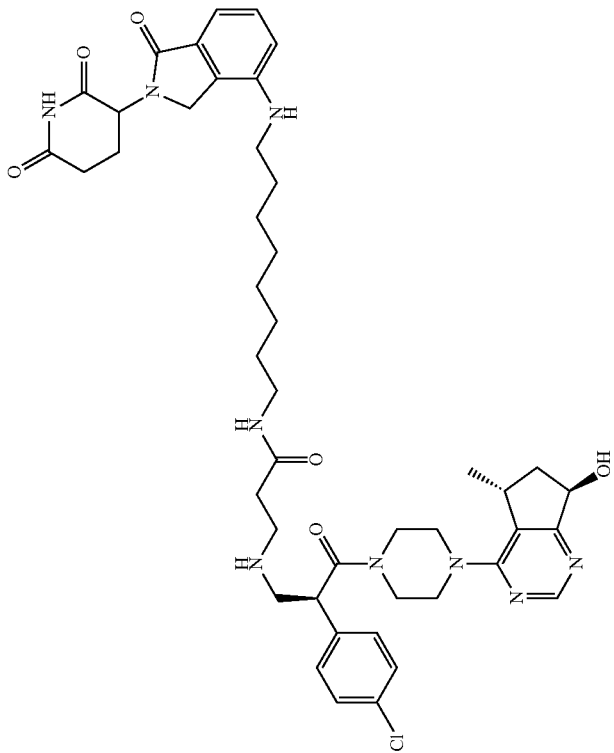 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(8-((2-(2,6-dioxopiperidin-3-yl)-1-oxoisoindolin-4-yl)amino)octyl)propanamide |

TABLE 1-continued

| Compound ID | Structure | Chemical Name |
|---|---|---|
| XF050-133 | 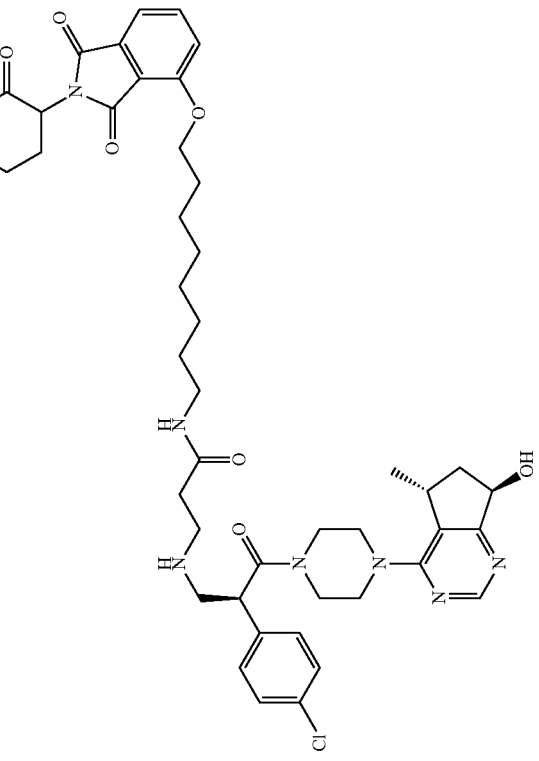 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(8-((2-(2,6-dioxopiperidin-3-yl)-1,3-dioxoisoindolin-4-yl)oxy)octyl)propanamide |
| XF050-134 | 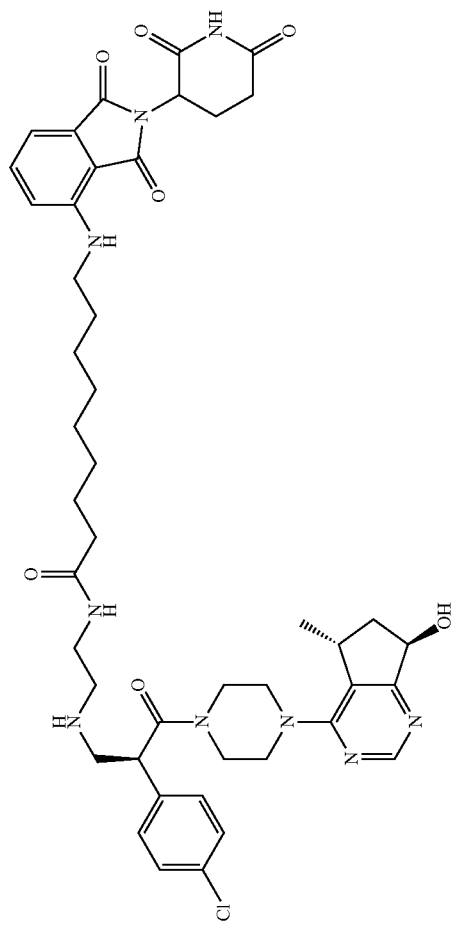 | N-(2-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)ethyl)-9-((2-(2,6-dioxopiperidin-3-yl)-1,3-dioxoisoindolin-4-yl)amino)nonanamide |

TABLE 1-continued
| Compound ID | Structure | Chemical Name |
|---|---|---|
| XF056-93 | 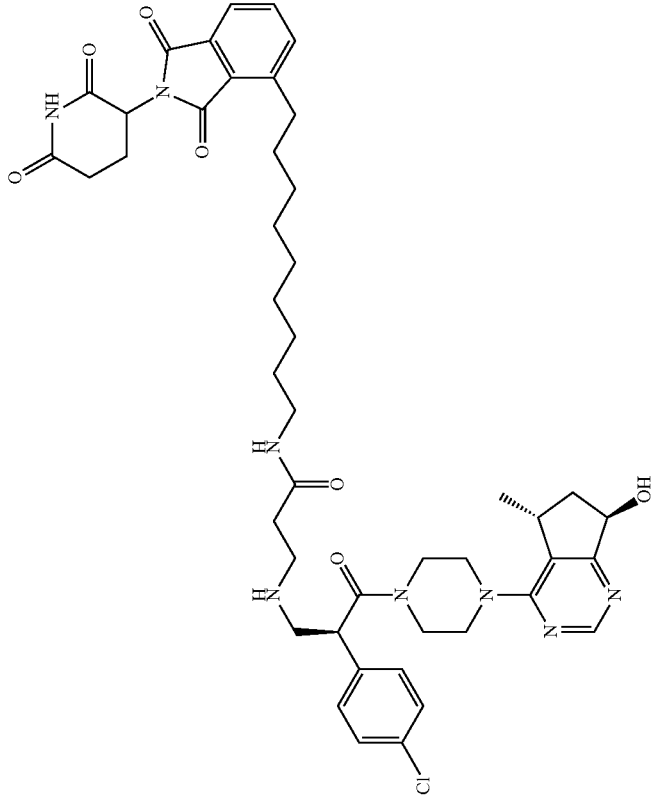 | 3-(((S)-2-(4-chlorophenyl)-3-(4-((5R,7R)-7-hydroxy-5-methyl-6,7-dihydro-5H-cyclopenta[d]pyrimidin-4-yl)piperazin-1-yl)-3-oxopropyl)amino)-N-(9-(2-(2,6-dioxopiperidin-3-yl)-1,3-dioxoisoindolin-4-yl)nonyl)propanamide |

TABLE 1-continued
| Compound ID | Structure | Chemical Name |
|---|---|---|
| XF050-143 | 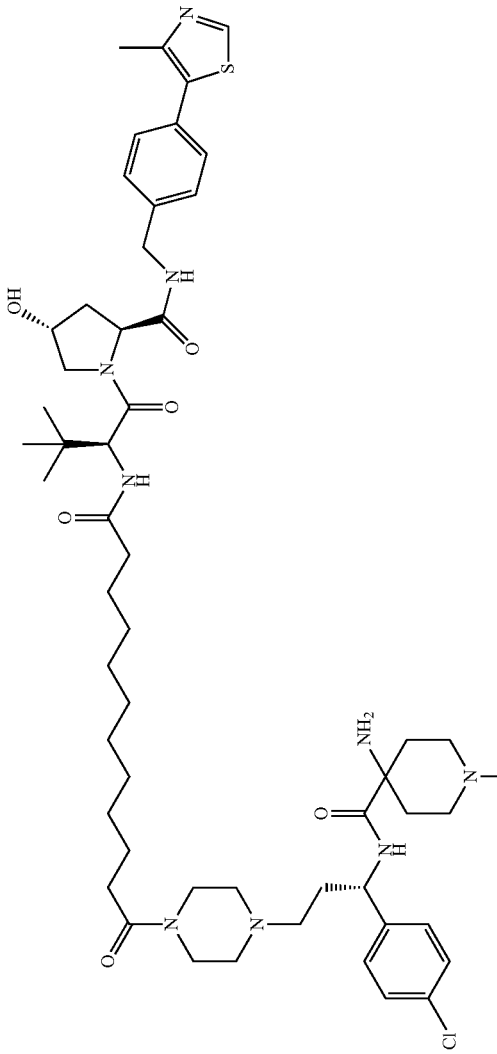 | 4-amino-N-((1S)-1-(4-chlorophenyl)-3-(4-(12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-144 | 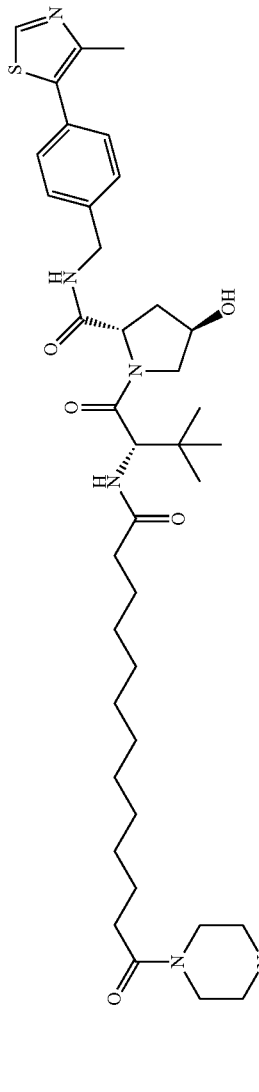 | 4-amino-N-((S)-1-(4-chlorophenyl)-3-(4-(13-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-13-oxotridecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-145 | 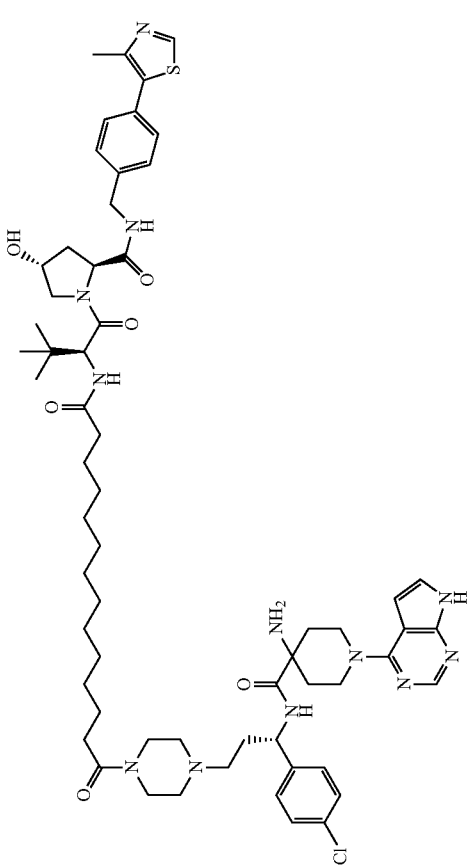 | 4-amino-N-((S)-1-(4-chlorophenyl)-3-(4-(14-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-14-oxotetradecanoyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF050-167 | 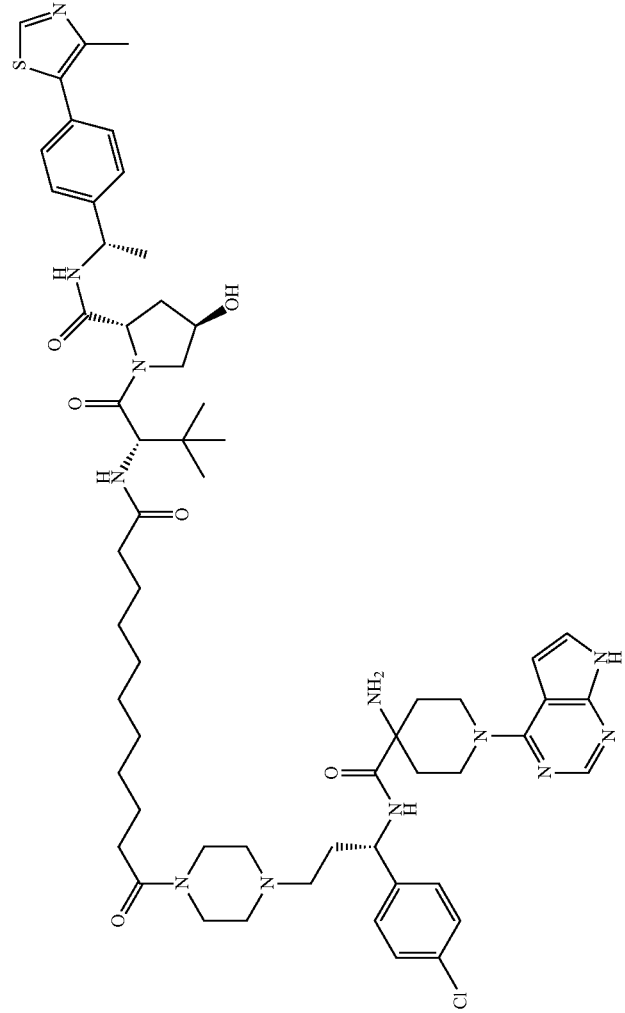 | 4-amino-N-((S)-1-(4-chlorophenyl)-3-(4-(11-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-11-oxoundecanoyl)piperazin-1-yl)propyl)-1-(7H-pyrrolo[2,3-d]pyrimidin-4-yl)piperidine-4-carboxamide |

TABLE 1-continued

| Compound ID | Structure | Chemical Name |
|---|---|---|
| XF056-33 | 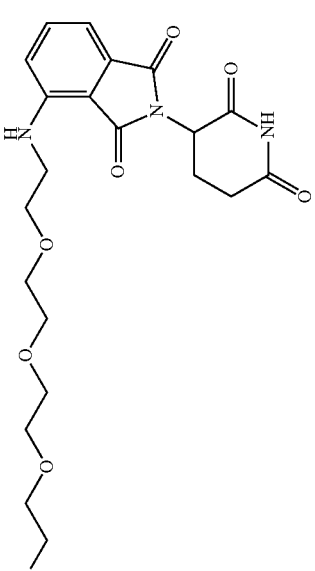 | 4-amino-N-((1S)-1-(4-chlorophenyl)-3-(4-(1-((2-(2,6-dioxopiperidin-3-yl)-1,3-dioxoisoindolin-4-yl)amino)-3,6,9,12,15,18-hexaoxahenicosan-21-oyl)piperazin-1-yl)propyl)-1-(7H-pyrrolo[2,3-d]pyrimidin-4-yl)piperidine-4-carboxamide |
| XF056-34 | 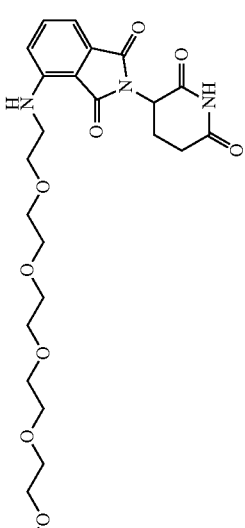 | 4-amino-N-((1S)-1-(4-chlorophenyl)-3-(4-(1-((2-(2,6-dioxopiperidin-3-yl)-1,3-dioxoisoindolin-4-yl)amino)-3,6,9,12,15,18,21,24-octaoxaheptacosan-27-oyl)piperazin-1-yl)propyl)-1-(7H-pyrrolo[2,3-d]pyrimidin-4-yl)piperidine-4-carboxamide |

| Compound ID | Structure | Chemical Name |
|---|---|---|
| XF056-35 | 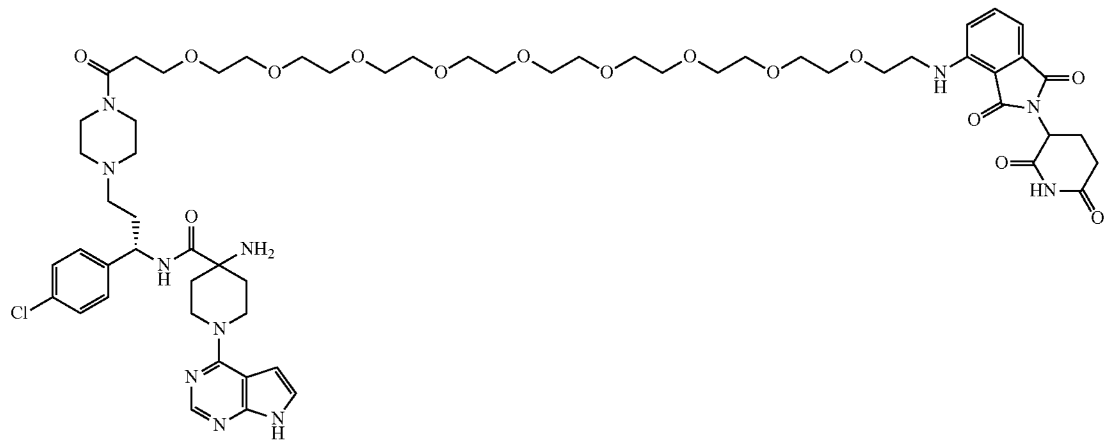 [SMILES: NC1(C(=O)N[C@@H](CCN2CCN(C(=O)CCOCCOCCOCCOCCOCCOCCOCCOCCOCCNc3cccc4c3C(=O)N(C3CCC(=O)NC3=O)C4=O)CC2)c2ccc(Cl)cc2)CCN(c2ncnc3[nH]ccc23)CC1] | 4-amino-N-((1S)-1-(4-chlorophenyl)-3-(4-(1-(2-(2,6-dioxopiperidin-3-yl)-1,3-dioxoisoindolin-4-yl)amino)-3,6,9,12,15,18,21,24,27-nonaoxatriacontan-30-oyl)piperazin-1-yl)propyl)-1-(7H-pyrrolo[2,3-d]pyrimidin-4-yl)piperidine-4-carboxamide |
| XF056-36 | 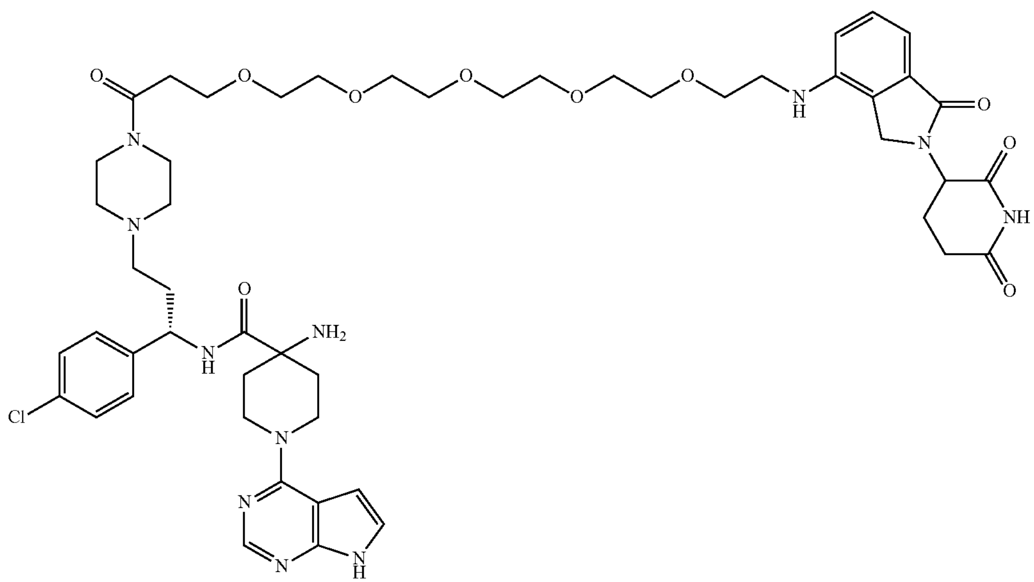 [SMILES: NC1(C(=O)N[C@@H](CCN2CCN(C(=O)CCOCCOCCOCCOCCOCCNc3cccc4c3CN(C3CCC(=O)NC3=O)C4=O)CC2)c2ccc(Cl)cc2)CCN(c2ncnc3[nH]ccc23)CC1] | 4-amino-N-((1S)-1-(4-chlorophenyl)-3-(4-(1-(2-(2,6-dioxopiperidin-3-yl)-1-oxoisoindolin-4-yl)amino)-3,6,9,12,15-pentaoxaoctadecan-18-oyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF056-37 | 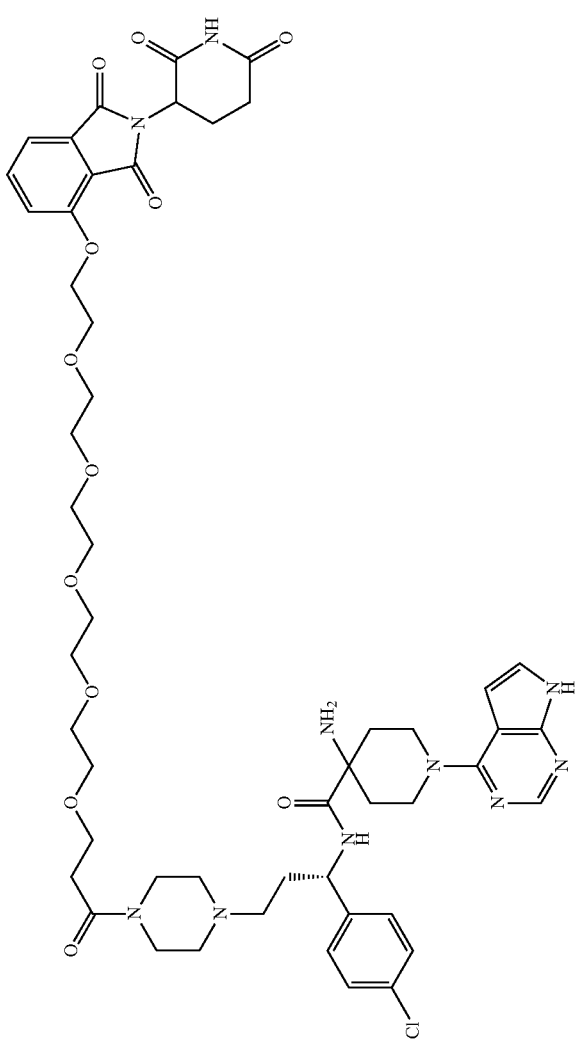 | 4-amino-N-((1S)-1-(4-chlorophenyl)-3-(4-(1-((2-(2,6-dioxopiperidin-3-yl)-1,3-dioxoisoindolin-4-yl)oxy)-3,6,9,12,15-pentaoxaoctadecan-18-oyl)piperazin-1-yl)propyl)-1-(7H-pyrrolo[2,3-d]pyrimidin-4-yl)piperidine-4-carboxamide |

TABLE 1-continued
| Compound ID | Structure | Chemical Name |
|---|---|---|
| XF056-73 | 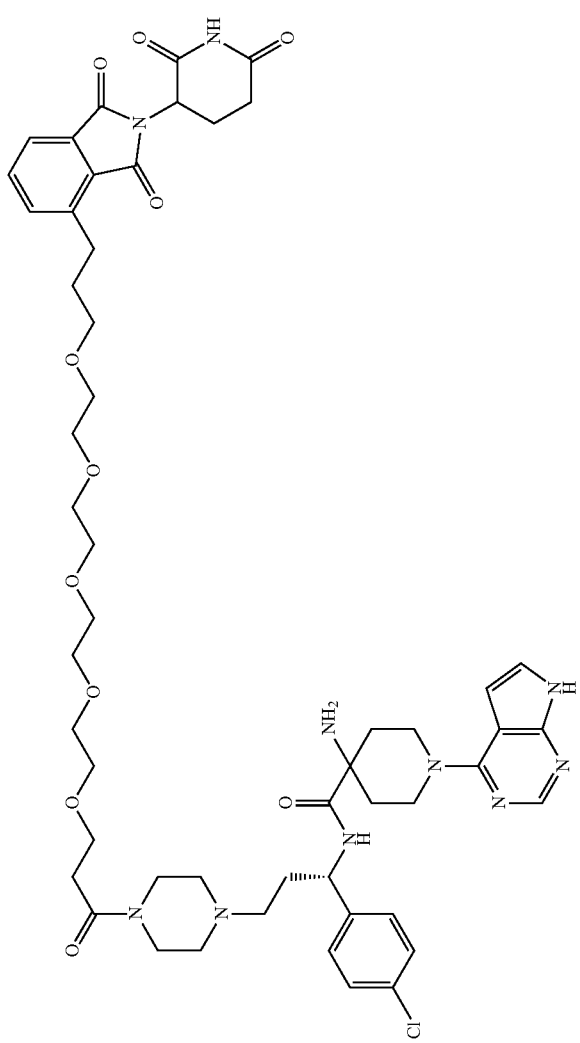 | 4-amino-N-((1S)-1-(4-chlorophenyl)-3-(4-(19-(2-(2,6-dioxopiperidin-3-yl)-1,3-dioxoisoindolin-4-yl)-4,7,10,13,16-pentaoxanonadecanoyl)piperazin-1-yl)propyl)-1-(7H-pyrrolo[2,3-d]pyrimidin-4-yl)piperidine-4-carboxamide |

TABLE 1-continued

| Compound ID | Structure | Chemical Name |
|---|---|---|
| XF061-10 | 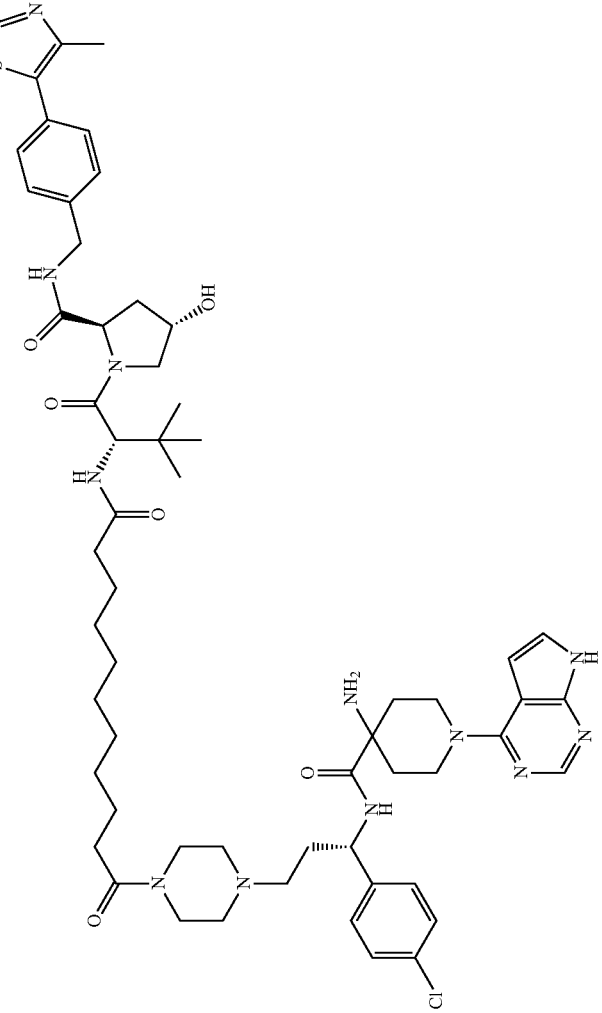 | 4-amino-N-((1S)-1-(4-chlorophenyl)-3-(4-(11-(((S)-1-((2R,4S)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)propyl)-1-(7H-pyrrolo[2,3-d]pyrimidin-4-yl)piperidine-4-carboxamide |
| XF067-1 | 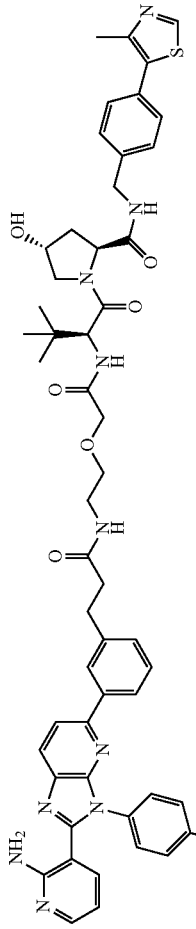 | (2S,4R)-1-((S)-2-(2-(3-(3-(4-(1-aminocyclobutyl)phenyl)-2-(2-aminopyridin-3-yl)-3H-imidazo[4,5-b]pyridin-5-yl)phenyl)propanamido)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-2 | 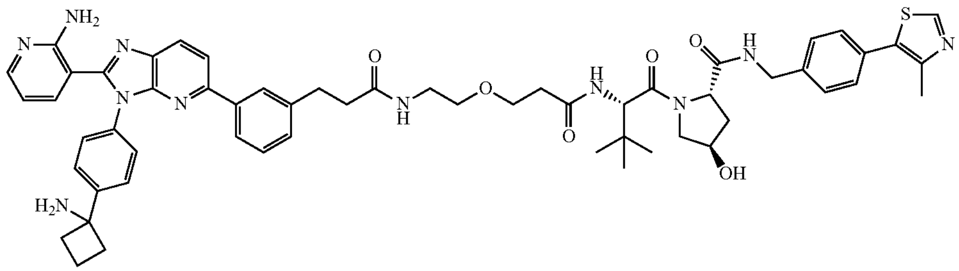 [SMILES: Cc1ncsc1-c1ccc(CNC(=O)[C@@H]2C[C@@H](O)CN2C(=O)[C@@H](NC(=O)CCOCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(3-(2-(3-(3-(4-(1-aminocyclobutyl)phenyl)-2-(2-aminopyridin-3-yl)-3H-imidazo[4,5-b]pyridin-5-yl)phenyl)propanamido)ethoxy)propanamido)-3,3-dimethylbutanoyl)-4-hydroxy-N-(4-(4-methylthiazol-5-yl)benzyl)pyrrolidine-2-carboxamide |
| XF067-3 | 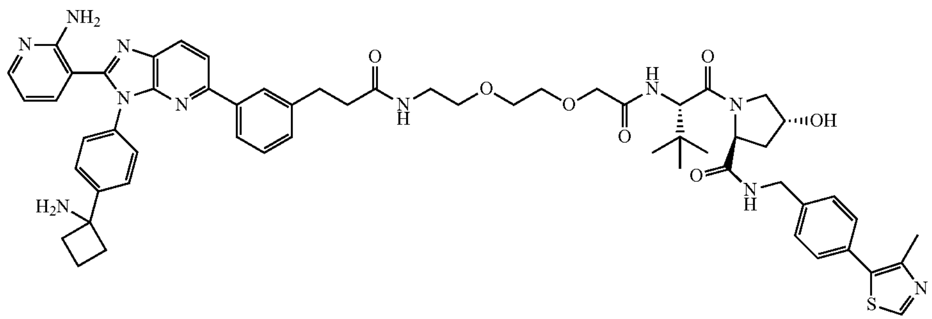 [SMILES: Cc1ncsc1-c1ccc(CNC(=O)[C@@H]2C[C@@H](O)CN2C(=O)[C@@H](NC(=O)COCCOCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-15-(3-(4-(1-aminocyclobutyl)phenyl)-2-(2-aminopyridin-3-yl)-3H-imidazo[4,5-b]pyridin-5-yl)phenyl)-2-(tert-butyl)-4,13-dioxo-6,9-dioxa-3,12-diazapentadecanoyl)-4-hydroxy-N-(4-(4-methylthiazol-5-yl)benzyl)pyrrolidine-2-carboxamide |
| XF067-4 | 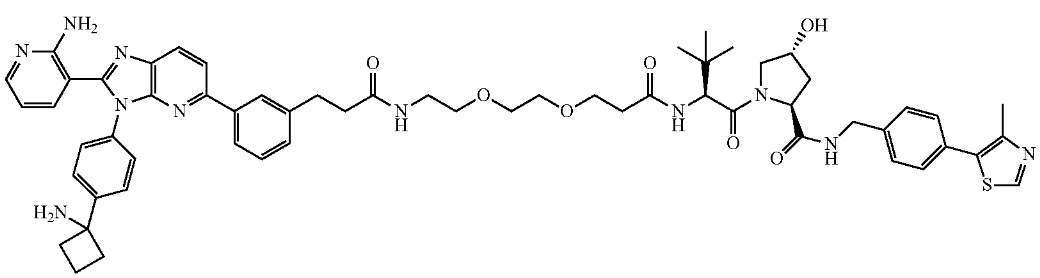 [SMILES: Cc1ncsc1-c1ccc(CNC(=O)[C@@H]2C[C@@H](O)CN2C(=O)[C@@H](NC(=O)CCOCCOCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-16-(3-(4-(1-aminocyclobutyl)phenyl)-2-(2-aminopyridin-3-yl)-3H-imidazo[4,5-b]pyridin-5-yl)phenyl)-2-(tert-butyl)-4,14-dioxo-7,10-dioxa-3,13-diazahexadecanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-5 | 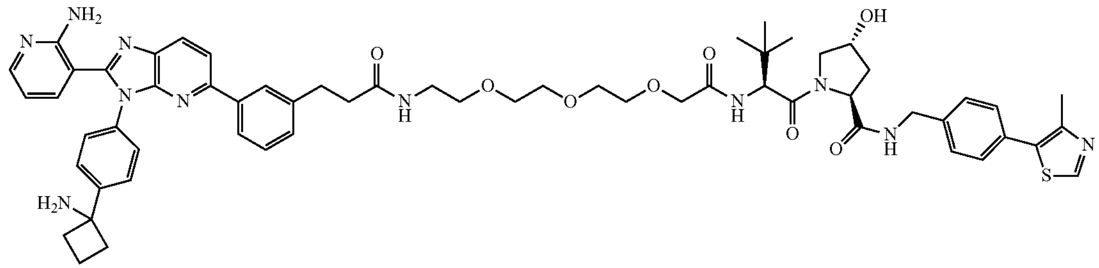 | (2S,4R)-1-((S)-18-(3-(4-(1-aminocyclobutyl)phenyl)-2-(2-aminopyridin-3-yl)-3H-imidazo[4,5-b]pyridin-5-yl)phenyl)-2-(tert-butyl)-4,16-dioxo-6,9,12-trioxa-3,15-diazaoctadecanoyl)-4-hydroxy-N-(4-(4-methylthiazol-5-yl)benzyl)pyrrolidine-2-carboxamide |
| XF067-6 | 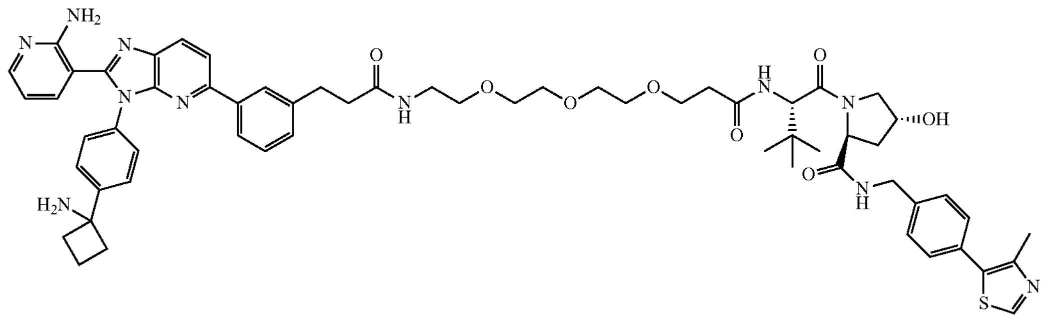 [SMILES: Cc1ncsc1-c1ccc(CNC(=O)[C@@H]2C[C@@H](O)CN2C(=O)[C@@H](NC(=O)CCOCCOCCOCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-19-(3-(4-(1-aminocyclobutyl)phenyl)-2-(2-aminopyridin-3-yl)-3H-imidazo[4,5-b]pyridin-5-yl)phenyl)-2-(tert-butyl)-4,17-dioxo-7,10,13-trioxa-3,16-diazanonadecanoyl)-4-hydroxy-N-(4-(4-methylthiazol-5-yl)benzyl)pyrrolidine-2-carboxamide |
| XF067-7 | 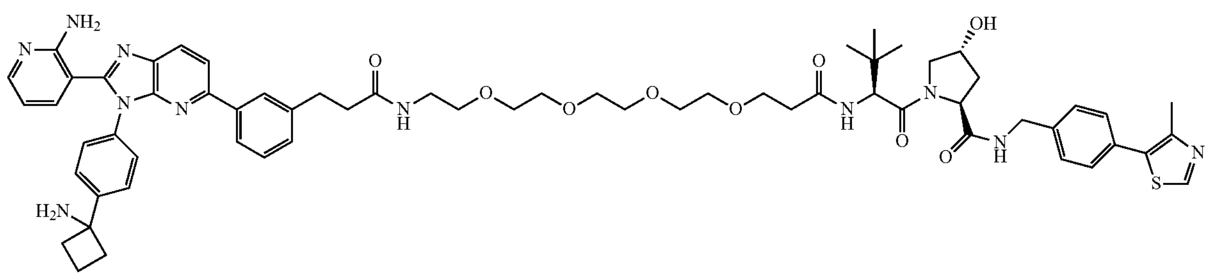 [SMILES: Cc1ncsc1-c1ccc(CNC(=O)[C@@H]2C[C@@H](O)CN2C(=O)[C@@H](NC(=O)CCOCCOCCOCCOCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-22-(3-(4-(1-aminocyclobutyl)phenyl)-2-(2-aminopyridin-3-yl)-3H-imidazo[4,5-b]pyridin-5-yl)phenyl)-2-(tert-butyl)-4,20-dioxo-7,10,13,16-tetraoxa-3,19-diazadocosanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-8 | 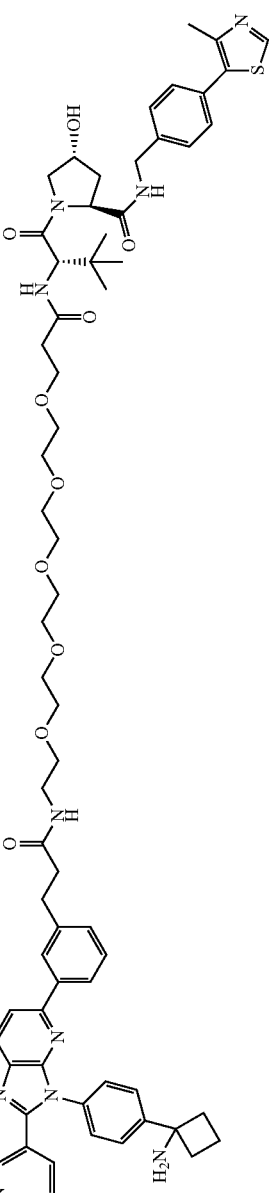 | (2S,4R)-1-((S)-25-(3-(3-(4-(1-aminocyclobutyl)phenyl)-2-(2-aminopyridin-3-yl)-3H-imidazo[4,5-b]pyridin-5-yl)phenyl)-2-(tert-butyl)-4,23-dioxo-7,10,13,16,19-pentaoxa-3,22-diazapentacosanoyl)-4-hydroxy-N-(4-(4-methylthiazol-5-yl)benzyl)pyrrolidine-2-carboxamide |
| XF067-9 | 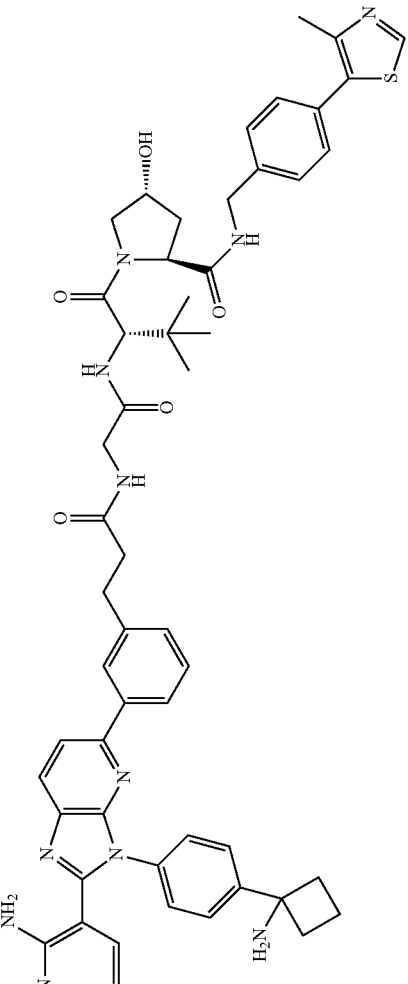 | (2S,4R)-1-((S)-2-(2-(3-(3-(4-(1-aminocyclobutyl)phenyl)-2-(2-aminopyridin-3-yl)-3H-imidazo[4,5-b]pyridin-5-yl)phenyl)propanamido)acetamido)-3,3-dimethylbutanoyl)-4-hydroxy-N-(4-(4-methylthiazol-5-yl)benzyl)pyrrolidine-2-carboxamide |
| XF067-10 | 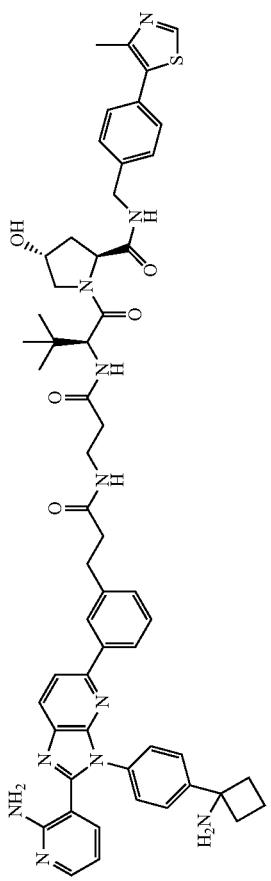 | (2S,4R)-1-((S)-2-(3-(3-(3-(4-(1-aminocyclobutyl)phenyl)-2-(2-aminopyridin-3-yl)-3H-imidazo[4,5-b]pyridin-5-yl)phenyl)propanamido)propanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-11 | 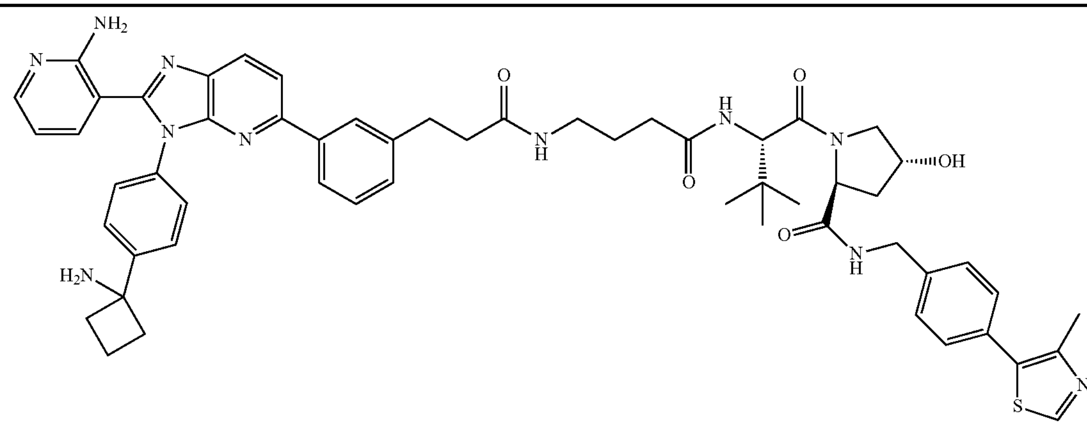 | (2S,4R)-1-((S)-2-(4-(3-(3-(4-(1-aminocyclobutyl)phenyl)-2-(2-aminopyridin-3-yl)-3H-imidazo[4,5-b]pyridin-5-yl)phenyl)propanamido)butanamido)-3,3-dimethylbutanoyl)-4-hydroxy-N-(4-(4-methylthiazol-5-yl)benzyl)pyrrolidine-2-carboxamide |
| XF067-12 | 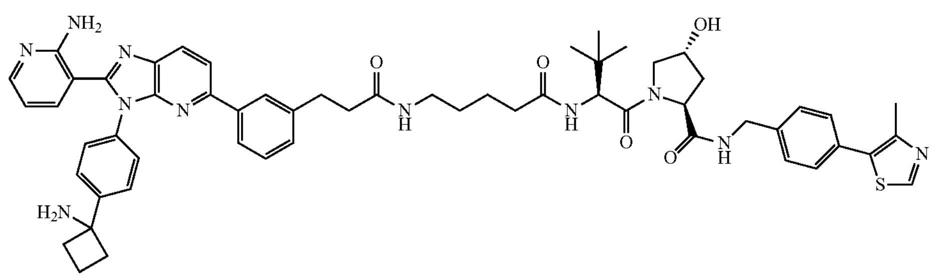 | (2S,4R)-1-((S)-2-(5-(3-(3-(4-(1-aminocyclobutyl)phenyl)-2-(2-aminopyridin-3-yl)-3H-imidazo[4,5-b]pyridin-5-yl)phenyl)propanamido)pentanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-13 | 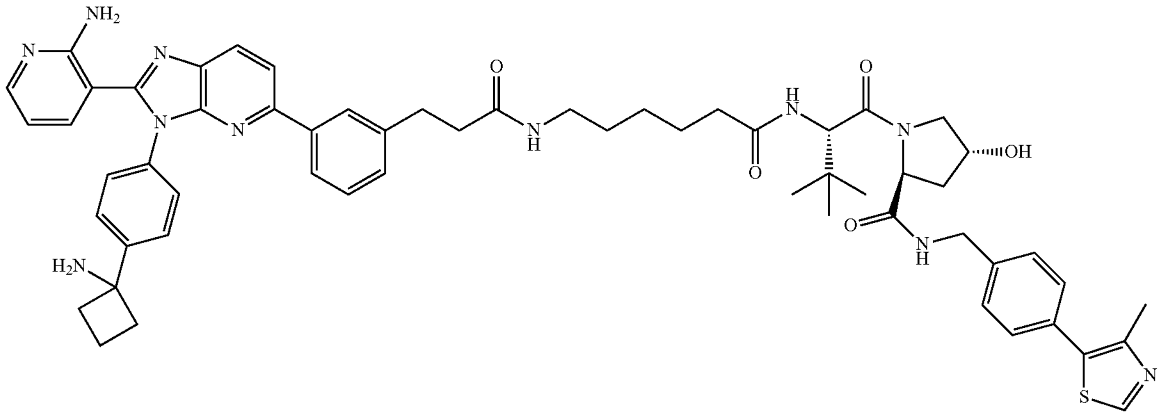 [SMILES: Cc1ncsc1-c1ccc(CNC(=O)[C@@H]2C[C@@H](O)CN2C(=O)[C@@H](NC(=O)CCCCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(6-(3-(3-(4-(1-aminocyclobutyl)phenyl)-2-(2-aminopyridin-3-yl)-3H-imidazo[4,5-b]pyridin-5-yl)phenyl)propanamido)hexanamido)-3,3-dimethylbutanoyl)-4-hydroxy-N-(4-(4-methylthiazol-5-yl)benzyl)pyrrolidine-2-carboxamide |
| XF067-14 | 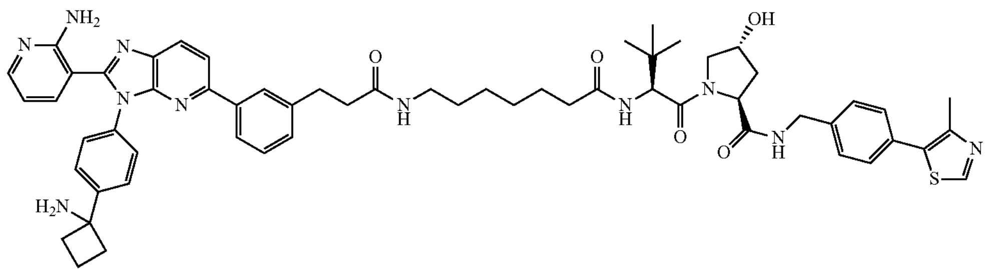 [SMILES: Cc1ncsc1-c1ccc(CNC(=O)[C@@H]2C[C@@H](O)CN2C(=O)[C@@H](NC(=O)CCCCCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(7-(3-(3-(4-(1-aminocyclobutyl)phenyl)-2-(2-aminopyridin-3-yl)-3H-imidazo[4,5-b]pyridin-5-yl)phenyl)propanamido)heptanamido)-3,3-dimethylbutanoyl)-4-hydroxy-N-(4-(4-methylthiazol-5-yl)benzyl)pyrrolidine-2-carboxamide |
| XF067-15 | 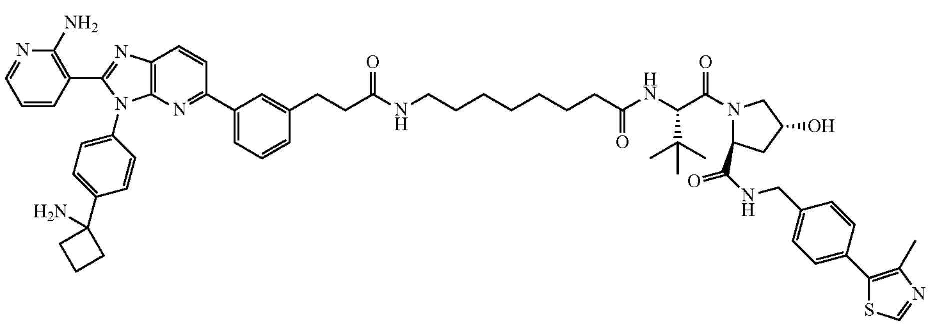 [SMILES: Cc1ncsc1-c1ccc(CNC(=O)[C@@H]2C[C@@H](O)CN2C(=O)[C@@H](NC(=O)CCCCCCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(8-(3-(3-(4-(1-aminocyclobutyl)phenyl)-2-(2-aminopyridin-3-yl)-3H-imidazo[4,5-b]pyridin-5-yl)phenyl)propanamido)octanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-16 | 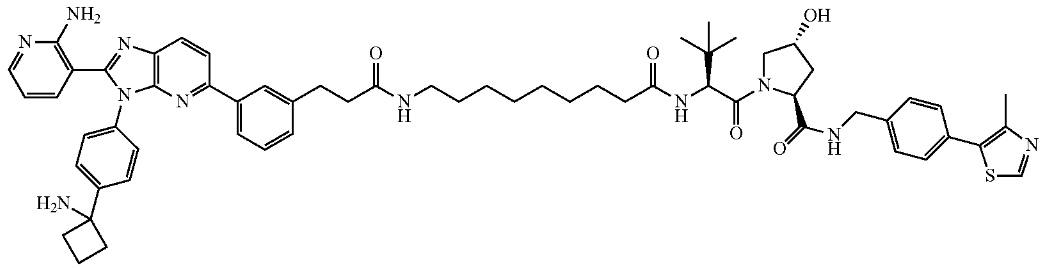 [SMILES: Cc1ncsc1-c1ccc(CNC(=O)[C@@H]2C[C@@H](O)CN2C(=O)[C@@H](NC(=O)CCCCCCCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(9-(3-(3-(4-(1-aminocyclobutyl)phenyl)-2-(2-aminopyridin-3-yl)-3H-imidazo[4,5-b]pyridin-5-yl)phenyl)propanamido)nonanamido)-3,3-dimethylbutanoyl)-4-hydroxy-N-(4-(4-methylthiazol-5-yl)benzyl)pyrrolidine-2-carboxamide |
| XF067-17 | 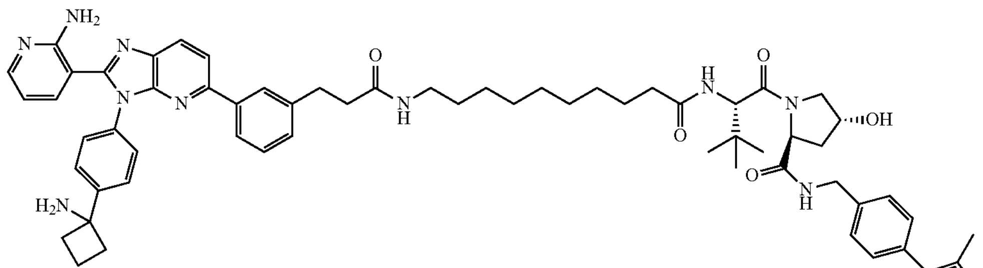 | (2S,4R)-1-((S)-2-(10-(3-(3-(4-(1-aminocyclobutyl)phenyl)-2-(2-aminopyridin-3-yl)-3H-imidazo[4,5-b]pyridin-5-yl)phenyl)propanamido)decanamido)-3,3-dimethylbutanoyl)-4-hydroxy-N-(4-(4-methylthiazol-5-yl)benzyl)pyrrolidine-2-carboxamide |
| XF067-18 | 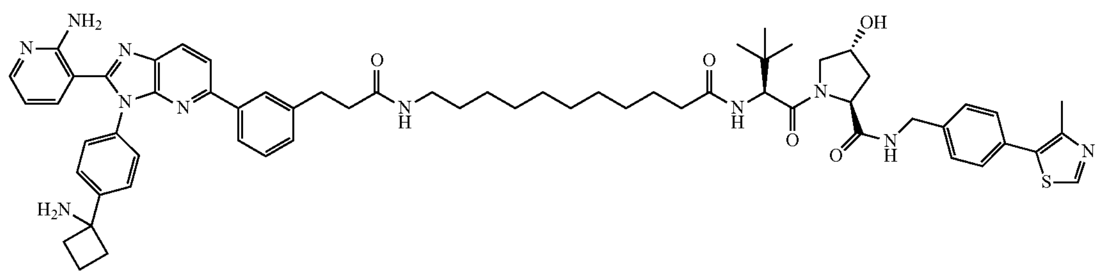 [SMILES: Cc1ncsc1-c1ccc(CNC(=O)[C@@H]2C[C@@H](O)CN2C(=O)[C@@H](NC(=O)CCCCCCCCCCNC(=O)CCc2cccc(-c3ccc4nc(-c5cccnc5N)n(-c5ccc(C6(N)CCC6)cc5)c4n3)c2)C(C)(C)C)cc1] | (2S,4R)-1-((S)-2-(11-(3-(3-(4-(1-aminocyclobutyl)phenyl)-2-(2-aminopyridin-3-yl)-3H-imidazo[4,5-b]pyridin-5-yl)phenyl)propanamido)undecanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-19 | 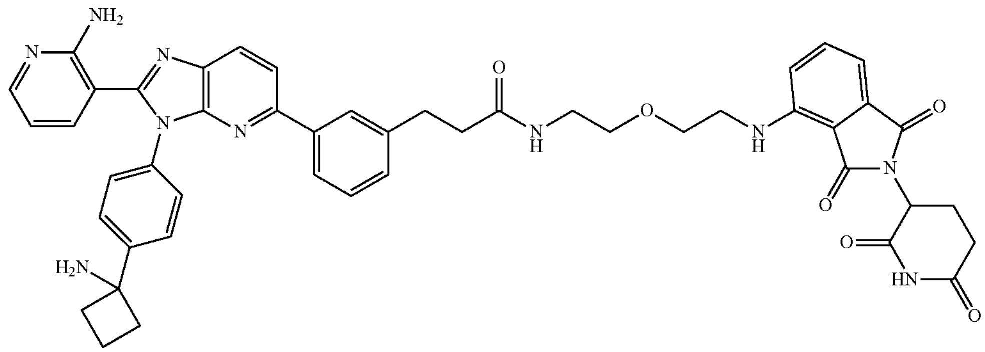 [SMILES: Nc1ncccc1-c1nc2ccc(-c3cccc(CCC(=O)NCCOCCNc4cccc5c4C(=O)N(C4CCC(=O)NC4=O)C5=O)c3)nc2n1-c1ccc(C2(N)CCC2)cc1] | 3-(3-(3-(4-(1-aminocyclobutyl)phenyl)-2-(2-aminopyridin-3-yl)-3H-imidazo[4,5-b]pyridin-5-yl)phenyl)-N-(2-(2-((2-(2,6-dioxopiperidin-3-yl)-1,3-dioxoisoindolin-4-yl)amino)ethoxy)ethyl)propanamide |
| XF067-20 | 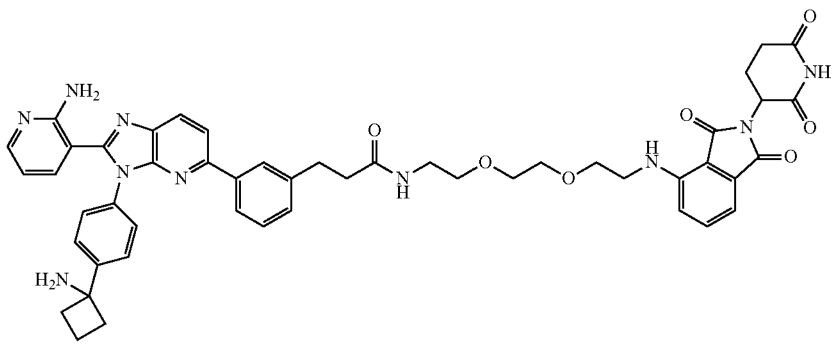 [SMILES: Nc1ncccc1-c1nc2ccc(-c3cccc(CCC(=O)NCCOCCOCCNc4cccc5c4C(=O)N(C4CCC(=O)NC4=O)C5=O)c3)nc2n1-c1ccc(C2(N)CCC2)cc1] | 3-(3-(3-(4-(1-aminocyclobutyl)phenyl)-2-(2-aminopyridin-3-yl)-3H-imidazo[4,5-b]pyridin-5-yl)phenyl)-N-(2-(2-(2-((2-(2,6-dioxopiperidin-3-yl)-1,3-dioxoisoindolin-4-yl)amino)ethoxy)ethoxy)ethyl)propanamide |
| XF067-21 | 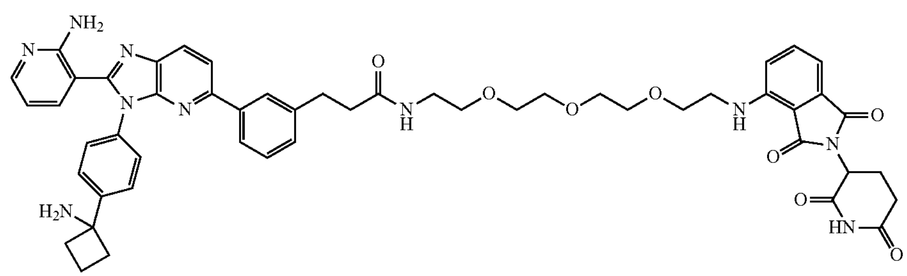 [SMILES: Nc1ncccc1-c1nc2ccc(-c3cccc(CCC(=O)NCCOCCOCCOCCNc4cccc5c4C(=O)N(C4CCC(=O)NC4=O)C5=O)c3)nc2n1-c1ccc(C2(N)CCC2)cc1] | 3-(3-(3-(4-(1-aminocyclobutyl)phenyl)-2-(2-aminopyridin-3-yl)-3H-imidazo[4,5-b]pyridin-5-yl)phenyl)-N-(2-(2-(2-((2-(2,6-dioxopiperidin-3-yl)-1,3-dioxoisoindolin-4-yl)amino)ethoxy)ethoxy)ethoxy)ethyl)propanamide |

TABLE 1-continued

| Compound ID | Structure | Chemical Name |
|---|---|---|
| XF067-22 | 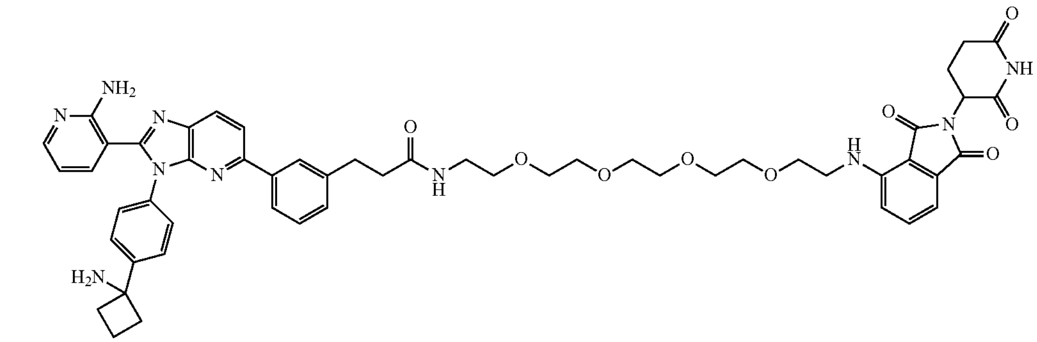 [SMILES: Nc1ncccc1-c1nc2ccc(-c3cccc(CCC(=O)NCCOCCOCCOCCOCCNc4cccc5c4C(=O)N(C4CCC(=O)NC4=O)C5=O)c3)nc2n1-c1ccc(C2(N)CCC2)cc1] | 3-(3-(4-(1-aminocyclobutyl)phenyl)-2-(2-aminopyridin-3-yl)-3H-imidazo[4,5-b]pyridin-5-yl)phenyl)-N-(14-((2-(2,6-dioxopiperidin-3-yl)-1,3-dioxoisoindolin-4-yl)amino)-3,6,9,12-tetraoxatetradecyl) propanamide |
| XF067-23 | 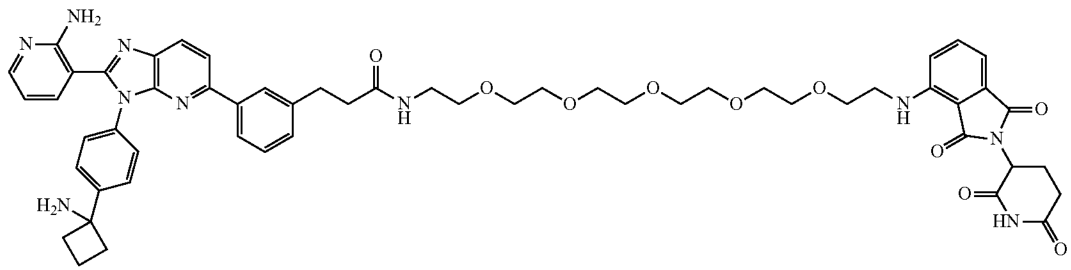 [SMILES: Nc1ncccc1-c1nc2ccc(-c3cccc(CCC(=O)NCCOCCOCCOCCOCCOCCNc4cccc5c4C(=O)N(C4CCC(=O)NC4=O)C5=O)c3)nc2n1-c1ccc(C2(N)CCC2)cc1] | 3-(3-(4-(1-aminocyclobutyl)phenyl)-2-(2-aminopyridin-3-yl)-3H-imidazo[4,5-b]pyridin-5-yl)phenyl)-N-(17-((2-(2,6-dioxopiperidin-3-yl)-1,3-dioxoisoindolin-4-yl)amino)-3,6,9,12,15-pentaoxaheptadecyl) propanamide |
| XF067-24 | 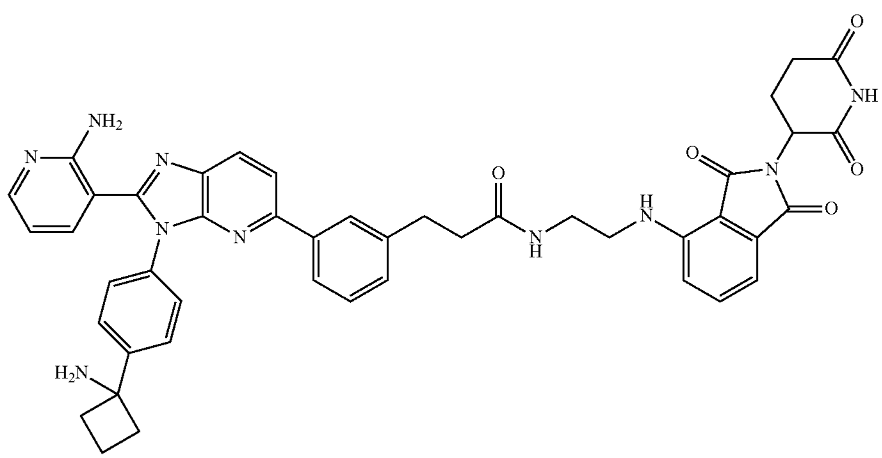 [SMILES: Nc1ncccc1-c1nc2ccc(-c3cccc(CCC(=O)NCCNc4cccc5c4C(=O)N(C4CCC(=O)NC4=O)C5=O)c3)nc2n1-c1ccc(C2(N)CCC2)cc1] | 3-(3-(4-(1-aminocyclobutyl)phenyl)-2-(2-aminopyridin-3-yl)-3H-imidazo[4,5-b]pyridin-5-yl)phenyl)-N-(2-((2-(2,6-dioxopiperidin-3-yl)-1,3-dioxoisoindolin-4-yl)amino)ethyl)propanamide |

TABLE 1-continued
| Compound ID | Structure | Chemical Name |
|---|---|---|
| XF067-25 | 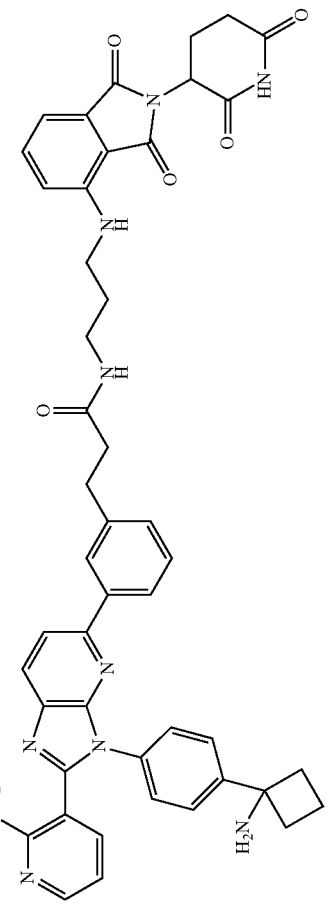 | 3-(3-(4-(1-aminocyclobutyl)phenyl)-2-(2-aminopyridin-3-yl)-3H-imidazo[4,5-b]pyridin-5-yl)phenyl)-N-(3-((2-(2,6-dioxopiperidin-3-yl)-1,3-dioxoisoindolin-4-yl)amino)propyl)propanamide |
| XF067-26 | 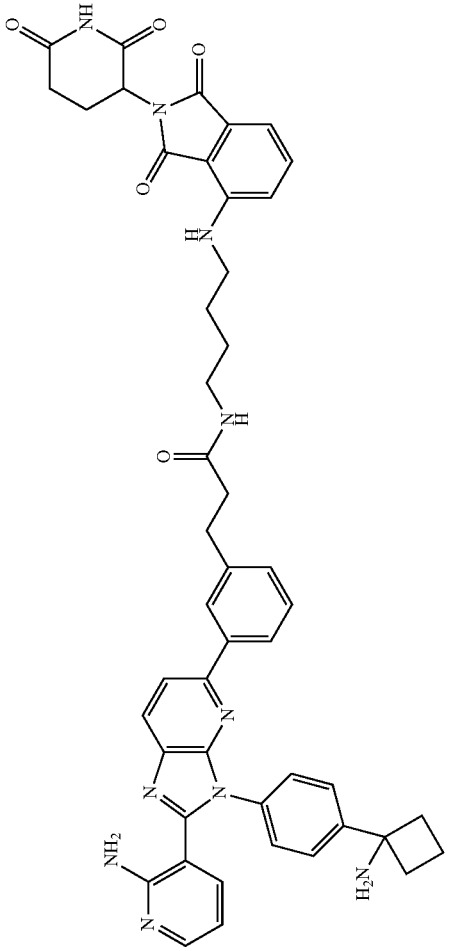 | 3-(3-(4-(1-aminocyclobutyl)phenyl)-2-(2-aminopyridin-3-yl)-3H-imidazo[4,5-b]pyridin-5-yl)phenyl)-N-(4-((2-(2,6-dioxopiperidin-3-yl)-1,3-dioxoisoindolin-4-yl)amino)butyl)propanamide |

TABLE 1-continued
| Compound ID | Structure | Chemical Name |
|---|---|---|
| XF067-27 | 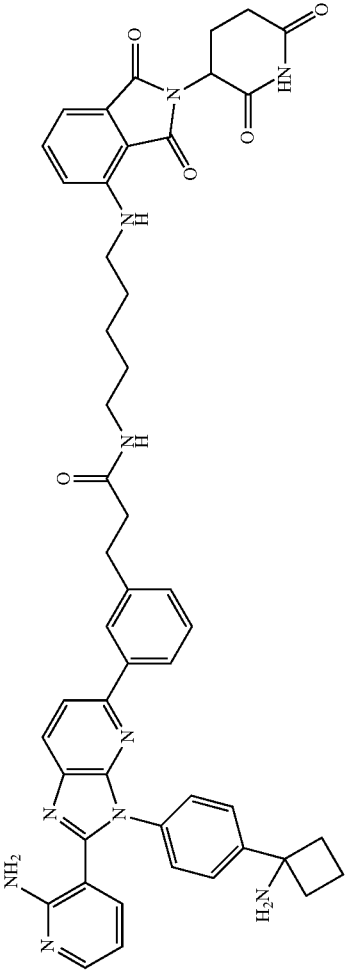 | 3-(3-(4-(1-aminocyclobutyl)phenyl)-2-(2-aminopyridin-3-yl)-3H-imidazo[4,5-b]pyridin-5-yl)phenyl)-N-(5-((2-(2,6-dioxopiperidin-3-yl)-1,3-dioxoisoindolin-4-yl)amino)pentyl)propanamide |
| XF067-28 | 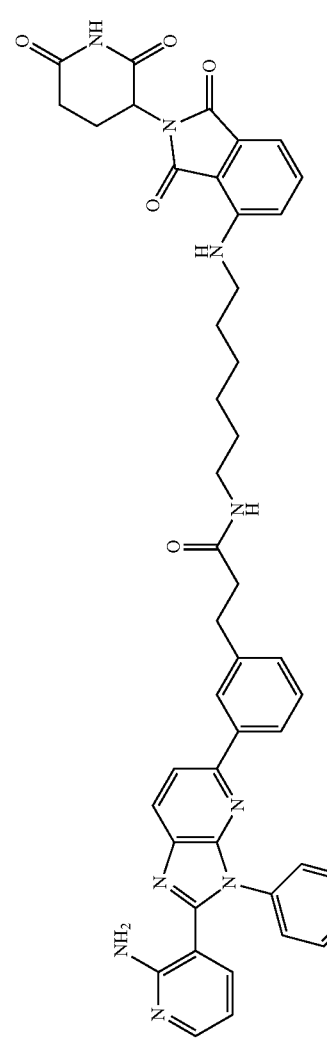 | 3-(3-(4-(1-aminocyclobutyl)phenyl)-2-(2-aminopyridin-3-yl)-3H-imidazo[4,5-b]pyridin-5-yl)phenyl)-N-(6-((2-(2,6-dioxopiperidin-3-yl)-1,3-dioxoisoindolin-4-yl)amino)hexyl)propanamide |

TABLE 1-continued

| Compound ID | Structure | Chemical Name |
|---|---|---|
| XF067-29 | 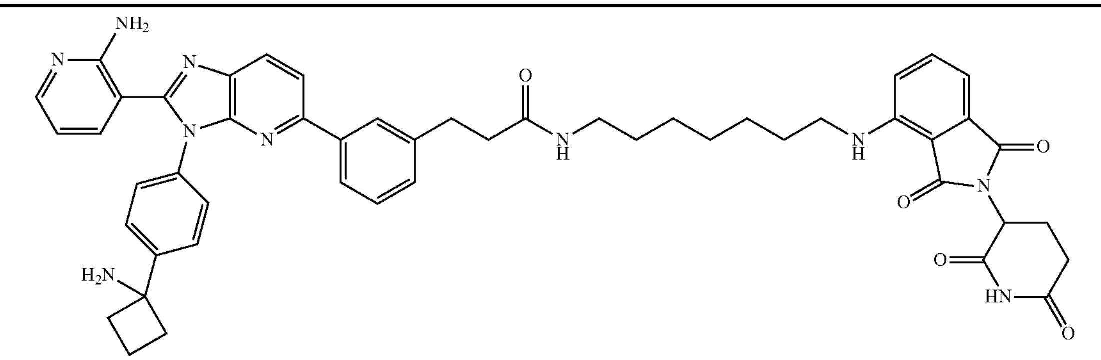 | 3-(3-(3-(4-(1-aminocyclobutyl)phenyl)-2-(2-aminopyridin-3-yl)-3H-imidazo[4,5-b]pyridin-5-yl)phenyl)-N-(7-((2-(2,6-dioxopiperidin-3-yl)-1,3-dioxoisoindolin-4-yl)amino)heptyl)propanamide |
| XF067-30 | 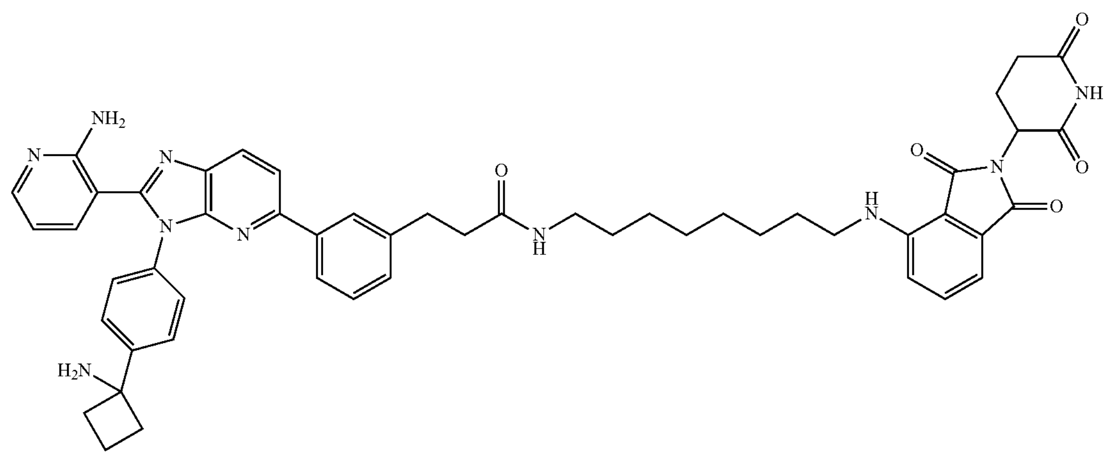 [SMILES: Nc1ncccc1-c1nc2ccc(-c3cccc(CCC(=O)NCCCCCCCCNc4cccc5c4C(=O)N(C4CCC(=O)NC4=O)C5=O)c3)nc2n1-c1ccc(C2(N)CCC2)cc1] | 3-(3-(3-(4-(1-aminocyclobutyl)phenyl)-2-(2-aminopyridin-3-yl)-3H-imidazo[4,5-b]pyridin-5-yl)phenyl)-N-(8-((2-(2,6-dioxopiperidin-3-yl)-1,3-dioxoisoindolin-4-yl)amino)octyl)propanamide |
| XF067-31 | 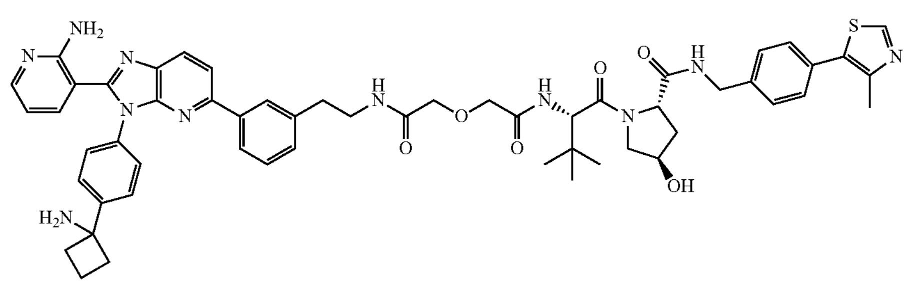 [SMILES: Cc1ncsc1-c1ccc(CNC(=O)[C@@H]2C[C@@H](O)CN2C(=O)[C@@H](NC(=O)COCC(=O)NCCc2cccc(-c3ccc4nc(-c5cccnc5N)n(-c5ccc(C6(N)CCC6)cc5)c4n3)c2)C(C)(C)C)cc1] | (2S,4R)-1-((S)-2-(2-(2-(3-(3-(4-(1-aminocyclobutyl)phenyl)-2-(2-aminopyridin-3-yl)-3H-imidazo[4,5-b]pyridin-5-yl)phenethyl)amino)-2-oxoethoxy)acetamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-32 | 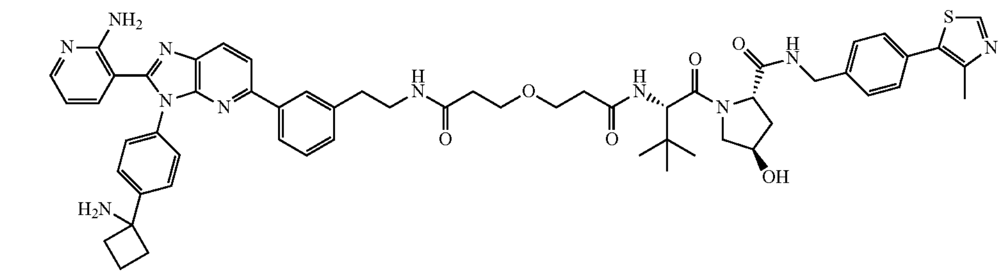 | (2S,4R)-1-((S)-2-(3-(3-(4-(1-aminocyclobutyl)phenyl)-2-(2-aminopyridin-3-yl)-3H-imidazo[4,5-b]pyridin-5-yl)phenethyl)amino)-3-oxopropoxy)propanamido)-3,3-dimethylbutanoyl)-4-hydroxy-N-(4-(4-methylthiazol-5-yl)benzyl)pyrrolidine-2-carboxamide |
| XF067-33 | 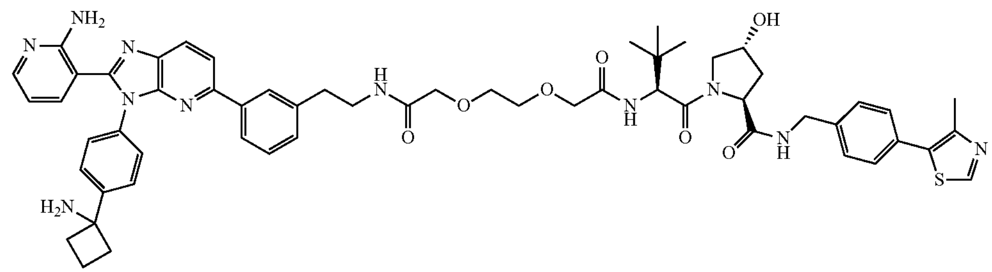 [SMILES: Cc1ncsc1-c1ccc(CNC(=O)[C@@H]2C[C@@H](O)CN2C(=O)[C@@H](NC(=O)COCCOCC(=O)NCCc2cccc(-c3ccc4nc(-c5cccnc5N)n(-c5ccc(C6(N)CCC6)cc5)c4n3)c2)C(C)(C)C)cc1] | (2S,4R)-1-((S)-14-(3-(3-(4-(1-aminocyclobutyl)phenyl)-2-(2-aminopyridin-3-yl)-3H-imidazo[4,5-b]pyridin-5-yl)phenyl)-2-(tert-butyl)-4,11-dioxo-6,9-dioxa-3,12-diazatetradecanoyl)-4-hydroxy-N-(4-(4-methylthiazol-5-yl)benzyl)pyrrolidine-2-carboxamide |
| XF067-34 | 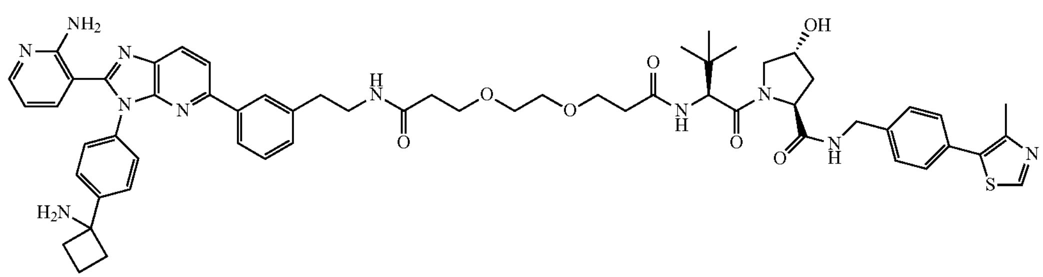 [SMILES: Cc1ncsc1-c1ccc(CNC(=O)[C@@H]2C[C@@H](O)CN2C(=O)[C@@H](NC(=O)CCOCCOCCC(=O)NCCc2cccc(-c3ccc4nc(-c5cccnc5N)n(-c5ccc(C6(N)CCC6)cc5)c4n3)c2)C(C)(C)C)cc1] | (2S,4R)-1-((S)-16-(3-(3-(4-(1-aminocyclobutyl)phenyl)-2-(2-aminopyridin-3-yl)-3H-imidazo[4,5-b]pyridin-5-yl)phenyl)-2-(tert-butyl)-4,13-dioxo-7,10-dioxa-3,14-diazahexadecanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-35 | 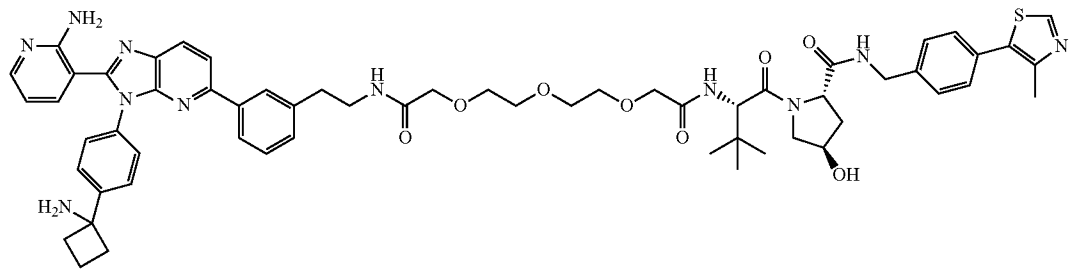 | (2S,4R)-1-((S)-17-(3-(4-(1-aminocyclobutyl)phenyl)-2-(2-aminopyridin-3-yl)-3H-imidazo[4,5-b]pyridin-5-yl)phenyl)-2-(tert-butyl)-4,14-dioxo-6,9,12-trioxa-3,15-diazaheptadecanoyl)-4-hydroxy-N-(4-(4-methylthiazol-5-yl)benzyl)pyrrolidine-2-carboxamide |
| XF067-36 | 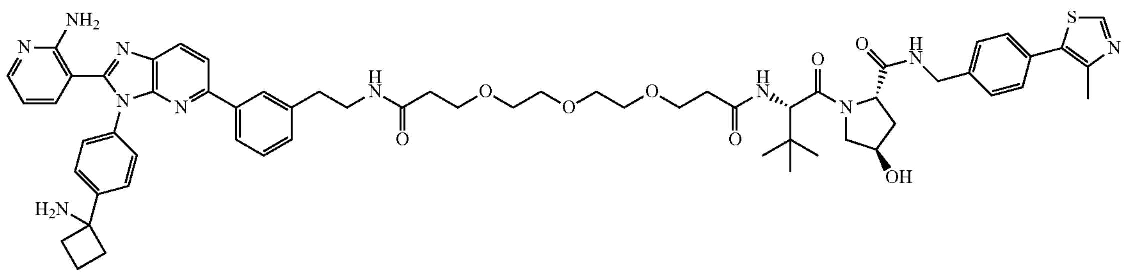 [SMILES: Cc1ncsc1-c1ccc(CNC(=O)[C@@H]2C[C@@H](O)CN2C(=O)[C@@H](NC(=O)CCOCCOCCOCCC(=O)NCCc2cccc(-c3ccc4nc(-c5cccnc5N)n(-c5ccc(C6(N)CCC6)cc5)c4n3)c2)C(C)(C)C)cc1] | (2S,4R)-1-((S)-19-(3-(4-(1-aminocyclobutyl)phenyl)-2-(2-aminopyridin-3-yl)-3H-imidazo[4,5-b]pyridin-5-yl)phenyl)-2-(tert-butyl)-4,16-dioxo-7,10,13-trioxa-3,17-diazanonadecanoyl)-4-hydroxy-N-(4-(4-methylthiazol-5-yl)benzyl)pyrrolidine-2-carboxamide |
| XF067-37 | 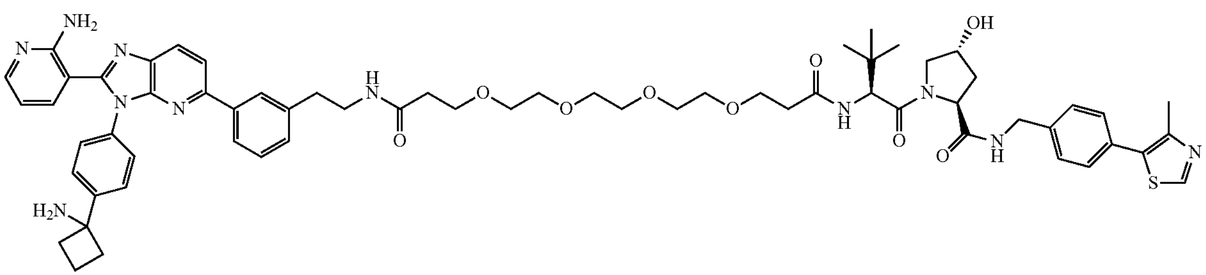 [SMILES: Cc1ncsc1-c1ccc(CNC(=O)[C@@H]2C[C@@H](O)CN2C(=O)[C@@H](NC(=O)CCOCCOCCOCCOCCC(=O)NCCc2cccc(-c3ccc4nc(-c5cccnc5N)n(-c5ccc(C6(N)CCC6)cc5)c4n3)c2)C(C)(C)C)cc1] | $N^1$-(3-(4-(1-aminocyclobutyl)phenyl)-2-(2-aminopyridin-3-yl)-3H-imidazo[4,5-b]pyridin-5-yl)phenethyl)-$N^{16}$-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide |

| Compound ID | Structure | Chemical Name |
|---|---|---|
| XF067-38 | 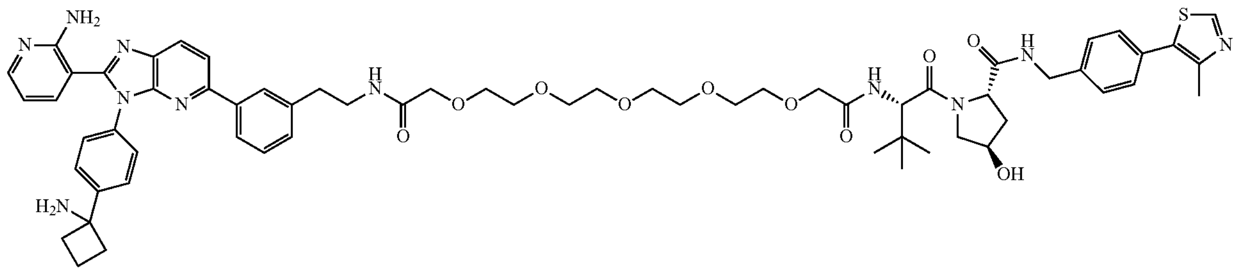 [SMILES: Cc1ncsc1-c1ccc(CNC(=O)[C@@H]2C[C@@H](O)CN2C(=O)[C@@H](NC(=O)COCCOCCOCCOCCOCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N¹⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-3,6,9,12,15-pentaoxaheptadecanediamide |
| XF067-39 | 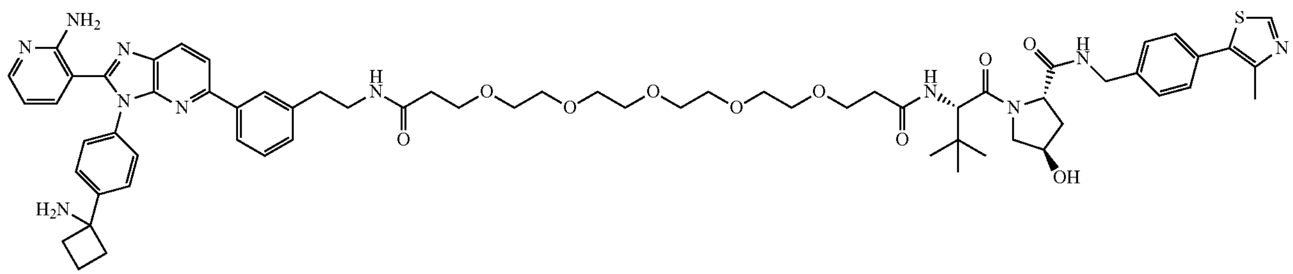 [SMILES: Cc1ncsc1-c1ccc(CNC(=O)[C@@H]2C[C@@H](O)CN2C(=O)[C@@H](NC(=O)CCOCCOCCOCCOCCOCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N¹⁰-((1S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-4,7,10,13,16-pentaoxanonadecanediamide |
| XF067-40 | 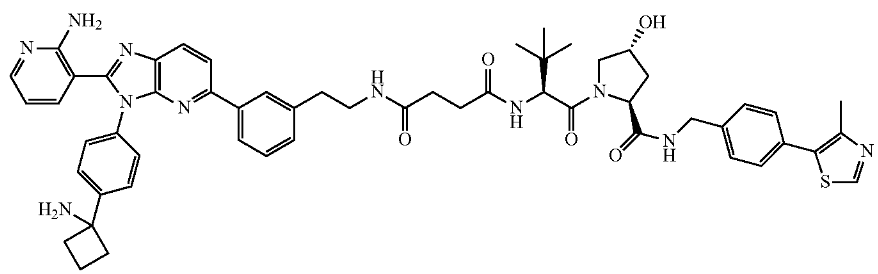 [SMILES: Cc1ncsc1-c1ccc(CNC(=O)[C@@H]2C[C@@H](O)CN2C(=O)[C@@H](NC(=O)CCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N⁴-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)succinamide |

TABLE 1-continued

| Compound ID | Structure | Chemical Name |
|---|---|---|
| XF067-41 | 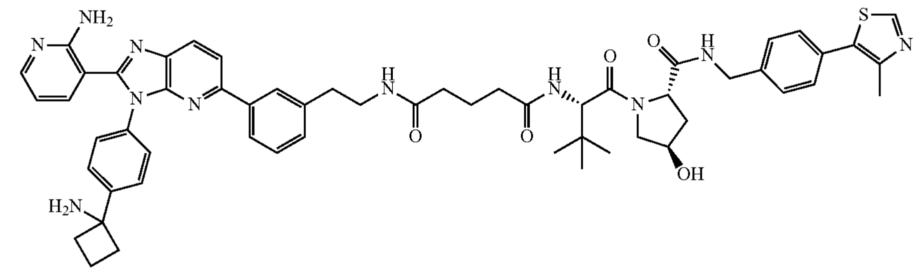 | N¹-(3-(4-(1-aminocyclobutyl)phenyl)-2-(2-aminopyridin-3-yl)-3H-imidazo[4,5-b]pyridin-5-yl)phenethyl)-N⁵-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)glutaramide |
| XF067-42 | 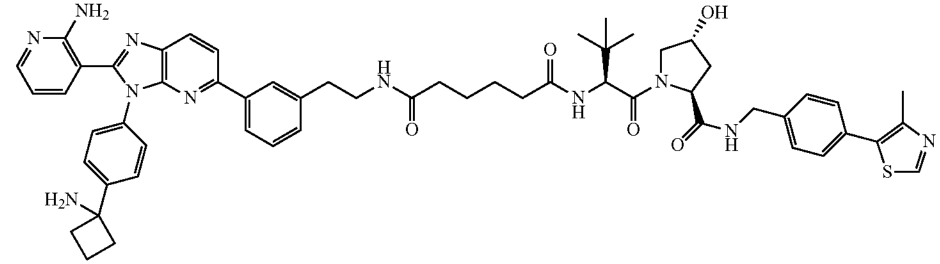 [SMILES: Cc1ncsc1-c1ccc(CNC(=O)[C@@H]2C[C@@H](O)CN2C(=O)[C@@H](NC(=O)CCCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N⁶-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)adipamide |
| XF067-43 | 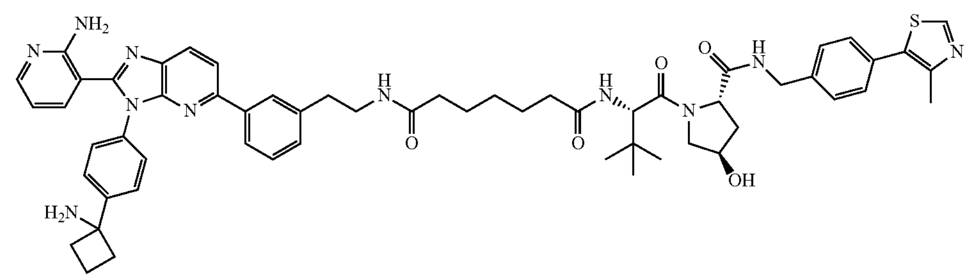 [SMILES: Cc1ncsc1-c1ccc(CNC(=O)[C@@H]2C[C@@H](O)CN2C(=O)[C@@H](NC(=O)CCCCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N⁷-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)heptanediamide |

TABLE 1-continued

| Compound ID | Structure | Chemical Name |
|---|---|---|
| XF067-44 | 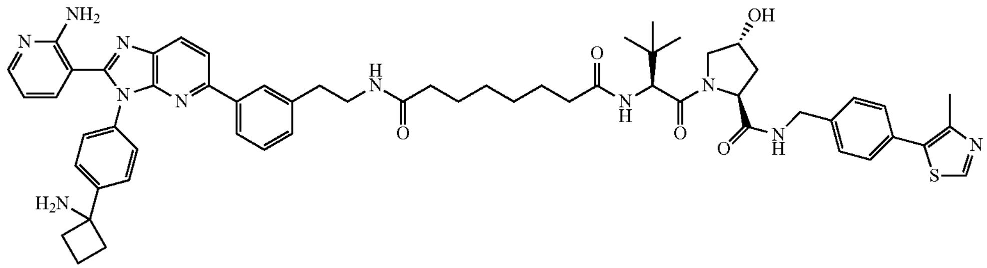 [SMILES: Cc1ncsc1-c1ccc(CNC(=O)[C@@H]2C[C@@H](O)CN2C(=O)[C@@H](NC(=O)CCCCCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N⁸-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)octanediamide |
| XF067-45 | 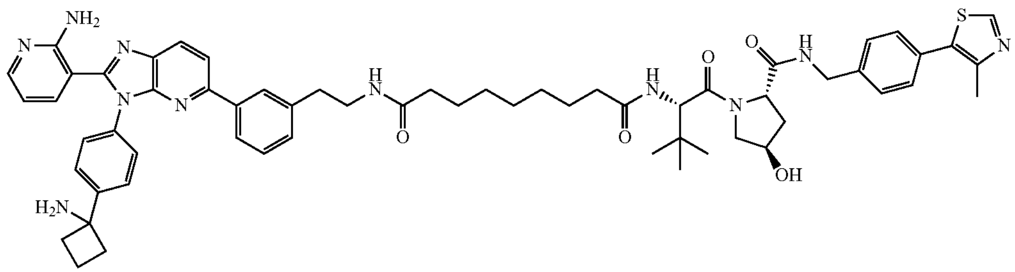 [SMILES: Cc1ncsc1-c1ccc(CNC(=O)[C@@H]2C[C@@H](O)CN2C(=O)[C@@H](NC(=O)CCCCCCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N⁹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)nonanediamide |
| XF067-46 | 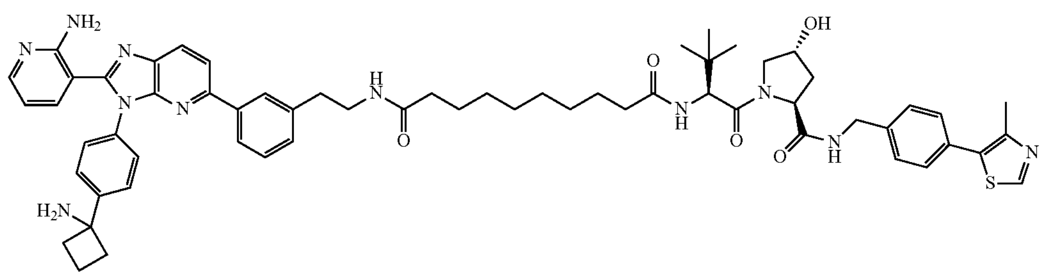 | N¹-(3-(4-(1-aminocyclobutyl)phenyl)-2-(2-aminopyridin-3-yl)-3H-imidazo[4,5-b]pyridin-5-yl)phenethyl)-N¹⁰-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |

TABLE 1-continued

| Compound ID | Structure | Chemical Name |
|---|---|---|
| XF067-47 | 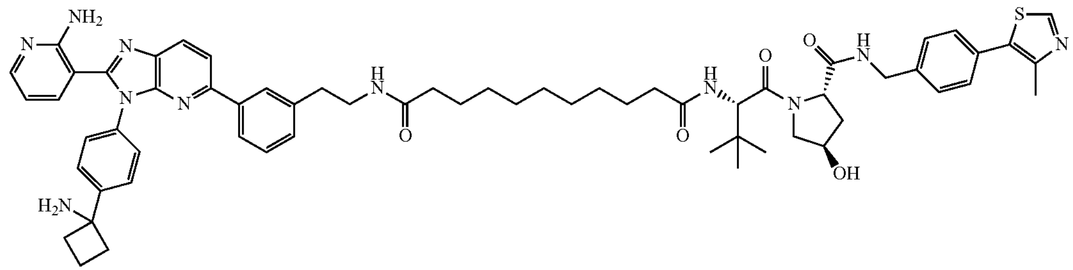 [SMILES: Cc1ncsc1-c1ccc(CNC(=O)[C@@H]2C[C@@H](O)CN2C(=O)[C@@H](NC(=O)CCCCCCCCCC(=O)NCCc2cccc(-c3ccc4nc(-c5cccnc5N)n(-c5ccc(C6(N)CCC6)cc5)c4n3)c2)C(C)(C)C)cc1] | N¹-(3-(4-(1-aminocyclobutyl)phenyl)-2-(2-aminopyridin-3-yl)-3H-imidazo[4,5-b]pyridin-5-yl)phenethyl)-N¹¹-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)undecanediamide |
| XF067-48 | 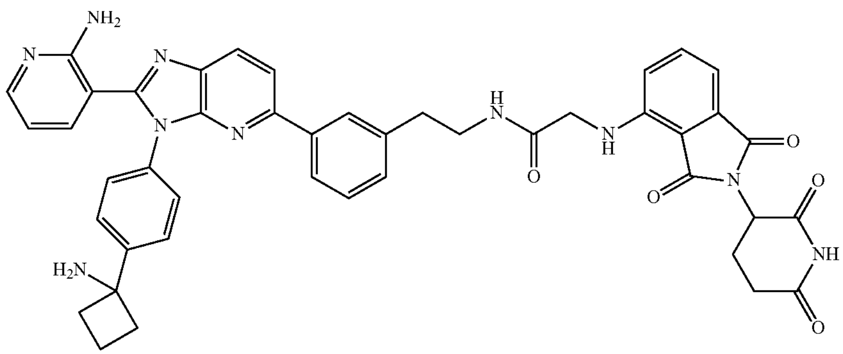 [SMILES: Nc1ncccc1-c1nc2ccc(-c3cccc(CCNC(=O)CNc4cccc5c4C(=O)N(C4CCC(=O)NC4=O)C5=O)c3)nc2n1-c1ccc(C2(N)CCC2)cc1] | N¹-(3-(4-(1-aminocyclobutyl)phenyl)-2-(2-aminopyridin-3-yl)-3H-imidazo[4,5-b]pyridin-5-yl)phenethyl)-2-(2-(2,6-dioxopiperidin-3-yl)-1,3-dioxoisoindolin-4-yl)amino)acetamide |
| XF067-49 | 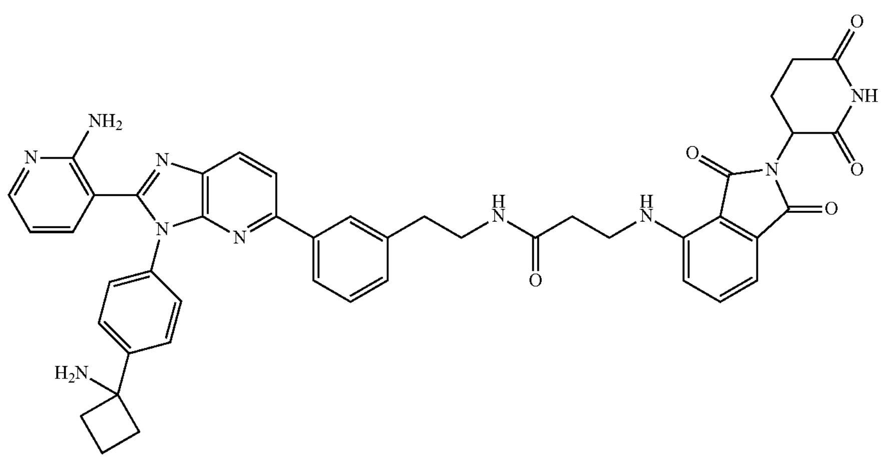 [SMILES: Nc1ncccc1-c1nc2ccc(-c3cccc(CCNC(=O)CCNc4cccc5c4C(=O)N(C4CCC(=O)NC4=O)C5=O)c3)nc2n1-c1ccc(C2(N)CCC2)cc1] | N¹-(3-(4-(1-aminocyclobutyl)phenyl)-2-(2-aminopyridin-3-yl)-3H-imidazo[4,5-b]pyridin-5-yl)phenethyl)-3-((2-(2,6-dioxopiperidin-3-yl)-1,3-dioxoisoindolin-4-yl)amino)propanamide |

| Compound ID | Structure | Chemical Name |
|---|---|---|
| XF067-50 | 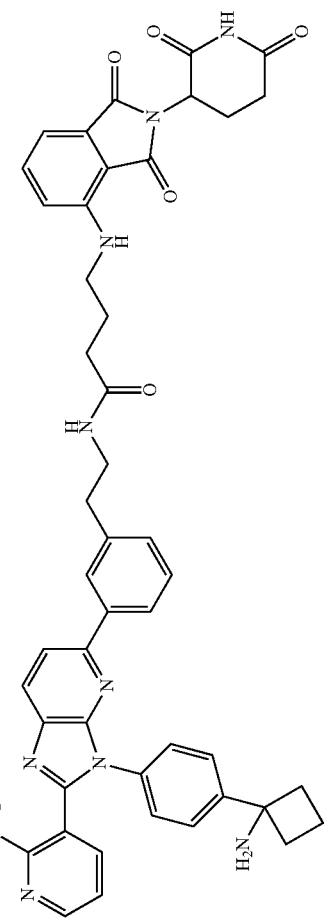 | N¹-(3-(4-(1-aminocyclobutyl)phenyl)-2-(2-aminopyridin-3-yl)-3H-imidazo[4,5-b]pyridin-5-yl)phenethyl)-4-((2-(2,6-dioxopiperidin-3-yl)-1,3-dioxoisoindolin-4-yl)amino)butanamide |
| XF067-51 | 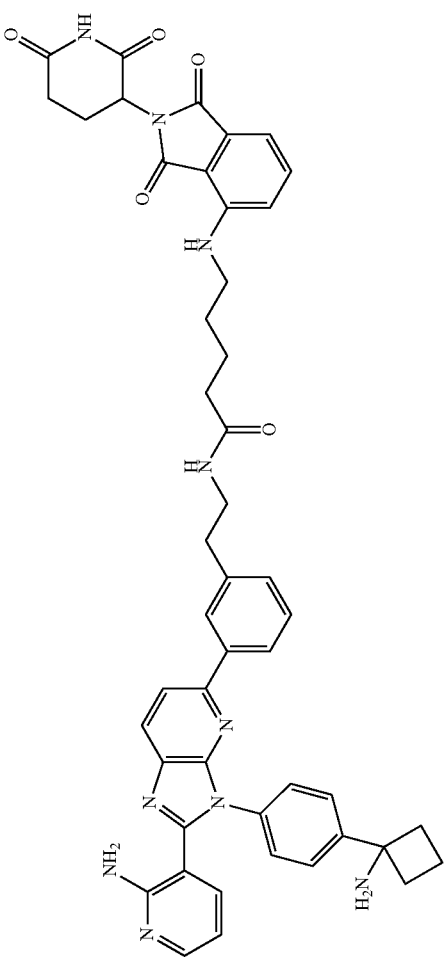 | N¹-(3-(4-(1-aminocyclobutyl)phenyl)-2-(2-aminopyridin-3-yl)-3H-imidazo[4,5-b]pyridin-5-yl)phenethyl)-5-((2-(2,6-dioxopiperidin-3-yl)-1,3-dioxoisoindolin-4-yl)amino)pentanamide |

TABLE 1-continued

| Compound ID | Structure | Chemical Name |
|---|---|---|
| XF067-52 | 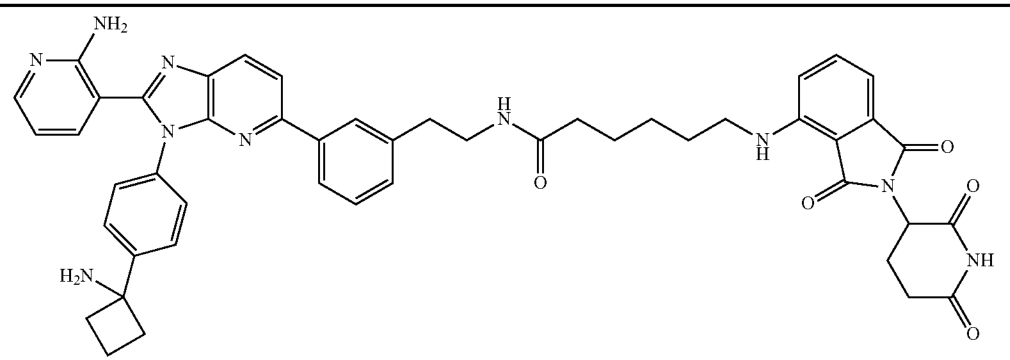 | N-(3-(3-(4-(1-aminocyclobutyl)phenyl)-2-(2-aminopyridin-3-yl)-3H-imidazo[4,5-b]pyridin-5-yl)phenethyl)-6-((2-(2,6-dioxopiperidin-3-yl)-1,3-dioxoisoindolin-4-yl)amino)hexanamide |
| XF067-53 | 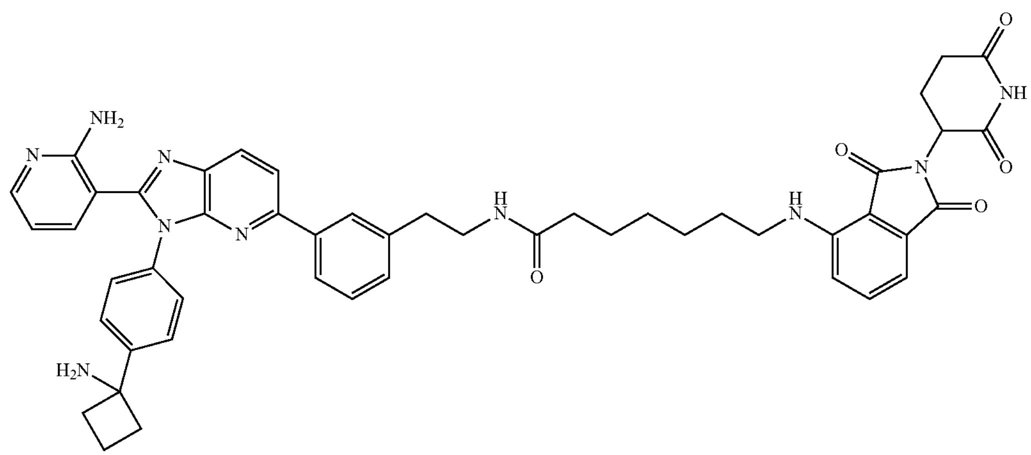 [SMILES: Nc1ncccc1-c1nc2ccc(-c3cccc(CCNC(=O)CCCCCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-7-((2-(2,6-dioxopiperidin-3-yl)-1,3-dioxoisoindolin-4-yl)amino)heptanamide |

TABLE 1-continued

| Compound ID | Structure | Chemical Name |
|---|---|---|
| XF067-54 | 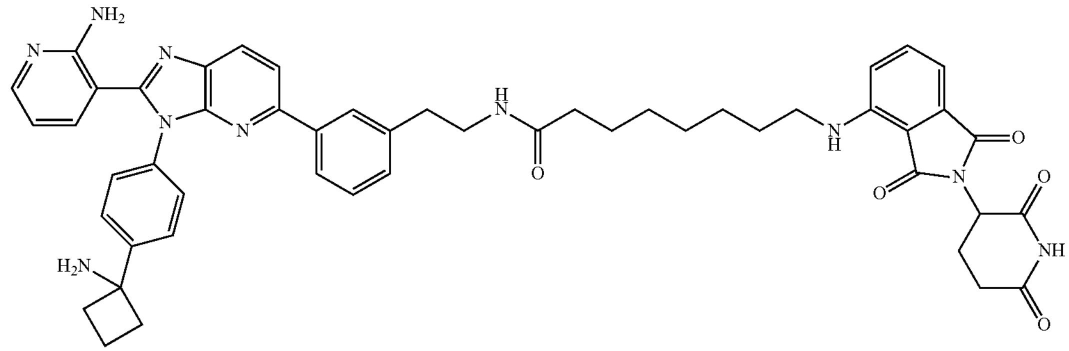 [SMILES: Nc1ncccc1-c1nc2ccc(-c3cccc(CCNC(=O)CCCCCCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-8-((2-(2,6-dioxopiperidin-3-yl)-1,3-dioxoisoindolin-4-yl)amino)octanamide |
| XF067-55 | 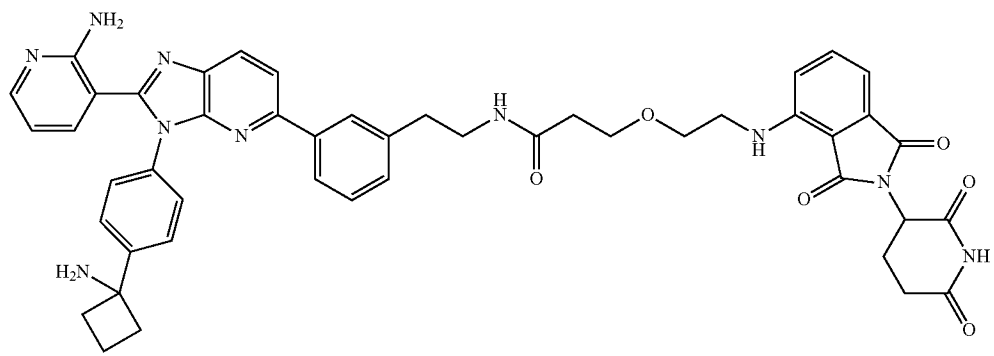 [SMILES: Nc1ncccc1-c1nc2ccc(-c3cccc(CCNC(=O)CCOCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-3-(2-((2-(2,6-dioxopiperidin-3-yl)-1,3-dioxoisoindolin-4-yl)amino)ethoxy)propanamide |

TABLE 1-continued

| Compound ID | Structure | Chemical Name |
|---|---|---|
| XF067-56 | 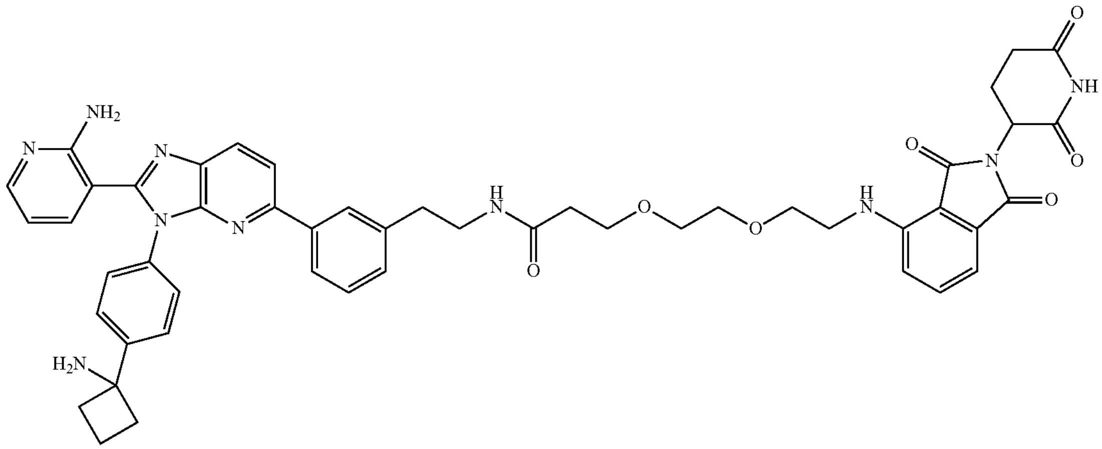 [SMILES: Nc1ncccc1-c1nc2ccc(-c3cccc(CCNC(=O)CCOCCOCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-3-(2-(2-((2-(2,6-dioxopiperidin-3-yl)-1,3-dioxoisoindolin-4-yl)amino)ethoxy)ethoxy)propanamid |
| XF067-57 | 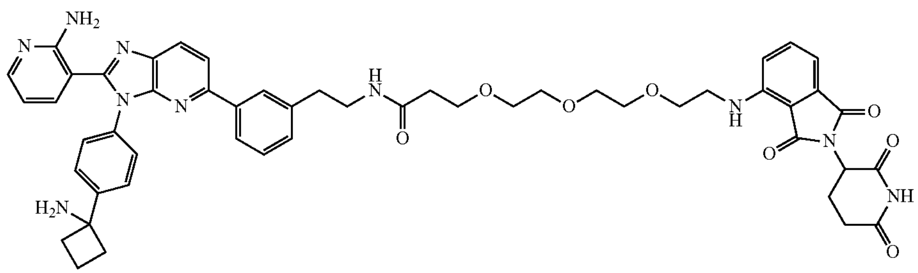 [SMILES: Nc1ncccc1-c1nc2ccc(-c3cccc(CCNC(=O)CCOCCOCCOCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-3-(2-(2-(2-((2-(2,6-dioxopiperidin-3-yl)-1,3-dioxoisoindolin-4-yl)amino)ethoxy)ethoxy)ethoxy)propanamide |
| XF067-58 | 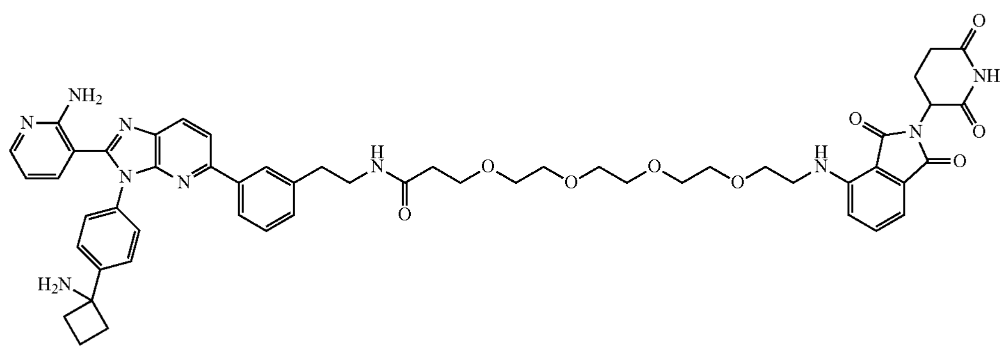 [SMILES: Nc1ncccc1-c1nc2ccc(-c3cccc(CCNC(=O)CCOCCOCCOCCOCCNc4cccc5c4C(=O)N(C4CCC(=O)NC4=O)C5=O)c3)nc2n1-c1ccc(C2(N)CCC2)cc1] | N-(3-(3-(4-(1-aminocyclobutyl)phenyl)-2-(2-aminopyridin-3-yl)-3H-imidazo[4,5-b]pyridin-5-yl)phenethyl)-1-((2-(2,6-dioxopiperidin-3-yl)-1,3-dioxoisoindolin-4-yl)amino)-3,6,9,12-tetraoxapentadecan-15-amide |

| Compound ID | Structure | Chemical Name |
|---|---|---|
| XF067-59 | 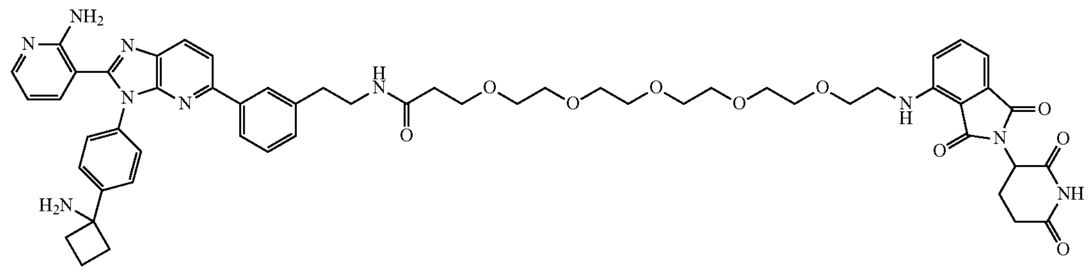 [SMILES: Nc1ncccc1-c1nc2ccc(-c3cccc(CCNC(=O)CCOCCOCCOCCOCCOCCNc4cccc5c4C(=O)N(C4CCC(=O)NC4=O)C5=O)c3)nc2n1-c1ccc(C2(N)CCC2)cc1] | N-(3-(4-(1-aminocyclobutyl)phenyl)-2-(2-aminopyridin-3-yl)-3H-imidazo[4,5-b]pyridin-5-yl)phenethyl)-1-((2-(2,6-dioxopiperidin-3-yl)-1,3-dioxoisoindolin-4-yl)amino)-3,6,9,12,15-pentaoxaoctadecan-18-amide |
| XF067-84 | 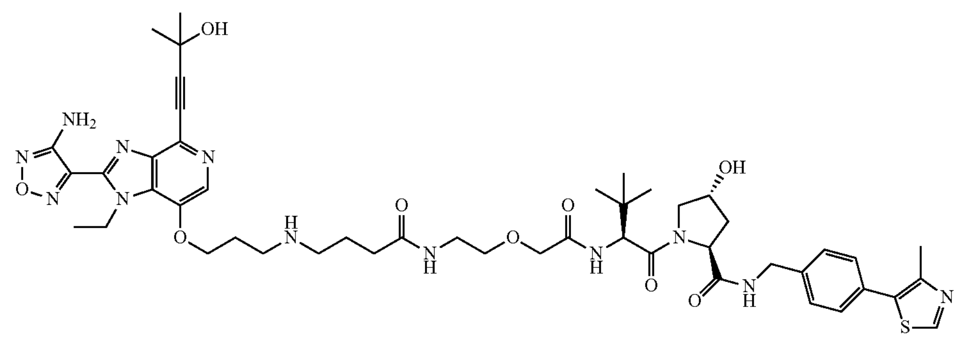 [SMILES: CCn1c(-c2nonc2N)nc2c(C#CC(C)(C)O)ncc(OCCCNCCCC(=O)NCCOCC(=O)N[C@H](C(=O)N3C[C@H](O)C[C@H]3C(=O)NCc3ccc(-c4scnc4C)cc3)C(C)(C)C)c21] | (2S,4R)-1-((S)-17-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,10-dioxo-6-oxa-3,9,14-triazaheptadecanoyl)-4-hydroxy-N-(4-(4-methylthiazol-5-yl)benzyl)pyrrolidine-2-carboxamide |
| XF067-85 | 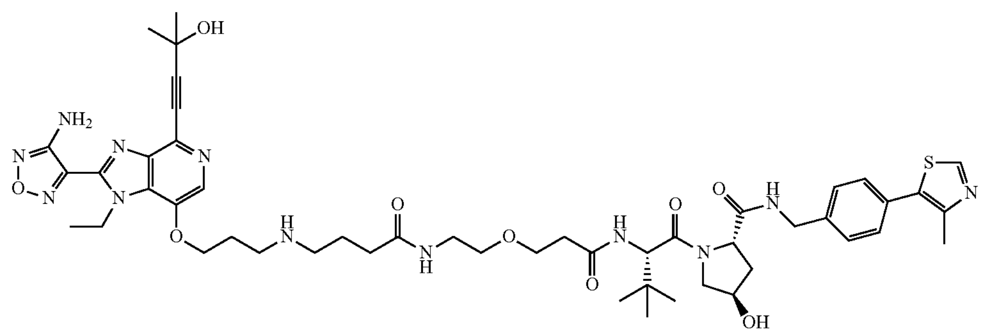 [SMILES: CCn1c(-c2nonc2N)nc2c(C#CC(C)(C)O)ncc(OCCCNCCCC(=O)NCCOCCC(=O)N[C@H](C(=O)N3C[C@H](O)C[C@H]3C(=O)NCc3ccc(-c4scnc4C)cc3)C(C)(C)C)c21] | (2S,4R)-1-((S)-18-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,11-dioxo-7-oxa-3,10,15-triazaoctadecanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-86 | 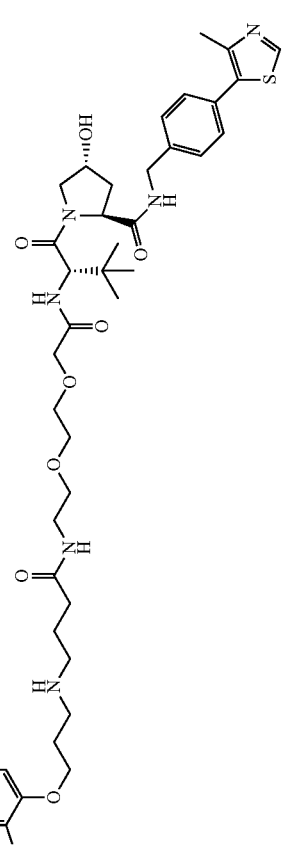 | (2S,4R)-1-((S)-20-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,13-dioxo-6,9-dioxa-3,12,17-triazaicosanoyl)-4-hydroxy-N-(4-(4-methylthiazol-5-yl)benzyl)pyrrolidine-2-carboxamide |
| XF067-87 | 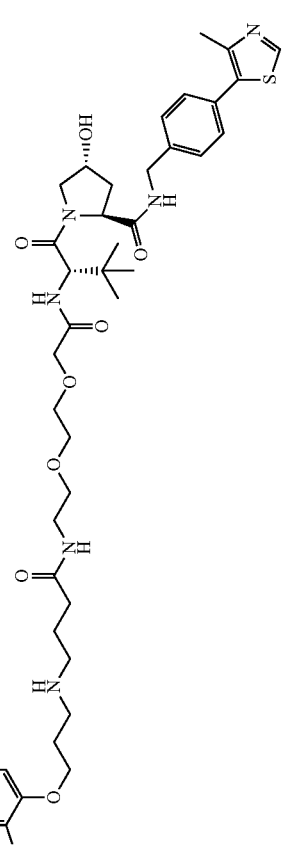 | (2S,4R)-1-((S)-21-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,14-dioxo-7,10-dioxa-3,13,18-triazahenicosanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-88 | 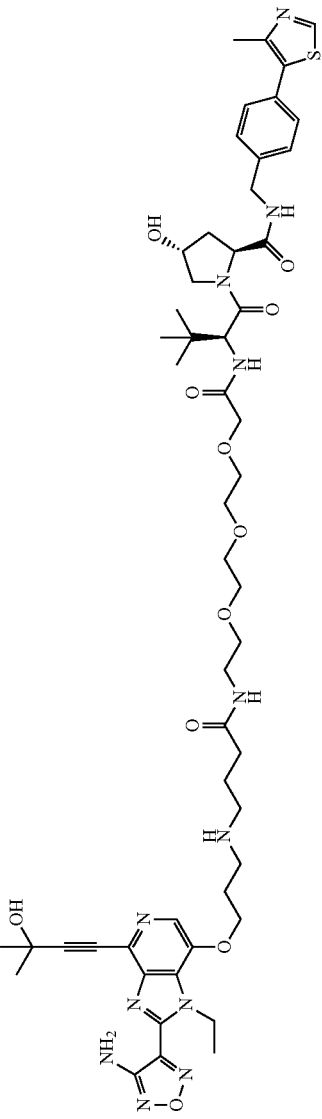 | (2S,4R)-1-((S)-23-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,16-dioxo-6,9,12-trioxa-3,15,20-triazatricosanoyl)-4-hydroxy-N-(4-(4-methylthiazol-5-yl)benzyl)pyrrolidine-2-carboxamide |
| XF067-89 | 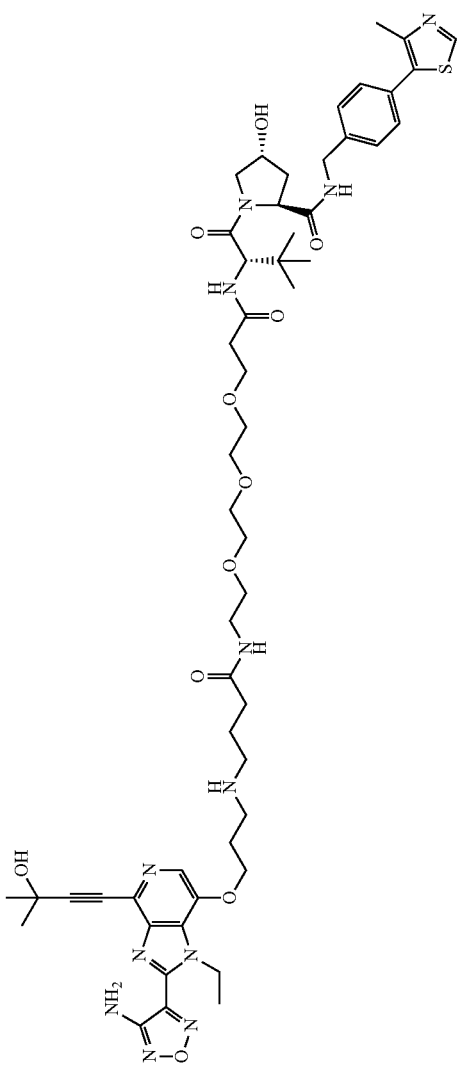 | (2S,4R)-1-((S)-24-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,17-dioxo-7,10,13-trioxa-3,16,21-triazatetracosanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-90 | 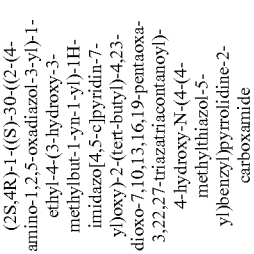 | (2S,4R)-1-((S)-27-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,20-dioxo-7,10,13,16-tetraoxa-3,19,24-triazaheptacosanoyl)-4-hydroxy-N-(4-(4-methylthiazol-5-yl)benzyl)pyrrolidine-2-carboxamide |
| XF067-91 | 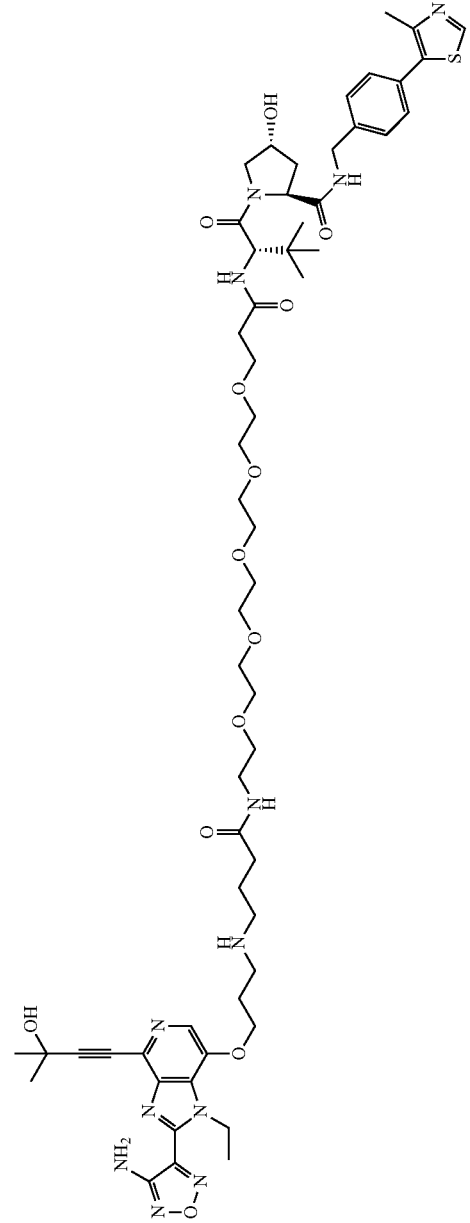 | (2S,4R)-1-((S)-30-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)-2-(tert-butyl)-4,23-dioxo-7,10,13,16,19-pentaoxa-3,22,27-triazatriacontanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-92 | 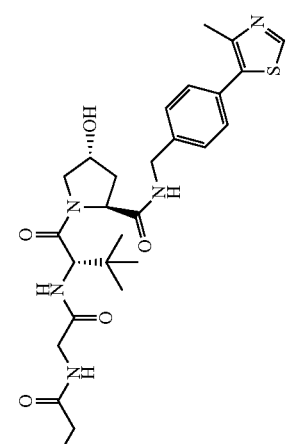 | (2S,4R)-1-((S)-2-(2-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)acetamido)-3,3-dimethylbutanoyl)-4-hydroxy-N-(4-(4-methylthiazol-5-yl)benzyl)pyrrolidine-2-carboxamide |
| XF067-93 | 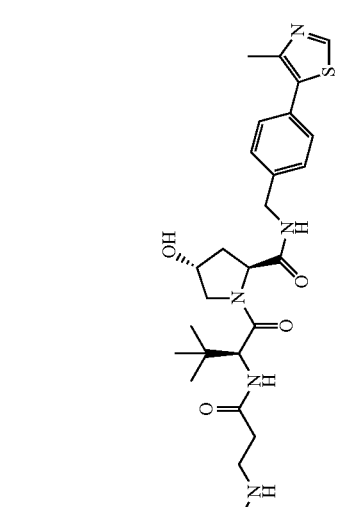 | (2S,4R)-1-((S)-2-(3-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)propanamido)-3,3-dimethylbutanoyl)-4-hydroxy-N-(4-(4-methylthiazol-5-yl)benzyl)pyrrolidine-2-carboxamide |

| Compound ID | Structure | Chemical Name |
|---|---|---|
| XF067-94 | 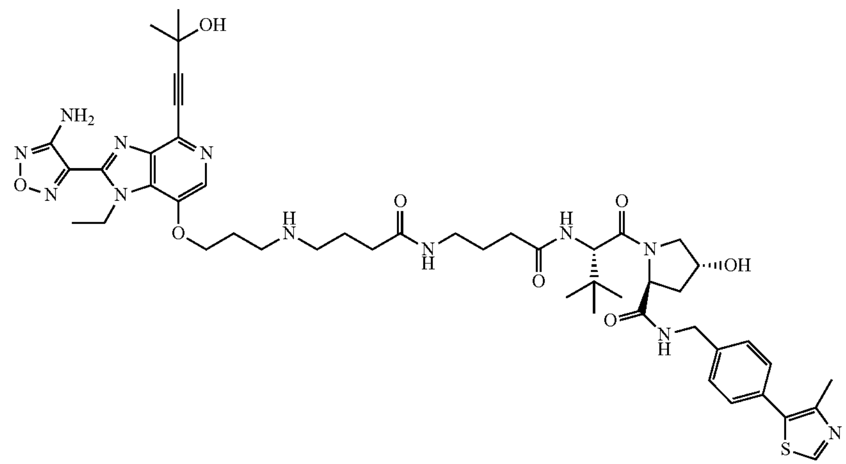 [SMILES: CCn1c(-c2nonc2N)nc2c(C#CC(C)(C)O)ncc(OCCCNCCCC(=O)NCCCC(=O)N[C@H](C(=O)N3C[C@H](O)C[C@H]3C(=O)NCc3ccc(-c4scnc4C)cc3)C(C)(C)C)c21] | (2S,4R)-1-((S)-2-(4-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)butanoyl)-3,3-dimethylbutanoyl)-4-hydroxy-N-(4-(4-methylthiazol-5-yl)benzyl)pyrrolidine-2-carboxamide |
| XF067-95 | 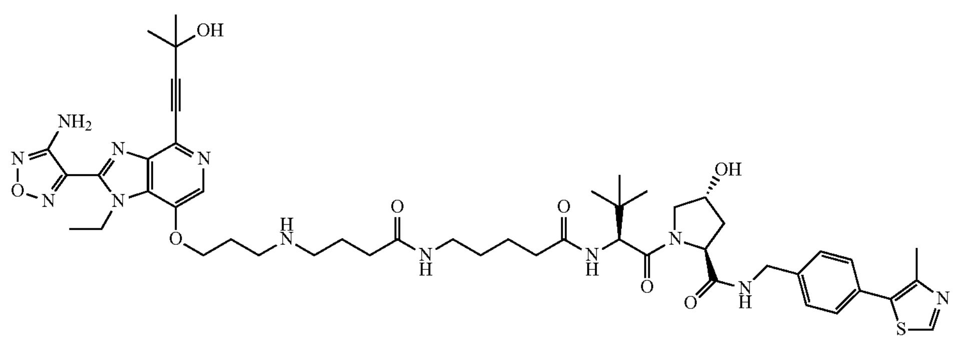 [SMILES: CCn1c(-c2nonc2N)nc2c(C#CC(C)(C)O)ncc(OCCCNCCCC(=O)NCCCCC(=O)N[C@H](C(=O)N3C[C@H](O)C[C@H]3C(=O)NCc3ccc(-c4scnc4C)cc3)C(C)(C)C)c21] | (2S,4R)-1-((S)-2-(5-(4-((3-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)pentanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-96 | 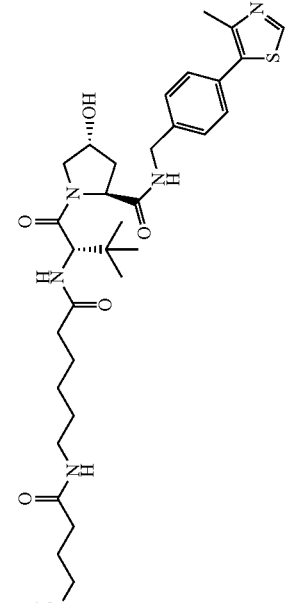 | (2S,4R)-1-((S)-2-(6-(4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)hexanamido)-3,3-dimethylbutanoyl)-4-hydroxy-N-(4-(4-methylthiazol-5-yl)benzyl)pyrrolidine-2-carboxamide |
| XF067-97 | 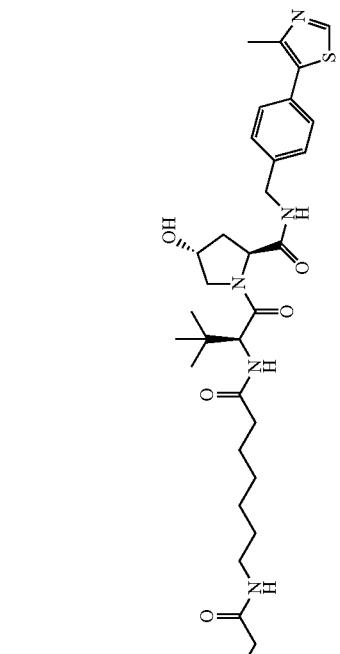 | (2S,4R)-1-((S)-2-(7-(4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)heptanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-98 | 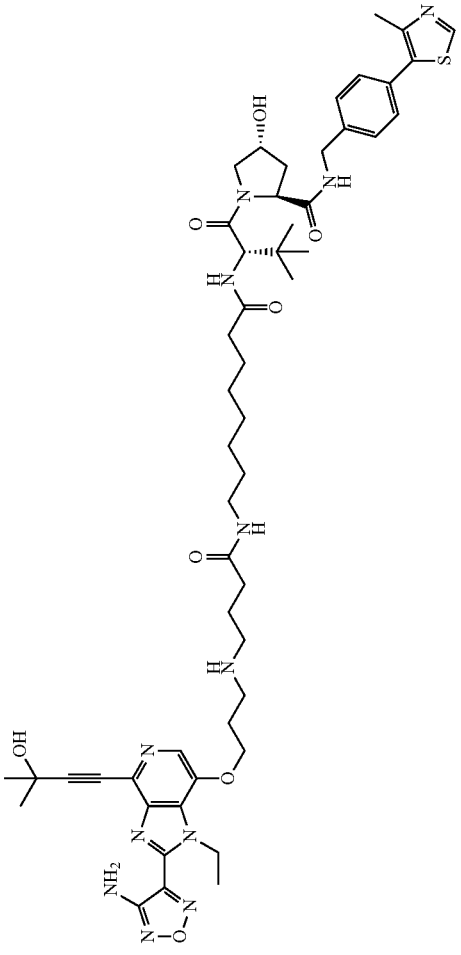 | (2S,4R)-1-((S)-2-(8-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)octanamido)-3,3-dimethylbutanoyl)-4-hydroxy-N-(4-(4-methylthiazol-5-yl)benzyl)pyrrolidine-2-carboxamide |
| XF067-99 | 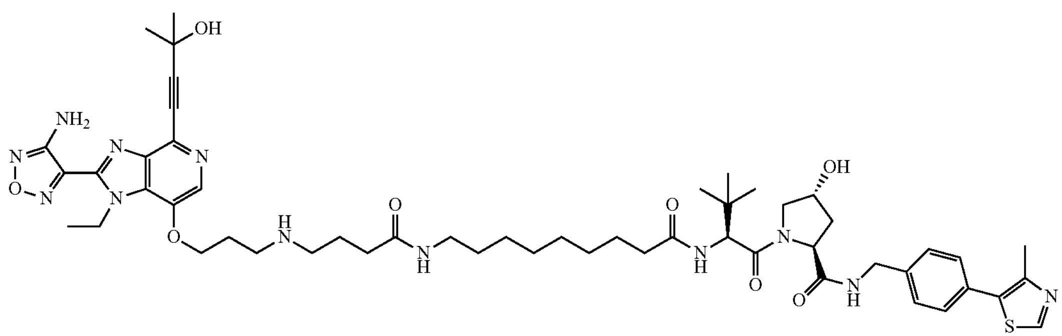 | (2S,4R)-1-((S)-2-(9-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)nonanamido)-3,3-dimethylbutanoyl)-4-hydroxy-N-(4-(4-methylthiazol-5-yl)benzyl)pyrrolidine-2-carboxamide |

| Compound ID | Structure | Chemical Name |
|---|---|---|
| XF067-100 | 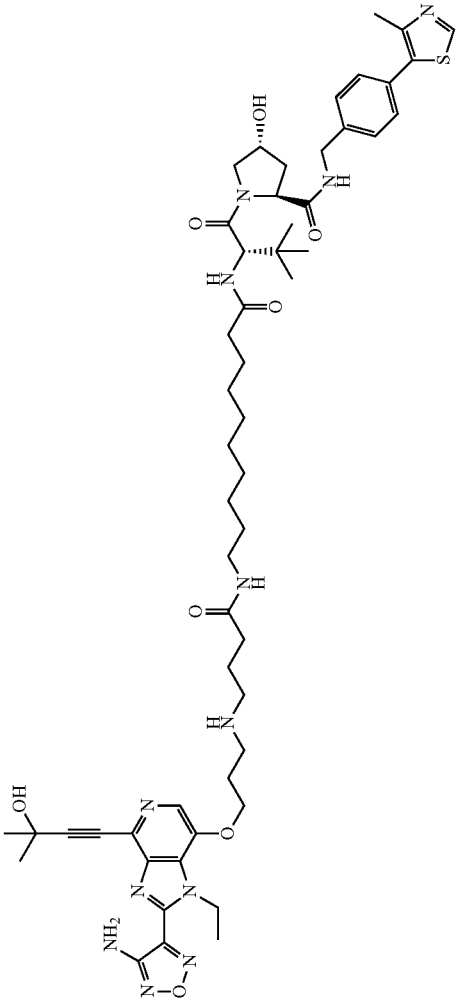 | (2S,4R)-1-((S)-2-(10-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)decanamido)-3,3-dimethylbutanoyl)-4-hydroxy-N-(4-(4-methylthiazol-5-yl)benzyl)pyrrolidine-2-carboxamide |
| XF067-101 | 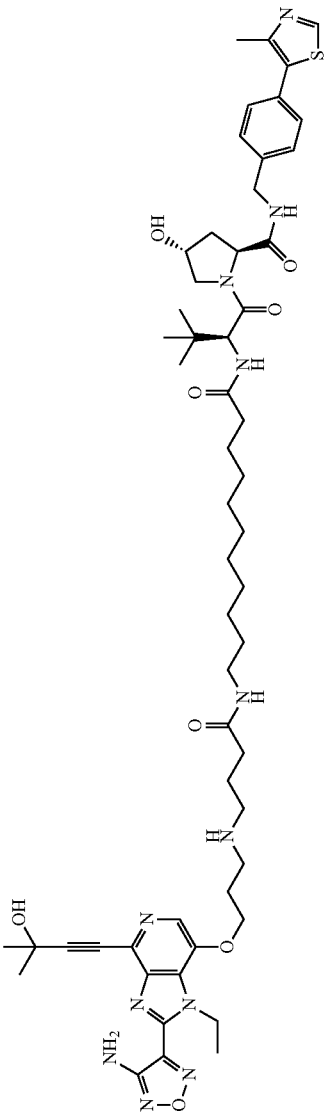 | (2S,4R)-1-((S)-2-(11-(4-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)butanamido)undecanamido)-3,3-dimethylbutanoyl)-4-hydroxy-N-(4-(4-methylthiazol-5-yl)benzyl)pyrrolidine-2-carboxamide |

TABLE 1-continued

| Compound ID | Structure | Chemical Name |
|---|---|---|
| XF067-102 | 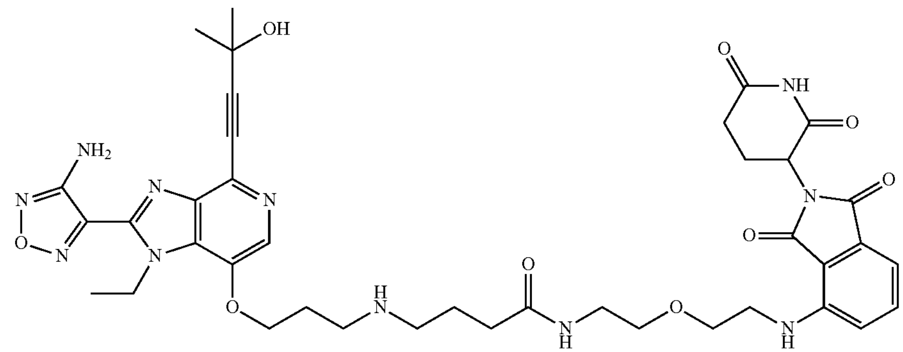 [SMILES: CCn1c(-c2nonc2N)nc2c(C#CC(C)(C)O)ncc(OCCCNCCCC(=O)NCCOCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(2-(2-((2,6-dioxopiperidin-3-yl)-1,3-dioxoisoindolin-4-yl)amino)ethoxy)ethyl)butanamide |
| XF067-103 | 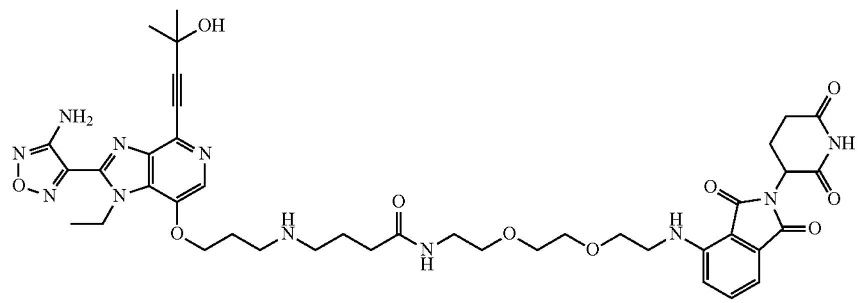 [SMILES: CCn1c(-c2nonc2N)nc2c(C#CC(C)(C)O)ncc(OCCCNCCCC(=O)NCCOCCOCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(2-(2-((2-(2,6-dioxopiperidin-3-yl)-1,3-dioxoisoindolin-4-yl)amino)ethoxy)ethoxy)ethyl)butanamide |
| XF067-104 | 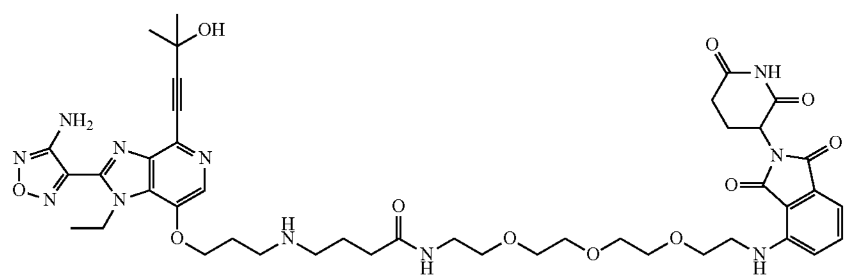 [SMILES: CCn1c(-c2nonc2N)nc2c(C#CC(C)(C)O)ncc(OCCCNCCCC(=O)NCCOCCOCCOCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(2-(2-((2-(2,6-dioxopiperidin-3-yl)-1,3-dioxoisoindolin-4-yl)amino)ethoxy)ethoxy)ethyl)butanamide |

TABLE 1-continued

| Compound ID | Structure | Chemical Name |
|---|---|---|
| XF067-105 | 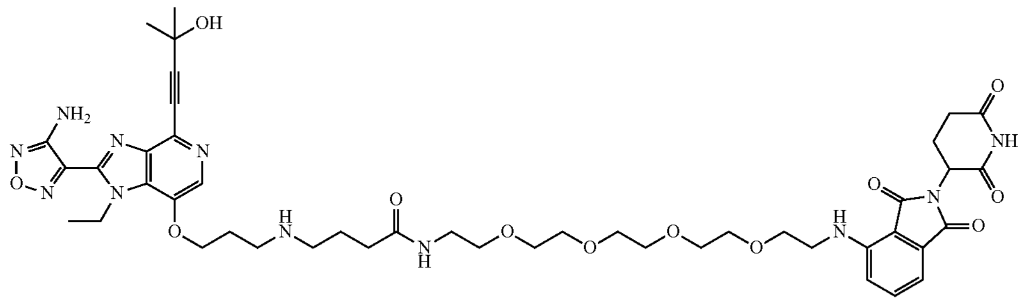 [SMILES: CCn1c(-c2nonc2N)nc2c(C#CC(C)(C)O)ncc(OCCCNCCCC(=O)NCCOCCOCCOCCOCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(14-((2-(2,6-dioxopiperidin-3-yl)-1,3-dioxoisoindolin-4-yl)amino)-3,6,9,12-tetraoxatetradecyl)butanamide |
| XF067-106 | 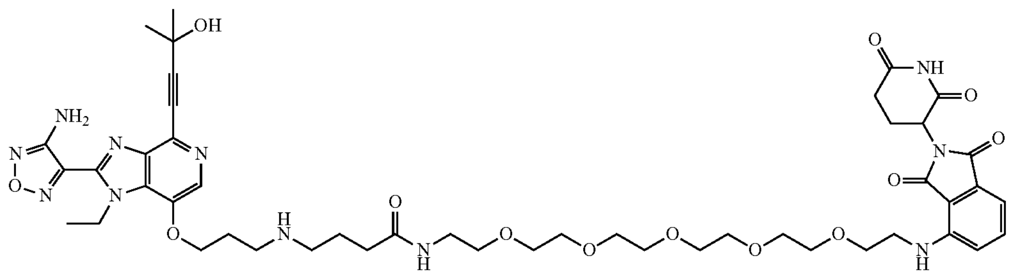 [SMILES: CCn1c(-c2nonc2N)nc2c(C#CC(C)(C)O)ncc(OCCCNCCCC(=O)NCCOCCOCCOCCOCCOCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(17-((2-(2,6-dioxopiperidin-3-yl)-1,3-dioxoisoindolin-4-yl)amino)-3,6,9,12,15-pentaoxaheptadecyl)butanamide |
| XF067-107 | 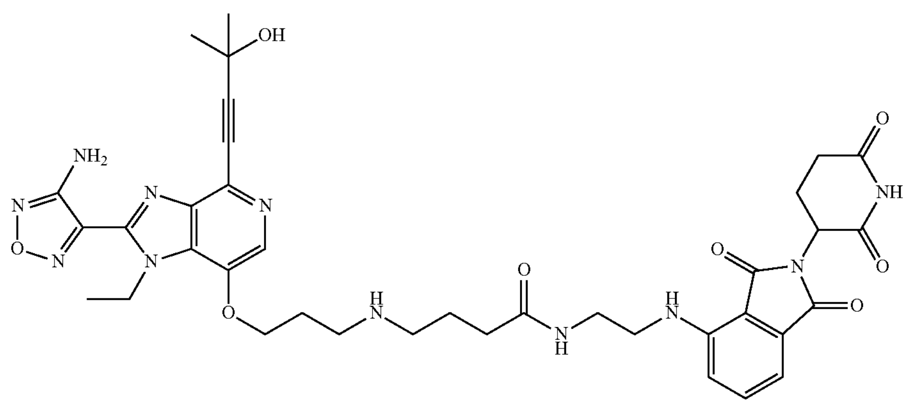 [SMILES: CCn1c(-c2nonc2N)nc2c(C#CC(C)(C)O)ncc(OCCCNCCCC(=O)NCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(2-((2-(2,6-dioxopiperidin-3-yl)-1,3-dioxoisoindolin-4-yl)amino)ethyl)butanamide |

| Compound ID | Structure | Chemical Name |
|---|---|---|
| XF067-108 | 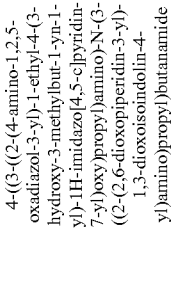 | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(3-((2-(2,6-dioxopiperidin-3-yl)-1,3-dioxoisoindolin-4-yl)amino)propyl)butanamide |
| XF067-109 | 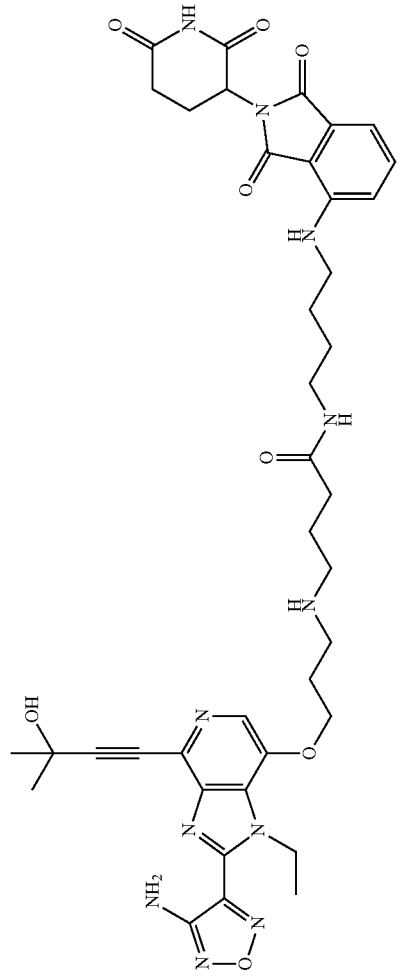 | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino-N-(4-((2-(2,6-dioxopiperidin-3-yl)-1,3-dioxoisoindolin-4-yl)amino)butyl)butanamide |

TABLE 1-continued

| Compound ID | Structure | Chemical Name |
|---|---|---|
| XF067-110 | 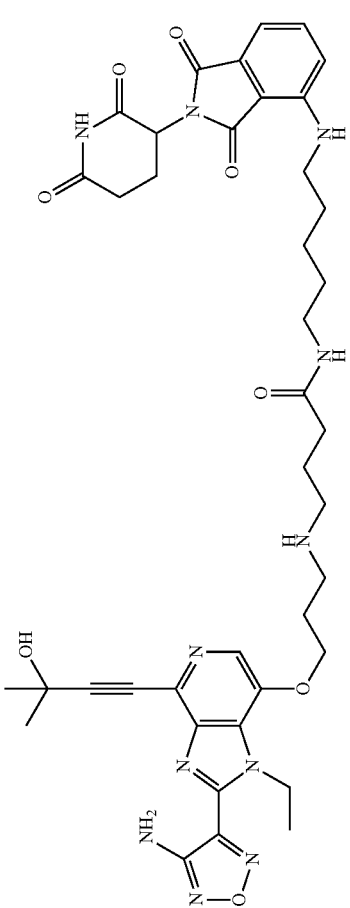 | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(5-((2-(2,6-dioxopiperidin-3-yl)-1,3-dioxoisoindolin-4-yl)amino)pentyl)butanamide |
| XF067-111 | 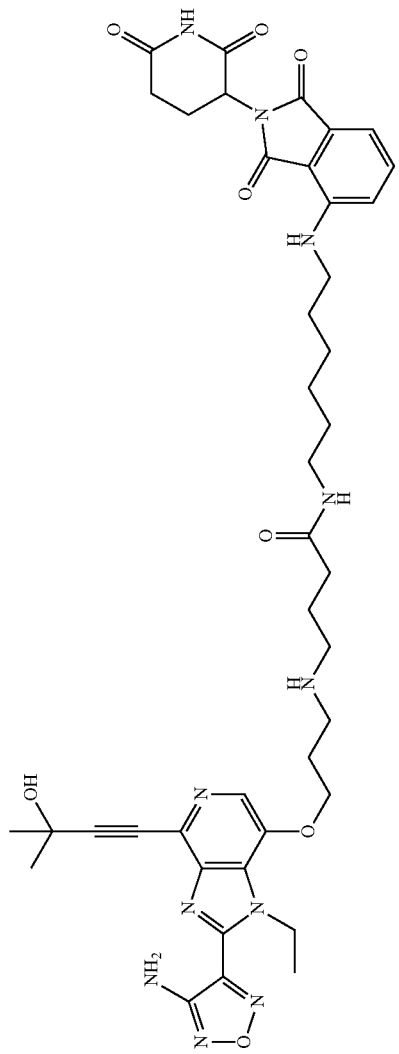 | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(6-((2-(2,6-dioxopiperidin-3-yl)-1,3-dioxoisoindolin-4-yl)amino)hexyl)butanamide |

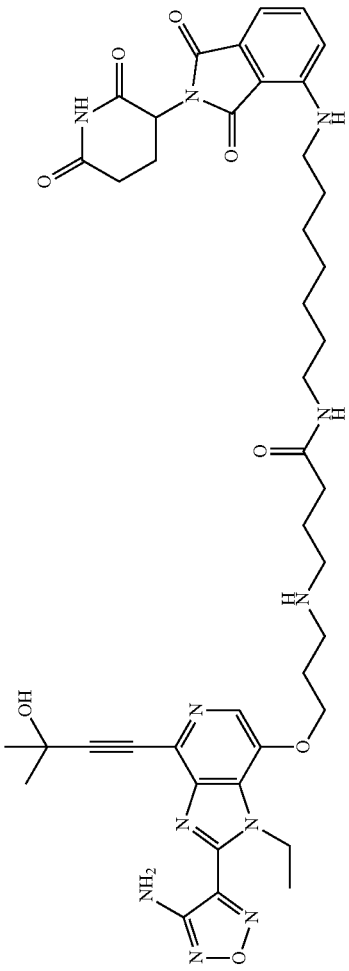

TABLE 1-continued

| Compound ID | Structure | Chemical Name |
|---|---|---|
| XF067-112 | 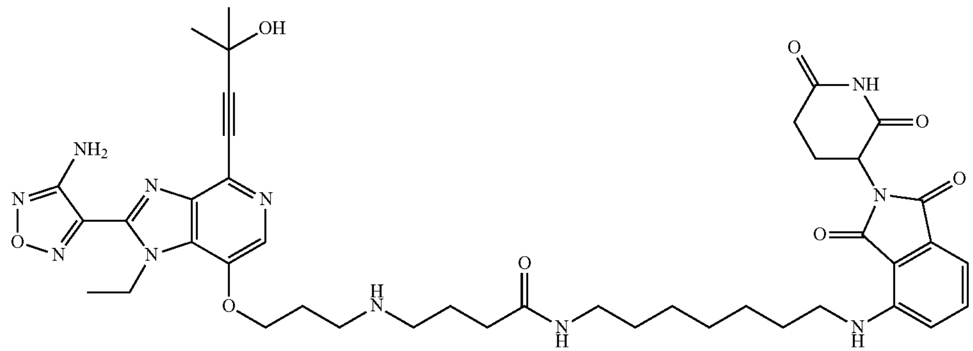 [SMILES: CCn1c(-c2nonc2N)nc2c(C#CC(C)(C)O)ncc(OCCCNCCCC(=O)NCCCCCCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(7-((2-(2,6-dioxopiperidin-3-yl)-1,3-dioxoisoindolin-4-yl)amino)heptyl)butanamide |
| XF067-113 | 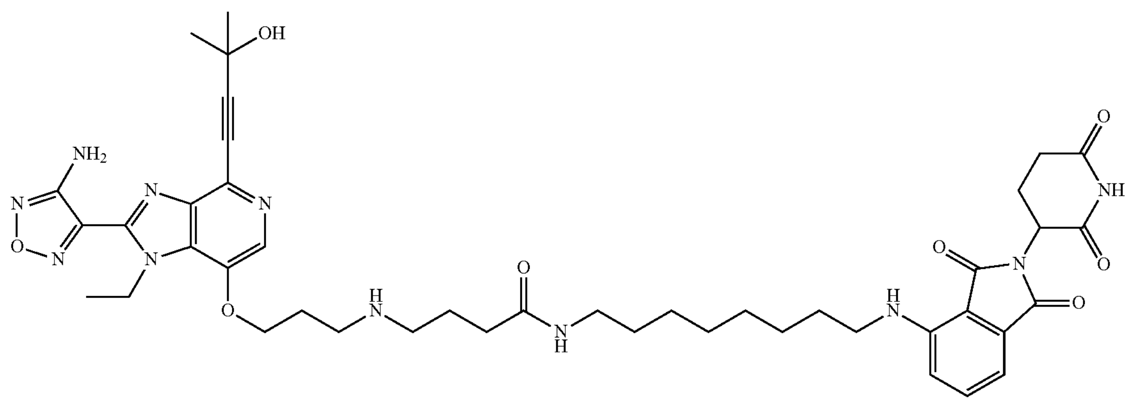 [SMILES: CCn1c(-c2nonc2N)nc2c(C#CC(C)(C)O)ncc(OCCCNCCCC(=O)NCCCCCCCCNc3cccc4c3C(=O)N(C3CCC(=O)NC3=O)C4=O)c21] | 4-((3-((2-(4-amino-1,2,5-oxadiazol-3-yl)-1-ethyl-4-(3-hydroxy-3-methylbut-1-yn-1-yl)-1H-imidazo[4,5-c]pyridin-7-yl)oxy)propyl)amino)-N-(8-((2-(2,6-dioxopiperidin-3-yl)-1,3-dioxoisoindolin-4-yl)amino)octyl)butanamide |

As used herein, in case of discrepancy between the structure and chemical name provided for a particular compound, the structure shall control.

Example 167. AKT Degraders Reduced AKT Protein Levels in BT474 Cells (FIG. 1)

BT474 cells were treated with DMSO or indicated compounds at 1 µM, 5 µM, or 10 µM for 24 h. The Western blot results showed that various AKT degraders significantly reduced AKT protein levels at 1 µM, while the AKT activity inhibitor GDC0068 had no effect on AKT protein levels but increased pAKT levels.

Example 168. AKT Degraders Reduced AKT Protein Levels in BT474 Cells in a Time-Dependent Manner (FIG. 2)

BT474 cells were treated with DMSO or the indicated compounds at a fixed concentration of 1 µM for 1, 2, 3, 6, 12, or 24 h. The maximum degradation of AKT and inhibition of downstream signaling were observed after 12 h of treatment.

Example 169. AKT Degraders Reduced AKT Protein Levels in BT474 Cells (FIG. 3)

BT474 cells were treated with DMSO or indicated compounds at 1 µM, 5 µM, or 10 µM for 24 h. The Western blot results showed that various AKT degraders significantly reduced AKT protein levels at 1 µM, while the AKT activity inhibitor AZD5363 had no effect on AKT protein levels but increased pAKT levels.

Example 170. AKT Degraders Reduced AKT Protein Levels in BT474 Cells (FIG. 4)

Figure 4A:
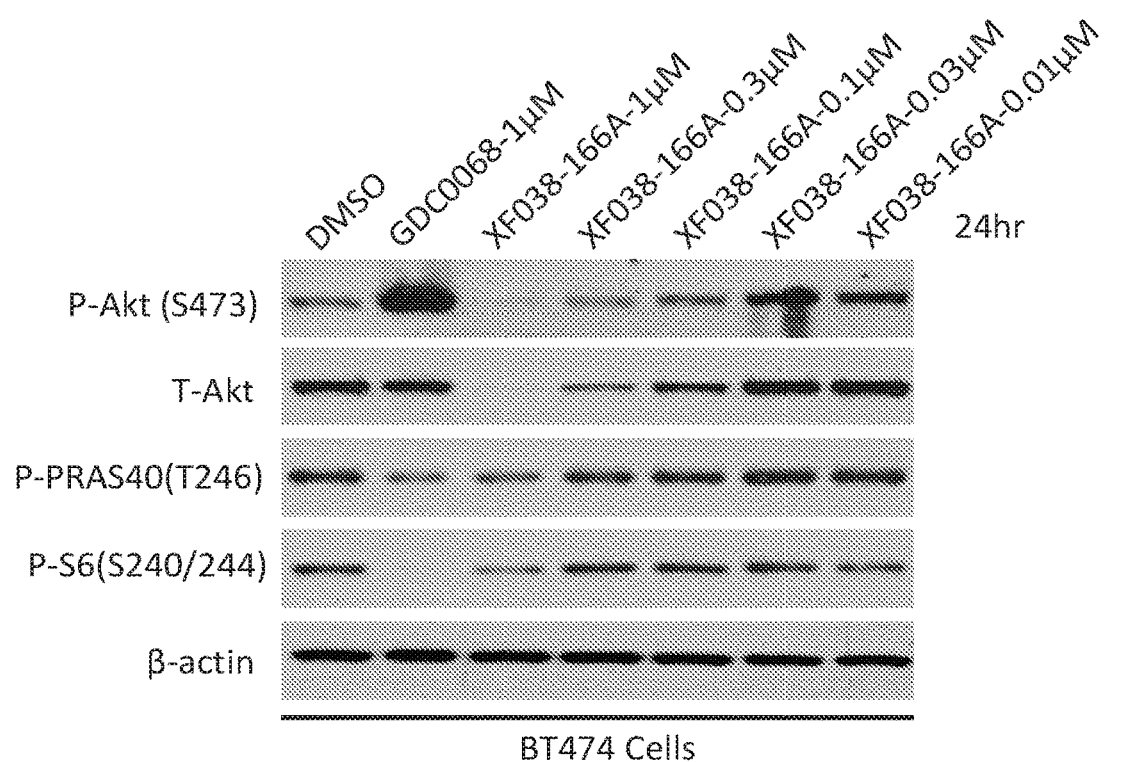
FIG. 4A is a series of Western blots showing the effect of selected AKT degraders on reducing AKT, p-AKT, P-PRAS40 (T246), and P-S6 (S240/244) protein levels at various concentrations in BT474 cells.
Figure 1:
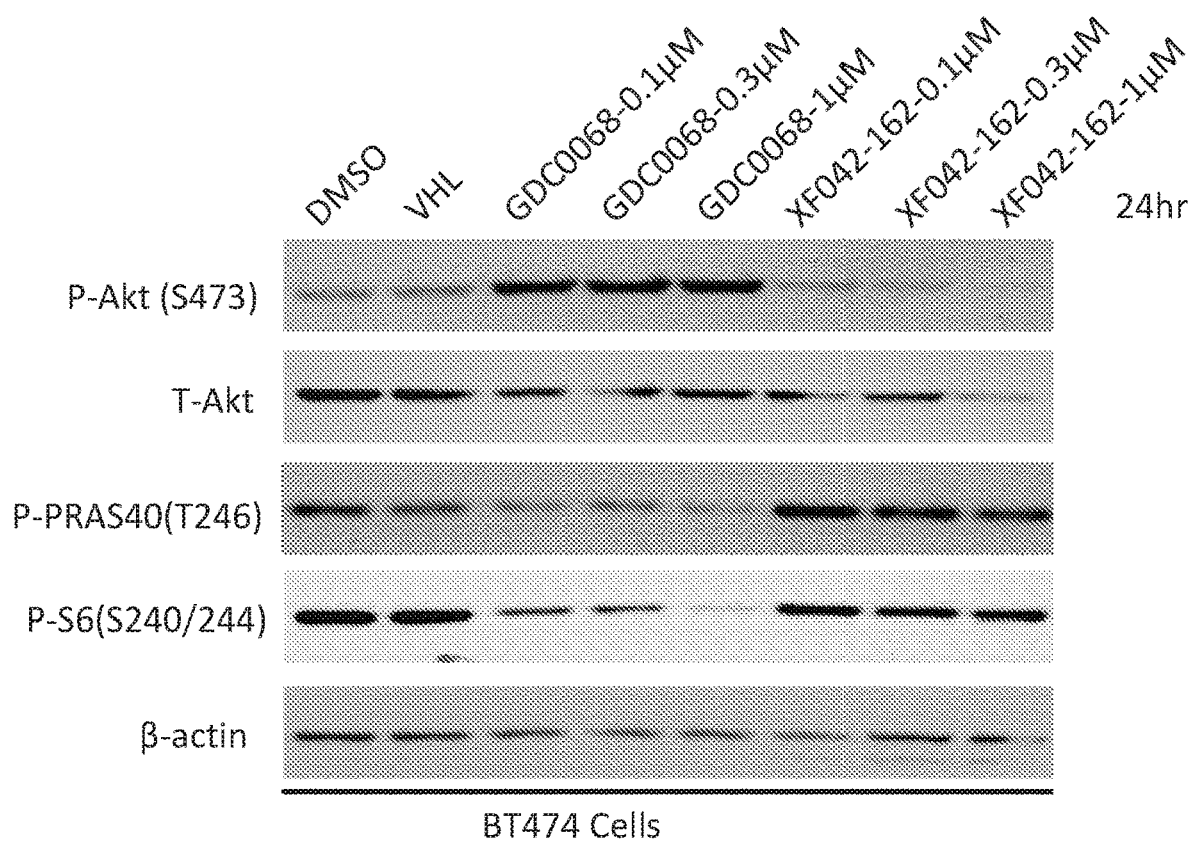
Figure 4A:
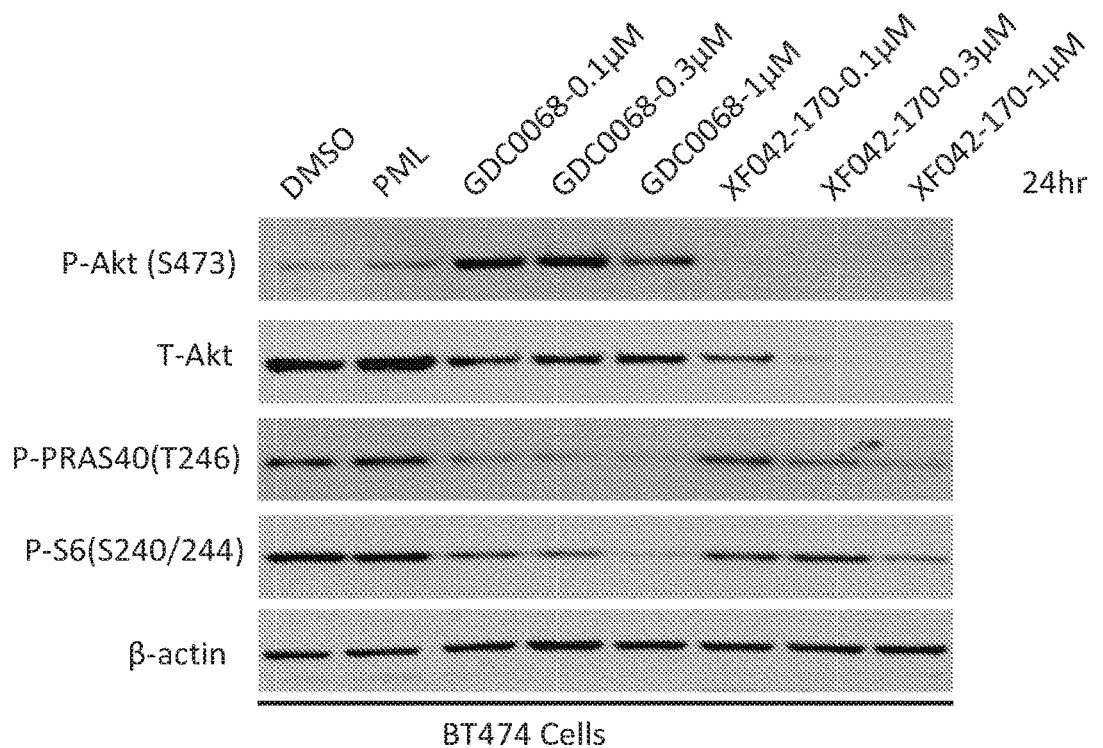
Figure 2:
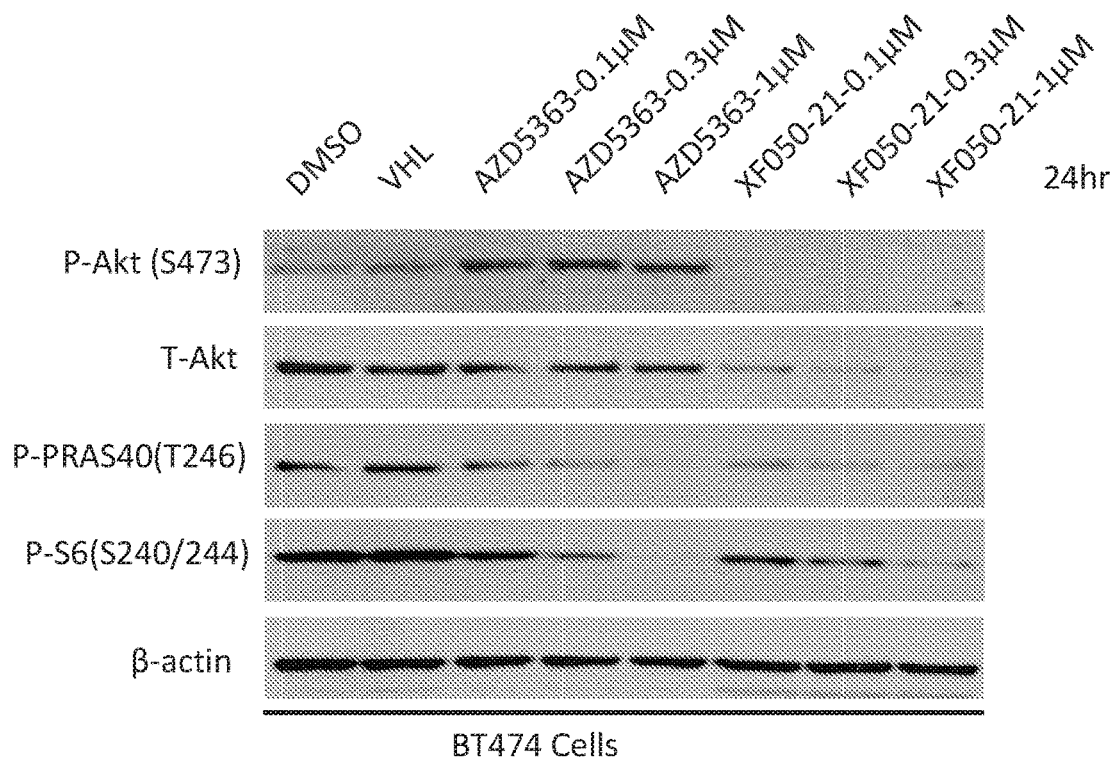
Figures 3, 4A:
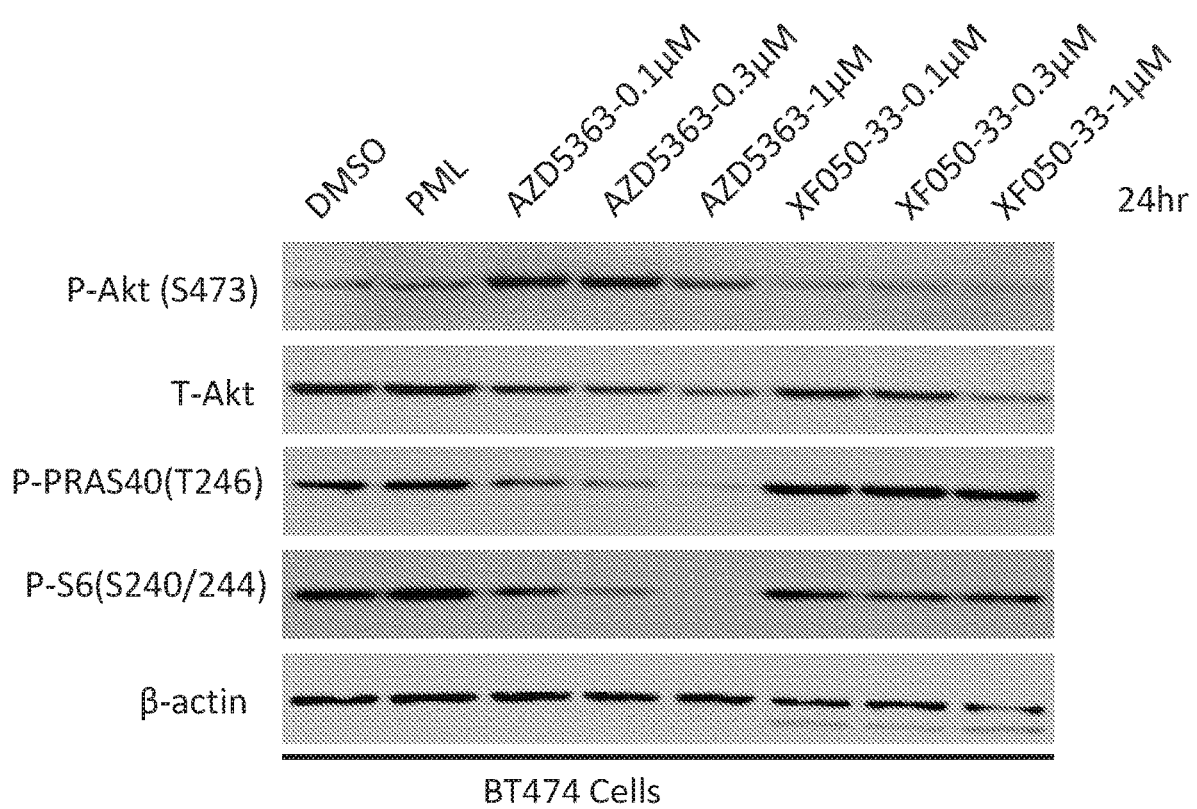
Figures 1, 4B:
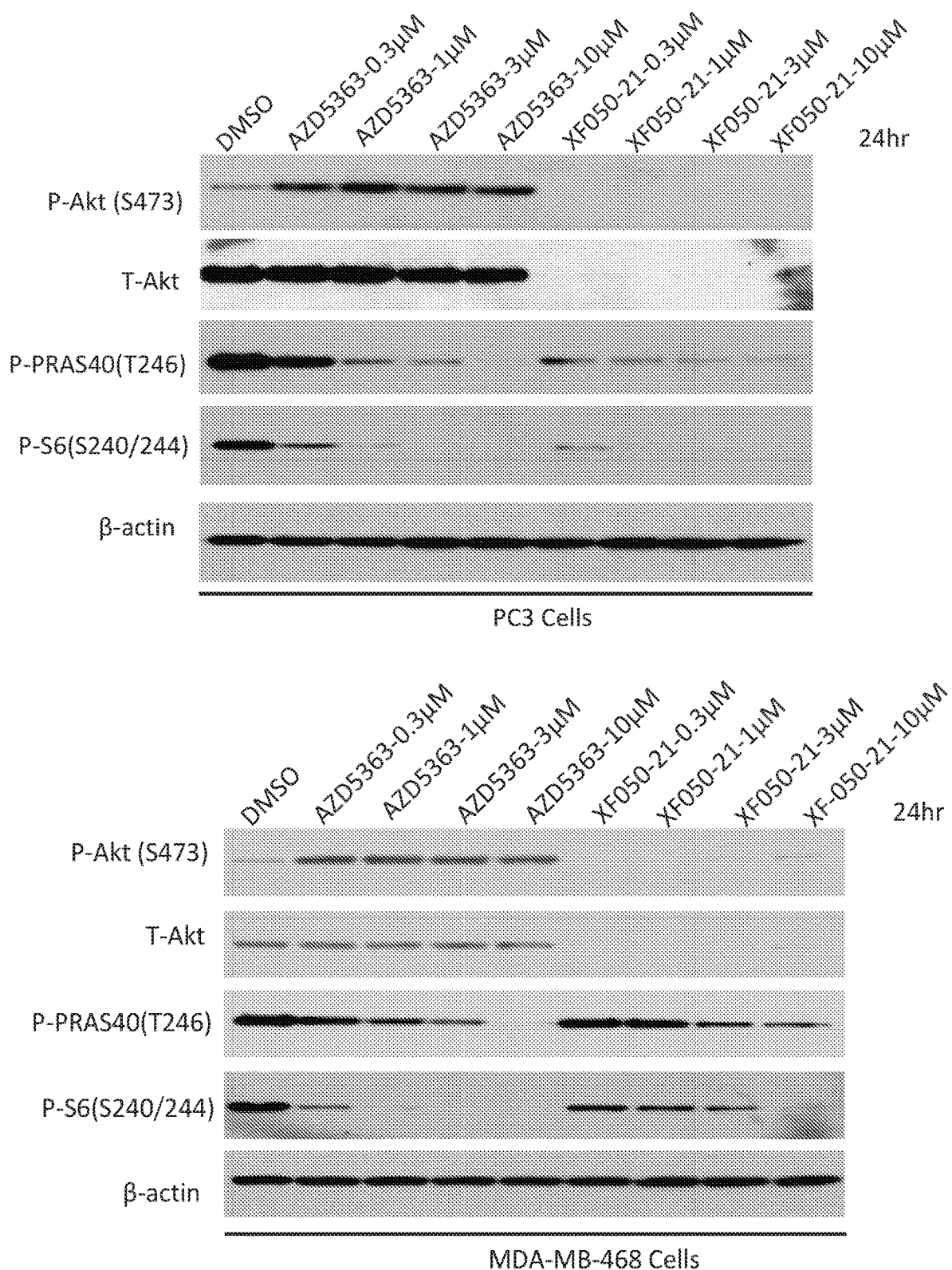
FIG. 4B is a series of Western blots showing the effect of XF050-21 on reducing AKT, p-AKT, P-PRAS40 (T246), and P-S6 (S240/244) protein levels at various concentrations in PC-3, MDA-MB-468, and U87MG cells.
Figures 2, 4B:
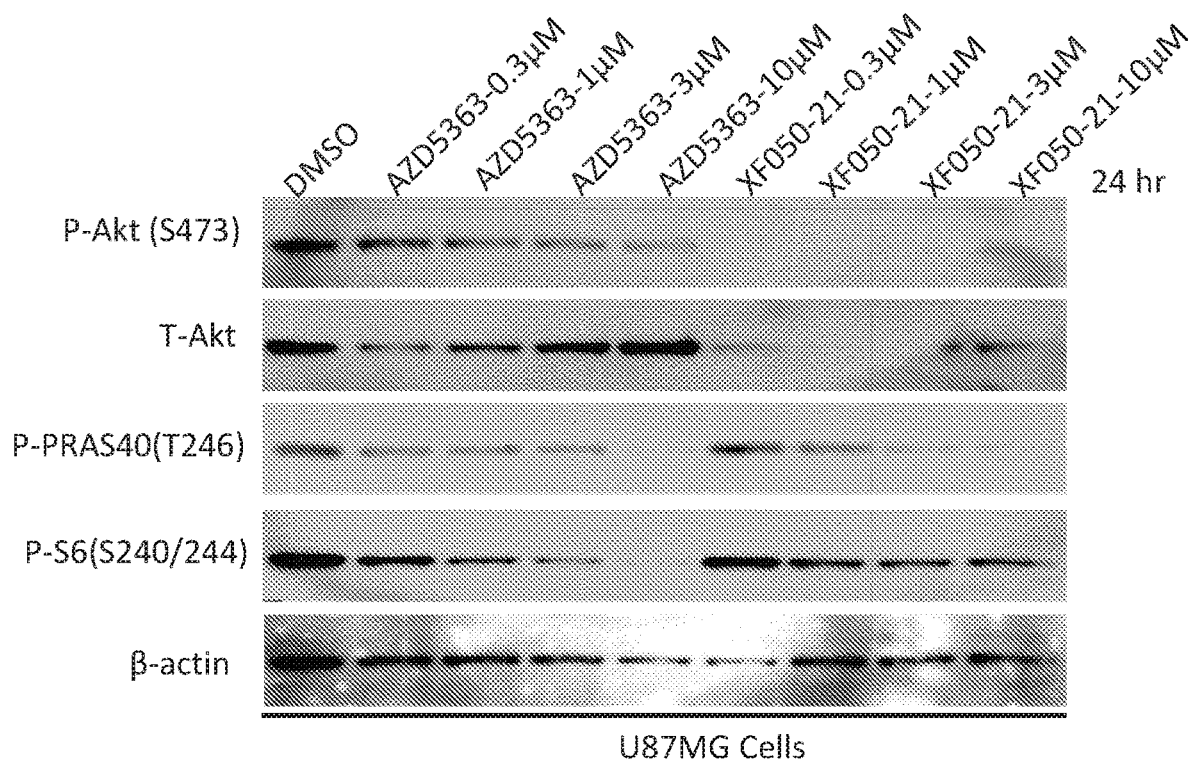

BT474 cells were treated with DMSO or indicated compounds at 0.01 µM, 0.03 µM, 0.1 µM, 0.3 µM, or 1 µM for 24 h. The Western blot results showed that various AKT degraders significantly reduced AKT protein levels at 1 µM, while the AKT activity inhibitor AZD5363 or GDC0068 had no effect on AKT protein levels but increased pAKT levels (FIG. 4A). PC-3 cells, MDA-MB-468 cells, U87MG cells were treated with DMSO or indicated compounds at 0.3 µM, 1 µM, 3 µM, or 10 µM for 24 h. The Western blot results showed that AKT degrader XF050-21 significantly reduced AKT protein levels in these cell lines, while the AKT activity inhibitor AZD5363 had no effect on AKT protein levels but increased pAKT levels (FIG. 4B).

Example 171. AKT Degraders Reduced AKT Protein Levels in BT474 Cells and PC-3 Cells in a Time-Dependent Manner (FIG. 5)

Figure 5A:
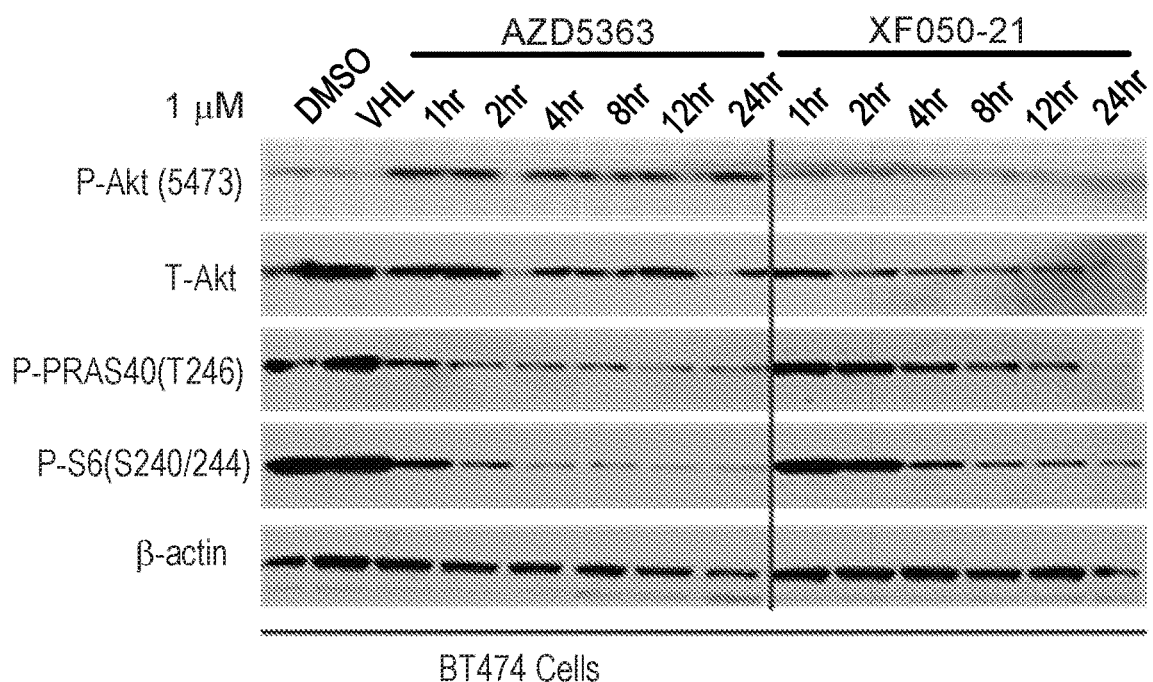
FIG. 5A is a series of Western blots showing that XF050-21, XF050-33, XF042-162 and XF042-170 time-dependently reduce AKT, p-AKT, P-PRAS40 (T246), and P-S6 (S240/244) protein levels in BT474 cells.
Figure 1:
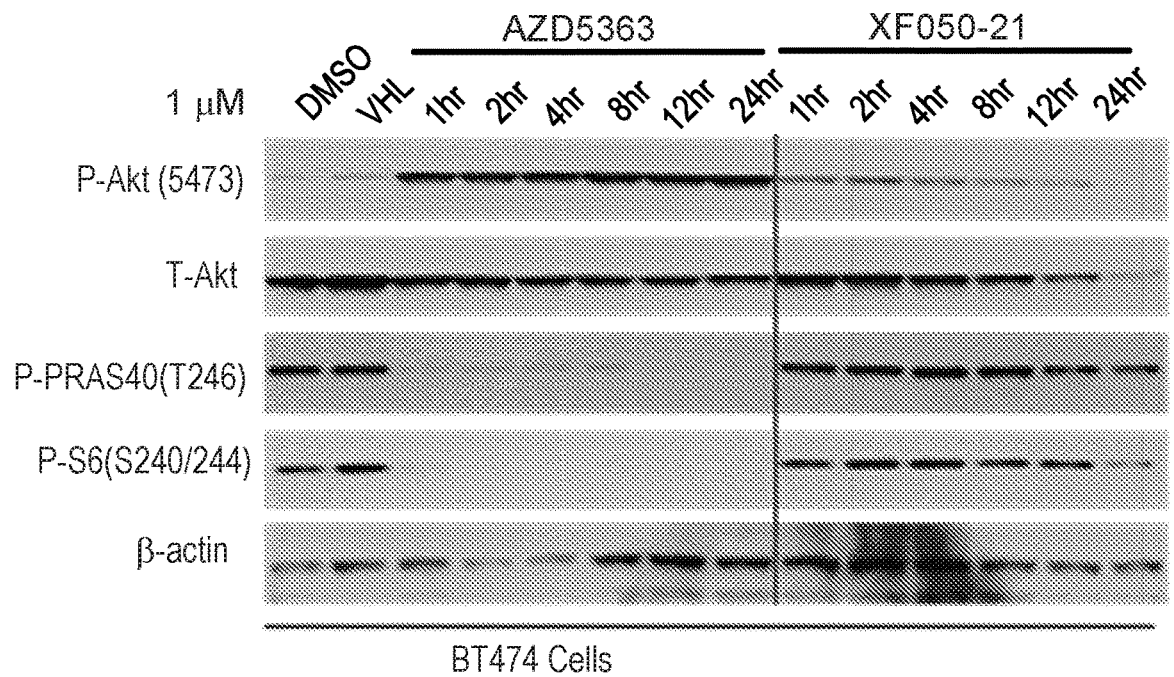
Figures 2, 5A:
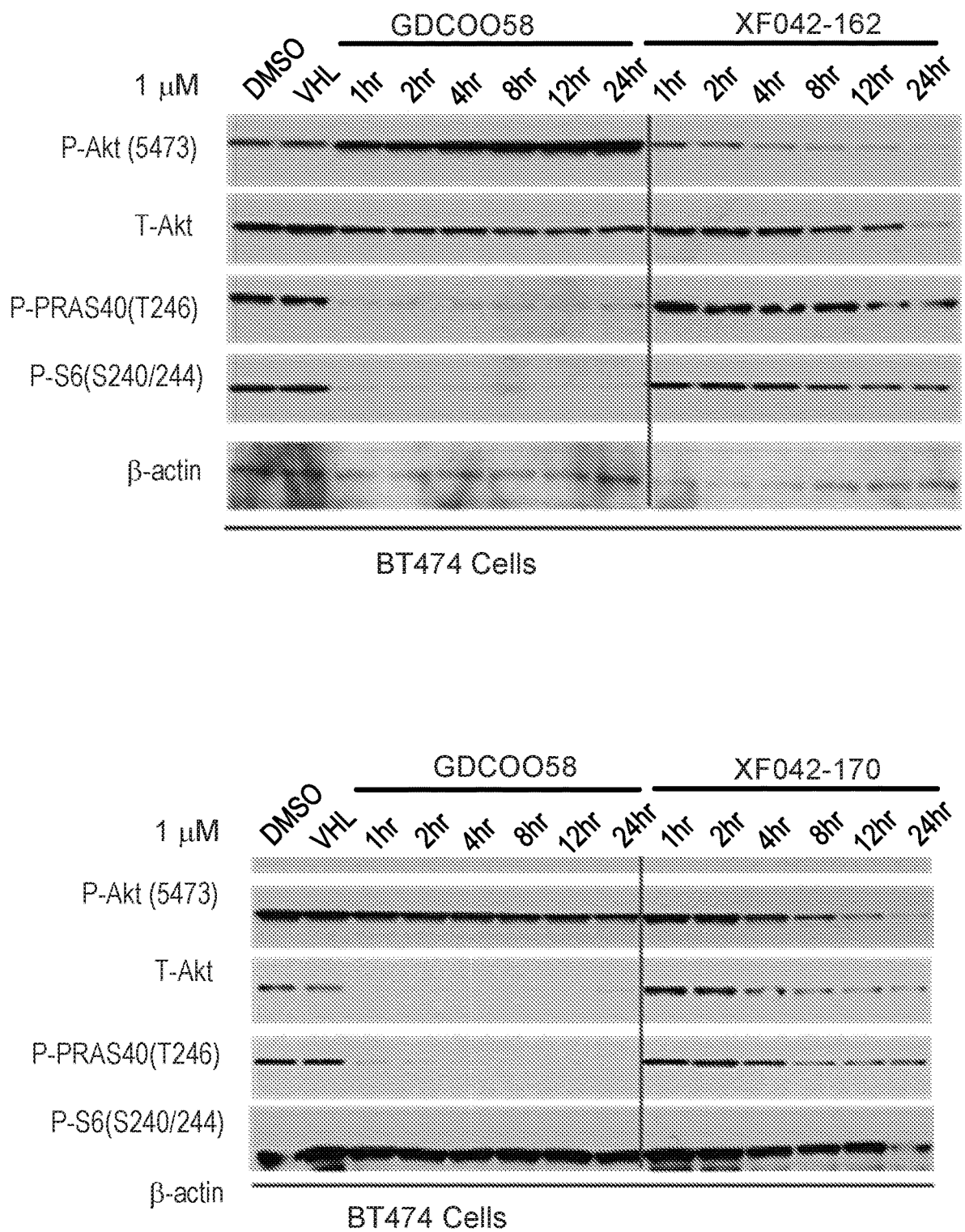
Figure 5B:
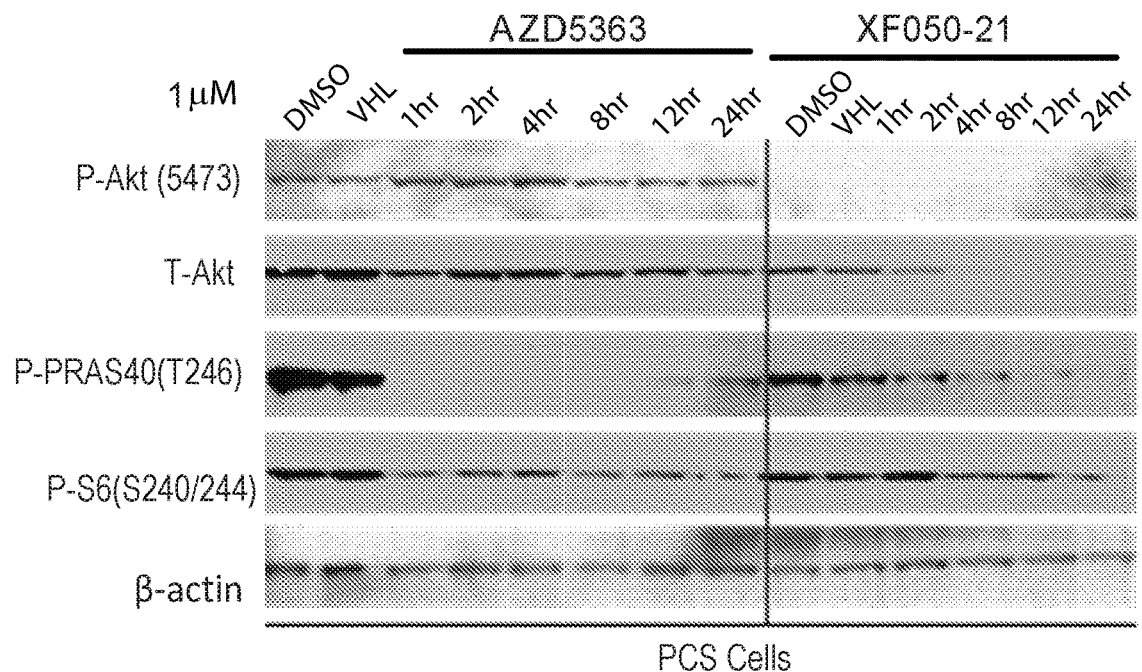
FIG. 5B is a Western blot showing that XF050-21 time-dependently reduces AKT, p-AKT, P-PRAS40 (T246), and P-S6 (S240/244) protein levels in PC3 cells.

BT474 cells and PC-3 cells were treated with DMSO or the indicated compounds at a fixed concentration of 1 µM for 1, 2, 4, 8, 12, or 24 h. The maximum degradation of AKT and inhibition of downstream signaling were observed after 24 h of treatment in BT474 cells (FIG. 5A). The maximum degradation of AKT and inhibition of downstream signaling were observed after 12 h of treatment in PC-3 cells (FIG. 5B).

Example 172. AKT Degraders Reduced AKT Protein Levels Through E3 Ubiquitin Ligase (FIG. 6)

BT474 Cells were pre-treated with DMSO, VHL-1 (1 mM), MLN4924 (1 µM), MG-132 (20 µM) or AZD5363 (1 µM) for 2 h, before being treated with the 1 µM XF050-21 compounds for 24 h. XF050-21 induced AKT protein degradation is mediated by hijacking the E3 ubiquitin ligase VHL, and it can be rescued by VHL-1, MLN4924, MG-132 or AZD5363 pretreatment.

Example 173: AKT Degraders Inhibit Cancer Cell Proliferation (FIG. 7)

$1-3 \times 10^3$ PC-3 or MDA-MB-468 cells were seeded in 96-well plates in triplicates and treated at the indicated compound concentrations. Cells were monitored using the IncuCyte® live cell imaging system (Essen Bioscience™, Ann Arbor, Mich.) which was placed in a cell culture incubator operated at 37° C. and 5% $CO_2$. Cell confluence was determined using calculations derived from phase-contrast images. The concentration for 50% of maximal inhibition of cell proliferation (GI50) values were determined by fitting to a standard four-parameter logistic using GraphPad Prism® v5. Graphs depicting the $GI_{50}$ of AKT degraders XF050-21 for these cancer cell lines are shown in FIG. 7.

Example 174. AKT Degraders Inhibit Cancer Cell Proliferation (FIG. 8)

PC-3, MDA-MB-468, HCC1143, and MDA-MB-231 cells were treated with DMSO, AZD5363 or XF050-21 at 0.1 µM, 0.3 µM, 1 µM, 3 µM, or 10 µM for 2 weeks. Cells were stained with Crystal Violet and the Bright field imaging indicated that XF050-21 was more effective in inhibiting cancer cell proliferation than AZD5363 at the same concentration in these cells.

Example 175. Combination Treatment of an AKT Degrader and an mTOR Inhibitor Reduced AKT Protein Levels and Inhibited Downstream Signaling in BT474 Cells (FIG. 9)

BT474 cells were treated with DMSO or indicated compounds combination at indicated concentration for 24 h. The Western blot results showed that the combination treatment of AKT degrader (XF050-21 or XF042-170) and an mTOR inhibitor (Torin1 or Rapamycin) reduced AKT protein levels and inhibited downstream signaling in BT474 cells.

Example 176. XF050-21 was Bioavailable in Mice (FIG. 10)

Standard PK studies were conducted using male Swiss Albino mice. A single 75 mg/kg intraperitoneal (IP) injection of XF050-21 was evaluated. Plasma concentrations of XF050-21 reported at each of the six time points (30 min, 1 h, 2 h, 4 h, 8 h, and 12 h post dosing) are the average values from 3 test animals. There were no abnormal clinical observations noted during the course of the study.

Example 177. AKT Degraders Reduced AKT Protein Levels in PC-3 Cells (FIG. 11)

PC-3 cells were treated with DMSO or indicated compounds at 1 µM for 24 h. The Western blot results showed that various AKT degraders significantly reduced AKT protein levels at 1 µM, while the AKT activity inhibitor ARQ-092 had no effect on reducing AKT protein levels.

Example 178. AKT Degraders Reduced AKT Protein Levels in PC-3 Cells (FIG. 12)

PC-3 cells were treated with DMSO or indicated compounds at 1 µM for 24 h. The Western blot results showed that various AKT degraders significantly reduced AKT protein levels at 1 µM, while the AKT activity inhibitor GSK690693 had no effect on reducing AKT protein levels.

Materials and Methods:

General Chemistry Methods

HPLC spectra for all compounds were acquired using an Agilent 1200 Series system with DAD detector. Chromatography was performed on a 2.1×150 mm Zorbax 300SB-C18 5 µm column with water containing 0.1% formic acid as solvent A and acetonitrile containing 0.1% formic acid as solvent B at a flow rate of 0.4 ml/min. The gradient program was as follows: 1% B (0-1 min), 1-99% B (1-4 min), and 99% B (4-8 min). High-resolution mass spectra (HRMS) data were acquired in positive ion mode using an Agilent G1969A API-TOF with an electrospray ionization (ESI) source. Nuclear Magnetic Resonance (NMR) spectra were acquired on a Bruker DRX-600 spectrometer with 600 MHz for proton ($^1$H NMR) and 150 MHz for carbon ($^{13}$C NMR); chemical shifts are reported in (6). Preparative HPLC was performed on Agilent Prep 1200 series with UV detector set to 254 nm. Samples were injected onto a Phenomenex Luna 250×30 mm, 5 µm, $C_{18}$ column at room temperature. The flow rate was 40 ml/min. A linear gradient was used with 10% (or 50%) of MeOH (A) in $H_2O$ (with 0.1% TFA) (B) to 100% of MeOH (A). HPLC was used to establish the purity of target compounds. All final compounds had >95% purity using the HPLC methods described above.

Cell Culture and Treatment

PC-3, U87MG, HCC1143, MDA-MB-231, MDA-MB-468, BT474 and MCF-7 cell lines were purchased from ATCC. Cell lines were regularly tested in the lab for mycoplasma. All cells were cultured at 37° C. and 5% $CO_2$. PC-3, U87MG, MDA-MB-231, MCF-7 and BT474 cells were cultured in 1×DMEM (Corning, 10-013-CV) with 10% fetal bovine serum (Atlanta Biologicals S11150) and 1× Penicillin/Streptomycin. HCC1143 cells were cultured in RPMI (Corning, 10-040-CV) medium with 10% fetal bovine serum (Atlanta Biologicals S11150) and 1× Penicillin/Streptomycin. Cells were split using 0.05% or 0.25% trypsin (Corning 25-051-Cl or 25-053-Cl, respectively) before they reached full confluence and media was changed every 3-4 days. Cells were treated with compounds individually at different concentrations for 24 hrs. Cells were treated with DMSO, VHL, or PML alone as controls.

Immunoblotting

Cells were lysed in 2× sample buffer (125 mM Tris-HCl at pH 6.8, 10% βME, 2% SDS, 20% glycerol, 0.05% Bromophenol Blue, 8 M urea). Protein lysates were loaded into 4-12% Bis-Tris gels and resolved by electrophoresis. Samples were then blotted on PVDF membrane (Millipore IPVH00010) using the wet transfer technique (Invitrogen). Membranes were blocked in 5% milk-TBST for 1 hour, washed in TBST for 10 min, and incubated in primary antibody in 5% milk-TBST or 5% BSA-TBST at 4° C. for 16 h. Membranes were rinsed (3×6 min) in TBST and incubated in horseradish peroxidase-conjugated secondary antibodies in 5% milk-TBST for 1 hour and rinsed again in TBST (3×6 min). Membranes were visualized using the chemiluminescence system (Thermo 34080, 37075) on autoradiography film (Denville E3018). Primary Antibodies: R-actin (Sigma A5316), p-AKT (Ser473 CST-9721), total AKT (CST-9272), p-S6 (Ser240/244, CST-5364), p-PRAS40 (Thr246, CST-2997). Secondary Antibodies: Mouse (Thermo 31432), Rabbit (Thermo 31460).

Cell Viability Assay

Cells were cultured for 12-17 days in the presence of different compounds. Media with compound was replenished every two days. At the end of the experiment, media was aspirated and viable cells were stained with 0.5% crystal violet dye.

Proliferation and Apoptosis Assays

Experiments were carried out in 96-well plates in triplicates. A total of 1-3×10$^3$ cells per well were grown in the presence of 1 µM of AZD5363 (Selleckchem), 1 µM of selected degrader compounds. Cells were then monitored for 3-4 days using the IncuCyte live cell imaging system (Essen BioScience, Ann Arbor, Mich., USA), which was placed in a cell culture incubator operated at 37° C. and 5% $CO_2$. Cell confluence was determined using calculations derived from phase-contrast images. For measurement of cell death DRAQ7 (Cell Signaling #7406) at 1.5 µM was included in the medium and apoptotic red counts were measured in IncuCyte™ FLR automated incubator microscope.

Xenograft Studies

Thirty male immunocompromised nu/nu mice (The Jackson Laboratory) was engrafted with PC-3 human prostate cancer cells that have never been passed through animals and was used under blood-born pathogen laboratory procedures. After tumor volumes reach ~100 mm$^3$, 3 treatment arms (10 animals per group) were administrated with vehicle control, AZD5363, or a selected degrader compound daily for 3-4 weeks via intraperitoneal (IP) injections. Tumor volume was calculated as follows: tumor size (mm$^3$)= (longer measurement×shorter measurement$^2$)×0.5. Tumor sizes were recorded every other day over the course of the studies. Engraftment and monitoring of tumor growth and toxicity in mice were be performed. Treatments would be discontinued if toxicity or distress is encountered. All procedures involving mice and experimental protocols (LA13-00024) were approved by the Institutional Animal Care and Use Committee (IACUC) of Icahn School of Medicine at Mount Sinai (ISMMS).

Immunohistochemistry

Paraffin sections were dewaxed as previously described. If necessary, antigen retrieval was performed, typically, the sections were boiled in 0.01M sodium citrate, pH 6.0, 0.05% Tween-20 twice for 10 min, and then cooled at room temperature for 20 min. After that, the sections were washed with dd $H_2O$ for 3 times of 5 min each and then washed with PBS for 5 min. HRP conjugated secondary antibody was used to detect the signal. Endogenous HRP was blocked with 3% $H_2O_2$ in PBS or methanol for 10 min. Then the slide was washed in PBS for 3 times of 5 mins each. At this time, the section on slide was circled with a PAP pen. For cryosections, the sections were warmed from −80° C. freezer to room temperature and dried at room temperature for 30 mins or 15 mins at 50° C. Then sections were fixed in ice-cold acetone for 5 min on ice, and then air dried at room temperature for 30 mins, followed by washing with 1×PBS for 5 mins. Afterwards, the endogenous HRP was blocked with 3% $H_2O_2$ if necessary. The sections were washed again with PBS for 3 times of 5 mins each before circled with a PAP pen.

Statistics

No statistical methods were used to determine sample size, and experiments were not randomized. The experimenters were not blinded. Aside from traditional Mann-Whitney (non-parametric), Spearman correlation test (non-parametric), student t-tests (parametric) to compare two data sets, and Chi-squared test (non-parametric), parametric statistical methods were used in order to make appropriate multiple comparisons of repeated measures of data (following 1-way or 2-way ANOVA). Graphpad Prism was used to make these simple predetermined statistical comparisons. Tukey's Multiple Comparisons Correction: Used for making all possible pairwise comparisons in a data set. Dunnett's Multiple Comparisons Correction: Used for comparing all samples to a control sample, but not for comparing the non-control samples to one another. Sidak's Multiple Comparisons Correction: Used when specific multiple comparisons are pre-selected. Fischer's Exact Test: Used to analyze items in a contingency table.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

Addie, M., Ballard, P., Buttar, D., Crafter, C., Currie, G., Davies, B. R., Debreczeni, J., Dry, H., Dudley, P., Greenwood, R., et al. (2013). Discovery of 4-amino-N-[(1S)-1-(4-chlorophenyl)-3-hydroxypropyl]-1-(7H-pyrrolo[2,3-d]pyrimidin-4-yl)piperidine-4-carboxamide (AZD5363), an orally bioavailable, potent inhibitor of Akt kinases. J Med Chem 56, 2059-2073.

Aguilar, A., Lu, J., Liu, L., Du, D., Bernard, D., McEachem, D., Przybranowski, S., Li, X., Luo, R., Wen, B., et al. (2017). Discovery of 4-((3'R,4'S,5'R)-6''-Chloro-4'-(3-chloro-2-fluorophenyl)-1'-ethyl-2''-oxodispiro[cyclohexane-1,2'-pyrrolidine-3',3''-indoline]-5'-carboxamido) bicyclo[2.2.2]octane-1-carboxylic Acid (AA-115/APG-115): A Potent and Orally Active Murine Double Minute 2 (MDM2) Inhibitor in Clinical Development. J Med Chem 60, 2819-2839.

Blake, J. F., Xu, R., Bencsik, J. R., Xiao, D., Kallan, N.C., Schlachter, S., Mitchell, I. S., Spencer, K. L., Banka, A. L., Wallace, E. M., et al. (2012). Discovery and preclinical pharmacology of a selective ATP-competitive Akt inhibitor (GDC-0068) for the treatment of human tumors. J Med Chem 55, 8110-8127.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Buckley, D. L., and Crews, C. M. (2014). Small-molecule control of intracellular protein levels through modulation of the ubiquitin proteasome system. Angew Chem Int Ed Engl 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIF1alpha. Angew Chem Int Ed Engl 51, 11463-11467.

Buckley, D. L., Raina, K., Darricarrere, N., Hines, J., Gustafson, J. L., Smith, I. E., Miah, A. H., Harling, J. D., and Crews, C. M. (2015). HaloPROTACS: Use of Small Molecule PROTACs to Induce Degradation of HaloTag Fusion Proteins. ACS Chem Biol 10, 1831-1837.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-1alpha interaction. J Am Chem Soc 134, 4465-4468.

Chamberlain, P. P., Lopez-Girona, A., Miller, K., Carmel, G., Pagarigan, B., Chie-Leon, B., Rychak, E., Corral, L. G., Ren, Y. J., Wang, M., et al. (2014). Structure of the human Cereblon-DDB1-lenalidomide complex reveals basis for responsiveness to thalidomide analogs. Nat Struct Mol Biol 21, 803-809.

Dumble, M., Crouthamel, M. C., Zhang, S. Y., Schaber, M., Levy, D., Robell, K., Liu, Q., Figueroa, D. J., Minthorn, E. A., Seefeld, M. A., et al. (2014). Discovery of novel AKT inhibitors with enhanced anti-tumor effects in combination with the MEK inhibitor. PLoS One 9, e100880.

E. Wakeling, A. (1995). Use of pure antioestrogens to elucidate the mode of action of oestrogens. Biochem Pharmacol 49, 1545-1549.

Fischer, E. S., Bohm, K., Lydeard, J. R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Heerding, D. A., Rhodes, N., Leber, J. D., Clark, T. J., Keenan, R. M., Lafrance, L. V., Li, M., Safonov, I. G., Takata, D. T., Venslavsky, J. W., et al. (2008). Identification of 4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol (GSK690693), a novel inhibitor of AKT kinase. J Med Chem 51, 5663-5679.

Henning, R. K., Varghese, J. O., Das, S., Nag, A., Tang, G., Tang, K., Sutherland, A. M., and Heath, J. R. (2016). Degradation of Akt using protein-catalyzed capture agents. J Pept Sci 22, 196-200.

Hirai, H., Sootome, H., Nakatsuru, Y., Miyama, K., Taguchi, S., Tsujioka, K., Ueno, Y., Hatch, H., Majumder, P. K., Pan, B. S., et al. (2010). MK-2206, an allosteric Akt inhibitor, enhances antitumor efficacy by standard chemotherapeutic agents or molecular targeted drugs in vitro and in vivo. Mol Cancer Ther 9, 1956-1967.

Hiroyuki Suda, Tomohisa Takita, Takaaki Aoyagi, and Umezawa, H. (1976). The structure of bestatin. The Journal of Antibiotic 20, 100-101.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Lai, A. C., Toure, M., Hellerschmied, D., Salami, J., Jaime-Figueroa, S., Ko, E., Hines, J., and Crews, C. M. (2016). Modular PROTAC Design for the Degradation of Oncogenic BCR-ABL. Angew Chem Int Ed Engl 55, 807-810.

Lapierre, J. M., Eathiraj, S., Vensel, D., Liu, Y., Bull, C. O., Cornell-Kennon, S., Iimura, S., Kelleher, E. W., Kizer, D. E., Koerner, S., et al. (2016). Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor. J Med Chem 59, 6455-6469.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chemistry & biology 22, 755-763.

Maniaci, C., Hughes, S. J., Testa, A., Chen, W., Lamont, D. J., Rocha, S., Alessi, D. R., Romeo, R., and Ciulli, A. (2017). Homo-PROTACs: bivalent small-molecule dimerizers of the VHL E3 ubiquitin ligase to induce self-degradation. Nat Commun 8, 830.

Manning, B. D., and Toker, A. (2017). AKT/PKB Signaling: Navigating the Network. Cell 169, 381-405.

Pretre, V., and Wicki, A. (2017). Inhibition of Akt and other AGC kinases: A target for clinical cancer therapy? Semin Cancer Biol.

Saura, C., Roda, D., Rosello, S., Oliveira, M., Macarulla, T., Perez-Fidalgo, J. A., Morales-Barrera, R., Sanchis-Garcia, J. M., Musib, L., Budha, N., et al. (2017). A First-in-Human Phase I Study of the ATP-Competitive AKT Inhibitor Ipatasertib Demonstrates Robust and Safe Targeting of AKT in Patients with Solid Tumors. Cancer Discov 7, 102-113.

Sun, D., Li, Z., Rew, Y., Gribble, M., Bartberger, M. D., Beck, H. P., Canon, J., Chen, A., Chen, X., Chow, D., et al. (2014). Discovery of AMG 232, a potent, selective, and orally bioavailable MDM2-p53 inhibitor in clinical development. J Med Chem 57, 1454-1472.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., et al. (2007). IAP antagonists induce autoubiquitination of c-IAPs, NF-kappaB activation, and TNFalpha-dependent apoptosis. Cell 131, 669-681.

Vassilev, L. T., Vu, B. T., Graves, B., Carvajal, D., Podlaski, F., Filipovic, Z., Kong, N., Kammlott, U., Lukacs, C., Klein, C., et al. (2004). In vivo activation of the p53 pathway by small-molecule antagonists of MDM2. Science 303, 844-848.

Vu, B., Wovkulich, P., Pizzolato, G., Lovey, A., Ding, Q., Jiang, N., Liu, J. J., Zhao, C., Glenn, K., Wen, Y., et al. (2013). Discovery of RG7112: A Small-Molecule MDM2 Inhibitor in Clinical Development. ACS Med Chem Lett 4, 466-469.

Weisberg, E., Ray, A., Barrett, R., Nelson, E., Christie, A. L., Porter, D., Straub, C., Zawel, L., Daley, J. F., Lazo-Kallanian, S., et al. (2010). Smac mimetics: implications for enhancement of targeted therapies in leukemia. Leukemia 24, 2100-2109.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Xie, T., Lim, S. M., Westover, K. D., Dodge, M. E., Ercan, D., Ficarro, S. B., Udayakumar, D., Gurbani, D., Tae, H. S., Riddle, S. M., et al. (2014). Pharmacological targeting of the pseudokinase Her3. Nat Chem Biol 10, 1006-1012.

Yu, Y., Savage, R. E., Eathiraj, S., Meade, J., Wick, M. J., Hall, T., Abbadessa, G., and Schwartz, B. (2015). Targeting AKT1-E17K and the PI3K/AKT Pathway with an Allosteric AKT Inhibitor, ARQ 092. PLoS One 10, e0140479.

Zengerle, M., Chan, K. H., and Ciulli, A. (2015). Selective Small Molecule Induced Degradation of the BET Bromodomain Protein BRD4. ACS Chem Biol 10, 1770-1777.

What is claimed is:

1. A bivalent compound comprising a serine threonine kinase AKT ligand conjugated to a degradation/disruption tag through a linker, said linker selected from the group consisting of:

a.

FORMULA 9 wherein

A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, R" and $R^2$ together with the atom to which they are connected form a 3-20 membered cycloalkyl or 4-20 membered heterocyclyl ring; and m is 0 to 15;

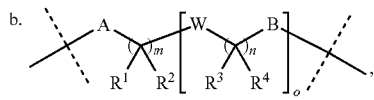

FORMULA 9A wherein
- $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-10 membered cycloalkoxy, optionally substituted 3-10 membered carbocyclylamino, optionally substituted 4-8 membered heterocyclyl, optionally substituted aryl, and optionally substituted heteroaryl, or
- $R^1$ and $R^2$, $R^3$ and $R^4$ together with the atom to which they are connected form a 3-20 membered cycloalkyl or 4-20 membered heterocyclyl ring;
- A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR'COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein
  - R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;
- $R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;
- R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;
- m is 0 to 15;
- n, at each occurrence, is 0 to 15; and
- o is 0 to 15;

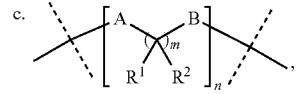

FORMULA 9B wherein
- $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-10 membered cycloalkoxy, optionally substituted 3-10 membered carbocyclylamino, optionally substituted 4-10 membered heterocyclyl, optionally substituted aryl, and optionally substituted heteroaryl, or
- $R^1$ and $R^2$ together with the atom to which they are connected form a 3-20 membered cycloalkyl or 4-20 membered heterocyclyl ring;
- A and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR"R$^1$, R'NR"R$^1$, R'NR'COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein
  - R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;
- $R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

each m is 0 to 15; and n is 0 to 15;

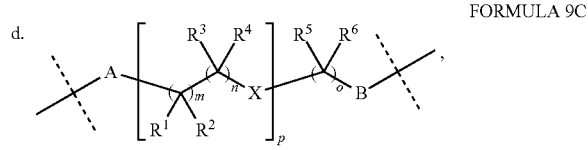
FORMULA 9C wherein

X is selected from O, NH, and $NR^7$;

$R^1$, $R^2$, $R^3$, $R^4$, $R^5$, $R^6$, and $R^7$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-10 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'$CO_2$R", R'C(O)NR"$R^1$, R'C(S)NR"$R^1$, R'OR", R'OC(O)R", R'OC(O)OR", R'OCONR$^1$R", R'SR", R'SOR", R'$SO_2$R", R'$SO_2$NR"$R^1$, R'NR"$R^1$, R'NR"$^1$COR", R'NR$^1$C(O)OR", R'NR$^1$CONR"$R^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;

m, at each occurrence, is 0 to 15;

n, at each occurrence, is 0 to 15;

o is 0 to 15; and p is 0 to 15;

e. the linker comprises one or more rings selected from the group consisting of a 3 to 13 membered ring, a 3 to 13 membered fused ring, a 3 to 13 membered bridged ring, and a 3 to 13 membered spiro ring;

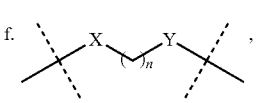
FORMULA A wherein

X is C=O or $CH_2$,

Y is C=O or $CH_2$, and n is 0-15;

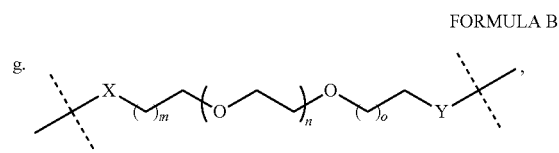
FORMULA B wherein

X is C=O or $CH_2$,

Y is C=O or $CH_2$, m is 0-15, n is 0-6, and o is 0-15; and

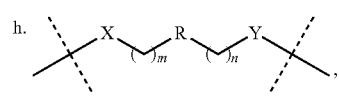
Formula C wherein

X is C=O or $CH_2$,

Y is C=O or $CH_2$,

R is —$CH_2$—, —$CF_2$—, —CH($C_{1-3}$ alkyl)-, —C($C_{1-3}$ alkyl)($C_{1-3}$ alkyl)-, —CH=CH—, —C($C_{1-3}$ alkyl)=C($C_{1-3}$ alkyl)-, —C=C—, —O—, —NH—, —N($C_{1-3}$ alkyl)-, —C(O)NH—, —C(O)N($C_{1-3}$ alkyl)-, a 3-13 membered ring, a 3-13 membered fused ring, a 3-13 membered bridged ring, and/or a 3-13 membered spiro ring, m is 0-15, and n is 0-15 and pharmaceutically acceptable salts and enantiomers thereof.

2. The bivalent compound of claim 1, wherein the linker comprises:

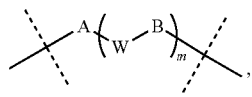

FORMULA 9 wherein

A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR$^1$R", R'SR", R'SOR", R'SO$_2$R", R'SO$_2$NR$^1$R", R'NR"R$^1$, R'NR$^1$COR", R'NR$^1$C(O)OR", R'NR$^1$CONR"R$^2$, R'NR$^1$C(S)R", R'NR$^1$S(O)R", R'NR$^1$S(O)$_2$R", and R'NR$^1$S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

R$^1$ and R$^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", R$^1$ and R$^2$, R' and R$^1$, R' and R$^2$, R" and R$^1$, R" and R$^2$ together with the atom to which they are connected form a 3-20 membered cycloalkyl or 4-20 membered heterocyclyl ring; and m is 0 to 15.

3. The bivalent compound of claim 1, wherein the linker comprises:

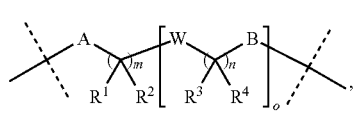

FORMULA 9A wherein

R$^1$, R$^2$, R$^3$ and R$^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-10 membered cycloalkoxy, optionally substituted 3-10 membered carbocyclylamino, optionally substituted 4-8 membered heterocyclyl, optionally substituted aryl, and optionally substituted heteroaryl, or R$^1$ and R$^2$, R$^3$ and R$^4$ together with the atom to which they are connected form a 3-20 membered cycloalkyl or 4-20 membered heterocyclyl ring;

A, W and B, at each occurrence, are independently selected from null, or bivalent moiety selected from R'—R", R'COR", R'CO$_2$R", R'C(O)NR"R$^1$, R'C(S)NR"R$^1$, R'OR", R'OC(O)R", R'OC(O)OR", R'OCONR'R", R'SR", R'SOR", R'SO$_2$R", R'SO$_2$NR"R$^1$, R'NR"R$^1$, R'NR'COR", R'NR'C(O)OR", R'NR'CONR"R$^2$, R'NR'C(S)R", R'NR'S(O)R", R'NR$^1$S(O)$_2$R", and R'NR$^1$S(O)NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

R$^5$ and R$^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;

n, at each occurrence, is 0 to 15; and o is 0 to 15.

4. The bivalent compound of claim 1, wherein the linker comprises

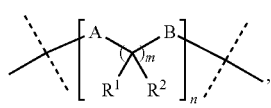

FORMULA 9B wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-10 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'CO$_2$R", R'C(O)NR"$R^1$, R'C(S)NR"$R^1$, R'OR", R'OC(O)R", R'OC(O)OR", R'OCONR'R", R'SR", R'SOR", R'SO$_2$R", R'SO$_2$NR"$R^1$, R'NR"$R^1$, R'NR'COR", R'NR'C(O)OR", R'NR'CONR"$R^2$, R'NR'C(S)R", R'NR'S(O)R", R'NR'S(O)$_2$R", and R'NR'S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

each m is 0 to 15; and n is 0 to 15.

5. The bivalent compound of claim 1, wherein the linker comprises:

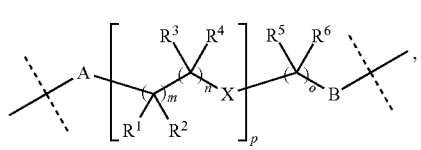

FORMULA 9C wherein

X is selected from O, NH, and NR$^7$;

$R^1$, $R^2$, $R^3$, $R^4$, $R^5$, $R^6$, and $R^7$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-10 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'CO$_2$R", R'C(O)NR"$R^1$, R'C(S)NR"$R^1$, R'OR", R'OC(O)R", R'OC(O)OR", R'OCONR'R", R'SR", R'SOR", R'SO$_2$R", R'SO$_2$NR"$R^1$, R'NR"$R^1$, R'NR'COR", R'NR'C(O)OR", R'NR'CONR"$R^2$, R'NR'C(S)R", R'NR'S(O)R", R'NR'S(O)$_2$R", and R'NR'S(O)$_2$NR$^2$R", wherein R' and R" are independently selected from null, or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;

m, at each occurrence, is 0 to 15;
n, at each occurrence, is 0 to 15;
o is 0 to 15; and
p is 0 to 15.

6. The bivalent compound according to claim 1, wherein the linker comprises one or more rings selected from the group consisting of:

FORMULA C1

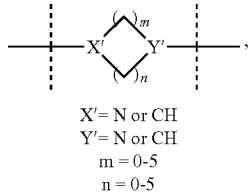
(a)

X' = N or CH
Y' = N or CH
m = 0-5
n = 0-5

FORMULA C2

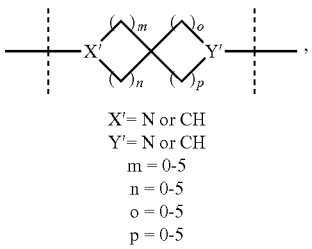
(b)

X' = N or CH
Y' = N or CH
m = 0-5
n = 0-5
o = 0-5
p = 0-5

FORMULA C3

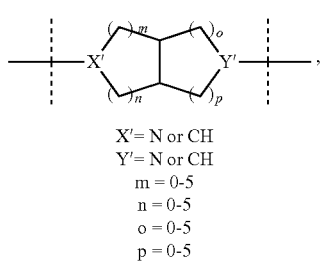
(c)

X' = N or CH
Y' = N or CH
m = 0-5
n = 0-5
o = 0-5
p = 0-5

FORMULA C4

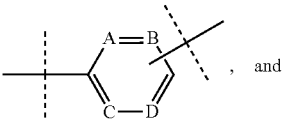
(d)
, and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N

FORMULA C5

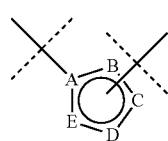
(e)

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3alkyl), O, S.

7. The bivalent compound of claim 1, wherein the linker comprises:

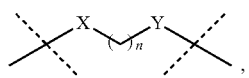
FORMULA A wherein
X is C=O or $CH_2$,
Y is C=O or $CH_2$, and
n is 0-15.

8. The bivalent compound of claim 1, wherein the linker comprises:

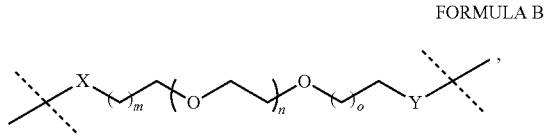
FORMULA B wherein
X is C=O or $CH_2$,
Y is C=O or $CH_2$,
m is 0-15,
n is 0-6, and
o is 0-15.

9. The bivalent compound of claim 1, wherein the linker comprises:

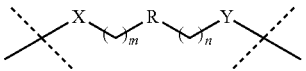
FORMULA C wherein
X is C=O or CH₂,
Y is C=O or CH₂,
R is —CH₂—, —CF₂—, —CH(C$_{1-3}$ alkyl)-, —C(C$_{1-3}$ alkyl)(C$_{1-3}$ alkyl)-, —CH=CH—, —C(C$_{1-3}$ alkyl)=C(C$_{1-3}$ alkyl)-, —C≡C—, —O—, —NH—, —N(C$_{1-3}$ alkyl)-, —C(O)NH—, —C(O)N(C$_{1-3}$ alkyl)-, a 3-13 membered ring, a 3-13 membered fused ring, a 3-13 membered bridged ring, and/or a 3-13 membered spiro ring,
m is 0-15, and
n is 0-15.

10. The bivalent compound of claim 1, wherein the AKT ligand is selected from the group consisting of:

a.

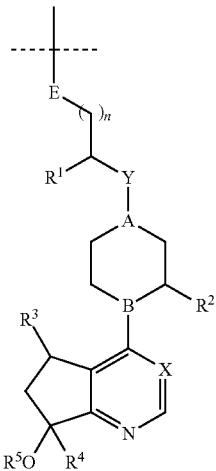

FORMULA 1 wherein
A, B, and X are independently N, CH, or CR⁶,
Y is CH₂, CO, SO, SO₂, CR⁷R⁸, CONR⁷, or SO₂NR⁷,
E is NH, NR⁹, O, C$_1$-C$_8$ alkyl, C$_1$-C$_8$ alkoxy, C$_1$-C$_8$ alkoxyalkyl, C$_1$-C$_8$ haloalkyl, C$_1$-C$_8$ hydroxyalkyl, C$_3$-C$_8$ cycloalkyl, C$_3$-C$_7$ heterocyclyl, C$_2$-C$_8$ alkenyl, C$_2$-C$_8$ alkynyl, OR⁹, SR⁹, NR⁹R¹⁰, CN, NO₂, (CR⁹R¹⁰)$_m$ NR¹¹R¹², (CR⁹R¹⁰)$_m$C(O)R¹¹, (NR⁹R¹⁰)$_m$NR¹¹R¹², (NR⁹R¹⁰)$_m$C(O)R'', COR⁹, CO₂R⁹, CONR⁹R¹⁰, NR⁹COR¹⁰, NR⁹SOR¹⁰, NR⁹SO₂R¹⁰, SOR⁹, SO₂R⁹, SO₂NR⁹R¹⁰, (CR⁹R¹⁰)$_m$-aryl, or (CR⁹R¹⁰)$_m$-heteroaryl,
R¹ is H, C$_1$-C$_8$ alkyl, C$_3$-C$_8$ cycloalkyl, C$_1$-C$_8$ alkoxy, C$_1$-C$_8$ alkoxyalkyl, aryl, C$_1$-C$_8$ alkylaryl, haloaryl, arylalkyl, heteroaryl, or heteroarylalkyl,
R², R³, R⁴, and R⁶ are independently hydrogen, halogen, amino, C$_1$-C$_8$ alkylamino, arylamino, C$_1$-C$_8$ alkyl, C$_3$-C$_8$ cycloalkyl, C$_1$-C$_8$ alkoxy, or C$_1$-C$_8$ alkoxyalkyl,
R⁵, R⁷, and R⁸ are independently H, C$_1$-C$_8$ alkyl, C$_3$-C$_8$ cycloalkyl, or C$_1$-C$_8$ alkoxyalkyl,
R⁹, R¹⁰, R¹¹, and R¹² are independently H, C$_1$-C$_8$ alkyl, C$_3$-C$_8$ cycloalkyl, C$_1$-C$_8$ alkoxy, C$_2$-C$_8$ alkenyl, C$_2$-C$_8$ alkynyl, arylalkyl, cycloalkyl, heterocycloalkyl, aryl, heteroaryl, or heteroarylalkyl, R⁹ and R¹⁰, R¹¹ and R¹² can independently form 4-8 membered alkyl or heterocyclyl rings, m=0-8,
and
n=0-8;

b.

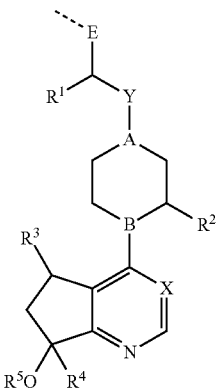

FORMULA 2 wherein
A, B and X are independently selected from N and CR⁶, wherein
R⁶ is independently selected from hydrogen, halogen, cyano, nitro, hydroxyl, amino, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxy C$_1$-C$_8$ alkyl, optionally substituted amino, optionally substituted C$_1$-C$_8$ alkylamino, optionally substituted C$_1$-C$_8$ alkylaminoC$_1$-C$_8$ alkyl, optionally substituted 3-10 membered carbocyclyl, and optionally substituted 4-10 membered heterocyclyl;
Y is selected from CR⁷R⁸, CO, SO, SO₂, CONR⁷, and SO₂NR⁷, wherein
R⁷ and R⁸ is independently selected from hydrogen, halogen, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ alkoxy, optionally substituted C$_1$-C$_8$ alkoxy C$_1$-C$_8$ alkyl; optionally substituted C$_1$-C$_8$ alkylamino, optionally substituted C$_1$-C$_8$ alkylamino C$_1$-C$_8$ alkyl, optionally substituted 3 to 10 membered carbocyclyl, and optionally substituted 4-10 membered heterocyclyl, or
R⁷ and R⁸ together with the atom to which they are connected form an optionally substituted 3-10 membered carbocyclyl or an optionally substituted 4-10 membered heterocyclyl ring;
E is connected to the "linker" moiety of the bivalent compound, and is selected from null, R'—R'' R'OR'', R'SR'', R'NR⁹R'', R'OC(O)R'', R'OC(O)OR'', R'OCONR⁹R'', R'C(O)R'', R'C(O)OR'', R'CONR⁹R'', R'S(O)R'', R'S(O)₂R'', R'SO₂NR⁹R'', R'NR¹⁰C(O)OR'', R'NR¹⁰C(O)R'', R'NR¹⁰C(O)NR⁹R'', R'NR¹⁰S(O)R'', R'NR¹⁰S(O)₂R'', and R'NR¹⁰S(O)₂NR⁹R'', wherein
R' and R'' are independently selected from null, optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C₂-C₈ alkenylene, optionally substituted C₂-C₈ alkynylene, optionally substituted C₁-C₈ haloalkylene, optionally substituted C₁-C₈ hydroxyalkylene, optionally substituted C₁-C₈alkoxyC₁-C₈alkylene, optionally substituted C₁-C₈alkylaminoC₁-C₈alkylene, optionally substituted (C₁-C₈ alkylene)O(C₁-C₈ alkylene), optionally substituted (C₁-C₈ alkylene)N(C₁-C₈ alkylene), optionally substituted 3-10 membered carbocyclyl, optionally substituted 4-10 membered heterocyclyl, optionally substituted C₃-C₁₃ fused carbocyclyl, optionally substituted C₃-C₁₃ fused heterocyclyl, optionally substituted C₃-C₁₃ bridged carbocyclyl, optionally substituted C₃-C₁₃ bridged heterocyclyl, optionally substituted C₃-C₁₃ spiro carbocyclyl, optionally substituted C₃-C₁₃ spiro heterocyclyl, optionally substituted aryl, and optionally substituted heteroaryl;

$R^9$ and $R^{10}$ are independently selected from hydrogen, optionally substituted C₁-C₈ alkyl, optionally substituted C₂-C₈ alkenyl, optionally substituted C₂-C₈ alkynyl, optionally substituted C₁-C₈alkoxyC₁-C₈alkyl, optionally substituted C₁-C₈alkylaminoC₁-C₈alkyl, optionally substituted 3-10 membered carbocyclyl, optionally substituted 4-10 membered heterocyclyl, optionally substituted aryl, and optionally substituted heteroaryl;

R' and R'', $R^9$ and $R^{10}$, R' and $R^9$, R' and $R^{10}$, R'' and $R^9$, R'' and $R^{10}$ together with the atom to which they are connected form a 4-20 membered heterocyclyl ring;

$R^1$ is selected from hydrogen, halogen, and optionally substituted C₁-C₈ alkyl, optionally substituted C₂-C₈ alkenyl, optionally substituted C₂-C₈ alkynyl, optionally substituted C₁-C₈ alkoxy, optionally substituted C₁-C₈ alkoxy C₁-C₈ alkyl, optionally substituted C₁-C₈ alkylamino, optionally substituted C₁-C₈ alkylamino C₁-C₈ alkyl, optionally substituted 3-10 membered carbocyclyl, optionally substituted 4-10 membered heterocyclyl, optionally substituted aryl, and optionally substituted heteroaryl;

$R^2$, $R^3$ and $R^4$ are independently selected from hydrogen, halogen, cyano, nitro, hydroxyl, optionally substituted C₁-C₈ alkyl, optionally substituted C₂-C₈ alkenyl, optionally substituted C₂-C₈ alkynyl, optionally substituted C₁-C₈ alkoxy, optionally substituted aryloxy, optionally substituted C₁-C₈ alkoxyC₁-C₈ alkyl, optionally substituted amino, optionally substituted C₁-C₈ alkylamino, optionally substituted C₁-C₈ alkylaminoC₁-C₈ alkyl, optionally substituted arylamino, optionally substituted 3-10 membered carbocyclyl, and optionally substituted 4-10 membered heterocyclyl;

$R^5$ is selected from hydrogen, optionally substituted C₁-C₈ alkyl, optionally substituted C₂-C₈ alkenyl, optionally substituted C₂-C₈ alkynyl, optionally substituted C₁-C₈ alkoxyC₁-C₈ alkyl, optionally substituted C₁-C₈ alkylaminoC₁-C₈ alkyl, optionally substituted 3-10 membered carbocyclyl, and optionally substituted 4-10 membered heterocyclyl;

c.

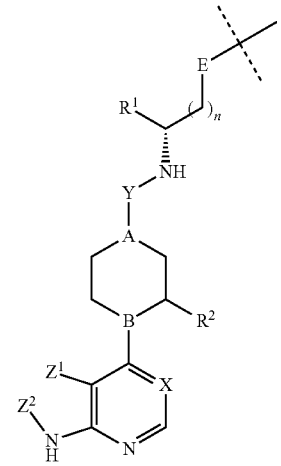

FORMULA 3 wherein
A, B, and X are independently N or $CR^3$,
Y is $CH_2$, CO, SO, $SO_2$, $CR^4R^5$, $CONR^4$, or $SO_2NR^4$,
E is NH, $NR^6$, O, C₁-C₈ alkyl, C₁-C₈ alkoxy, C₁-C₈ alkoxyalkyl, C₁-C₈ haloalkyl, C₁-C₈ hydroxyalkyl, C₃-C₈ cycloalkyl, C₃-C₈ heterocyclyl, C₂-C₈ alkenyl, C₂-C₈ alkynyl, $OR^6$, $SR^6$, $NR^6R^7$, CN, $NO_2$, $(CR^6R^7)_m NR^8R^9$, $(CR^6R^7)_m C(O)R^8$, $(NR^6R^7)_m NR^8R^9$, $(NR^6R^7)_m C(O)R^8$, $COR^6$, $CO_2R^6$, $CONR^6R^7$, $NR^6COR^7$, $NR^6SOR^7$, $NR^6SO_2R^7$, $SOR^6$, $SO_2R^6$, $SO_2NR^6R^7$, $(CR^6R^7)_m$-aryl, or $(CR^6R^7)_m$-heteroaryl,
$Z^1$-$Z^2$ is $CR^{10}$=CH, N+CH, or $CR^{10}$=N,
$R^1$ is hydrogen, C₁-C₈ alkyl, C₃-C₈ cycloalkyl, C₁-C₈ alkoxy, C₁-C₈ alkoxyalkyl, aryl, C₁-C₈ alkylaryl, haloaryl, arylalkyl, heteroaryl, or heteroarylalkyl,
$R^2$, $R^3$, and $R^4$ are independently hydrogen, halogen, amino, C₁-C₈ alkylamino, arylamino, C₁-C₈ alkyl, C₃-C₈ cycloalkyl, C₁-C₈ alkoxy, or C₁-C₈ alkoxyalkyl,
$R^6$, $R^7$, $R^8$, and $R^9$ are independently H, C₁-C₈ alkyl, C₃-C₈ cycloalkyl, C₁-C₈ alkoxy, C₂-C₈ alkenyl, C₂-C₈ alkynyl, arylalkyl, cycloalkyl, heterocycloalkyl, aryl, heteroaryl, or heteroarylalkyl, $R^6$ and $R^7$, $R^8$ and $R^9$ can independently form 4-8 membered alkyl or heterocyclyl rings,
$R^{10}$ is hydrogen, halogen, C₁-C₈ alkyl, C₃-C₈ cycloalkyl, C₁-C₈ alkoxy, C₁-C₈ alkoxyalkyl, and
n=0-8;

d.

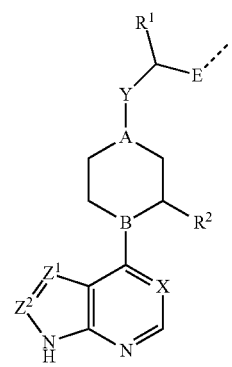

FORMULA 4 wherein

A, B and X are independently selected from N and $CR^3$, wherein $R^3$ is independently selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino $C_1$-$C_8$ alkyl, optionally substituted 3-10 membered carbocyclyl, and optionally substituted 4-10 membered heterocyclyl;

$Z^1$ is selected from $CR^8$ and N, wherein $R^8$ is selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3-10 membered carbocyclyl, and optionally substituted 4-10 membered heterocyclyl;

$Z^2$ is selected from CH and N;

Y is selected from CO, SO, $SO_2$, $CR^4R^5$, $CONR^4$, and $SO_2NR^4$, wherein $R^4$ and $R^5$ is independently selected from hydrogen and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3 to 10 membered carbocyclyl, and optionally substituted 4-10 membered heterocyclyl;

E is connected to the "linker" moiety of the bivalent compound, and is selected from null, R'—R", R'OR", R'SR", R'NR$^6$R", R'OC(O)R", R'OC(O)OR", R'OCONR$^6$R", R'C(O)R", R'C(O)OR", R'CONR$^6$R", R'S(O)R", R'S(O)$_2$R", R'SO$_2$NR$^6$R", R'NR$^7$C(O)OR", R'NR$^7$C(O)R", R'NR$^7$C(O)NR$^6$R", R'NR$^7$S(O)R", R'NR$^7$S(O)$_2$R", and R'NR$^7$S(O)$_2$NR$^6$R", wherein R' and R" are independently selected from null, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ haloalkylene, optionally substituted $C_1$-$C_8$ hydroxyalkylene, optionally substituted $C_1$-$C_8$alkoxy$C_1$-$C_8$alkylene, optionally substituted ($C_1$-$C_8$ alkylene)O($C_1$-$C_8$ alkylene), optionally substituted ($C_1$-$C_8$ alkylene)N($C_1$-$C_8$ alkylene), optionally substituted 3-10 membered carbocyclyl, optionally substituted 4-10 membered heterocyclyl, optionally substituted $C_3$-$C_{13}$ fused carbocyclyl, optionally substituted $C_3$-$C_{13}$ fused heterocyclyl, optionally substituted $C_3$-$C_{13}$ bridged carbocyclyl, optionally substituted $C_3$-$C_{13}$ bridged heterocyclyl, optionally substituted $C_3$-$C_{13}$ spiro carbocyclyl, optionally substituted $C_3$-$C_{13}$ spiro heterocyclyl, optionally substituted aryl, and optionally substituted heteroaryl;

$R^6$ and $R^7$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$alkoxy$C_1$-$C_8$alkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl, or R' and R", $R^6$ and $R^7$, R' and $R^6$, R' and $R^7$, R" and $R^6$, R" and $R^7$ together with the atom to which they are connected form a 4-20 membered heterocyclyl ring;

$R^1$ is selected from selected from hydrogen, halogen, and optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy$C_1$-$C_8$ alkyl, optionally substituted amino, optionally substituted $C_1$-$C_8$ alkylamino$C_1$-$C_8$ alkyl, optionally substituted 3-10 membered carbocyclyl, optionally substituted 4-10 membered heterocyclyl, optionally substituted aryl, and optionally substituted heteroaryl; and $R^2$ is selected from hydrogen, halogen, cyano, nitro, hydroxyl, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, or optionally substituted $C_1$-$C_8$ alkoxy $C_1$-$C_8$ alkyl, optionally substituted amino, optionally substituted $C_1$-$C_8$ alkylamino$C_1$-$C_8$ alkyl, optionally substituted 3-10 membered carbocyclyl, and optionally substituted 4-10 membered heterocyclyl; and e. a compound selected from the group consisting of:

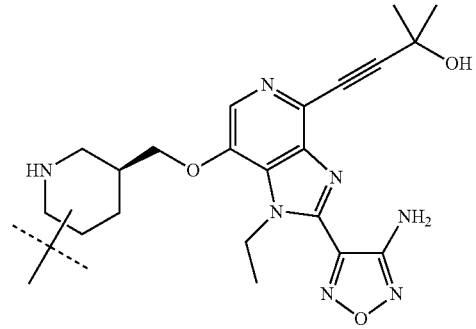

FORMULA 3A

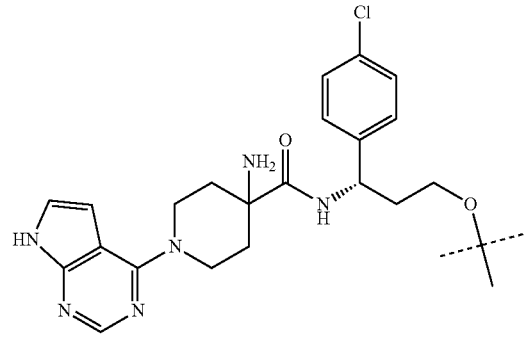

FORMULA 3B

FORMULA 3C
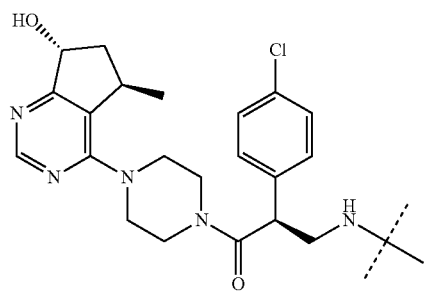
FORMULA 3D
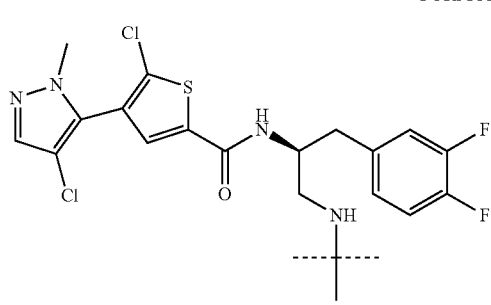
FORMULA 3E
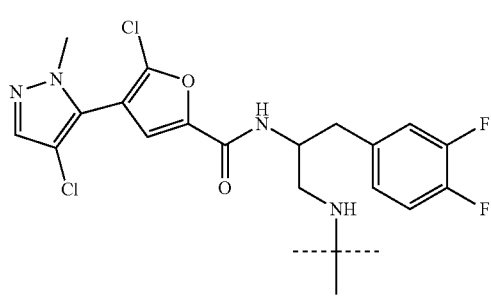
FORMULA 3F
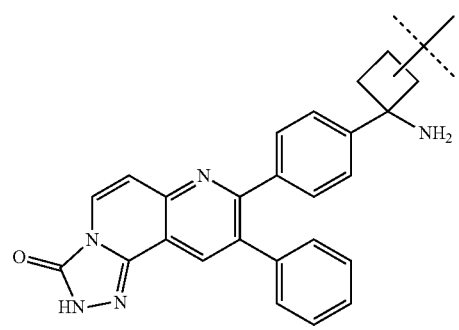
FORMULA 3G
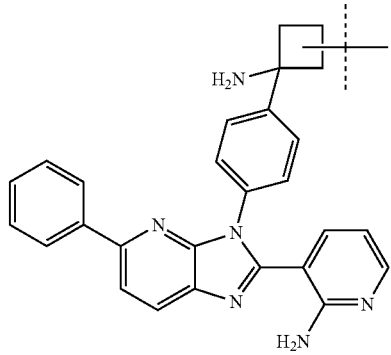
FORMULA 3H
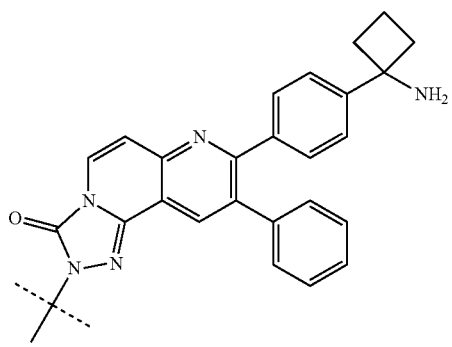
FORMULA 3I
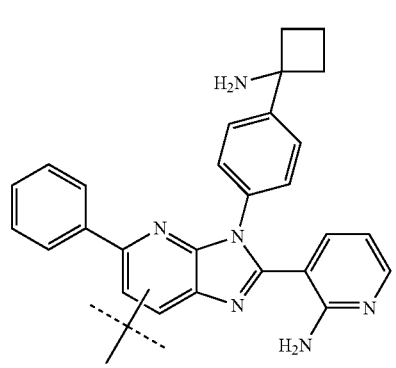
FORMULA 3J
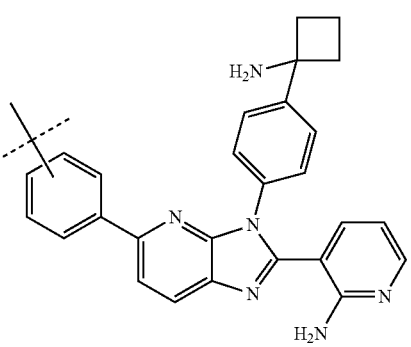
FORMULA 3K
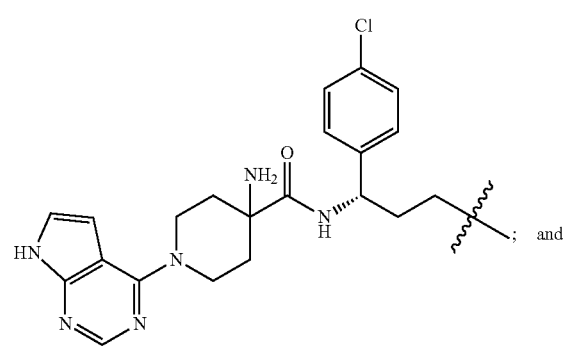
; and 12. The bivalent compound of claim 10 wherein the AKT ligand comprises:

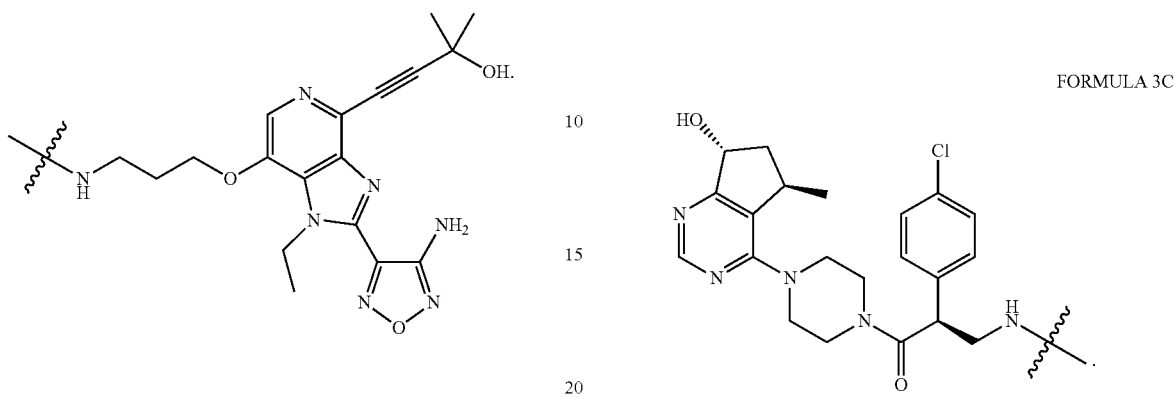

FORMULA 3C

11. The bivalent ligand of claim 10 wherein the AKT ligand comprises:

13. The bivalent ligand of claim 10 wherein the AKT ligand comprises:

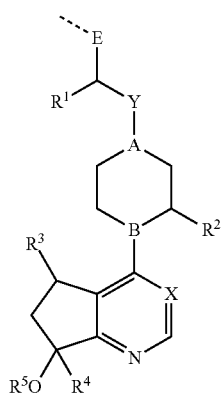

FORMULA 2

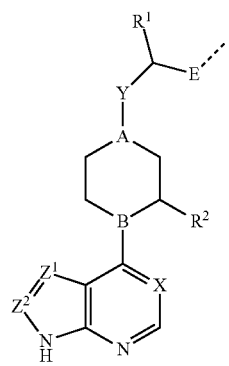

FORMULA 4 wherein

A, B and X are each N;

Y is CO;

E is connected to the "linker" moiety of the bivalent compound, and is R'NR⁹R", wherein R' is optionally substituted $C_1$-$C_8$ alkyl;

R⁹ is hydrogen;

R" is null;

R¹ is optionally substituted aryl;

R² is hydrogen;

R³ is optionally substituted $C_1$-$C_8$ alkyl;

R⁴ is hydrogen; and

R⁵ is hydrogen.

wherein

A is CR³, wherein

B and X are each N, wherein

R³ is optionally substituted amino;

Z¹ is CR, wherein

R⁸ is hydrogen;

Z² is CH;

Y is CONR⁴, wherein

R⁴ is hydrogen;

E is connected to the "linker" moiety of the bivalent compound, and is R'—R", wherein R' is optionally substituted $C_1$-$C_8$ alkyl;

R" is null;

R¹ is optionally substituted aryl; and

R² is hydrogen.

14. The bivalent compound of claim 10 wherein the AKT ligand comprises:

FORMULA 3K

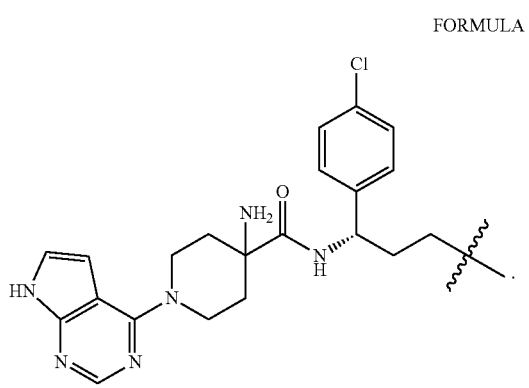

15. The bivalent compound of claim 10, wherein the AKT ligand comprises:

FORMULA 3L

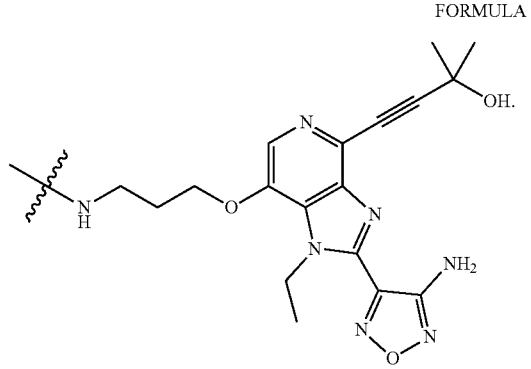

16. The bivalent compound of claim 10, wherein the AKT ligand comprises:

FORMULA 3J

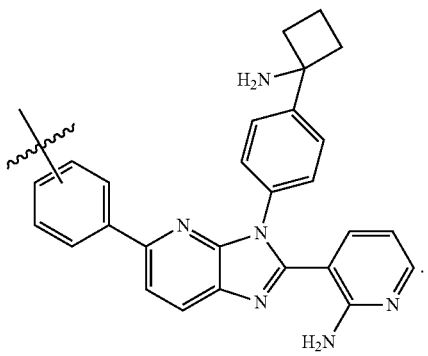

17. The bivalent compound of claim 10, wherein the AKT ligand comprises:

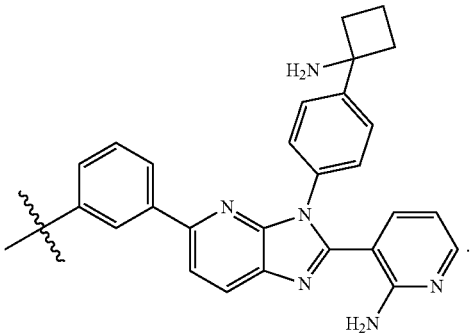 [SMILES: *c1cccc(-c2ccc3nc(-c4cccnc4N)n(-c4ccc(C5(N)CCC5)cc4)c3n2)c1]

18. The bivalent compound of claim 1, wherein the degradation/disruption tag is selected from the group consisting of:

a.

FORMULA 5A

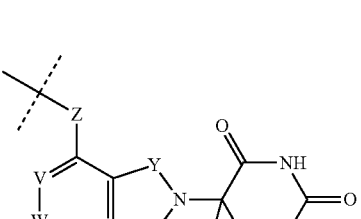

FORMULA 5B

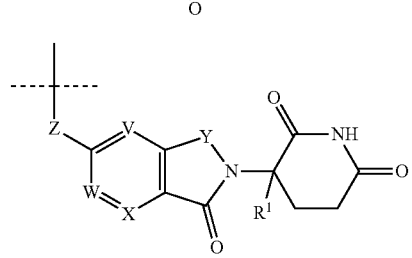

FORMULA 5C

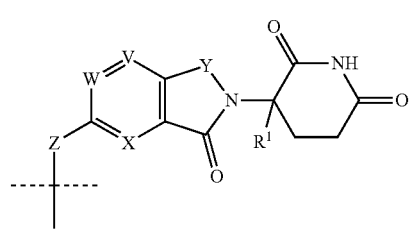

FORMULA 5D

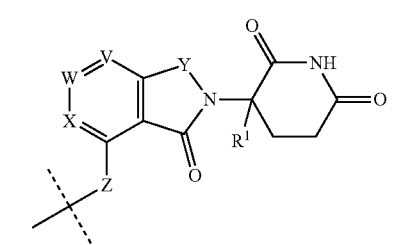

wherein
V, W, and X are independently selected from $CR^2$ and N;
Y is selected from CO, $CH_2$, and N=N;
Z is selected from $CH_2$, NH and O; and R¹ and R² are independently selected from hydrogen, halogen, cyano, nitro, and $C_1$-$C_5$ alkyl;

b.

FORMULA 6

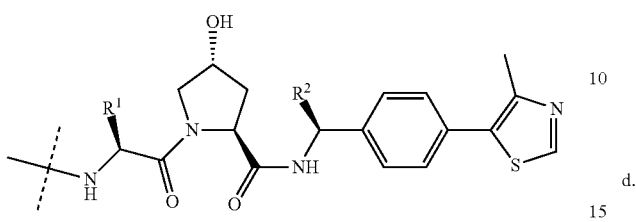

wherein
R¹ and R² are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl;

c.

FORMULA 7

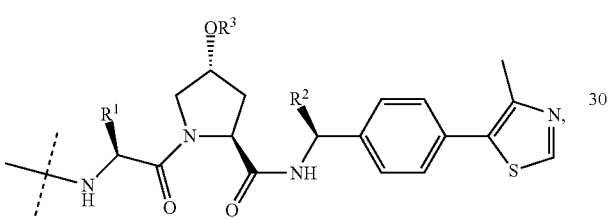

wherein
R¹ and R² are independently selected from hydrogen, hydroxyl, amino, cyano, nitro, optionally substituted $C_1$-$C_8$ alkyl, optionally substituted $C_2$-$C_8$ alkenyl, and optionally substituted $C_2$-$C_8$ alkynyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted 3-10 membered carbocyclyl, and optionally substituted 4-10 membered heterocyclyl;
R³ is selected from hydrogen, optionally substituted C(O) $C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)(3-10 membered carbocyclyl), optionally substituted C(O)(4-10 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$ aminoalkyl, optionally substituted C(O)O$C_1$-$C_8$alkylamino$C_1$-$C_8$alkyl, optionally substituted C(O)O(3-10 membered carbocyclyl), optionally substituted C(O)O(4-10 membered heterocyclyl), optionally substituted C(O)O$C_2$-$C_8$ alkenyl, optionally substituted C(O)O$C_2$-$C_8$ alkynyl, optionally substituted C(O)N$C_1$-$C_8$alkoxy$C_1$-$C_8$alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O) N$C_1$-$C_8$alkylamino$C_1$-$C_8$alkyl, optionally substituted C(O)N(3-10 membered carbocyclyl), optionally substituted C(O)N(4-10 membered heterocyclyl), optionally substituted C(O)N$C_2$-$C_8$ alkenyl, optionally substituted C(O)N$C_2$-$C_8$ alkynyl, optionally substituted P(O) (OH)₂, optionally substituted P(O)(O$C_1$-$C_8$ alkyl)₂, and optionally substituted P(O)(O$C_1$-$C_8$ aryl)₂;

d.

FORMULA 8

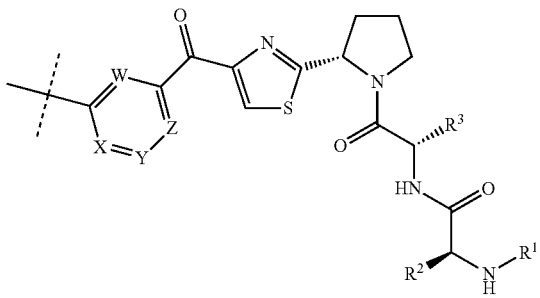

wherein
V, W, X, and Z are independently selected from CR⁴ and N; and
R¹, R², R³, and R⁴ are independently selected from hydrogen, halogen, cyano, nitro, optionally substituted $C_1$-$C_8$ alkyl, optionally substituted $C_2$-$C_8$ alkenyl, and optionally substituted $C_2$-$C_8$ alkynyl; optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkoxy, optionally substituted $C_1$-$C_8$alkylamino, optionally substituted 3-10 membered carbocyclyl, and optionally substituted 4-10 membered heterocyclyl;

e. a compound selected from the group consisting of:

FORMULA 8A

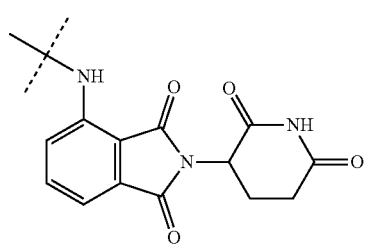

FORMULA 8B

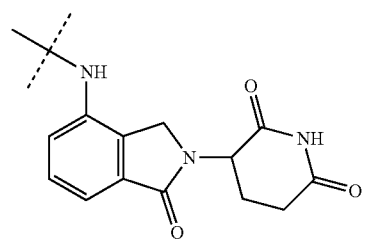

FORMULA 8C
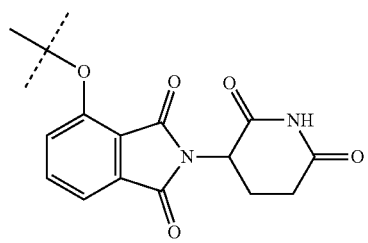
FORMULA 8D
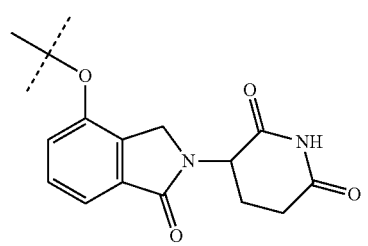
FORMULA 8E
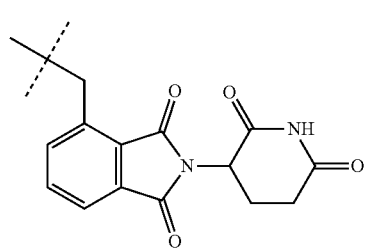
FORMULA 8F
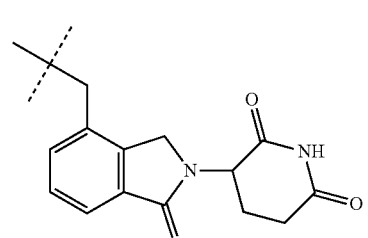
FORMULA 8G
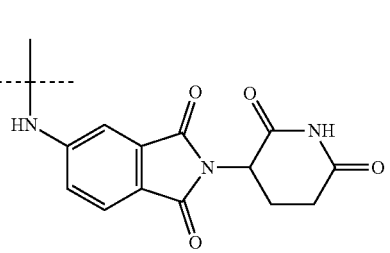
FORMULA 8H
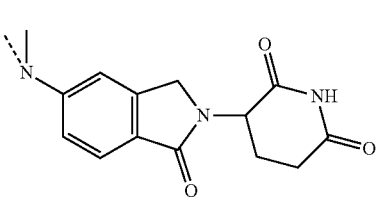
FORMULA 8I
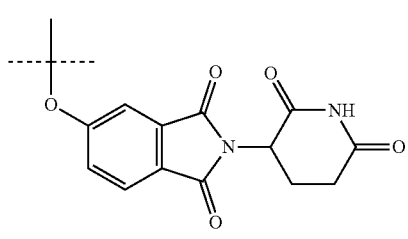
FORMULA 8J
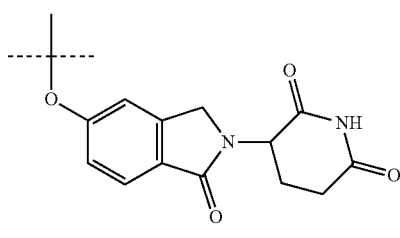
FORMULA 8K
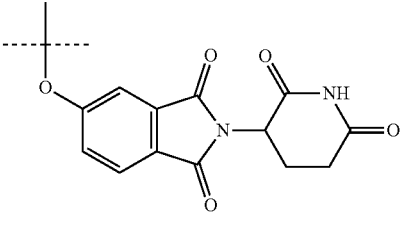
FORMULA 8L
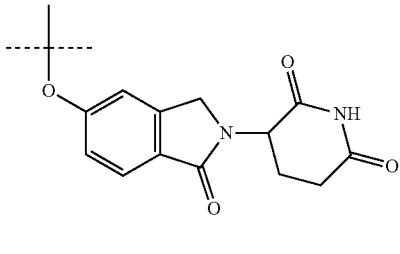
FORMULA 8M
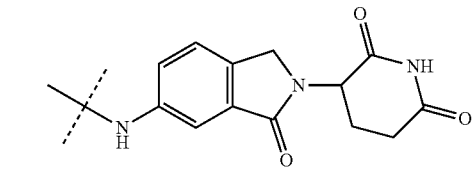
FORMULA 8N
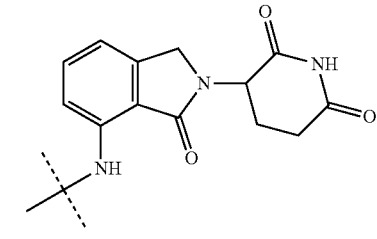
FORMULA 8O
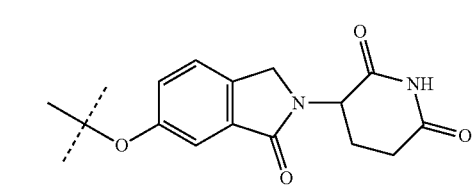
FORMULA 8P
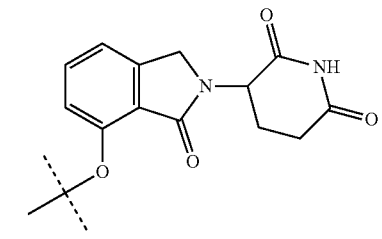

FORMULA 8Q
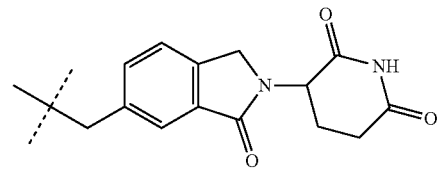
FORMULA 8R
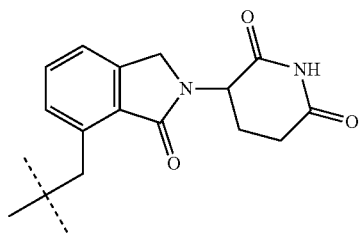
FORMULA 8S
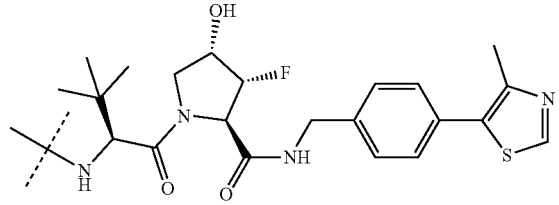
FORMULA 8T
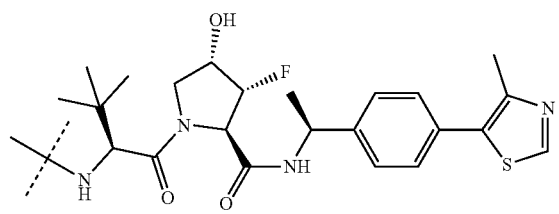
FORMULA 8U
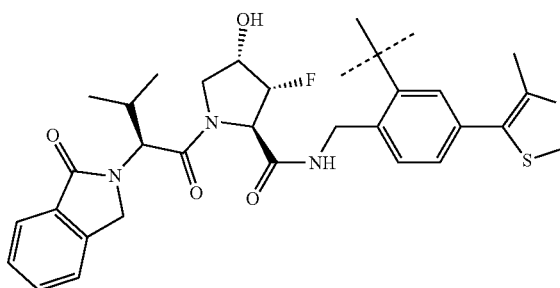
FORMULA 8V
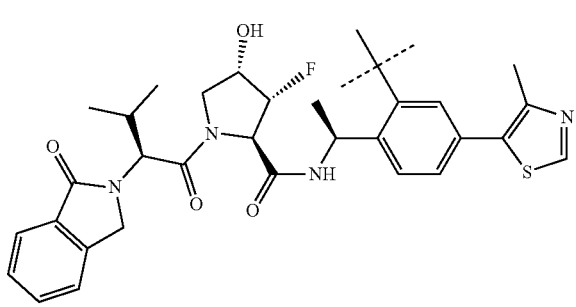
FORMULA 8W
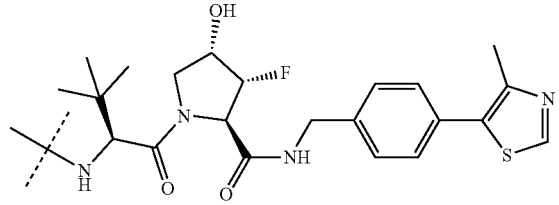
FORMULA 8X
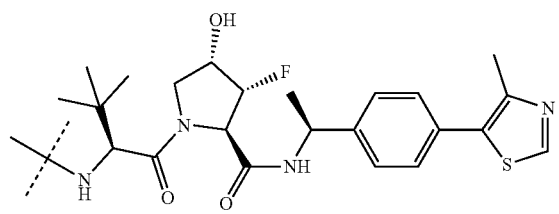
FORMULA 8Y
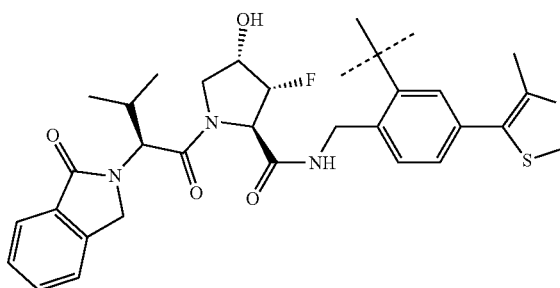
FORMULA 8Z
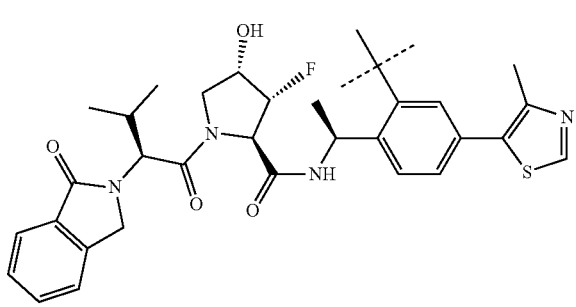
FORMULA 8AA
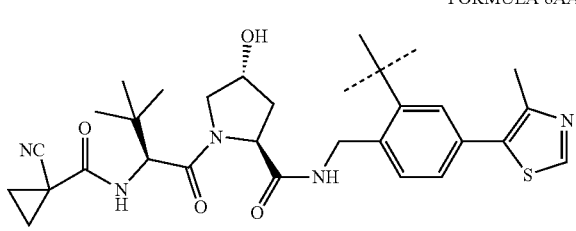
FORMULA 8AB
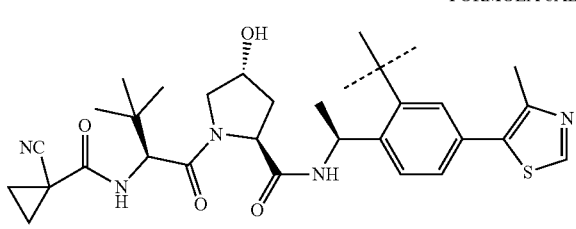

FORMULA 8AC
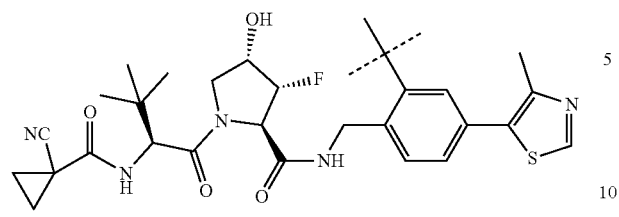
FORMULA 8AD
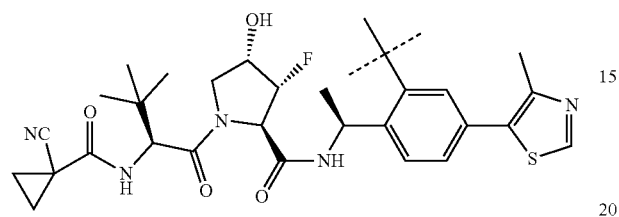
FORMULA 8AE
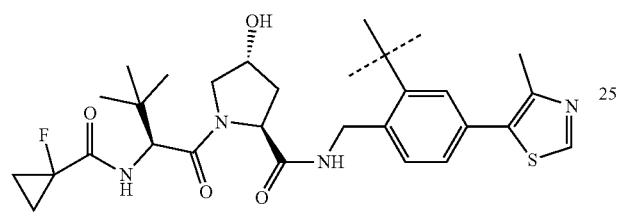
FORMULA 8AF
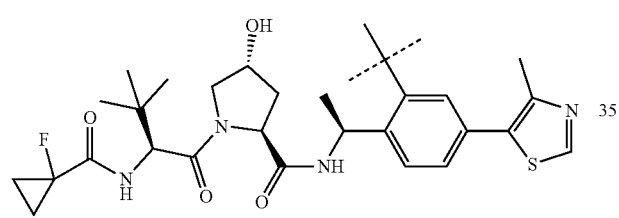
FORMULA 8AG
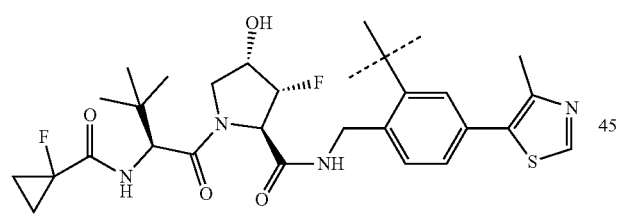
FORMULA 8AH
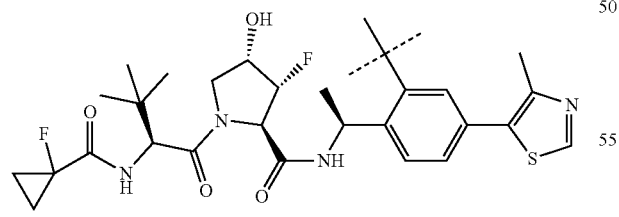
FORMULA 8AI
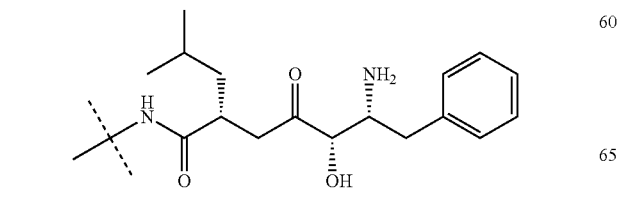
FORMULA 8AJ
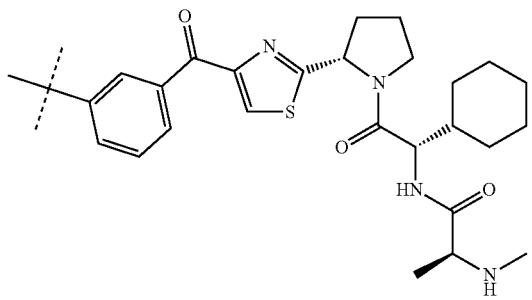
FORMULA 8AK
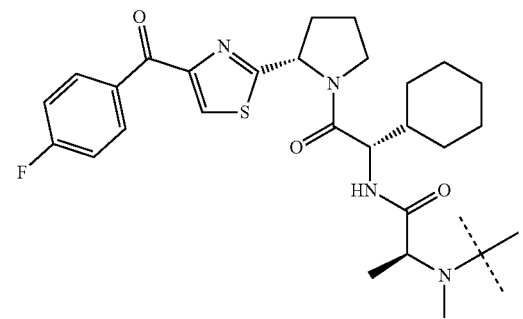
FORMULA 8AL
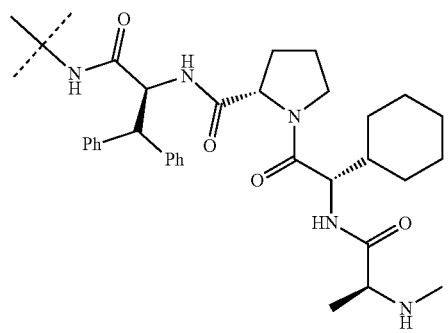
FORMULA 8AM
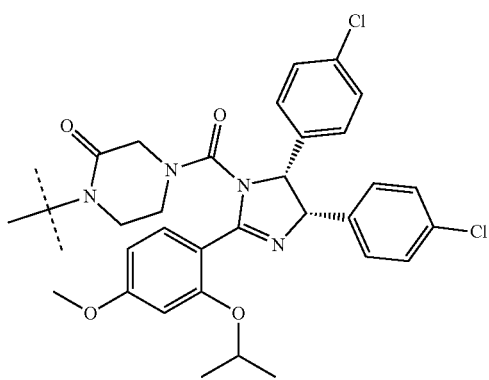

649

-continued

FORMULA 8AN

FORMULA 8AO

FORMULA 8AP and
f. a compound selected from the group consisting of:

thalidomide pomalidomide

650

-continued lenalidomide bestatin

MV₁

LCL161 nutlin-3a

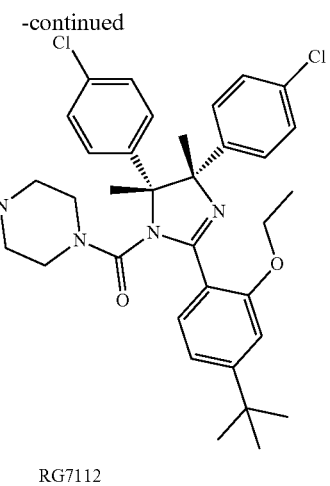
RG7112

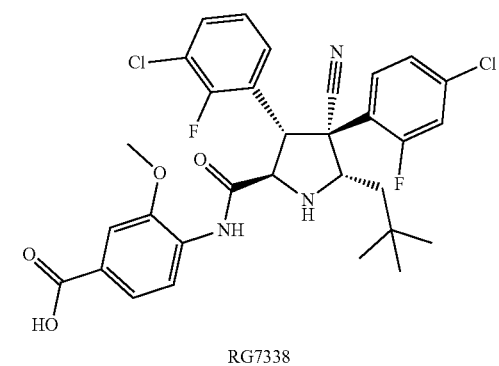
RG7338

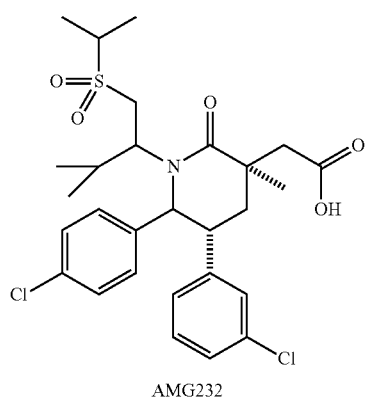
AMG232

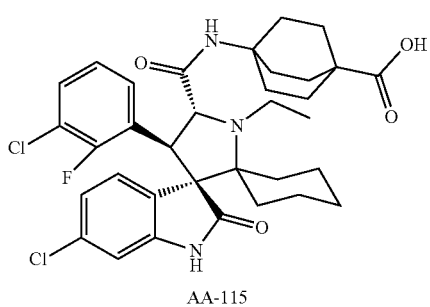
AA-115

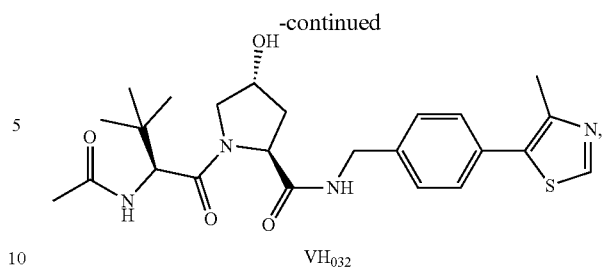
VH₀₃₂ or a pharmaceutically acceptable salt thereof.

19. The bivalent compound of claim 1, wherein the bivalent compound is selected from the group consisting of: XF038-157A, XF038-158A, XF038-159A, XF038-160A, XF038-161A, XF038-162A, XF038-164A, XF038-165A, XF038-166A, XF038-176A, XF038-177A, XF042-162, XF042-164, XF042-165, XF042-166, XF042-167, XF042-168, XF042-170, XF042-171, XF048-1, XF048-2, XF048-3, XF048-4, XF048-5, XF048-7, XF048-8, XF050-5, XF050-6, XF050-7, XF050-8, XF050-9, XF050-10, XF050-11, XF050-12, XF050-13, XF050-14, XF050-15, XF050-16, XF050-17, XF050-18, XF050-19, XF050-20, XF050-21, XF050-22, XF050-23, XF050-24, XF050-25, XF050-26, XF050-27, XF050-28, XF050-29, XF050-30, XF050-31, XF050-32, XF050-33, XF050-98, XF050-132, XF050-133, XF050-134, XF056-93, XF050-143, XF050-144, XF050-145, XF050-167, XF056-33, XF056-34, XF056-35, XF056-36, XF056-37, XF056-73, XF061-10, XF067-1, XF067-2, XF067-3, XF067-4, XF067-5, XF067-6, XF067-7, XF067-8, XF067-9, XF067-10, XF067-11, XF067-12, XF067-13, XF067-14, XF067-15, XF067-16, XF067-17, XF067-18, XF067-19, XF067-20, XF067-21, XF067-22, XF067-23, XF067-24, XF067-25, XF067-26, XF067-27, XF067-28, XF067-29, XF067-30, XF067-31, XF067-32, XF067-33, XF067-34, XF067-35, XF067-36, XF067-37, XF067-38, XF067-39, XF067-40, XF067-41, XF067-42, XF067-43, XF067-44, XF067-45, XF067-46, XF067-47, XF067-48, XF067-49, XF067-50, XF067-51, XF067-52, XF067-53, XF067-54, XF067-55, XF067-56, XF067-57, XF067-58, XF067-59, XF067-84, XF067-85, XF067-86, XF067-87, XF067-88, XF067-89, XF067-90, XF067-91, XF067-92, XF067-93, XF067-94, XF067-95, XF067-96, XF067-97, XF067-98, XF067-99, XF067-100, XF067-101, XF067-102, XF067-103, XF067-104, XF067-105, XF067-106, XF067-107, XF067-108, XF067-109, XF067-110, XF067-111, XF067-112, XF067-113, and pharmaceutically acceptable salts and enantiomers thereof.

20. A method of treating a serine threonine kinase (AKT)-mediated disease, comprising administering, to a subject with an AKT-mediated disease, a bivalent compound comprising an AKT ligand conjugated to a degradation/disruption tag through a linker.

21. A bivalent compound comprising a serine threonine kinase (AKT) ligand conjugated to a degradation/disruption tag through a linker.

22. The bivalent compound of claim 21, wherein the AKT ligand is selected from the group consisting of GSK690693, GSK2110183, GSK2141795, AZD5363, GDC-0068, MK-2206, and ARQ-092.

23. The bivalent compound of claim 21, wherein the degradation/disruption tag is selected from the group consisting of pomalidomide, thalidomide, lenalidomide, VHL-1, adamantane, 1-((4,4,5,5,5-pentafluoropentyl)sulfinyl) nonane, nutlin-3a, RG7112, RG7338, AMG232, AA-115, bestatin, MV-1, and LCL161.

24. The bivalent compound of claim 21, wherein the AKT ligand [PI] comprises:

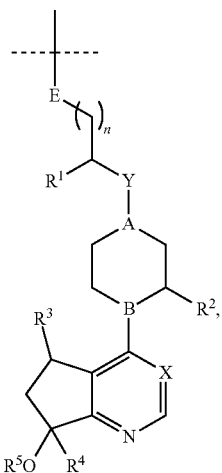

FORMULA 1 wherein

A, B, and X are independently N, CH, or $CR^6$,

Y is $CH_2$, CO, SO, $SO_2$, $CR^7R^8$, $CONR^7$, or $SO_2NR^7$, E is NH, $NR^9$, O, $C_1$-$C_8$ alkyl, $C_1$-$C_8$ alkoxy, $C_1$-$C_8$ alkoxyalkyl, $C_1$-$C_8$ haloalkyl, $C_1$-$C_8$ hydroxyalkyl, $C_3$-$C_8$ cycloalkyl, $C_3$-$C_7$ heterocyclyl, $C_2$-$C_8$ alkenyl, $C_2$-$C_8$ alkynyl, $OR^9$, $SR^9$, $NR^9R^{10}$, CN, $NO_2$, $(CR^9R^{10})_m$ $NR^{11}R^{12}$, $(CR^9R^{10})_m C(O)R^{11}$, $(NR^9R^{10})_m$ $NR^{11}R^{12}$, $(NR^9R^{10})_m C(O)R^{11}$, $COR^9$, $CO_2R^9$, $CONR^9R^{10}$, $NR^9COR^{10}$, $NR^9SOR^{10}$, $NR^9SO_2R^{10}$, $SOR^9$, $SO_2R^9$, $SO_2NR^9R^{10}$, $(CR^9R^{10})_m$-aryl, or $(CR^9R^{10})_m$-heteroaryl, $R^1$ is H, $C_1$-$C_8$ alkyl, $C_3$-$C_8$ cycloalkyl, $C_1$-$C_8$ alkoxy, $C_1$-$C_8$ alkoxyalkyl, aryl, $C_1$-$C_8$ alkylaryl, haloaryl, arylalkyl, heteroaryl, or heteroarylalkyl, $R^2$, $R^3$, $R^4$, and $R^6$ are independently hydrogen, halogen, amino, $C_1$-$C_8$ alkylamino, arylamino, $C_1$-$C_8$ alkyl, $C_3$-$C_8$ cycloalkyl, $C_1$-$C_8$ alkoxy, or $C_1$-$C_8$ alkoxyalkyl, $R^5$, $R^7$, and $R^8$ are independently H, $C_1$-$C_8$ alkyl, $C_3$-$C_8$ cycloalkyl, or $C_1$-$C_8$ alkoxyalkyl, $R^9$, $R^{10}$, $R^{11}$, and $R^{12}$ are independently H, $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, arylalkyl, cycloalkyl, heterocycloalkyl, aryl, heteroaryl, or heteroarylalkyl, $R^9$ and $R^{10}$, $R^{11}$ and $R^{12}$ can independently form 4-8 membered alkyl or heterocyclyl rings, m=0-8, and n=0-8.

25. The bivalent compound of claim 21, wherein the AKT ligand [PI] comprises:

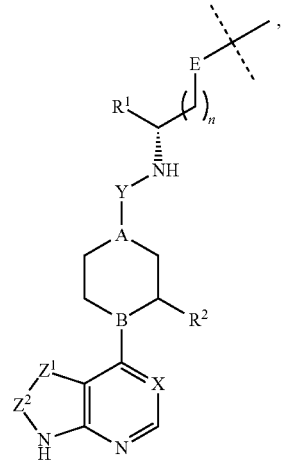

FORMULA 3 wherein

A, B, and X are independently N or $CR^3$,

Y is $CH_2$, CO, SO, $SO_2$, $CR^4R^5$, $CONR^4$, or $SO_2NR^4$,

E is NH, $NR^6$, O, $C_1$-$C_8$ alkyl, $C_1$-$C_8$ alkoxy, $C_1$-$C_8$ alkoxyalkyl, $C_1$-$C_8$ haloalkyl, $C_1$-$C_8$ hydroxyalkyl, $C_3$-$C_8$ cycloalkyl, $C_3$-$C_8$ heterocyclyl, $C_2$-$C_8$ alkenyl, $C_2$-$C_8$ alkynyl, $OR^6$, $SR^6$, $NR^6R^7$, CN, $NO_2$, $(CR^6R^7)_m NR^8R^9$, $(CR^6R^7)_m C(O)R^8$, $(NR^6R^7)_m NR^8R^9$, $(NR^6R^7)_m C(O)R^8$, $COR^6$, $CO_2R^6$, $CONR^6R^7$, $NR^6COR^7$, $NR^6SOR^7$, $NR^6SO_2R^7$, $SOR^6$, $SO_2R^6$, $SO_2NR^6R^7$, $(CR^6R^7)_m$-aryl, or $(CR^6R^7)_m$-heteroaryl, $Z^1$-$Z^2$ is $CR^{10}$=CH, N+CH, or $CR^{10}$=N, $R^1$ is hydrogen, $C_1$-$C_8$ alkyl, $C_3$-$C_8$ cycloalkyl, $C_1$-$C_8$ alkoxy, $C_1$-$C_8$ alkoxyalkyl, aryl, $C_1$-$C_8$ alkylaryl, haloaryl, arylalkyl, heteroaryl, or heteroarylalkyl, $R^2$, $R^3$, and $R^4$ are independently hydrogen, halogen, amino, $C_1$-$C_8$ alkylamino, arylamino, $C_1$-$C_8$ alkyl, $C_3$-$C_8$ cycloalkyl, $C_1$-$C_8$ alkoxy, or $C_1$-$C_8$ alkoxyalkyl, $R^6$, $R^7$, $R^8$, and $R^9$ are independently H, $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, arylalkyl, cycloalkyl, heterocycloalkyl, aryl, heteroaryl, or heteroarylalkyl, $R^6$ and $R^7$, $R^8$ and $R^9$ can independently form 4-8 membered alkyl or heterocyclyl rings, $R^{10}$ is hydrogen, halogen, $C_1$-$C_8$ alkyl, $C_3$-$C_8$ cycloalkyl, $C_1$-$C_8$ alkoxy, $C_1$-$C_8$ alkoxyalkyl, m=0-8, and n=0-8.

26. The bivalent compound of claim 21, wherein [PI] the AKT ligand is selected from the group consisting of:

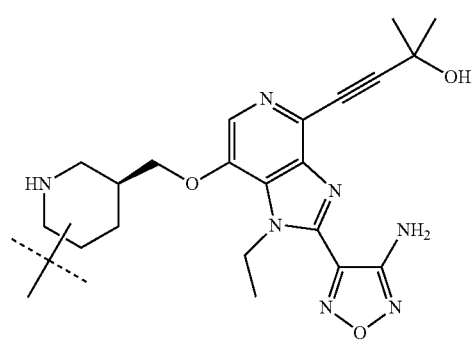

FORMULA 3A

FORMULA 3B

FORMULA 3C

FORMULA 3D

FORMULA 3E

FORMULA 3F

FORMULA 3G

FORMULA 3H

FORMULA 3I

GSK690693

AZD5363
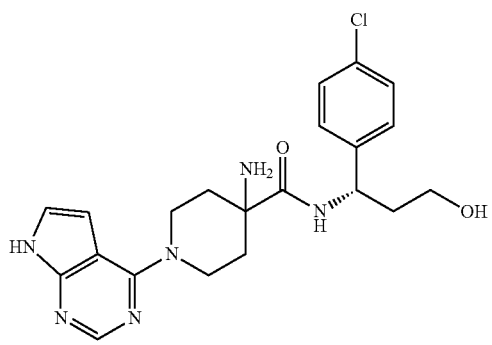
ARQ 092
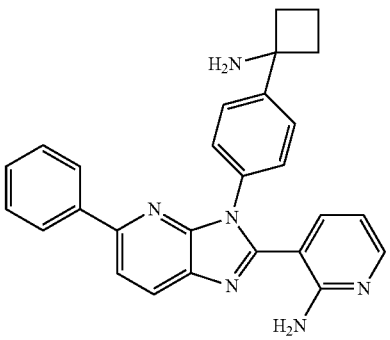
27. The bivalent compound of claim 21, wherein the degradation tag [EL] is selected from the group consisting of:
GDC0068
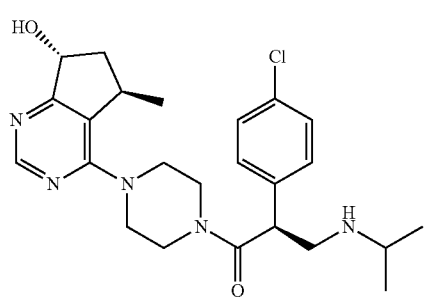
FORMULA 5A
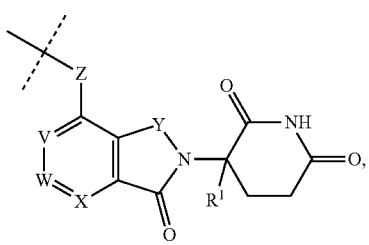
GSK2110183
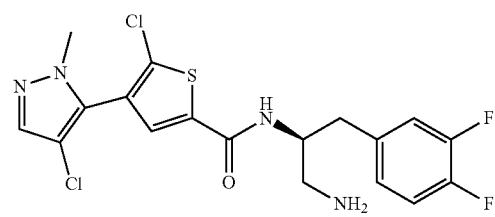
FORMULA 5B
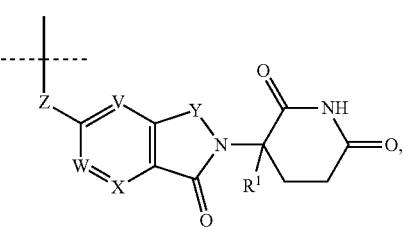
GSK2141795
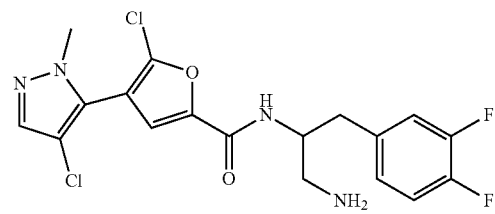
FORMULA 5C
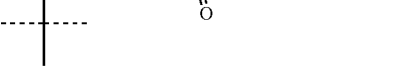
MK2206
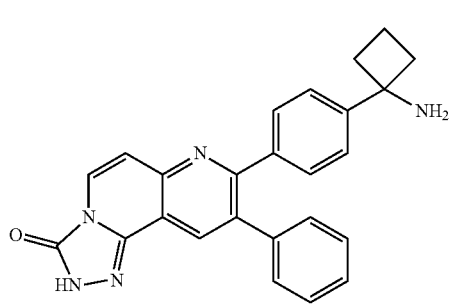
FORMULA 5D
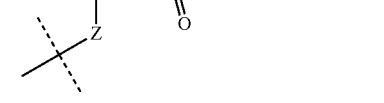
wherein
V, W, and X are independently $CR^2$ or N,
Y is CO or $CH_2$,
Z is $CH_2$, NH, or O,
$R^1$ is hydrogen, methyl, or fluoro, and
$R^2$ is hydrogen, halogen, or $C_1$-$C_8$ alkyl;

FORMULA 6

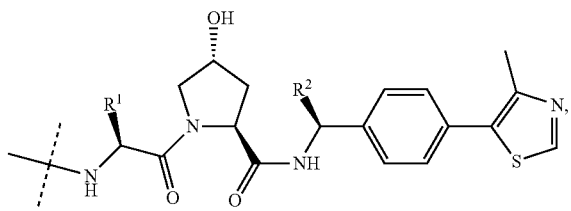

wherein R[1] and R[2] are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl; and

FORMULA 8

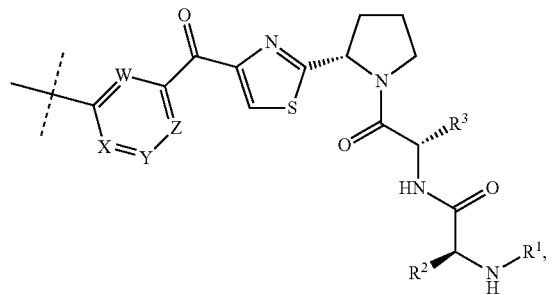

wherein R[1], R[2], R[3], and R[4] are independently hydrogen, $C_1$-$C_8$ alkyl, $C_1$-$C_8$ alkoxyalkyl, $C_1$-$C_8$ haloalkyl, $C_1$-$C_8$ hydroxyalkyl, $C_3$-$C_7$ cycloalkyl, $C_3$-$C_7$ heterocyclyl, $C_2$-$C_8$ alkenyl, or $C_2$-$C_8$ alkynyl, and V, W, X, and Z are independently CR[4] or N.

28. The bivalent compound of claim 21, wherein the linker is selected from the group consisting of:

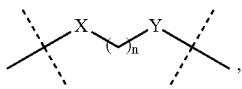

Formula A wherein X is C=O or $CH_2$,
Y is C=O or $CH_2$, and
n is 0-15;

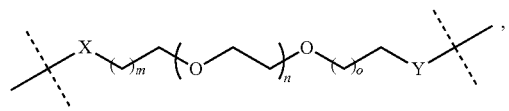

Formula B wherein X is C=O or $CH_2$,
Y is C=O or $CH_2$,
m is 0-15,
n is 0-6, and
o is 0-15; and

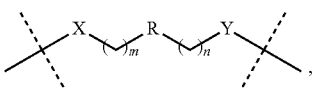

Formula C wherein
X is C=O or $CH_2$,
Y is C=O or $CH_2$,
R is —$CH_2$—, —$CF_2$—, —CH($C_{1-3}$ alkyl)-, —C($C_{1-3}$ alkyl)($C_{1-3}$ alkyl)-, —CH=CH—, —C($C_{1-3}$ alkyl)=C($C_{1-3}$ alkyl)-, —C≡C—, —O—, —NH—, —N($C_{1-3}$ alkyl)-, —C(O)NH—, —C(O)N($C_{1-3}$ alkyl)-, a 3-13 membered ring, a 3-13 membered fused ring, a 3-13 membered bridged ring, or a 3-13 membered spiro ring,
m is 0-15, and
n is 0-15.

29. The bivalent compound of claim 21, wherein the linker is Formula C and R is selected from the group consisting of:

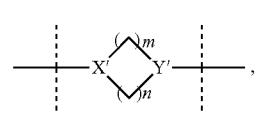

Formula C1

X' = N or CH
Y' = N or CH
m = 0-5
n = 0-5

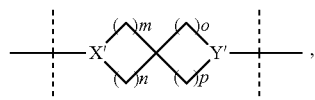

Formula C2

X' = N or CH
Y' = N or CH
m = 0-5
n = 0-5
o = 0-5
p = 0-5

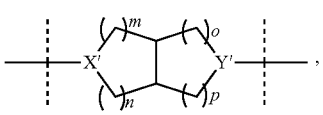

Formula C3

X' = N or CH
Y' = N or CH
m = 0-5
n = 0-5
o = 0-5
p = 0-5

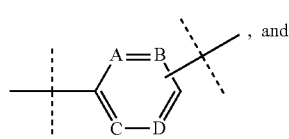

Formula C4, and

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N

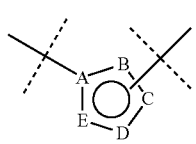

Formula C5

A = C, CH, C(C$_{1-3}$ alkyl), N, NH, N(C$_{1-3}$ alkyl), O, S
B = C, CH, C(C$_{1-3}$ alkyl), N, NH, N(C$_{1-3}$ alkyl), O, S
C = C, CH, C(C$_{1-3}$ alkyl), N, NH, N(C$_{1-3}$ alkyl), O, S
D = C, CH, C(C$_{1-3}$ alkyl), N, NH, N(C$_{1-3}$ alkyl), O, S
E = C, CH, C(C1-3 alkyl), N, NH, N(C1-3 alkyl), O, S.

30. A method for identifying a bivalent compound which mediates degradation/disruption of AKT, the method comprising:
providing a heterobifunctional test compound comprising an AKT ligand conjugated to a degradation/disruption tag through a linker;
contacting the heterobifunctional test compound with a cell comprising a ubiquitin ligase and AKT;
determining whether AKT levels decrease in the cell; and
identifying the heterobifunctional test compound as a bivalent compound which mediates degradation/reduction of AKT levels decrease in the cell.

* * * * *